(12) United States Patent
Sage et al.

(10) Patent No.: US 7,242,443 B2
(45) Date of Patent: Jul. 10, 2007

(54) TRIBOLUMINESCENT MATERIALS AND DEVICES

(75) Inventors: Ian C Sage, Worcester (GB); Wendy H Howie, Worcester (GB); Ian D Brotherston, Worcester (GB)

(73) Assignee: Qinetiq Limited, London (GB)

( * ) Notice: Subject to any disclaimer, the term of this patent is extended or adjusted under 35 U.S.C. 154(b) by 506 days.

(21) Appl. No.: 10/486,964

(22) PCT Filed: Aug. 6, 2002

(86) PCT No.: PCT/GB02/03615

§ 371 (c)(1),
(2), (4) Date: Feb. 17, 2004

(87) PCT Pub. No.: WO03/016428

PCT Pub. Date: Feb. 27, 2003

(65) Prior Publication Data

US 2004/0233347 A1 Nov. 25, 2004

(30) Foreign Application Priority Data

Aug. 14, 2001 (GB) ............................... 01197929.2

(51) Int. Cl.
*G02F 1/1333* (2006.01)

(52) U.S. Cl. .................... 349/56; 428/1.1; 73/800; 252/301.16

(58) Field of Classification Search ............ 252/301.16
See application file for complete search history.

(56) References Cited

U.S. PATENT DOCUMENTS

| 5,504,195 | A | 4/1996 | Leedham et al. |
| 6,071,632 | A * | 6/2000 | Hall-Goulle ............... 428/690 |
| 6,524,727 | B1 | 2/2003 | Kathirgamanathan |
| 6,605,317 | B1 | 8/2003 | Kathirgamanathan |
| 2004/0233347 | A1 | 11/2004 | Sage et al. |

FOREIGN PATENT DOCUMENTS

| EP | 1 009 033 A | 6/2000 |
| EP | 1 035 160 A | 9/2000 |
| GB | 2 232 119 A | 12/1990 |
| GB | 2232119 A | 12/1990 |
| GB | 2 325 883 A | 12/1998 |
| WO | 96/20942 A | 7/1996 |
| WO | 97/18451 A | 5/1997 |
| WO | 02/062914 A1 | 8/2002 |
| WO | 02/062915 A1 | 8/2002 |

OTHER PUBLICATIONS

Zhu et al; "Red Mechanoluminescence and Photoluminescenece From Novel Europium Complexes"; Chinese Chemical Letters, vol. 11, No. 7, 2000, pp. 635-638, XP008009596.
Brandl: "Das Phaenomen Der Triboluminszenz"; Mathemathische UND Naturwissenschaftliche Unterricht, Duemmler, Bonn, DE, Jun. 1, 1992, pp. 195-202, XP001078983.
Zhu Wenxiang et al; "Triboluminescent Complexes of Rare Earth. (I). Ternary Complexes of Samarium (3+), Europium (3+) and Terbium (3+) with Thenoyltrifluoroacetone and Triphenylphosphine Oxide"; CAPLUS, XP002217570.
Zhu Wenxiang et al; "Rare Earth Triboluminescent Complexes. Part II, Mixed Complexes Between Europium (3+), TTA and Pyridine-Type N-Oxide Compounds"; Retrieved from STN Database Accession No. 114:1771144 CA, XP002217712.
Ala-Kleme et al; "Y (III)-Enhanced Dy (III) and Sm (III)-Specific Electrogenerated Luminescence of Heterrodinuclear 1-Y(III)-Dy(111)-1 and 1-Y(III)-Sm(III)-1 Chelates"; Journal of Alloys and Compounds, vol. 275-277, 1998, pp. 911-914, XP002217711.
Akiyama et al; "Influence of Eu, Dy Co-Doped Strontium Aluminate Composition on Mechanoluminescence Intensity"; Journal of Luminescence, Amsterdam, NL, vol. 97, No. 1, Apr. 2002, pp. 13-18, XP004347383.
Takada et al; "Mechanoluminescent Properties of Europium Complexes"; Synthetic Metals, Elsevier Sequoia, Lausanne, CH, vol. 91, No. 1/3, Dec. 1997, pp. 351-354, XP000866433.
Patent Abstracts of Japan, vol. 006, No. 011 (C-088), Jan. 22, 1982 & JP 56 136874 A, Oct. 26, 1981, Abstract.
Chinese Chemical Letters, vol. 11, No. 7, pp. 635-638, 2000.
Zhu et al, "Synthesis and Fluorescent Properties of New Binuclear . . . ", Chinese Chemical Letters vol. 10, No. 7, pp. 603-606, 1999.
Reyes et al, "Growth and Characterization of OLED with Samarium Complex as Emitting and Electron Transporting Layer", Thin Solid Films 420-421 (2002) 23-29.

* cited by examiner

*Primary Examiner*—Kamal A. Saeed
(74) *Attorney, Agent, or Firm*—Nixon & Vanderhye P.C.

(57) ABSTRACT

The invention relates to various materials and their use in applications which exploit the triboluminescent effect.

6 Claims, 3 Drawing Sheets

TRIBOLUMINESCENT MATERIALS AND DEVICES

This application is the US national phase of international application PCT/GB02/03615, filed in English on 06 Aug. 2002, which designated the US. PCT/GB02/03615 claims priority to GB Application No. 0119729.2 filed 14 Aug. 2001. The entire contents of these applications are incorporated herein by reference.

This invention relates to novel Triboluminescent (TL) materials and their use in devices which exploit the triboluminescent effect.

Triboluminescent materials are known—(L M Sweeting & J L Guido, J. of Luminescence, 33, (1985), p167, N Kitamura et al, Chem Phys Letts, 125, (1986), p360, B P Shandra, et al Pramana-J Phys, 29, (1987), p399, C R Hurt, et al Nature, 212, (1966), p179; L M Sweeting & A L Rheingold, J Am Chem Soc, 109, (1987), p2652 M B Hocking, et al, J. of Luminescence, 43, (1989), p309).

Triboluminescence is the effect seen when a material emits light when particles of the material are damaged/fractured or strained.

Chinese Chemical Letters, vol 11, no 7 pp635-38, 2000 discloses a number of compounds that exhibit mechanoluminescence (ML). The property of mechanoluminescence is effectively the same property as triboluminescence. More specifically two 1:1 binuclear (europium and lanthanum) β-diketonate complexes are disclosed. The complexes further comprise 1,10-phenanthroline and an anion of thenoyltrifluoroacetone (HTTA).

Soden in J. Appl. Phys., 32, (1961) 750 discloses the effects of rare-earth substitutions on the fluorescence of Terbium Hexa-Antipyrine tri-iodide.

PCT GB96/02778 and corresponding U.S. Pat. No. 5,905,260 describe the use of triboluminescent compounds in an environment where they are used to detect damage to objects.

Preferably for use in damage sensing equipment triboluminescent compounds exhibit some or all of the following properties:

Bright emission

High stability to temperature and high melting point

Compatibility with structural and adhesive resins

Emission at wavelengths which are different from those provided by known materials Emission of light having other features distinguishable from known materials, such as luminescence lifetime, bandwidth etc.

Clearly it is also advantageous that triboluminescent compounds, if they are to be used commercially, are not prohibitively expensive.

There is a continued need for triboluminescent materials for use in such an environment and it is an object of the present invention inter alia to provide alternative compounds suitable for use in a range of applications/devices which are capable of exploiting the triboluminescence effect particularly sensing damage applications.

The current invention provides for the use of a range of compounds in a number of devices/applications which exploit the triboluminescent effect and it is believed that some of these compounds are novel and inventive per se.

According to a first aspect of this invention a method of making paper that emits light when torn and/or pressed and/or gripped and/or folded comprises the steps of coating and/or impregnating the paper with triboluminescent material comprising M wherein M is chosen from Tb, Eu, Sm, Dy and 0.01%-99.99% of M is replaced by at least one of Y, Gd, La or Lu.

When coating and/or impregnating the paper it may be necessary to apply the triboluminescent material in one or more of a number of ways, for example:

in an adhesive composition, in addition the triboluminescent material may be glued onto the paper either directly and/or in an encapsulant such as a polymer;

in a solvent followed by solvent evaporation;

by melting the triboluminescent material such that it soaks into the paper;

by incorporating the triboluminescent material together with the pulp, fibre etc., during manufacture of the paper.

Preferably the solvent will be an organic solvent though this will be a function of the solvation properties of the triboluminescent material.

Examples of suitable polymers for use in encapsulation include the following:

Acrylic and methacrylic resins, polyimides, polyamides, melamine/formaldehyde resins, urea formaldehyde resins, epoxy resins, poly(p-xylylene), gelatin, poly(lactic acid), polyester resins and alkyd resins.

Typical adhesives include:

Epoxy adhesives based on adducts of bisphenol-A and epichlorhydrin cured by polyamine or anhydride initiators, and similar adhesives based on other epoxides, UV curable and thermally curable adhesives based on acrylic, vinylic, styrenic, or thiol/ene monomer systems, cyanoacrylate adhesives, pressure sensitive adhesives, hot melt adhesives, latex based adhesives, PVA adhesives, solvent based adhesives, urea formaldehyde and melamine formaldehyde adhesives, anaerobic adhesives, bis-diallyamine derived adhesives etc.

In addition to the adhesive and triboluminescent material the adhesive composition may also comprise one or more of the following additional reagents such as solvents, dispersants, plasticisers, curing agents, dyes, fillers, stabilisers, anti-oxidants etc as is understood in the art. The compositions may include water as a solvent or dispersant or an organic solvent such as dichloromethane, acetone, tetrahydrofuran etc. may be present in order to ensure that the composition is homogenous and will spread well.

According to a second aspect of this invention paper is provided which comprises one or more triboluminescent materials according to the first aspect of the present invention such that the paper triboluminesces when the paper is torn and/or pressed and/or gripped and/or folded.

Such paper is obtainable by the method of the first aspect of the invention.

For all of the above aspects of the invention the term paper is also taken to include paper-like products such as cardboard, kitchen-roll, tissue and the like.

According to a third aspect of the invention a product comprising the paper of the second aspect of the invention is provided.

According to a fourth aspect of this invention an adhesive composition comprising an adhesive and one or more triboluminescent materials according to the first aspect of the present invention is provided.

According to a fifth aspect of this invention a method of adhering two surfaces together comprises the steps of:

applying an adhesive composition to one or more surfaces and bringing the surfaces into contact such that adhesion occurs wherein the adhesive composition comprises an adhesive and one or more triboluminescent materials according to the first aspect of the present invention.

According to a sixth aspect of this invention a method of making adhesive tape that flashes when used comprises the steps of:

selecting a substantially transparent substrate, optionally depositing an adhesion promoter on the substrate, depositing an adhesive composition comprising a triboluminescent material according to the first aspect of the present invention on to the substrate, optionally drying the adhesive composition, optionally depositing a further laminating sheet on top of the adhesive composition before or after any drying stage.

The laminating sheet, if applied, may be treated with a release layer.

By flashes when used it is meant that the adhesive tape may flash when it is removed from a roll of adhesive tape or it may flash when it is removed from the object to which it has been applied. The adhesive tape may also flash when it is cut. How many times a particular piece of adhesive tape flashes will depend on the nature of the briboluminescent materials used and the adhesive and the substrate to which it has been adhered.

Drying may be carried out using any of the known techniques—these include:

Solvent removal, removal of a dispersant phase, chemical polymerisation or cross linking, chemical reaction or condensation and may be aided by known methods such as application of heat or UV light.

The substrate may comprise triboluminescent material itself, typically this would be carried out during formation of the substrate.

There are various uses to which the adhesive compositions and methods of the present invention may be put. Included are adhesive compositions when used on envelopes and tape and the like for indicating whether or not an envelope or package has been previously opened. Alternatively, seals on containers may comprise adhesive/triboluminesecent compositions according to the present invention so it is evident whether or not a container has been tampered with or damaged such that the seal has been broken in some way. For some of these particular type applications the adhesive and triboluminescent materials may with advantage be selected such that the composition only triboluminesces once.

Hence a seventh aspect of this invention provides a method for detecting tampering of a sealed article comprising the steps of:

coating a part of an unsealed article with an adhesive composition, sealing the article, wherein the adhesive composition further comprises one or more triboluminescent materials according to the first aspect of the present invention such that on breaking the seal triboluminescence will be observed.

The article may be any type of suitable container, for example an envelope or packaging or a bottle and top.

In the above method it is also possible for the adhesive/triboluminescent mixture to be applied once the article has been sealed in some way. An example of this could be a bottle with a screw top wherein the adhesive/triboluminescent mixture could be added once the top has been screwed on to the bottle. The mixture could also be added before and after the sealing.

The present invention also provides for opening packages, envelopes and the like with added aesthetic appeal. It is an objective of the present invention to provide aesthetic effects in relation to adhesives/adhesive tape, paper and paper-like products through the use of technical structures and/or other technical means.

Further aspects of the invention include articles produced by the above methods.

Typical adhesives include:

Epoxy adhesives based on adducts of bisphenol-A and epichlorhydrin cured by polyamine or anhydride initiators, and similar adhesives based on other epoxides, UV curable and thermally curable adhesives based on acrylic, vinylic, styrenic, or thiol/ene monomer systems, cyanoacrylate adhesives, pressure sensitive adhesives, hot melt adhesives, latex based adhesives, PVA adhesives, solvent based adhesives, urea formaldehyde and melamine formaldehyde adhesives, anaerobic adhesives, bis-diallyamine derived adhesives etc.

In addition to the adhesive and triboluminescent material the adhesive composition may also comprise one or more of the following additional components such as solvents, wetting agents, flow modifiers, plasticisers, curing agents, dyes, fillers, stabilisers, anti-oxidants etc as is understood in the art. The compositions may include water as a solvent or dispersant or an organic solvent such as dichloromethane, acetone, tetrahydrofuran etc. may be present in order to ensure that the composition is homogenous and will spread well.

In all of the above aspects preferably the triboluminescent materials are chosen from the following general Formulae I, II and III:

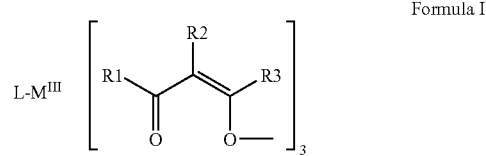

Formula I

Wherein M is Eu, Tb, Dy or Sm and 0.01%-99.99% of M is replaced by at least one of Y, Gd, La or Lu;

R2 is H or C1-C6 alkyl or phenyl;

R1 and R3 are independently of each other selected from phenyl, naphthyl, H and C1-C6 branched or straight chain alkyl, thiophene and C1-C6 fluorinated alkyl herein the fluorination may be in 1 or all positions or any intermediate value, substituted phenyl wherein the substituents are independently selected from C1-C4 straight or branched chain alkyl, Cl, Br, F, I and the phenyl group may be substituted in 1, 2 or 3 positions;

L is p-N,N-dimethylaminopyridine, N-methylimidazole, p-methoxypyridine-N-oxide, 4 phenyl pyridine, 2,2' bipyridyl, phenanthroline, bathophenanthroline, bathocuproine, 3-cyanopyridine, 4 cyanopyridine and for L their N-oxides;

L is also given by the following general Formula IA:

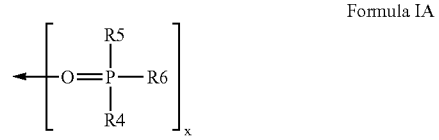

Formula IA

Wherein the arrow indicates that the oxygen coordinates to M wherein x is 1 or 2

R4 and R5 are independently of each other selected from phenyl, tolyl, naphthyl, C1-C6 branched or straight chain alkyl and substituted phenyl wherein the substituents are independently selected from C1-C4 straight or branched chain alkyl and the phenyl group may be substituted in 1, 2 or 3 positions;

R6 is selected from phenyl, tolyl, naphthyl, C1-C6 branched or straight chain alkyl, —$(CH_2)_nP(O)R7R8$, wherein n=1 to 4 and —$N=(PR7R8R9)$, wherein R7, R8 and R9 are independently selected from phenyl, naphthyl, C1-C6 branched or straight chain alkyl and substituted phenyl wherein the substituents are independently selected from C1-C4 straight or branched chain alkyl and the phenyl group may be substituted in 1, 2 or 3 positions;

R6 is also selected from substituted phenyl wherein the substituents are independently selected from C1-C4 straight or branched chain alkyl and the phenyl group may be substituted in 1, 2 or 3 positions;

It is understood in the definition of R6 that the phosphine oxide group, [included in —$(CH_2)_nP(O)R7R8$] if present, may be coordinated to the metal atom M or to another equivalent metal atom as a bridging group.

For Formulae I and IA the C1-C6 alkyl groups can be straight chain or branched and are typically methyl, ethyl, n-propyl, isopropyl, n-butyl, sec-butyl, isobutyl, ter-butyl or the different positional isomers of pentyl and hexyl, cyclopentyl, cyclohexyl or methyl cyclopentyl.

Preferably the alkyl groups contain 1-4 carbon atoms.

Preferably M is Eu, Tb or Dy.

R2 is preferably H.

Most preferably R1 and R3 are each tert-butyl or phenyl.

The synthesis of compounds of Formula I is described in WO 96/20942 and references therein including Eisentraut et al, Inorg. Syn. 11, 1968, 94.

Hexa-antipyrine tri-iodide compounds of Formula II:

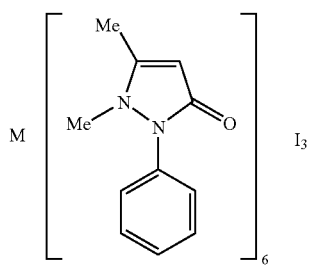

Formula II wherein M is Eu, Tb, Dy or Sm wherein 0.01%-99.99% of M is replaced by at least one of Y, Gd, La or Lu.

Preferably M is Tb.

Compounds of Formula III:

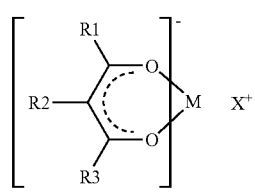

Formula III wherein M is Eu, Tb, Dy or Sm wherein 0.01%-99.99% of M is replaced by at least one of Y, Gd, La or Lu;

and wherein R1 and R2 and R3 are independently chosen from H, $C_1$-$C_{12}$ alkyl, including straight and branched chain which may be fluorinated in one, or any interim amount and up to all positions, $C_1$-$C_{12}$ cycloalkyl, aryl, thiophene, pyrrole, pyridine, pyrimidine, furan, benzoxazole, benzothiazole.

$X^+$ is selected from:

Morpholinium;

Pyridinium optionally substituted by phenyl, C1-C6 alkyl, Cl, Br, F, I, CN, $NO_2$;

$HNR_1R_2R_3$ wherein $R_1$, $R_2$ and $R_3$ are independently selected from H, C1-C12 alkyl, phenyl and benzyl.

According to an eighth aspect of this invention a damage-sensing device comprises at least one light sensor and at least one triboluminescent material comprising M wherein M is chosen from Tb, Eu, Sm, Dy and 0.01%-99.99% of M is replaced by at least one of Y, Gd, La or Lu; provided that other than when the triboluminescent material is selected from Formula I or Formula II or Formula III; when, with respect to M, only La and Eu are present then La is present in an amount of at least 75%;

The light sensor may be connected directly to the triboluminescent material or via light guiding means such as optical fibres.

The sensor may be embedded within a structure, such as a composite plastics material, or fixed externally to such structure. Several sensors may be embedded within one structure. Light output from the triboluminescent material may be detected directly, or such light output may be absorbed by photo excitable dye material whose subsequent luminescence is detected. Different triboluminescent material described by the present invention and or different dyes may be used in different parts of a structure so that damage location is readily determined from the wavelength of emission. The detector may be directly connected to each different triboluminescent or dye material, or one or more detectors used with filters or wavelength detection means to determine the location of damage at several sites.

Additionally the damage site may be located by timing receipt of pulses. The intensity of emission may also be measured to give an indication of the severity of impact and hence damage.

The light guiding means may be single or multimode optical fibres, optical transparent sheet or slab within a composite material. The sheet material may have waveguides defined by rib, in diffusion, or etching etc, and may contain secondary emitters.

The detectors may be photo multipliers, photo diodes, as single detectors or in arrays.

Use of the materials of the present invention may be incorporated into the devices described in U.S. Pat. No. 5,905,260 the contents of which are incorporated herein by reference.

With respect to the eighth aspect of the present invention preferably the triboluminescent materials are chosen from the following general Formulae I arid II and III:

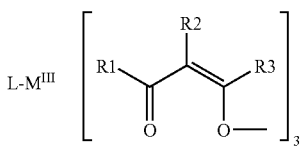

Formula I

Wherein M is Eu, Tb, Dy or Sm and 0.01%-99.99% of M is replaced by at least one of Y, Gd, La or Lu;

R2 is H or C1-C6 alkyl or phenyl;

R1 and R3 are independently of each other selected from phenyl, naphthyl, H and C1-C6 branched or straight chain alkyl, thiophene and C1-C6 fluorinated alkyl wherein the fluorination may be in 1 or all positions or any intermediate value, substituted phenyl wherein the substituents are independently selected from C1-C4 straight or branched chain alkyl, Cl, Br, F, I and the phenyl group may be substituted in 1, 2 or 3 positions;

L is p-N,N-dimethylaminopyridine, N-methylimidazole, p-methoxypyridine-N-oxide, 4 phenyl pyridine, 2,2' bipyridyl, phenanthroline, bathophenanthroline, bathocuproine, 3-cyanopyridine, 4 cyanopyridine and for L their N-oxides;

L is also given by the following general Formula IA:

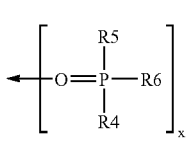

Formula IA

Wherein the arrow indicates that the oxygen coordinates to M wherein x is 1 or 2

R4 and R5 are independently of each other selected from phenyl, tolyl, naphthyl, C1-C6 branched or straight chain alkyl and substituted phenyl wherein the substituents are independently selected from C1-C4 straight or branched chain alkyl and the phenyl group may be substituted in 1, 2 or 3 positions;

R6 is selected from phenyl, tolyl, naphthyl, C1-C6 branched or straight chain alkyl, —(CH$_2$)$_n$P(O)R7R8, wherein n=1 to 4 and —N=(P R7R8R9), wherein R7, R8 and R9 are independently selected from phenyl, naphthyl, C1-C6 branched or straight chain alkyl and substituted phenyl wherein the substituents are independently selected from C1-C4 straight or branched chain alkyl and the phenyl group may be substituted in 1, 2 or 3 positions;

R6 is also selected from substituted phenyl wherein the substituents are independently selected from C1-C4 straight or branched chain alkyl and the phenyl group may be substituted in 1, 2 or 3 positions;

It is understood in the definition of R6 that the phosphine oxide group, [included in —(CH$_2$)$_n$P(O)R7R8] if present, may be coordinated to the metal atom M or to another equivalent metal atom as a bridging group.

For Formulae I and IA the C1-C6 alkyl groups can be straight chain or branched and are typically methyl, ethyl, n-propyl, isopropyl, n-butyl, sec-butyl, isobutyl, ter-butyl or the different positional isomers of pentyl and hexyl, cyclopentyl, cyclohexyl or methyl cyclopentyl.

Preferably the alkyl groups contain 1-4 carbon atoms.

Preferably M is Eu, Tb or Dy.

R2 is preferably H.

Most preferably R1 and R3 are each tert-butyl or phenyl.

The synthesis of compounds of Formula I is described in WO 96/20942 and references therein including Eisentraut et al, Inorg. Syn. 11, 1968, 94.

Hexa-antipyrine tri-iodide compounds of Formula II:

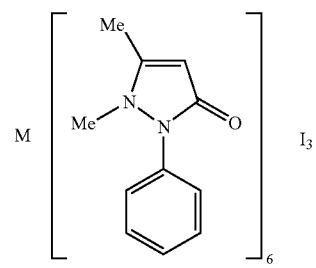

Formula II wherein M is Eu, Tb, Dy or Sm wherein 0.01%-99.99% of M is replaced by at least one of Y, Gd, La or Lu.

Compounds of Formula III:

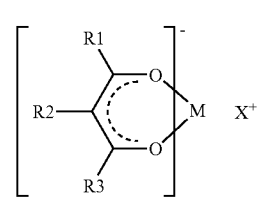

Formula III wherein M is Eu, Tb, Dy or Sm wherein 0.01%-99.99% of M is replaced by at least one of Y, Gd, La or Lu;

and wherein R1 and R2 and R3 are independently chosen from H, $C_1$-$C_{12}$ alkyl, including straight and branched chain which may be fluorinated in one, or any interim amount and up to all positions, $C_1$-$C_{12}$ cycloalkyl, aryl, thiophene, pyrrole, pyridine, pyrimidine, furan, benzoxazole, benzothiazole.

$X^+$ is selected from:

Morpholinium;

Pyridinium optionally substituted by phenyl, C1-C6 alkyl, Cl, Br, F, I, CN, NO$_2$; HNR$_1$R$_2$R$_3$ wherein R$_1$, R$_2$ and R$_3$ are independently selected from H, C1-C12 alkyl, phenyl and benzyl.

According to a ninth aspect of the present invention triboluminescent materials comprising M wherein M is chosen from Tb, Eu, Sm, Dy and 0.01%-99.99% of M is replaced by at least one of Y, Gd, La or Lu are provided, provided that:

other than when the triboluminescent material is selected from Formula I or Formula II or Formula III; when, with respect to M, only La and Eu are present then La is present in an amount of at least 75%;

when the triboluminescent material is given by Formula II and M is Tb then M is replaced by at least one of La or Lu.

Preferably the triboluminescent materials are chosen from the following general Formulae I and II and III:

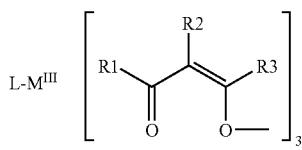

Formula I

Wherein M is Eu, Tb, Dy or Sm and 0.01%-99.99% of M is replaced by at least one of Y, Gd, La or Lu:
R2 is H or C1-C6 alkyl or phenyl;
R1 and R3 are independently of each other selected from phenyl, naphthyl, H and C1-C6 branched or straight chain alkyl, thiophene and C1-C6 fluorinated alkyl wherein the fluorination may be in 1 or all positions or any intermediate value, substituted phenyl wherein the substituents are independently selected from C1-C4 straight or branched chain alkyl, Cl, Br, F, I and the phenyl group may be substituted in 1, 2 or 3 positions;
L is p-N,N-dimethylaminopyridine, N-methylimidazole, p-methoxypyridine-N-oxide, 4 phenyl pyridine, 2,2' bipyridyl, phenanthroline, bathophenanthroline, bathocuproine, 3-cyanopyridine, 4 cyanopyridine and for L their N-oxides;
L is also given by the following general Formula IA:

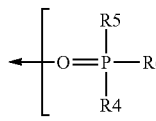

Formula IA

Wherein the arrow indicates that the oxygen coordinates to M
wherein
x is 1 or 2
R4 and R5 are independently of each other selected from phenyl, tolyl, naphthyl, C1-C6 branched or straight chain alkyl and substituted phenyl wherein the substituents are independently selected from C1-C4 straight or branched chain alkyl and the phenyl group may be substituted in 1, 2 or 3 positions;
R6 is selected from phenyl, tolyl, naphthyl, C1-C6 branched or straight chain alkyl, —$(CH_2)_n$P(O)R7R8, wherein n=1 to 4 and —N=(PR7R8R9), wherein R7, R8 and R9 are independently selected from phenyl, naphthyl, C1-C6 branched or straight chain alkyl and substituted phenyl wherein the substituents are independently selected from C1-C4 straight or branched chain alkyl and the phenyl group may be substituted in 1, 2 or 3 positions;
R6 is also selected from substituted phenyl wherein the substituents are independently selected from C1-C4 straight or branched chain alkyl and the phenyl group may be substituted in 1, 2 or 3 positions;
It is understood in the definition of R6 that the phosphine oxide group, [included in —$(CH_2)_n$P(O)R7R8] if present, may be coordinated to the metal atom M or to another equivalent metal atom as a bridging group.
In formula I and IA the C1-C6 alkyl groups can be straight chain or branched and are typically methyl, ethyl, n-propyl, isopropyl, n-butyl, sec-butyl, isobutyl, ter-butyl or the different positional isomers of pentyl and hexyl, cyclopentyl, cyclohexyl or methyl cyclopentyl.
Preferably the alkyl groups contain 1-4 carbon atoms.
Preferably M is Eu, Tb or Dy.
R2 is preferably H.

Most preferably R1 and R3 are each tert-butyl or phenyl.
The synthesis of compounds of formula I is described in WO 96/20942 and references therein including Eisentraut et al, Inorg. Syn. 11, 1968, 94.
Hexa-antipyrine tri-iodide compounds of Formula II:

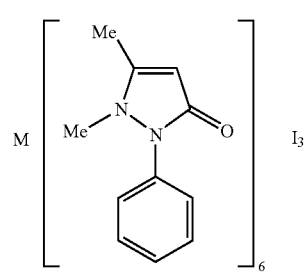

Formula II wherein M is Eu, Tb, Dy or Sm wherein 0.01%-99.99% of M is replaced by at least one of Y, Gd, La or Lu provided that:
when the triboluminescent material is given by Formula II and M is Tb then M is replaced by at least one of La or Lu.
Compounds of Formula III:

Formula III wherein M is Eu, Tb, Dy or Sm wherein 0.01%-99.99% of M is replaced by at least one of Y, Gd, La or Lu;
and wherein R1 and R2 and R3 are independently chosen from H, $C_1$-$C_{12}$ alkyl, including straight and branched chain which may be fluorinated in one, or any interim amount and up to all positions, $C_1$-$C_{12}$ cycloalkyl, aryl, thiophene, pyrrole, pyridine, pyrimidine, furan, benzoxazole, benzothiazole.
$X^+$ is selected from:
Morpholinium;
Pyridinium optionally substituted by phenyl, C1-C6 alkyl, Cl, Br, F, I, CN, $NO_2$; $HNR_1R_2R_3$ wherein $R_1$, $R_2$ and $R_3$ are independently selected from H, C1-C12 alkyl, phenyl and benzyl.
The ability of the materials of the present invention, to provide intense triboluminescence even when a high proportion of luminescent metal ie europium, terbium, dysprosium, samarium is replaced by a metal having a f0, f7 or f14 configuration ie yttrium, lanthanum, gadolinium or lutetium is unexpected and the origin of the effect in the compounds of the invention cannot be given with certainty. The mechanism of triboluminescence itself is not well understood. In the majority of bright triboluminescent compounds, it is probable that the origin lies in a non-centrosymmetric crystal structure. Fracture of the crystal then produces an electrical charge separation at the newly formed surfaces, and an electric discharge occurs which either excites the material by electron impact or produces ultra violet light by discharge through nitrogen present in the crystal or in the air. In the latter case, the ultra violet light must be absorbed by the triboluminescent compound and re-emitted at a longer wavelength to provide bright emission.

In either of the above cases, the initial excitation of the luminescent complex occurs in the organic ligands which surround the metal ion. The excitation energy may then be transferred to the metal ion, which emits light as a visible luminescence. This effect can be highly efficient because of the short distance between the ligands and the metal ion. In the case that a substantially non-emissive metal such as yttrium, lanthanum, gadolinium or lutetium is present in the molecule which receives the initial excitation, the excitation energy must be transferred the much greater distance to a neighbouring molecule which does contain the luminescent ion, before emission can take place. Under these conditions, the probability of a non-radiative process intervening to convert the excitation energy into heat, rather than light is increased.

A single binuclear triboluminescent complex containing not more than a 1:1 ratio of lanthanum to europium has been described previously—Chinese Chemical Letters, vol 11, no 7 pp635-38, 2000, indicating the general expectation that more than a single transfer of energy in this way will lead to loss of triboluminescent effectiveness.

It has unexpectedly been found by the current inventors that in the compounds of the invention, such an intermolecular transfer of the excitation energy produced by triboluminescence can occur not only once, but on average many times before the emission takes place and yet remain highly efficient. For example (reported in detail below), a sample of triethylammonium metal tetrakis dibenzoylmethide in which the metal is 10% europium and 90% lanthanum shows excellent bright triboluminescence despite the fact that on average the excitation energy must undergo no less than 9 intermolecular transfers before it reaches a luminescent centre. High triboluminescence activity can be achieved in the compounds of the invention even when 99% or more of the luminescent metal is replaced by a non-luminescent metal ion.

In other cases the crystals of triboluminescent compounds belong to a centrosymmetric class, and no such mechanisms as the above can be invoked. In these cases there is no secure explanation of the origin of the triboluminescence and the triboluminescent activity of these complexes cannot be inferred at all from the behaviour of the non-centrosymmetric classes, nor vice versa. The presence of photoluminescence, phosphorescence, thermoluminescence, cathodoluminescence etc in a compound are not necessarily useful guides to its triboluminescent activity. The compounds of this invention encompass both centrosymmetric and non-centrosymmetric types.

These unexpected results provide a particular benefit for applications of triboluminescent materials by providing a reduced materials cost.

Typically any triboluminescent compound comprising M also comprises a ligand—the current invention with respect to all aspects preferably comprises M plus ligand.

THE INVENTION WILL NOW BE DESCRIBED, BY WAY OF EXAMPLE ONLY, WITH REFERENCE TO THE ACCOMPANYING DRAWINGS OF WHICH

Figure 1:
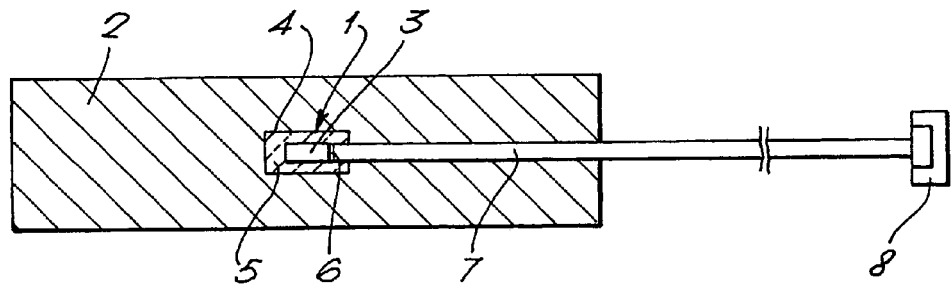
FIG. 1 is a sectional view of a sensor embedded within a structure.

As seen in FIG. 1 a sensor 1 is embedded in a composite material 2 such as a glass or carbon fibre matrix layered material. The sensor 1 comprises a small crystal 3 of a triboluminescent (TL) material as described by the present invention held within a cavity 4 by epoxy resin 5 and optically connected by optical cement such as a UV curing glue 6 from the Norland™ range to an optical fibre 7 which transmits light to an externally mounted detector 8. This detector 8 may be a photo diode or part of an array linked to several crystals.

The composite material 2, may have different triboluminescent materials 3 with their characteristic emissions arranged at different positions within the composite 2. The detectors 8 detect such different wavelengths thereby giving positional information about damage location In operation, e.g. in an aircraft, impact of objects on the composite 2 above a redetermined known energy level will damage the crystal 3 causing it to emit light; high impact energy results in higher light output. The detected light may either be transmitted as a signal directly to the pilot if a serious damage had occurred or stored by computer and read by a maintenance crew at a later stage for damage repair. If the recorded detection indicates composite damage, then that part of the composite may be repaired or replaced before the next aircraft flight.

Thus several different materials constructed as in FIG. 1 may be used as shown in different parts of a structure and a single detector used. In this case the detector must be able to distinguish different wavelengths to indicate which area of the structure has received damage.

Figure 2:
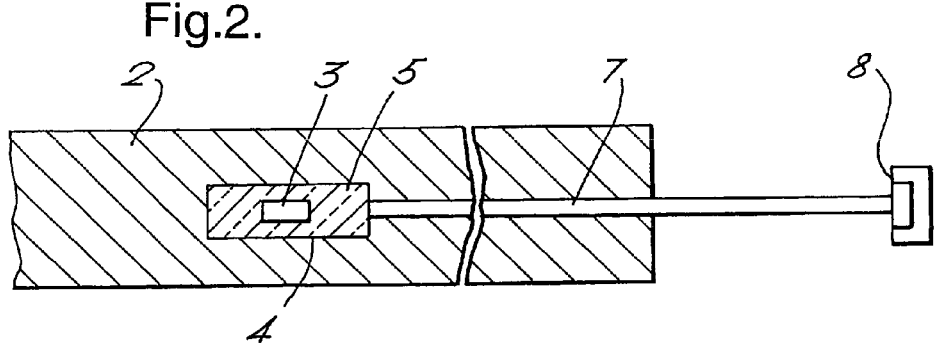
FIG. 2 is similar to and a variation of FIG. 1.

FIG. 2 is similar to FIG. 1 and given like reference numeral. In this example the optical fibre 7 optically connects to glue 5 holding the crystal 3 within the cavity 4. The glue 5 is optically transparent and may be a polymer matrix.

Figure 3:
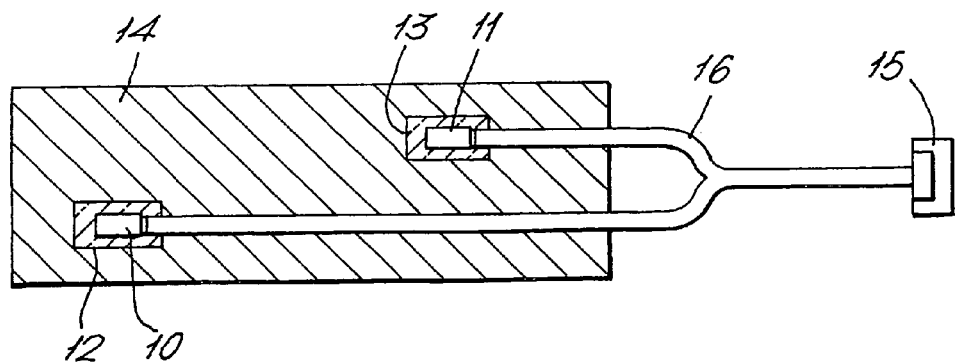
FIG. 3 is a sectional view of two sensors embedded within a structure, with optical fibre readout to a single detector.

FIG. 3 shows different TL crystals 10, 11 (two only shown, but may be many more) located in cavities 12, 13 in different parts of a composite material 14. A single detector 15 connects with each crystal 10, 11 via an optical fibre network 16 and is sensitive to the different emissions of the crystals 10, 11, and can therefore indicate the location of any damage. Such an arrangement reduces the number of cavities needed within the composite material 14.

Figure 4:
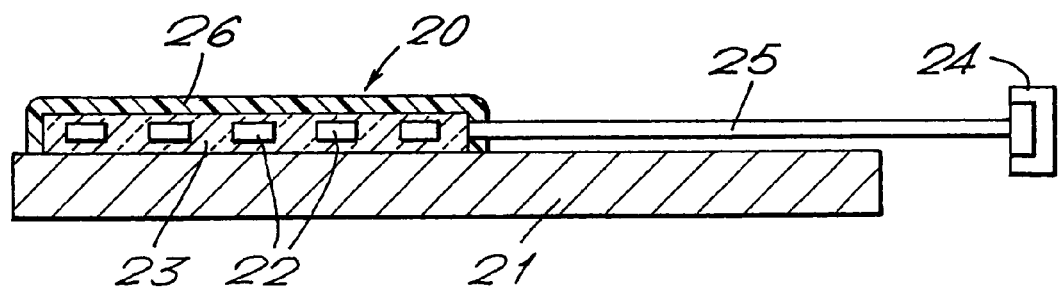
FIG. 4 is a sectional view of a sensor mounted on a surface of a structure.

FIG. 4 shows how a sensor 20 can be mounted externally on a composite material 21. As before one or more TL crystals 22 are encapsulated within an optically transparent glue or resin 23 and coupled to a detector 24 via an optical fibre 25. When a plurality of different crystals 22 are used, the detector 24 is arranged to distinguish between their different emissions wavelengths to give an indication of damage location. A protective layer 26 of opaque material covers the glue 23.

Figure 5:
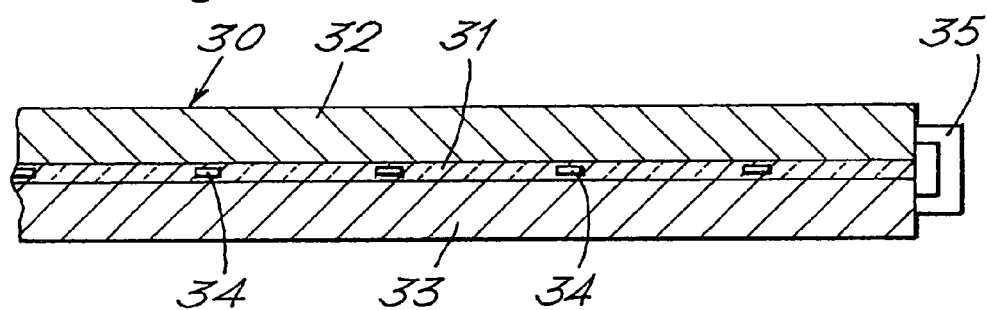
FIG. 5 is a sectional view of several triboluminescent materials and a light guiding layer embedded within a structure.

FIG. 5 shows a composite material 30 in which a layer 31 of a guiding material is sandwiched between two layers 32, 33. Embedded within the light guiding layer 31 are one or more TL crystals 34. A detector 35 is mounted on the edge of the composite material 30. Suitable materials for the light guiding layer 31 include:- UV curing glues, sol-gel, optically transparent polymers, resins or glues.

Figure 6:
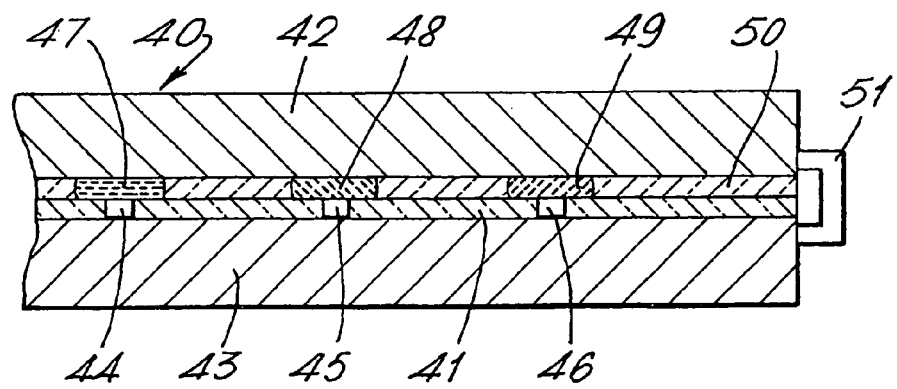
FIG. 6 is similar to that of FIG. 5, but in addition has a different photo excitable dye associated with each triboluminescent material.

FIG. 6 shows a composite material 40 in which a layer 41 of a light guiding material is sandwiched between two layers 42, 43. Embedded within the layer 41 are three TL crystals 44, 45, 46. Above each crystal 44, 45, 46 is a volume of three different photo excitable dyes 47, 48, 49 contained within a second layer 50 of a light guiding material. A detector 51 is sensitive to the outputs of each dye volume 47, 48, 49. When damage occurs, an appropriate crystal 44, 45, 46 will emit light and cause an associated dye volume 47, 48, 49 respectively to emit light at a characteristic wavelength which is guided by the layer 50 to the detector 51.

Figure 7:
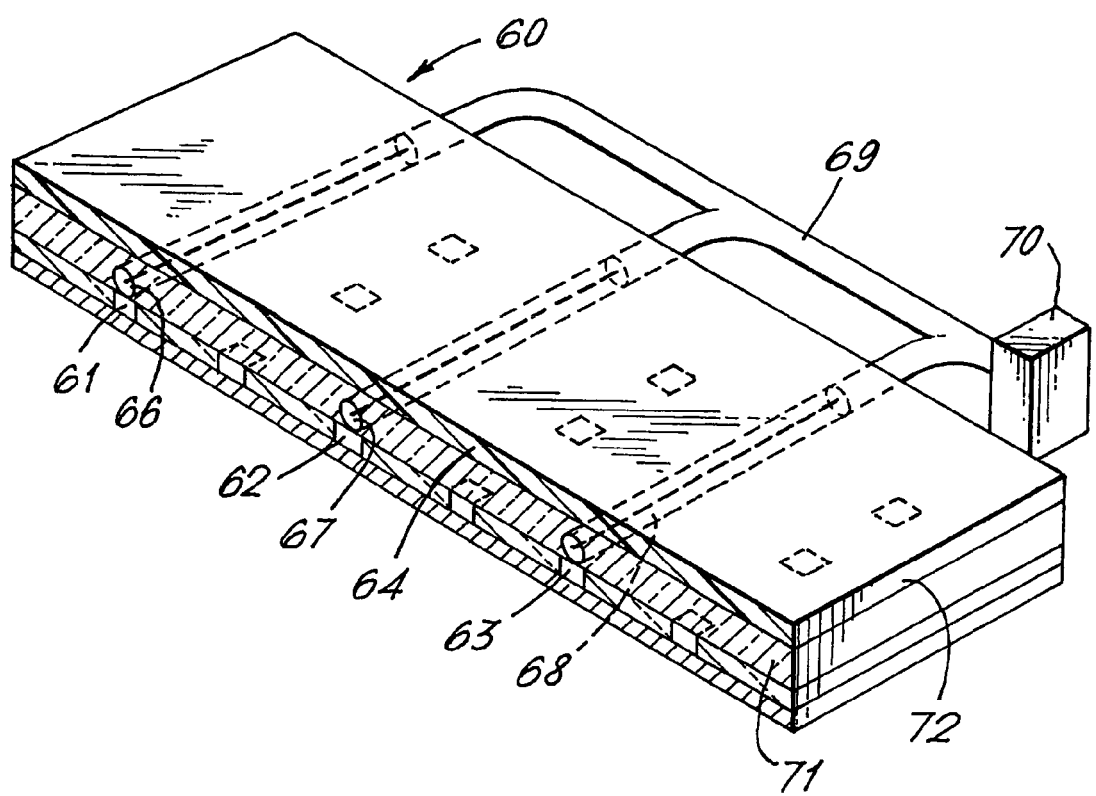
FIG. 7 is a perspective view of a sensor employing three differently doped fibres each directing light from several triboluminescent materials to a single detector.

FIG. 7 shows a composite layer material 60 in which several TL crystals 61, 62, 63 are embedded in rows within a layer 64. Optical fibres 66, 67, 68 containing photo excitable dyes are in optical contact with these rows of crystals 61, 62, 63 and connect via an optical fibre network 69 to one or more detectors 70. The fibres 66, 67, 68 are embedded in an optically transparent layer 71 and covered with a protective layer 72 of composite fibre. The crystals 61, 62, 63 may be one of the adducts of the present invention, the fibres 66, 67, 68 maybe glass single or multi mode fibres, or polymer fibres; the glues may be RS™ bipax epoxy, Araldite™ fast setting, or Norland UV curing flues.

In a modification of FIG. 7 an additional set of differently doped optical fibres is arranged in columns so that an x,y matrix of differently doped optical fibres lies within a composite material. The column fibres are connected to one or more detectors as in FIG. 7. Signals from these two detectors indicate where in the matrix, light is being received.

A flashing form of paper, (e.g. writing paper, tissue or cardboard) according to the present invention may be fabricated as follows. Paper is soaked in a solution of triboluminescent material and any excess solvent is evaporated off. The paper may then be torn, folded or crumpled to test for a triboluminescent effect.

An alternative method of fabrication involves melting the triboluminescent material and allowing the melt to soak into the paper.

An alternative method of fabrication involves gluing triboluminescent material to the surface of the paper, alternatively the triboluminescent material is encapsulated, for example, in polymer which may then be coated on to the surface of the paper. Examples of suitable polymer include poly vinyl alcohol. The polymer may be applied whilst still in monomer form and subsequently cured.

A flashing form of adhesive tape according to the present invention may be fabricated as follows. An adhesive compound which may be cured via any of the known methods of curing including by uv polymerisation and a triboluminescent material are placed on to a sheet of plastic material. A further sheet of plastic is pressed on top of the first sheet, sandwiching the adhesive/triboluminescent mixture. The sheets plus mixture are then subject to curing such that the monomer polymerises—it may be the case that an amount of the monomer remains unpolymerised. In order to assess the tape the sheets may be pulled apart to reveal bright flashes.

It is not necessarily the case that the adhesive is a monomer system—any type of adhesive known to those skilled in the art would be suitable. The mixture need not necessarily require curing.

In all aspects of the present invention preferably at least 75% of M is replaced, more preferably at least 85% is replaced and even more preferably at least 95% and up to and including 99% is replaced. Preferred ranges are 75-99%, 85-99%, 95-99%.

In addition to binary complexes, ternary complexes and tertiary complexes are included in the present invention in relation to M.

In all of the aspects of the present invention the choice of which metal is used to substitute for Eu, Tb, Sm or Dy may be made according to the desired outcome which is to be achieved. In many cases, substitution of an alternative metal selected from Y, La, Gd or Lu for some proportion of Eu, Tb, Sm or Dy will allow the preparation of a triboluminescent material having substantially similar or improved brightness, while using starting materials of lower cost or easier availability. In some cases the performance of the product is substantially similar to that of the parent compound, whichever metal of Y, La, Gd or Lu is selected for the substitution. In this case, the selection of the metal may be made solely on grounds of cost or availability. In a few cases, the different ionic radii of the metals may cause a change in crystalline form and consequent change in triboluminescent behaviour when certain substitutions are made. In the latter case, the substituent metal may with advantage be selected from Gd and Y, which have ionic radii close to those of the luminescent ions of Eu, Tb, Sm and Dy.

Example triboluminescent complexes according to the invention were prepared by the methods described below. In assessing the relative brightnesses of triboluminescent materials, it is understood by those skilled in the art that quantitative comparisons are made difficult by the dependancy of the triboluminescent emission intensity on such factors as the crystalline particle size and crystal habit of the sample, the force applied to the sample, traces of different impurities which may occur in the sample, the geometry of the optical detector and its wavelength sensitivity. For the purpose of evaluating the usefulness of the compounds of the invention, a semi-quantitative scale was employed based on observation of the triboluminescent emission from the samples by eye, while the materials in the form of crystalline powders were crushed in a soda lime glass sample tube under hand pressure with a stainless steel spatula. The brightness is then assessed according to the highest level of ambient illumination, in the presence of which the triboluminescent emission becomes visible. The scale employed is:

| Brightness Scale | Maximum ambient light for observation |
| --- | --- |
| 10 | Full daylight |
| 9 | Diffuse daylight |
| 8 | Bright room lighting |
| 7 | Subdued room lighting |
| 6 | Dim artificial light |
| 5 | Semi-darkness |
| 4 | Darkness, without dark adaptation of the eye |
| 3 | Darkness, with up to 2 mins dark adaptation |
| 2 | Darkness, with up to 10 mins dark adaptation |
| 1 | Visible with fully dark adapted eye |
| 0 | No observable triboluminescence |

Terbium tris(2,2,6,6-tetramethylheptane-3,5-dionate) (0.1 gm) and gadolinium tris(2,2,6,6-tetramethylheptane-3,5-dionate) (0.9 gm) were dissolved in 3 ml of warm anhydrous ethanol. Solid 4-dimethylamino pyridine (0.18 gm) was added and the solution was raised briefly to reflux. The solution was allowed to cool, and then placed in a refrigerator at 5° C. overnight. The colourless crystals which separated were filtered, washed with a small quantity of cold anhydrous ethanol, and dried to furnish tris 2,2,6,6-tetramethylheptanedionato Tb0.1, Gd0.9 dimethylaminopyridine as almost colourless crystals. The triboluminescent properties of the product were tested by crushing a small quantity alongside a similar sample of the corresponding product containing 100% terbium. Substantially Identical brightness of emitted light was observed from each sample.

By the same method, the following compounds were prepared:

tris acetylacetonato Tb dimethylaminopyridine (comparative example)
tris acetylacetonato Tb 4-picoline-N-oxide (comparative example)
tris acetylacetonato Tb 4-phenylpyridine (comparative example)
tris acetylacetonato Tb 4-cyanopyridine (comparative example)
tris acetylacetonato Tb 4-phenylpyridine-N-oxide (comparative example)
tris acetylacetonato Tb 1-methylimidazole (comparative example)
tris acetylacetonato Tb triphenylphosphine oxide (comparative example)
tris acetylacetonato Tb 2,2-bipyridyl (comparative example)
tris acetylacetonato Tb 2,2-bipyridyl-N,N-dioxide (comparative example)
tris acetylacetonato Tb phenanthroline (comparative example)
tris acetylacetonato Tb bathocuproine (comparative example)
tris acetylacetonato Tb bathophenanthroline (comparative example)
tris dibenzoylmethanato Tb dimethylaminopyridine (comparative example)
tris dibenzoylmethanato Tb 4-picoline-N-oxide (comparative example)
tris dibenzoylmethanato Tb 4-phenylpyridine (comparative example)
tris dibenzoylmethanato Tb 4-cyanopyridine (comparative example)
tris dibenzoylmethanato Tb 4-phenylpyridine-N-oxide (comparative example)
tris dibenzoylmethanato Tb 1-methylimidazole (comparative example)
tris dibenzoylmethanato Tb triphenylphosphine oxide (comparative example)
tris dibenzoylmethanato Tb 2,2-bipyridyl (comparative example)
tris dibenzoylmethanato Tb 2,2-bipyridyl-N,N-dioxide (comparative example)
tris dibenzoylmethanato Tb phenanthroline (comparative example)
tris dibenzoylmethanato Tb bathocuproine (comparative example)
tris dibenzoylmethanato Tb bathophenanthroline (comparative example)
tris thenoyltrifluoroacetonato Tb dimethylaminopyridine (comparative example)
tris thenoyltrifluoroacetonato Tb 4-picoline-N-oxide (comparative example)
tris thenoyltrifluoroacetonato Tb 4-phenylpyridine (comparative example)
tris thenoyltrifluoroacetonato Tb 4-cyanopyridine (comparative example)
tris thenoyltrifluoroacetonato Tb 4-phenylpyridine-N-oxide (comparative example)
tris thenoyltrifluoroacetonato Tb 1-methylimidazole (comparative example)
tris thenoyltrifluoroacetonato Tb triphenylphosphine oxide (comparative example)
tris thenoyltrifluoroacetonato Tb 2,2-bipyridyl (comparative example)
tris thenoyltrifluoroacetonato Tb 2,2-bipyridyl-N,N-dioxide (comparative example)
tris thenoyltrifluoroacetonato Tb phenanthroline (comparative example)
tris thenoyltrifluoroacetonato Tb bathocuproine (comparative example)
tris thenoyltrifluoroacetonato Tb bathophenanthroline (comparative example)
tris 2,2,6,6-tetramethylheptanedionato Tb dimethylaminopyridine (comparative example); brightness=10
tris 2,2,6,6-tetramethylheptanedionato Tb 4-picoline-N-oxide (comparative example); brightness=4
tris 2,2,6,6-tetramethylheptanedionato Tb 4-phenylpyridine (comparative example) brightness=3
tris 2,2,6,6-tetramethylheptanedionato Tb 4-cyanopyridine (comparative example); brightness=4
tris 2,2,6,6-tetramethylheptanedionato Tb 4-phenylpyridine-N-oxide (comparative example)
tris 2,2,6,6-tetramethylheptanedionato Tb 1-methylimidazole (comparative example)
tris 2,2,6,6-tetramethylheptanedionato Tb triphenylphosphine oxide (comparative example)
tris 2,2,6,6-tetramethylheptanedionato Tb 2,2-bipyridyl (comparative example); brightness=6
tris 2,2,66-tetramethylheptanedionato Tb 2,2-bipyridyl-N,N-dioxide (comparative example)
tris 2,2,6,6-tetramethylheptanedionato Tb phenanthroline (comparative example)
tris 2,2,6,6-tetramethylheptanedionato Tb bathocuproine (comparative example)
tris 2,2,6,6-tetramethylheptanedionato Tb bathophenanthroline (comparative example)
tris 3-methylpentane-2,4-dionato Tb dimethylaminopyridine (comparative example)
tris 3-methylpentane-2,4-dionato Tb 4-picoline-N-oxide (comparative example)
tris 3-methylpentane-2,4-dionato Tb 4-phenylpyridine (comparative example)
tris 3-methylpentane-2,4-dionato Tb 4-cyanopyridine (comparative example)
tris 3-methylpentane-2,4-dionato Tb 4-phenylpyridine-N-oxide (comparative example)
tris 3-methylpentane-2,4-dionato Tb 1-methylimidazole (comparative example)
tris 3-methylpentane-2,4-dionato Tb triphenylphosphine oxide (comparative example); brightness=4
tris 3-methylpentane-2,4-dionato Tb 2,2-bipyridyl (comparative example)
tris 3-methylpentane-2,4-dionato Tb 2,2-bipyridyl-N,N-dioxide (comparative example)
tris 3-methylpentane-2,4-dionato Tb phenanthroline (comparative example)
tris 3-methylpentane-2,4-dionato Tb bathocuproine (comparative example)
tris 3-methylpentane-2,4-dionato Tb bathophenanthroline (comparative example)
tris 3-ethylpentane-2,4-dionato Tb dimethylaminopyridine (comparative example)

tris 3-ethylpentane-2,4-dionato Tb 4-picoline-N-oxide (comparative example)
tris 3-ethylpentane-2,4-dionato Tb 4-phenylpyridine (comparative example)
tris 3-ethylpentane-2,4-dionato Tb 4-cyanopyridine (comparative example)
tris 3-ethylpentane-2,4-dionato Tb 4-phenylpyridine-N-oxide (comparative example)
tris 3-ethylpentane-2,4-dionato Tb 1-methylimidazole (comparative example)
tris 3-ethylpentane-2,4-dionato Tb triphenylphosphine oxide (comparative example)
tris 3-ethylpentane-2,4-dionato Tb 2,2-bipyridyl (comparative example)
tris 3-ethylpentane-2,4-dionato Tb 2,2-bipyridyl-N,N-dioxide (comparative example)
tris 3-ethylpentane-2,4-dionato Tb phenanthroline (comparative example)
tris 3-ethylpentane-2,4-dionato Tb bathocuproine (comparative example)
tris 3-ethylpentane-2,4-dionato Tb bathophenanthroline (comparative example)
tris pivaloyltrifluoroacetonato Tb dimethylaminopyridine (comparative example)
tris pivaloyltrifluoroacetonato Tb 4-picoline-N-oxide (comparative example)
tris pivaloyltrifluoroacetonato Tb 4-phenylpyridine (comparative example)
tris pivaloyltrifluoroacetonato Tb 4-cyanopyridine (comparative example)
tris pivaloyltrifluoroacetonato Tb 4-phenylpyridine-N-oxide (comparative example)
tris pivaloyltrifluoroacetonato Tb 1-methylimidazole (comparative example)
tris pivaloyltrifluoroacetonato Tb triphenylphosphine oxide (comparative example)
tris pivaloyltrifluoroacetonato Tb 2,2-bipyridyl (comparative example)
tris pivaloyltrifluoroacetonato Tb 2,2-bipyridyl-N,N-dioxide (comparative example)
tris pivaloyltrifluoroacetonato Tb phenanthroline (comparative example)
tris pivaloyltrifluoroacetonato Tb bathocuproine (comparative example)
tris pivaloyltrifluoroacetonato Tb bathophenanthroline (comparative example)
tris trifluoroacetylacetonato Tb dimethylaminopyridine (comparative example)
tris trifluoroacetylacetonato Tb 4-picoline-N-oxide (comparative example)
tris trifluoroacetylacetonato Tb 4-phenylpyridine (comparative example)
tris trifluoroacetylacetonato Tb 4-cyanopyridine (comparative example)
tris trifluoroacetylacetonato Tb 4-phenylpyridine-N-oxide (comparative example)
tris trifluoroacetylacetonato Tb 1-methylimidazole (comparative example)
tris trifluoroacetylacetonato Tb triphenylphosphine oxide (comparative example)
tris trifluoroacetylacetonato Tb 2,2-bipyridyl (comparative example)
tris trifluoroacetylacetonato Tb 2,2-bipyridyl-N,N-dioxide (comparative example)
tris trifluoroacetylacetonato Tb phenanthroline (comparative example)
tris trifluoroacetylacetonato Tb bathocuproine (comparative example)
tris trifluoroacetylacetonato Tb bathophenanthroline (comparative example)
tris hexafluoroacetylacetonato Tb dimethylaminopyridine (comparative example)
tris hexafluoroacetylacetonato Tb 4-picoline-N-oxide (comparative example)
tris hexafluoroacetylacetonato Tb 4-phenylpyridine (comparative example)
tris hexafluoroacetylacetonato Tb 4-cyanopyridine (comparative example)
tris hexafluoroacetylacetonato Tb 4-phenylpyridine-N-oxide (comparative example)
tris hexafluoroacetylacetonato Tb 1-methylimidazole (comparative example)
tris hexafluoroacetylacetonato Tb triphenylphosphine oxide (comparative example)
tris hexafluoroacetylacetonato Tb 2,2-bipyridyl (comparative example)
tris hexafluoroacetylacetonato Tb 2,2-bipyridyl-N,N-dioxide (comparative example)
tris hexafluoroacetylacetonato Tb phenanthroline (comparative example)
tris hexafluoroacetylacetonato Tb bathocuproine (comparative example)
tris hexafluoroacetylacetonato Tb bathophenanthroline (comparative example)
tris 6,6,7,7,8,8,8-heptafluoro-2,2-dimethyloctanedionato Tb dimethylaminopyridine (comparative example)
tris 6,6,7,7,8,8,8-heptafluoro-2,2-dimethyloctanedionato Tb 4-picoline-N-oxide (comparative example)
tris 6,6,7,7,8,8,8-heptafluoro-2,2-dimethyloctanedionato Tb 4-phenylpyridine (comparative example)
tris 6,6,7,7,8,8,8-heptafluoro-2,2-dimethyloctanedionato Tb 4-cyanopyridine (comparative example)
tris 6,6,7,7,8,8,8-heptafluoro-2,2-dimethyloctanedionato Tb 4-phenylpyridine-N-oxide (comparative example)
tris 6,6,7,7,8,8,8-heptafluoro-2,2-dimethyloctanedionato Tb 1-methylimidazole (comparative example)
tris 6,6,7,7,8,8,8-heptafluoro-2,2-dimethyloctanedionato Tb triphenylphosphine oxide (comparative example)
tris 6,6,7,7,8,8,8-heptafluoro-2,2-dimethyloctanedionato Tb 2,2-bipyridyl (comparative example)
tris 6,6,7,7,8,8,8-heptafluoro-2,2-dimethyloctanedionato Tb 2,2-bipyridyl-N,N-dioxide (comparative example)
tris 6,6,7,7,8,8,8-heptafluoro-2,2-dimethyloctanedionato Tb phenanthroline (comparative example)
tris 6,6,7,7,8,8,8-heptafluoro-2,2-dimethyloctanedionato Tb bathocuproine (comparative example)
tris 6,6,7,7,8,8,8-heptafluoro-2,2-dimethyloctanedionato Tb bathophenanthroline (comparative example)
tris 1-phenyl-1,3-butanedionato Tb dimethylaminopyridine (comparative example)
tris 1-phenyl-1,3-butanedionato Tb 4-picoline-N-oxide (comparative example)
tris 1-phenyl-1,3-butanedionato Tb 4-phenylpyridine (comparative example)
tris 1-phenyl-1,3-butanedionato Tb 4-cyanopyridine (comparative example)
tris 1-phenyl-1,3-butanedionato Tb 4-phenylpyridine-N-oxide (comparative example)
tris 1-phenyl-1,3-butanedionato Tb 1-methylimidazole (comparative example)
tris 1-phenyl-1,3-butanedionato Tb triphenylphosphine oxide (comparative example)

tris 1-phenyl-1,3-butanedionato Tb 2,2-bipyridyl (comparative example)
tris 1-phenyl-1,3-butanedionato Tb 2,2-bipyridyl-N,N-dioxide (comparative example)
tris 1-phenyl-1,3-butanedionato Tb phenanthroline (comparative example)
tris 1-phenyl-1,3-butanedionato Tb bathocuproine (comparative example)
tris 1-phenyl-1,3-butanedionato Tb bathophenanthroline (comparative example)
tris acetylacetonato Eu dimethylaminopyridine (comparative example)
tris acetylacetonato Eu 4-picoline-N-oxide (comparative example)
tris acetylacetonato Eu 4-phenylpyridine (comparative example)
tris acetylacetonato Eu 4-cyanopyridine (comparative example)
tris acetylacetonato Eu 4-phenylpyridine-N-oxide (comparative example)
tris acetylacetonato Eu 1-methylimidazole (comparative example)
tris acetylacetonato Eu triphenylphosphine oxide (comparative example)
tris acetylacetonato Eu 2,2-bipyridyl (comparative example)
tris acetylacetonato Eu 2,2-bipyridyl-N,N-dioxide (comparative example)
tris acetylacetonato Eu phenanthroline (comparative example)
tris acetylacetonato Eu bathocuproine (comparative example)
tris acetylacetonato Eu bathophenanthroline (comparative example)
tris dibenzoylmethanato Eu dimethylaminopyridine (comparative example)
tris dibenzoylmethanato Eu 4-picoline-N-oxide (comparative example)
tris dibenzoylmethanato Eu 4-phenylpyridine (comparative example)
tris dibenzoylmethanato Eu 4-cyanopyridine (comparative example)
tris dibenzoylmethanato Eu 4-phenylpyridine-N-oxide (comparative example)
tris dibenzoylmethanato Eu 1-methylimidazole (comparative example)
tris dibenzoylmethanato Eu triphenylphosphine oxide (comparative example)
tris dibenzoylmethanato Eu 2,2-bipyridyl (comparative example)
tris dibenzoylmethanato Eu 2,2-bipyridyl-N,N-dioxide (comparative example)
tris dibenzoylmethanato Eu phenanthroline (comparative example)
tris dibenzoylmethanato Eu bathocuproine (comparative example)
tris dibenzoylmethanato Eu bathophenanthroline (comparative example)
tris thenoyltrifluoroacetonato Eu dimethylaminopyridine (comparative example)
tris thenoyltrifluoroacetonato Eu 4-picoline-N-oxide (comparative example)
tris thenoyltrifluoroacetonato Eu 4-phenylpyridine (comparative example)
tris thenoyltrifluoroacetonato Eu 4-cyanopyridine (comparative example)
tris thenoyltrifluoroacetonato Eu 4-phenylpyridine-N-oxide (comparative example)
tris thenoyltrifluoroacetonato Eu 1-methylimidazole (comparative example)
tris thenoyltrifluoroacetonato Eu triphenylphosphine oxide (comparative example)
tris thenoyltrifluoroacetonato Eu 2,2-bipyridyl (comparative example)
tris thenoyltrifluoroacetonato Eu 2,2-bipyridyl-N,N-dioxide (comparative example)
tris thenoyltrifluoroacetonato Eu phenanthroline (comparative example); brightness=9
tris thenoyltrifluoroacetonato Eu bathocuproine (comparative example)
tris thenoyltrifluoroacetonato Eu bathophenanthroline (comparative example)
tris 2,2,6,6-tetramethylheptanedionato Eu dimethylaminopyridine (comparative example); brightness=7
tris 2,2,6,6-tetramethylheptanedionato Eu 4-picoline-N-oxide (comparative example)
tris 2,2,6,6-tetramethylheptanedionato Eu 4-phenylpyridine (comparative example)
tris 2,2,6,6-tetramethylheptanedionato Eu 4-cyanopyridine (comparative example)
tris 2,2,6,6-tetramethylheptanedionato Eu 4-phenylpyridine-N-oxide (comparative example)
tris 2,2,6,6-tetramethylheptanedionato Eu 1-methylimidazole (comparative example)
tris 2,2,6,6-tetramethylheptanedionato Eu triphenyiphosphine oxide (comparative example)
tris 2,2,6,6-tetramethylheptanedionato Eu 2,2-bipyridyl (comparative example)
tris 2,2,6,6-tetramethylheptanedionato Eu 2,2-bipyridyl-N,N-dioxide (comparative example)
tris 2,2,6,6-tetramethylheptanedionato Eu phenanthroline (comparative example)
tris 2,2,6,6-tetramethylheptanedionato Eu bathocuproine (comparative example)
tris 2,2,6,6-tetramethylheptanedionato Eu bathophenanthroline (comparative example)
tris 3-methylpentane-2,4-dionato Eu dimethylaminopyridine (comparative example)
tris 3-methylpentane-2,4-dionato Eu 4-picoline-N-oxide (comparative example)
tris 3-methylpentane-2,4-dionato Eu 4-phenylpyridine (comparative example)
tris 3-methylpentane-2,4-dionato Eu 4-cyanopyridine (comparative example)
tris 3-methylpentane-2,4-dionato Eu 4-phenylpyridine-N-oxide (comparative example)
tris 3-methylpentane-2,4-dionato Eu 1-methylimidazole (comparative example)
tris 3-methylpentane-2,4-dionato Eu triphenylphosphine oxide (comparative example)
tris 3-methylpentane-2,4-dionato Eu 2,2-bipyridyl (comparative example)
tris 3-methylpentane-2,4-dionato Eu 2,2-bipyridyl-N,N-dioxide (comparative example)
tris 3-methylpentane-2,4-dionato Eu phenanthroline (comparative example)
tris 3-methylpentane-2,4-dionato Eu bathocuproine (comparative example)
tris 3-methylpentane-2,4-dionato Eu bathophenanthroline (comparative example)
tris 3-ethylpentane-2,4-dionato Eu dimethylaminopyridine (comparative example)
tris 3-ethylpentane-2,4-dionato Eu 4-picoline-N-oxide (comparative example)

tris 3-ethylpentane-2,4-dionato Eu 4-phenylpyridine (comparative example)
tris 3-ethylpentane-2,4-dionato Eu 4-cyanopyridine (comparative example)
tris 3-ethylpentane-2,4-dionato Eu 4-phenylpyridine-N-oxide (comparative example)
tris 3-ethylpentane-2,4-dionato Eu 1-methylimidazole (comparative example)
tris 3-ethylpentane-2,4-dionato Eu triphenylphosphine oxide (comparative example)
tris 3-ethylpentane-2,4-dionato Eu 2,2-bipyridyl (comparative example)
tris 3-ethylpentane-2,4-dionato Eu 2,2-bipyridyl-N,N-dioxide (comparative example)
tris 3-ethylpentane-2,4-dionato Eu phenanthroline (comparative example)
tris 3-ethylpentane-2,4-dionato Eu bathocuproine (comparative example)
tris 3-ethylpentane-2,4-dionato Eu bathophenanthroline (comparative example)
tris pivaloyltrifluoroacetonato Eu dimethylaminopyridine (comparative example)
tris pivaloyltrifluoroacetonato Eu 4-picoline-N-oxide (comparative example)
tris pivaloyltrifluoroacetonato Eu 4-phenylpyridine (comparative example)
tris pivaloyltrifluoroacetonato Eu 4-cyanopyridine (comparative example)
tris pivaloyltrifluoroacetonato Eu 4-phenylpyridine-N-oxide (comparative example)
tris pivaloyltrifluoroacetonato Eu 1-methylimidazole (comparative example)
tris pivaloyltrifluoroacetonato Eu triphenylphosphine oxide (comparative example)
tris pivaloyltrifluoroacetonato Eu 2,2-bipyridyl (comparative example)
tris pivaloyltrifluoroacetonato Eu 2,2-bipyridyl-N,N-dioxide (comparative example)
tris pivaloyltrifluoroacetonato Eu phenanthroline (comparative example)
tris pivaloyltrifluoroacetonato Eu bathocuproine (comparative example)
tris pivaloyltrifluoroacetonato Eu bathophenanthroline (comparative example)
tris trifluoroacetylacetonato Eu dimethylaminopyridine (comparative example)
tris trifluoroacetylacetonato Eu 4-picoline-N-oxide (comparative example)
tris trifluoroacetylacetonato Eu 4-phenylpyridine (comparative example)
tris trifluoroacetylacetonato Eu 4-cyanopyridine (comparative example)
tris trifluoroacetylacetonato Eu 4-phenylpyridine-N-oxide (comparative example)
tris trifluoroacetylacetonato Eu 1-methylimidazole (comparative example)
tris trifluoroacetylacetonato Eu triphenylphosphine oxide (comparative example)
tris trifluoroacetylacetonato Eu 2,2-bipyridyl (comparative example)
tris trifluoroacetylacetonato Eu 2,2-bipyridyl-N,N-dioxide (comparative example)
tris trifluoroacetylacetonato Eu phenanthroline (comparative example)
tris trifluoroacetylacetonato Eu bathocuproine (comparative example)
tris trifluoroacetylacetonato Eu bathophenanthroline (comparative example)
tris hexafluoroacetylacetonato Eu dimethylaminopyridine (comparative example)
tris hexafluoroacetylacetonato Eu 4-picoline-N-oxide (comparative example)
tris hexafluoroacetylacetonato Eu 4-phenylpyridine (comparative example)
tris hexafluoroacetylacetonato Eu 4-cyanopyridine (comparative example)
tris hexafluoroacetylacetonato Eu 4-phenylpyridine-N-oxide (comparative example)
tris hexafluoroacetylacetonato Eu 1-methylimidazole (comparative example)
tris hexafluoroacetylacetonato Eu triphenylphosphine oxide (comparative example)
tris hexafluoroacetylacetonato Eu 2,2-bipyridyl (comparative example)
tris hexafluoroacetylacetonato Eu 2,2-bipyridyl-N,N-dioxide (comparative example)
tris hexafluoroacetylacetonato Eu phenanthroline (comparative example)
tris hexafluoroacetylacetonato Eu bathocuproine (comparative example)
tris hexafluoroacetylacetonato Eu bathophenanthroline (comparative example)
tris 6,6,7,7,8,8,8-heptafluoro-2,2-dimethyloctanedionato Eu dimethylaminopyridine (comparative example)
tris 6,6,7,7,8,8,8-heptafluoro-2,2-dimethyloctanedionato Eu 4-picoline-N-oxide (comparative example)
tris 6,6,7,7,8,8,8-heptafluoro-2,2-dimethyloctanedionato Eu 4-phenylpyridine (comparative example)
tris 6,6,7,7,8,8,8-heptafluoro-2,2-dimethyloctanedionato Eu 4-cyanopyridine (comparative example)
tris 6,6,7,7,8,8,8-heptafluoro-2,2-dimethyloctanedionato Eu 4-phenylpyridine-N-oxide (comparative example)
tris 6,6,7,7,8,8,8-heptafluoro-2,2-dimethyloctanedionato Eu 1-methylimidazole (comparative example)
tris 6,6,7,7,8,8,8-heptafluoro-2,2-dimethyloctanedionato Eu triphenylphosphine oxide (comparative example)
tris 6,6,7,7,8,8,8-heptafluoro-2,2-dimethyloctanedionato Eu 2,2-bipyridyl (comparative example)
tris 6,6,7,7,8,8,8-heptafluoro-2,2-dimethyloctanedionato Eu 2,2-bipyridyl-N,N-dioxide (comparative example)
tris 6,6,7,7,8,8,8-heptafluoro-2,2-dimethyloctanedionato Eu phenanthroline (comparative example).
tris 6,6,7,7,8,8,8-heptafluoro-2,2-dimethyloctanedionato Eu bathocuproine comparative example)
tris 6,6,7,7,8,8,8-heptafluoro-2,2-dimethyloctanedionato Eu bathophenanthroline comparative example)
tris 1-phenyl-1,3-butanedionato Eu dimethylaminopyridine (comparative example)
tris 1-phenyl-1,3-butanedionato Eu 4-picoline-N-oxide (comparative example)
tris 1-phenyl-1,3-butanedionato Eu 4-phenylpyridine (comparative example)
tris 1-phenyl-1,3-butanedionato Eu 4-cyanopyridine (comparative example)
tris 1-phenyl-1,3-butanedionato Eu 4-phenylpyridine-N-oxide (comparative example)
tris 1-phenyl-1,3-butanedionato Eu 1-methylimidazole (comparative example)
tris 1-phenyl-1,3-butanedionato Eu triphenylphosphine oxide (comparative example)
tris 1-phenyl-1,3-butanedionato Eu 2,2-bipyridyl (comparative example)

tris 1-phenyl-1,3-butanedionato Eu 2,2-bipyridyl-N,N-dioxide (comparative example)
tris 1-phenyl-1,3-butanedionato Eu phenanthroline (comparative example)
tris 1-phenyl-1,3-butanedionato Eu bathocuproine (comparative example)
tris 1-phenyl-1,3-butanedionato Eu bathophenanthroline (comparative example)
tris acetylacetonato Sm dimethylaminopyridine (comparative example)
tris acetylacetonato Sm 4-picoline-N-oxide (comparative example)
tris acetylacetonato Sm 4-phenylpyridine (comparative example)
tris acetylacetonato Sm 4-cyanopyridine (comparative example)
tris acetylacetonato Sm 4-phenylpyridine-N-oxide (comparative example)
tris acetylacetonato Sm 1-methylimidazole (comparative example)
tris acetylacetonato Sm triphenylphosphine oxide (comparative example)
tris acetylacetonato Sm 2,2-bipyridyl (comparative example)
tris acetylacetonato Sm 2,2-bipyridyl-N,N-dioxide (comparative example)
tris acetylacetonato Sm phenanthroline (comparative example)
tris acetylacetonato Sm bathocuproine (comparative example)
tris acetylacetonato Sm bathophenanthroline (comparative example)
tris dibenzoylmethanato Sm dimethylaminopyridine (comparative example)
tris dibenzoylmethanato Sm 4-picoline-N-oxide (comparative example)
tris dibenzoylmethanato Sm 4-phenylpyridine (comparative example)
tris dibenzoylmethanato Sm 4-cyanopyridine (comparative example)
tris dibenzoylmethanato Sm 4-phenylpyridine-N-oxide (comparative example)
tris dibenzoylmethanato Sm 1-methylimidazole (comparative example)
tris dibenzoylmethanato Sm triphenylphosphine oxide (comparative example)
tris dibenzoylmethanato Sm 2,2-bipyridyl (comparative example)
tris dibenzoylmethanato Sm 2,2-bipyridyl-N,N-dioxide (comparative example)
tris dibenzoylmethanato Sm phenanthroline (comparative example)
tris dibenzoylmethanato Sm bathocuproine (comparative example)
tris dibenzoylmethanato Sm bathophenanthroline (comparative example)
tris thenoyltrifluoroacetonato Sm dimethylaminopyridine (comparative example)
tris thenoyltrifluoroacetonato Sm 4-picoline-N-oxide (comparative example)
tris thenoyltrifluoroacetonato Sm 4-phenylpyridine (comparative example)
tris thenoyltrifluoroacetonato Sm 4-cyanopyridine (comparative example)
tris thenoyltrifluoroacetonato Sm 4-phenylpyridine-N-oxide (comparative example)
tris thenoyltrifluoroacetonato Sm 1-methylimidazole (comparative example)
tris thenoyltrifluoroacetonato Sm triphenylphosphine oxide (comparative example)
tris thenoyltrifluoroacetonato Sm 2,2-bipyridyl (comparative example)
tris thenoyltrifluoroacetonato Sm 2,2-bipyridyl-N,N-dioxide (comparative example)
tris thenoyltrifluoroacetonato Sm phenanthroline (comparative example)
tris thenoyltrifluoroacetonato Sm bathocuproine (comparative example)
tris thenoyltrifluoroacetonato Sm bathophenanthroline (comparative example)
tris 2,2,6,6-tetramethylheptanedionato Sm dimethylaminopyridine (comparative example)
tris 2,2,6,6-tetramethylheptanedionato Sm 4-picoline-N-oxide (comparative example)
tris 2,2,6,6-tetramethylheptanedionato Sm 4-phenylpyridine (comparative example)
tris 2,2,6,6-tetramethylheptanedionato Sm 4-cyanopyridine (comparative example)
tris 2,2,6,6-tetramethylheptanedionato Sm 4-phenylpyridine-N-oxide (comparative example)
tris 2,2,6,6-tetramethylheptanedionato Sm 1-methylimidazole (comparative example)
tris 2,2,6,6-tetramethylheptanedionato Sm triphenylphosphine oxide (comparative example)
tris 2,2,6,6-tetramethylheptanedionato Sm 2,2-bipyridyl (comparative example)
tris 2,2,6,6-tetramethylheptanedionato Sm 2,2-bipyridyl-N,N-dioxide (comparative example)
tris 2,2,6,6-tetramethylheptanedionato Sm phenanthroline (comparative example)
tris 2,2,6,6-tetramethylheptanedionato Sm bathocuproine (comparative example)
tris 2,2,6,6-tetramethylheptanedionato Sm bathophenanthroline (comparative example)
tris 3-methylpentane-2,4-dionato Sm dimethylaminopyridine (comparative example)
tris 3-methylpentane-2,4-dionato Sm 4-picoline-N-oxide (comparative example)
tris 3-methylpentane-2,4-dionato Sm 4-phenylpyridine (comparative example)
tris 3-methylpentane-2,4-dionato Sm 4-cyanopyridine (comparative example)
tris 3-methylpentane-2,4-dionato Sm 4-phenylpyridine-N-oxide (comparative example)
tris 3-methylpentane-2,4-dionato Sm 1-methylimidazole (comparative example)
tris 3-methylpentane-2,4-dionato Sm triphenylphosphine oxide (comparative example)
tris 3-methylpentane-2,4-dionato Sm 2,2-bipyridyl (comparative example)
tris 3-methylpentane-2,4-dionato Sm 2,2-bipyridyl-N,N-dioxide (comparative example)
tris 3-methylpentane-2,4-dionato Sm phenanthroline (comparative example)
tris 3-methylpentane-2,4-dionato Sm bathocuproine (comparative example)
tris 3-methylpentane-2,4-dionato Sm bathophenanthroline (comparative example)
tris 3-ethylpentane-2,4-dionato Sm dimethylaminopyridine (comparative example)
tris 3-ethylpentane-2,4-dionato Sm 4-picoline-N-oxide (comparative example)

tris 3-ethylpentane-2,4-dionato Sm 4-phenylpyridine (comparative example)
tris 3-ethylpentane-2,4-dionato Sm 4-cyanopyridine (comparative example)
tris 3-ethylpentane-2,4-dionato Sm 4-phenylpyridine-N-oxide (comparative example)
tris 3-ethylpentane-2,4-dionato Sm 1-methylimidazole (comparative example)
tris 3-ethylpentane-2,4-dionato Sm triphenylphosphine oxide (comparative example)
tris 3-ethylpentane-2,4-dionato Sm 2,2-bipyridyl (comparative example)
tris 3-ethylpentane-2,4-dionato Sm 2,2-bipyridyl-N,N-dioxide (comparative example)
tris 3-ethylpentane-2,4-dionato Sm phenanthroline (comparative example)
tris 3-ethylpentane-2,4-dionato Sm bathocuproine (comparative example)
tris 3-ethylpentane-2,4-dionato Sm bathophenanthroline (comparative example)
tris pivaloyltrifluoroacetonato Sm dimethylaminopyridine (comparative example)
tris pivaloyltrifluoroacetonato Sm 4-picoline-N-oxide (comparative example)
tris pivaloyltrifluoroacetonato Sm 4-phenylpyridine (comparative example)
tris pivaloyltrifluoroacetonato Sm 4-cyanopyridine (comparative example)
tris pivaloyltrifluoroacetonato Sm 4-phenylpyridine-N-oxide (comparative example)
tris pivaloyltrifluoroacetonato Sm 1-methylimidazole (comparative example)
tris pivaloyltrifluoroacetonato Sm triphenylphosphine oxide (comparative example)
tris pivaloyltrifluoroacetonato Sm 2,2-bipyridyl (comparative example)
tris pivaloyltrifluoroacetonato Sm 2,2-bipyridyl-N,N-dioxide (comparative example)
tris pivaloyltrifluoroacetonato Sm phenanthroline (comparative example)
tris pivaloyltrifluoroacetonato Sm bathocuproine (comparative example)
tris pivaloyltrifluoroacetonato Sm bathophenanthroline (comparative example)
tris trifluoroacetylacetonato Sm dimethylaminopyridine (comparative example)
tris trifluoroacetylacetonato Sm 4-picoline-N-oxide (comparative example)
tris trifluoroacetylacetonato Sm 4-phenylpyridine (comparative example)
tris trifluoroacetylacetonato Sm 4-cyanopyridine (comparative example)
tris trifluoroacetylacetonato Sm 4-phenylpyridine-N-oxide (comparative example)
tris trifluoroacetylacetonato Sm 1-methylimidazole (comparative example)
tris trifluoroacetylacetonato Sm triphenylphosphine oxide (comparative example)
tris trifluoroacetylacetonato Sm 2,2-bipyridyl (comparative example)
tris trifluoroacetylacetonato Sm 2,2-bipyridyl-N,N-dioxide (comparative example)
tris trifluoroacetylacetonato Sm phenanthroline (comparative example)
tris trifluoroacetylacetonato Sm bathocuproine (comparative example)
tris trifluoroacetylacetonato Sm bathophenanthroline (comparative example)
tris hexafluoroacetylacetonato Sm dimethylaminopyridine (comparative example)
tris hexafluoroacetylacetonato Sm 4-picoline-N-oxide (comparative example)
tris hexafluoroacetylacetonato Sm 4-phenylpyridine (comparative example)
tris hexafluoroacetylacetonato Sm 4-cyanopyridine (comparative example)
tris hexafluoroacetylacetonato Sm 4-phenylpyridine-N-oxide (comparative example)
tris hexafluoroacetylacetonato Sm 1-methylimidazole (comparative example)
tris hexafluoroacetylacetonato Sm triphenylphosphine oxide (comparative example)
tris hexafluoroacetylacetonato Sm 2,2-bipyridyl (comparative example)
tris hexafluoroacetylacetonato Sm 2,2-bipyridyl-N,N-dioxide (comparative example)
tris hexafluoroacetylacetonato Sm phenanthroline (comparative example)
tris hexafluoroacetylacetonato Sm bathocuproine (comparative example)
tris hexafluoroacetylacetonato Sm bathophenanthroline (comparative example)
tris 6,6,7,7,8,8,8-heptafluoro-2,2-dimethyloctanedionato Sm dimethylaminopyridine (comparative example)
tris 6,6,7,7,8,8,8-heptafluoro-2,2-dimethyloctanedionato Sm 4-picoline-N-oxide (comparative example)
tris 6,6,7,7,8,8,8-heptafluoro-2,2-dimethyloctanedionato Sm 4-phenylpyridine (comparative example)
tris 6,6,7,7,8,8,8-heptafluoro-2,2-dimethyloctanedionato Sm 4-cyanopyridine (comparative example)
tris 6,6,7,7,8,8,8-heptafluoro-2,2-dimethyloctanedionato Sm 4-phenylpyridine-N-oxide (comparative example)
tris 6,6,7,7,8,8,8-heptafluoro-2,2-dimethyloctanedionato Sm 1-methylimidazole (comparative example)
tris 6,6,7,7,8,8,8-heptafluoro-2,2-dimethyloctanedionato Sm triphenylphosphine oxide (comparative example)
tris 6,6,7,7,8,8,8-heptafluoro-2,2-dimethyloctanedionato Sm 2,2-bipyridyl (comparative example)
tris 6,6,7,7,8,8,8-heptafluoro-2,2-dimethyloctanedionato Sm 2,2-bipyridyl-N,N-dioxide (comparative example)
tris 6,6,7,7,8,8,8-heptafluoro-2,2-dimethyloctanedionato Sm phenanthroline (comparative example)
tris 6,6,7,7,8,8,8-heptafluoro-2,2-dimethyloctanedionato Sm bathocuproine (comparative example)
tris 6,6,7,7,8,8,8-heptafluoro-2,2-dimethyloctanedionato Sm bathophenanthroline (comparative example)
tris 1-phenyl-1,3-butanedionato Sm dimethylaminopyridine (comparative example)
tris 1-phenyl-1,3-butanedionato Sm 4-picoline-N-oxide (comparative example)
tris 1-phenyl-1,3-butanedionato Sm 4-phenylpyridine (comparative example)
tris 1-phenyl-1,3-butanedionato Sm 4-cyanopyridine (comparative example)
tris 1-phenyl-1,3-butanedionato Sm 4-phenylpyridine-N-oxide (comparative example)
tris 1-phenyl-1,3-butanedionato Sm 1-methylimidazole (comparative example)
tris 1-phenyl-1,3-butanedionato Sm triphenylphosphine oxide (comparative example)
tris 1-phenyl-1,3-butanedionato Sm 2,2-bipyridyl (comparative example)

tris 1-phenyl-1,3-butanedionato Sm 2,2-bipyridyl-N,N-dioxide (comparative example)
tris 1-phenyl-1,3-butanedionato Sm phenanthroline (comparative example)
tris 1-phenyl-1,3-butanedionato Sm bathocuproine (comparative example)
tris 1-phenyl-1,3-butanedionato Sm bathophenanthroline (comparative example)
tris acetylacetonato Dy dimethylaminopyridine (comparative example)
tris acetylacetonato Dy 4-picoline-N-oxide (comparative example)
tris acetylacetonato Dy 4-phenylpyridine (comparative example)
tris acetylacetonato Dy 4-cyanopyridine (comparative example)
tris acetylacetonato Dy 4-phenylpyridine-N-oxide (comparative example)
tris acetylacetonato Dy 1-methylimidazole (comparative example)
tris acetylacetonato Dy triphenylphosphine oxide (comparative example)
tris acetylacetonato Dy 2,2-bipyridyl (comparative example)
tris acetylacetonato Dy 2,2-bipyridyl-N,N-dioxide (comparative example)
tris acetylacetonato Dy phenanthroline (comparative example)
tris acetylacetonato Dy bathocuproine (comparative example)
tris acetylacetonato Dy bathophenanthroline (comparative example)
tris dibenzoylmethanato Dy dimethylaminopyridine (comparative example)
tris dibenzoylmethanato Dy 4-picoline-N-oxide (comparative example)
tris dibenzoylmethanato Dy 4-phenylpyridine (comparative example)
tris dibenzoylmethanato Dy 4-cyanopyridine (comparative example)
tris dibenzoylmethanato Dy 4-phenylpyridine-N-oxide (comparative example)
tris dibenzoylmethanato Dy 1-methylimidazole (comparative example)
tris dibenzoylmethanato Dy triphenylphosphine oxide (comparative example)
tris dibenzoylmethanato Dy 2,2-bipyridyl (comparative example)
tris dibenzoylmethanato Dy 2,2-bipyridyl-N,N-dioxide (comparative example)
tris dibenzoylmethanato Dy phenanthroline (comparative example)
tris dibenzoylmethanato Dy bathocuproine (comparative example)
tris dibenzoylmethanato Dy bathophenanthroline (comparative example)
tris thenoyltrifluoroacetonato Dy dimethylaminopyridine (comparative example)
tris thenoyltrifluoroacetonato Dy 4-picoline-N-oxide (comparative example)
tris thenoyltrifluoroacetonato Dy 4-phenylpyridine (comparative example)
tris thenoyltrifluoroacetonato Dy 4-cyanopyridine (comparative example)
tris thenoyltrifluoroacetonato Dy 4-phenylpyridine-N-oxide (comparative example)
tris thenoyltrifluoroacetonato Dy 1-methylimidazole (comparative example)
tris thenoyltrifluoroacetonato Dy triphenylphosphine oxide (comparative example)
tris thenoyltrifluoroacetonato Dy 2,2-bipyridyl (comparative example)
tris thenoyltrifluoroacetonato Dy 2,2-bipyridyl-N,N-dioxide (comparative example)
tris thenoyltrifluoroacetonato Dy phenanthroline (comparative example)
tris thenoyltrifluoroacetonato Dy bathocuproine (comparative example)
tris thenoyltrifluoroacetonato Dy bathophenanthroline (comparative example)
tris 2,2,6,6-tetramethylheptanedionato Dy dimethylaminopyridine (comparative example)
tris 2,2,6,6-tetramethylheptanedionato Dy 4-picoline-N-oxide (comparative example)
tris 2,2,6,6-tetramethylheptanedionato Dy 4-phenylpyridine (comparative example)
tris 2,2,6,6-tetramethylheptanedionato Dy 4-cyanopyridine (comparative example)
tris 2,2,6,6-tetramethylheptanedionato Dy 4-phenylpyridine-N-oxide (comparative example)
tris 2,2,6,6-tetramethylheptanedionato Dy 1-methylimidazole (comparative example)
tris 2,2,6,6-tetramethylheptanedionato Dy triphenylphosphine oxide (comparative example)
tris 2,2,6,6-tetramethylheptanedionato Dy 2,2-bipyridyl (comparative example)
tris 2,2,6,6-tetramethylheptanedionato Dy 2,2-bipyridyl-N,N-dioxide (comparative example)
tris 2,2,6,6-tetramethylheptanedionato Dy phenanthroline (comparative example)
tris 2,2,6,6-tetramethylheptanedionato Dy bathocuproine (comparative example)
tris 2,2,6,6-tetramethylheptanedionato Dy bathophenanthroline (comparative example)
tris 3-methylpentane-2,4-dionato Dy dimethylaminopyridine (comparative example)
tris 3-methylpentane-2,4-dionato Dy 4-picoline-N-oxide (comparative example)
tris 3-methylpentane-2,4-dionato Dy 4-phenylpyridine (comparative example)
tris 3-methylpentane-2,4-dionato Dy 4-cyanopyridine (comparative example)
tris 3-methylpentane-2,4-dionato Dy 4-phenylpyridine-N-oxide (comparative example)
tris 3-methylpentane-2,4-dionato Dy 1-methylimidazole (comparative example)
tris 3-methylpentane-2,4-dionato Dy triphenylphosphine oxide (comparative example)
tris 3-methylpentane-2,4-dionato Dy 2,2-bipyridyl (comparative example)
tris 3-methylpentane-2,4-dionato Dy 2,2-bipyridyl-N,N-dioxide (comparative example)
tris 3-methylpentane-2,4-dionato Dy phenanthroline (comparative example)
tris 3-methylpentane-2,4-dionato Dy bathocuproine (comparative example)
tris 3-methylpentane-2,4-dionato Dy bathophenanthroline (comparative example)
tris 3-ethylpentane-2,4-dionato Dy dimethylaminopyridine (comparative example)
tris 3-ethylpentane-2,4-dionato Dy 4-picoline-N-oxide (comparative example)
tris 3-ethylpentane-2,4-dionato Dy 4-phenylpyridine (comparative example)

tris 3-ethylpentane-2,4-dionato Dy 4-cyanopyridine (comparative example)
tris 3-ethylpentane-2,4-dionato Dy 4-phenylpyridine-N-oxide (comparative example)
tris 3-ethylpentane-2,4-dionato Dy 1-methylimidazole (comparative example)
tris 3-ethylpentane-2,4-dionato Dy triphenylphosphine oxide (comparative example)
tris 3-ethylpentane-2,4-dionato Dy 2,2-bipyridyl (comparative example)
tris 3-ethylpentane-2,4-dionato Dy 2,2-bipyridyl-N,N-dioxide (comparative example)
tris 3-ethylpentane-2,4-dionato Dy phenanthroline (comparative example)
tris 3-ethylpentane-2,4-dionato Dy bathocuproine (comparative example)
tris 3-ethylpentane-2,4-dionato Dy bathophenanthroline (comparative example)
tris pivaloyltrifluoroacetonato Dy dimethylaminopyridine (comparative example)
tris pivaloyltrifluoroacetonato Dy 4-picoline-N-oxide (comparative example)
tris pivaloyltrifluoroacetonato Dy 4-phenylpyridine (comparative example)
tris pivaloyltrifluoroacetonato Dy 4-cyanopyridine (comparative example)
tris pivaloyltrifluoroacetonato Dy 4-phenylpyridine-N-oxide (comparative example)
tris pivaloyltrifluoroacetonato Dy 1-methylimidazole (comparative example)
tris pivaloyltrifluoroacetonato Dy triphenylphosphine oxide (comparative example)
tris pivaloyltrifluoroacetonato Dy 2,2-bipyridyl (comparative example)
tris pivaloyltrifluoroacetonato Dy 2,2-bipyridyl-N,N-dioxide (comparative example)
tris pivaloyltrifluoroacetonato Dy phenanthroline (comparative example)
tris pivaloyltrifluoroacetonato Dy bathocuproine (comparative example)
tris pivaloyltrifluoroacetonato Dy bathophenanthroline (comparative example)
tris trifluoroacetylacetonato Dy dimethylaminopyridine (comparative example)
tris trifluoroacetylacetonato Dy 4-picoline-N-oxide (comparative example)
tris trifluoroacetylacetonato Dy 4-phenylpyridine (comparative example)
tris trifluoroacetylacetonato Dy 4-cyanopyridine (comparative example)
tris trifluoroacetylacetonato Dy 4-phenylpyridine-N-oxide (comparative example)
tris trifluoroacetylacetonato Dy 1-methylimidazole (comparative example)
tris trifluoroacetylacetonato Dy triphenylphosphine oxide (comparative example)
tris trifluoroacetylacetonato Dy 2,2-bipyridyl (comparative example)
tris trifluoroacetylacetonato Dy 2,2-bipyridyl-N,N-dioxide (comparative example)
tris trifluoroacetylacetonato Dy phenanthroline (comparative example)
tris trifluoroacetylacetonato Dy bathocuproine (comparative example)
tris trifluoroacetylacetonato Dy bathophenanthroline (comparative example)
tris hexafluoroacetylacetonato Dy dimethylaminopyridine (comparative example)
tris hexafluoroacetylacetonato Dy 4-picoline-N-oxide (comparative example)
tris hexafluoroacetylacetonato Dy 4-phenylpyridine (comparative example)
tris hexafluoroacetylacetonato Dy 4-cyanopyridine (comparative example)
tris hexafluoroacetylacetonato Dy 4-phenylpyridine-N-oxide (comparative example)
tris hexafluoroacetylacetonato Dy 1-methylimidazole (comparative example)
tris hexafluoroacetylacetonato Dy triphenylphosphine oxide (comparative example)
tris hexafluoroacetylacetonato Dy 2,2-bipyridyl (comparative example)
tris hexafluoroacetylacetonato Dy 2,2-bipyridyl-N,N-dioxide (comparative example)
tris hexafluoroacetylacetonato Dy phenanthroline (comparative example)
tris hexafluoroacetylacetonato Dy bathocuproine (comparative example)
tris hexafluoroacetylacetonato Dy bathophenanthroline (comparative example)
tris 6,6,7,7,8,8,8-heptafluoro-2,2-dimethyloctanedionato Dy dimethylaminopyridine (comparative example)
tris 6,6,7,7,8,8,8-heptafluoro-2,2-dimethyloctanedionato Dy 4-picoline-N-oxide (comparative example)
tris 6,6,7,7,8,8,8-heptafluoro-2,2-dimethyloctanedionato Dy 4-phenylpyridine (comparative example)
tris 6,6,7,7,8,8,8-heptafluoro-2,2-dimethyloctanedionato Dy 4-cyanopyridine (comparative example)
tris 6,6,7,7,8,8,8-heptafluoro-2,2-dimethyloctanedionato Dy 4-phenylpyridine-N-oxide (comparative example)
tris 6,6,7,7,8,8,8-heptafluoro-2,2-dimethyloctanedionato Dy 1-methylimidazole (comparative example)
tris 6,6,7,7,8,8,8-heptafluoro-2,2-dimethyloctanedionato Dy triphenylphosphine oxide (comparative example)
tris 6,6,7,7,8,8,8-heptafluoro-2,2-dimethyloctanedionato Dy 2,2-bipyridyl (comparative example)
tris 6,6,7,7,8,8,8-heptafluoro-2,2-dimethyloctanedionato Dy 2,2-bipyridyl-N,N-dioxide (comparative example)
tris 6,6,7,7,8,8,8-heptafluoro-2,2-dimethyloctanedionato Dy phenanthroline (comparative example)
tris 6,6,7,7,8,8,8-heptafluoro-2,2-dimethyloctanedionato Dy bathocuproine (comparative example)
tris 6,6,7,7,8,8,8-heptafluoro-2,2-dimethyloctanedionato Dy bathophenanthroline (comparative example)
tris 1-phenyl-1,3-butanedionato Dy dimethylaminopyridine (comparative example)
tris 1-phenyl-1,3-butanedionato Dy 4-picoline-N-oxide (comparative example)
tris 1-phenyl-1,3-butanedionato Dy 4-phenylpyridine (comparative example)
tris 1-phenyl-1,3-butanedionato Dy 4-cyanopyridine (comparative example)
tris 1-phenyl-1,3-butanedionato Dy 4-phenylpyridine-N-oxide (comparative example)
tris 1-phenyl-1,3-butanedionato Dy 1-methylimidazole (comparative example)
tris 1-phenyl-1,3-butanedionato Dy triphenylphosphine oxide (comparative example)
tris 1-phenyl-1,3-butanedionato Dy 2,2-bipyridyl (comparative example)
tris 1-phenyl-1,3-butanedionato Dy 2,2-bipyridyl-N,N-dioxide (comparative example)

tris 1-phenyl-1,3-butanedionato Dy phenanthroline (comparative example)
tris 1-phenyl-1,3-butanedionato Dy bathocuproine (comparative example)
tris 1-phenyl-1,3-butanedionato Dy bathophenanthroline (comparative example)
tris acetylacetonato Tb0.5, Y0.5 dimethylaminopyridine
tris acetylacetonato Tb0.5, Y0.5 4-picoline-N-oxide
tris acetylacetonato Tb0.5, Y0.5 4-phenylpyridine
tris acetylacetonato Tb0.5, Y0.5 4-cyanopyridine
tris acetylacetonato Tb0.5, Y0.5 4-phenylpyridine-N-oxide
tris acetylacetonato Tb0.5, Y0.5 1-methylimidazole
tris acetylacetonato Tb0.5, Y0.5 triphenylphosphine oxide
tris acetylacetonato Tb0.5, Y0.5 2,2-bipyridyl
tris acetylacetonato Tb0.5, Y0.5 2,2-bipyridyl-N,N-dioxide
tris acetylacetonato Tb0.5, Y0.5 phenanthroline
tris acetylacetonato Tb0.5, Y0.5 bathocuproine
tris acetylacetonato Tb0.5, Y0.5 bathophenanthroline
tris dibenzoylmethanato Tb0.5, Y0.5 dimethylaminopyridine
tris dibenzoylmethanato Tb0.5, Y0.5 4-picoline-N-oxide
tris dibenzoylmethanato Tb0.5, Y0.5 4-phenylpyridine
tris dibenzoylmethanato Tb0.5, Y0.5 4-cyanopyridine
tris dibenzoylmethanato Tb0.5, Y0.5 4-phenylpyridine-N-oxide
tris dibenzoylmethanato Tb0.5, Y0.5 1-methylimidazole
tris dibenzoylmethanato Tb0.5, Y0.5 triphenylphosphine oxide
tris dibenzoylmethanato Tb0.5, Y0.5 2,2-bipyridyl
tris dibenzoylmethanato Tb0.5, Y0.5 2,2-bipyridyl-N,N-dioxide
tris dibenzoylmethanato Tb0.5, Y0.5 phenanthroline
tris dibenzoylmethanato Tb0.5, Y0.5 bathocuproine
tris dibenzoylmethanato Tb0.5, Y0.5 bathophenanthroline
tris thenoyltrifluoroacetonato Tb0.5, Y0.5 dimethylaminopyridine
tris thenoyltrifluoroacetonato Tb0.5, Y0.5 4-picoline-N-oxide
tris thenoyltrifluoroacetonato Tb0.5, Y0.5 4-phenylpyridine
tris thenoyltrifluoroacetonato Tb0.5, Y0.5 4-cyanopyridine
tris thenoyltrifluoroacetonato Tb0.5, Y0.5 4-phenylpyridine-N-oxide
tris thenoyltrifluoroacetonato Tb0.5, Y0.5 1-methylimidazole
tris thenoyltrifluoroacetonato Tb0.5, Y0.5 triphenylphosphine oxide
tris thenoyltrifluoroacetonato Tb0.5, Y0.5 2,2-bipyridyl
tris thenoyltrifluoroacetonato Tb0.5, Y0.5 2,2-bipyridyl-N,N-dioxide
tris thenoyltrifluoroacetonato Tb0.5, Y0.5 phenanthroline
tris thenoyltrifluoroacetonato Tb0.5, Y0.5 bathocuproine
tris thenoyltrifluoroacetonato Tb0.5, Y0.5 bathophenanthroline
tris 2,2,6,6-tetramethylheptanedionato Tb0.5, Y0.5 dimethylaminopyridine
tris 2,2,6,6-tetramethylheptanedionato Tb0.5, Y0.5 4-picoline-N-oxide
tris 2,2,6,6-tetramethylheptanedionato Tb0.5, Y0.5 4-phenylpyridine
tris 2,2,6,6-tetramethylheptanedionato Tb0.5, Y0.5 4-cyanopyridine
tris 2,2,6,6-tetramethylheptanedionato Tb0.5, Y0.5 4-phenylpyridine-N-oxide
tris 2,2,6,6-tetramethylheptanedionato Tb0.5, Y0.5 1-methylimidazole
tris 2,2,6,6-tetramethylheptanedionato Tb0.5, Y0.5 triphenylphosphine oxide
tris 2,2,6,6-tetramethylheptanedionato Tb0.5, Y0.5 2,2-bipyridyl
tris 2,2,6,6-tetramethylheptanedionato Tb0.5, Y0.5 2,2-bipyridyl-N,N-dioxide
tris 2,2,6,6-tetramethylheptanedionato Tb0.5, Y0.5 phenanthroline
tris 2,2,6,6-tetramethylheptanedionato Tb0.5, Y0.5 bathocuproine
tris 2,2,6,6-tetramethylheptanedionato Tb0.5, Y0.5 bathophenanthroline
tris 3-methylpentane-2,4-dionato Tb0.5, Y0.5 dimethylaminopyridine
tris 3-methylpentane-2,4-dionato Tb0.5, Y0.5 4-picoline-N-oxide
tris 3-methylpentane-2,4-dionato Tb0.5, Y0.5 4-phenylpyridine
tris 3-methylpentane-2,4-dionato Tb0.5, Y0.5 4-cyanopyridine
tris 3-methylpentane-2,4-dionato Tb0.5, Y0.5 4-phenylpyridine-N-oxide
tris 3-methylpentane-2,4-dionato Tb0.5, Y0.5 1-methylimidazole
tris 3-methylpentane-2,4-dionato Tb0.5, Y0.5 triphenylphosphine oxide
tris 3-methylpentane-2,4-dionato Tb0.5, Y0.5 2,2-bipyridyl
tris 3-methylpentane-2,4-dionato Tb0.5, Y0.5 2,2-bipyridyl-N,N-dioxide
tris 3-methylpentane-2,4-dionato Tb0.5, Y0.5 phenanthroline
tris 3-methylpentane-2,4-dionato Tb0.5, Y0.5 bathocuproine
tris 3-methylpentane-2,4-dionato Tb0.5, Y0.5 bathophenanthroline
tris 3-ethylpentane-2,4-dionato Tb0.5, Y0.5 dimethylaminopyridine
tris 3-ethylpentane-2,4-dionato Tb0.5, Y0.5 4-picoline-N-oxide
tris 3-ethylpentane-2,4-dionato Tb0.5, Y0.5 4-phenylpyridine
tris 3-ethylpentane-2,4-dionato Tb0.5, Y0.5 4-cyanopyridine
tris 3-ethylpentane-2,4-dionato Tb0.5, Y0.5 4-phenylpyridine-N-oxide
tris 3-ethylpentane-2,4-dionato Tb0.5, Y0.5 1-methylimidazole
tris 3-ethylpentane-2,4-dionato Tb0.5, Y0.5 triphenylphosphine oxide
tris 3-ethylpentane-2,4-dionato Tb0.5, Y0.5 2,2-bipyridyl
tris 3-ethylpentane-2,4-dionato Tb0.5, Y0.5 2,2-bipyridyl-N,N-dioxide
tris 3-ethylpentane-2,4-dionato Tb0.5, Y0.5 phenanthroline
tris 3-ethylpentane-2,4-dionato Tb0.5, Y0.5 bathocuproine
tris 3-ethylpentane-2,4-dionato Tb0.5, Y0.5 bathophenanthroline
tris pivaloyltrifluoroacetonato Tb0.5, Y0.5 dimethylaminopyridine
tris pivaloyltrifluoroacetonato Tb0.5, Y0.5 4-picoline-N-oxide
tris pivaloyltrifluoroacetonato Tb0.5, Y0.5 4-phenylpyridine
tris pivaloyltrifluoroacetonato Tb0.5, Y0.5 4-cyanopyridine
tris pivaloyltrifluoroacetonato Tb0.5, Y0.5 4-phenylpyridine-N-oxide
tris pivaloyltrifluoroacetonato Tb0.5, Y0.5 1-methylimidazole
tris pivaloyltrifluoroacetonato Tb0.5, Y0.5 triphenylphosphine oxide
tris pivaloyltrifluoroacetonato Tb0.5, Y0.5 2,2-bipyridyl tris pivaloyltrifluoroacetonato Tb0.5, Y0.5 2,2-bipyridyl-N,N-dioxide
tris pivaloyltrifluoroacetonato Tb0.5, Y0.5 phenanthroline
tris pivaloyltrifluoroacetonato Tb0.5, Y0.5 bathocuproine
tris pivaloyltrifluoroacetonato Tb0.5, Y0.5 bathophenanthroline
tris trifluoroacetylacetonato Tb0.5, Y0.5 dimethylaminopyridine
tris trifluoroacetylacetonato Tb0.5, Y0.5 4-picoline-N-oxide
tris trifluoroacetylacetonato Tb0.5, Y0.5 4-phenylpyridine
tris trifluoroacetylacetonato Tb0.5, Y0.5 4-cyanopyridine
tris trifluoroacetylacetonato Tb0.5, Y0.5 4-phenylpyridine-N-oxide
tris trifluoroacetylacetonato Tb0.5, Y0.5 1-methylimidazole
tris trifluoroacetylacetonato Tb0.5, Y0.5 triphenylphosphine oxide
tris trifluoroacetylacetonato Tb0.5, Y0.5 2,2-bipyridyl
tris trifluoroacetylacetonato Tb0.5, Y0.5 2,2-bipyridyl-N,N-dioxide
tris trifluoroacetylacetonato Tb0.5, Y0.5 phenanthroline
tris trifluoroacetylacetonato Tb0.5, Y0.5 bathocuproine
tris trifluoroacetylacetonato Tb0.5, Y0.5 bathophenanthroline
tris hexafluoroacetylacetonato Tb0.5, Y0.5 dimethylaminopyridine
tris hexafluoroacetylacetonato Tb0.5, Y0.5 4-picoline-N-oxide
tris hexafluoroacetylacetonato Tb0.5, Y0.5 4-phenylpyridine
tris hexafluoroacetylacetonato Tb0.5, Y0.5 4-cyanopyridine
tris hexafluoroacetylacetonato Tb0.5, Y0.5 4-phenylpyridine-N-oxide
tris hexafluoroacetylacetonato Tb0.5, Y0.5 1-methylimidazole
tris hexafluoroacetylacetonato Tb0.5, Y0.5 triphenylphosphine oxide
tris hexafluoroacetylacetonato Tb0.5, Y0.5 2,2-bipyridyl
tris hexafluoroacetylacetonato Tb0.5, Y0.5 2,2-bipyridyl-N,N-dioxide
tris hexafluoroacetylacetonato Tb0.5, Y0.5 phenanthroline
tris hexafluoroacetylacetonato Tb0.5, Y0.5 bathocuproine
tris hexafluoroacetylacetonato Tb0.5, Y0.5 bathophenanthroline
tris 6,6,7,7,8,8,8-heptafluoro-2,2-dimethyloctanedionato Tb0.5, Y0.5 dimethylaminopyridine
tris 6,6,7,7,8,8,8-heptafluoro-2,2-dimethyloctanedionato Tb0.5, Y0.5 4-picoline-N-oxide
tris 6,6,7,7,8,8,8-heptafluoro-2,2-dimethyloctanedionato Tb0.5, Y0.5 4-phenylpyridine
tris 6,6,7,7,8,8,8-heptafluoro-2,2-dimethyloctanedionato Tb0.5, Y0.5 4-cyanopyridine
tris 6,6,7,7,8,8,8-heptafluoro-2,2-dimethyloctanedionato Tb0.5, Y0.5 4-phenylpyridine-N-oxide
tris 6,6,7,7,8,8,8-heptafluoro-2,2-dimethyloctanedionato Tb0.5, Y0.5 1-methylimidazole
tris 6,6,7,7,8,8,8-heptafluoro-2,2-dimethyloctanedionato Tb0.5, Y0.5 triphenylphosphine oxide
tris 6,6,7,7,8,8,8-heptafluoro-2,2-dimethyloctanedionato Tb0.5, Y0.5 2,2-bipyridyl
tris 6,6,7,7,8,8,8-heptafluoro-2,2-dimethyloctanedionato Tb0.5, Y0.5 2,2-bipyridyl-N,N-dioxide
tris 6,6,7,7,8,8,8-heptafluoro-2,2-dimethyloctanedionato Tb0.5, Y0.5 phenanthroline
tris 6,6,7,7,8,8,8-heptafluoro-2,2-dimethyloctanedionato Tb0.5, Y0.5 bathocuproine
tris 6,6,7,7,8,8,8-heptafluoro-2,2-dimethyloctanedionato Tb0.5, Y0.5 bathophenanthroline
tris 1-phenyl-1,3-butanedionato Tb0.5, Y0.5 dimethylaminopyridine
tris 1-phenyl-1,3-butanedionato Tb0.5, Y0.5 4-picoline-N-oxide
tris 1-phenyl-1,3-butanedionato Tb0.5, Y0.5 4-phenylpyridine
tris 1-phenyl-1,3-butanedionato Tb0.5, Y0.5 4-cyanopyridine
tris 1-phenyl-1,3-butanedionato Tb0.5, Y0.5 4-phenylpyridine-N-oxide
tris 1-phenyl-1,3-butanedionato Tb0.5, Y0.5 1-methylimidazole
tris 1-phenyl-1,3-butanedionato Tb0.5, Y0.5 triphenylphosphine oxide
tris 1-phenyl-1,3-butanedionato Tb0.5, Y0.5 2,2-bipyridyl
tris 1-phenyl-1,3-butanedionato Tb0.5, Y0.5 2,2-bipyridyl-N,N-dioxide
tris 1-phenyl-1,3-butanedionato Tb0.5, Y0.5 phenanthroline
tris 1-phenyl-1,3-butanedionato Tb0.5, Y0.5 bathocuproine
tris 1-phenyl-1,3-butanedionato Tb0.5, Y0.5 bathophenanthroline
tris acetylacetonato Tb0.2, Y0.8 dimethylaminopyridine
tris acetylacetonato Tb0.2, Y0.8 4-picoline-N-oxide
tris acetylacetonato Tb0.2, Y0.8 4-phenylpyridine
tris acetylacetonato Tb0.2, Y0.8 4-cyanopyridine
tris acetylacetonato Tb0.2, Y0.8 4-phenylpyridine-N-oxide
tris acetylacetonato Tb0.2, Y0.8 1-methylimidazole
tris acetylacetonato Tb0.2, Y0.8 triphenyiphosphine oxide
tris acetylacetonato Tb0.2, Y0.8 2,2-bipyridyl
tris acetylacetonato Tb0.2, Y0.8 2,2-bipyridyl-N,N-dioxide
tris acetylacetonato Tb0.2, Y0.8 phenanthroline
tris acetylacetonato Tb0.2, Y0.8 bathocuproine
tris acetylacetonato Tb0.2, Y0.8 bathophenanthroline
tris dibenzoylmethanato Tb0.2, Y0.8 dimethylaminopyridine
tris dibenzoylmethanato Tb0.2, Y0.8 4-picoline-N-oxide
tris dibenzoylmethanato Tb0.2, Y0.8 4-phenylpyridine
tris dibenzoylmethanato Tb0.2, Y0.8 4-cyanopyridine
tris dibenzoylmethanato Tb0.2, Y0.8 4-phenylpyridine-N-oxide
tris dibenzoylmethanato Tb0.2, Y0.8 1-methylimidazole
tris dibenzoylmethanato Tb0.2, Y0.8 triphenylphosphine oxide
tris dibenzoylmethanato Tb0.2, Y0.8 2,2-bipyridyl
tris dibenzoylmethanato Tb0.2, Y0.8 2,2-bipyridyl-N,N-dioxide
tris dibenzoylmethanato Tb0.2, Y0.8 phenanthroline
tris dibenzoylmethanato Tb0.2, Y0.8 bathocuproine
tris dibenzoylmethanato Tb0.2, Y0.8 bathophenanthroline
tris thenoyltrifluoroacetonato Tb0.2, Y0.8 dimethylaminopyridine
tris thenoyltrifluoroacetonato Tb0.2, Y0.8 4-picoline-N-oxide
tris thenoyltrifluoroacetonato Tb0.2, Y0.8 4-phenylpyridine
tris thenoyltrifluoroacetonato Tb0.2, Y0.8 4-cyanopyridine
tris thenoyltrifluoroacetonato Tb0.2, Y0.8 4-phenylpyridine-N-oxide
tris thenoyltrifluoroacetonato Tb0.2, Y0.8 1-methylimidazole
tris thenoyltrifluoroacetonato Tb0.2, Y0.8 triphenylphosphine oxide
tris thenoyltrifluoroacetonato Tb0.2, Y0.8 2,2-bipyridyl
tris thenoyltrifluoroacetonato Tb0.2, Y0.8 2,2-bipyridyl-N,N-dioxide
tris thenoyltrifluoroacetonato Tb0.2, Y0.8 phenanthroline
tris thenoyltrifluoroacetonato Tb0.2, Y0.8 bathocuproine tris thenoyltrifluoroacetonato Tb0.2, Y0.8 bathophenanthroline
tris 2,2,6,6-tetramethylheptanedionato Tb0.2, Y0.8 dimethylaminopyridine
tris 2,2,6,6-tetramethylheptanedionato Tb0.2, Y0.8 4-picoline-N-oxide
tris 2,2,6,6-tetramethylheptanedionato Tb0.2, Y0.8 4-phenylpyridine
tris 2,2,6,6-tetramethylheptanedionato Tb0.2, Y0.8 4-cyanopyridine
tris 2,2,6,6-tetramethylheptanedionato Tb0.2, Y0.8 4-phenylpyridine-N-oxide
tris 2,2,6,6-tetramethylheptanedionato Tb0.2, Y0.8 1-methylimidazole
tris 2,2,6,6-tetramethylheptanedionato Tb0.2, Y0.8 triphenylphosphine oxide
tris 2,2,6,6-tetramethylheptanedionato Tb0.2, Y0.8 2,2-bipyridyl
tris 2,2,6,6-tetramethylheptanedionato Tb0.2, Y0.8 2,2-bipyridyl-N,N-dioxide
tris 2,2,6,6-tetramethylheptanedionato Tb0.2, Y0.8 phenanthroline
tris 2,2,6,6-tetramethylheptanedionato Tb0.2, Y0.8 bathocuproine
tris 2,2,6,6-tetramethylheptanedionato Tb0.2, Y0.8 bathophenanthroline
tris 3-methylpentane-2,4-dionato Tb0.2, Y0.8 dimethylaminopyridine
tris 3-methylpentane-2,4-dionato Tb0.2, Y0.8 4-picoline-N-oxide
tris 3-methylpentane-2,4-dionato Tb0.2, Y0.8 4-phenylpyridine
tris 3-methylpentane-2,4-dionato Tb0.2, Y0.8 4-cyanopyridine
tris 3-methylpentane-2,4-dionato Tb0.2, Y0.8 4-phenylpyridine-N-oxide
tris 3-methylpentane-2,4-dionato Tb0.2, Y0.8 1-methylimidazole
tris 3-methylpentane-2,4-dionato Tb0.2, Y0.8 triphenylphosphine oxide
tris 3-methylpentane-2,4-dionato Tb0.2, Y0.8 2,2-bipyridyl
tris 3-methylpentane-2,4-dionato Tb0.2, Y0.8 2,2-bipyridyl-N,N-dioxide
tris 3-methylpentane-2,4-dionato Tb0.2, Y0.8 phenanthroline
tris 3-methylpentane-2,4-dionato Tb0.2, Y0.8 bathocuproine
tris 3-methylpentane-2,4-dionato Tb0.2, Y0.8 bathophenanthroline
tris 3-ethylpentane-2,4-dionato Tb0.2, Y0.8 dimethylaminopyridine
tris 3-ethylpentane-2,4-dionato Tb0.2, Y0.8 4-picoline-N-oxide
tris 3-ethylpentane-2,4-dionato Tb0.2, Y0.8 4-phenylpyridine
tris 3-ethylpentane-2,4-dionato Tb0.2, Y0.8 4-cyanopyridine
tris 3-ethylpentane-2,4-dionato Tb0.2, Y0.8 4-phenylpyridine-N-oxide
tris 3-ethylpentane-2,4-dionato Tb0.2, Y0.8 1-methylimidazole
tris 3-ethylpentane-2,4-dionato Tb0.2, Y0.8 triphenylphosphine oxide
tris 3-ethylpentane-2,4-dionato Tb0.2, Y0.8 2,2-bipyridyl
tris 3-ethylpentane-2,4-dionato Tb0.2, Y0.8 2,2-bipyridyl-N,N-dioxide
tris 3-ethylpentane-2,4-dionato Tb0.2, Y0.8 phenanthroline
tris 3-ethylpentane-2,4-dionato Tb0.2, Y0.8 bathocuproine
tris 3-ethylpentane-2,4-dionato Tb0.2, Y0.8 bathophenanthroline
tris pivaloyltrifluoroacetonato Tb0.2, Y0.8 dimethylaminopyridine
tris pivaloyltrifluoroacetonato Tb0.2, Y0.8 4-picoline-N-oxide
tris pivaloyltrifluoroacetonato Tb0.2, Y0.8 4-phenylpyridine
tris pivaloyltrifluoroacetonato Tb0.2, Y0.8 4-cyanopyridine
tris pivaloyltrifluoroacetonato Tb0.2, Y0.8 4-phenylpyridine-N-oxide
tris pivaloyltrifluoroacetonato Tb0.2, Y0.8 1-methylimidazole
tris pivaloyltrifluoroacetonato Tb0.2, Y0.8 triphenylphosphine oxide
tris pivaloyltrifluoroacetonato Tb0.2, Y0.8 2,2-bipyridyl
tris pivaloyltrifluoroacetonato Tb0.2, Y0.8 2,2-bipyridyl-N,N-dioxide
tris pivaloyltrifluoroacetonato Tb0.2, Y0.8 phenanthroline
tris pivaloyltrifluoroacetonato Tb0.2, Y0.8 bathocuproine
tris pivaloyltrifluoroacetonato Tb0.2, Y0.8 bathophenanthroline
tris trifluoroacetylacetonato Tb0.2, Y0.8 dimethylaminopyridine
tris trifluoroacetylacetonato Tb0.2, Y0.8 4-picoline-N-oxide
tris trifluoroacetylacetonato Tb0.2, Y0.8 4-phenylpyridine
tris trifluoroacetylacetonato Tb0.2, Y0.8 4-cyanopyridine
tris trifluoroacetylacetonato Tb0.2, Y0.8 4-phenylpyridine-N-oxide
tris trifluoroacetylacetonato Tb0.2, Y0.8 1-methylimidazole
tris trifluoroacetylacetonato Tb0.2, Y0.8 triphenylphosphine oxide
tris trifluoroacetylacetonato Tb0.2, Y0.8 2,2-bipyridyl
tris trifluoroacetylacetonato Tb0.2, Y0.8 2,2-bipyridyl-N,N-dioxide
tris trifluoroacetylacetonato Tb0.2, Y0.8 phenanthroline
tris trifluoroacetylacetonato Tb0.2, Y0.8 bathocuproine
tris trifluoroacetylacetonato Tb0.2, Y0.8 bathophenanthroline
tris hexafluoroacetylacetonato Tb0.2, Y0.8 dimethylaminopyridine
tris hexafluoroacetylacetonato Tb0.2, Y0.8 4-picoline-N-oxide
tris hexafluoroacetylacetonato Tb0.2, Y0.8 4-phenylpyridine
tris hexafluoroacetylacetonato Tb0.2, Y0.8 4-cyanopyridine
tris hexafluoroacetylacetonato Tb0.2, Y0.8 4-phenylpyridine-N-oxide
tris hexafluoroacetylacetonato Tb0.2, Y0.8 1-methylimidazole
tris hexafluoroacetylacetonato Tb0.2, Y0.8 triphenylphosphine oxide
tris hexafluoroacetylacetonato Tb0.2, Y0.8 2,2-bipyridyl
tris hexafluoroacetylacetonato Tb0.2, Y0.8 2,2-bipyridyl-N,N-dioxide
tris hexafluoroacetylacetonato Tb0.2, Y0.8 phenanthroline
tris hexafluoroacetylacetonato Tb0.2, Y0.8 bathocuproine
tris hexafluoroacetylacetonato Tb0.2, Y0.8 bathophenanthroline
tris 6,6,7,7,8,8,8-heptafluoro-2,2-dimethyloctanedionato Tb0.2, Y0.8 dimethylaminopyridine
tris 6,6,7,7,8,8,8-heptafluoro-2,2-dimethyloctanedionato Tb0.2, Y0.8 4-picoline-N-oxide
tris 6,6,7,7,8,8,8-heptafluoro-2,2-dimethyloctanedionato Tb0.2, Y0.8 4-phenylpyridine
tris 6,6,7,7,8,8,8-heptafluoro-2,2-dimethyloctanedionato Tb0.2, Y0.8 4-cyanopyridine
tris 6,6,7,7,8,8,8-heptafluoro-2,2-dimethyloctanedionato Tb0.2, Y0.8 4-phenylpyridine-N-oxide tris 6,6,7,7,8,8-heptafluoro-2,2-dimethyloctanedionato Tb0.2, Y0.8 1-methylimidazole
tris 6,6,7,7,8,8-heptafluoro-2,2-dimethyloctanedionato Tb0.2, Y0.8 triphenylphosphine oxide
tris 6,6,7,7,8,8-heptafluoro-2,2-dimethyloctanedionato Tb0.2, Y0.8 2,2-bipyridyl
tris 6,6,7,7,8,8-heptafluoro-2,2-dimethyloctanedionato Tb0.2, Y0.8 2,2-bipyridyl-N,N-dioxide
tris 6,6,7,7,8,8-heptafluoro-2,2-dimethyloctanedionato Tb0.2, Y0.8 phenanthroline
tris 6,6,7,7,8,8-heptafluoro-2,2-dimethyloctanedionato Tb0.2, Y0.8 bathocuproine
tris 6,6,7,7,8,8-heptafluoro-2,2-dimethyloctanedionato Tb0.2, Y0.8 bathophenanthroline
tris 1-phenyl-1,3-butanedionato Tb0.2, Y0.8 dimethylaminopyridine
tris 1-phenyl-1,3-butanedionato Tb0.2, Y0.8 4-picoline-N-oxide
tris 1-phenyl-1,3-butanedionato Tb0.2, Y0.8 4-phenylpyridine
tris 1-phenyl-1,3-butanedionato Tb0.2, Y0.8 4-cyanopyridine
tris 1-phenyl-1,3-butanedionato Tb0.2, Y0.8 4-phenylpyridine-N-oxide
tris 1-phenyl-1,3-butanedionato Tb0.2, Y0.8 1-methylimidazole
tris 1-phenyl-1,3-butanedionato Tb0.2, Y0.8 triphenylphosphine oxide
tris 1-phenyl-1,3-butanedionato Tb0.2, Y0.8 2,2-bipyridyl
tris 1-phenyl-1,3-butanedionato Tb0.2, Y0.8 2,2-bipyridyl-N,N-dioxide
tris 1-phenyl-1,3-butanedionato Tb0.2, Y0.8 phenanthroline
tris 1-phenyl-1,3-butanedionato Tb0.2, Y0.8 bathocuproine
tris 1-phenyl-1,3-butanedionato Tb0.2, Y0.8 bathophenanthroline
tris acetylacetonato Tb0.1, Y0.9 dimethylaminopyridine
tris acetylacetonato Tb0.1, Y0.9 4-picoline-N-oxide
tris acetylacetonato Tb0.1, Y0.9 4-phenylpyridine
tris acetylacetonato Tb0.1, Y0.9 4-cyanopyridine
tris acetylacetonato Tb0.1, Y0.9 4-phenylpyridine-N-oxide
tris acetylacetonato Tb0.1, Y0.9 1-methylimidazole
tris acetylacetonato Tb0.1, Y0.9 triphenylphosphine oxide
tris acetylacetonato Tb0.1, Y0.9 2,2-bipyridyl
tris acetylacetonato Tb0.1, Y0.9 2,2-bipyridyl-N,N-dioxide
tris acetylacetonato Tb0.1, Y0.9 phenanthroline
tris acetylacetonato Tb0.1, Y0.9 bathocuproine
tris acetylacetonato Tb0.1, Y0.9 bathophenanthroline
tris dibenzoylmethanato Tb0.1, Y0.9 dimethylaminopyridine
tris dibenzoylmethanato Tb0.1, Y0.9 4-picoline-N-oxide
tris dibenzoylmethanato Tb0.1, Y0.9 4-phenylpyridine
tris dibenzoylmethanato Tb0.1, Y0.9 4-cyanopyridine
tris dibenzoylmethanato Tb0.1, Y0.9 4-phenylpyridine-N-oxide
tris dibenzoylmethanato Tb0.1, Y0.9 1-methylimidazole
tris dibenzoylmethanato Tb0.1, Y0.9 triphenylphosphine oxide
tris dibenzoylmethanato Tb0.1, Y0.9 2,2-bipyridyl
tris dibenzoylmethanato Tb0.1, Y0.9 2,2-bipyridyl-N,N-dioxide
tris dibenzoylmethanato Tb0.1, Y0.9 phenanthroline
tris dibenzoylmethanato Tb0.1, Y0.9 bathocuproine
tris dibenzoylmethanato Tb0.1, Y0.9 bathophenanthroline
tris thenoyltrifluoroacetonato Tb0.1, Y0.9 dimethylaminopyridine
tris thenoyltrifluoroacetonato Tb0.1, Y0.9 4-picoline-N-oxide
tris thenoyltrifluoroacetonato Tb0.1, Y0.9 4-phenylpyridine
tris thenoyltrifluoroacetonato Tb0.1, Y0.9 4-cyanopyridine
tris thenoyltrifluoroacetonato Tb0.1, Y0.9 4-phenylpyridine-N-oxide
tris thenoyltrifluoroacetonato Tb0.1, Y0.9 1-methylimidazole
tris thenoyltrifluoroacetonato Tb0.1, Y0.9 triphenylphosphine oxide
tris thenoyltrifluoroacetonato Tb0.1, Y0.9 2,2-bipyridyl
tris thenoyltrifluoroacetonato Tb0.1, Y0.9 2,2-bipyridyl-N,N-dioxide
tris thenoyltrifluoroacetonato Tb0.1, Y0.9 phenanthroline
tris thenoyltrifluoroacetonato Tb0.1, Y0.9 bathocuproine
tris thenoyltrifluoroacetonato Tb0.1, Y0.9 bathophenanthroline
tris 2,2,6,6-tetramethylheptanedionato Tb0.1, Y0.9 dimethylaminopyridine
tris 2,2,6,6-tetramethylheptanedionato Tb0.1, Y0.9 4-picoline-N-oxide
tris 2,2,6,6-tetramethylheptanedionato Tb0.1, Y0.9 4-phenylpyridine
tris 2,2,6,6-tetramethylheptanedionato Tb0.1, Y0.9 4-cyanopyridine
tris 2,2,6,6-tetramethylheptanedionato Tb0.1, Y0.9 4-phenylpyridine-N-oxide
tris 2,2,6,6-tetramethylheptanedionato Tb0.1, Y0.9 1-methylimidazole
tris 2,2,6,6-tetramethylheptanedionato Tb0.1, Y0.9 triphenylphosphine oxide
tris 2,2,6,6-tetramethylheptanedionato Tb0.1, Y0.9 2,2-bipyridyl
tris 2,2,6,6-tetramethylheptanedionato Tb0.1, Y0.9 2,2-bipyridyl-N,N-dioxide
tris 2,2,6,6-tetramethylheptanedionato Tb0.1, Y0.9 phenanthroline
tris 2,2,6,6-tetramethylheptanedionato Tb0.1, Y0.9 bathocuproine
tris 2,2,6,6-tetramethylheptanedionato Tb0.1, Y0.9 bathophenanthroline
tris 3-methylpentane-2,4-dionato Tb0.1, Y0.9 dimethylaminopyridine
tris 3-methylpentane-2,4-dionato Tb0.1, Y0.9 4-picoline-N-oxide
tris 3-methylpentane-2,4-dionato Tb0.1, Y0.9 4-phenylpyridine
tris 3-methylpentane-2,4-dionato Tb0.1, Y0.9 4-cyanopyridine
tris 3-methylpentane-2,4-dionato Tb0.1, Y0.9 4-phenylpyridine-N-oxide
tris 3-methylpentane-2,4-dionato Tb0.1, Y0.9 1-methylimidazole
tris 3-methylpentane-2,4-dionato Tb0.1, Y0.9 triphenylphosphine oxide
tris 3-methylpentane-2,4-dionato Tb0.1, Y0.9 2,2-bipyridyl
tris 3-methylpentane-2,4-dionato Tb0.1, Y0.9 2,2-bipyridyl-N,N-dioxide
tris 3-methylpentane-2,4-dionato Tb0.1, Y0.9 phenanthroline
tris 3-methylpentane-2,4-dionato Tb0.1, Y0.9 bathocuproine
tris 3-methylpentane-2,4-dionato Tb0.1, Y0.9 bathophenanthroline
tris 3-ethylpentane-2,4-dionato Tb0.1, Y0.9 dimethylaminopyridine
tris 3-ethylpentane-2,4-dionato Tb0.1, Y0.9 4-picoline-N-oxide
tris 3-ethylpentane-2,4-dionato Tb0.1, Y0.9 4-phenylpyridine tris 3-ethylpentane-2,4-dionato Tb0.1, Y0.9 4-cyanopyridine
tris 3-ethylpentane-2,4-dionato Tb0.1, Y0.9 4-phenylpyridine-N-oxide
tris 3-ethylpentane-2,4-dionato Tb0.1, Y0.9 1-methylimidazole
tris 3-ethylpentane-2,4-dionato Tb0.1, Y0.9 triphenylphosphine oxide
tris 3-ethylpentane-2,4-dionato Tb0.1, Y0.9 2,2-bipyridyl
tris 3-ethylpentane-2,4-dionato Tb0.1, Y0.9 2,2-bipyridyl-N,N-dioxide
tris 3-ethylpentane-2,4-dionato Tb0.1, Y0.9 phenanthroline
tris 3-ethylpentane-2,4-dionato Tb0.1, Y0.9 bathocuproine
tris 3-ethylpentane-2,4-dionato Tb0.1, Y0.9 bathophenanthroline
tris pivaloyltrifluoroacetonato Tb0.1, Y0.9 dimethylaminopyridine
tris pivaloyltrifluoroacetonato Tb0.1, Y0.9 4-picoline-N-oxide
tris pivaloyltrifluoroacetonato Tb0.1, Y0.9 4-phenylpyridine
tris pivaloyltrifluoroacetonato Tb0.1, Y0.9 4-cyanopyridine
tris pivaloyltrifluoroacetonato Tb0.1, Y0.9 4-phenylpyridine-N-oxide
tris pivaloyltrifluoroacetonato Tb0.1, Y0.9 1-methylimidazole
tris pivaloyltrifluoroacetonato Tb0.1, Y0.9 triphenylphosphine oxide
tris pivaloyltrifluoroacetonato Tb0.1, Y0.9 2,2-bipyridyl
tris pivaloyltrifluoroacetonato Tb0.1, Y0.9 2,2-bipyridyl-N,N-dioxide
tris pivaloyltrifluoroacetonato Tb0.1, Y0.9 phenanthroline
tris pivaloyltrifluoroacetonato Tb0.1, Y0.9 bathocuproine
tris pivaloyltrifluoroacetonato Tb0.1, Y0.9 bathophenanthroline
tris trifluoroacetylacetonato Tb0.1, Y0.9 dimethylaminopyridine
tris trifluoroacetylacetonato Tb0.1, Y0.9 4-picoline-N-oxide
tris trifluoroacetylacetonato Tb0.1, Y0.9 4-phenylpyridine
tris trifluoroacetylacetonato Tb0.1, Y0.9 4-cyanopyridine
tris trifluoroacetylacetonato Tb0.1, Y0.9 4-phenylpyridine-N-oxide
tris trifluoroacetylacetonato Tb0.1, Y0.9 1-methylimidazole
tris trifluoroacetylacetonato Tb0.1, Y0.9 triphenylphosphine oxide
tris trifluoroacetylacetonato Tb0.1, Y0.9 2,2-bipyridyl
tris trifluoroacetylacetonato Tb0.1, Y0.9 2,2-bipyridyl-N,N-dioxide
tris trifluoroacetylacetonato Tb0.1, Y0.9 phenanthroline
tris trifluoroacetylacetonato Tb0.1, Y0.9 bathocuproine
tris trifluoroacetylacetonato Tb0.1, Y0.9 bathophenanthroline
tris hexafluoroacetylacetonato Tb0.1, Y0.9 dimethylaminopyridine
tris hexafluoroacetylacetonato Tb0.1, Y0.9 4-picoline-N-oxide
tris hexafluoroacetylacetonato Tb0.1, Y0.9 4-phenylpyridine
tris hexafluoroacetylacetonato Tb0.1, Y0.9 4-cyanopyridine
tris hexafluoroacetylacetonato Tb0.1, Y0.9 4-phenylpyridine-N-oxide
tris hexafluoroacetylacetonato Tb0.1, Y0.9 1-methylimidazole
tris hexafluoroacetylacetonato Tb0.1, Y0.9 triphenylphosphine oxide
tris hexafluoroacetylacetonato Tb0.1, Y0.9 2,2-bipyridyl
tris hexafluoroacetylacetonato Tb0.1, Y0.9 2,2-bipyridyl-N,N-dioxide
tris hexafluoroacetylacetonato Tb0.1, Y0.9 phenanthroline
tris hexafluoroacetylacetonato Tb0.1, Y0.9 bathocuproine
tris hexafluoroacetylacetonato Tb0.1, Y0.9 bathophenanthroline
tris 6,6,7,7,8,8,8-heptafluoro-2,2-dimethyloctanedionato Tb0.1, Y0.9 dimethylaminopyridine
tris 6,6,7,7,8,8,8-heptafluoro-2,2-dimethyloctanedionato Tb0.1, Y0.9 4-picoline-N-oxide
tris 6,6,7,7,8,8,8-heptafluoro-2,2-dimethyloctanedionato Tb0.1, Y0.9 4-phenylpyridine
tris 6,6,7,7,8,8,8-heptafluoro-2,2-dimethyloctanedionato Tb0.1, Y0.9 4-cyanopyridine
tris 6,6,7,7,8,8,8-heptafluoro-2,2-dimethyloctanedionato Tb0.1, Y0.9 4-phenylpyridine-N-oxide
tris 6,6,7,7,8,8,8-heptafluoro-2,2-dimethyloctanedionato Tb0.1, Y0.9 1-methylimidazole
tris 6,6,7,7,8,8,8-heptafluoro-2,2-dimethyloctanedionato Tb0.1, Y0.9 triphenylphosphine oxide
tris 6,6,7,7,8,8,8-heptafluoro-2,2-dimethyloctanedionato Tb0.1, Y0.9 2,2-bipyridyl
tris 6,6,7,7,8,8,8-heptafluoro-2,2-dimethyloctanedionato Tb0.1, Y0.9 2,2-bipyridyl-N,N-dioxide
tris 6,6,7,7,8,8,8-heptafluoro-2,2-dimethyloctanedionato Tb0.1, Y0.9 phenanthroline
tris 6,6,7,7,8,8,8-heptafluoro-2,2-dimethyloctanedionato Tb0.1, Y0.9 bathocuproine
tris 6,6,7,7,8,8,8-heptafluoro-2,2-dimethyloctanedionato Tb0.1, Y0.9 bathophenanthroline
tris 1-phenyl-1,3-butanedionato Tb0.1, Y0.9 dimethylaminopyridine
tris 1-phenyl-1,3-butanedionato Tb0.1, Y0.9 4-picoline-N-oxide
tris 1-phenyl-1,3-butanedionato Tb0.1, Y0.9 4-phenylpyridine
tris 1-phenyl-1,3-butanedionato Tb0.1, Y0.9 4-cyanopyridine
tris 1-phenyl-1,3-butanedionato Tb0.1, Y0.9 4-phenylpyridine-N-oxide
tris 1-phenyl-1,3-butanedionato Tb0.1, Y0.9 1-methylimidazole
tris 1-phenyl-1,3-butanedionato Tb0.1, Y0.9 triphenylphosphine oxide
tris 1-phenyl-1,3-butanedionato Tb0.1, Y0.9 2,2-bipyridyl
tris 1-phenyl-1,3-butanedionato Tb0.1, Y0.9 2,2-bipyridyl-N,N-dioxide
tris 1-phenyl-1,3-butanedionato Tb0.1, Y0.9 phenanthroline
tris 1-phenyl-1,3-butanedionato Tb0.1, Y0.9 bathocuproine
tris 1-phenyl-1,3-butanedionato Tb0.1, Y0.9 bathophenanthroline
tris acetylacetonato Tb0.01, Y0.99 dimethylaminopyridine
tris acetylacetonato Tb0.01, Y0.99 4-picoline-N-oxide
tris acetylacetonato Tb0.01, Y0.99 4-phenylpyridine
tris acetylacetonato Tb0.01, Y0.99 4-cyanopyridine
tris acetylacetonato Tb0.01, Y0.99 4-phenylpyridine-N-oxide
tris acetylacetonato Tb0.01, Y0.99 1-methylimidazole
tris acetylacetonato Tb0.01, Y0.99 triphenylphosphine oxide
tris acetylacetonato Tb0.01, Y0.99 2,2-bipyridyl
tris acetylacetonato Tb0.01, Y0.99 2,2-bipyridyl-N,N-dioxide
tris acetylacetonato Tb0.01, Y0.99 phenanthroline
tris acetylacetonato Tb0.01, Y0.99 bathocuproine
tris acetylacetonato Tb0.01, Y0.99 bathophenanthroline
tris dibenzoylmethanato Tb0.01, Y0.99 dimethylaminopyridine
tris dibenzoylmethanato Tb0.01, Y0.99 4-picoline-N-oxide
tris dibenzoylmethanato Tb0.01, Y0.99 4-phenylpyridine
tris dibenzoylmethanato Tb0.01, Y0.99 4-cyanopyridine tris dibenzoylmethanato Tb0.01, Y0.99 4-phenylpyridine-N-oxide
tris dibenzoylmethanato Tb0.01, Y0.99 1-methylimidazole
tris dibenzoylmethanato Tb0.01, Y0.99 triphenylphosphine oxide
tris dibenzoylmethanato Tb0.01, Y0.99 2,2-bipyridyl
tris dibenzoylmethanato Tb0.01, Y0.99 2,2-bipyridyl-N,N-dioxide
tris dibenzoylmethanato Tb0.01, Y0.99 phenanthroline
tris dibenzoylmethanato Tb0.01, Y0.99 bathocuproine
tris dibenzoylmethanato Tb0.01, Y0.99 bathophenanthroline
tris thenoyltrifluoroacetonato Tb0.01, Y0.99 dimethylaminopyridine
tris thenoyltrifluoroacetonato Tb0.01, Y0.99 4-picoline-N-oxide
tris thenoyltrifluoroacetonato Tb0.01, Y0.99 4-phenylpyridine
tris thenoyltrifluoroacetonato Tb0.01, Y0.99 4-cyanopyridine
tris thenoyltrifluoroacetonato Tb0.01, Y0.99 4-phenylpyridine-N-oxide
tris thenoyltrifluoroacetonato Tb0.01, Y0.99 1-methylimidazole
tris thenoyltrifluoroacetonato Tb0.01, Y0.99 triphenylphosphine oxide
tris thenoyltrifluoroacetonato Tb0.01, Y0.99 2,2-bipyridyl
tris thenoyltrifluoroacetonato Tb0.01, Y0.99 2,2-bipyridyl-N,N-dioxide
tris thenoyltrifluoroacetonato Tb0.01, Y0.99 phenanthroline
tris thenoyltrifluoroacetonato Tb0.01, Y0.99 bathocuproine
tris thenoyltrifluoroacetonato Tb0.01, Y0.99 bathophenanthroline
tris 2,2,6,6-tetramethylheptanedionato Tb0.01, Y0.99 dimethylaminopyridine
tris 2,2,6,6-tetramethylheptanedionato Tb0.01, Y0.99 4-picoline-N-oxide
tris 2,2,6,6-tetramethylheptanedionato Tb0.01, Y0.99 4-phenylpyridine
tris 2,2,6,6-tetramethylheptanedionato Tb0.01, Y0.99 4-cyanopyridine
tris 2,2,6,6-tetramethylheptanedionato Tb0.01, Y0.99 4-phenylpyridine-N-oxide
tris 2,2,6,6-tetramethylheptanedionato Tb0.01, Y0.99 1-methylimidazole
tris 2,2,6,6-tetramethylheptanedionato Tb0.01, Y0.99 triphenylphosphine oxide
tris 2,2,6,6-tetramethylheptanedionato Tb0.01, Y0.99 2,2-bipyridyl
tris 2,2,6,6-tetramethylheptanedionato Tb0.01, Y0.99 2,2-bipyridyl-N,N-dioxide
tris 2,2,6,6-tetramethylheptanedionato Tb0.01, Y0.99 phenanthroline
tris 2,2,6,6-tetramethylheptanedionato Tb0.01, Y0.99 bathocuproine
tris 2,2,6,6-tetramethylheptanedionato Tb0.01, Y0.99 bathophenanthroline
tris 3-methylpentane-2,4-dionato Tb0.01, Y0.99 dimethylaminopyridine
tris 3-methylpentane-2,4-dionato Tb0.01, Y0.99 4-picoline-N-oxide
tris 3-methylpentane-2,4-dionato Tb0.01, Y0.99 4-phenylpyridine
tris 3-methylpentane-2,4-dionato Tb0.01, Y0.99 4-cyanopyridine
tris 3-methylpentane-2,4-dionato Tb0.01, Y0.99 4-phenylpyridine-N-oxide
tris 3-methylpentane-2,4-dionato Tb0.01, Y0.99 1-methylimidazole
tris 3-methylpentane-2,4-dionato Tb0.01, Y0.99 triphenylphosphine oxide
tris 3-methylpentane-2,4-dionato Tb0.01, Y0.99 2,2-bipyridyl
tris 3-methylpentane-2,4-dionato Tb0.01, Y0.99 2,2-bipyridyl-N,N-dioxide
tris 3-methylpentane-2,4-dionato Tb0.01, Y0.99 phenanthroline
tris 3-methylpentane-2,4-dionato Tb0.01, Y0.99 bathocuproine
tris 3-methylpentane-2,4-dionato Tb0.01, Y0.99 bathophenanthroline
tris 3-ethylpentane-2,4-dionato Tb0.01, Y0.99 dimethylaminopyridine
tris 3-ethylpentane-2,4-dionato Tb0.01, Y0.99 4-picoline-N-oxide
tris 3-ethylpentane-2,4-dionato Tb0.01, Y0.99 4-phenylpyridine
tris 3-ethylpentane-2,4-dionato Tb0.01, Y0.99 4-cyanopyridine
tris 3-ethylpentane-2,4-dionato Tb0.01, Y0.99 4-phenylpyridine-N-oxide
tris 3-ethylpentane-2,4-dionato Tb0.01, Y0.99 1-methylimidazole
tris 3-ethylpentane-2,4-dionato Tb0.01, Y0.99 triphenylphosphine oxide
tris 3-ethylpentane-2,4-dionato Tb0.01, Y0.99 2,2-bipyridyl
tris 3-ethylpentane-2,4-dionato Tb0.01, Y0.99 2,2-bipyridyl-N,N-dioxide
tris 3-ethylpentane-2,4-dionato Tb0.01, Y0.99 phenanthroline
tris 3-ethylpentane-2,4-dionato Tb0.01, Y0.99 bathocuproine
tris 3-ethylpentane-2,4-dionato Tb0.01, Y0.99 bathophenanthroline
tris pivaloyltrifluoroacetonato Tb0.01, Y0.99 dimethylaminopyridine
tris pivaloyltrifluoroacetonato Tb0.01, Y0.99 4-picoline-N-oxide
tris pivaloyltrifluoroacetonato Tb0.01, Y0.99 4-phenylpyridine
tris pivaloyltrifluoroacetonato Tb0.01, Y0.99 4-cyanopyridine
tris pivaloyltrifluoroacetonato Tb0.01, Y0.99 4-phenylpyridine-N-oxide
tris pivaloyltrifluoroacetonato Tb0.01, Y0.99 1-methylimidazole
tris pivaloyltrifluoroacetonato Tb0.01, Y0.99 triphenylphosphine oxide
tris pivaloyltrifluoroacetonato Tb0.01, Y0.99 2,2-bipyridyl
tris pivaloyltrifluoroacetonato Tb0.01, Y0.99 2,2-bipyridyl-N,N-dioxide
tris pivaloyltrifluoroacetonato Tb0.01, Y0.99 phenanthroline
tris pivaloyltrifluoroacetonato Tb0.01, Y0.99 bathocuproine
tris pivaloyltrifluoroacetonato Tb0.01, Y0.99 bathophenanthroline
tris trifluoroacetylacetonato Tb0.01, Y0.99 dimethylaminopyridine
tris trifluoroacetylacetonato Tb0.01, Y0.99 4-picoline-N-oxide
tris trifluoroacetylacetonato Tb0.01, Y0.99 4-phenylpyridine
tris trifluoroacetylacetonato Tb0.01, Y0.99 4-cyanopyridine
tris trifluoroacetylacetonato Tb0.01, Y0.99 4-phenylpyridine-N-oxide tris trifluoroacetylacetonato Tb0.01, Y0.99 1-methylimidazole
tris trifluoroacetylacetonato Tb0.01, Y0.99 triphenylphosphine oxide
tris trifluoroacetylacetonato Tb0.01, Y0.99 2,2-bipyridyl
tris trifluoroacetylacetonato Tb0.01, Y0.99 2,2-bipyridyl-N,N-dioxide
tris trifluoroacetylacetonato Tb0.01, Y0.99 phenanthroline
tris trifluoroacetylacetonato Tb0.01, Y0.99 bathocuproine
tris trifluoroacetylacetonato Tb0.01, Y0.99 bathophenanthroline
tris hexafluoroacetylacetonato Tb0.01, Y0.99 dimethylaminopyridine
tris hexafluoroacetylacetonato Tb0.01, Y0.99 4-picoline-N-oxide
tris hexafluoroacetylacetonato Tb0.01, Y0.99 4-phenylpyridine
tris hexafluoroacetylacetonato Tb0.01, Y0.99 4-cyanopyridine
tris hexafluoroacetylacetonato Tb0.01, Y0.99 4-phenylpyridine-N-oxide
tris hexafluoroacetylacetonato Tb0.01, Y0.99 1-methylimidazole
tris hexafluoroacetylacetonato Tb0.01, Y0.99 triphenylphosphine oxide
tris hexafluoroacetylacetonato Tb0.01, Y0.99 2,2-bipyridyl
tris hexafluoroacetylacetonato Tb0.01, Y0.99 2,2-bipyridyl-N,N-dioxide
tris hexafluoroacetylacetonato Tb0.01, Y0.99 phenanthroline
tris hexafluoroacetylacetonato Tb0.01, Y0.99 bathocuproine
tris hexafluoroacetylacetonato Tb0.01, Y0.99 bathophenanthroline
tris 6,6,7,7,8,8,8-heptafluoro-2,2-dimethyloctanedionato Tb0.01, Y0.99 dimethylaminopyridine
tris 6,6,7,7,8,8,8-heptafluoro-2,2-dimethyloctanedionato Tb0.01, Y0.99 4-picoline-N-oxide
tris 6,6,7,7,8,8,8-heptafluoro-2,2-dimethyloctanedionato Tb0.01, Y0.99 4-phenylpyridine
tris 6,6,7,7,8,8,8-heptafluoro-2,2-dimethyloctanedionato Tb0.01, Y0.99 4-cyanopyridine
tris 6,6,7,7,8,8,8-heptafluoro-2,2-dimethyloctanedionato Tb0.01, Y0.99 4-phenylpyridine-N-oxide
tris 6,6,7,7,8,8,8-heptafluoro-2,2-dimethyloctanedionato Tb0.01, Y0.99 1-methylimidazole
tris 6,6,7,7,8,8,8-heptafluoro-2,2-dimethyloctanedionato Tb0.01, Y0.99 triphenylphosphine oxide
tris 6,6,7,7,8,8,8-heptafluoro-2,2-dimethyloctanedionato Tb0.01, Y0.99 2,2-bipyridyl
tris 6,6,7,7,8,8,8-heptafluoro-2,2-dimethyloctanedionato Tb0.01, Y0.99 2,2-bipyridyl-N,N-dioxide
tris 6,6,7,7,8,8,8-heptafluoro-2,2-dimethyloctanedionato Tb0.01, Y0.99 phenanthroline
tris 6,6,7,7,8,8,8-heptafluoro-2,2-dimethyloctanedionato Tb0.01, Y0.99 bathocuproine
tris 6,6,7,7,8,8,8-heptafluoro-2,2-dimethyloctanedionato Tb0.01, Y0.99 bathophenanthroline
tris 1-phenyl-1,3-butanedionato Tb0.01, Y0.99 dimethylaminopyridine
tris 1-phenyl-1,3-butanedionato Tb0.01, Y0.99 4-picoline-N-oxide
tris 1-phenyl-1,3-butanedionato Tb0.01, Y0.99 4-phenylpyridine
tris 1-phenyl-1,3-butanedionato Tb0.01, Y0.99 4-cyanopyridine
tris 1-phenyl-1,3-butanedionato Tb0.01, Y0.99 4-phenylpyridine-N-oxide
tris 1-phenyl-1,3-butanedionato Tb0.01, Y0.99 1-methylimidazole
tris 1-phenyl-1,3-butanedionato Tb0.01, Y0.99 triphenylphosphine oxide
tris 1-phenyl-1,3-butanedionato Tb0.01, Y0.99 2,2-bipyridyl
tris 1-phenyl-1,3-butanedionato Tb0.01, Y0.99 2,2-bipyridyl-N,N-dioxide
tris 1-phenyl-1,3-butanedionato Tb0.01, Y0.99 phenanthroline
tris 1-phenyl-1,3-butanedionato Tb0.01, Y0.99 bathocuproine
tris 1-phenyl-1,3-butanedionato Tb0.01, Y0.99 bathophenanthroline
tris acetylacetonato Eu0.5, Y0.5 dimethylaminopyridine
tris acetylacetonato Eu0.5, Y0.5 4-picoline-N-oxide
tris acetylacetonato Eu0.5, Y0.5 4-phenylpyridine
tris acetylacetonato Eu0.5, Y0.5 4-cyanopyridine
tris acetylacetonato Eu0.5, Y0.5 4-phenylpyridine-N-oxide
tris acetylacetonato Eu0.5, Y0.5 1-methylimidazole
tris acetylacetonato Eu0.5, Y0.5 triphenylphosphine oxide
tris acetylacetonato Eu0.5, Y0.5 2,2-bipyridyl
tris acetylacetonato Eu0.5, Y0.5 2,2-bipyridyl-N,N-dioxide
tris acetylacetonato Eu0.5, Y0.5 phenanthroline
tris acetylacetonato Eu0.5, Y0.5 bathocuproine
tris acetylacetonato Eu0.5, Y0.5 bathophenanthroline
tris dibenzoylmethanato Eu0.5, Y0.5 dimethylaminopyridine
tris dibenzoylmethanato Eu0.5, Y0.5 4-picoline-N-oxide
tris dibenzoylmethanato Eu0.5, Y0.5 4-phenylpyridine
tris dibenzoylmethanato Eu0.5, Y0.5 4-cyanopyridine
tris dibenzoylmethanato Eu0.5, Y0.5 4-phenylpyridine-N-oxide
tris dibenzoylmethanato Eu0.5, Y0.5 1-methylimidazole
tris dibenzoylmethanato Eu0.5, Y0.5 triphenylphosphine oxide
tris dibenzoylmethanato Eu0.5, Y0.5 2,2-bipyridyl
tris dibenzoylmethanato Eu0.5, Y0.5 2,2-bipyridyl-N,N-dioxide
tris dibenzoylmethanato Eu0.5, Y0.5 phenanthroline
tris dibenzoylmethanato Eu0.5, Y0.5 bathocuproine
tris dibenzoylmethanato Eu0.5, Y0.5 bathophenanthroline
tris thenoyltrifluoroacetonato Eu0.5, Y0.5 dimethylaminopyridine
tris thenoyltrifluoroacetonato Eu0.5, Y0.5 4-picoline-N-oxide
tris thenoyltrifluoroacetonato Eu0.5, Y0.5 4-phenylpyridine
tris thenoyltrifluoroacetonato Eu0.5, Y0.5 4-cyanopyridine
tris thenoyltrifluoroacetonato Eu0.5, Y0.5 4-phenylpyridine-N-oxide
tris thenoyltrifluoroacetonato Eu0.5, Y0.5 1-methylimidazole
tris thenoyltrifluoroacetonato Eu0.5, Y0.5 triphenylphosphine oxide
tris thenoyltrifluoroacetonato Eu0.5, Y0.5 2,2-bipyridyl
tris thenoyltrifluoroacetonato Eu0.5, Y0.5 2,2-bipyridyl-N,N-dioxide
tris thenoyltrifluoroacetonato Eu0.5, Y0.5 phenanthroline
tris thenoyltrifluoroacetonato Eu0.5, Y0.5 bathocuproine
tris thenoyltrifluoroacetonato Eu0.5, Y0.5 bathophenanthroline
tris 2,2,6,6-tetramethylheptanedionato Eu0.5, Y0.5 dimethylaminopyridine
tris 2,2,6,6-tetramethylheptanedionato Eu0.5, Y0.5 4-picoline-N-oxide
tris 2,2,6,6-tetramethylheptanedionato Eu0.5, Y0.5 4-phenylpyridine tris 2,2,6,6-tetramethylheptanedionato Eu0.5, Y0.5 4-cyanopyridine
tris 2,2,6,6-tetramethylheptanedionato Eu0.5, Y0.5 4-phenylpyridine-N-oxide
tris 2,2,6,6-tetramethylheptanedionato Eu0.5, Y0.5 1-methylimidazole
tris 2,2,6,6-tetramethylheptanedionato Eu0.5, Y0.5 triphenylphosphine oxide
tris 2,2,6,6-tetramethylheptanedionato Eu0.5, Y0.5 2,2-bipyridyl
tris 2,2,6,6-tetramethylheptanedionato Eu0.5, Y0.5 2,2-bipyridyl-N,N-dioxide
tris 2,2,6,6-tetramethylheptanedionato Eu0.5, Y0.5 phenanthroline
tris 2,2,6,6-tetramethylheptanedionato Eu0.5, Y0.5 bathocuproine
tris 2,2,6,6-tetramethylheptanedionato Eu0.5, Y0.5 bathophenanthroline
tris 3-methylpentane-2,4-dionato Eu0.5, Y0.5 dimethylaminopyridine
tris 3-methylpentane-2,4-dionato Eu0.5, Y0.5 4-picoline-N-oxide
tris 3-methylpentane-2,4-dionato Eu0.5, Y0.5 4-phenylpyridine
tris 3-methylpentane-2,4-dionato Eu0.5, Y0.5 4-cyanopyridine
tris 3-methylpentane-2,4-dionato Eu0.5, Y0.5 4-phenylpyridine-N-oxide
tris 3-methylpentane-2,4-dionato Eu0.5, Y0.5 1-methylimidazole
tris 3-methylpentane-2,4-dionato Eu0.5, Y0.5 triphenylphosphine oxide
tris 3-methylpentane-2,4-dionato Eu0.5, Y0.5 2,2-bipyridyl
tris 3-methylpentane-2,4-dionato Eu0.5, Y0.5 2,2-bipyridyl-N,N-dioxide
tris 3-methylpentane-2,4-dionato Eu0.5, Y0.5 phenanthroline
tris 3-methylpentane-2,4-dionato Eu0.5, Y0.5 bathocuproine
tris 3-methylpentane-2,4-dionato Eu0.5, Y0.5 bathophenanthroline
tris 3-ethylpentane-2,4-dionato Eu0.5, Y0.5 dimethylaminopyridine
tris 3-ethylpentane-2,4-dionato Eu0.5, Y0.5 4-picoline-N-oxide
tris 3-ethylpentane-2,4-dionato Eu0.5, Y0.5 4-phenylpyridine
tris 3-ethylpentane-2,4-dionato Eu0.5, Y0.5 4-cyanopyridine
tris 3-ethylpentane-2,4-dionato Eu0.5, Y0.5 4-phenylpyridine-N-oxide
tris 3-ethylpentane-2,4-dionato Eu0.5, Y0.5 1-methylimidazole
tris 3-ethylpentane-2,4-dionato Eu0.5, Y0.5 triphenylphosphine oxide
tris 3-ethylpentane-2,4-dionato Eu0.5, Y0.5 2,2-bipyridyl
tris 3-ethylpentane-2,4-dionato Eu0.5, Y0.5 2,2-bipyridyl-N,N-dioxide
tris 3-ethylpentane-2,4-dionato Eu0.5, Y0.5 phenanthroline
tris 3-ethylpentane-2,4-dionato Eu0.5, Y0.5 bathocuproine
tris 3-ethylpentane-2,4-dionato Eu0.5, Y0.5 bathophenanthroline
tris pivaloyltrifluoroacetonato Eu0.5, Y0.5 dimethylaminopyridine
tris pivaloyltrifluoroacetonato Eu0.5, Y0.5 4-picoline-N-oxide
tris pivaloyltrifluoroacetonato Eu0.5, Y0.5 4-phenylpyridine
tris pivaloyltrifluoroacetonato Eu0.5, Y0.5 4-cyanopyridine
tris pivaloyltrifluoroacetonato Eu0.5, Y0.5 4-phenylpyridine-N-oxide
tris pivaloyltrifluoroacetonato Eu0.5, Y0.5 1-methylimidazole
tris pivaloyltrifluoroacetonato Eu0.5, Y0.5 triphenylphosphine oxide
tris pivaloyltrifluoroacetonato Eu0.5, Y0.5 2,2-bipyridyl
tris pivaloyltrifluoroacetonato Eu0.5, Y0.5 2,2-bipyridyl-N,N-dioxide
tris pivaloyltrifluoroacetonato Eu0.5, Y0.5 phenanthroline
tris pivaloyltrifluoroacetonato Eu0.5, Y0.5 bathocuproine
tris pivaloyltrifluoroacetonato Eu0.5, Y0.5 bathophenanthroline
tris trifluoroacetylacetonato Eu0.5, Y0.5 dimethylaminopyridine
tris trifluoroacetylacetonato Eu0.5, Y0.5 4-picoline-N-oxide
tris trifluoroacetylacetonato Eu0.5, Y0.5 4-phenylpyridine
tris trifluoroacetylacetonato Eu0.5, Y0.5 4-cyanopyridine
tris trifluoroacetylacetonato Eu0.5, Y0.5 4-phenylpyridine-N-oxide
tris trifluoroacetylacetonato Eu0.5, Y0.5 1-methylimidazole
tris trifluoroacetylacetonato Eu0.5, Y0.5 triphenylphosphine oxide
tris trifluoroacetylacetonato Eu0.5, Y0.5 2,2-bipyridyl
tris trifluoroacetylacetonato Eu0.5, Y0.5 2,2-bipyridyl-N,N-dioxide
tris trifluoroacetylacetonato Eu0.5, Y0.5 phenanthroline
tris trifluoroacetylacetonato Eu0.5, Y0.5 bathocuproine
tris trifluoroacetylacetonato Eu0.5, Y0.5 bathophenanthroline
tris hexafluoroacetylacetonato Eu0.5, Y0.5 dimethylaminopyridine
tris hexafluoroacetylacetonato Eu0.5, Y0.5 4-picoline-N-oxide
tris hexafluoroacetylacetonato Eu0.5, Y0.5 4-phenylpyridine
tris hexafluoroacetylacetonato Eu0.5, Y0.5 4-cyanopyridine
tris hexafluoroacetylacetonato Eu0.5, Y0.5 4-phenylpyridine-N-oxide
tris hexafluoroacetylacetonato Eu0.5, Y0.5 1-methylimidazole
tris hexafluoroacetylacetonato Eu0.5, Y0.5 triphenylphosphine oxide
tris hexafluoroacetylacetonato Eu0.5, Y0.5 2,2-bipyridyl
tris hexafluoroacetylacetonato Eu0.5, Y0.5 2,2-bipyridyl-N,N-dioxide
tris hexafluoroacetylacetonato Eu0.5, Y0.5 phenanthroline
tris hexafluoroacetylacetonato Eu0.5, Y0.5 bathocuproine
tris hexafluoroacetylacetonato Eu0.5, Y0.5 bathophenanthroline
tris 6,6,7,7,8,8,8-heptafluoro-2,2-dimethyloctanedionato Eu0.5, Y0.5 dimethylaminopyridine
tris 6,6,7,7,8,8,8-heptafluoro-2,2-dimethyloctanedionato Eu0.5, Y0.5 4-picoline-N-oxide
tris 6,6,7,7,8,8,8-heptafluoro-2,2-dimethyloctanedionato Eu0.5, Y0.5 4-phenylpyridine
tris 6,6,7,7,8,8,8-heptafluoro-2,2-dimethyloctanedionato Eu0.5, Y0.5 4-cyanopyridine
tris 6,6,7,7,8,8,8-heptafluoro-2,2-dimethyloctanedionato Eu0.5, Y0.5 4-phenylpyridine-N-oxide
tris 6,6,7,7,8,8,8-heptafluoro-2,2-dimethyloctanedionato Eu0.5, Y0.5 1-methylimidazole
tris 6,6,7,7,8,8,8-heptafluoro-2,2-dimethyloctanedionato Eu0.5, Y0.5 triphenylphosphine oxide
tris 6,6,7,7,8,8,8-heptafluoro-2,2-dimethyloctanedionato Eu0.5, Y0.5 2,2-bipyridyl tris 6,6,7,7,8,8,8-heptafluoro-2,2-dimethyloctanedionato Eu0.5, Y0.5 2,2-bipyridyl-N,N-dioxide
tris 6,6,7,7,8,8,8-heptafluoro-2,2-dimethyloctanedionato Eu0.5, Y0.5 phenanthroline
tris 6,6,7,7,8,8,8-heptafluoro-2,2-dimethyloctanedionato Eu0.5, Y0.5 bathocuproine
tris 6,6,7,7,8,8,8-heptafluoro-2,2-dimethyloctanedionato Eu0.5, Y0.5 bathophenanthroline
tris 1-phenyl-1,3-butanedionato Eu0.5, Y0.5 dimethylaminopyridine
tris 1-phenyl-1,3-butanedionato Eu0.5, Y0.5 4-picoline-N-oxide
tris 1-phenyl-1,3-butanedionato Eu0.5, Y0.5 4-phenylpyridine
tris 1-phenyl-1,3-butanedionato Eu0.5, Y0.5 4-cyanopyridine
tris 1-phenyl-1,3-butanedionato Eu0.5, Y0.5 4-phenylpyridine-N-oxide
tris 1-phenyl-1,3-butanedionato Eu0.5, Y0.5 1-methylimidazole
tris 1-phenyl-1,3-butanedionato Eu0.5, Y0.5 triphenylphosphine oxide
tris 1-phenyl-1,3-butanedionato Eu0.5, Y0.5 2,2-bipyridyl
tris 1-phenyl-1,3-butanedionato Eu0.5, Y0.5 2,2-bipyridyl-N,N-dioxide
tris 1-phenyl-1,3-butanedionato Eu0.5, Y0.5 phenanthroline
tris 1-phenyl-1,3-butanedionato Eu0.5, Y0.5 bathocuproine
tris 1-phenyl-1,3-butanedionato Eu0.5, Y0.5 bathophenanthroline
tris acetylacetonato Eu0.2, Y0.8 dimethylaminopyridine
tris acetylacetonato Eu0.2, Y0.8 4-picoline-N-oxide
tris acetylacetonato Eu0.2, Y0.8 4-phenylpyridine
tris acetylacetonato Eu0.2, Y0.8 4-cyanopyridine
tris acetylacetonato Eu0.2, Y0.8 4-phenylpyridine-N-oxide
tris acetylacetonato Eu0.2, Y0.8 1-methylimidazole
tris acetylacetonato Eu0.2, Y0.8 triphenylphosphine oxide
tris acetylacetonato Eu0.2, Y0.8 2,2-bipyridyl
tris acetylacetonato Eu0.2, Y0.8 2,2-bipyridyl-N,N-dioxide
tris acetylacetonato Eu0.2, Y0.8 phenanthroline
tris acetylacetonato Eu0.2, Y0.8 bathocuproine
tris acetylacetonato Eu0.2, Y0.8 bathophenanthroline
tris dibenzoylmethanato Eu0.2, Y0.8 dimethylaminopyridine
tris dibenzoylmethanato Eu0.2, Y0.8 4-picoline-N-oxide
tris dibenzoylmethanato Eu0.2, Y0.8 4-phenylpyridine
tris dibenzoylmethanato Eu0.2, Y0.8 4-cyanopyridine
tris dibenzoylmethanato Eu0.2, Y0.8 4-phenylpyridine-N-oxide
tris dibenzoylmethanato Eu0.2, Y0.8 1-methylimidazole
tris dibenzoylmethanato Eu0.2, Y0.8 triphenylphosphine oxide
tris dibenzoylmethanato Eu0.2, Y0.8 2,2-bipyridyl
tris dibenzoylmethanato Eu0.2, Y0.8 2,2-bipyridyl-N,N-dioxide
tris dibenzoylmethanato Eu0.2, Y0.8 phenanthroline
tris dibenzoylmethanato Eu0.2, Y0.8 bathocuproine
tris dibenzoylmethanato Eu0.2, Y0.8 bathophenanthroline
tris thenoyltrifluoroacetonato Eu0.2, Y0.8 dimethylaminopyridine
tris thenoyltrifluoroacetonato Eu0.2, Y0.8 4-picoline-N-oxide
tris thenoyltrifluoroacetonato Eu0.2, Y0.8 4-phenylpyridine
tris thenoyltrifluoroacetonato Eu0.2, Y0.8 4-cyanopyridine
tris thenoyltrifluoroacetonato Eu0.2, Y0.8 4-phenylpyridine-N-oxide
tris thenoyltrifluoroacetonato Eu0.2, Y0.8 1-methylimidazole
tris thenoyltrifluoroacetonato Eu0.2, Y0.8 triphenylphosphine oxide
tris thenoyltrifluoroacetonato Eu0.2, Y0.8 2,2-bipyridyl
tris thenoyltrifluoroacetonato Eu0.2, Y0.8 2,2-bipyridyl-N,N-dioxide
tris thenoyltrifluoroacetonato Eu0.2, Y0.8 phenanthroline
tris thenoyltrifluoroacetonato Eu0.2, Y0.8 bathocuproine
tris thenoyltrifluoroacetonato Eu0.2, Y0.8 bathophenanthroline
tris 2,2,6,6-tetramethylheptanedionato Eu0.2, Y0.8 dimethylaminopyridine
tris 2,2,6,6-tetramethylheptanedionato Eu0.2, Y0.8 4-picoline-N-oxide
tris 2,2,6,6-tetramethylheptanedionato Eu0.2, Y0.8 4-phenylpyridine
tris 2,2,6,6-tetramethylheptanedionato Eu0.2, Y0.8 4-cyanopyridine
tris 2,2,6,6-tetramethylheptanedionato Eu0.2, Y0.8 4-phenylpyridine-N-oxide
tris 2,2,6,6-tetramethylheptanedionato Eu0.2, Y0.8 1-methylimidazole
tris 2,2,6,6-tetramethylheptanedionato Eu0.2, Y0.8 triphenylphosphine oxide
tris 2,2,6,6-tetramethylheptanedionato Eu0.2, Y0.8 2,2-bipyridyl
tris 2,2,6,6-tetramethylheptanedionato Eu0.2, Y0.8 2,2-bipyridyl-N,N-dioxide
tris 2,2,6,6-tetramethylheptanedionato Eu0.2, Y0.8 phenanthroline
tris 2,2,6,6-tetramethylheptanedionato Eu0.2, Y0.8 bathocuproine
tris 2,2,6,6-tetramethylheptanedionato Eu0.2, Y0.8 bathophenanthroline
tris 3-methylpentane-2,4-dionato Eu0.2, Y0.8 dimethylaminopyridine
tris 3-methylpentane-2,4-dionato Eu0.2, Y0.8 4-picoline-N-oxide
tris 3-methylpentane-2,4-dionato Eu0.2, Y0.8 4-phenylpyridine
tris 3-methylpentane-2,4-dionato Eu0.2, Y0.8 4-cyanopyridine
tris 3-methylpentane-2,4-dionato Eu0.2, Y0.8 4-phenylpyridine-N-oxide
tris 3-methylpentane-2,4-dionato Eu0.2, Y0.8 1-methylimidazole
tris 3-methylpentane-2,4-dionato Eu0.2, Y0.8 triphenylphosphine oxide
tris 3-methylpentane-2,4-dionato Eu0.2, Y0.8 2,2-bipyridyl
tris 3-methylpentane-2,4-dionato Eu0.2, Y0.8 2,2-bipyridyl-N,N-dioxide
tris 3-methylpentane-2,4-dionato Eu0.2, Y0.8 phenanthroline
tris 3-methylpentane-2,4-dionato Eu0.2, Y0.8 bathocuproine
tris 3-methylpentane-2,4-dionato Eu0.2, Y0.8 bathophenanthroline
tris 3-ethylpentane-2,4-dionato Eu0.2, Y0.8 dimethylaminopyridine
tris 3-ethylpentane-2,4-dionato Eu0.2, Y0.8 4-picoline-N-oxide
tris 3-ethylpentane-2,4-dionato Eu0.2, Y0.8 4-phenylpyridine
tris 3-ethylpentane-2,4-dionato Eu0.2, Y0.8 4-cyanopyridine
tris 3-ethylpentane-2,4-dionato Eu0.2, Y0.8 4-phenylpyridine-N-oxide
tris 3-ethylpentane-2,4-dionato Eu0.2, Y0.8 1-methylimidazole tris 3-ethylpentane-2,4-dionato Eu0.2, Y0.8 triphenylphosphine oxide
tris 3-ethylpentane-2,4-dionato Eu0.2, Y0.8 2,2-bipyridyl
tris 3-ethylpentane-2,4-dionato Eu0.2, Y0.8 2,2-bipyridyl-N,N-dioxide
tris 3-ethylpentane-2,4-dionato Eu0.2, Y0.8 phenanthroline
tris 3-ethylpentane-2,4-dionato Eu0.2, Y0.8 bathocuproine
tris 3-ethylpentane-2,4-dionato Eu0.2, Y0.8 bathophenanthroline
tris pivaloyltrifluoroacetonato Eu0.2, Y0.8 dimethylaminopyridine
tris pivaloyltrifluoroacetonato Eu0.2, Y0.8 4-picoline-N-oxide
tris pivaloyltrifluoroacetonato Eu0.2, Y0.8 4-phenylpyridine
tris pivaloyltrifluoroacetonato Eu0.2, Y0.8 4-cyanopyridine
tris pivaloyltrifluoroacetonato Eu0.2, Y0.8 4-phenylpyridine-N-oxide
tris pivaloyltrifluoroacetonato Eu0.2, Y0.8 1-methylimidazole
tris pivaloyltrifluoroacetonato Eu0.2, Y0.8 triphenylphosphine oxide
tris pivaloyltrifluoroacetonato Eu0.2, Y0.8 2,2-bipyridyl
tris pivaloyltrifluoroacetonato Eu0.2, Y0.8 2,2-bipyridyl-N,N-dioxide
tris pivaloyltrifluoroacetonato Eu0.2, Y0.8 phenanthroline
tris pivaloyltrifluoroacetonato Eu0.2, Y0.8 bathocuproine
tris pivaloyltrifluoroacetonato Eu0.2, Y0.8 bathophenanthroline
tris trifluoroacetylacetonato Eu0.2, Y0.8 dimethylaminopyridine
tris trifluoroacetylacetonato Eu0.2, Y0.8 4-picoline-N-oxide
tris trifluoroacetylacetonato Eu0.2, Y0.8 4-phenylpyridine
tris trifluoroacetylacetonato Eu0.2, Y0.8 4-cyanopyridine
tris trifluoroacetylacetonato Eu0.2, Y0.8 4-phenylpyridine-N-oxide
tris trifluoroacetylacetonato Eu0.2, Y0.8 1-methylimidazole
tris trifluoroacetylacetonato Eu0.2, Y0.8 triphenylphosphine oxide
tris trifluoroacetylacetonato Eu0.2, Y0.8 2,2-bipyridyl
tris trifluoroacetylacetonato Eu0.2, Y0.8 2,2-bipyridyl-N,N-dioxide
tris trifluoroacetylacetonato Eu0.2, Y0.8 phenanthroline
tris trifluoroacetylacetonato Eu0.2, Y0.8 bathocuproine
tris trifluoroacetylacetonato Eu0.2, Y0.8 bathophenanthroline
tris hexafluoroacetylacetonato Eu0.2, Y0.8 dimethylaminopyridine
tris hexafluoroacetylacetonato Eu0.2, Y0.8 4-picoline-N-oxide
tris hexafluoroacetylacetonato Eu0.2, Y0.8 4-phenylpyridine
tris hexafluoroacetylacetonato Eu0.2, Y0.8 4-cyanopyridine
tris hexafluoroacetylacetonato Eu0.2, Y0.8 4-phenylpyridine-N-oxide
tris hexafluoroacetylacetonato Eu0.2, Y0.8 1-methylimidazole
tris hexafluoroacetylacetonato Eu0.2, Y0.8 triphenylphosphine oxide
tris hexafluoroacetylacetonato Eu0.2, Y0.8 2,2-bipyridyl
tris hexafluoroacetylacetonato Eu0.2, Y0.8 2,2-bipyridyl-N,N-dioxide
tris hexafluoroacetylacetonato Eu0.2, Y0.8 phenanthroline
tris hexafluoroacetylacetonato Eu0.2, Y0.8 bathocuproine
tris hexafluoroacetylacetonato Eu0.2, Y0.8 bathophenanthroline
tris 6,6,7,7,8,8,8-heptafluoro-2,2-dimethyloctanedionato Eu0.2, Y0.8 dimethylaminopyridine
tris 6,6,7,7,8,8,8-heptafluoro-2,2-dimethyloctanedionato Eu0.2, Y0.8 4-picoline-N-oxide
tris 6,6,7,7,8,8,8-heptafluoro-2,2-dimethyloctanedionato Eu0.2, Y0.8 4-phenylpyridine
tris 6,6,7,7,8,8,8-heptafluoro-2,2-dimethyloctanedionato Eu0.2, Y0.8 4-cyanopyridine
tris 6,6,7,7,8,8,8-heptafluoro-2,2-dimethyloctanedionato Eu0.2, Y0.8 4-phenylpyridine-N-oxide
tris 6,6,7,7,8,8,8-heptafluoro-2,2-dimethyloctanedionato Eu0.2, Y0.8 1-methylimidazole
tris 6,6,7,7,8,8,8-heptafluoro-2,2-dimethyloctanedionato Eu0.2, Y0.8 triphenylphosphine oxide
tris 6,6,7,7,8,8,8-heptafluoro-2,2-dimethyloctanedionato Eu0.2, Y0.8 2,2-bipyridyl
tris 6,6,7,7,8,8,8-heptafluoro-2,2-dimethyloctanedionato Eu0.2, Y0.8 2,2-bipyridyl-N,N-dioxide
tris 6,6,7,7,8,8,8-heptafluoro-2,2-dimethyloctanedionato Eu0.2, Y0.8 phenanthroline
tris 6,6,7,7,8,8,8-heptafluoro-2,2-dimethyloctanedionato Eu0.2, Y0.8 bathocuproine
tris 6,6,7,7,8,8,8-heptafluoro-2,2-dimethyloctanedionato Eu0.2, Y0.8 bathophenanthroline
tris 1-phenyl-1,3-butanedionato Eu0.2, Y0.8 dimethylaminopyridine
tris 1-phenyl-1,3-butanedionato Eu0.2, Y0.8 4-picoline-N-oxide
tris 1-phenyl-1,3-butanedionato Eu0.2, Y0.8 4-phenylpyridine
tris 1-phenyl-1,3-butanedionato Eu0.2, Y0.8 4-cyanopyridine
tris 1-phenyl-1,3-butanedionato Eu0.2, Y0.8 4-phenylpyridine-N-oxide
tris 1-phenyl-1,3-butanedionato Eu0.2, Y0.8 1-methylimidazole
tris 1-phenyl-1,3-butanedionato Eu0.2, Y0.8 triphenylphosphine oxide
tris 1-phenyl-1,3-butanedionato Eu0.2, Y0.8 2,2-bipyridyl
tris 1-phenyl-1,3-butanedionato Eu0.2, Y0.8 2,2-bipyridyl-N,N-dioxide
tris 1-phenyl-1,3-butanedionato Eu0.2, Y0.8 phenanthroline
tris 1-phenyl-1,3-butanedionato Eu0.2, Y0.8 bathocuproine
tris 1-phenyl-1,3-butanedionato Eu0.2, Y0.8 bathophenanthroline
tris acetylacetonato Eu0.1, Y0.9 dimethylaminopyridine
tris acetylacetonato Eu0.1, Y0.9 4-picoline-N-oxide
tris acetylacetonato Eu0.1, Y0.9 4-phenylpyridine
tris acetylacetonato Eu0.1, Y0.9 4-cyanopyridine
tris acetylacetonato Eu0.1, Y0.9 4-phenylpyridine-N-oxide
tris acetylacetonato Eu0.1, Y0.9 1-methylimidazole
tris acetylacetonato Eu0.1, Y0.9 triphenylphosphine oxide
tris acetylacetonato Eu0.1, Y0.9 2,2-bipyridyl
tris acetylacetonato Eu0.1, Y0.9 2,2-bipyridyl-N,N-dioxide
tris acetylacetonato Eu0.1, Y0.9 phenanthroline
tris acetylacetonato Eu0.1, Y0.9 bathocuproine
tris acetylacetonato Eu0.1, Y0.9 bathophenanthroline
tris dibenzoylmethanato Eu0.1, Y0.9 dimethylaminopyridine
tris dibenzoylmethanato Eu0.1, Y0.9 4-picoline-N-oxide
tris dibenzoylmethanato Eu0.1, Y0.9 4-phenylpyridine
tris dibenzoylmethanato Eu0.1, Y0.9 4-cyanopyridine
tris dibenzoylmethanato Eu0.1, Y0.9 4-phenylpyridine-N-oxide
tris dibenzoylmethanato Eu0.1, Y0.9 1-methylimidazole
tris dibenzoylmethanato Eu0.1, Y0.9 triphenylphosphine oxide
tris dibenzoylmethanato Eu0.1, Y0.9 2,2-bipyridyl tris dibenzoylmethanato Eu0.1, Y0.9 2,2-bipyridyl-N,N-dioxide
tris dibenzoylmethanato Eu0.1, Y0.9 phenanthroline
tris dibenzoylmethanato Eu0.1, Y0.9 bathocuproine
tris dibenzoylmethanato Eu0.1, Y0.9 bathophenanthroline
tris thenoyltrifluoroacetonato Eu0.1, Y0.9 dimethylaminopyridine
tris thenoyltrifluoroacetonato Eu0.1, Y0.9 4-picoline-N-oxide
tris thenoyltrifluoroacetonato Eu0.1, Y0.9 4-phenylpyridine
tris thenoyltrifluoroacetonato Eu0.1, Y0.9 4-cyanopyridine
tris thenoyltrifluoroacetonato Eu0.1, Y0.9 4-phenylpyridine-N-oxide
tris thenoyltrifluoroacetonato Eu0.1, Y0.9 1-methylimidazole
tris thenoyltrifluoroacetonato Eu0.1, Y0.9 triphenylphosphine oxide
tris thenoyltrifluoroacetonato Eu0.1, Y0.9 2,2-bipyridyl
tris thenoyltrifluoroacetonato Eu0.1, Y0.9 2,2-bipyridyl-N,N-dioxide
tris thenoyltrifluoroacetonato Eu0.1, Y0.9 phenanthroline
tris thenoyltrifluoroacetonato Eu0.1, Y0.9 bathocuproine
tris thenoyltrifluoroacetonato Eu0.1, Y0.9 bathophenanthroline
tris 2,2,6,6-tetramethylheptanedionato Eu0.1, Y0.9 dimethylaminopyridine
tris 2,2,6,6-tetramethylheptanedionato Eu0.1, Y0.9 4-picoline-N-oxide
tris 2,2,6,6-tetramethylheptanedionato Eu0.1, Y0.9 4-phenylpyridine
tris 2,2,6,6-tetramethylheptanedionato Eu0.1, Y0.9 4-cyanopyridine
tris 2,2,6,6-tetramethylheptanedionato Eu0.1, Y0.9 4-phenylpyridine-N-oxide
tris 2,2,6,6-tetramethylheptanedionato Eu0.1, Y0.9 1-methylimidazole
tris 2,2,6,6-tetramethylheptanedionato Eu0.1, Y0.9 triphenylphosphine oxide
tris 2,2,6,6-tetramethylheptanedionato Eu0.1, Y0.9 2,2-bipyridyl
tris 2,2,6,6-tetramethylheptanedionato Eu0.1, Y0.9 2,2-bipyridyl-N,N-dioxide
tris 2,2,6,6-tetramethylheptanedionato Eu0.1, Y0.9 phenanthroline
tris 2,2,6,6-tetramethylheptanedionato Eu0.1, Y0.9 bathocuproine
tris 2,2,6,6-tetramethylheptanedionato Eu0.1, Y0.9 bathophenanthroline
tris 3-methylpentane-2,4-dionato Eu0.1, Y0.9 dimethylaminopyridine
tris 3-methylpentane-2,4-dionato Eu0.1, Y0.9 4-picoline-N-oxide
tris 3-methylpentane-2,4-dionato Eu0.1, Y0.9 4-phenylpyridine
tris 3-methylpentane-2,4-dionato Eu0.1, Y0.9 4-cyanopyridine
tris 3-methylpentane-2,4-dionato Eu0.1, Y0.9 4-phenylpyridine-N-oxide
tris 3-methylpentane-2,4-dionato Eu0.1, Y0.9 1-methylimidazole
tris 3-methylpentane-2,4-dionato Eu0.1, Y0.9 triphenylphosphine oxide
tris 3-methylpentane-2,4-dionato Eu0.1, Y0.9 2,2-bipyridyl
tris 3-methylpentane-2,4-dionato Eu0.1, Y0.9 2,2-bipyridyl-N,N-dioxide
tris 3-methylpentane-2,4-dionato Eu0.1, Y0.9 phenanthroline
tris 3-methylpentane-2,4-dionato Eu0.1, Y0.9 bathocuproine
tris 3-methylpentane-2,4-dionato Eu0.1, Y0.9 bathophenanthroline
tris 3-ethylpentane-2,4-dionato Eu0.1, Y0.9 dimethylaminopyridine
tris 3-ethylpentane-2,4-dionato Eu0.1, Y0.9 4-picoline-N-oxide
tris 3-ethylpentane-2,4-dionato Eu0.1, Y0.9 4-phenylpyridine
tris 3-ethylpentane-2,4-dionato Eu0.1, Y0.9 4-cyanopyridine
tris 3-ethylpentane-2,4-dionato Eu0.1, Y0.9 4-phenylpyridine-N-oxide
tris 3-ethylpentane-2,4-dionato Eu0.1, Y0.9 1-methylimidazole
tris 3-ethylpentane-2,4-dionato Eu0.1, Y0.9 triphenylphosphine oxide
tris 3-ethylpentane-2,4-dionato Eu0.1, Y0.9 2,2-bipyridyl
tris 3-ethylpentane-2,4-dionato Eu0.1, Y0.9 2,2-bipyridyl-N,N-dioxide
tris 3-ethylpentane-2,4-dionato Eu0.1, Y0.9 phenanthroline
tris 3-ethylpentane-2,4-dionato Eu0.1, Y0.9 bathocuproine
tris 3-ethylpentane-2,4-dionato Eu0.1, Y0.9 bathophenanthroline
tris pivaloyltrifluoroacetonato Eu0.1, Y0.9 dimethylaminopyridine
tris pivaloyltrifluoroacetonato Eu0.1, Y0.9 4-picoline-N-oxide
tris pivaloyltrifluoroacetonato Eu0.1, Y0.9 4-phenylpyridine
tris pivaloyltrifluoroacetonato Eu0.1, Y0.9 4-cyanopyridine
tris pivaloyltrifluoroacetonato Eu0.1, Y0.9 4-phenylpyridine-N-oxide
tris pivaloyltrifluoroacetonato Eu0.1, Y0.9 1-methylimidazole
tris pivaloyltrifluoroacetonato Eu0.1, Y0.9 triphenylphosphine oxide
tris pivaloyltrifluoroacetonato Eu0.1, Y0.9 2,2-bipyridyl
tris pivaloyltrifluoroacetonato Eu0.1, Y0.9 2,2-bipyridyl-N,N-dioxide
tris pivaloyltrifluoroacetonato Eu0.1, Y0.9 phenanthroline
tris pivaloyltrifluoroacetonato Eu0.1, Y0.9 bathocuproine
tris pivaloyltrifluoroacetonato Eu0.1, Y0.9 bathophenanthroline
tris trifluoroacetylacetonato Eu0.1, Y0.9 dimethylaminopyridine
tris trifluoroacetylacetonato Eu0.1, Y0.9 4-picoline-N-oxide
tris trifluoroacetylacetonato Eu0.1, Y0.9 4-phenylpyridine
tris trifluoroacetylacetonato Eu0.1, Y0.9 4-cyanopyridine
tris trifluoroacetylacetonato Eu0.1, Y0.9 4-phenylpyridine-N-oxide
tris trifluoroacetylacetonato Eu0.1, Y0.9 1-methylimidazole
tris trifluoroacetylacetonato Eu0.1, Y0.9 triphenylphosphine oxide
tris trifluoroacetylacetonato Eu0.1, Y0.9 2,2-bipyridyl
tris trifluoroacetylacetonato Eu0.1, Y0.9 2,2-bipyridyl-N,N-dioxide
tris trifluoroacetylacetonato Eu0.1, Y0.9 phenanthroline
tris trifluoroacetylacetonato Eu0.1, Y0.9 bathocuproine
tris trifluoroacetylacetonato Eu0.1, Y0.9 bathophenanthroline
tris hexafluoroacetylacetonato Eu0.1, Y0.9 dimethylaminopyridine
tris hexafluoroacetylacetonato Eu0.1, Y0.9 4-picoline-N-oxide
tris hexafluoroacetylacetonato Eu0.1, Y0.9 4-phenylpyridine
tris hexafluoroacetylacetonato Eu0.1, Y0.9 4-cyanopyridine tris hexafluoroacetylacetonato Eu0.1, Y0.9 4-phenylpyridine-N-oxide
tris hexafluoroacetylacetonato Eu0.1, Y0.9 1-methylimidazole
tris hexafluoroacetylacetonato Eu0.1, Y0.9 triphenylphosphine oxide
tris hexafluoroacetylacetonato Eu0.1, Y0.9 2,2-bipyridyl
tris hexafluoroacetylacetonato Eu0.1, Y0.9 2,2-bipyridyl-N,N-dioxide
tris hexafluoroacetylacetonato Eu0.1, Y0.9 phenanthroline
tris hexafluoroacetylacetonato Eu0.1, Y0.9 bathocuproine
tris hexafluoroacetylacetonato Eu0.1, Y0.9 bathophenanthroline
tris 6,6,7,7,8,8,8-heptafluoro-2,2-dimethyloctanedionato Eu0.1, Y0.9 dimethylaminopyridine
tris 6,6,7,7,8,8,8-heptafluoro-2,2-dimethyloctanedionato Eu0.1, Y0.9 4-picoline-N-oxide
tris 6,6,7,7,8,8,8-heptafluoro-2,2-dimethyloctanedionato Eu0.1, Y0.9 4-phenylpyridine
tris 6,6,7,7,8,8,8-heptafluoro-2,2-dimethyloctanedionato Eu0.1, Y0.9 4-cyanopyridine
tris 6,6,7,7,8,8,8-heptafluoro-2,2-dimethyloctanedionato Eu0.1, Y0.9 4-phenylpyridine-N-oxide
tris 6,6,7,7,8,8,8-heptafluoro-2,2-dimethyloctanedionato Eu0.1, Y0.9 1-methylimidazole
tris 6,6,7,7,8,8,8-heptafluoro-2,2-dimethyloctanedionato Eu0.1, Y0.9 triphenylphosphine oxide
tris 6,6,7,7,8,8,8-heptafluoro-2,2-dimethyloctanedionato Eu0.1, Y0.9 2,2-bipyridyl
tris 6,6,7,7,8,8,8-heptafluoro-2,2-dimethyloctanedionato Eu0.1, Y0.9 2,2-bipyridyl-N,N-dioxide
tris 6,6,7,7,8,8,8-heptafluoro-2,2-dimethyloctanedionato Eu0.1, Y0.9 phenanthroline
tris 6,6,7,7,8,8,8-heptafluoro-2,2-dimethyloctanedionato Eu0.1, Y0.9 bathocuproine
tris 6,6,7,7,8,8,8-heptafluoro-2,2-dimethyloctanedionato Eu0.1, Y0.9 bathophenanthroline
tris 1-phenyl-1,3-butanedionato Eu0.1, Y0.9 dimethylaminopyridine
tris 1-phenyl-1,3-butanedionato Eu0.1, Y0.9 4-picoline-N-oxide
tris 1-phenyl-1,3-butanedionato Eu0.1, Y0.9 4-phenylpyridine
tris 1-phenyl-1,3-butanedionato Eu0.1, Y0.9 4-cyanopyridine
tris 1-phenyl-1,3-butanedionato Eu0.1, Y0.9 4-phenylpyridine-N-oxide
tris 1-phenyl-1,3-butanedionato Eu0.1, Y0.9 1-methylimidazole
tris 1-phenyl-1,3-butanedionato Eu0.1, Y0.9 triphenylphosphine oxide
tris 1-phenyl-1,3-butanedionato Eu0.1, Y0.9 2,2-bipyridyl
tris 1-phenyl-1,3-butanedionato Eu0.1, Y0.9 2,2-bipyridyl-N,N-dioxide
tris 1-phenyl-1,3-butanedionato Eu0.1, Y0.9 phenanthroline
tris 1-phenyl-1,3-butanedionato Eu0.1, Y0.9 bathocuproine
tris 1-phenyl-1,3-butanedionato Eu0.1, Y0.9 bathophenanthroline
tris acetylacetonato Eu0.01, Y0.99 dimethylaminopyridine
tris acetylacetonato Eu0.01, Y0.99 4-picoline-N-oxide
tris acetylacetonato Eu0.01, Y0.99 4-phenylpyridine
tris acetylacetonato Eu0.01, Y0.99 4-cyanopyridine
tris acetylacetonato Eu0.01, Y0.99 4-phenylpyridine-N-oxide
tris acetylacetonato Eu0.01, Y0.99 1-methylimidazole
tris acetylacetonato Eu0.01, Y0.99 triphenylphosphine oxide
tris acetylacetonato Eu0.01, Y0.99 2,2-bipyridyl
tris acetylacetonato Eu0.01, Y0.99 2,2-bipyridyl-N,N-dioxide
tris acetylacetonato Eu0.01, Y0.99 phenanthroline
tris acetylacetonato Eu0.01, Y0.99 bathocuproine
tris acetylacetonato Eu0.01, Y0.99 bathophenanthroline
tris dibenzoylmethanato Eu0.01, Y0.99 dimethylaminopyridine
tris dibenzoylmethanato Eu0.01, Y0.99 4-picoline-N-oxide
tris dibenzoylmethanato Eu0.01, Y0.99 4-phenylpyridine
tris dibenzoylmethanato Eu0.01, Y0.99 4-cyanopyridine
tris dibenzoylmethanato Eu0.01, Y0.99 4-phenylpyridine-N-oxide
tris dibenzoylmethanato Eu0.01, Y0.99 1-methylimidazole
tris dibenzoylmethanato Eu0.01, Y0.99 triphenylphosphine oxide
tris dibenzoylmethanato Eu0.01, Y0.99 2,2-bipyridyl
tris dibenzoylmethanato Eu0.01, Y0.99 2,2-bipyridyl-N,N-dioxide
tris dibenzoylmethanato Eu0.01, Y0.99 phenanthroline
tris dibenzoylmethanato Eu0.01, Y0.99 bathocuproine
tris dibenzoylmethanato Eu0.01, Y0.99 bathophenanthroline
tris thenoyltrifluoroacetonato Eu0.01, Y0.99 dimethylaminopyridine
tris thenoyltrifluoroacetonato Eu0.01, Y0.99 4-picoline-N-oxide
tris thenoyltrifluoroacetonato Eu0.01, Y0.99 4-phenylpyridine
tris thenoyltrifluoroacetonato Eu0.01, Y0.99 4-cyanopyridine
tris thenoyltrifluoroacetonato Eu0.01, Y0.99 4-phenylpyridine-N-oxide
tris thenoyltrifluoroacetonato Eu0.01, Y0.99 1-methylimidazole
tris thenoyltrifluoroacetonato Eu0.01, Y0.99 triphenylphosphine oxide
tris thenoyltrifluoroacetonato Eu0.01, Y0.99 2,2-bipyridyl
tris thenoyltrifluoroacetonato Eu0.01, Y0.99 2,2-bipyridyl-N,N-dioxide
tris thenoyltrifluoroacetonato Eu0.01, Y0.99 phenanthroline
tris thenoyltrifluoroacetonato Eu0.01, Y0.99 bathocuproine
tris thenoyltrifluoroacetonato Eu0.01, Y0.99 bathophenanthroline
tris 2,2,6,6-tetramethylheptanedionato Eu0.01, Y0.99 dimethylaminopyridine
tris 2,2,6,6-tetramethylheptanedionato Eu0.01, Y0.99 4-picoline-N-oxide
tris 2,2,6,6-tetramethylheptanedionato Eu0.01, Y0.99 4-phenylpyridine
tris 2,2,6,6-tetramethylheptanedionato Eu0.01, Y0.99 4-cyanopyridine
tris 2,2,6,6-tetramethylheptanedionato Eu0.01, Y0.99 4-phenylpyridine-N-oxide
tris 2,2,6,6-tetramethylheptanedionato Eu0.01, Y0.99 1-methylimidazole
tris 2,2,6,6-tetramethylheptanedionato Eu0.01, Y0.99 triphenylphosphine oxide
tris 2,2,6,6-tetramethylheptanedionato Eu0.01, Y0.99 2,2-bipyridyl
tris 2,2,6,6-tetramethylheptanedionato Eu0.01, Y0.99 2,2-bipyridyl-N,N-dioxide
tris 2,2,6,6-tetramethylheptanedionato Eu0.01, Y0.99 phenanthroline
tris 2,2,6,6-tetramethylheptanedionato Eu0.01, Y0.99 bathocuproine
tris 2,2,6,6-tetramethylheptanedionato Eu0.01, Y0.99 bathophenanthroline tris 3-methylpentane-2,4-dionato Eu0.01, Y0.99 dimethylaminopyridine
tris 3-methylpentane-2,4-dionato Eu0.01, Y0.99 4-picoline-N-oxide
tris 3-methylpentane-2,4-dionato Eu0.01, Y0.99 4-phenylpyridine
tris 3-methylpentane-2,4-dionato Eu0.01, Y0.99 4-cyanopyridine
tris 3-methylpentane-2,4-dionato Eu0.01, Y0.99 4-phenylpyridine-N-oxide
tris 3-methylpentane-2,4-dionato Eu0.01, Y0.99 1-methylimidazole
tris 3-methylpentane-2,4-dionato Eu0.01, Y0.99 triphenylphosphine oxide
tris 3-methylpentane-2,4-dionato Eu0.01, Y0.99 2,2-bipyridyl
tris 3-methylpentane-2,4-dionato Eu0.01, Y0.99 2,2-bipyridyl-N,N-dioxide
tris 3-methylpentane-2,4-dionato Eu0.01, Y0.99 phenanthroline
tris 3-methylpentane-2,4-dionato Eu0.01, Y0.99 bathocuproine
tris 3-methylpentane-2,4-dionato Eu0.01, Y0.99 bathophenanthroline
tris 3-ethylpentane-2,4-dionato Eu0.01, Y0.99 dimethylaminopyridine
tris 3-ethylpentane-2,4-dionato Eu0.01, Y0.99 4-picoline-N-oxide
tris 3-ethylpentane-2,4-dionato Eu0.01, Y0.99 4-phenylpyridine
tris 3-ethylpentane-2,4-dionato Eu0.01, Y0.99 4-cyanopyridine
tris 3-ethylpentane-2,4-dionato Eu0.01, Y0.99 4-phenylpyridine-N-oxide
tris 3-ethylpentane-2,4-dionato Eu0.01, Y0.99 1-methylimidazole
tris 3-ethylpentane-2,4-dionato Eu0.01, Y0.99 triphenylphosphine oxide
tris 3-ethylpentane-2,4-dionato Eu0.01, Y0.99 2,2-bipyridyl
tris 3-ethylpentane-2,4-dionato Eu0.01, Y0.99 2,2-bipyridyl-N,N-dioxide
tris 3-ethylpentane-2,4-dionato Eu0.01, Y0.99 phenanthroline
tris 3-ethylpentane-2,4-dionato Eu0.01, Y0.99 bathocuproine
tris 3-ethylpentane-2,4-dionato Eu0.01, Y0.99 bathophenanthroline
tris pivaloyltrifluoroacetonato Eu0.01, Y0.99 dimethylaminopyridine
tris pivaloyltrifluoroacetonato Eu0.01, Y0.99 4-picoline-N-oxide
tris pivaloyltrifluoroacetonato Eu0.01, Y0.99 4-phenylpyridine
tris pivaloyltrifluoroacetonato Eu0.01, Y0.99 4-cyanopyridine
tris pivaloyltrifluoroacetonato Eu0.01, Y0.99 4-phenylpyridine-N-oxide
tris pivaloyltrifluoroacetonato Eu0.01, Y0.99 1-methylimidazole
tris pivaloyltrifluoroacetonato Eu0.01, Y0.99 triphenylphosphine oxide
tris pivaloyltrifluoroacetonato Eu0.01, Y0.99 2,2-bipyridyl
tris pivaloyltrifluoroacetonato Eu0.01, Y0.99 2,2-bipyridyl-N,N-dioxide
tris pivaloyltrifluoroacetonato Eu0.01, Y0.99 phenanthroline
tris pivaloyltrifluoroacetonato Eu0.01, Y0.99 bathocuproine
tris pivaloyltrifluoroacetonato Eu0.01, Y0.99 bathophenanthroline
tris trifluoroacetylacetonato Eu0.01, Y0.99 dimethylaminopyridine
tris trifluoroacetylacetonato Eu0.01, Y0.99 4-picoline-N-oxide
tris trifluoroacetylacetonato Eu0.01, Y0.99 4-phenylpyridine
tris trifluoroacetylacetonato Eu0.01, Y0.99 4-cyanopyridine
tris trifluoroacetylacetonato Eu0.01, Y0.99 4-phenylpyridine-N-oxide
tris trifluoroacetylacetonato Eu0.01, Y0.99 1-methylimidazole
tris trifluoroacetylacetonato Eu0.01, Y0.99 triphenylphosphine oxide
tris trifluoroacetylacetonato Eu0.01, Y0.99 2,2-bipyridyl
tris trifluoroacetylacetonato Eu0.01, Y0.99 2,2-bipyridyl-N,N-dioxide
tris trifluoroacetylacetonato Eu0.01, Y0.99 phenanthroline
tris trifluoroacetylacetonato Eu0.01, Y0.99 bathocuproine
tris trifluoroacetylacetonato Eu0.01, Y0.99 bathophenanthroline
tris hexafluoroacetylacetonato Eu0.01, Y0.99 dimethylaminopyridine
tris hexafluoroacetylacetonato Eu0.01, Y0.99 4-picoline-N-oxide
tris hexafluoroacetylacetonato Eu0.01, Y0.99 4-phenylpyridine
tris hexafluoroacetylacetonato Eu0.01, Y0.99 4-cyanopyridine
tris hexafluoroacetylacetonato Eu0.01, Y0.99 4-phenylpyridine-N-oxide
tris hexafluoroacetylacetonato Eu0.01, Y0.99 1-methylimidazole
tris hexafluoroacetylacetonato Eu0.01, Y0.99 triphenylphosphine oxide
tris hexafluoroacetylacetonato Eu0.01, Y0.99 2,2-bipyridyl
tris hexafluoroacetylacetonato Eu0.01, Y0.99 2,2-bipyridyl-N,N-dioxide
tris hexafluoroacetylacetonato Eu0.01, Y0.99 phenanthroline
tris hexafluoroacetylacetonato Eu0.01, Y0.99 bathocuproine
tris hexafluoroacetylacetonato Eu0.01, Y0.99 bathophenanthroline
tris 6,6,7,7,8,8,8-heptafluoro-2,2-dimethyloctanedionato Eu0.01, Y0.99 dimethylaminopyridine
tris 6,6,7,7,8,8,8-heptafluoro-2,2-dimethyloctanedionato Eu0.01, Y0.99 4-picoline-N-oxide
tris 6,6,7,7,8,8,8-heptafluoro-2,2-dimethyloctanedionato Eu0.01, Y0.99 4-phenylpyridine
tris 6,6,7,7,8,8,8-heptafluoro-2,2-dimethyloctanedionato Eu0.01, Y0.99 4-cyanopyridine
tris 6,6,7,7,8,8,8-heptafluoro-2,2-dimethyloctanedionato Eu0.01, Y0.99 4-phenylpyridine-N-oxide
tris 6,6,7,7,8,8,8-heptafluoro-2,2-dimethyloctanedionato Eu0.01, Y0.99 1-methylimidazole
tris 6,6,7,7,8,8,8-heptafluoro-2,2-dimethyloctanedionato Eu0.01, Y0.99 triphenylphosphine oxide
tris 6,6,7,7,8,8,8-heptafluoro-2,2-dimethyloctanedionato Eu0.01, Y0.99 2,2-bipyridyl
tris 6,6,7,7,8,8,8-heptafluoro-2,2-dimethyloctanedionato Eu0.01, Y0.99 2,2-bipyridyl-N,N-dioxide
tris 6,6,7,7,8,8,8-heptafluoro-2,2-dimethyloctanedionato Eu0.01, Y0.99 phenanthroline
tris 6,6,7,7,8,8,8-heptafluoro-2,2-dimethyloctanedionato Eu0.01, Y0.99 bathocuproine tris 6,6,7,7,8,8,8-heptafluoro-2,2-dimethyloctanedionato Eu0.01, Y0.99 bathophenanthroline
tris 1-phenyl-1,3-butanedionato Eu0.01, Y0.99 dimethylaminopyridine
tris 1-phenyl-1,3-butanedionato Eu0.01, Y0.99 4-picoline-N-oxide
tris 1-phenyl-1,3-butanedionato Eu0.01, Y0.99 4-phenylpyridine
tris 1-phenyl-1,3-butanedionato Eu0.01, Y0.99 4-cyanopyridine
tris 1-phenyl-1,3-butanedionato Eu0.01, Y0.99 4-phenylpyridine-N-oxide
tris 1-phenyl-1,3-butanedionato Eu0.01, Y0.99 1-methylimidazole
tris 1-phenyl-1,3-butanedionato Eu0.01, Y0.99 triphenylphosphine oxide
tris 1-phenyl-1,3-butanedionato Eu0.01, Y0.99 2,2-bipyridyl
tris 1-phenyl-1,3-butanedionato Eu0.01, Y0.99 2,2-bipyridyl-N,N-dioxide
tris 1-phenyl-1,3-butanedionato Eu0.01, Y0.99 phenanthroline
tris 1-phenyl-1,3-butanedionato Eu0.01, Y0.99 bathocuproine
tris 1-phenyl-1,3-butanedionato Eu0.01, Y0.99 bathophenanthroline
tris acetylacetonato Eu0.5, Y0.5 dimethylaminopyridine
tris acetylacetonato Eu0.5, Y0.5 4-picoline-N-oxide
tris acetylacetonato Eu0.5, Y0.5 4-phenylpyridine
tris acetylacetonato Eu0.5, Y0.5 4-cyanopyridine
tris acetylacetonato Eu0.5, Y0.5 4-phenylpyridine-N-oxide
tris acetylacetonato Eu0.5, Y0.5 1-methylimidazole
tris acetylacetonato Eu0.5, Y0.5 triphenylphosphine oxide
tris acetylacetonato Eu0.5, Y0.5 2,2-bipyridyl
tris acetylacetonato Eu0.5, Y0.5 2,2-bipyridyl-N,N-dioxide
tris acetylacetonato Eu0.5, Y0.5 phenanthroline
tris acetylacetonato Eu0.5, Y0.5 bathocuproine
tris acetylacetonato Eu0.5, Y0.5 bathophenanthroline
tris dibenzoylmethanato Eu0.5, Y0.5 dimethylaminopyridine
tris dibenzoylmethanato Eu0.5, Y0.5 4-picoline-N-oxide
tris dibenzoylmethanato Eu0.5, Y0.5 4-phenylpyridine
tris dibenzoylmethanato Eu0.5, Y0.5 4-cyanopyridine
tris dibenzoylmethanato Eu0.5, Y0.5 4-phenylpyridine-N-oxide
tris dibenzoylmethanato Eu0.5, Y0.5 1-methylimidazole
tris dibenzoylmethanato Eu0.5, Y0.5 triphenylphosphine oxide
tris dibenzoylmethanato Eu0.5, Y0.5 2,2-bipyridyl
tris dibenzoylmethanato Eu0.5, Y0.5 2,2-bipyridyl-N,N-dioxide
tris dibenzoylmethanato Eu0.5, Y0.5 phenanthroline
tris dibenzoylmethanato Eu0.5, Y0.5 bathocuproine
tris dibenzoylmethanato Eu0.5, Y0.5 bathophenanthroline
tris thenoyltrifluoroacetonato Eu0.5, Y0.5 dimethylaminopyridine
tris thenoyltrifluoroacetonato Eu0.5, Y0.5 4-picoline-N-oxide
tris thenoyltrifluoroacetonato Eu0.5, Y0.5 4-phenylpyridine
tris thenoyltrifluoroacetonato Eu0.5, Y0.5 4-cyanopyridine
tris thenoyltrifluoroacetonato Eu0.5, Y0.5 4-phenylpyridine-N-oxide
tris thenoyltrifluoroacetonato Eu0.5, Y0.5 1-methylimidazole
tris thenoyltrifluoroacetonato Eu0.5, Y0.5 triphenylphosphine oxide
tris thenoyltrifluoroacetonato Eu0.5, Y0.5 2,2-bipyridyl
tris thenoyltrifluoroacetonato Eu0.5, Y0.5 2,2-bipyridyl-N,N-dioxide
tris thenoyltrifluoroacetonato Eu0.5, Y0.5 phenanthroline
tris thenoyltrifluoroacetonato Eu0.5, Y0.5 bathocuproine
tris thenoyltrifluoroacetonato Eu0.5, Y0.5 bathophenanthroline
tris 2,2,6,6-tetramethylheptanedionato Eu0.5, Y0.5 dimethylaminopyridine
tris 2,2,6,6-tetramethylheptanedionato Eu0.5, Y0.5 4-picoline-N-oxide
tris 2,2,6,6-tetramethylheptanedionato Eu0.5, Y0.5 4-phenylpyridine
tris 2,2,6,6-tetramethylheptanedionato Eu0.5, Y0.5 4-cyanopyridine
tris 2,2,6,6-tetramethylheptanedionato Eu0.5, Y0.5 4-phenylpyridine-N-oxide
tris 2,2,6,6-tetramethylheptanedionato Eu0.5, Y0.5 1-methylimidazole
tris 2,2,6,6-tetramethylheptanedionato Eu0.5, Y0.5 triphenylphosphine oxide
tris 2,2,6,6-tetramethylheptanedionato Eu0.5, Y0.5 2,2-bipyridyl
tris 2,2,6,6-tetramethylheptanedionato Eu0.5, Y0.5 2,2-bipyridyl-N,N-dioxide
tris 2,2,6,6-tetramethylheptanedionato Eu0.5, Y0.5 phenanthroline
tris 2,2,6,6-tetramethylheptanedionato Eu0.5, Y0.5 bathocuproine
tris 2,2,6,6-tetramethylheptanedionato Eu0.5, Y0.5 bathophenanthroline
tris 3-methylpentane-2,4-dionato Eu0.5, Y0.5 dimethylaminopyridine
tris 3-methylpentane-2,4-dionato Eu0.5, Y0.5 4-picoline-N-oxide
tris 3-methylpentane-2,4-dionato Eu0.5, Y0.5 4-phenylpyridine
tris 3-methylpentane-2,4-dionato Eu0.5, Y0.5 4-cyanopyridine
tris 3-methylpentane-2,4-dionato Eu0.5, Y0.5 4-phenylpyridine-N-oxide
tris 3-methylpentane-2,4-dionato Eu0.5, Y0.5 1-methylimidazole
tris 3-methylpentane-2,4-dionato Eu0.5, Y0.5 triphenylphosphine oxide
tris 3-methylpentane-2,4-dionato Eu0.5, Y0.5 2,2-bipyridyl
tris 3-methylpentane-2,4-dionato Eu0.5, Y0.5 2,2-bipyridyl-N,N-dioxide
tris 3-methylpentane-2,4-dionato Eu0.5, Y0.5 phenanthroline
tris 3-methylpentane-2,4-dionato Eu0.5, Y0.5 bathocuproine
tris 3-methylpentane-2,4-dionato Eu0.5, Y0.5 bathophenanthroline
tris 3-ethylpentane-2,4-dionato Eu0.5, Y0.5 dimethylaminopyridine
tris 3-ethylpentane-2,4-dionato Eu0.5, Y0.5 4-picoline-N-oxide
tris 3-ethylpentane-2,4-dionato Eu0.5, Y0.5 4-phenylpyridine
tris 3-ethylpentane-2,4-dionato Eu0.5, Y0.5 4-cyanopyridine
tris 3-ethylpentane-2,4-dionato Eu0.5, Y0.5 4-phenylpyridine-N-oxide
tris 3-ethylpentane-2,4-dionato Eu0.5, Y0.5 1-methylimidazole
tris 3-ethylpentane-2,4-dionato Eu0.5, Y0.5 triphenylphosphine oxide
tris 3-ethylpentane-2,4-dionato Eu0.5, Y0.5 2,2-bipyridyl tris 3-ethylpentane-2,4-dionato Eu0.5, Y0.5 2,2-bipyridyl-N,N-dioxide
tris 3-ethylpentane-2,4-dionato Eu0.5, Y0.5 phenanthroline
tris 3-ethylpentane-2,4-dionato Eu0.5, Y0.5 bathocuproine
tris 3-ethylpentane-2,4-dionato Eu0.5, Y0.5 bathophenanthroline
tris pivaloyltrifluoroacetonato Eu0.5, Y0.5 dimethylaminopyridine
tris pivaloyltrifluoroacetonato Eu0.5, Y0.5 4-picoline-N-oxide
tris pivaloyltrifluoroacetonato Eu0.5, Y0.5 4-phenylpyridine
tris pivaloyltrifluoroacetonato Eu0.5, Y0.5 4-cyanopyridine
tris pivaloyltrifluoroacetonato Eu0.5, Y0.5 4-phenylpyridine-N-oxide
tris pivaloyltrifluoroacetonato Eu0.5, Y0.5 1-methylimidazole
tris pivaloyltrifluoroacetonato Eu0.5, Y0.5 triphenylphosphine oxide
tris pivaloyltrifluoroacetonato Eu0.5, Y0.5 2,2-bipyridyl
tris pivaloyltrifluoroacetonato Eu0.5, Y0.5 2,2-bipyridyl-N,N-dioxide
tris pivaloyltrifluoroacetonato Eu0.5, Y0.5 phenanthroline
tris pivaloyltrifluoroacetonato Eu0.5, Y0.5 bathocuproine
tris pivaloyltrifluoroacetonato Eu0.5, Y0.5 bathophenanthroline
tris trifluoroacetylacetonato Eu0.5, Y0.5 dimethylaminopyridine
tris trifluoroacetylacetonato Eu0.5, Y0.5 4-picoline-N-oxide
tris trifluoroacetylacetonato Eu0.5, Y0.5 4-phenylpyridine
tris trifluoroacetylacetonato Eu0.5, Y0.5 4-cyanopyridine
tris trifluoroacetylacetonato Eu0.5, Y0.5 4-phenylpyridine-N-oxide
tris trifluoroacetylacetonato Eu0.5, Y0.5 1-methylimidazole
tris trifluoroacetylacetonato Eu0.5, Y0.5 triphenylphosphine oxide
tris trifluoroacetylacetonato Eu0.5, Y0.5 2,2-bipyridyl
tris trifluoroacetylacetonato Eu0.5, Y0.5 2,2-bipyridyl-N,N-dioxide
tris trifluoroacetylacetonato Eu0.5, Y0.5 phenanthroline
tris trifluoroacetylacetonato Eu0.5, Y0.5 bathocuproine
tris trifluoroacetylacetonato Eu0.5, Y0.5 bathophenanthroline
tris hexafluoroacetylacetonato Eu0.5, Y0.5 dimethylaminopyridine
tris hexafluoroacetylacetonato Eu0.5, Y0.5 4-picoline-N-oxide
tris hexafluoroacetylacetonato Eu0.5, Y0.5 4-phenylpyridine
tris hexafluoroacetylacetonato Eu0.5, Y0.5 4-cyanopyridine
tris hexafluoroacetylacetonato Eu0.5, Y0.5 4-phenylpyridine-N-oxide
tris hexafluoroacetylacetonato Eu0.5, Y0.5 1-methylimidazole
tris hexafluoroacetylacetonato Eu0.5, Y0.5 triphenylphosphine oxide
tris hexafluoroacetylacetonato Eu0.5, Y0.5 2,2-bipyridyl
tris hexafluoroacetylacetonato Eu0.5, Y0.5 2,2-bipyridyl-N,N-dioxide
tris hexafluoroacetylacetonato Eu0.5, Y0.5 phenanthroline
tris hexafluoroacetylacetonato Eu0.5, Y0.5 bathocuproine
tris hexafluoroacetylacetonato Eu0.5, Y0.5 bathophenanthroline
tris 6,6,7,7,8,8,8-heptafluoro-2,2-dimethyloctanedionato Eu0.5, Y0.5 dimethylaminopyridine
tris 6,6,7,7,8,8,8-heptafluoro-2,2-dimethyloctanedionato Eu0.5, Y0.5 4-picoline-N-oxide
tris 6,6,7,7,8,8,8-heptafluoro-2,2-dimethyloctanedionato Eu0.5, Y0.5 4-phenylpyridine
tris 6,6,7,7,8,8,8-heptafluoro-2,2-dimethyloctanedionato Eu0.5, Y0.5 4-cyanopyridine
tris 6,6,7,7,8,8,8-heptafluoro-2,2-dimethyloctanedionato Eu0.5, Y0.5 4-phenylpyridine-N-oxide
tris 6,6,7,7,8,8,8-heptafluoro-2,2-dimethyloctanedionato Eu0.5, Y0.5 1-methylimidazole
tris 6,6,7,7,8,8,8-heptafluoro-2,2-dimethyloctanedionato Eu0.5, Y0.5 triphenylphosphine oxide
tris 6,6,7,7,8,8,8-heptafluoro-2,2-dimethyloctanedionato Eu0.5, Y0.5 2,2-bipyridyl
tris 6,6,7,7,8,8,8-heptafluoro-2,2-dimethyloctanedionato Eu0.5, Y0.5 2,2-bipyridyl-N,N-dioxide
tris 6,6,7,7,8,8,8-heptafluoro-2,2-dimethyloctanedionato Eu0.5, Y0.5 phenanthroline
tris 6,6,7,7,8,8,8-heptafluoro-2,2-dimethyloctanedionato Eu0.5, Y0.5 bathocuproine
tris 6,6,7,7,8,8,8-heptafluoro-2,2-dimethyloctanedionato Eu0.5, Y0.5 bathophenanthroline
tris 1-phenyl-1,3-butanedionato Eu0.5, Y0.5 dimethylaminopyridine
tris 1-phenyl-1,3-butanedionato Eu0.5, Y0.5 4-picoline-N-oxide
tris 1-phenyl-1,3-butanedionato Eu0.5, Y0.5 4-phenylpyridine
tris 1-phenyl-1,3-butanedionato Eu0.5, Y0.5 4-cyanopyridine
tris 1-phenyl-1,3-butanedionato Eu0.5, Y0.5 4-phenylpyridine-N-oxide
tris 1-phenyl-1,3-butanedionato Eu0.5, Y0.5 1-methylimidazole
tris 1-phenyl-1,3-butanedionato Eu0.5, Y0.5 triphenylphosphine oxide
tris 1-phenyl-1,3-butanedionato Eu0.5, Y0.5 2,2-bipyridyl
tris 1-phenyl-1,3-butanedionato Eu0.5, Y0.5 2,2-bipyridyl-N,N-dioxide
tris 1-phenyl-1,3-butanedionato Eu0.5, Y0.5 phenanthroline
tris 1-phenyl-1,3-butanedionato Eu0.5, Y0.5 bathocuproine
tris 1-phenyl-1,3-butanedionato Eu0.5, Y0.5 bathophenanthroline
tris acetylacetonato Eu0.2, Y0.8 dimethylaminopyridine
tris acetylacetonato Eu0.2, Y0.8 4-picoline-N-oxide
tris acetylacetonato Eu0.2, Y0.8 4-phenylpyridine
tris acetylacetonato Eu0.2, Y0.8 4-cyanopyridine
tris acetylacetonato Eu0.2, Y0.8 4-phenylpyridine-N-oxide
tris acetylacetonato Eu0.2, Y0.8 1-methylimidazole
tris acetylacetonato Eu0.2, Y0.8 triphenylphosphine oxide
tris acetylacetonato Eu0.2, Y0.8 2,2-bipyridyl
tris acetylacetonato Eu0.2, Y0.8 2,2-bipyridyl-N,N-dioxide
tris acetylacetonato Eu0.2, Y0.8 phenanthroline
tris acetylacetonato Eu0.2, Y0.8 bathocuproine
tris acetylacetonato Eu0.2, Y0.8 bathophenanthroline
tris dibenzoylmethanato Eu0.2, Y0.8 dimethylaminopyridine
tris dibenzoylmethanato Eu0.2, Y0.8 4-picoline-N-oxide
tris dibenzoylmethanato Eu0.2, Y0.8 4-phenylpyridine
tris dibenzoylmethanato Eu0.2, Y0.8 4-cyanopyridine
tris dibenzoylmethanato Eu0.2, Y0.8 4-phenylpyridine-N-oxide
tris dibenzoylmethanato Eu0.2, Y0.8 1-methylimidazole
tris dibenzoylmethanato Eu0.2, Y0.8 triphenylphosphine oxide
tris dibenzoylmethanato Eu0.2, Y0.8 2,2-bipyridyl
tris dibenzoylmethanato Eu0.2, Y0.8 2,2-bipyridyl-N,N-dioxide
tris dibenzoylmethanato Eu0.2, Y0.8 phenanthroline tris dibenzoylmethanato Eu0.2, Y0.8 bathocuproine
tris dibenzoylmethanato Eu0.2, Y0.8 bathophenanthroline
tris thenoyltrifluoroacetonato Eu0.2, Y0.8 dimethylaminopyridine
tris thenoyltrifluoroacetonato Eu0.2, Y0.8 4-picoline-N-oxide
tris thenoyltrifluoroacetonato Eu0.2, Y0.8 4-phenylpyridine
tris thenoyltrifluoroacetonato Eu0.2, Y0.8 4-cyanopyridine
tris thenoyltrifluoroacetonato Eu0.2, Y0.8 4-phenylpyridine-N-oxide
tris thenoyltrifluoroacetonato Eu0.2, Y0.8 1-methylimidazole
tris thenoyltrifluoroacetonato Eu0.2, Y0.8 triphenylphosphine oxide
tris thenoyltrifluoroacetonato Eu0.2, Y0.8 2,2-bipyridyl
tris thenoyltrifluoroacetonato Eu0.2, Y0.8 2,2-bipyridyl-N,N-dioxide
tris thenoyltrifluoroacetonato Eu0.2, Y0.8 phenanthroline
tris thenoyltrifluoroacetonato Eu0.2, Y0.8 bathocuproine
tris thenoyltrifluoroacetonato Eu0.2, Y0.8 bathophenanthroline
tris 2,2,6,6-tetramethylheptanedionato Eu0.2, Y0.8 dimethylaminopyridine
tris 2,2,6,6-tetramethylheptanedionato Eu0.2, Y0.8 4-picoline-N-oxide
tris 2,2,6,6-tetramethylheptanedionato Eu0.2, Y0.8 4-phenylpyridine
tris 2,2,6,6-tetramethylheptanedionato Eu0.2, Y0.8 4-cyanopyridine
tris 2,2,6,6-tetramethylheptanedionato Eu0.2, Y0.8 4-phenylpyridine-N-oxide
tris 2,2,6,6-tetramethylheptanedionato Eu0.2, Y0.8 1-methylimidazole
tris 2,2,6,6-tetramethylheptanedionato Eu0.2, Y0.8 triphenylphosphine oxide
tris 2,2,6,6-tetramethylheptanedionato Eu0.2, Y0.8 2,2-bipyridyl
tris 2,2,6,6-tetramethylheptanedionato Eu0.2, Y0.8 2,2-bipyridyl-N,N-dioxide
tris 2,2,6,6-tetramethylheptanedionato Eu0.2, Y0.8 phenanthroline
tris 2,2,6,6-tetramethylheptanedionato Eu0.2, Y0.8 bathocuproine
tris 2,2,6,6-tetramethylheptanedionato Eu0.2, Y0.8 bathophenanthroline
tris 3-methylpentane-2,4-dionato Eu0.2, Y0.8 dimethylaminopyridine
tris 3-methylpentane-2,4-dionato Eu0.2, Y0.8 4-picoline-N-oxide
tris 3-methylpentane-2,4-dionato Eu0.2, Y0.8 4-phenylpyridine
tris 3-methylpentane-2,4-dionato Eu0.2, Y0.8 4-cyanopyridine
tris 3-methylpentane-2,4-dionato Eu0.2, Y0.8 4-phenylpyridine-N-oxide
tris 3-methylpentane-2,4-dionato Eu0.2, Y0.8 1-methylimidazole
tris 3-methylpentane-2,4-dionato Eu0.2, Y0.8 triphenylphosphine oxide
tris 3-methylpentane-2,4-dionato Eu0.2, Y0.8 2,2-bipyridyl
tris 3-methylpentane-2,4-dionato Eu0.2, Y0.8 2,2-bipyridyl-N,N-dioxide
tris 3-methylpentane-2,4-dionato Eu0.2, Y0.8 phenanthroline
tris 3-methylpentane-2,4-dionato Eu0.2, Y0.8 bathocuproine
tris 3-methylpentane-2,4-dionato Eu0.2, Y0.8 bathophenanthroline
tris 3-ethylpentane-2,4-dionato Eu0.2, Y0.8 dimethylaminopyridine
tris 3-ethylpentane-2,4-dionato Eu0.2, Y0.8 4-picoline-N-oxide
tris 3-ethylpentane-2,4-dionato Eu0.2, Y0.8 4-phenylpyridine
tris 3-ethylpentane-2,4-dionato Eu0.2, Y0.8 4-cyanopyridine
tris 3-ethylpentane-2,4-dionato Eu0.2, Y0.8 4-phenylpyridine-N-oxide
tris 3-ethylpentane-2,4-dionato Eu0.2, Y0.8 1-methylimidazole
tris 3-ethylpentane-2,4-dionato Eu0.2, Y0.8 triphenylphosphine oxide
tris 3-ethylpentane-2,4-dionato Eu0.2, Y0.8 2,2-bipyridyl
tris 3-ethylpentane-2,4-dionato Eu0.2, Y0.8 2,2-bipyridyl-N,N-dioxide
tris 3-ethylpentane-2,4-dionato Eu0.2, Y0.8 phenanthroline
tris 3-ethylpentane-2,4-dionato Eu0.2, Y0.8 bathocuproine
tris 3-ethylpentane-2,4-dionato Eu0.2, Y0.8 bathophenanthroline
tris pivaloyltrifluoroacetonato Eu0.2, Y0.8 dimethylaminopyridine
tris pivaloyltrifluoroacetonato Eu0.2, Y0.8 4-picoline-N-oxide
tris pivaloyltrifluoroacetonato Eu0.2, Y0.8 4-phenylpyridine
tris pivaloyltrifluoroacetonato Eu0.2, Y0.8 4-cyanopyridine
tris pivaloyltrifluoroacetonato Eu0.2, Y0.8 4-phenylpyridine-N-oxide
tris pivaloyltrifluoroacetonato Eu0.2, Y0.8 1-methylimidazole
tris pivaloyltrifluoroacetonato Eu0.2, Y0.8 triphenylphosphine oxide
tris pivaloyltrifluoroacetonato Eu0.2, Y0.8 2,2-bipyridyl
tris pivaloyltrifluoroacetonato Eu0.2, Y0.8 2,2-bipyridyl-N,N-dioxide
tris pivaloyltrifluoroacetonato Eu0.2, Y0.8 phenanthroline
tris pivaloyltrifluoroacetonato Eu0.2, Y0.8 bathocuproine
tris pivaloyltrifluoroacetonato Eu0.2, Y0.8 bathophenanthroline
tris trifluoroacetylacetonato Eu0.2, Y0.8 dimethylaminopyridine
tris trifluoroacetylacetonato Eu0.2, Y0.8 4-picoline-N-oxide
tris trifluoroacetylacetonato Eu0.2, Y0.8 4-phenylpyridine
tris trifluoroacetylacetonato Eu0.2, Y0.8 4-cyanopyridine
tris trifluoroacetylacetonato Eu0.2, Y0.8 4-phenylpyridine-N-oxide
tris trifluoroacetylacetonato Eu0.2, Y0.8 1-methylimidazole
tris trifluoroacetylacetonato Eu0.2, Y0.8 triphenylphosphine oxide
tris trifluoroacetylacetonato Eu0.2, Y0.8 2,2-bipyridyl
tris trifluoroacetylacetonato Eu0.2, Y0.8 2,2-bipyridyl-N,N-dioxide
tris trifluoroacetylacetonato Eu0.2, Y0.8 phenanthroline
tris trifluoroacetylacetonato Eu0.2, Y0.8 bathocuproine
tris trifluoroacetylacetonato Eu0.2, Y0.8 bathophenanthroline
tris hexafluoroacetylacetonato Eu0.2, Y0.8 dimethylaminopyridine
tris hexafluoroacetylacetonato Eu0.2, Y0.8 4-picoline-N-oxide
tris hexafluoroacetylacetonato Eu0.2, Y0.8 4-phenylpyridine
tris hexafluoroacetylacetonato Eu0.2, Y0.8 4-cyanopyridine
tris hexafluoroacetylacetonato Eu0.2, Y0.8 4-phenylpyridine-N-oxide tris hexafluoroacetylacetonato Eu0.2, Y0.8 1-methylimidazole
tris hexafluoroacetylacetonato Eu0.2, Y0.8 triphenylphosphine oxide
tris hexafluoroacetylacetonato Eu0.2, Y0.8 2,2-bipyridyl
tris hexafluoroacetylacetonato Eu0.2, Y0.8 2,2-bipyridyl-N,N-dioxide
tris hexafluoroacetylacetonato Eu0.2, Y0.8 phenanthroline
tris hexafluoroacetylacetonato Eu0.2, Y0.8 bathocuproine
tris hexafluoroacetylacetonato Eu0.2, Y0.8 bathophenanthroline
tris 6,6,7,7,8,8,8-heptafluoro-2,2-dimethyloctanedionato Eu0.2, Y0.8 dimethylaminopyridine
tris 6,6,7,7,8,8,8-heptafluoro-2,2-dimethyloctanedionato Eu0.2, Y0.8 4-picoline-N-oxide
tris 6,6,7,7,8,8,8-heptafluoro-2,2-dimethyloctanedionato Eu0.2, Y0.8 4-phenylpyridine
tris 6,6,7,7,8,8,8-heptafluoro-2,2-dimethyloctanedionato Eu0.2, Y0.8 4-cyanopyridine
tris 6,6,7,7,8,8,8-heptafluoro-2,2-dimethyloctanedionato Eu0.2, Y0.8 4-phenylpyridine-N-oxide
tris 6,6,7,7,8,8,8-heptafluoro-2,2-dimethyloctanedionato Eu0.2, Y0.8 1-methylimidazole
tris 6,6,7,7,8,8,8-heptafluoro-2,2-dimethyloctanedionato Eu0.2, Y0.8 triphenylphosphine oxide
tris 6,6,7,7,8,8,8-heptafluoro-2,2-dimethyloctanedionato Eu0.2, Y0.8 2,2-bipyridyl
tris 6,6,7,7,8,8,8-heptafluoro-2,2-dimethyloctanedionato Eu0.2, Y0.8 2,2-bipyridyl-N,N-dioxide
tris 6,6,7,7,8,8,8-heptafluoro-2,2-dimethyloctanedionato Eu0.2, Y0.8 phenanthroline
tris 6,6,7,7,8,8,8-heptafluoro-2,2-dimethyloctanedionato Eu0.2, Y0.8 bathocuproine
tris 6,6,7,7,8,8,8-heptafluoro-2,2-dimethyloctanedionato Eu0.2, Y0.8 bathophenanthroline
tris 1-phenyl-1,3-butanedionato Eu0.2, Y0.8 dimethylaminopyridine
tris 1-phenyl-1,3-butanedionato Eu0.2, Y0.8 4-picoline-N-oxide
tris 1-phenyl-1,3-butanedionato Eu0.2, Y0.8 4-phenylpyridine
tris 1-phenyl-1,3-butanedionato Eu0.2, Y0.8 4-cyanopyridine
tris 1-phenyl-1,3-butanedionato Eu0.2, Y0.8 4-phenylpyridine-N-oxide
tris 1-phenyl-1,3-butanedionato Eu0.2, Y0.8 1-methylimidazole
tris 1-phenyl-1,3-butanedionato Eu0.2, Y0.8 triphenylphosphine oxide
tris 1-phenyl-1,3-butanedionato Eu0.2, Y0.8 2,2-bipyridyl
tris 1-phenyl-1,3-butanedionato Eu0.2, Y0.8 2,2-bipyridyl-N,N-dioxide
tris 1-phenyl-1,3-butanedionato Eu0.2, Y0.8 phenanthroline
tris 1-phenyl-1,3-butanedionato Eu0.2, Y0.8 bathocuproine
tris 1-phenyl-1,3-butanedionato Eu0.2, Y0.8 bathophenanthroline
tris acetylacetonato Eu0.1, Y0.9 dimethylaminopyridine
tris acetylacetonato Eu0.1, Y0.9 4-picoline-N-oxide
tris acetylacetonato Eu0.1, Y0.9 4-phenylpyridine
tris acetylacetonato Eu0.1, Y0.9 4-cyanopyridine
tris acetylacetonato Eu0.1, Y0.9 4-phenylpyridine-N-oxide
tris acetylacetonato Eu0.1, Y0.9 1-methylimidazole
tris acetylacetonato Eu0.1, Y0.9 triphenylphosphine oxide
tris acetylacetonato Eu0.1, Y0.9 2,2-bipyridyl
tris acetylacetonato Eu0.1, Y0.9 2,2-bipyridyl-N,N-dioxide
tris acetylacetonato Eu0.1, Y0.9 phenanthroline
tris acetylacetonato Eu0.1, Y0.9 bathocuproine
tris acetylacetonato Eu0.1, Y0.9 bathophenanthroline
tris dibenzoylmethanato Eu0.1, Y0.9 dimethylaminopyridine
tris dibenzoylmethanato Eu0.1, Y0.9 4-picoline-N-oxide
tris dibenzoylmethanato Eu0.1, Y0.9 4-phenylpyridine
tris dibenzoylmethanato Eu0.1, Y0.9 4-cyanopyridine
tris dibenzoylmethanato Eu0.1, Y0.9 4-phenylpyridine-N-oxide
tris dibenzoylmethanato Eu0.1, Y0.9 1-methylimidazole
tris dibenzoylmethanato Eu0.1, Y0.9 triphenylphosphine oxide
tris dibenzoylmethanato Eu0.1, Y0.9 2,2-bipyridyl
tris dibenzoylmethanato Eu0.1, Y0.9 2,2-bipyridyl-N,N-dioxide
tris dibenzoylmethanato Eu0.1, Y0.9 phenanthroline
tris dibenzoylmethanato Eu0.1, Y0.9 bathocuproine
tris dibenzoylmethanato Eu0.1, Y0.9 bathophenanthroline
tris thenoyltrifluoroacetonato Eu0.1, Y0.9 dimethylaminopyridine
tris thenoyltrifluoroacetonato Eu0.1, Y0.9 4-picoline-N-oxide
tris thenoyltrifluoroacetonato Eu0.1, Y0.9 4-phenylpyridine
tris thenoyltrifluoroacetonato Eu0.1, Y0.9 4-cyanopyridine
tris thenoyltrifluoroacetonato Eu0.1, Y0.9 4-phenylpyridine-N-oxide
tris thenoyltrifluoroacetonato Eu0.1, Y0.9 1-methylimidazole
tris thenoyltrifluoroacetonato Eu0.1, Y0.9 triphenylphosphine oxide
tris thenoyltrifluoroacetonato Eu0.1, Y0.9 2,2-bipyridyl
tris thenoyltrifluoroacetonato Eu0.1, Y0.9 2,2-bipyridyl-N,N-dioxide
tris thenoyltrifluoroacetonato Eu0.1, Y0.9 phenanthroline
tris thenoyltrifluoroacetonato Eu0.1, Y0.9 bathocuproine
tris thenoyltrifluoroacetonato Eu0.1, Y0.9 bathophenanthroline
tris 2,2,6,6-tetramethylheptanedionato Eu0.1, Y0.9 dimethylaminopyridine
tris 2,2,6,6-tetramethylheptanedionato Eu0.1, Y0.9 4-picoline-N-oxide
tris 2,2,6,6-tetramethylheptanedionato Eu0.1, Y0.9 4-phenylpyridine
tris 2,2,6,6-tetramethylheptanedionato Eu0.1, Y0.9 4-cyanopyridine
tris 2,2,6,6-tetramethylheptanedionato Eu0.1, Y0.9 4-phenylpyridine-N-oxide
tris 2,2,6,6-tetramethylheptanedionato Eu0.1, Y0.9 1-methylimidazole
tris 2,2,6,6-tetramethylheptanedionato Eu0.1, Y0.9 triphenylphosphine oxide
tris 2,2,6,6-tetramethylheptanedionato Eu0.1, Y0.9 2,2-bipyridyl
tris 2,2,6,6-tetramethylheptanedionato Eu0.1, Y0.9 2,2-bipyridyl-N,N-dioxide
tris 2,2,6,6-tetramethylheptanedionato Eu0.1, Y0.9 phenanthroline
tris 2,2,6,6-tetramethylheptanedionato Eu0.1, Y0.9 bathocuproine
tris 2,2,6,6-tetramethylheptanedionato Eu0.1, Y0.9 bathophenanthroline
tris 3-methylpentane-2,4-dionato Eu0.1, Y0.9 dimethylaminopyridine
tris 3-methylpentane-2,4-dionato Eu0.1, Y0.9 4-picoline-N-oxide
tris 3-methylpentane-2,4-dionato Eu0.1, Y0.9 4-phenylpyridine tris 3-methylpentane-2,4-dionato Eu0.1, Y0.9 4-cyanopyridine
tris 3-methylpentane-2,4-dionato Eu0.1, Y0.9 4-phenylpyridine-N-oxide
tris 3-methylpentane-2,4-dionato Eu0.1, Y0.9 1-methylimidazole
tris 3-methylpentane-2,4-dionato Eu0.1, Y0.9 triphenylphosphine oxide
tris 3-methylpentane-2,4-dionato Eu0.1, Y0.9 2,2-bipyridyl
tris 3-methylpentane-2,4-dionato Eu0.1, Y0.9 2,2-bipyridyl-N,N-dioxide
tris 3-methylpentane-2,4-dionato Eu0.1, Y0.9 phenanthroline
tris 3-methylpentane-2,4-dionato Eu0.1, Y0.9 bathocuproine
tris 3-methylpentane-2,4-dionato Eu0.1, Y0.9 bathophenanthroline
tris 3-ethylpentane-2,4-dionato Eu0.1, Y0.9 dimethylaminopyridine
tris 3-ethylpentane-2,4-dionato Eu0.1, Y0.9 4-picoline-N-oxide
tris 3-ethylpentane-2,4-dionato Eu0.1, Y0.9 4-phenylpyridine
tris 3-ethylpentane-2,4-dionato Eu0.1, Y0.9 4-cyanopyridine
tris 3-ethylpentane-2,4-dionato Eu0.1, Y0.9 4-phenylpyridine-N-oxide
tris 3-ethylpentane-2,4-dionato Eu0.1, Y0.9 1-methylimidazole
tris 3-ethylpentane-2,4-dionato Eu0.1, Y0.9 triphenylphosphine oxide
tris 3-ethylpentane-2,4-dionato Eu0.1, Y0.9 2,2-bipyridyl
tris 3-ethylpentane-2,4-dionato Eu0.1, Y0.9 2,2-bipyridyl-N,N-dioxide
tris 3-ethylpentane-2,4-dionato Eu0.1, Y0.9 phenanthroline
tris 3-ethylpentane-2,4-dionato Eu0.1, Y0.9 bathocuproine
tris 3-ethylpentane-2,4-dionato Eu0.1, Y0.9 bathophenanthroline
tris pivaloyltrifluoroacetonato Eu0.1, Y0.9 dimethylaminopyridine
tris pivaloyltrifluoroacetonato Eu0.1, Y0.9 4-picoline-N-oxide
tris pivaloyltrifluoroacetonato Eu0.1, Y0.9 4-phenylpyridine
tris pivaloyltrifluoroacetonato Eu0.1, Y0.9 4-cyanopyridine
tris pivaloyltrifluoroacetonato Eu0.1, Y0.9 4-phenylpyridine-N-oxide
tris pivaloyltrifluoroacetonato Eu0.1, Y0.9 1-methylimidazole
tris pivaloyltrifluoroacetonato Eu0.1, Y0.9 triphenylphosphine oxide
tris pivaloyltrifluoroacetonato Eu0.1, Y0.9 2,2-bipyridyl
tris pivaloyltrifluoroacetonato Eu0.1, Y0.9 2,2-bipyridyl-N,N-dioxide
tris pivaloyltrifluoroacetonato Eu0.1, Y0.9 phenanthroline
tris pivaloyltrifluoroacetonato Eu0.1, Y0.9 bathocuproine
tris pivaloyltrifluoroacetonato Eu0.1, Y0.9 bathophenanthroline
tris trifluoroacetylacetonato Eu0.1, Y0.9 dimethylaminopyridine
tris trifluoroacetylacetonato Eu0.1, Y0.9 4-picoline-N-oxide
tris trifluoroacetylacetonato Eu0.1, Y0.9 4-phenylpyridine
tris trifluoroacetylacetonato Eu0.1, Y0.9 4-cyanopyridine
tris trifluoroacetylacetonato Eu0.1, Y0.9 4-phenylpyridine-N-oxide
tris trifluoroacetylacetonato Eu0.1, Y0.9 1-methylimidazole
tris trifluoroacetylacetonato Eu0.1, Y0.9 triphenylphosphine oxide
tris trifluoroacetylacetonato Eu0.1, Y0.9 2,2-bipyridyl
tris trifluoroacetylacetonato Eu0.1, Y0.9 2,2-bipyridyl-N,N-dioxide
tris trifluoroacetylacetonato Eu0.1, Y0.9 phenanthroline
tris trifluoroacetylacetonato Eu0.1, Y0.9 bathocuproine
tris trifluoroacetylacetonato Eu0.1, Y0.9 bathophenanthroline
tris hexafluoroacetylacetonato Eu0.1, Y0.9 dimethylaminopyridine
tris hexafluoroacetylacetonato Eu0.1, Y0.9 4-picoline-N-oxide
tris hexafluoroacetylacetonato Eu0.1, Y0.9 4-phenylpyridine
tris hexafluoroacetylacetonato Eu0.1, Y0.9 4-cyanopyridine
tris hexafluoroacetylacetonato Eu0.1, Y0.9 4-phenylpyridine-N-oxide
tris hexafluoroacetylacetonato Eu0.1, Y0.9 1-methylimidazole
tris hexafluoroacetylacetonato Eu0.1, Y0.9 triphenylphosphine oxide
tris hexafluoroacetylacetonato Eu0.1, Y0.9 2,2-bipyridyl
tris hexafluoroacetylacetonato Eu0.1, Y0.9 2,2-bipyridyl-N,N-dioxide
tris hexafluoroacetylacetonato Eu0.1, Y0.9 phenanthroline
tris hexafluoroacetylacetonato Eu0.1, Y0.9 bathocuproine
tris hexafluoroacetylacetonato Eu0.1, Y0.9 bathophenanthroline
tris 6,6,7,7,8,8,8-heptafluoro-2,2-dimethyloctanedionato Eu0.1, Y0.9 dimethylaminopyridine
tris 6,6,7,7,8,8,8-heptafluoro-2,2-dimethyloctanedionato Eu0.1, Y0.9 4-picoline-N-oxide
tris 6,6,7,7,8,8,8-heptafluoro-2,2-dimethyloctanedionato Eu0.1, Y0.9 4-phenylpyridine
tris 6,6,7,7,8,8,8-heptafluoro-2,2-dimethyloctanedionato Eu0.1, Y0.9 4-cyanopyridine
tris 6,6,7,7,8,8,8-heptafluoro-2,2-dimethyloctanedionato Eu0.1, Y0.9 4-phenylpyridine-N-oxide
tris 6,6,7,7,8,8,8-heptafluoro-2,2-dimethyloctanedionato Eu0.1, Y0.9 1-methylimidazole
tris 6,6,7,7,8,8,8-heptafluoro-2,2-dimethyloctanedionato Eu0.1, Y0.9 triphenylphosphine oxide
tris 6,6,7,7,8,8,8-heptafluoro-2,2-dimethyloctanedionato Eu0.1, Y0.9 2,2-bipyridyl
tris 6,6,7,7,8,8,8-heptafluoro-2,2-dimethyloctanedionato Eu0.1, Y0.9 2,2-bipyridyl-N,N-dioxide
tris 6,6,7,7,8,8,8-heptafluoro-2,2-dimethyloctanedionato Eu0.1, Y0.9 phenanthroline
tris 6,6,7,7,8,8,8-heptafluoro-2,2-dimethyloctanedionato Eu0.1, Y0.9 bathocuproine
tris 6,6,7,7,8,8,8-heptafluoro-2,2-dimethyloctanedionato Eu0.1, Y0.9 bathophenanthroline
tris 1-phenyl-1,3-butanedionato Eu0.1, Y0.9 dimethylaminopyridine
tris 1-phenyl-1,3-butanedionato Eu0.1, Y0.9 4-picoline-N-oxide
tris 1-phenyl-1,3-butanedionato Eu0.1, Y0.9 4-phenylpyridine
tris 1-phenyl-1,3-butanedionato Eu0.1, Y0.9 4-cyanopyridine
tris 1-phenyl-1,3-butanedionato Eu0.1, Y0.9 4-phenylpyridine-N-oxide
tris 1-phenyl-1,3-butanedionato Eu0.1, Y0.9 1-methylimidazole
tris 1-phenyl-1,3-butanedionato Eu0.1, Y0.9 triphenylphosphine oxide
tris 1-phenyl-1,3-butanedionato Eu0.1, Y0.9 2,2-bipyridyl
tris 1-phenyl-1,3-butanedionato Eu0.1, Y0.9 2,2-bipyridyl-N,N-dioxide tris 1-phenyl-1,3-butanedionato Eu0.1, Y0.9 phenanthroline
tris 1-phenyl-1,3-butanedionato Eu0.1, Y0.9 bathocuproine
tris 1-phenyl-1,3-butanedionato Eu0.1, Y0.9 bathophenanthroline
tris acetylacetonato Eu0.01, Y0.99 dimethylaminopyridine
tris acetylacetonato Eu0.01, Y0.99 4-picoline-N-oxide
tris acetylacetonato Eu0.01, Y0.99 4-phenylpyridine
tris acetylacetonato Eu0.01, Y0.99 4-cyanopyridine
tris acetylacetonato Eu0.01, Y0.99 4-phenylpyridine-N-oxide
tris acetylacetonato Eu0.01, Y0.99 1-methylimidazole
tris acetylacetonato Eu0.01, Y0.99 triphenylphosphine oxide
tris acetylacetonato Eu0.01, Y0.99 2,2-bipyridyl
tris acetylacetonato Eu0.01, Y0.99 2,2-bipyridyl-N,N-dioxide
tris acetylacetonato Eu0.01, Y0.99 phenanthroline
tris acetylacetonato Eu0.01, Y0.99 bathocuproine
tris acetylacetonato Eu0.01, Y0.99 bathophenanthroline
tris dibenzoylmethanato Eu0.01, Y0.99 dimethylaminopyridine
tris dibenzoylmethanato Eu0.01, Y0.99 4-picoline-N-oxide
tris dibenzoylmethanato Eu0.01, Y0.99 4-phenylpyridine
tris dibenzoylmethanato Eu0.01, Y0.99 4-cyanopyridine
tris dibenzoylmethanato Eu0.01, Y0.99 4-phenylpyridine-N-oxide
tris dibenzoylmethanato Eu0.01, Y0.99 1-methylimidazole
tris dibenzoylmethanato Eu0.01, Y0.99 triphenylphosphine oxide
tris dibenzoylmethanato Eu0.01, Y0.99 2,2-bipyridyl
tris dibenzoylmethanato Eu0.01, Y0.99 2,2-bipyridyl-N,N-dioxide
tris dibenzoylmethanato Eu0.01, Y0.99 phenanthroline
tris dibenzoylmethanato Eu0.01, Y0.99 bathocuproine
tris dibenzoylmethanato Eu0.01, Y0.99 bathophenanthroline
tris thenoyltrifluoroacetonato Eu0.01, Y0.99 dimethylaminopyridine
tris thenoyltrifluoroacetonato Eu0.01, Y0.99 4-picoline-N-oxide
tris thenoyltrifluoroacetonato Eu0.01, Y0.99 4-phenylpyridine
tris thenoyltrifluoroacetonato Eu0.01, Y0.99 4-cyanopyridine
tris thenoyltrifluoroacetonato Eu0.01, Y0.99 4-phenylpyridine-N-oxide
tris thenoyltrifluoroacetonato Eu0.01, Y0.99 1-methylimidazole
tris thenoyltrifluoroacetonato Eu0.01, Y0.99 triphenylphosphine oxide
tris thenoyltrifluoroacetonato Eu0.01, Y0.99 2,2-bipyridyl
tris thenoyltrifluoroacetonato Eu0.01, Y0.99 2,2-bipyridyl-N,N-dioxide
tris thenoyltrifluoroacetonato Eu0.01, Y0.99 phenanthroline
tris thenoyltrifluoroacetonato Eu0.01, Y0.99 bathocuproine
tris thenoyltrifluoroacetonato Eu0.01, Y0.99 bathophenanthroline
tris 2,2,6,6-tetramethylheptanedionato Eu0.01, Y0.99 dimethylaminopyridine
tris 2,2,6,6-tetramethylheptanedionato Eu0.01, Y0.99 4-picoline-N-oxide
tris 2,2,6,6-tetramethylheptanedionato Eu0.01, Y0.99 4-phenylpyridine
tris 2,2,6,6-tetramethylheptanedionato Eu0.01, Y0.99 4-cyanopyridine
tris 2,2,6,6-tetramethylheptanedionato Eu0.01, Y0.99 4-phenylpyridine-N-oxide
tris 2,2,6,6-tetramethylheptanedionato Eu0.01, Y0.99 1-methylimidazole
tris 2,2,6,6-tetramethylheptanedionato Eu0.01, Y0.99 triphenylphosphine oxide
tris 2,2,6,6-tetramethylheptanedionato Eu0.01, Y0.99 2,2-bipyridyl
tris 2,2,6,6-tetramethylheptanedionato Eu0.01, Y0.99 2,2-bipyridyl-N,N-dioxide
tris 2,2,6,6-tetramethylheptanedionato Eu0.01, Y0.99 phenanthroline
tris 2,2,6,6-tetramethylheptanedionato Eu0.01, Y0.99 bathocuproine
tris 2,2,6,6-tetramethylheptanedionato Eu0.01, Y0.99 bathophenanthroline
tris 3-methylpentane-2,4-dionato Eu0.01, Y0.99 dimethylaminopyridine
tris 3-methylpentane-2,4-dionato Eu0.01, Y0.99 4-picoline-N-oxide
tris 3-methylpentane-2,4-dionato Eu0.01, Y0.99 4-phenylpyridine
tris 3-methylpentane-2,4-dionato Eu0.01, Y0.99 4-cyanopyridine
tris 3-methylpentane-2,4-dionato Eu0.01, Y0.99 4-phenylpyridine-N-oxide
tris 3-methylpentane-2,4-dionato Eu0.01, Y0.99 1-methylimidazole
tris 3-methylpentane-2,4-dionato Eu0.01, Y0.99 triphenylphosphine oxide
tris 3-methylpentane-2,4-dionato Eu0.01, Y0.99 2,2-bipyridyl
tris 3-methylpentane-2,4-dionato Eu0.01, Y0.99 2,2-bipyridyl-N,N-dioxide
tris 3-methylpentane-2,4-dionato Eu0.01, Y0.99 phenanthroline
tris 3-methylpentane-2,4-dionato Eu0.01, Y0.99 bathocuproine
tris 3-methylpentane-2,4-dionato Eu0.01, Y0.99 bathophenanthroline
tris 3-ethylpentane-2,4-dionato Eu0.01, Y0.99 dimethylaminopyridine
tris 3-ethylpentane-2,4-dionato Eu0.01, Y0.99 4-picoline-N-oxide
tris 3-ethylpentane-2,4-dionato Eu0.01, Y0.99 4-phenylpyridine
tris 3-ethylpentane-2,4-dionato Eu0.01, Y0.99 4-cyanopyridine
tris 3-ethylpentane-2,4-dionato Eu0.01, Y0.99 4-phenylpyridine-N-oxide
tris 3-ethylpentane-2,4-dionato Eu0.01, Y0.99 1-methylimidazole
tris 3-ethylpentane-2,4-dionato Eu0.01, Y0.99 triphenylphosphine oxide
tris 3-ethylpentane-2,4-dionato Eu0.01, Y0.99 2,2-bipyridyl
tris 3-ethylpentane-2,4-dionato Eu0.01, Y0.99 2,2-bipyridyl-N,N-dioxide
tris 3-ethylpentane-2,4-dionato Eu0.01, Y0.99 phenanthroline
tris 3-ethylpentane-2,4-dionato Eu0.01, Y0.99 bathocuproine
tris 3-ethylpentane-2,4-dionato Eu0.01, Y0.99 bathophenanthroline
tris pivaloyltrifluoroacetonato Eu0.01, Y0.99 dimethylaminopyridine
tris pivaloyltrifluoroacetonato Eu0.01, Y0.99 4-picoline-N-oxide
tris pivaloyltrifluoroacetonato Eu0.01, Y0.99 4-phenylpyridine
tris pivaloyltrifluoroacetonato Eu0.01, Y0.99 4-cyanopyridine tris pivaloyltrifluoroacetonato Eu0.01, Y0.99 4-phenylpyridine-N-oxide
tris pivaloyltrifluoroacetonato Eu0.01, Y0.99 1-methylimidazole
tris pivaloyltrifluoroacetonato Eu0.01, Y0.99 triphenylphosphine oxide
tris pivaloyltrifluoroacetonato Eu0.01, Y0.99 2,2-bipyridyl
tris pivaloyltrifluoroacetonato Eu0.01, Y0.99 2,2-bipyridyl-N,N-dioxide
tris pivaloyltrifluoroacetonato Eu0.01, Y0.99 phenanthroline
tris pivaloyltrifluoroacetonato Eu0.01, Y0.99 bathocuproine
tris pivaloyltrifluoroacetonato Eu0.01, Y0.99 bathophenanthroline
tris trifluoroacetylacetonato Eu0.01, Y0.99 dimethylaminopyridine
tris trifluoroacetylacetonato Eu0.01, Y0.99 4-picoline-N-oxide
tris trifluoroacetylacetonato Eu0.01, Y0.99 4-phenylpyridine
tris trifluoroacetylacetonato Eu0.01, Y0.99 4-cyanopyridine
tris trifluoroacetylacetonato Eu0.01, Y0.99 4-phenylpyridine-N-oxide
tris trifluoroacetylacetonato Eu0.01, Y0.99 1-methylimidazole
tris trifluoroacetylacetonato Eu0.01, Y0.99 triphenylphosphine oxide
tris trifluoroacetylacetonato Eu0.01, Y0.99 2,2-bipyridyl
tris trifluoroacetylacetonato Eu0.01, Y0.99 2,2-bipyridyl-N,N-dioxide
tris trifluoroacetylacetonato Eu0.01, Y0.99 phenanthroline
tris trifluoroacetylacetonato Eu0.01, Y0.99 bathocuproine
tris trifluoroacetylacetonato Eu0.01, Y0.99 bathophenanthroline
tris hexafluoroacetylacetonato Eu0.01, Y0.99 dimethylaminopyridine
tris hexafluoroacetylacetonato Eu0.01, Y0.99 4-picoline-N-oxide
tris hexafluoroacetylacetonato Eu0.01, Y0.99 4-phenylpyridine
tris hexafluoroacetylacetonato Eu0.01, Y0.99 4-cyanopyridine
tris hexafluoroacetylacetonato Eu0.01, Y0.99 4-phenylpyridine-N-oxide
tris hexafluoroacetylacetonato Eu0.01, Y0.99 1-methylimidazole
tris hexafluoroacetylacetonato Eu0.01, Y0.99 triphenylphosphine oxide
tris hexafluoroacetylacetonato Eu0.01, Y0.99 2,2-bipyridyl
tris hexafluoroacetylacetonato Eu0.01, Y0.99 2,2-bipyridyl-N,N-dioxide
tris hexafluoroacetylacetonato Eu0.01, Y0.99 phenanthroline
tris hexafluoroacetylacetonato Eu0.01, Y0.99 bathocuproine
tris hexafluoroacetylacetonato Eu0.01, Y0.99 bathophenanthroline
tris 6,6,7,7,8,8,8-heptafluoro-2,2-dimethyloctanedionato Eu0.01, Y0.99 dimethylaminopyridine
tris 6,6,7,7,8,8,8-heptafluoro-2,2-dimethyloctanedionato Eu0.01, Y0.99 4-picoline-N-oxide
tris 6,6,7,7,8,8,8-heptafluoro-2,2-dimethyloctanedionato Eu0.01, Y0.99 4-phenylpyridine
tris 6,6,7,7,8,8,8-heptafluoro-2,2-dimethyloctanedionato Eu0.01, Y0.99 4-cyanopyridine
tris 6,6,7,7,8,8,8-heptafluoro-2,2-dimethyloctanedionato Eu0.01, Y0.99 4-phenylpyridine-N-oxide
tris 6,6,7,7,8,8,8-heptafluoro-2,2-dimethyloctanedionato Eu0.01, Y0.99 1-methylimidazole
tris 6,6,7,7,8,8,8-heptafluoro-2,2-dimethyloctanedionato Eu0.01, Y0.99 triphenylphosphine oxide
tris 6,6,7,7,8,8,8-heptafluoro-2,2-dimethyloctanedionato Eu0.01, Y0.99 2,2-bipyridyl
tris 6,6,7,7,8,8,8-heptafluoro-2,2-dimethyloctanedionato Eu0.01, Y0.99 2,2-bipyridyl-N,N-dioxide
tris 6,6,7,7,8,8,8-heptafluoro-2,2-dimethyloctanedionato Eu0.01, Y0.99 phenanthroline
tris 6,6,7,7,8,8,8-heptafluoro-2,2-dimethyloctanedionato Eu0.01, Y0.99 bathocuproine
tris 6,6,7,7,8,8,8-heptafluoro-2,2-dimethyloctanedionato Eu0.01, Y0.99 bathophenanthroline
tris 1-phenyl-1,3-butanedionato Eu0.01, Y0.99 dimethylaminopyridine
tris 1-phenyl-1,3-butanedionato Eu0.01, Y0.99 4-picoline-N-oxide
tris 1-phenyl-1,3-butanedionato Eu0.01, Y0.99 4-phenylpyridine
tris 1-phenyl-1,3-butanedionato Eu0.01, Y0.99 4-cyanopyridine
tris 1-phenyl-1,3-butanedionato Eu0.01, Y0.99 4-phenylpyridine-N-oxide
tris 1-phenyl-1,3-butanedionato Eu0.01, Y0.99 1-methylimidazole
tris 1-phenyl-1,3-butanedionato Eu0.01, Y0.99 triphenylphosphine oxide
tris 1-phenyl-1,3-butanedionato Eu0.01, Y0.99 2,2-bipyridyl
tris 1-phenyl-1,3-butanedionato Eu0.01, Y0.99 2,2-bipyridyl-N,N-dioxide
tris 1-phenyl-1,3-butanedionato Eu0.01, Y0.99 phenanthroline
tris 1-phenyl-1,3-butanedionato Eu0.01, Y0.99 bathocuproine
tris 1-phenyl-1,3-butanedionato Eu0.01, Y0.99 bathophenanthroline
tris acetylacetonato Tb0.5, La0.5 dimethylaminopyridine
tris acetylacetonato Tb0.5, La0.5 4-picoline-N-oxide
tris acetylacetonato Tb0.5, La0.5 4-phenylpyridine
tris acetylacetonato Tb0.5, La0.5 4-cyanopyridine
tris acetylacetonato Tb0.5, La0.5 4-phenylpyridine-N-oxide
tris acetylacetonato Tb0.5, La0.5 1-methylimidazole
tris acetylacetonato Tb0.5, La0.5 triphenylphosphine oxide
tris acetylacetonato Tb0.5, La0.5 2,2-bipyridyl
tris acetylacetonato Tb0.5, La0.5 2,2-bipyridyl-N,N-dioxide
tris acetylacetonato Tb0.5, La0.5 phenanthroline
tris acetylacetonato Tb0.5, La0.5 bathocuproine
tris acetylacetonato Tb0.5, La0.5 bathophenanthroline
tris dibenzoylmethanato Tb0.5, La0.5 dimethylaminopyridine
tris dibenzoylmethanato Tb0.5, La0.5 4-picoline-N-oxide
tris dibenzoylmethanato Tb0.5, La0.5 4-phenylpyridine
tris dibenzoylmethanato Tb0.5, La0.5 4-cyanopyridine
tris dibenzoylmethanato Tb0.5, La0.5 4-phenylpyridine-N-oxide
tris dibenzoylmethanato Tb0.5, La0.5 1-methylimidazole
tris dibenzoylmethanato Tb0.5, La0.5 triphenylphosphine oxide
tris dibenzoylmethanato Tb0.5, La0.5 2,2-bipyridyl
tris dibenzoylmethanato Tb0.5, La0.5 2,2-bipyridyl-N,N-dioxide
tris dibenzoylmethanato Tb0.5, La0.5 phenanthroline
tris dibenzoylmethanato Tb0.5, La0.5 bathocuproine
tris dibenzoylmethanato Tb0.5, La0.5 bathophenanthroline tris thenoyltrifluoroacetonato Tb0.5, La0.5 dimethylaminopyridine
tris thenoyltrifluoroacetonato Tb0.5, La0.5 4-picoline-N-oxide
tris thenoyltrifluoroacetonato Tb0.5, La0.5 4-phenylpyridine
tris thenoyltrifluoroacetonato Tb0.5, La0.5 4-cyanopyridine
tris thenoyltrifluoroacetonato Tb0.5, La0.5 4-phenylpyridine-N-oxide
tris thenoyltrifluoroacetonato Tb0.5, La0.5 1-methylimidazole
tris thenoyltrifluoroacetonato Tb0.5, La0.5 triphenylphosphine oxide
tris thenoyltrifluoroacetonato Tb0.5, La0.5 2,2-bipyridyl
tris thenoyltrifluoroacetonato Tb0.5, La0.5 2,2-bipyridyl-N,N-dioxide
tris thenoyltrifluoroacetonato Tb0.5, La0.5 phenanthroline
tris thenoyltrifluoroacetonato Tb0.5, La0.5 bathocuproine
tris thenoyltrifluoroacetonato Tb0.5, La0.5 bathophenanthroline
tris 2,2,6,6-tetramethylheptanedionato Tb0.5, La0.5 dimethylaminopyridine
tris 2,2,6,6-tetramethylheptanedionato Tb0.5, La0.5 4-picoline-N-oxide
tris 2,2,6,6-tetramethylheptanedionato Tb0.5, La0.5 4-phenylpyridine
tris 2,2,6,6-tetramethylheptanedionato Tb0.5, La0.5 4-cyanopyridine
tris 2,2,6,6-tetramethylheptanedionato Tb0.5, La0.5 4-phenylpyridine-N-oxide
tris 2,2,6,6-tetramethylheptanedionato Tb0.5, La0.5 1-methylimidazole
tris 2,2,6,6-tetramethylheptanedionato Tb0.5, La0.5 triphenylphosphine oxide
tris 2,2,6,6-tetramethylheptanedionato Tb0.5, La0.5 2,2-bipyridyl
tris 2,2,6,6-tetramethylheptanedionato Tb0.5, La0.5 2,2-bipyridyl-N,N-dioxide
tris 2,2,6,6-tetramethylheptanedionato Tb0.5, La0.5 phenanthroline
tris 2,2,6,6-tetramethylheptanedionato Tb0.5, La0.5 bathocuproine
tris 2,2,6,6-tetramethylheptanedionato Tb0.5, La0.5 bathophenanthroline
tris 3-methylpentane-2,4-dionato Tb0.5, La0.5 dimethylaminopyridine
tris 3-methylpentane-2,4-dionato Tb0.5, La0.5 4-picoline-N-oxide
tris 3-methylpentane-2,4-dionato Tb0.5, La0.5 4-phenylpyridine
tris 3-methylpentane-2,4-dionato Tb0.5, La0.5 4-cyanopyridine
tris 3-methylpentane-2,4-dionato Tb0.5, La0.5 4-phenylpyridine-N-oxide
tris 3-methylpentane-2,4-dionato Tb0.5, La0.5 1-methylimidazole
tris 3-methylpentane-2,4-dionato Tb0.5, La0.5 triphenylphosphine oxide
tris 3-methylpentane-2,4-dionato Tb0.5, La0.5 2,2-bipyridyl
tris 3-methylpentane-2,4-dionato Tb0.5, La0.5 2,2-bipyridyl-N,N-dioxide
tris 3-methylpentane-2,4-dionato Tb0.5, La0.5 phenanthroline
tris 3-methylpentane-2,4-dionato Tb0.5, La0.5 bathocuproine
tris 3-methylpentane-2,4-dionato Tb0.5, La0.5 bathophenanthroline
tris 3-ethylpentane-2,4-dionato Tb0.5, La0.5 dimethylaminopyridine
tris 3-ethylpentane-2,4-dionato Tb0.5, La0.5 4-picoline-N-oxide
tris 3-ethylpentane-2,4-dionato Tb0.5, La0.5 4-phenylpyridine
tris 3-ethylpentane-2,4-dionato Tb0.5, La0.5 4-cyanopyridine
tris 3-ethylpentane-2,4-dionato Tb0.5, La0.5 4-phenylpyridine-N-oxide
tris 3-ethylpentane-2,4-dionato Tb0.5, La0.5 1-methylimidazole
tris 3-ethylpentane-2,4-dionato Tb0.5, La0.5 triphenylphosphine oxide
tris 3-ethylpentane-2,4-dionato Tb0.5, La0.5 2,2-bipyridyl
tris 3-ethylpentane-2,4-dionato Tb0.5, La0.5 2,2-bipyridyl-N,N-dioxide
tris 3-ethylpentane-2,4-dionato Tb0.5, La0.5 phenanthroline
tris 3-ethylpentane-2,4-dionato Tb0.5, La0.5 bathocuproine
tris 3-ethylpentane-2,4-dionato Tb0.5, La0.5 bathophenanthroline
tris pivaloyltrifluoroacetonato Tb0.5, La0.5 dimethylaminopyridine
tris pivaloyltrifluoroacetonato Tb0.5, La0.5 4-picoline-N-oxide
tris pivaloyltrifluoroacetonato Tb0.5, La0.5 4-phenylpyridine
tris pivaloyltrifluoroacetonato Tb0.5, La0.5 4-cyanopyridine
tris pivaloyltrifluoroacetonato Tb0.5, La0.5 4-phenylpyridine-N-oxide
tris pivaloyltrifluoroacetonato Tb0.5, La0.5 1-methylimidazole
tris pivaloyltrifluoroacetonato Tb0.5, La0.5 triphenylphosphine oxide
tris pivaloyltrifluoroacetonato Tb0.5, La0.5 2,2-bipyridyl
tris pivaloyltrifluoroacetonato Tb0.5, La0.5 2,2-bipyridyl-N,N-dioxide
tris pivaloyltrifluoroacetonato Tb0.5, La0.5 phenanthroline
tris pivaloyltrifluoroacetonato Tb0.5, La0.5 bathocuproine
tris pivaloyltrifluoroacetonato Tb0.5, La0.5 bathophenanthroline
tris trifluoroacetylacetonato Tb0.5, La0.5 dimethylaminopyridine
tris trifluoroacetylacetonato Tb0.5, La0.5 4-picoline-N-oxide
tris trifluoroacetylacetonato Tb0.5, La0.5 4-phenylpyridine
tris trifluoroacetylacetonato Tb0.5, La0.5 4-cyanopyridine
tris trifluoroacetylacetonato Tb0.5, La0.5 4-phenylpyridine-N-oxide
tris trifluoroacetylacetonato Tb0.5, La0.5 1-methylimidazole
tris trifluoroacetylacetonato Tb0.5, La0.5 triphenylphosphine oxide
tris trifluoroacetylacetonato Tb0.5, La0.5 2,2-bipyridyl
tris trifluoroacetylacetonato Tb0.5, La0.5 2,2-bipyridyl-N,N-dioxide
tris trifluoroacetylacetonato Tb0.5, La0.5 phenanthroline
tris trifluoroacetylacetonato Tb0.5, La0.5 bathocuproine
tris trifluoroacetylacetonato Tb0.5, La0.5 bathophenanthroline
tris hexafluoroacetylacetonato Tb0.5, La0.5 dimethylaminopyridine
tris hexafluoroacetylacetonato Tb0.5, La0.5 4-picoline-N-oxide
tris hexafluoroacetylacetonato Tb0.5, La0.5 4-phenylpyridine tris hexafluoroacetylacetonato Tb0.5, La0.5 4-cyanopyridine
tris hexafluoroacetylacetonato Tb0.5, La0.5 4-phenylpyridine-N-oxide
tris hexafluoroacetylacetonato Tb0.5, La0.5 1-methylimidazole
tris hexafluoroacetylacetonato Tb0.5, La0.5 triphenylphosphine oxide
tris hexafluoroacetylacetonato Tb0.5, La0.5 2,2-bipyridyl
tris hexafluoroacetylacetonato Tb0.5, La0.5 2,2-bipyridyl-N,N-dioxide
tris hexafluoroacetylacetonato Tb0.5, La0.5 phenanthroline
tris hexafluoroacetylacetonato Tb0.5, La0.5 bathocuproine
tris hexafluoroacetylacetonato Tb0.5, La0.5 bathophenanthroline
tris 6,6,7,7,8,8,8-heptafluoro-2,2-dimethyloctanedionato Tb0.5, La0.5 dimethylaminopyridine
tris 6,6,7,7,8,8,8-heptafluoro-2,2-dimethyloctanedionato Tb0.5, La0.5 4-picoline-N-oxide
tris 6,6,7,7,8,8,8-heptafluoro-2,2-dimethyloctanedionato Tb0.5, La0.5 4-phenylpyridine
tris 6,6,7,7,8,8,8-heptafluoro-2,2-dimethyloctanedionato Tb0.5, La0.5 4-cyanopyridine
tris 6,6,7,7,8,8,8-heptafluoro-2,2-dimethyloctanedionato Tb0.5, La0.5 4-phenylpyridine-N-oxide
tris 6,6,7,7,8,8,8-heptafluoro-2,2-dimethyloctanedionato Tb0.5, La0.5 1-methylimidazole
tris 6,6,7,7,8,8,8-heptafluoro-2,2-dimethyloctanedionato Tb0.5, La0.5 triphenylphosphine oxide
tris 6,6,7,7,8,8,8-heptafluoro-2,2-dimethyloctanedionato Tb0.5, La0.5 2,2-bipyridyl
tris 6,6,7,7,8,8,8-heptafluoro-2,2-dimethyloctanedionato Tb0.5, La0.5 2,2-bipyridyl-N,N-dioxide
tris 6,6,7,7,8,8,8-heptafluoro-2,2-dimethyloctanedionato Tb0.5, La0.5 phenanthroline
tris 6,6,7,7,8,8,8-heptafluoro-2,2-dimethyloctanedionato Tb0.5, La0.5 bathocuproine
tris 6,6,7,7,8,8,8-heptafluoro-2,2-dimethyloctanedionato Tb0.5, La0.5 bathophenanthroline
tris 1-phenyl-1,3-butanedionato Tb0.5, La0.5 dimethylaminopyridine
tris 1-phenyl-1,3-butanedionato Tb0.5, La0.5 4-picoline-N-oxide
tris 1-phenyl-1,3-butanedionato Tb0.5, La0.5 4-phenylpyridine
tris 1-phenyl-1,3-butanedionato Tb0.5, La0.5 4-cyanopyridine
tris 1-phenyl-1,3-butanedionato Tb0.5, La0.5 4-phenylpyridine-N-oxide
tris 1-phenyl-1,3-butanedionato Tb0.5, La0.5 1-methylimidazole
tris 1-phenyl-1,3-butanedionato Tb0.5, La0.5 triphenylphosphine oxide
tris 1-phenyl-1,3-butanedionato Tb0.5, La0.5 2,2-bipyridyl
tris 1-phenyl-1,3-butanedionato Tb0.5, La0.5 2,2-bipyridyl-N,N-dioxide
tris 1-phenyl-1,3-butanedionato Tb0.5, La0.5 phenanthroline
tris 1-phenyl-1,3-butanedionato Tb0.5, La0.5 bathocuproine
tris 1-phenyl-1,3-butanedionato Tb0.5, La0.5 bathophenanthroline
tris acetylacetonato Tb0.2, La0.8 dimethylaminopyridine
tris acetylacetonato Tb0.2, La0.8 4-picoline-N-oxide
tris acetylacetonato Tb0.2, La0.8 4-phenylpyridine
tris acetylacetonato Tb0.2, La0.8 4-cyanopyridine
tris acetylacetonato Tb0.2, La0.8 4-phenylpyridine-N-oxide
tris acetylacetonato Tb0.2, La0.8 1-methylimidazole
tris acetylacetonato Tb0.2, La0.8 triphenylphosphine oxide
tris acetylacetonato Tb0.2, La0.8 2,2-bipyridyl
tris acetylacetonato Tb0.2, La0.8 2,2-bipyridyl-N,N-dioxide
tris acetylacetonato Tb0.2, La0.8 phenanthroline
tris acetylacetonato Tb0.2, La0.8 bathocuproine
tris acetylacetonato Tb0.2, La0.8 bathophenanthroline
tris dibenzoylmethanato Tb0.2, La0.8 dimethylaminopyridine
tris dibenzoylmethanato Tb0.2, La0.8 4-picoline-N-oxide
tris dibenzoylmethanato Tb0.2, La0.8 4-phenylpyridine
tris dibenzoylmethanato Tb0.2, La0.8 4-cyanopyridine
tris dibenzoylmethanato Tb0.2, La0.8 4-phenylpyridine-N-oxide
tris dibenzoylmethanato Tb0.2, La0.8 1-methylimidazole
tris dibenzoylmethanato Tb0.2, La0.8 triphenylphosphine oxide
tris dibenzoylmethanato Tb0.2, La0.8 2,2-bipyridyl
tris dibenzoylmethanato Tb0.2, La0.8 2,2-bipyridyl-N,N-dioxide
tris dibenzoylmethanato Tb0.2, La0.8 phenanthroline
tris dibenzoylmethanato Tb0.2, La0.8 bathocuproine
tris dibenzoylmethanato Tb0.2, La0.8 bathophenanthroline
tris thenoyltrifluoroacetonato Tb0.2, La0.8 dimethylaminopyridine
tris thenoyltrifluoroacetonato Tb0.2, La0.8 4-picoline-N-oxide
tris thenoyltrifluoroacetonato Tb0.2, La0.8 4-phenylpyridine
tris thenoyltrifluoroacetonato Tb0.2, La0.8 4-cyanopyridine
tris thenoyltrifluoroacetonato Tb0.2, La0.8 4-phenylpyridine-N-oxide
tris thenoyltrifluoroacetonato Tb0.2, La0.8 1-methylimidazole
tris thenoyltrifluoroacetonato Tb0.2, La0.8 triphenylphosphine oxide
tris thenoyltrifluoroacetonato Tb0.2, La0.8 2,2-bipyridyl
tris thenoyltrifluoroacetonato Tb0.2, La0.8 2,2-bipyridyl-N,N-dioxide
tris thenoyltrifluoroacetonato Tb0.2, La0.8 phenanthroline
tris thenoyltrifluoroacetonato Tb0.2, La0.8 bathocuproine
tris thenoyltrifluoroacetonato Tb0.2, La0.8 bathophenanthroline
tris 2,2,6,6-tetramethylheptanedionato Tb0.2, La0.8 dimethylaminopyridine
tris 2,2,6,6-tetramethylheptanedionato Tb0.2, La0.8 4-picoline-N-oxide
tris 2,2,6,6-tetramethylheptanedionato Tb0.2, La0.8 4-phenylpyridine
tris 2,2,6,6-tetramethylheptanedionato Tb0.2, La0.8 4-cyanopyridine
tris 2,2,6,6-tetramethylheptanedionato Tb0.2, La0.8 4-phenylpyridine-N-oxide
tris 2,2,6,6-tetramethylheptanedionato Tb0.2, La0.8 1-methylimidazole
tris 2,2,6,6-tetramethylheptanedionato Tb0.2, La0.8 triphenylphosphine oxide
tris 2,2,6,6-tetramethylheptanedionato Tb0.2, La0.8 2,2-bipyridyl
tris 2,2,6,6-tetramethylheptanedionato Tb0.2, La0.8 2,2-bipyridyl-N,N-dioxide
tris 2,2,6,6-tetramethylheptanedionato Tb0.2, La0.8 phenanthroline
tris 2,2,6,6-tetramethylheptanedionato Tb0.2, La0.8 bathocuproine
tris 2,2,6,6-tetramethylheptanedionato Tb0.2, La0.8 bathophenanthroline
tris 3-methylpentane-2,4-dionato Tb0.2, La0.8 dimethylaminopyridine tris 3-methylpentane-2,4-dionato Tb0.2, La0.8 4-picoline-N-oxide
tris 3-methylpentane-2,4-dionato Tb0.2, La0.8 4-phenylpyridine
tris 3-methylpentane-2,4-dionato Tb0.2, La0.8 4-cyanopyridine
tris 3-methylpentane-2,4-dionato Tb0.2, La0.8 4-phenylpyridine-N-oxide
tris 3-methylpentane-2,4-dionato Tb0.2, La0.8 1-methylimidazole
tris 3-methylpentane-2,4-dionato Tb0.2, La0.8 triphenylphosphine oxide
tris 3-methylpentane-2,4-dionato Tb0.2, La0.8 2,2-bipyridyl
tris 3-methylpentane-2,4-dionato Tb0.2, La0.8 2,2-bipyridyl-N,N-dioxide
tris 3-methylpentane-2,4-dionato Tb0.2, La0.8 phenanthroline
tris 3-methylpentane-2,4-dionato Tb0.2, La0.8 bathocuproine
tris 3-methylpentane-2,4-dionato Tb0.2, La0.8 bathophenanthroline
tris 3-ethylpentane-2,4-dionato Tb0.2, La0.8 dimethylaminopyridine
tris 3-ethylpentane-2,4-dionato Tb0.2, La0.8 4-picoline-N-oxide
tris 3-ethylpentane-2,4-dionato Tb0.2, La0.8 4-phenylpyridine
tris 3-ethylpentane-2,4-dionato Tb0.2, La0.8 4-cyanopyridine
tris 3-ethylpentane-2,4-dionato Tb0.2, La0.8 4-phenylpyridine-N-oxide
tris 3-ethylpentane-2,4-dionato Tb0.2, La0.8 1-methylimidazole
tris 3-ethylpentane-2,4-dionato Tb0.2, La0.8 triphenylphosphine oxide
tris 3-ethylpentane-2,4-dionato Tb0.2, La0.8 2,2-bipyridyl
tris 3-ethylpentane-2,4-dionato Tb0.2, La0.8 2,2-bipyridyl-N,N-dioxide
tris 3-ethylpentane-2,4-dionato Tb0.2, La0.8 phenanthroline
tris 3-ethylpentane-2,4-dionato Tb0.2, La0.8 bathocuproine
tris 3-ethylpentane-2,4-dionato Tb0.2, La0.8 bathophenanthroline
tris pivaloyltrifluoroacetonato Tb0.2, La0.8 dimethylaminopyridine
tris pivaloyltrifluoroacetonato Tb0.2, La0.8 4-picoline-N-oxide
tris pivaloyltrifluoroacetonato Tb0.2, La0.8 4-phenylpyridine
tris pivaloyltrifluoroacetonato Tb0.2, La0.8 4-cyanopyridine
tris pivaloyltrifluoroacetonato Tb0.2, La0.8 4-phenylpyridine-N-oxide
tris pivaloyltrifluoroacetonato Tb0.2, La0.8 1-methylimidazole
tris pivaloyltrifluoroacetonato Tb0.2, La0.8 triphenylphosphine oxide
tris pivaloyltrifluoroacetonato Tb0.2, La0.8 2,2-bipyridyl
tris pivaloyltrifluoroacetonato Tb0.2, La0.8 2,2-bipyridyl-N,N-dioxide
tris pivaloyltrifluoroacetonato Tb0.2, La0.8 phenanthroline
tris pivaloyltrifluoroacetonato Tb0.2, La0.8 bathocuproine
tris pivaloyltrifluoroacetonato Tb0.2, La0.8 bathophenanthroline
tris trifluoroacetylacetonato Tb0.2, La0.8 dimethylaminopyridine
tris trifluoroacetylacetonato Tb0.2, La0.8 4-picoline-N-oxide
tris trifluoroacetylacetonato Tb0.2, La0.8 4-phenylpyridine
tris trifluoroacetylacetonato Tb0.2, La0.8 4-cyanopyridine
tris trifluoroacetylacetonato Tb0.2, La0.8 4-phenylpyridine-N-oxide
tris trifluoroacetylacetonato Tb0.2, La0.8 1-methylimidazole
tris trifluoroacetylacetonato Tb0.2, La0.8 triphenylphosphine oxide
tris trifluoroacetylacetonato Tb0.2, La0.8 2,2-bipyridyl
tris trifluoroacetylacetonato Tb0.2, La0.8 2,2-bipyridyl-N,N-dioxide
tris trifluoroacetylacetonato Tb0.2, La0.8 phenanthroline
tris trifluoroacetylacetonato Tb0.2, La0.8 bathocuproine
tris trifluoroacetylacetonato Tb0.2, La0.8 bathophenanthroline
tris hexafluoroacetylacetonato Tb0.2, La0.8 dimethylaminopyridine
tris hexafluoroacetylacetonato Tb0.2, La0.8 4-picoline-N-oxide
tris hexafluoroacetylacetonato Tb0.2, La0.8 4-phenylpyridine
tris hexafluoroacetylacetonato Tb0.2, La0.8 4-cyanopyridine
tris hexafluoroacetylacetonato Tb0.2, La0.8 4-phenylpyridine-N-oxide
tris hexafluoroacetylacetonato Tb0.2, La0.8 1-methylimidazole
tris hexafluoroacetylacetonato Tb0.2, La0.8 triphenylphosphine oxide
tris hexafluoroacetylacetonato Tb0.2, La0.8 2,2-bipyridyl
tris hexafluoroacetylacetonato Tb0.2, La0.8 2,2-bipyridyl-N,N-dioxide
tris hexafluoroacetylacetonato Tb0.2, La0.8 phenanthroline
tris hexafluoroacetylacetonato Tb0.2, La0.8 bathocuproine
tris hexafluoroacetylacetonato Tb0.2, La0.8 bathophenanthroline
tris 6,6,7,7,8,8,8-heptafluoro-2,2-dimethyloctanedionato Tb0.2, La0.8 dimethylaminopyridine
tris 6,6,7,7,8,8,8-heptafluoro-2,2-dimethyloctanedionato Tb0.2, La0.8 4-picoline-N-oxide
tris 6,6,7,7,8,8,8-heptafluoro-2,2-dimethyloctanedionato Tb0.2, La0.8 4-phenylpyridine
tris 6,6,7,7,8,8,8-heptafluoro-2,2-dimethyloctanedionato Tb0.2, La0.8 4-cyanopyridine
tris 6,6,7,7,8,8,8-heptafluoro-2,2-dimethyloctanedionato Tb0.2, La0.8 4-phenylpyridine-N-oxide
tris 6,6,7,7,8,8,8-heptafluoro-2,2-dimethyloctanedionato Tb0.2, La0.8 1-methylimidazole
tris 6,6,7,7,8,8,8-heptafluoro-2,2-dimethyloctanedionato Tb0.2, La0.8 triphenylphosphine oxide
tris 6,6,7,7,8,8,8-heptafluoro-2,2-dimethyloctanedionato Tb0.2, La0.8 2,2-bipyridyl
tris 6,6,7,7,8,8,8-heptafluoro-2,2-dimethyloctanedionato Tb0.2, La0.8 2,2-bipyridyl-N,N-dioxide
tris 6,6,7,7,8,8,8-heptafluoro-2,2-dimethyloctanedionato Tb0.2, La0.8 phenanthroline
tris 6,6,7,7,8,8,8-heptafluoro-2,2-dimethyloctanedionato Tb0.2, La0.8 bathocuproine
tris 6,6,7,7,8,8,8-heptafluoro-2,2-dimethyloctanedionato Tb0.2, La0.8 bathophenanthroline
tris 1-phenyl-1,3-butanedionato Tb0.2, La0.8 dimethylaminopyridine
tris 1-phenyl-1,3-butanedionato Tb0.2, La0.8 4-picoline-N-oxide
tris 1-phenyl-1,3-butanedionato Tb0.2, La0.8 4-phenylpyridine
tris 1-phenyl-1,3-butanedionato Tb0.2, La0.8 4-cyanopyridine tris 1-phenyl-1,3-butanedionato Tb0.2, La0.8 4-phenylpyridine-N-oxide
tris 1-phenyl-1,3-butanedionato Tb0.2, La0.8 1-methylimidazole
tris 1-phenyl-1,3-butanedionato Tb0.2, La0.8 triphenylphosphine oxide
tris 1-phenyl-1,3-butanedionato Tb0.2, La0.8 2,2-bipyridyl
tris 1-phenyl-1,3-butanedionato Tb0.2, La0.8 2,2-bipyridyl-N,N-dioxide
tris 1-phenyl-1,3-butanedionato Tb0.2, La0.8 phenanthroline
tris 1-phenyl-1,3-butanedionato Tb0.2, La0.8 bathocuproine
tris 1-phenyl-1,3-butanedionato Tb0.2, La0.8 bathophenanthroline
tris acetylacetonato Tb0.1, La0.9 dimethylaminopyridine
tris acetylacetonato Tb0.1, La0.9 4-picoline-N-oxide
tris acetylacetonato Tb0.1, La0.9 4-phenylpyridine
tris acetylacetonato Tb0.1, La0.9 4-cyanopyridine
tris acetylacetonato Tb0.1, La0.9 4-phenylpyridine-N-oxide
tris acetylacetonato Tb0.1, La0.9 1-methylimidazole
tris acetylacetonato Tb0.1, La0.9 triphenylphosphine oxide
tris acetylacetonato Tb0.1, La0.9 2,2-bipyridyl
tris acetylacetonato Tb0.1, La0.9 2,2-bipyridyl-N,N-dioxide
tris acetylacetonato Tb0.1, La0.9 phenanthroline
tris acetylacetonato Tb0.1, La0.9 bathocuproine
tris acetylacetonato Tb0.1, La0.9 bathophenanthroline
tris dibenzoylmethanato Tb0.1, La0.9 dimethylaminopyridine
tris dibenzoylmethanato Tb0.1, La0.9 4-picoline-N-oxide
tris dibenzoylmethanato Tb0.1, La0.9 4-phenylpyridine
tris dibenzoylmethanato Tb0.1, La0.9 4-cyanopyridine
tris dibenzoylmethanato Tb0.1, La0.9 4-phenylpyridine-N-oxide
tris dibenzoylmethanato Tb0.1, La0.9 1-methylimidazole
tris dibenzoylmethanato Tb0.1, La0.9 triphenylphosphine oxide
tris dibenzoylmethanato Tb0.1, La0.9 2,2-bipyridyl
tris dibenzoylmethanato Tb0.1, La0.9 2,2-bipyridyl-N,N-dioxide
tris dibenzoylmethanato Tb0.1, La0.9 phenanthroline
tris dibenzoylmethanato Tb0.1, La0.9 bathocuproine
tris dibenzoylmethanato Tb0.1, La0.9 bathophenanthroline
tris thenoyltrifluoroacetonato Tb0.1, La0.9 dimethylaminopyridine
tris thenoyltrifluoroacetonato Tb0.1, La0.9 4-picoline-N-oxide
tris thenoyltrifluoroacetonato Tb0.1, La0.9 4-phenylpyridine
tris thenoyltrifluoroacetonato Tb0.1, La0.9 4-cyanopyridine
tris thenoyltrifluoroacetonato Tb0.1, La0.9 4-phenylpyridine-N-oxide
tris thenoyltrifluoroacetonato Tb0.1, La0.9 1-methylimidazole
tris thenoyltrifluoroacetonato Tb0.1, La0.9 triphenylphosphine oxide
tris thenoyltrifluoroacetonato Tb0.1, La0.9 2,2-bipyridyl
tris thenoyltrifluoroacetonato Tb0.1, La0.9 2,2-bipyridyl-N,N-dioxide
tris thenoyltrifluoroacetonato Tb0.1, La0.9 phenanthroline
tris thenoyltrifluoroacetonato Tb0.1, La0.9 bathocuproine
tris thenoyltrifluoroacetonato Tb0.1, La0.9 bathophenanthroline
tris 2,2,6,6-tetramethylheptanedionato Tb0.1, La0.9 dimethylaminopyridine
tris 2,2,6,6-tetramethylheptanedionato Tb0.1, La0.9 4-picoline-N-oxide
tris 2,2,6,6-tetramethylheptanedionato Tb0.1, La0.9 4-phenylpyridine
tris 2,2,6,6-tetramethylheptanedionato Tb0.1, La0.9 4-cyanopyridine
tris 2,2,6,6-tetramethylheptanedionato Tb0.1, La0.9 4-phenylpyridine-N-oxide
tris 2,2,6,6-tetramethylheptanedionato Tb0.1, La0.9 1-methylimidazole
tris 2,2,6,6-tetramethylheptanedionato Tb0.1, La0.9 triphenylphosphine oxide
tris 2,2,6,6-tetramethylheptanedionato Tb0.1, La0.9 2,2-bipyridyl
tris 2,2,6,6-tetramethylheptanedionato Tb0.1, La0.9 2,2-bipyridyl-N,N-dioxide
tris 2,2,6,6-tetramethylheptanedionato Tb0.1, La0.9 phenanthroline
tris 2,2,6,6-tetramethylheptanedionato Tb0.1, La0.9 bathocuproine
tris 2,2,6,6-tetramethylheptanedionato Tb0.1, La0.9 bathophenanthroline
tris 3-methylpentane-2,4-dionato Tb0.1, La0.9 dimethylaminopyridine
tris 3-methylpentane-2,4-dionato Tb0.1, La0.9 4-picoline-N-oxide
tris 3-methylpentane-2,4-dionato Tb0.1, La0.9 4-phenylpyridine
tris 3-methylpentane-2,4-dionato Tb0.1, La0.9 4-cyanopyridine
tris 3-methylpentane-2,4-dionato Tb0.1, La0.9 4-phenylpyridine-N-oxide
tris 3-methylpentane-2,4-dionato Tb0.1, La0.9 1-methylimidazole
tris 3-methylpentane-2,4-dionato Tb0.1, La0.9 triphenylphosphine oxide
tris 3-methylpentane-2,4-dionato Tb0.1, La0.9 2,2-bipyridyl
tris 3-methylpentane-2,4-dionato Tb0.1, La0.9 2,2-bipyridyl-N,N-dioxide
tris 3-methylpentane-2,4-dionato Tb0.1, La0.9 phenanthroline
tris 3-methylpentane-2,4-dionato Tb0.1, La0.9 bathocuproine
tris 3-methylpentane-2,4-dionato Tb0.1, La0.9 bathophenanthroline
tris 3-ethylpentane-2,4-dionato Tb0.1, La0.9 dimethylaminopyridine
tris 3-ethylpentane-2,4-dionato Tb0.1, La0.9 4-picoline-N-oxide
tris 3-ethylpentane-2,4-dionato Tb0.1, La0.9 4-phenylpyridine
tris 3-ethylpentane-2,4-dionato Tb0.1, La0.9 4-cyanopyridine
tris 3-ethylpentane-2,4-dionato Tb0.1, La0.9 4-phenylpyridine-N-oxide
tris 3-ethylpentane-2,4-dionato Tb0.1, La0.9 1-methylimidazole
tris 3-ethylpentane-2,4-dionato Tb0.1, La0.9 triphenylphosphine oxide
tris 3-ethylpentane-2,4-dionato Tb0.1, La0.9 2,2-bipyridyl
tris 3-ethylpentane-2,4-dionato Tb0.1, La0.9 2,2-bipyridyl-N,N-dioxide
tris 3-ethylpentane-2,4-dionato Tb0.1, La0.9 phenanthroline
tris 3-ethylpentane-2,4-dionato Tb0.1, La0.9 bathocuproine
tris 3-ethylpentane-2,4-dionato Tb0.1, La0.9 bathophenanthroline
tris pivaloyltrifluoroacetonato Tb0.1, La0.9 dimethylaminopyridine
tris pivaloyltrifluoroacetonato Tb0.1, La0.9 4-picoline-N-oxide tris pivaloyltrifluoroacetonato Tb0.1, La0.9 4-phenylpyridine
tris pivaloyltrifluoroacetonato Tb0.1, La0.9 4-cyanopyridine
tris pivaloyltrifluoroacetonato Tb0.1, La0.9 4-phenylpyridine-N-oxide
tris pivaloyltrifluoroacetonato Tb0.1, La0.9 1-methylimidazole
tris pivaloyltrifluoroacetonato Tb0.1, La0.9 triphenylphosphine oxide
tris pivaloyltrifluoroacetonato Tb0.1, La0.9 2,2-bipyridyl
tris pivaloyltrifluoroacetonato Tb0.1, La0.9 2,2-bipyridyl-N,N-dioxide
tris pivaloyltrifluoroacetonato Tb0.1, La0.9 phenanthroline
tris pivaloyltrifluoroacetonato Tb0.1, La0.9 bathocuproine
tris pivaloyltrifluoroacetonato Tb0.1, La0.9 bathophenanthroline
tris trifluoroacetylacetonato Tb0.1, La0.9 dimethylaminopyridine
tris trifluoroacetylacetonato Tb0.1, La0.9 4-picoline-N-oxide
tris trifluoroacetylacetonato Tb0.1, La0.9 4-phenylpyridine
tris trifluoroacetylacetonato Tb0.1, La0.9 4-cyanopyridine
tris trifluoroacetylacetonato Tb0.1, La0.9 4-phenylpyridine-N-oxide
tris trifluoroacetylacetonato Tb0.1, La0.9 1-methylimidazole
tris trifluoroacetylacetonato Tb0.1, La0.9 triphenylphosphine oxide
tris trifluoroacetylacetonato Tb0.1, La0.9 2,2-bipyridyl
tris trifluoroacetylacetonato Tb0.1, La0.9 2,2-bipyridyl-N,N-dioxide
tris trifluoroacetylacetonato Tb0.1, La0.9 phenanthroline
tris trifluoroacetylacetonato Tb0.1, La0.9 bathocuproine
tris trifluoroacetylacetonato Tb0.1, La0.9 bathophenanthroline
tris hexafluoroacetylacetonato Tb0.1, La0.9 dimethylaminopyridine
tris hexafluoroacetylacetonato Tb0.1, La0.9 4-picoline-N-oxide
tris hexafluoroacetylacetonato Tb0.1, La0.9 4-phenylpyridine
tris hexafluoroacetylacetonato Tb0.1, La0.9 4-cyanopyridine
tris hexafluoroacetylacetonato Tb0.1, La0.9 4-phenylpyridine-N-oxide
tris hexafluoroacetylacetonato Tb0.1, La0.9 1-methylimidazole
tris hexafluoroacetylacetonato Tb0.1, La0.9 triphenylphosphine oxide
tris hexafluoroacetylacetonato Tb0.1, La0.9 2,2-bipyridyl
tris hexafluoroacetylacetonato Tb0.1, La0.9 2,2-bipyridyl-N,N-dioxide
tris hexafluoroacetylacetonato Tb0.1, La0.9 phenanthroline
tris hexafluoroacetylacetonato Tb0.1, La0.9 bathocuproine
tris hexafluoroacetylacetonato Tb0.1, La0.9 bathophenanthroline
tris 6,6,7,7,8,8,8-heptafluoro-2,2-dimethyloctanedionato Tb0.1, La0.9 dimethylaminopyridine
tris 6,6,7,7,8,8,8-heptafluoro-2,2-dimethyloctanedionato Tb0.1, La0.9 4-picoline-N-oxide
tris 6,6,7,7,8,8,8-heptafluoro-2,2-dimethyloctanedionato Tb0.1, La0.9 4-phenylpyridine
tris 6,6,7,7,8,8,8-heptafluoro-2,2-dimethyloctanedionato Tb0.1, La0.9 4-cyanopyridine
tris 6,6,7,7,8,8,8-heptafluoro-2,2-dimethyloctanedionato Tb0.1, La0.9 4-phenylpyridine-N-oxide
tris 6,6,7,7,8,8,8-heptafluoro-2,2-dimethyloctanedionato Tb0.1, La0.9 1-methylimidazole
tris 6,6,7,7,8,8,8-heptafluoro-2,2-dimethyloctanedionato Tb0.1, La0.9 triphenylphosphine oxide
tris 6,6,7,7,8,8,8-heptafluoro-2,2-dimethyloctanedionato Tb0.1, La0.9 2,2-bipyridyl
tris 6,6,7,7,8,8,8-heptafluoro-2,2-dimethyloctanedionato Tb0.1, La0.9 2,2-bipyridyl-N,N-dioxide
tris 6,6,7,7,8,8,8-heptafluoro-2,2-dimethyloctanedionato Tb0.1, La0.9 phenanthroline
tris 6,6,7,7,8,8,8-heptafluoro-2,2-dimethyloctanedionato Tb0.1, La0.9 bathocuproine
tris 6,6,7,7,8,8,8-heptafluoro-2,2-dimethyloctanedionato Tb0.1, La 0.9 bathophenanthroline
tris 1-phenyl-1,3-butanedionato Tb0.1, La0.9 dimethylaminopyridine
tris 1-phenyl-1,3-butanedionato Tb0.1, La0.9 4-picoline-N-oxide
tris 1-phenyl-1,3-butanedionato Tb0.1, La0.9 4-phenylpyridine
tris 1-phenyl-1,3-butanedionato Tb0.1, La0.9 4-cyanopyridine
tris 1-phenyl-1,3-butanedionato Tb0.1, La0.9 4-phenylpyridine-N-oxide
tris 1-phenyl-1,3-butanedionato Tb0.1, La0.9 1-methylimidazole
tris 1-phenyl-1,3-butanedionato Tb0.1, La0.9 triphenylphosphine oxide
tris 1-phenyl-1,3-butanedionato Tb0.1, La0.9 2,2-bipyridyl
tris 1-phenyl-1,3-butanedionato Tb0.1, La0.9 2,2-bipyridyl-N,N-dioxide
tris 1-phenyl-1,3-butanedionato Tb0.1, La0.9 phenanthroline
tris 1-phenyl-1,3-butanedionato Tb0.1, La0.9 bathocuproine
tris 1-phenyl-1,3-butanedionato Tb0.1, La0.9 bathophenanthroline
tris acetylacetonato Tb0.01, La0.99 dimethylaminopyridine
tris acetylacetonato Tb0.01, La0.99 4-picoline-N-oxide
tris acetylacetonato Tb0.01, La0.99 4-phenylpyridine
tris acetylacetonato Tb0.01, La0.99 4-cyanopyridine
tris acetylacetonato Tb0.01, La0.99 4-phenylpyridine-N-oxide
tris acetylacetonato Tb0.01, La0.99 1-methylimidazole
tris acetylacetonato Tb0.01, La0.99 triphenylphosphine oxide
tris acetylacetonato Tb0.01, La0.99 2,2-bipyridyl
tris acetylacetonato Tb0.01, La0.99 2,2-bipyridyl-N,N-dioxide
tris acetylacetonato Tb0.01, La0.99 phenanthroline
tris acetylacetonato Tb0.01, La0.99 bathocuproine
tris acetylacetonato Tb0.01, La0.99 bathophenanthroline
tris dibenzoylmethanato Tb0.01, La0.99 dimethylaminopyridine
tris dibenzoylmethanato Tb0.01, La0.99 4-picoline-N-oxide
tris dibenzoylmethanato Tb0.01, La0.99 4-phenylpyridine
tris dibenzoylmethanato Tb0.01, La0.99 4-cyanopyridine
tris dibenzoylmethanato Tb0.01, La0.99 4-phenylpyridine-N-oxide
tris dibenzoylmethanato Tb0.01, La0.99 1-methylimidazole
tris dibenzoylmethanato Tb0.01, La0.99 triphenylphosphine oxide
tris dibenzoylmethanato Tb0.01, La0.99 2,2-bipyridyl
tris dibenzoylmethanato Tb0.01, La0.99 2,2-bipyridyl-N,N-dioxide
tris dibenzoylmethanato Tb0.01, La0.99 phenanthroline
tris dibenzoylmethanato Tb0.01, La0.99 bathocuproine tris dibenzoylmethanato Tb0.01, La0.99 bathophenanthroline
tris thenoyltrifluoroacetonato Tb0.01, La0.99 dimethylaminopyridine
tris thenoyltrifluoroacetonato Tb0.01, La0.99 4-picoline-N-oxide
tris thenoyltrifluoroacetonato Tb0.01, La0.99 4-phenylpyridine
tris thenoyltrifluoroacetonato Tb0.01, La0.99 4-cyanopyridine
tris thenoyltrifluoroacetonato Tb0.01, La0.99 4-phenylpyridine-N-oxide
tris thenoyltrifluoroacetonato Tb0.01, La0.99 1-methylimidazole
tris thenoyltrifluoroacetonato Tb0.01, La0.99 triphenylphosphine oxide
tris thenoyltrifluoroacetonato Tb0.01, La0.99 2,2-bipyridyl
tris thenoyltrifluoroacetonato Tb0.01, La0.99 2,2-bipyridyl-N,N-dioxide
tris thenoyltrifluoroacetonato Tb0.01, La0.99 phenanthroline
tris thenoyltrifluoroacetonato Tb0.01, La0.99 bathocuproine
tris thenoyltrifluoroacetonato Tb0.01, La0.99 bathophenanthroline
tris 2,2,6,6-tetramethylheptanedionato Tb0.01, La0.99 dimethylaminopyridine
tris 2,2,6,6-tetramethylheptanedionato Tb0.01, La0.99 4-picoline-N-oxide
tris 2,2,6,6-tetramethylheptanedionato Tb0.01, La0.99 4-phenylpyridine
tris 2,2,6,6-tetramethylheptanedionato Tb0.01, La0.99 4-cyanopyridine
tris 2,2,6,6-tetramethylheptanedionato Tb0.01, La0.99 4-phenylpyridine-N-oxide
tris 2,2,6,6-tetramethylheptanedionato Tb0.01, La0.99 1-methylimidazole
tris 2,2,6,6-tetramethylheptanedionato Tb0.01, La0.99 triphenylphosphine oxide
tris 2,2,6,6-tetramethylheptanedionato Tb0.01, La0.99 2,2-bipyridyl
tris 2,2,6,6-tetramethylheptanedionato Tb0.01, La0.99 2,2-bipyridyl-N,N-dioxide
tris 2,2,6,6-tetramethylheptanedionato Tb0.01, La0.99 phenanthroline
tris 2,2,6,6-tetramethylheptanedionato Tb0.01, La0.99 bathocuproine
tris 2,2,6,6-tetramethylheptanedionato Tb0.01, La0.99 bathophenanthroline
tris 3-methylpentane-2,4-dionato Tb0.01, La0.99 dimethylaminopyridine
tris 3-methylpentane-2,4-dionato Tb0.01, La0.99 4-picoline-N-oxide
tris 3-methylpentane-2,4-dionato Tb0.01, La0.99 4-phenylpyridine
tris 3-methylpentane-2,4-dionato Tb0.01, La0.99 4-cyanopyridine
tris 3-methylpentane-2,4-dionato Tb0.01, La0.99 4-phenylpyridine-N-oxide
tris 3-methylpentane-2,4-dionato Tb0.01, La0.99 1-methylimidazole
tris 3-methylpentane-2,4-dionato Tb0.01, La0.99 triphenylphosphine oxide
tris 3-methylpentane-2,4-dionato Tb0.01, La0.99 2,2-bipyridyl
tris 3-methylpentane-2,4-dionato Tb0.01, La0.99 2,2-bipyridyl-N,N-dioxide
tris 3-methylpentane-2,4-dionato Tb0.01, La0.99 phenanthroline
tris 3-methylpentane-2,4-dionato Tb0.01, La0.99 bathocuproine
tris 3-methylpentane-2,4-dionato Tb0.01, La0.99 bathophenanthroline
tris 3-ethylpentane-2,4-dionato Tb0.01, La0.99 dimethylaminopyridine
tris 3-ethylpentane-2,4-dionato Tb0.01, La0.99 4-picoline-N-oxide
tris 3-ethylpentane-2,4-dionato Tb0.01, La0.99 4-phenylpyridine
tris 3-ethylpentane-2,4-dionato Tb0.01, La0.99 4-cyanopyridine
tris 3-ethylpentane-2,4-dionato Tb0.01, La0.99 4-phenylpyridine-N-oxide
tris 3-ethylpentane-2,4-dionato Tb0.01, La0.99 1-methylimidazole
tris 3-ethylpentane-2,4-dionato Tb0.01, La0.99 triphenylphosphine oxide
tris 3-ethylpentane-2,4-dionato Tb0.01, La0.99 2,2-bipyridyl
tris 3-ethylpentane-2,4-dionato Tb0.01, La0.99 2,2-bipyridyl-N,N-dioxide
tris 3-ethylpentane-2,4-dionato Tb0.01, La0.99 phenanthroline
tris 3-ethylpentane-2,4-dionato Tb0.01, La0.99 bathocuproine
tris 3-ethylpentane-2,4-dionato Tb0.01, La0.99 bathophenanthroline
tris pivaloyltrifluoroacetonato Tb0.01, La0.99 dimethylaminopyridine
tris pivaloyltrifluoroacetonato Tb0.01, La0.99 4-picoline-N-oxide
tris pivaloyltrifluoroacetonato Tb0.01, La0.99 4-phenylpyridine
tris pivaloyltrifluoroacetonato Tb0.01, La0.99 4-cyanopyridine
tris pivaloyltrifluoroacetonato Tb0.01, La0.99 4-phenylpyridine-N-oxide
tris pivaloyltrifluoroacetonato Tb0.01, La0.99 1-methylimidazole
tris pivaloyltrifluoroacetonato Tb0.01, La0.99 triphenylphosphine oxide
tris pivaloyltrifluoroacetonato Tb0.01, La0.99 2,2-bipyridyl
tris pivaloyltrifluoroacetonato Tb0.01, La0.99 2,2-bipyridyl-N,N-dioxide
tris pivaloyltrifluoroacetonato Tb0.01, La0.99 phenanthroline
tris pivaloyltrifluoroacetonato Tb0.01, La0.99 bathocuproine
tris pivaloyltrifluoroacetonato Tb0.01, La0.99 bathophenanthroline
tris trifluoroacetylacetonato Tb0.01, La0.99 dimethylaminopyridine
tris trifluoroacetylacetonato Tb0.01, La0.99 4-picoline-N-oxide
tris trifluoroacetylacetonato Tb0.01, La0.99 4-phenylpyridine
tris trifluoroacetylacetonato Tb0.01, La0.99 4-cyanopyridine
tris trifluoroacetylacetonato Tb0.01, La0.99 4-phenylpyridine-N-oxide
tris trifluoroacetylacetonato Tb0.01, La0.99 1-methylimidazole
tris trifluoroacetylacetonato Tb0.01, La0.99 triphenylphosphine oxide tris trifluoroacetylacetonato Tb0.01, La0.99 2,2-bipyridyl
tris trifluoroacetylacetonato Tb0.01, La0.99 2,2-bipyridyl-N,N-dioxide
tris trifluoroacetylacetonato Tb0.01, La0.99 phenanthroline
tris trifluoroacetylacetonato Tb0.01, La0.99 bathocuproine
tris trifluoroacetylacetonato Tb0.01, La0.99 bathophenanthroline
tris hexafluoroacetylacetonato Tb0.01, La0.99 dimethylaminopyridine
tris hexafluoroacetylacetonato Tb0.01, La0.99 4-picoline-N-oxide
tris hexafluoroacetylacetonato Tb0.01, La0.99 4-phenylpyridine
tris hexafluoroacetylacetonato Tb0.01, La0.99 4-cyanopyridine
tris hexafluoroacetylacetonato Tb0.01, La0.99 4-phenylpyridine-N-oxide
tris hexafluoroacetylacetonato Tb0.01, La0.99 1-methylimidazole
tris hexafluoroacetylacetonato Tb0.01, La0.99 triphenylphosphine oxide
tris hexafluoroacetylacetonato Tb0.01, La0.99 2,2-bipyridyl
tris hexafluoroacetylacetonato Tb0.01, La0.99 2,2-bipyridyl-N,N-dioxide
tris hexafluoroacetylacetonato Tb0.01, La0.99 phenanthroline
tris hexafluoroacetylacetonato Tb0.01, La0.99 bathocuproine
tris hexafluoroacetylacetonato Tb0.01, La0.99 bathophenanthroline
tris 6,6,7,7,8,8,8-heptafluoro-2,2-dimethyloctanedionato Tb0.01, La0.99 dimethylaminopyridine
tris 6,6,7,7,8,8,8-heptafluoro-2,2-dimethyloctanedionato Tb0.01, La0.99 4-picoline-N-oxide
tris 6,6,7,7,8,8,8-heptafluoro-2,2-dimethyloctanedionato Tb0.01, La0.99 4-phenylpyridine
tris 6,6,7,7,8,8,8-heptafluoro-2,2-dimethyloctanedionato Tb0.01, La0.99 4-cyanopyridine
tris 6,6,7,7,8,8,8-heptafluoro-2,2-dimethyloctanedionato Tb0.01, La0.99 4-phenylpyridine-N-oxide
tris 6,6,7,7,8,8,8-heptafluoro-2,2-dimethyloctanedionato Tb0.01, La0.99 1-methylimidazole
tris 6,6,7,7,8,8,8-heptafluoro-2,2-dimethyloctanedionato Tb0.01, La0.99 triphenylphosphine oxide
tris 6,6,7,7,8,8,8-heptafluoro-2,2-dimethyloctanedionato Tb0.01, La0.99 2,2-bipyridyl
tris 6,6,7,7,8,8,8-heptafluoro-2,2-dimethyloctanedionato Tb0.01, La0.99 2,2-bipyridyl-N,N-dioxide
tris 6,6,7,7,8,8,8-heptafluoro-2,2-dimethyloctanedionato Tb0.01, La0.99 phenanthroline
tris 6,6,7,7,8,8,8-heptafluoro-2,2-dimethyloctanedionato Tb0.01, La0.99 bathocuproine
tris 6,6,7,7,8,8,8-heptafluoro-2,2-dimethyloctanedionato Tb0.01, La0.99 bathophenanthroline
tris 1-phenyl-1,3-butanedionato Tb0.01, La0.99 dimethylaminopyridine
tris 1-phenyl-1,3-butanedionato Tb0.01, La0.99 4-picoline-N-oxide
tris 1-phenyl-1,3-butanedionato Tb0.01, La0.99 4-phenylpyridine
tris 1-phenyl-1,3-butanedionato Tb0.01, La0.99 4-cyanopyridine
tris 1-phenyl-1,3-butanedionato Tb0.01, La0.99 4-phenylpyridine-N-oxide
tris 1-phenyl-1,3-butanedionato Tb0.01, La0.99 1-methylimidazole
tris 1-phenyl-1,3-butanedionato Tb0.01, La0.99 triphenylphosphine oxide
tris 1-phenyl-1,3-butanedionato Tb0.01, La0.99 2,2-bipyridyl
tris 1-phenyl-1,3-butanedionato Tb0.01, La0.99 2,2-bipyridyl-N,N-dioxide
tris 1-phenyl-1,3-butanedionato Tb0.01, La0.99 phenanthroline
tris 1-phenyl-1,3-butanedionato Tb0.01, La0.99 bathocuproine
tris 1-phenyl-1,3-butanedionato Tb0.01, La0.99 bathophenanthroline
tris acetylacetonato Eu0.5, La0.5 dimethylaminopyridine
tris acetylacetonato Eu0.5, La0.5 4-picoline-N-oxide
tris acetylacetonato Eu0.5, La0.5 4-phenylpyridine
tris acetylacetonato Eu0.5, La0.5 4-cyanopyridine
tris acetylacetonato Eu0.5, La0.5 4-phenylpyridine-N-oxide
tris acetylacetonato Eu0.5, La0.5 1-methylimidazole
tris acetylacetonato Eu0.5, La0.5 triphenylphosphine oxide
tris acetylacetonato Eu0.5, La0.5 2,2-bipyridyl
tris acetylacetonato Eu0.5, La0.5 2,2-bipyridyl-N,N-dioxide
tris acetylacetonato Eu0.5, La0.5 phenanthroline
tris acetylacetonato Eu0.5, La0.5 bathocuproine
tris acetylacetonato Eu0.5, La0.5 bathophenanthroline
tris dibenzoylmethanato Eu0.5, La0.5 dimethylaminopyridine
tris dibenzoylmethanato Eu0.5, La0.5 4-picoline-N-oxide
tris dibenzoylmethanato Eu0.5, La0.5 4-phenylpyridine
tris dibenzoylmethanato Eu0.5, La0.5 4-cyanopyridine
tris dibenzoylmethanato Eu0.5, La0.5 4-phenylpyridine-N-oxide
tris dibenzoylmethanato Eu0.5, La0.5 1-methylimidazole
tris dibenzoylmethanato Eu0.5, La0.5 triphenylphosphine oxide
tris dibenzoylmethanato Eu0.5, La0.5 2,2-bipyridyl
tris dibenzoylmethanato Eu0.5, La0.5 2,2-bipyridyl-N,N-dioxide
tris dibenzoylmethanato Eu0.5, La0.5 phenanthroline
tris dibenzoylmethanato Eu0.5, La0.5 bathocuproine
tris dibenzoylmethanato Eu0.5, La0.5 bathophenanthroline
tris thenoyltrifluoroacetonato Eu0.5, La0.5 dimethylaminopyridine
tris thenoyltrifluoroacetonato Eu0.5, La0.5 4-picoline-N-oxide
tris thenoyltrifluoroacetonato Eu0.5, La0.5 4-phenylpyridine
tris thenoyltrifluoroacetonato Eu0.5, La0.5 4-cyanopyridine
tris thenoyltrifluoroacetonato Eu0.5, La0.5 4-phenylpyridine-N-oxide
tris thenoyltrifluoroacetonato Eu0.5, La0.5 1-methylimidazole
tris thenoyltrifluoroacetonato Eu0.5, La0.5 triphenylphosphine oxide
tris thenoyltrifluoroacetonato Eu0.5, La0.5 2,2-bipyridyl
tris thenoyltrifluoroacetonato Eu0.5, La0.5 2,2-bipyridyl-N,N-dioxide
tris thenoyltrifluoroacetonato Eu0.5, La0.5 phenanthroline
tris thenoyltrifluoroacetonato Eu0.5, La0.5 bathocuproine
tris thenoyltrifluoroacetonato Eu0.5, La0.5 bathophenanthroline
tris 2,2,6,6-tetramethylheptanedionato Eu0.5, La0.5 dimethylaminopyridine
tris 2,2,6,6-tetramethylheptanedionato Eu0.5, La0.5 4-picoline-N-oxide
tris 2,2,6,6-tetramethylheptanedionato Eu0.5, La0.5 4-phenylpyridine
tris 2,2,6,6-tetramethylheptanedionato Eu0.5, La0.5 4-cyanopyridine tris 2,2,6,6-tetramethylheptanedionato Eu0.5, La0.5 4-phenylpyridine-N-oxide
tris 2,2,6,6-tetramethylheptanedionato Eu0.5, La0.5 1-methylimidazole
tris 2,2,6,6-tetramethylheptanedionato Eu0.5, La0.5 triphenylphosphine oxide
tris 2,2,6,6-tetramethylheptanedionato Eu0.5, La0.5 2,2-bipyridyl
tris 2,2,6,6-tetramethylheptanedionato Eu0.5, La0.5 2,2-bipyridyl-N,N-dioxide
tris 2,2,6,6-tetramethylheptanedionato Eu0.5, La0.5 phenanthroline
tris 2,2,6,6-tetramethylheptanedionato Eu0.5, La0.5 bathocuproine
tris 2,2,6,6-tetramethylheptanedionato Eu0.5, La0.5 bathophenanthroline
tris 3-methylpentane-2,4-dionato Eu0.5, La0.5 dimethylaminopyridine
tris 3-methylpentane-2,4-dionato Eu0.5, La0.5 4-picoline-N-oxide
tris 3-methylpentane-2,4-dionato Eu0.5, La0.5 4-phenylpyridine
tris 3-methylpentane-2,4-dionato Eu0.5, La0.5 4-cyanopyridine
tris 3-methylpentane-2,4-dionato Eu0.5, La0.5 4-phenylpyridine-N-oxide
tris 3-methylpentane-2,4-dionato Eu0.5, La0.5 1-methylimidazole
tris 3-methylpentane-2,4-dionato Eu0.5, La0.5 triphenylphosphine oxide
tris 3-methylpentane-2,4-dionato Eu0.5, La0.5 2,2-bipyridyl
tris 3-methylpentane-2,4-dionato Eu0.5, La0.5 2,2-bipyridyl-N,N-dioxide
tris 3-methylpentane-2,4-dionato Eu0.5, La0.5 phenanthroline
tris 3-methylpentane-2,4-dionato Eu0.5, La0.5 bathocuproine
tris 3-methylpentane-2,4-dionato Eu0.5, La0.5 bathophenanthroline
tris 3-ethylpentane-2,4-dionato Eu0.5, La0.5 dimethylaminopyridine
tris 3-ethylpentane-2,4-dionato Eu0.5, La0.5 4-picoline-N-oxide
tris 3-ethylpentane-2,4-dionato Eu0.5, La0.5 4-phenylpyridine
tris 3-ethylpentane-2,4-dionato Eu0.5, La0.5 4-cyanopyridine
tris 3-ethylpentane-2,4-dionato Eu0.5, La0.5 4-phenylpyridine-N-oxide
tris 3-ethylpentane-2,4-dionato Eu0.5, La0.5 1-methylimidazole
tris 3-ethylpentane-2,4-dionato Eu0.5, La0.5 triphenylphosphine oxide
tris 3-ethylpentane-2,4-dionato Eu0.5, La0.5 2,2-bipyridyl
tris 3-ethylpentane-2,4-dionato Eu0.5, La0.5 2,2-bipyridyl-N,N-dioxide
tris 3-ethylpentane-2,4-dionato Eu0.5, La0.5 phenanthroline
tris 3-ethylpentane-2,4-dionato Eu0.5, La0.5 bathocuproine
tris 3-ethylpentane-2,4-dionato Eu0.5, La0.5 bathophenanthroline
tris pivaloyltrifluoroacetonato Eu0.5, La0.5 dimethylaminopyridine
tris pivaloyltrifluoroacetonato Eu0.5, La0.5 4-picoline-N-oxide
tris pivaloyltrifluoroacetonato Eu0.5, La0.5 4-phenylpyridine
tris pivaloyltrifluoroacetonato Eu0.5, La0.5 4-cyanopyridine
tris pivaloyltrifluoroacetonato Eu0.5, La0.5 4-phenylpyridine-N-oxide
tris pivaloyltrifluoroacetonato Eu0.5, La0.5 1-methylimidazole
tris pivaloyltrifluoroacetonato Eu0.5, La0.5 triphenylphosphine oxide
tris pivaloyltrifluoroacetonato Eu0.5, La0.5 2,2-bipyridyl
tris pivaloyltrifluoroacetonato Eu0.5, La0.5 2,2-bipyridyl-N,N-dioxide
tris pivaloyltrifluoroacetonato Eu0.5, La0.5 phenanthroline
tris pivaloyltrifluoroacetonato Eu0.5, La0.5 bathocuproine
tris pivaloyltrifluoroacetonato Eu0.5, La0.5 bathophenanthroline
tris trifluoroacetylacetonato Eu0.5, La0.5 dimethylaminopyridine
tris trifluoroacetylacetonato Eu0.5, La0.5 4-picoline-N-oxide
tris trifluoroacetylacetonato Eu0.5, La0.5 4-phenylpyridine
tris trifluoroacetylacetonato Eu0.5, La0.5 4-cyanopyridine
tris trifluoroacetylacetonato Eu0.5, La0.5 4-phenylpyridine-N-oxide
tris trifluoroacetylacetonato Eu0.5, La0.5 1-methylimidazole
tris trifluoroacetylacetonato Eu0.5, La0.5 triphenylphosphine oxide
tris trifluoroacetylacetonato Eu0.5, La0.5 2,2-bipyridyl
tris trifluoroacetylacetonato Eu0.5, La0.5 2,2-bipyridyl-N,N-dioxide
tris trifluoroacetylacetonato Eu0.5, La0.5 phenanthroline
tris trifluoroacetylacetonato Eu0.5, La0.5 bathocuproine
tris trifluoroacetylacetonato Eu0.5, La0.5 bathophenanthroline
tris hexafluoroacetylacetonato Eu0.5, La0.5 dimethylaminopyridine
tris hexafluoroacetylacetonato Eu0.5, La0.5 4-picoline-N-oxide
tris hexafluoroacetylacetonato Eu0.5, La0.5 4-phenylpyridine
tris hexafluoroacetylacetonato Eu0.5, La0.5 4-cyanopyridine
tris hexafluoroacetylacetonato Eu0.5, La0.5 4-phenylpyridine-N-oxide
tris hexafluoroacetylacetonato Eu0.5, La0.5 1-methylimidazole
tris hexafluoroacetylacetonato Eu0.5, La0.5 triphenylphosphine oxide
tris hexafluoroacetylacetonato Eu0.5, La0.5 2,2-bipyridyl
tris hexafluoroacetylacetonato Eu0.5, La0.5 2,2-bipyridyl-N,N-dioxide
tris hexafluoroacetylacetonato Eu0.5, La0.5 phenanthroline
tris hexafluoroacetylacetonato Eu0.5, La0.5 bathocuproine
tris hexafluoroacetylacetonato Eu0.5, La0.5 bathophenanthroline
tris 6,6,7,7,8,8,8-heptafluoro-2,2-dimethyloctanedionato Eu0.5, La0.5 dimethylaminopyridine
tris 6,6,7,7,8,8,8-heptafluoro-2,2-dimethyloctanedionato Eu0.5, La0.5 4-picoline-N-oxide
tris 6,6,7,7,8,8,8-heptafluoro-2,2-dimethyloctanedionato Eu0.5, La0.5 4-phenylpyridine
tris 6,6,7,7,8,8,8-heptafluoro-2,2-dimethyloctanedionato Eu0.5, La0.5 4-cyanopyridine
tris 6,6,7,7,8,8,8-heptafluoro-2,2-dimethyloctanedionato Eu0.5, La0.5 4-phenylpyridine-N-oxide
tris 6,6,7,7,8,8,8-heptafluoro-2,2-dimethyloctanedionato Eu0.5, La0.5 1-methylimidazole
tris 6,6,7,7,8,8,8-heptafluoro-2,2-dimethyloctanedionato Eu0.5, La0.5 triphenylphosphine oxide tris 6,6,7,7,8,8,8-heptafluoro-2,2-dimethyloctanedionato Eu0.5, La0.5 2,2-bipyridyl
tris 6,6,7,7,8,8,8-heptafluoro-2,2-dimethyloctanedionato Eu0.5, La0.5 2,2-bipyridyl-N,N-dioxide
tris 6,6,7,7,8,8,8-heptafluoro-2,2-dimethyloctanedionato Eu0.5, La0.5 phenanthroline
tris 6,6,7,7,8,8,8-heptafluoro-2,2-dimethyloctanedionato Eu0.5, La0.5 bathocuproine
tris 6,6,7,7,8,8,8-heptafluoro-2,2-dimethyloctanedionato Eu0.5, La0.5 bathophenanthroline
tris 1-phenyl-1,3-butanedionato Eu0.5, La0.5 dimethylaminopyridine
tris 1-phenyl-1,3-butanedionato Eu0.5, La0.5 4-picoline-N-oxide
tris 1-phenyl-1,3-butanedionato Eu0.5, La0.5 4-phenylpyridine
tris 1-phenyl-1,3-butanedionato Eu0.5, La0.5 4-cyanopyridine
tris 1-phenyl-1,3-butanedionato Eu0.5, La0.5 4-phenylpyridine-N-oxide
tris 1-phenyl-1,3-butanedionato Eu0.5, La0.5 1-methylimidazole
tris 1-phenyl-1,3-butanedionato Eu0.5, La0.5 triphenylphosphine oxide
tris 1-phenyl-1,3-butanedionato Eu0.5, La0.5 2,2-bipyridyl
tris 1-phenyl-1,3-butanedionato Eu0.5, La0.5 2,2-bipyridyl-N,N-dioxide
tris 1-phenyl-1,3-butanedionato Eu0.5, La0.5 phenanthroline
tris 1-phenyl-1,3-butanedionato Eu0.5, La0.5 bathocuproine
tris 1-phenyl-1,3-butanedionato Eu0.5, La0.5 bathophenanthroline
tris acetylacetonato Eu0.2, La0.8 dimethylaminopyridine
tris acetylacetonato Eu0.2, La0.8 4-picoline-N-oxide
tris acetylacetonato Eu0.2, La0.8 4-phenylpyridine
tris acetylacetonato Eu0.2, La0.8 4-cyanopyridine
tris acetylacetonato Eu0.2, La0.8 4-phenylpyridine-N-oxide
tris acetylacetonato Eu0.2, La0.8 1-methylimidazole
tris acetylacetonato Eu0.2, La0.8 triphenylphosphine oxide
tris acetylacetonato Eu0.2, La0.8 2,2-bipyridyl
tris acetylacetonato Eu0.2, La0.8 2,2-bipyridyl-N,N-dioxide
tris acetylacetonato Eu0.2, La0.8 phenanthroline
tris acetylacetonato Eu0.2, La0.8 bathocuproine
tris acetylacetonato Eu0.2, La0.8 bathophenanthroline
tris dibenzoylmethanato Eu0.2, La0.8 dimethylaminopyridine
tris dibenzoylmethanato Eu0.2, La0.8 4-picoline-N-oxide
tris dibenzoylmethanato Eu0.2, La0.8 4-phenylpyridine
tris dibenzoylmethanato Eu0.2, La0.8 4-cyanopyridine
tris dibenzoylmethanato Eu0.2, La0.8 4-phenylpyridine-N-oxide
tris dibenzoylmethanato Eu0.2, La0.8 1-methylimidazole
tris dibenzoylmethanato Eu0.2, La0.8 triphenylphosphine oxide
tris dibenzoylmethanato Eu0.2, La0.8 2,2-bipyridyl
tris dibenzoylmethanato Eu0.2, La0.8 2,2-bipyridyl-N,N-dioxide
tris dibenzoylmethanato Eu0.2, La0.8 phenanthroline
tris dibenzoylmethanato Eu0.2, La0.8 bathocuproine
tris dibenzoylmethanato Eu0.2, La0.8 bathophenanthroline
tris thenoyltrifluoroacetonato Eu0.2, La0.8 dimethylaminopyridine
tris thenoyltrifluoroacetonato Eu0.2, La0.8 4-picoline-N-oxide
tris thenoyltrifluoroacetonato Eu0.2, La0.8 4-phenylpyridine
tris thenoyltrifluoroacetonato Eu0.2, La0.8 4-cyanopyridine
tris thenoyltrifluoroacetonato Eu0.2, La0.8 4-phenylpyridine-N-oxide
tris thenoyltrifluoroacetonato Eu0.2, La0.8 1-methylimidazole
tris thenoyltrifluoroacetonato Eu0.2, La0.8 triphenylphosphine oxide
tris thenoyltrifluoroacetonato Eu0.2, La0.8 2,2-bipyridyl
tris thenoyltrifluoroacetonato Eu0.2, La0.8 2,2-bipyridyl-N,N-dioxide
tris thenoyltrifluoroacetonato Eu0.2, La0.8 phenanthroline
tris thenoyltrifluoroacetonato Eu0.2, La0.8 bathocuproine
tris thenoyltrifluoroacetonato Eu0.2, La0.8 bathophenanthroline
tris 2,2,6,6-tetramethylheptanedionato Eu0.2, La0.8 dimethylaminopyridine
tris 2,2,6,6-tetramethylheptanedionato Eu0.2, La0.8 4-picoline-N-oxide
tris 2,2,6,6-tetramethylheptanedionato Eu0.2, La0.8 4-phenylpyridine
tris 2,2,6,6-tetramethylheptanedionato Eu0.2, La0.8 4-cyanopyridine
tris 2,2,6,6-tetramethylheptanedionato Eu0.2, La0.8 4-phenylpyridine-N-oxide
tris 2,2,6,6-tetramethylheptanedionato Eu0.2, La0.8 1-methylimidazole
tris 2,2,6,6-tetramethylheptanedionato Eu0.2, La0.8 triphenylphosphine oxide
tris 2,2,6,6-tetramethylheptanedionato Eu0.2, La0.8 2,2-bipyridyl
tris 2,2,6,6-tetramethylheptanedionato Eu0.2, La0.8 2,2-bipyridyl-N,N-dioxide
tris 2,2,6,6-tetramethylheptanedionato Eu0.2, La0.8 phenanthroline
tris 2,2,6,6-tetramethylheptanedionato Eu0.2, La0.8 bathocuproine
tris 2,2,6,6-tetramethylheptanedionato Eu0.2, La0.8 bathophenanthroline
tris 3-methylpentane-2,4-dionato Eu0.2, La0.8 dimethylaminopyridine
tris 3-methylpentane-2,4-dionato Eu0.2, La0.8 4-picoline-N-oxide
tris 3-methylpentane-2,4-dionato Eu0.2, La0.8 4-phenylpyridine
tris 3-methylpentane-2,4-dionato Eu0.2, La0.8 4-cyanopyridine
tris 3-methylpentane-2,4-dionato Eu0.2, La0.8 4-phenylpyridine-N-oxide
tris 3-methylpentane-2,4-dionato Eu0.2, La0.8 1-methylimidazole
tris 3-methylpentane-2,4-dionato Eu0.2, La0.8 triphenylphosphine oxide
tris 3-methylpentane-2,4-dionato Eu0.2, La0.8 2,2-bipyridyl
tris 3-methylpentane-2,4-dionato Eu0.2, La0.8 2,2-bipyridyl-N,N-dioxide
tris 3-methylpentane-2,4-dionato Eu0.2, La0.8 phenanthroline
tris 3-methylpentane-2,4-dionato Eu0.2, La0.8 bathocuproine
tris 3-methylpentane-2,4-dionato Eu0.2, La0.8 bathophenanthroline
tris 3-ethylpentane-2,4-dionato Eu0.2, La0.8 dimethylaminopyridine
tris 3-ethylpentane-2,4-dionato Eu0.2, La0.8 4-picoline-N-oxide
tris 3-ethylpentane-2,4-dionato Eu0.2, La0.8 4-phenylpyridine tris 3-ethylpentane-2,4-dionato Eu0.2, La0.8 4-cyanopyridine
tris 3-ethylpentane-2,4-dionato Eu0.2, La0.8 4-phenylpyridine-N-oxide
tris 3-ethylpentane-2,4-dionato Eu0.2, La0.8 1-methylimidazole
tris 3-ethylpentane-2,4-dionato Eu0.2, La0.8 triphenylphosphine oxide
tris 3-ethylpentane-2,4-dionato Eu0.2, La0.8 2,2-bipyridyl
tris 3-ethylpentane-2,4-dionato Eu0.2, La0.8 2,2-bipyridyl-N,N-dioxide
tris 3-ethylpentane-2,4-dionato Eu0.2, La0.8 phenanthroline
tris 3-ethylpentane-2,4-dionato Eu0.2, La0.8 bathocuproine
tris 3-ethylpentane-2,4-dionato Eu0.2, La0.8 bathophenanthroline
tris pivaloyltrifluoroacetonato Eu0.2, La0.8 dimethylaminopyridine
tris pivaloyltrifluoroacetonato Eu0.2, La0.8 4-picoline-N-oxide
tris pivaloyltrifluoroacetonato Eu0.2, La0.8 4-phenylpyridine
tris pivaloyltrifluoroacetonato Eu0.2, La0.8 4-cyanopyridine
tris pivaloyltrifluoroacetonato Eu0.2, La0.8 4-phenylpyridine-N-oxide
tris pivaloyltrifluoroacetonato Eu0.2, La0.8 1-methylimidazole
tris pivaloyltrifluoroacetonato Eu0.2, La0.8 triphenylphosphine oxide
tris pivaloyltrifluoroacetonato Eu0.2, La0.8 2,2-bipyridyl
tris pivaloyltrifluoroacetonato Eu0.2, La0.8 2,2-bipyridyl-N,N-dioxide
tris pivaloyltrifluoroacetonato Eu0.2, La0.8 phenanthroline
tris pivaloyltrifluoroacetonato Eu0.2, La0.8 bathocuproine
tris pivaloyltrifluoroacetonato Eu0.2, La0.8 bathophenanthroline
tris trifluoroacetylacetonato Eu0.2, La0.8 dimethylaminopyridine
tris trifluoroacetylacetonato Eu0.2, La0.8 4-picoline-N-oxide
tris trifluoroacetylacetonato Eu0.2, La0.8 4-phenylpyridine
tris trifluoroacetylacetonato Eu0.2, La0.8 4-cyanopyridine
tris trifluoroacetylacetonato Eu0.2, La0.8 4-phenylpyridine-N-oxide
tris trifluoroacetylacetonato Eu0.2, La0.8 1-methylimidazole
tris trifluoroacetylacetonato Eu0.2, La0.8 triphenylphosphine oxide
tris trifluoroacetylacetonato Eu0.2, La0.8 2,2-bipyridyl
tris trifluoroacetylacetonato Eu0.2, La0.8 2,2-bipyridyl-N,N-dioxide
tris trifluoroacetylacetonato Eu0.2, La0.8 phenanthroline
tris trifluoroacetylacetonato Eu0.2, La0.8 bathocuproine
tris trifluoroacetylacetonato Eu0.2, La0.8 bathophenanthroline
tris hexafluoroacetylacetonato Eu0.2, La0.8 dimethylaminopyridine
tris hexafluoroacetylacetonato Eu0.2, La0.8 4-picoline-N-oxide
tris hexafluoroacetylacetonato Eu0.2, La0.8 4-phenylpyridine
tris hexafluoroacetylacetonato Eu0.2, La0.8 4-cyanopyridine
tris hexafluoroacetylacetonato Eu0.2, La0.8 4-phenylpyridine-N-oxide
tris hexafluoroacetylacetonato Eu0.2, La0.8 1-methylimidazole
tris hexafluoroacetylacetonato Eu0.2, La0.8 triphenylphosphine oxide
tris hexafluoroacetylacetonato Eu0.2, La0.8 2,2-bipyridyl
tris hexafluoroacetylacetonato Eu0.2, La0.8 2,2-bipyridyl-N,N-dioxide
tris hexafluoroacetylacetonato Eu0.2, La0.8 phenanthroline
tris hexafluoroacetylacetonato Eu0.2, La0.8 bathocuproine
tris hexafluoroacetylacetonato Eu0.2, La0.8 bathophenanthroline
tris 6,6,7,7,8,8-heptafluoro-2,2-dimethyloctanedionato Eu0.2, La0.8 dimethylaminopyridine
tris 6,6,7,7,8,8-heptafluoro-2,2-dimethyloctanedionato Eu0.2, La0.8 4-picoline-N-oxide
tris 6,6,7,7,8,8-heptafluoro-2,2-dimethyloctanedionato Eu0.2, La0.8 4-phenylpyridine
tris 6,6,7,7,8,8-heptafluoro-2,2-dimethyloctanedionato Eu0.2, La0.8 4-cyanopyridine
tris 6,6,7,7,8,8-heptafluoro-2,2-dimethyloctanedionato Eu0.2, La0.8 4-phenylpyridine-N-oxide
tris 6,6,7,7,8,8-heptafluoro-2,2-dimethyloctanedionato Eu0.2, La0.8 1-methylimidazole
tris 6,6,7,7,8,8-heptafluoro-2,2-dimethyloctanedionato Eu0.2, La0.8 triphenylphosphine oxide
tris 6,6,7,7,8,8-heptafluoro-2,2-dimethyloctanedionato Eu0.2, La0.8 2,2-bipyridyl
tris 6,6,7,7,8,8-heptafluoro-2,2-dimethyloctanedionato Eu0.2, La0.8 2,2-bipyridyl-N,N-dioxide
tris 6,6,7,7,8,8-heptafluoro-2,2-dimethyloctanedionato Eu0.2, La0.8 phenanthroline
tris 6,6,7,7,8,8-heptafluoro-2,2-dimethyloctanedionato Eu0.2, La0.8 bathocuproine
tris 6,6,7,7,8,8-heptafluoro-2,2-dimethyloctanedionato Eu0.2, La0.8 bathophenanthroline
tris 1-phenyl-1,3-butanedionato Eu0.2, La0.8 dimethylaminopyridine
tris 1-phenyl-1,3-butanedionato Eu0.2, La0.8 4-picoline-N-oxide
tris 1-phenyl-1,3-butanedionato Eu0.2, La0.8 4-phenylpyridine
tris 1-phenyl-1,3-butanedionato Eu0.2, La0.8 4-cyanopyridine
tris 1-phenyl-1,3-butanedionato Eu0.2, La0.8 4-phenylpyridine-N-oxide
tris 1-phenyl-1,3-butanedionato Eu0.2, La0.8 1-methylimidazole
tris 1-phenyl-1,3-butanedionato Eu0.2, La0.8 triphenylphosphine oxide
tris 1-phenyl-1,3-butanedionato Eu0.2, La0.8 2,2-bipyridyl
tris 1-phenyl-1,3-butanedionato Eu0.2, La0.8 2,2-bipyridyl-N,N-dioxide
tris 1-phenyl-1,3-butanedionato Eu0.2, La0.8 phenanthroline
tris 1-phenyl-1,3-butanedionato Eu0.2, La0.8 bathocuproine
tris 1-phenyl-1,3-butanedionato Eu0.2, La0.8 bathophenanthroline
tris acetylacetonato Eu0.25, La0.75 dimethylaminopyridine
tris acetylacetonato Eu0.25, La0.75 4-picoline-N-oxide
tris acetylacetonato Eu0.25, La0.75 4-phenylpyridine
tris acetylacetonato Eu0.25, La0.75 4-cyanopyridine
tris acetylacetonato Eu0.25, La0.75 4-phenylpyridine-N-oxide
tris acetylacetonato Eu0.25, La0.75 1-methylimidazole
tris acetylacetonato Eu0.25, La0.75 triphenylphosphine oxide
tris acetylacetonato Eu0.25, La0.75 2,2-bipyridyl
tris acetylacetonato Eu0.25, La0.75 2,2-bipyridyl-N,N-dioxide tris acetylacetonato Eu0.25, La0.75 phenanthroline
tris acetylacetonato Eu0.25, La0.75 bathocuproine
tris acetylacetonato Eu0.25, La0.75 bathophenanthroline
tris dibenzoylmethanato Eu0.25, La0.75 dimethylaminopyridine
tris dibenzoylmethanato Eu0.25, La0.75 4-picoline-N-oxide
tris dibenzoylmethanato Eu0.25, La0.75 4-phenylpyridine
tris dibenzoylmethanato Eu0.25, La0.75 4-cyanopyridine
tris dibenzoylmethanato Eu0.25, La0.75 4-phenylpyridine-N-oxide
tris dibenzoylmethanato Eu0.25, La0.75 1-methylimidazole
tris dibenzoylmethanato Eu0.25, La0.75 triphenylphosphine oxide
tris dibenzoylmethanato Eu0.25, La0.75 2,2-bipyridyl
tris dibenzoylmethanato Eu0.25, La0.75 2,2-bipyridyl-N,N-dioxide
tris dibenzoylmethanato Eu0.25, La0.75 phenanthroline
tris dibenzoylmethanato Eu0.25, La0.75 bathocuproine
tris dibenzoylmethanato Eu0.25, La0.75 bathophenanthroline
tris thenoyltrifluoroacetonato Eu0.25, La0.75 dimethylaminopyridine
tris thenoyltrifluoroacetonato Eu0.25, La0.75 4-picoline-N-oxide
tris thenoyltrifluoroacetonato Eu0.25, La0.75 4-phenylpyridine
tris thenoyltrifluoroacetonato Eu0.25, La0.75 4-cyanopyridine
tris thenoyltrifluoroacetonato Eu0.25, La0.75 4-phenylpyridine-N-oxide
tris thenoyltrifluoroacetonato Eu0.25, La0.75 1-methylimidazole
tris thenoyltrifluoroacetonato Eu0.25, La0.75 triphenylphosphine oxide
tris thenoyltrifluoroacetonato Eu0.25, La0.75 2,2-bipyridyl
tris thenoyltrifluoroacetonato Eu0.25, La0.75 2,2-bipyridyl-N,N-dioxide
tris thenoyltrifluoroacetonato Eu0.25, La0.75 phenanthroline
tris thenoyltrifluoroacetonato Eu0.25, La0.75 bathocuproine
tris thenoyltrifluoroacetonato Eu0.25, La0.75 bathophenanthroline
tris 2,2,6,6-tetramethylheptanedionato Eu0.25, La0.75 dimethylaminopyridine
tris 2,2,6,6-tetramethylheptanedionato Eu0.25, La0.75 4-picoline-N-oxide
tris 2,2,6,6-tetramethylheptanedionato Eu0.25, La0.75 4-phenylpyridine
tris 2,2,6,6-tetramethylheptanedionato Eu0.25, La0.75 4-cyanopyridine
tris 2,2,6,6-tetramethylheptanedionato Eu0.25, La0.75 4-phenylpyridine-N-oxide
tris 2,2,6,6-tetramethylheptanedionato Eu0.25, La0.75 1-methylimidazole
tris 2,2,6,6-tetramethylheptanedionato Eu0.25, La0.75 triphenylphosphine oxide
tris 2,2,6,6-tetramethylheptanedionato Eu0.25, La0.75 2,2-bipyridyl
tris 2,2,6,6-tetramethylheptanedionato Eu0.25, La0.75 2,2-bipyridyl-N,N-dioxide
tris 2,2,6,6-tetramethylheptanedionato Eu0.25, La0.75 phenanthroline
tris 2,2,6,6-tetramethylheptanedionato Eu0.25, La0.75 bathocuproine
tris 2,2,6,6-tetramethylheptanedionato Eu0.25, La0.75 bathophenanthroline
tris 3-methylpentane-2,4-dionato Eu0.25, La0.75 dimethylaminopyridine
tris 3-methylpentane-2,4-dionato Eu0.25, La0.75 4-picoline-N-oxide
tris 3-methylpentane-2,4-dionato Eu0.25, La0.75 4-phenylpyridine
tris 3-methylpentane-2,4-dionato Eu0.25, La0.75 4-cyanopyridine
tris 3-methylpentane-2,4-dionato Eu0.25, La0.75 4-phenylpyridine-N-oxide
tris 3-methylpentane-2,4-dionato Eu0.25, La0.75 1-methylimidazole
tris 3-methylpentane-2,4-dionato Eu0.25, La0.75 triphenylphosphine oxide
tris 3-methylpentane-2,4-dionato Eu0.25, La0.75 2,2-bipyridyl
tris 3-methylpentane-2,4-dionato Eu0.25, La0.75 2,2-bipyridyl-N,N-dioxide
tris 3-methylpentane-2,4-dionato Eu0.25, La0.75 phenanthroline
tris 3-methylpentane-2,4-dionato Eu0.25, La0.75 bathocuproine
tris 3-methylpentane-2,4-dionato Eu0.25, La0.75 bathophenanthroline
tris 3-ethylpentane-2,4-dionato Eu0.25, La0.75 dimethylaminopyridine
tris 3-ethylpentane-2,4-dionato Eu0.25, La0.75 4-picoline-N-oxide
tris 3-ethylpentane-2,4-dionato Eu0.25, La0.75 4-phenylpyridine
tris 3-ethylpentane-2,4-dionato Eu0.25, La0.75 4-cyanopyridine
tris 3-ethylpentane-2,4-dionato Eu0.25, La0.75 4-phenylpyridine-N-oxide
tris 3-ethylpentane-2,4-dionato Eu0.25, La0.75 1-methylimidazole
tris 3-ethylpentane-2,4-dionato Eu0.25, La0.75 triphenylphosphine oxide
tris 3-ethylpentane-2,4-dionato Eu0.25, La0.75 2,2-bipyridyl
tris 3-ethylpentane-2,4-dionato Eu0.25, La0.75 2,2-bipyridyl-N,N-dioxide
tris 3-ethylpentane-2,4-dionato Eu0.25, La0.75 phenanthroline
tris 3-ethylpentane-2,4-dionato Eu0.25, La0.75 bathocuproine
tris 3-ethylpentane-2,4-dionato Eu0.25, La0.75 bathophenanthroline
tris pivaloyltrifluoroacetonato Eu0.25, La0.75 dimethylaminopyridine
tris pivaloyltrifluoroacetonato Eu0.25, La0.75 4-picoline-N-oxide
tris pivaloyltrifluoroacetonato Eu0.25, La0.75 4-phenylpyridine
tris pivaloyltrifluoroacetonato Eu0.25, La0.75 4-cyanopyridine
tris pivaloyltrifluoroacetonato Eu0.25, La0.75 4-phenylpyridine-N-oxide
tris pivaloyltrifluoroacetonato Eu0.25, La0.75 1-methylimidazole
tris pivaloyltrifluoroacetonato Eu0.25, La0.75 triphenylphosphine oxide
tris pivaloyltrifluoroacetonato Eu0.25, La0.75 2,2-bipyridyl
tris pivaloyltrifluoroacetonato Eu0.25, La0.75 2,2-bipyridyl-N,N-dioxide
tris pivaloyltrifluoroacetonato Eu0.25, La0.75 phenanthroline tris pivaloyltrifluoroacetonato Eu0.25, La0.75 bathocuproine
tris pivaloyltrifluoroacetonato Eu0.25, La0.75 bathophenanthroline
tris trifluoroacetylacetonato Eu0.25, La0.75 dimethylaminopyridine
tris trifluoroacetylacetonato Eu0.25, La0.75 4-picoline-N-oxide
tris trifluoroacetylacetonato Eu0.25, La0.75 4-phenylpyridine
tris trifluoroacetylacetonato Eu0.25, La0.75 4-cyanopyridine
tris trifluoroacetylacetonato Eu0.25, La0.75 4-phenylpyridine-N-oxide
tris trifluoroacetylacetonato Eu0.25, La0.75 1-methylimidazole
tris trifluoroacetylacetonato Eu0.25, La0.75 triphenylphosphine oxide
tris trifluoroacetylacetonato Eu0.25, La0.75 2,2-bipyridyl
tris trifluoroacetylacetonato Eu0.25, La0.75 2,2-bipyridyl-N,N-dioxide
tris trifluoroacetylacetonato Eu0.25, La0.75 phenanthroline
tris trifluoroacetylacetonato Eu0.25, La0.75 bathocuproine
tris trifluoroacetylacetonato Eu0.25, La0.75 bathophenanthroline
tris hexafluoroacetylacetonato Eu0.25, La0.75 dimethylaminopyridine
tris hexafluoroacetylacetonato Eu0.25, La0.75 4-picoline-N-oxide
tris hexafluoroacetylacetonato Eu0.25, La0.75 4-phenylpyridine
tris hexafluoroacetylacetonato Eu0.25, La0.75 4-cyanopyridine
tris hexafluoroacetylacetonato Eu0.25, La0.75 4-phenylpyridine-N-oxide
tris hexafluoroacetylacetonato Eu0.25, La0.75 1-methylimidazole
tris hexafluoroacetylacetonato Eu0.25, La0.75 triphenylphosphine oxide
tris hexafluoroacetylacetonato Eu0.25, La0.75 2,2-bipyridyl
tris hexafluoroacetylacetonato Eu0.25, La0.75 2,2-bipyridyl-N,N-dioxide
tris hexafluoroacetylacetonato Eu0.25, La0.75 phenanthroline
tris hexafluoroacetylacetonato Eu0.25, La0.75 bathocuproine
tris hexafluoroacetylacetonato Eu0.25, La0.75 bathophenanthroline
tris 6,6,7,7,8,8,8-heptafluoro-2,2-dimethyloctanedionato Eu0.25, La0.75 dimethylaminopyridine
tris 6,6,7,7,8,8,8-heptafluoro-2,2-dimethyloctanedionato Eu0.25, La0.75 4-picoline-N-oxide
tris 6,6,7,7,8,8,8-heptafluoro-2,2-dimethyloctanedionato Eu0.25, La0.75 4-phenylpyridine
tris 6,6,7,7,8,8,8-heptafluoro-2,2-dimethyloctanedionato Eu0.25, La0.75 4-cyanopyridine
tris 6,6,7,7,8,8,8-heptafluoro-2,2-dimethyloctanedionato Eu0.25, La0.75 4-phenylpyridine-N-oxide
tris 6,6,7,7,8,8,8-heptafluoro-2,2-dimethyloctanedionato Eu0.25, La0.75 1-methylimidazole
tris 6,6,7,7,8,8,8-heptafluoro-2,2-dimethyloctanedionato Eu0.25, La0.75 triphenylphosphine oxide
tris 6,6,7,7,8,8,8-heptafluoro-2,2-dimethyloctanedionato Eu0.25, La0.75 2,2-bipyridyl
tris 6,6,7,7,8,8,8-heptafluoro-2,2-dimethyloctanedionato Eu0.25, La0.75 2,2-bipyridyl-N,N-dioxide
tris 6,6,7,7,8,8,8-heptafluoro-2,2-dimethyloctanedionato Eu0.25, La0.75 phenanthroline
tris 6,6,7,7,8,8,8-heptafluoro-2,2-dimethyloctanedionato Eu0.25, La0.75 bathocuproine
tris 6,6,7,7,8,8,8-heptafluoro-2,2-dimethyloctanedionato Eu0.25, La0.75 bathophenanthroline
tris 1-phenyl-1,3-butanedionato Eu0.25, La0.75 dimethylaminopyridine
tris 1-phenyl-1,3-butanedionato Eu0.25, La0.75 4-picoline-N-oxide
tris 1-phenyl-1,3-butanedionato Eu0.25, La0.75 4-phenylpyridine
tris 1-phenyl-1,3-butanedionato Eu0.25, La0.75 4-cyanopyridine
tris 1-phenyl-1,3-butanedionato Eu0.25, La0.75 4-phenylpyridine-N-oxide
tris 1-phenyl-1,3-butanedionato Eu0.25, La0.75 1-methylimidazole
tris 1-phenyl-1,3-butanedionato Eu0.25, La0.75 triphenylphosphine oxide
tris 1-phenyl-1,3-butanedionato Eu0.25, La0.75 2,2-bipyridyl
tris 1-phenyl-1,3-butanedionato Eu0.25, La0.75 2,2-bipyridyl-N,N-dioxide
tris 1-phenyl-1,3-butanedionato Eu0.25, La0.75 phenanthroline
tris 1-phenyl-1,3-butanedionato Eu0.25, La0.75 bathocuproine
tris 1-phenyl-1,3-butanedionato Eu0.25, La0.75 bathophenanthroline
tris acetylacetonato Eu0.1, La0.9 dimethylaminopyridine
tris acetylacetonato Eu0.1, La0.9 4-picoline-N-oxide
tris acetylacetonato Eu0.1, La0.9 4-phenylpyridine
tris acetylacetonato Eu0.1, La0.9 4-cyanopyridine
tris acetylacetonato Eu0.1, La0.9 4-phenylpyridine-N-oxide
tris acetylacetonato Eu0.1, La0.9 1-methylimidazole
tris acetylacetonato Eu0.1, La0.9 triphenylphosphine oxide
tris acetylacetonato Eu0.1, La0.9 2,2-bipyridyl
tris acetylacetonato Eu0.1, La0.9 2,2-bipyridyl-N,N-dioxide
tris acetylacetonato Eu0.1, La0.9 phenanthroline
tris acetylacetonato Eu0.1, La0.9 bathocuproine
tris acetylacetonato Eu0.1, La0.9 bathophenanthroline
tris dibenzoylmethanato Eu0.1, La0.9 dimethylaminopyridine
tris dibenzoylmethanato Eu0.1, La0.9 4-picoline-N-oxide
tris dibenzoylmethanato Eu0.1, La0.9 4-phenylpyridine
tris dibenzoylmethanato Eu0.1, La0.9 4-cyanopyridine
tris dibenzoylmethanato Eu0.1, La0.9 4-phenylpyridine-N-oxide
tris dibenzoylmethanato Eu0.1, La0.9 1-methylimidazole
tris dibenzoylmethanato Eu0.1, La0.9 triphenylphosphine oxide
tris dibenzoylmethanato Eu0.1, La0.9 2,2-bipyridyl
tris dibenzoylmethanato Eu0.1, La0.9 2,2-bipyridyl-N,N-dioxide
tris dibenzoylmethanato Eu0.1, La0.9 phenanthroline
tris dibenzoylmethanato Eu0.1, La0.9 bathocuproine
tris dibenzoylmethanato Eu0.1, La0.9 bathophenanthroline
tris thenoyltrifluoroacetonato Eu0.1, La0.9 dimethylaminopyridine
tris thenoyltrifluoroacetonato Eu0.1, La0.9 4-picoline-N-oxide
tris thenoyltrifluoroacetonato Eu0.1, La0.9 4-phenylpyridine
tris thenoyltrifluoroacetonato Eu0.1, La0.9 4-cyanopyridine
tris thenoyltrifluoroacetonato Eu0.1, La0.9 4-phenylpyridine-N-oxide tris thenoyltrifluoroacetonato Eu0.1, La0.9 1-methylimidazole
tris thenoyltrifluoroacetonato Eu0.1, La0.9 triphenylphosphine oxide
tris thenoyltrifluoroacetonato Eu0.1, La0.9 2,2-bipyridyl
tris thenoyltrifluoroacetonato Eu0.1, La0.9 2,2-bipyridyl-N,N-dioxide
tris thenoyltrifluoroacetonato Eu0.1, La0.9 phenanthroline
tris thenoyltrifluoroacetonato Eu0.1, La0.9 bathocuproine
tris thenoyltrifluoroacetonato Eu0.1, La0.9 bathophenanthroline
tris 2,2,6,6-tetramethylheptanedionato Eu0.1, La0.9 dimethylaminopyridine
tris 2,2,6,6-tetramethylheptanedionato Eu0.1, La0.9 4-picoline-N-oxide
tris 2,2,6,6-tetramethylheptanedionato Eu0.1, La0.9 4-phenylpyridine
tris 2,2,6,6-tetramethylheptanedionato Eu0.1, La0.9 4-cyanopyridine
tris 2,2,6,6-tetramethylheptanedionato Eu0.1, La0.9 4-phenylpyridine-N-oxide
tris 2,2,6,6-tetramethylheptanedionato Eu0.1, La0.9 1-methylimidazole
tris 2,2,6,6-tetramethylheptanedionato Eu0.1, La0.9 triphenylphosphine oxide
tris 2,2,6,6-tetramethylheptanedionato Eu0.1, La0.9 2,2-bipyridyl
tris 2,2,6,6-tetramethylheptanedionato Eu0.1, La0.9 2,2-bipyridyl-N,N-dioxide
tris 2,2,6,6-tetramethylheptanedionato Eu0.1, La0.9 phenanthroline
tris 2,2,6,6-tetramethylheptanedionato Eu0.1, La0.9 bathocuproine
tris 2,2,6,6-tetramethylheptanedionato Eu0.1, La0.9 bathophenanthroline
tris 3-methylpentane-2,4-dionato Eu0.1, La0.9 dimethylaminopyridine
tris 3-methylpentane-2,4-dionato Eu0.1, La0.9 4-picoline-N-oxide
tris 3-methylpentane-2,4-dionato Eu0.1, La0.9 4-phenylpyridine
tris 3-methylpentane-2,4-dionato Eu0.1, La0.9 4-cyanopyridine
tris 3-methylpentane-2,4-dionato Eu0.1, La0.9 4-phenylpyridine-N-oxide
tris 3-methylpentane-2,4-dionato Eu0.1, La0.9 1-methylimidazole
tris 3-methylpentane-2,4-dionato Eu0.1, La0.9 triphenylphosphine oxide
tris 3-methylpentane-2,4-dionato Eu0.1, La0.9 2,2-bipyridyl
tris 3-methylpentane-2,4-dionato Eu0.1, La0.9 2,2-bipyridyl-N,N-dioxide
tris 3-methylpentane-2,4-dionato Eu0.1, La0.9 phenanthroline
tris 3-methylpentane-2,4-dionato Eu0.1, La0.9 bathocuproine
tris 3-methylpentane-2,4-dionato Eu0.1, La0.9 bathophenanthroline
tris 3-ethylpentane-2,4-dionato Eu0.1, La0.9 dimethylaminopyridine
tris 3-ethylpentane-2,4-dionato Eu0.1, La0.9 4-picoline-N-oxide
tris 3-ethylpentane-2,4-dionato Eu0.1, La0.9 4-phenylpyridine
tris 3-ethylpentane-2,4-dionato Eu0.1, La0.9 4-cyanopyridine
tris 3-ethylpentane-2,4-dionato Eu0.1, La0.9 4-phenylpyridine-N-oxide
tris 3-ethylpentane-2,4-dionato Eu0.1, La0.9 1-methylimidazole
tris 3-ethylpentane-2,4-dionato Eu0.1, La0.9 triphenylphosphine oxide
tris 3-ethylpentane-2,4-dionato Eu0.1, La0.9 2,2-bipyridyl
tris 3-ethylpentane-2,4-dionato Eu0.1, La0.9 2,2-bipyridyl-N,N-dioxide
tris 3-ethylpentane-2,4-dionato Eu0.1, La0.9 phenanthroline
tris 3-ethylpentane-2,4-dionato Eu0.1, La0.9 bathocuproine
tris 3-ethylpentane-2,4-dionato Eu0.1, La0.9 bathophenanthroline
tris pivaloyltrifluoroacetonato Eu0.1, La0.9 dimethylaminopyridine
tris pivaloyltrifluoroacetonato Eu0.1, La0.9 4-picoline-N-oxide
tris pivaloyltrifluoroacetonato Eu0.1, La0.9 4-phenylpyridine
tris pivaloyltrifluoroacetonato Eu0.1, La0.9 4-cyanopyridine
tris pivaloyltrifluoroacetonato Eu0.1, La0.9 4-phenylpyridine-N-oxide
tris pivaloyltrifluoroacetonato Eu0.1, La0.9 1-methylimidazole
tris pivaloyltrifluoroacetonato Eu0.1, La0.9 triphenylphosphine oxide
tris pivaloyltrifluoroacetonato Eu0.1, La0.9 2,2-bipyridyl
tris pivaloyltrifluoroacetonato Eu0.1, La0.9 2,2-bipyridyl-N,N-dioxide
tris pivaloyltrifluoroacetonato Eu0.1, La0.9 phenanthroline
tris pivaloyltrifluoroacetonato Eu0.1, La0.9 bathocuproine
tris pivaloyltrifluoroacetonato Eu0.1, La0.9 bathophenanthroline
tris trifluoroacetylacetonato Eu0.1, La0.9 dimethylaminopyridine
tris trifluoroacetylacetonato Eu0.1, La0.9 4-picoline-N-oxide
tris trifluoroacetylacetonato Eu0.1, La0.9 4-phenylpyridine
tris trifluoroacetylacetonato Eu0.1, La0.9 4-cyanopyridine
tris trifluoroacetylacetonato Eu0.1, La0.9 4-phenylpyridine-N-oxide
tris trifluoroacetylacetonato Eu0.1, La0.9 1-methylimidazole
tris trifluoroacetylacetonato Eu0.1, La0.9 triphenylphosphine oxide
tris trifluoroacetylacetonato Eu0.1, La0.9 2,2-bipyridyl
tris trifluoroacetylacetonato Eu0.1, La0.9 2,2-bipyridyl-N,N-dioxide
tris trifluoroacetylacetonato Eu0.1, La0.9 phenanthroline
tris trifluoroacetylacetonato Eu0.1, La0.9 bathocuproine
tris trifluoroacetylacetonato Eu0.1, La0.9 bathophenanthroline
tris hexafluoroacetylacetonato Eu0.1, La0.9 dimethylaminopyridine
tris hexafluoroacetylacetonato Eu0.1, La0.9 4-picoline-N-oxide
tris hexafluoroacetylacetonato Eu0.1, La0.9 4-phenylpyridine
tris hexafluoroacetylacetonato Eu0.1, La0.9 4-cyanopyridine
tris hexafluoroacetylacetonato Eu0.1, La0.9 4-phenylpyridine-N-oxide
tris hexafluoroacetylacetonato Eu0.1, La0.9 1-methylimidazole
tris hexafluoroacetylacetonato Eu0.1, La0.9 triphenylphosphine oxide
tris hexafluoroacetylacetonato Eu0.1, La0.9 2,2-bipyridyl tris hexafluoroacetylacetonato Eu0.1, La0.9 2,2-bipyridyl-N,N-dioxide
tris hexafluoroacetylacetonato Eu0.1, La0.9 phenanthroline
tris hexafluoroacetylacetonato Eu0.1, La0.9: bathocuproine
tris hexafluoroacetylacetonato Eu0.1, La0.9 bathophenanthroline
tris 6,6,7,7,8,8,8-heptafluoro-2,2-dimethyloctanedionato Eu0.1, La0.9 dimethylaminopyridine
tris 6,6,7,7,8,8,8-heptafluoro-2,2-dimethyloctanedionato Eu0.1, La0.9 4-picoline-N-oxide
tris 6,6,7,7,8,8,8-heptafluoro-2,2-dimethyloctanedionato Eu0.1, La0.9 4-phenylpyridine
tris 6,6,7,7,8,8,8-heptafluoro-2,2-dimethyloctanedionato Eu0.1, La0.9 4-cyanopyridine
tris 6,6,7,7,8,8,8-heptafluoro-2,2-dimethyloctanedionato Eu0.1, La0.9 4-phenylpyridine-N-oxide
tris 6,6,7,7,8,8,8-heptafluoro-2,2-dimethyloctanedionato Eu0.1, La0.9 1-methylimidazole
tris 6,6,7,7,8,8,8-heptafluoro-2,2-dimethyloctanedionato Eu0.1, La0.9 triphenylphosphine oxide
tris 6,6,7,7,8,8,8-heptafluoro-2,2-dimethyloctanedionato Eu0.1, La0.9 2,2-bipyridyl
tris 6,6,7,7,8,8,8-heptafluoro-2,2-dimethyloctanedionato Eu0.1, La0.9 2,2-bipyridyl-N,N-dioxide
tris 6,6,7,7,8,8,8-heptafluoro-2,2-dimethyloctanedionato Eu0.1, La0.9 phenanthroline
tris 6,6,7,7,8,8,8-heptafluoro-2,2-dimethyloctanedionato Eu0.1, La0.9 bathocuproine
tris 6,6,7,7,8,8,8-heptafluoro-2,2-dimethyloctanedionato Eu0.1, La0.9 bathophenanthroline
tris 1-phenyl-1,3-butanedionato Eu0.1, La0.9 dimethylaminopyridine
tris 1-phenyl-1,3-butanedionato Eu0.1, La0.9 4-picoline-N-oxide
tris 1-phenyl-1,3-butanedionato Eu0.1, La0.9 4-phenylpyridine
tris 1-phenyl-1,3-butanedionato Eu0.1, La0.9 4-cyanopyridine
tris 1-phenyl-1,3-butanedionato Eu0.1, La0.9 4-phenylpyridine-N-oxide
tris 1-phenyl-1,3-butanedionato Eu0.1, La0.9 1-methylimidazole
tris 1-phenyl-1,3-butanedionato Eu0.1, La0.9 triphenylphosphine oxide
tris 1-phenyl-1,3-butanedionato Eu0.1, La0.9 2,2-bipyridyl
tris 1-phenyl-1,3-butanedionato Eu0.1, La0.9 2,2-bipyridyl-N,N-dioxide
tris 1-phenyl-1,3-butanedionato Eu0.1, La0.9 phenanthroline
tris 1-phenyl-1,3-butanedionato Eu0.1, La0.9 bathocuproine
tris 1-phenyl-1,3-butanedionato Eu0.1, La0.9 bathophenanthroline
tris acetylacetonato Eu0.01, La0.99 dimethylaminopyridine
tris acetylacetonato Eu0.01, La0.99 4-picoline-N-oxide
tris acetylacetonato Eu0.01, La0.99 4-phenylpyridine
tris acetylacetonato Eu0.01, La0.99 4-cyanopyridine
tris acetylacetonato Eu0.01, La0.99 4-phenylpyridine-N-oxide
tris acetylacetonato Eu0.01, La0.99 1-methylimidazole
tris acetylacetonato Eu0.01, La0.99 triphenylphosphine oxide
tris acetylacetonato Eu0.01, La0.99 2,2-bipyridyl
tris acetylacetonato Eu0.01, La0.99 2,2-bipyridyl-N,N-dioxide
tris acetylacetonato Eu0.01, La0.99 phenanthroline
tris acetylacetonato Eu0.01, La0.99 bathocuproine
tris acetylacetonato Eu0.01, La0.99 bathophenanthroline
tris dibenzoylmethanato Eu0.01, La0.99 dimethylaminopyridine
tris dibenzoylmethanato Eu0.01, La0.99 4-picoline-N-oxide
tris dibenzoylmethanato Eu0.01, La0.99 4-phenylpyridine
tris dibenzoylmethanato Eu0.01, La0.99 4-cyanopyridine
tris dibenzoylmethanato Eu0.01, La0.99 4-phenylpyridine-N-oxide
tris dibenzoylmethanato Eu0.01, La0.99 1-methylimidazole
tris dibenzoylmethanato Eu0.01, La0.99 triphenylphosphine oxide
tris dibenzoylmethanato Eu0.01, La0.99 2,2-bipyridyl
tris dibenzoylmethanato Eu0.01, La0.99 2,2-bipyridyl-N,N-dioxide
tris dibenzoylmethanato Eu0.01, La0.99 phenanthroline
tris dibenzoylmethanato Eu0.01, La0.99 bathocuproine
tris dibenzoylmethanato Eu0.01, La0.99 bathophenanthroline
tris thenoyltrifluoroacetonato Eu0.01, La0.99 dimethylaminopyridine
tris thenoyltrifluoroacetonato Eu0.01, La0.99 4-picoline-N-oxide
tris thenoyltrifluoroacetonato Eu0.01, La0.99 4-phenylpyridine
tris thenoyltrifluoroacetonato Eu0.01, La0.99 4-cyanopyridine
tris thenoyltrifluoroacetonato Eu0.01, La0.99 4-phenylpyridine-N-oxide
tris thenoyltrifluoroacetonato Eu0.01, La0.99 1-methylimidazole
tris thenoyltrifluoroacetonato Eu0.01, La0.99 triphenylphosphine oxide
tris thenoyltrifluoroacetonato Eu0.01, La0.99 2,2-bipyridyl
tris thenoyltrifluoroacetonato Eu0.01, La0.99 2,2-bipyridyl-N,N-dioxide
tris thenoyltrifluoroacetonato Eu0.01, La0.99 phenanthroline
tris thenoyltrifluoroacetonato Eu0.01, La0.99 bathocuproine
tris thenoyltrifluoroacetonato Eu0.01, La0.99 bathophenanthroline
tris 2,2,6,6-tetramethylheptanedionato Eu0.01, La0.99 dimethylaminopyridine
tris 2,2,6,6-tetramethylheptanedionato Eu0.01, La0.99 4-picoline-N-oxide
tris 2,2,6,6-tetramethylheptanedionato Eu0.01, La0.99 4-phenylpyridine
tris 2,2,6,6-tetramethylheptanedionato Eu0.01, La0.99 4-cyanopyridine
tris 2,2,6,6-tetramethylheptanedionato Eu0.01, La0.99 4-phenylpyridine-N-oxide
tris 2,2,6,6-tetramethylheptanedionato Eu0.01, La0.99 1-methylimidazole
tris 2,2,6,6-tetramethylheptanedionato Eu0.01, La0.99 triphenylphosphine oxide
tris 2,2,6,6-tetramethylheptanedionato Eu0.01, La0.99 2,2-bipyridyl
tris 2,2,6,6-tetramethylheptanedionato Eu0.01, La0.99 2,2-bipyridyl-N,N-dioxide
tris 2,2,6,6-tetramethylheptanedionato Eu0.01, La0.99 phenanthroline
tris 2,2,6,6-tetramethylheptanedionato Eu0.01, La0.99 bathocuproine
tris 2,2,6,6-tetramethylheptanedionato Eu0.01, La0.99 bathophenanthroline
tris 3-methylpentane-2,4-dionato Eu0.01, La0.99 dimethylaminopyridine
tris 3-methylpentane-2,4-dionato Eu0.01, La0.99 4-picoline-N-oxide tris 3-methylpentane-2,4-dionato Eu0.01, La0.99 4-phenylpyridine
tris 3-methylpentane-2,4-dionato Eu0.01, La0.99 4-cyanopyridine
tris 3-methylpentane-2,4-dionato Eu0.01, La0.99 4-phenylpyridine-N-oxide
tris 3-methylpentane-2,4-dionato Eu0.01, La0.99 1-methylimidazole
tris 3-methylpentane-2,4-dionato Eu0.01, La0.99 triphenylphosphine oxide
tris 3-methylpentane-2,4-dionato Eu0.01, La0.99 2,2-bipyridyl
tris 3-methylpentane-2,4-dionato Eu0.01, La0.99 2,2-bipyridyl-N,N-dioxide
tris 3-methylpentane-2,4-dionato Eu0.01, La0.99 phenanthroline
tris 3-methylpentane-2,4-dionato Eu0.01, La0.99 bathocuproine
tris 3-methylpentane-2,4-dionato Eu0.01, La0.99 bathophenanthroline
tris 3-ethylpentane-2,4-dionato Eu0.01, La0.99 dimethylaminopyridine
tris 3-ethylpentane-2,4-dionato Eu0.01, La0.99 4-picoline-N-oxide
tris 3-ethylpentane-2,4-dionato Eu0.01, La0.99 4-phenylpyridine
tris 3-ethylpentane-2,4-dionato Eu0.01, La0.99 4-cyanopyridine
tris 3-ethylpentane-2,4-dionato Eu0.01, La0.99 4-phenylpyridine-N-oxide
tris 3-ethylpentane-2,4-dionato Eu0.01, La0.99 1-methylimidazole
tris 3-ethylpentane-2,4-dionato Eu0.01, La0.99 triphenylphosphine oxide
tris 3-ethylpentane-2,4-dionato Eu0.01, La0.99 2,2-bipyridyl
tris 3-ethylpentane-2,4-dionato Eu0.01, La0.99 2,2-bipyridyl-N,N-dioxide
tris 3-ethylpentane-2,4-dionato Eu0.01, La0.99 phenanthroline
tris 3-ethylpentane-2,4-dionato Eu0.01, La0.99 bathocuproine
tris 3-ethylpentane-2,4-dionato Eu0.01, La0.99 bathophenanthroline
tris pivaloyltrifluoroacetonato Eu0.01, La0.99 dimethylaminopyridine
tris pivaloyltrifluoroacetonato Eu0.01, La0.99 4-picoline-N-oxide
tris pivaloyltrifluoroacetonato Eu0.01, La0.99 4-phenylpyridine
tris pivaloyltrifluoroacetonato Eu0.01, La0.99 4-cyanopyridine
tris pivaloyltrifluoroacetonato Eu0.01, La0.99 4-phenylpyridine-N-oxide
tris pivaloyltrifluoroacetonato Eu0.01, La0.99 1-methylimidazole
tris pivaloyltrifluoroacetonato Eu0.01, La0.99 triphenylphosphine oxide
tris pivaloyltrifluoroacetonato Eu0.01, La0.99 2,2-bipyridyl
tris pivaloyltrifluoroacetonato Eu0.01, La0.99 2,2-bipyridyl-N,N-dioxide
tris pivaloyltrifluoroacetonato Eu0.01, La0.99 phenanthroline
tris pivaloyltrifluoroacetonato Eu0.01, La0.99 bathocuproine
tris pivaloyltrifluoroacetonato Eu0.01, La0.99 bathophenanthroline
tris trifluoroacetylacetonato Eu0.01, La0.99 dimethylaminopyridine
tris trifluoroacetylacetonato Eu0.01, La0.99 4-picoline-N-oxide
tris trifluoroacetylacetonato Eu0.01, La0.99 4-phenylpyridine
tris trifluoroacetylacetonato Eu0.01, La0.99 4-cyanopyridine
tris trifluoroacetylacetonato Eu0.01, La0.99 4-phenylpyridine-N-oxide
tris trifluoroacetylacetonato Eu0.01, La0.99 1-methylimidazole
tris trifluoroacetylacetonato Eu0.01, La0.99 triphenylphosphine oxide
tris trifluoroacetylacetonato Eu0.01, La0.99 2,2-bipyridyl
tris trifluoroacetylacetonato Eu0.01, La0.99 2,2-bipyridyl-N,N-dioxide
tris trifluoroacetylacetonato Eu0.01, La0.99 phenanthroline
tris trifluoroacetylacetonato Eu0.01, La0.99 bathocuproine
tris trifluoroacetylacetonato Eu0.01, La0.99 bathophenanthroline
tris hexafluoroacetylacetonato Eu0.01, La0.99 dimethylaminopyridine
tris hexafluoroacetylacetonato Eu0.01, La0.99 4-picoline-N-oxide
tris hexafluoroacetylacetonato Eu0.01, La0.99 4-phenylpyridine
tris hexafluoroacetylacetonato Eu0.01, La0.99 4-cyanopyridine
tris hexafluoroacetylacetonato Eu0.01, La0.99 4-phenylpyridine-N-oxide
tris hexafluoroacetylacetonato Eu0.01, La0.99 1-methylimidazole
tris hexafluoroacetylacetonato Eu0.01, La0.99 triphenylphosphine oxide
tris hexafluoroacetylacetonato Eu0.01, La0.99 2,2-bipyridyl
tris hexafluoroacetylacetonato Eu0.01, La0.99 2,2-bipyridyl-N,N-dioxide
tris hexafluoroacetylacetonato Eu0.01, La0.99 phenanthroline
tris hexafluoroacetylacetonato Eu0.01, La0.99 bathocuproine
tris hexafluoroacetylacetonato Eu0.01, La0.99 bathophenanthroline
tris 6,6,7,7,8,8,8-heptafluoro-2,2-dimethyloctanedionato Eu0.01, La0.99 dimethylaminopyridine
tris 6,6,7,7,8,8,8-heptafluoro-2,2-dimethyloctanedionato Eu0.01, La0.99 4-picoline-N-oxide
tris 6,6,7,7,8,8,8-heptafluoro-2,2-dimethyloctanedionato Eu0.01, La0.99 4-phenylpyridine
tris 6,6,7,7,8,8,8-heptafluoro-2,2-dimethyloctanedionato Eu0.01, La0.99 4-cyanopyridine
tris 6,6,7,7,8,8,8-heptafluoro-2,2-dimethyloctanedionato Eu0.01, La0.99 4-phenylpyridine-N-oxide
tris 6,6,7,7,8,8,8-heptafluoro-2,2-dimethyloctanedionato Eu0.01, La0.99 1-methylimidazole
tris 6,6,7,7,8,8,8-heptafluoro-2,2-dimethyloctanedionato Eu0.01, La0.99 triphenylphosphine oxide
tris 6,6,7,7,8,8,8-heptafluoro-2,2-dimethyloctanedionato Eu0.01, La0.99 2,2-bipyridyl
tris 6,6,7,7,8,8,8-heptafluoro-2,2-dimethyloctanedionato Eu0.01, La0.99 2,2-bipyridyl-N,N-dioxide
tris 6,6,7,7,8,8,8-heptafluoro-2,2-dimethyloctanedionato Eu0.01, La0.99 phenanthroline
tris 6,6,7,7,8,8,8-heptafluoro-2,2-dimethyloctanedionato Eu0.01, La0.99 bathocuproine tris 6,6,7,7,8,8,8-heptafluoro-2,2-dimethyloctanedionato Eu0.01, La0.99 bathophenanthroline
tris 1-phenyl-1,3-butanedionato Eu0.01, La0.99 dimethylaminopyridine
tris 1-phenyl-1,3-butanedionato Eu0.01, La0.99 4-picoline-N-oxide
tris 1-phenyl-1,3-butanedionato Eu0.01, La0.99 4-phenylpyridine
tris 1-phenyl-1,3-butanedionato Eu0.01, La0.99 4-cyanopyridine
tris 1-phenyl-1,3-butanedionato Eu0.01, La0.99 4-phenylpyridine-N-oxide
tris 1-phenyl-1,3-butanedionato Eu0.01, La0.99 1-methylimidazole
tris 1-phenyl-1,3-butanedionato Eu0.01, La0.99 triphenylphosphine oxide
tris 1-phenyl-1,3-butanedionato Eu0.01, La0.99 2,2-bipyridyl
tris 1-phenyl-1,3-butanedionato Eu0.01, La0.99 2,2-bipyridyl-N,N-dioxide
tris 1-phenyl-1,3-butanedionato Eu0.01, La0.99 phenanthroline
tris 1-phenyl-1,3-butanedionato Eu0.01, La0.99 bathocuproine
tris 1-phenyl-1,3-butanedionato Eu0.01, La0.99 bathophenanthroline
tris acetylacetonato Eu0.5, La0.5 dimethylaminopyridine
tris acetylacetonato Eu0.5, La0.5 4-picoline-N-oxide
tris acetylacetonato Eu0.5, La0.5 4-phenylpyridine
tris acetylacetonato Eu0.5, La0.5 4-cyanopyridine
tris acetylacetonato Eu0.5, La0.5 4-phenylpyridine-N-oxide
tris acetylacetonato Eu0.5, La0.5 1-methylimidazole
tris acetylacetonato Eu0.5, La0.5 triphenylphosphine oxide
tris acetylacetonato Eu0.5, La0.5 2,2-bipyridyl
tris acetylacetonato Eu0.5, La0.5 2,2-bipyridyl-N,N-dioxide
tris acetylacetonato Eu0.5, La0.5 phenanthroline
tris acetylacetonato Eu0.5, La0.5 bathocuproine
tris acetylacetonato Eu0.5, La0.5 bathophenanthroline
tris dibenzoylmethanato Eu0.5, La0.5 dimethylaminopyridine
tris dibenzoylmethanato Eu0.5, La0.5 4-picoline-N-oxide
tris dibenzoylmethanato Eu0.5, La0.5 4-phenylpyridine
tris dibenzoylmethanato Eu0.5, La0.5 4-cyanopyridine
tris dibenzoylmethanato Eu0.5, La0.5 4-phenylpyridine-N-oxide
tris dibenzoylmethanato Eu0.5, La0.5 1-methylimidazole
tris dibenzoylmethanato Eu0.5, La0.5 triphenylphosphine oxide
tris dibenzoylmethanato Eu0.5, La0.5 2,2-bipyridyl
tris dibenzoylmethanato Eu0.5, La0.5 2,2-bipyridyl-N,N-dioxide
tris dibenzoylmethanato Eu0.5, La0.5 phenanthroline
tris dibenzoylmethanato Eu0.5, La0.5 bathocuproine
tris dibenzoylmethanato Eu0.5, La0.5 bathophenanthroline
tris thenoyltrifluoroacetonato Eu0.5, La0.5 dimethylaminopyridine
tris thenoyltrifluoroacetonato Eu0.5, La0.5 4-picoline-N-oxide
tris thenoyltrifluoroacetonato Eu0.5, La0.5 4-phenylpyridine
tris thenoyltrifluoroacetonato Eu0.5, La0.5 4-cyanopyridine
tris thenoyltrifluoroacetonato Eu0.5, La0.5 4-phenylpyridine-N-oxide
tris thenoyltrifluoroacetonato Eu0.5, La0.5 1-methylimidazole
tris thenoyltrifluoroacetonato Eu0.5, La0.5 triphenylphosphine oxide
tris thenoyltrifluoroacetonato Eu0.5, La0.5 2,2-bipyridyl
tris thenoyltrifluoroacetonato Eu0.5, La0.5 2,2-bipyridyl-N,N-dioxide
tris thenoyltrifluoroacetonato Eu0.5, La0.5 phenanthroline
tris thenoyltrifluoroacetonato Eu0.5, La0.5 bathocuproine
tris thenoyltrifluoroacetonato Eu0.5, La0.5 bathophenanthroline
tris 2,2,6,6-tetramethylheptanedionato Eu0.5, La0.5 dimethylaminopyridine
tris 2,2,6,6-tetramethylheptanedionato Eu0.5, La0.5 4-picoline-N-oxide
tris 2,2,6,6-tetramethylheptanedionato Eu0.5, La0.5 4-phenylpyridine
tris 2,2,6,6-tetramethylheptanedionato Eu0.5, La0.5 4-cyanopyridine
tris 2,2,6,6-tetramethylheptanedionato Eu0.5, La0.5 4-phenylpyridine-N-oxide
tris 2,2,6,6-tetramethylheptanedionato Eu0.5, La0.5 1-methylimidazole
tris 2,2,6,6-tetramethylheptanedionato Eu0.5, La0.5 triphenylphosphine oxide
tris 2,2,6,6-tetramethylheptanedionato Eu0.5, La0.5 2,2-bipyridyl
tris 2,2,6,6-tetramethylheptanedionato Eu0.5, La0.5 2,2-bipyridyl-N,N-dioxide
tris 2,2,6,6-tetramethylheptanedionato Eu0.5, La0.5 phenanthroline
tris 2,2,6,6-tetramethylheptanedionato Eu0.5, La0.5 bathocuproine
tris 2,2,6,6-tetramethylheptanedionato Eu0.5, La0.5 bathophenanthroline
tris 3-methylpentane-2,4-dionato Eu0.5, La0.5 dimethylaminopyridine
tris 3-methylpentane-2,4-dionato Eu0.5, La0.5 4-picoline-N-oxide
tris 3-methylpentane-2,4-dionato Eu0.5, La0.5 4-phenylpyridine
tris 3-methylpentane-2,4-dionato Eu0.5, La0.5 4-cyanopyridine
tris 3-methylpentane-2,4-dionato Eu0.5, La0.5 4-phenylpyridine-N-oxide
tris 3-methylpentane-2,4-dionato Eu0.5, La0.5 1-methylimidazole
tris 3-methylpentane-2,4-dionato Eu0.5, La0.5 triphenylphosphine oxide
tris 3-methylpentane-2,4-dionato Eu0.5, La0.5 2,2-bipyridyl
tris 3-methylpentane-2,4-dionato Eu0.5, La0.5 2,2-bipyridyl-N,N-dioxide
tris 3-methylpentane-2,4-dionato Eu0.5, La0.5 phenanthroline
tris 3-methylpentane-2,4-dionato Eu0.5, La0.5 bathocuproine
tris 3-methylpentane-2,4-dionato Eu0.5, La0.5 bathophenanthroline
tris 3-ethylpentane-2,4-dionato Eu0.5, La0.5 dimethylaminopyridine
tris 3-ethylpentane-2,4-dionato Eu0.5, La0.5 4-picoline-N-oxide
tris 3-ethylpentane-2,4-dionato Eu0.5, La0.5 4-phenylpyridine
tris 3-ethylpentane-2,4-dionato Eu0.5, La0.5 4-cyanopyridine
tris 3-ethylpentane-2,4-dionato Eu0.5, La0.5 4-phenylpyridine-N-oxide
tris 3-ethylpentane-2,4-dionato Eu0.5, La0.5 1-methylimidazole
tris 3-ethylpentane-2,4-dionato Eu0.5, La0.5 triphenylphosphine oxide tris 3-ethylpentane-2,4-dionato Eu0.5, La0.5 2,2-bipyridyl
tris 3-ethylpentane-2,4-dionato Eu0.5, La0.5 2,2-bipyridyl-N,N-dioxide
tris 3-ethylpentane-2,4-dionato Eu0.5, La0.5 phenanthroline
tris 3-ethylpentane-2,4-dionato Eu0.5, La0.5 bathocuproine
tris 3-ethylpentane-2,4-dionato Eu0.5, La0.5 bathophenanthroline
tris pivaloyltrifluoroacetonato Eu0.5, La0.5 dimethylaminopyridine
tris pivaloyltrifluoroacetonato Eu0.5, La0.5 4-picoline-N-oxide
tris pivaloyltrifluoroacetonato Eu0.5, La0.5 4-phenylpyridine
tris pivaloyltrifluoroacetonato Eu0.5, La0.5 4-cyanopyridine
tris pivaloyltrifluoroacetonato Eu0.5, La0.5 4-phenylpyridine-N-oxide
tris pivaloyltrifluoroacetonato Eu0.5, La0.5 1-methylimidazole
tris pivaloyltrifluoroacetonato Eu0.5, La0.5 triphenylphosphine oxide
tris pivaloyltrifluoroacetonato Eu0.5, La0.5 2,2-bipyridyl
tris pivaloyltrifluoroacetonato Eu0.5, La0.5 2,2-bipyridyl-N,N-dioxide
tris pivaloyltrifluoroacetonato Eu0.5, La0.5 phenanthroline
tris pivaloyltrifluoroacetonato Eu0.5, La0.5 bathocuproine
tris pivaloyltrifluoroacetonato Eu0.5, La0.5 bathophenanthroline
tris trifluoroacetylacetonato Eu0.5, La0.5 dimethylaminopyridine
tris trifluoroacetylacetonato Eu0.5, La0.5 4-picoline-N-oxide
tris trifluoroacetylacetonato Eu0.5, La0.5 4-phenylpyridine
tris trifluoroacetylacetonato Eu0.5, La0.5 4-cyanopyridine
tris trifluoroacetylacetonato Eu0.5, La0.5 4-phenylpyridine-N-oxide
tris trifluoroacetylacetonato Eu0.5, La0.5 1-methylimidazole
tris trifluoroacetylacetonato Eu0.5, La0.5 triphenylphosphine oxide
tris trifluoroacetylacetonato Eu0.5, La0.5 2,2-bipyridyl
tris trifluoroacetylacetonato Eu0.5, La0.5 2,2-bipyridyl-N,N-dioxide
tris trifluoroacetylacetonato Eu0.5, La0.5 phenanthroline
tris trifluoroacetylacetonato Eu0.5, La0.5 bathocuproine
tris trifluoroacetylacetonato Eu0.5, La0.5 bathophenanthroline
tris hexafluoroacetylacetonato Eu0.5, La0.5 dimethylaminopyridine
tris hexafluoroacetylacetonato Eu0.5, La0.5 4-picoline-N-oxide
tris hexafluoroacetylacetonato Eu0.5, La0.5 4-phenylpyridine
tris hexafluoroacetylacetonato Eu0.5, La0.5 4-cyanopyridine
tris hexafluoroacetylacetonato Eu0.5, La0.5 4-phenylpyridine-N-oxide
tris hexafluoroacetylacetonato Eu0.5, La0.5 1-methylimidazole
tris hexafluoroacetylacetonato Eu0.5, La0.5 triphenylphosphine oxide
tris hexafluoroacetylacetonato Eu0.5, La0.5 2,2-bipyridyl
tris hexafluoroacetylacetonato Eu0.5, La0.5 2,2-bipyridyl-N,N-dioxide
tris hexafluoroacetylacetonato Eu0.5, La0.5 phenanthroline
tris hexafluoroacetylacetonato Eu0.5, La0.5 bathocuproine
tris hexafluoroacetylacetonato Eu0.5, La0.5 bathophenanthroline
tris 6,6,7,7,8,8,8-heptafluoro-2,2-dimethyloctanedionato Eu0.5, La0.5 dimethylaminopyridine
tris 6,6,7,7,8,8,8-heptafluoro-2,2-dimethyloctanedionato Eu0.5, La0.5 4-picoline-N-oxide
tris 6,6,7,7,8,8,8-heptafluoro-2,2-dimethyloctanedionato Eu0.5, La0.5 4-phenylpyridine
tris 6,6,7,7,8,8,8-heptafluoro-2,2-dimethyloctanedionato Eu0.5, La0.5 4-cyanopyridine
tris 6,6,7,7,8,8,8-heptafluoro-2,2-dimethyloctanedionato Eu0.5, La0.5 4-phenylpyridine-N-oxide
tris 6,6,7,7,8,8,8-heptafluoro-2,2-dimethyloctanedionato Eu0.5, La0.5 1-methylimidazole
tris 6,6,7,7,8,8,8-heptafluoro-2,2-dimethyloctanedionato Eu0.5, La0.5 triphenylphosphine oxide
tris 6,6,7,7,8,8,8-heptafluoro-2,2-dimethyloctanedionato Eu0.5, La0.5 2,2-bipyridyl
tris 6,6,7,7,8,8,8-heptafluoro-2,2-dimethyloctanedionato Eu0.5, La0.5 2,2-bipyridyl-N,N-dioxide
tris 6,6,7,7,8,8,8-heptafluoro-2,2-dimethyloctanedionato Eu0.5, La0.5 phenanthroline
tris 6,6,7,7,8,8,8-heptafluoro-2,2-dimethyloctanedionato Eu0.5, La0.5 bathocuproine
tris 6,6,7,7,8,8,8-heptafluoro-2,2-dimethyloctanedionato Eu0.5, La0.5 bathophenanthroline
tris 1-phenyl-1,3-butanedionato Eu0.5, La0.5 dimethylaminopyridine
tris 1-phenyl-1,3-butanedionato Eu0.5, La0.5 4-picoline-N-oxide
tris 1-phenyl-1,3-butanedionato Eu0.5, La0.5 4-phenylpyridine
tris 1-phenyl-1,3-butanedionato Eu0.5, La0.5 4-cyanopyridine
tris 1-phenyl-1,3-butanedionato Eu0.5, La0.5 4-phenylpyridine-N-oxide
tris 1-phenyl-1,3-butanedionato Eu0.5, La0.5 1-methylimidazole
tris 1-phenyl-1,3-butanedionato Eu0.5, La0.5 triphenylphosphine oxide
tris 1-phenyl-1,3-butanedionato Eu0.5, La0.5 2,2-bipyridyl
tris 1-phenyl-1,3-butanedionato Eu0.5, La0.5 2,2-bipyridyl-N,N-dioxide
tris 1-phenyl-1,3-butanedionato Eu0.5, La0.5 phenanthroline
tris 1-phenyl-1,3-butanedionato Eu0.5, La0.5 bathocuproine
tris 1-phenyl-1,3-butanedionato Eu0.5, La0.5 bathophenanthroline
tris acetylacetonato Eu0.2, La0.8 dimethylaminopyridine
tris acetylacetonato Eu0.2, La0.8 4-picoline-N-oxide
tris acetylacetonato Eu0.2, La0.8 4-phenylpyridine
tris acetylacetonato Eu0.2, La0.8 4-cyanopyridine
tris acetylacetonato Eu0.2, La0.8 4-phenylpyridine-N-oxide
tris acetylacetonato Eu0.2, La0.8 1-methylimidazole
tris acetylacetonato Eu0.2, La0.8 triphenylphosphine oxide
tris acetylacetonato Eu0.2, La0.8 2,2-bipyridyl
tris acetylacetonato Eu0.2, La0.8 2,2-bipyridyl-N,N-dioxide
tris acetylacetonato Eu0.2, La0.8 phenanthroline
tris acetylacetonato Eu0.2, La0.8 bathocuproine
tris acetylacetonato Eu0.2, La0.8 bathophenanthroline
tris dibenzoylmethanato Eu0.2, La0.8 dimethylaminopyridine
tris dibenzoylmethanato Eu0.2, La0.8 4-picoline-N-oxide
tris dibenzoylmethanato Eu0.2, La0.8 4-phenylpyridine
tris dibenzoylmethanato Eu0.2, La0.8 4-cyanopyridine
tris dibenzoylmethanato Eu0.2, La0.8 4-phenylpyridine-N-oxide
tris dibenzoylmethanato Eu0.2, La0.8 1-methylimidazole tris dibenzoylmethanato Eu0.2, La0.8 triphenylphosphine oxide
tris dibenzoylmethanato Eu0.2, La0.8 2,2-bipyridyl
tris dibenzoylmethanato Eu0.2, La0.8 2,2-bipyridyl-N,N-dioxide
tris dibenzoylmethanato Eu0.2, La0.8 phenanthroline
tris dibenzoylmethanato Eu0.2, La0.8 bathocuproine
tris dibenzoylmethanato Eu0.2, La0.8 bathophenanthroline
tris thenoyltrifluoroacetonato Eu0.2, La0.8 dimethylaminopyridine
tris thenoyltrifluoroacetonato Eu0.2, La0.8 4-picoline-N-oxide
tris thenoyltrifluoroacetonato Eu0.2, La0.8 4-phenylpyridine
tris thenoyltrifluoroacetonato Eu0.2, La0.8 4-cyanopyridine
tris thenoyltrifluoroacetonato Eu0.2, La0.8 4-phenylpyridine-N-oxide
tris thenoyltrifluoroacetonato Eu0.2, La0.8 1-methylimidazole
tris thenoyltrifluoroacetonato Eu0.2, La0.8 triphenylphosphine oxide
tris thenoyltrifluoroacetonato Eu0.2, La0.8 2,2-bipyridyl
tris thenoyltrifluoroacetonato Eu0.2, La0.8 2,2-bipyridyl-N,N-dioxide
tris thenoyltrifluoroacetonato Eu0.2, La0.8 phenanthroline
tris thenoyltrifluoroacetonato Eu0.2, La0.8 bathocuproine
tris thenoyltrifluoroacetonato Eu0.2, La0.8 bathophenanthroline
tris 2,2,6,6-tetramethylheptanedionato Eu0.2, La0.8 dimethylaminopyridine
tris 2,2,6,6-tetramethylheptanedionato Eu0.2, La0.8 4-picoline-N-oxide
tris 2,2,6,6-tetramethylheptanedionato Eu0.2, La0.8 4-phenylpyridine
tris 2,2,6,6-tetramethylheptanedionato Eu0.2, La0.8 4-cyanopyridine
tris 2,2,6,6-tetramethylheptanedionato Eu0.2, La0.8 4-phenylpyridine-N-oxide
tris 2,2,6,6-tetramethylheptanedionato Eu0.2, La0.8 1-methylimidazole
tris 2,2,6,6-tetramethylheptanedionato Eu0.2, La0.8 triphenylphosphine oxide
tris 2,2,6,6-tetramethylheptanedionato Eu0.2, La0.8 2,2-bipyridyl
tris 2,2,6,6-tetramethylheptanedionato Eu0.2, La0.8 2,2-bipyridyl-N,N-dioxide
tris 2,2,6,6-tetramethylheptanedionato Eu0.2, La0.8 phenanthroline
tris 2,2,6,6-tetramethylheptanedionato Eu0.2, La0.8 bathocuproine
tris 2,2,6,6-tetramethylheptanedionato Eu0.2, La0.8 bathophenanthroline
tris 3-methylpentane-2,4-dionato Eu0.2, La0.8 dimethylaminopyridine
tris 3-methylpentane-2,4-dionato Eu0.2, La0.8 4-picoline-N-oxide
tris 3-methylpentane-2,4-dionato Eu0.2, La0.8 4-phenylpyridine
tris 3-methylpentane-2,4-dionato Eu0.2, La0.8 4-cyanopyridine
tris 3-methylpentane-2,4-dionato Eu0.2, La0.8 4-phenylpyridine-N-oxide
tris 3-methylpentane-2,4-dionato Eu0.2, La0.8 1-methylimidazole
tris 3-methylpentane-2,4-dionato Eu0.2, La0.8 triphenylphosphine oxide
tris 3-methylpentane-2,4-dionato Eu0.2, La0.8 2,2-bipyridyl
tris 3-methylpentane-2,4-dionato Eu0.2, La0.8 2,2-bipyridyl-N,N-dioxide
tris 3-methylpentane-2,4-dionato Eu0.2, La0.8 phenanthroline
tris 3-methylpentane-2,4-dionato Eu0.2, La0.8 bathocuproine
tris 3-methylpentane-2,4-dionato Eu0.2, La0.8 bathophenanthroline
tris 3-ethylpentane-2,4-dionato Eu0.2, La0.8 dimethylaminopyridine
tris 3-ethylpentane-2,4-dionato Eu0.2, La0.8 4-picoline-N-oxide
tris 3-ethylpentane-2,4-dionato Eu0.2, La0.8 4-phenylpyridine
tris 3-ethylpentane-2,4-dionato Eu0.2, La0.8 4-cyanopyridine
tris 3-ethylpentane-2,4-dionato Eu0.2, La0.8 4-phenylpyridine-N-oxide
tris 3-ethylpentane-2,4-dionato Eu0.2, La0.8 1-methylimidazole
tris 3-ethylpentane-2,4-dionato Eu0.2, La0.8 triphenylphosphine oxide
tris 3-ethylpentane-2,4-dionato Eu0.2, La0.8 2,2-bipyridyl
tris 3-ethylpentane-2,4-dionato Eu0.2, La0.8 2,2-bipyridyl-N,N-dioxide
tris 3-ethylpentane-2,4-dionato Eu0.2, La0.8 phenanthroline
tris 3-ethylpentane-2,4-dionato Eu0.2, La0.8 bathocuproine
tris 3-ethylpentane-2,4-dionato Eu0.2, La0.8 bathophenanthroline
tris pivaloyltrifluoroacetonato Eu0.2, La0.8 dimethylaminopyridine
tris pivaloyltrifluoroacetonato Eu0.2, La0.8 4-picoline-N-oxide
tris pivaloyltrifluoroacetonato Eu0.2, La0.8 4-phenylpyridine
tris pivaloyltrifluoroacetonato Eu0.2, La0.8 4-cyanopyridine
tris pivaloyltrifluoroacetonato Eu0.2, La0.8 4-phenylpyridine-N-oxide
tris pivaloyltrifluoroacetonato Eu0.2, La0.8 1-methylimidazole
tris pivaloyltrifluoroacetonato Eu0.2, La0.8 triphenylphosphine oxide
tris pivaloyltrifluoroacetonato Eu0.2, La0.8 2,2-bipyridyl
tris pivaloyltrifluoroacetonato Eu0.2, La0.8 2,2-bipyridyl-N,N-dioxide
tris pivaloyltrifluoroacetonato Eu0.2, La0.8 phenanthroline
tris pivaloyltrifluoroacetonato Eu0.2, La0.8 bathocuproine
tris pivaloyltrifluoroacetonato Eu0.2, La0.8 bathophenanthroline
tris trifluoroacetylacetonato Eu0.2, La0.8 dimethylaminopyridine
tris trifluoroacetylacetonato Eu0.2, La0.8 4-picoline-N-oxide
tris trifluoroacetylacetonato Eu0.2, La0.8 4-phenylpyridine
tris trifluoroacetylacetonato Eu0.2, La0.8 4-cyanopyridine
tris trifluoroacetylacetonato Eu0.2, La0.8 4-phenylpyridine-N-oxide
tris trifluoroacetylacetonato Eu0.2, La0.8 1-methylimidazole
tris trifluoroacetylacetonato Eu0.2, La0.8 triphenylphosphine oxide
tris trifluoroacetylacetonato Eu0.2, La0.8 2,2-bipyridyl
tris trifluoroacetylacetonato Eu0.2, La0.8 2,2-bipyridyl-N,N-dioxide
tris trifluoroacetylacetonato Eu0.2, La0.8 phenanthroline
tris trifluoroacetylacetonato Eu0.2, La0.8 bathocuproine tris trifluoroacetylacetonato Eu0.2, La0.8 bathophenanthroline
tris hexafluoroacetylacetonato Eu0.2, La0.8 dimethylaminopyridine
tris hexafluoroacetylacetonato Eu0.2, La0.8 4-picoline-N-oxide
tris hexafluoroacetylacetonato Eu0.2, La0.8 4-phenylpyridine
tris hexafluoroacetylacetonato Eu0.2, La0.8 4-cyanopyridine
tris hexafluoroacetylacetonato Eu0.2, La0.8 4-phenylpyridine-N-oxide
tris hexafluoroacetylacetonato Eu0.2, La0.8 1-methylimidazole
tris hexafluoroacetylacetonato Eu0.2, La0.8 triphenylphosphine oxide
tris hexafluoroacetylacetonato Eu0.2, La0.8 2,2-bipyridyl
tris hexafluoroacetylacetonato Eu0.2, La0.8 2,2-bipyridyl-N,N-dioxide
tris hexafluoroacetylacetonato Eu0.2, La0.8 phenanthroline
tris hexafluoroacetylacetonato Eu0.2, La0.8 bathocuproine
tris hexafluoroacetylacetonato Eu0.2, La0.8 bathophenanthroline
tris 6,6,7,7,8,8,8-heptafluoro-2,2-dimethyloctanedionato Eu0.2, La0.8 dimethylaminopyridine
tris 6,6,7,7,8,8,8-heptafluoro-2,2-dimethyloctanedionato Eu0.2, La0.8 4-picoline-N-oxide
tris 6,6,7,7,8,8,8-heptafluoro-2,2-dimethyloctanedionato Eu0.2, La0.8 4-phenylpyridine
tris 6,6,7,7,8,8,8-heptafluoro-2,2-dimethyloctanedionato Eu0.2, La0.8 4-cyanopyridine
tris 6,6,7,7,8,8,8-heptafluoro-2,2-dimethyloctanedionato Eu0.2, La0.8 4-phenylpyridine-N-oxide
tris 6,6,7,7,8,8,8-heptafluoro-2,2-dimethyloctanedionato Eu0.2, La0.8 1-methylimidazole
tris 6,6,7,7,8,8,8-heptafluoro-2,2-dimethyloctanedionato Eu0.2, La0.8 triphenylphosphine oxide
tris 6,6,7,7,8,8,8-heptafluoro-2,2-dimethyloctanedionato Eu0.2, La0.8 2,2-bipyridyl
tris 6,6,7,7,8,8,8-heptafluoro-2,2-dimethyloctanedionato Eu0.2, La0.8 2,2-bipyridyl-N,N-dioxide
tris 6,6,7,7,8,8,8-heptafluoro-2,2-dimethyloctanedionato Eu0.2, La0.8 phenanthroline
tris 6,6,7,7,8,8,8-heptafluoro-2,2-dimethyloctanedionato Eu0.2, La0.8 bathocuproine
tris 6,6,7,7,8,8,8-heptafluoro-2,2-dimethyloctanedionato Eu0.2, La0.8 bathophenanthroline
tris 1-phenyl-1,3-butanedionato Eu0.2, La0.8 dimethylaminopyridine
tris 1-phenyl-1,3-butanedionato Eu0.2, La0.8 4-picoline-N-oxide
tris 1-phenyl-1,3-butanedionato Eu0.2, La0.8 4-phenylpyridine
tris 1-phenyl-1,3-butanedionato Eu0.2, La0.8 4-cyanopyridine
tris 1-phenyl-1,3-butanedionato Eu0.2, La0.8 4-phenylpyridine-N-oxide
tris 1-phenyl-1,3-butanedionato Eu0.2, La0.8 1-methylimidazole
tris 1-phenyl-1,3-butanedionato Eu0.2, La0.8 triphenylphosphine oxide
tris 1-phenyl-1,3-butanedionato Eu0.2, La0.8 2,2-bipyridyl
tris 1-phenyl-1,3-butanedionato Eu0.2, La0.8 2,2-bipyridyl-N,N-dioxide
tris 1-phenyl-1,3-butanedionato Eu0.2, La0.8 phenanthroline
tris 1-phenyl-1,3-butanedionato Eu0.2, La0.8 bathocuproine
tris 1-phenyl-1,3-butanedionato Eu0.2, La0.8 bathophenanthroline
tris acetylacetonato Eu0.1, La0.9 dimethylaminopyridine
tris acetylacetonato Eu0.1, La0.9 4-picoline-N-oxide
tris acetylacetonato Eu0.1, La0.9 4-phenylpyridine
tris acetylacetonato Eu0.1, La0.9 4-cyanopyridine
tris acetylacetonato Eu0.1, La0.9 4-phenylpyridine-N-oxide
tris acetylacetonato Eu0.1, La0.9 1-methylimidazole
tris acetylacetonato Eu0.1, La0.9 triphenylphosphine oxide
tris acetylacetonato Eu0.1, La0.9 2,2-bipyridyl
tris acetylacetonato Eu0.1, La0.9 2,2-bipyridyl-N,N-dioxide
tris acetylacetonato Eu0.1, La0.9 phenanthroline
tris acetylacetonato Eu0.1, La0.9 bathocuproine
tris acetylacetonato Eu0.1, La0.9 bathophenanthroline
tris dibenzoylmethanato Eu0.1, La0.9 dimethylaminopyridine
tris dibenzoylmethanato Eu0.1, La0.9 4-picoline-N-oxide
tris dibenzoylmethanato Eu0.1, La0.9 4-phenylpyridine
tris dibenzoylmethanato Eu0.1, La0.9 4-cyanopyridine
tris dibenzoylmethanato Eu0.1, La0.9 4-phenylpyridine-N-oxide
tris dibenzoylmethanato Eu0.1, La0.9 1-methylimidazole
tris dibenzoylmethanato Eu0.1, La0.9 triphenylphosphine oxide
tris dibenzoylmethanato Eu0.1, La0.9 2,2-bipyridyl
tris dibenzoylmethanato Eu0.1, La0.9 2,2-bipyridyl-N,N-dioxide
tris dibenzoylmethanato Eu0.1, La0.9 phenanthroline
tris dibenzoylmethanato Eu0.1, La0.9 bathocuproine
tris dibenzoylmethanato Eu0.1, La0.9 bathophenanthroline
tris thenoyltrifluoroacetonato Eu0.1, La0.9 dimethylaminopyridine
tris thenoyltrifluoroacetonato Eu0.1, La0.9 4-picoline-N-oxide
tris thenoyltrifluoroacetonato Eu0.1, La0.9 4-phenylpyridine
tris thenoyltrifluoroacetonato Eu0.1, La0.9 4-cyanopyridine
tris thenoyltrifluoroacetonato Eu0.1, La0.9 4-phenylpyridine-N-oxide
tris thenoyltrifluoroacetonato Eu0.1, La0.9 1-methylimidazole
tris thenoyltrifluoroacetonato Eu0.1, La0.9 triphenylphosphine oxide
tris thenoyltrifluoroacetonato Eu0.1, La0.9 2,2-bipyridyl
tris thenoyltrifluoroacetonato Eu0.1, La0.9 2,2-bipyridyl-N,N-dioxide
tris thenoyltrifluoroacetonato Eu0.1, La0.9 phenanthroline
tris thenoyltrifluoroacetonato Eu0.1, La0.9 bathocuproine
tris thenoyltrifluoroacetonato Eu0.1, La0.9 bathophenanthroline
tris 2,2,6,6-tetramethylheptanedionato Eu0.1, La0.9 dimethylaminopyridine
tris 2,2,6,6-tetramethylheptanedionato Eu0.1, La0.9 4-picoline-N-oxide
tris 2,2,6,6-tetramethylheptanedionato Eu0.1, La0.9 4-phenylpyridine
tris 2,2,6,6-tetramethylheptanedionato Eu0.1, La0.9 4-cyanopyridine
tris 2,2,6,6-tetramethylheptanedionato Eu0.1, La0.9 4-phenylpyridine-N-oxide
tris 2,2,6,6-tetramethylheptanedionato Eu0.1, La0.9 1-methylimidazole
tris 2,2,6,6-tetramethylheptanedionato Eu0.1, La0.9 triphenylphosphine oxide
tris 2,2,6,6-tetramethylheptanedionato Eu0.1, La0.9 2,2-bipyridyl
tris 2,2,6,6-tetramethylheptanedionato Eu0.1, La0.9 2,2-bipyridyl-N,N-dioxide tris 2,2,6,6-tetramethylheptanedionato Eu0.1, La0.9 phenanthroline
tris 2,2,6,6-tetramethylheptanedionato Eu0.1, La0.9 bathocuproine
tris 2,2,6,6-tetramethylheptanedionato Eu0.1, La0.9 bathophenanthroline
tris 3-methylpentane-2,4-dionato Eu0.1, La0.9 dimethylaminopyridine
tris 3-methylpentane-2,4-dionato Eu0.1, La0.9 4-picoline-N-oxide
tris 3-methylpentane-2,4-dionato Eu0.1, La0.9 4-phenylpyridine
tris 3-methylpentane-2,4-dionato Eu0.1, La0.9 4-cyanopyridine
tris 3-methylpentane-2,4-dionato Eu0.1, La0.9 4-phenylpyridine-N-oxide
tris 3-methylpentane-2,4-dionato Eu0.1, La0.9 1-methylimidazole
tris 3-methylpentane-2,4-dionato Eu0.1, La0.9 triphenylphosphine oxide
tris 3-methylpentane-2,4-dionato Eu0.1, La0.9 2,2-bipyridyl
tris 3-methylpentane-2,4-dionato Eu0.1, La0.9 2,2-bipyridyl-N,N-dioxide
tris 3-methylpentane-2,4-dionato Eu0.1, La0.9 phenanthroline
tris 3-methylpentane-2,4-dionato Eu0.1, La0.9 bathocuproine
tris 3-methylpentane-2,4-dionato Eu0.1, La0.9 bathophenanthroline
tris 3-ethylpentane-2,4-dionato Eu0.1, La0.9 dimethylaminopyridine
tris 3-ethylpentane-2,4-dionato Eu0.1, La0.9 4-picoline-N-oxide
tris 3-ethylpentane-2,4-dionato Eu0.1, La0.9 4-phenylpyridine
tris 3-ethylpentane-2,4-dionato Eu0.1, La0.9 4-cyanopyridine
tris 3-ethylpentane-2,4-dionato Eu0.1, La0.9 4-phenylpyridine-N-oxide
tris 3-ethylpentane-2,4-dionato Eu0.1, La0.9 1-methylimidazole
tris 3-ethylpentane-2,4-dionato Eu0.1, La0.9 triphenylphosphine oxide
tris 3-ethylpentane-2,4-dionato Eu0.1, La0.9 2,2-bipyridyl
tris 3-ethylpentane-2,4-dionato Eu0.1, La0.9 2,2-bipyridyl-N,N-dioxide
tris 3-ethylpentane-2,4-dionato Eu0.1, La0.9 phenanthroline
tris 3-ethylpentane-2,4-dionato Eu0.1, La0.9 bathocuproine
tris 3-ethylpentane-2,4-dionato Eu0.1, La0.9 bathophenanthroline
tris pivaloyltrifluoroacetonato Eu0.1, La0.9 dimethylaminopyridine
tris pivaloyltrifluoroacetonato Eu0.1, La0.9 4-picoline-N-oxide
tris pivaloyltrifluoroacetonato Eu0.1, La0.9 4-phenylpyridine
tris pivaloyltrifluoroacetonato Eu0.1, La0.9 4-cyanopyridine
tris pivaloyltrifluoroacetonato Eu0.1, La0.9 4-phenylpyridine-N-oxide
tris pivaloyltrifluoroacetonato Eu0.1, La0.9 1-methylimidazole
tris pivaloyltrifluoroacetonato Eu0.1, La0.9 triphenylphosphine oxide
tris pivaloyltrifluoroacetonato Eu0.1, La0.9 2,2-bipyridyl
tris pivaloyltrifluoroacetonato Eu0.1, La0.9 2,2-bipyridyl-N,N-dioxide
tris pivaloyltrifluoroacetonato Eu0.1, La0.9 phenanthroline
tris pivaloyltrifluoroacetonato Eu0.1, La0.9 bathocuproine
tris pivaloyltrifluoroacetonato Eu0.1, La0.9 bathophenanthroline
tris trifluoroacetylacetonato Eu0.1, La0.9 dimethylaminopyridine
tris trifluoroacetylacetonato Eu0.1, La0.9 4-picoline-N-oxide
tris trifluoroacetylacetonato Eu0.1, La0.9 4-phenylpyridine
tris trifluoroacetylacetonato Eu0.1, La0.9 4-cyanopyridine
tris trifluoroacetylacetonato Eu0.1, La0.9 4-phenylpyridine-N-oxide
tris trifluoroacetylacetonato Eu0.1, La0.9 1-methylimidazole
tris trifluoroacetylacetonato Eu0.1, La0.9 triphenylphosphine oxide
tris trifluoroacetylacetonato Eu0.1, La0.9 2,2-bipyridyl
tris trifluoroacetylacetonato Eu0.1, La0.9 2,2-bipyridyl-N,N-dioxide
tris trifluoroacetylacetonato Eu0.1, La0.9 phenanthroline
tris trifluoroacetylacetonato Eu0.1, La0.9 bathocuproine
tris trifluoroacetylacetonato Eu0.1, La0.9 bathophenanthroline
tris hexafluoroacetylacetonato Eu0.1, La0.9 dimethylaminopyridine
tris hexafluoroacetylacetonato Eu0.1, La0.9 4-picoline-N-oxide
tris hexafluoroacetylacetonato Eu0.1, La0.9 4-phenylpyridine
tris hexafluoroacetylacetonato Eu0.1, La0.9 4-cyanopyridine
tris hexafluoroacetylacetonato Eu0.1, La0.9 4-phenylpyridine-N-oxide
tris hexafluoroacetylacetonato Eu0.1, La0.9 1-methylimidazole
tris hexafluoroacetylacetonato Eu0.1, La0.9 triphenylphosphine oxide
tris hexafluoroacetylacetonato Eu0.1, La0.9 2,2-bipyridyl
tris hexafluoroacetylacetonato Eu0.1, La0.9 2,2-bipyridyl-N,N-dioxide
tris hexafluoroacetylacetonato Eu0.1, La0.9 phenanthroline
tris hexafluoroacetylacetonato Eu0.1, La0.9 bathocuproine
tris hexafluoroacetylacetonato Eu0.1, La0.9 bathophenanthroline
tris 6,6,7,7,8,8,8-heptafluoro-2,2-dimethyloctanedionato Eu0.1, La0.9 dimethylaminopyridine
tris 6,6,7,7,8,8,8-heptafluoro-2,2-dimethyloctanedionato Eu0.1, La0.9 4-picoline-N-oxide
tris 6,6,7,7,8,8,8-heptafluoro-2,2-dimethyloctanedionato Eu0.1, La0.9 4-phenylpyridine
tris 6,6,7,7,8,8,8-heptafluoro-2,2-dimethyloctanedionato Eu0.1, La0.9 4-cyanopyridine
tris 6,6,7,7,8,8,8-heptafluoro-2,2-dimethyloctanedionato Eu0.1, La0.9 4-phenylpyridine-N-oxide
tris 6,6,7,7,8,8,8-heptafluoro-2,2-dimethyloctanedionato Eu0.1, La0.9 1-methylimidazole
tris 6,6,7,7,8,8,8-heptafluoro-2,2-dimethyloctanedionato Eu0.1, La0.9 triphenylphosphine oxide
tris 6,6,7,7,8,8,8-heptafluoro-2,2-dimethyloctanedionato Eu0.1, La0.9 2,2-bipyridyl
tris 6,6,7,7,8,8,8-heptafluoro-2,2-dimethyloctanedionato Eu0.1, La0.9 2,2-bipyridyl-N,N-dioxide
tris 6,6,7,7,8,8,8-heptafluoro-2,2-dimethyloctanedionato Eu0.1, La0.9 phenanthroline
tris 6,6,7,7,8,8,8-heptafluoro-2,2-dimethyloctanedionato Eu0.1, La0.9 bathocuproine
tris 6,6,7,7,8,8,8-heptafluoro-2,2-dimethyloctanedionato Eu0.1, La0.9 bathophenanthroline tris 1-phenyl-1,3-butanedionato Eu0.1, La0.9 dimethylaminopyridine
tris 1-phenyl-1,3-butanedionato Eu0.1, La0.9 4-picoline-N-oxide
tris 1-phenyl-1,3-butanedionato Eu0.1, La0.9 4-phenylpyridine
tris 1-phenyl-1,3-butanedionato Eu0.1, La0.9 4-cyanopyridine
tris 1-phenyl-1,3-butanedionato Eu0.1, La0.9 4-phenylpyridine-N-oxide
tris 1-phenyl-1,3-butanedionato Eu0.1, La0.9 1-methylimidazole
tris 1-phenyl-1,3-butanedionato Eu0.1, La0.9 triphenylphosphine oxide
tris 1-phenyl-1,3-butanedionato Eu0.1, La0.9 2,2-bipyridyl
tris 1-phenyl-1,3-butanedionato Eu0.1, La0.9 2,2-bipyridyl-N,N-dioxide
tris 1-phenyl-1,3-butanedionato Eu0.1, La0.9 phenanthroline
tris 1-phenyl-1,3-butanedionato Eu0.1, La0.9 bathocuproine
tris 1-phenyl-1,3-butanedionato Eu0.1, La0.9 bathophenanthroline
tris acetylacetonato Eu0.01, La0.99 dimethylaminopyridine
tris acetylacetonato Eu0.01, La0.99 4-picoline-N-oxide
tris acetylacetonato Eu0.01, La0.99 4-phenylpyridine
tris acetylacetonato Eu0.01, La0.99 4-cyanopyridine
tris acetylacetonato Eu0.01, La0.99 4-phenylpyridine-N-oxide
tris acetylacetonato Eu0.01, La0.99 1-methylimidazole
tris acetylacetonato Eu0.01, La0.99 triphenylphosphine oxide
tris acetylacetonato Eu0.01, La0.99 2,2-bipyridyl
tris acetylacetonato Eu0.01, La0.99 2,2-bipyridyl-N,N-dioxide
tris acetylacetonato Eu0.01, La0.99 phenanthroline
tris acetylacetonato Eu0.01, La0.99 bathocuproine
tris acetylacetonato Eu0.01, La0.99 bathophenanthroline
tris dibenzoylmethanato Eu0.01, La0.99 dimethylaminopyridine
tris dibenzoylmethanato Eu0.01, La0.99 4-picoline-N-oxide
tris dibenzoylmethanato Eu0.01, La0.99 4-phenylpyridine
tris dibenzoylmethanato Eu0.01, La0.99 4-cyanopyridine
tris dibenzoylmethanato Eu0.01, La0.99 4-phenylpyridine-N-oxide
tris dibenzoylmethanato Eu0.01, La0.99 1-methylimidazole
tris dibenzoylmethanato Eu0.01, La0.99 triphenylphosphine oxide
tris dibenzoylmethanato Eu0.01, La0.99 2,2-bipyridyl
tris dibenzoylmethanato Eu0.01, La0.99 2,2-bipyridyl-N,N-dioxide
tris dibenzoylmethanato Eu0.01, La0.99 phenanthroline
tris dibenzoylmethanato Eu0.01, La0.99 bathocuproine
tris dibenzoylmethanato Eu0.01, La0.99 bathophenanthroline
tris thenoyltrifluoroacetonato Eu0.01, La0.99 dimethylaminopyridine
tris thenoyltrifluoroacetonato Eu0.01, La0.99 4-picoline-N-oxide
tris thenoyltrifluoroacetonato Eu0.01, La0.99 4-phenylpyridine
tris thenoyltrifluoroacetonato Eu0.01, La0.99 4-cyanopyridine
tris thenoyltrifluoroacetonato Eu0.01, La0.99 4-phenylpyridine-N-oxide
tris thenoyltrifluoroacetonato Eu0.01, La0.99 1-methylimidazole
tris thenoyltrifluoroacetonato Eu0.01, La0.99 triphenylphosphine oxide
tris thenoyltrifluoroacetonato Eu0.01, La0.99 2,2-bipyridyl
tris thenoyltrifluoroacetonato Eu0.01, La0.99 2,2-bipyridyl-N,N-dioxide
tris thenoyltrifluoroacetonato Eu0.01, La0.99 phenanthroline
tris thenoyltrifluoroacetonato Eu0.01, La0.99 bathocuproine
tris thenoyltrifluoroacetonato Eu0.01, La0.99 bathophenanthroline
tris 2,2,6,6-tetramethylheptanedionato Eu0.01, La0.99 dimethylaminopyridine
tris 2,2,6,6-tetramethylheptanedionato Eu0.01, La0.99 4-picoline-N-oxide
tris 2,2,6,6-tetramethylheptanedionato Eu0.01, La0.99 4-phenylpyridine
tris 2,2,6,6-tetramethylheptanedionato Eu0.01, La0.99 4-cyanopyridine
tris 2,2,6,6-tetramethylheptanedionato Eu0.01, La0.99 4-phenylpyridine-N-oxide
tris 2,2,6,6-tetramethylheptanedionato Eu0.01, La0.99 1-methylimidazole
tris 2,2,6,6-tetramethylheptanedionato Eu0.01, La0.99 triphenylphosphine oxide
tris 2,2,6,6-tetramethylheptanedionato Eu0.01, La0.99 2,2-bipyridyl
tris 2,2,6,6-tetramethylheptanedionato Eu0.01, La0.99 2,2-bipyridyl-N,N-dioxide
tris 2,2,6,6-tetramethylheptanedionato Eu0.01, La0.99 phenanthroline
tris 2,2,6,6-tetramethylheptanedionato Eu0.01, La0.99 bathocuproine
tris 2,2,6,6-tetramethylheptanedionato Eu0.01, La0.99 bathophenanthroline
tris 3-methylpentane-2,4-dionato Eu0.01, La0.99 dimethylaminopyridine
tris 3-methylpentane-2,4-dionato Eu0.01, La0.99 4-picoline-N-oxide
tris 3-methylpentane-2,4-dionato Eu0.01, La0.99 4-phenylpyridine
tris 3-methylpentane-2,4-dionato Eu0.01, La0.99 4-cyanopyridine
tris 3-methylpentane-2,4-dionato Eu0.01, La0.99 4-phenylpyridine-N-oxide
tris 3-methylpentane-2,4-dionato Eu0.01, La0.99 1-methylimidazole
tris 3-methylpentane-2,4-dionato Eu0.01, La0.99 triphenylphosphine oxide
tris 3-methylpentane-2,4-dionato Eu0.01, La0.99 2,2-bipyridyl
tris 3-methylpentane-2,4-dionato Eu0.01, La0.99 2,2-bipyridyl-N,N-dioxide
tris 3-methylpentane-2,4-dionato Eu0.01, La0.99 phenanthroline
tris 3-methylpentane-2,4-dionato Eu0.01, La0.99 bathocuproine
tris 3-methylpentane-2,4-dionato Eu0.01, La0.99 bathophenanthroline
tris 3-ethylpentane-2,4-dionato Eu0.01, La0.99 dimethylaminopyridine
tris 3-ethylpentane-2,4-dionato Eu0.01, La0.99 4-picoline-N-oxide
tris 3-ethylpentane-2,4-dionato Eu0.01, La0.99 4-phenylpyridine
tris 3-ethylpentane-2,4-dionato Eu0.01, La0.99 4-cyanopyridine tris 3-ethylpentane-2,4-dionato Eu0.01, La0.99 4-phenylpyridine-N-oxide
tris 3-ethylpentane-2,4-dionato Eu0.01, La0.99 1-methylimidazole
tris 3-ethylpentane-2,4-dionato Eu0.01, La0.99 triphenylphosphine oxide
tris 3-ethylpentane-2,4-dionato Eu0.01, La0.99 2,2-bipyridyl
tris 3-ethylpentane-2,4-dionato Eu0.01, La0.99 2,2-bipyridyl-N,N-dioxide
tris 3-ethylpentane-2,4-dionato Eu0.01, La0.99 phenanthroline
tris 3-ethylpentane-2,4-dionato Eu0.01, La0.99 bathocuproine
tris 3-ethylpentane-2,4-dionato Eu0.01, La0.99 bathophenanthroline
tris pivaloyltrifluoroacetonato Eu0.01, La0.99 dimethylaminopyridine
tris pivaloyltrifluoroacetonato Eu0.01, La0.99 4-picoline-N-oxide
tris pivaloyltrifluoroacetonato Eu0.01, La0.99 4-phenylpyridine
tris pivaloyltrifluoroacetonato Eu0.01, La0.99 4-cyanopyridine
tris pivaloyltrifluoroacetonato Eu0.01, La0.99 4-phenylpyridine-N-oxide
tris pivaloyltrifluoroacetonato Eu0.01, La0.99 1-methylimidazole
tris pivaloyltrifluoroacetonato Eu0.01, La0.99 triphenylphosphine oxide
tris pivaloyltrifluoroacetonato Eu0.01, La0.99 2,2-bipyridyl
tris pivaloyltrifluoroacetonato Eu0.01, La0.99 2,2-bipyridyl-N,N-dioxide
tris pivaloyltrifluoroacetonato Eu0.01, La0.99 phenanthroline
tris pivaloyltrifluoroacetonato Eu0.01, La0.99 bathocuproine
tris pivaloyltrifluoroacetonato Eu0.01, La0.99 bathophenanthroline
tris trifluoroacetylacetonato Eu0.01, La0.99 dimethylaminopyridine
tris trifluoroacetylacetonato Eu0.01, La0.99 4-picoline-N-oxide
tris trifluoroacetylacetonato Eu0.01, La0.99 4-phenylpyridine
tris trifluoroacetylacetonato Eu0.01, La0.99 4-cyanopyridine
tris trifluoroacetylacetonato Eu0.01, La0.99 4-phenylpyridine-N-oxide
tris trifluoroacetylacetonato Eu0.01, La0.99 1-methylimidazole
tris trifluoroacetylacetonato Eu0.01, La0.99 triphenylphosphine oxide
tris trifluoroacetylacetonato Eu0.01, La0.99 2,2-bipyridyl
tris trifluoroacetylacetonato Eu0.01, La0.99 2,2-bipyridyl-N,N-dioxide
tris trifluoroacetylacetonato Eu0.01, La0.99 phenanthroline
tris trifluoroacetylacetonato Eu0.01, La0.99 bathocuproine
tris trifluoroacetylacetonato Eu0.01, La0.99 bathophenanthroline
tris hexafluoroacetylacetonato Eu0.01, La0.99 dimethylaminopyridine
tris hexafluoroacetylacetonato Eu0.01, La0.99 4-picoline-N-oxide
tris hexafluoroacetylacetonato Eu0.01, La0.99 4-phenylpyridine
tris hexafluoroacetylacetonato Eu0.01, La0.99 4-cyanopyridine
tris hexafluoroacetylacetonato Eu0.01, La0.99 4-phenylpyridine-N-oxide
tris hexafluoroacetylacetonato Eu0.01, La0.99 1-methylimidazole
tris hexafluoroacetylacetonato Eu0.01, La0.99 triphenylphosphine oxide
tris hexafluoroacetylacetonato Eu0.01, La0.99 2,2-bipyridyl
tris hexafluoroacetylacetonato Eu0.01, La0.99 2,2-bipyridyl-N,N-dioxide
tris hexafluoroacetylacetonato Eu0.01, La0.99 phenanthroline
tris hexafluoroacetylacetonato Eu0.01, La0.99 bathocuproine
tris hexafluoroacetylacetonato Eu0.01, La0.99 bathophenanthroline
tris 6,6,7,7,8,8,8-heptafluoro-2,2-dimethyloctanedionato Eu0.01, La0.99 dimethylaminopyridine
tris 6,6,7,7,8,8,8-heptafluoro-2,2-dimethyloctanedionato Eu0.01, La0.99 4-picoline-N-oxide
tris 6,6,7,7,8,8,8-heptafluoro-2,2-dimethyloctanedionato Eu0.01, La0.99 4-phenylpyridine
tris 6,6,7,7,8,8,8-heptafluoro-2,2-dimethyloctanedionato Eu0.01, La0.99 4-cyanopyridine
tris 6,6,7,7,8,8,8-heptafluoro-2,2-dimethyloctanedionato Eu0.01, La0.99 4-phenylpyridine-N-oxide
tris 6,6,7,7,8,8,8-heptafluoro-2,2-dimethyloctanedionato Eu0.01, La0.99 1-methylimidazole
tris 6,6,7,7,8,8,8-heptafluoro-2,2-dimethyloctanedionato Eu0.01, La0.99 triphenylphosphine oxide
tris 6,6,7,7,8,8,8-heptafluoro-2,2-dimethyloctanedionato Eu0.01, La0.99 2,2-bipyridyl
tris 6,6,7,7,8,8,8-heptafluoro-2,2-dimethyloctanedionato Eu0.01, La0.99 2,2-bipyridyl-N,N-dioxide
tris 6,6,7,7,8,8,8-heptafluoro-2,2-dimethyloctanedionato Eu0.01, La0.99 phenanthroline
tris 6,6,7,7,8,8,8-heptafluoro-2,2-dimethyloctanedionato Eu0.01, La0.99 bathocuproine
tris 6,6,7,7,8,8,8-heptafluoro-2,2-dimethyloctanedionato Eu0.01, La0.99 bathophenanthroline
tris 1-phenyl-1,3-butanedionato Eu0.01, La0.99 dimethylaminopyridine
tris 1-phenyl-1,3-butanedionato Eu0.01, La0.99 4-picoline-N-oxide
tris 1-phenyl-1,3-butanedionato Eu0.01, La0.99 4-phenylpyridine
tris 1-phenyl-1,3-butanedionato Eu0.01, La0.99 4-cyanopyridine
tris 1-phenyl-1,3-butanedionato Eu0.01, La0.99 4-phenylpyridine-N-oxide
tris 1-phenyl-1,3-butanedionato Eu0.01, La0.99 1-methylimidazole
tris 1-phenyl-1,3-butanedionato Eu0.01, La0.99 triphenylphosphine oxide
tris 1-phenyl-1,3-butanedionato Eu0.01, La0.99 2,2-bipyridyl
tris 1-phenyl-1,3-butanedionato Eu0.01, La0.99 2,2-bipyridyl-N,N-dioxide
tris 1-phenyl-1,3-butanedionato Eu0.01, La0.99 phenanthroline
tris 1-phenyl-1,3-butanedionato Eu0.01, La0.99 bathocuproine
tris 1-phenyl-1,3-butanedionato Eu0.01, La0.99 bathophenanthroline
tris acetylacetonato Tb0.5, Gd0.5 dimethylaminopyridine
tris acetylacetonato Tb0.5, Gd0.5 4-picoline-N-oxide tris acetylacetonato Tb0.5, Gd0.5 4-phenylpyridine
tris acetylacetonato Tb0.5, Gd0.5 4-cyanopyridine
tris acetylacetonato Tb0.5, Gd0.5 4-phenylpyridine-N-oxide
tris acetylacetonato Tb0.5, Gd0.5 1-methylimidazole
tris acetylacetonato Tb0.5, Gd0.5 triphenylphosphine oxide
tris acetylacetonato Tb0.5, Gd0.5 2,2-bipyridyl
tris acetylacetonato Tb0.5, Gd0.5 2,2-bipyridyl-N,N-dioxide
tris acetylacetonato Tb0.5, Gd0.5 phenanthroline
tris acetylacetonato Tb0.5, Gd0.5 bathocuproine
tris acetylacetonato Tb0.5, Gd0.5 bathophenanthroline
tris dibenzoylmethanato Tb0.5, Gd0.5 dimethylaminopyridine
tris dibenzoylmethanato Tb0.5, Gd0.5 4-picoline-N-oxide
tris dibenzoylmethanato Tb0.5, Gd0.5 4-phenylpyridine
tris dibenzoylmethanato Tb0.5, Gd0.5 4-cyanopyridine
tris dibenzoylmethanato Tb0.5, Gd0.5 4-phenylpyridine-N-oxide
tris dibenzoylmethanato Tb0.5, Gd0.5 1-methylimidazole
tris dibenzoylmethanato Tb0.5, Gd0.5 triphenylphosphine oxide
tris dibenzoylmethanato Tb0.5, Gd0.5 2,2-bipyridyl
tris dibenzoylmethanato Tb0.5, Gd0.5 2,2-bipyridyl-N,N-dioxide
tris dibenzoylmethanato Tb0.5, Gd0.5 phenanthroline
tris dibenzoylmethanato Tb0.5, Gd0.5 bathocuproine
tris dibenzoylmethanato Tb0.5, Gd0.5 bathophenanthroline
tris thenoyltrifluoroacetonato Tb0.5, Gd0.5 dimethylaminopyridine
tris thenoyltrifluoroacetonato Tb0.5, Gd0.5 4-picoline-N-oxide
tris thenoyltrifluoroacetonato Tb0.5, Gd0.5 4-phenylpyridine
tris thenoyltrifluoroacetonato Tb0.5, Gd0.5 4-cyanopyridine
tris thenoyltrifluoroacetonato Tb0.5, Gd0.5 4-phenylpyridine-N-oxide
tris thenoyltrifluoroacetonato Tb0.5, Gd0.5 1-methylimidazole
tris thenoyltrifluoroacetonato Tb0.5, Gd0.5 triphenylphosphine oxide
tris thenoyltrifluoroacetonato Tb0.5, Gd0.5 2,2-bipyridyl
tris thenoyltrifluoroacetonato Tb0.5, Gd0.5 2,2-bipyridyl-N,N-dioxide
tris thenoyltrifluoroacetonato Tb0.5, Gd0.5 phenanthroline
tris thenoyltrifluoroacetonato Tb0.5, Gd0.5 bathocuproine
tris thenoyltrifluoroacetonato Tb0.5, Gd0.5 bathophenanthroline
tris 2,2,6,6-tetramethylheptanedionato Tb0.5, Gd0.5 dimethylaminopyridine
tris 2,2,6,6-tetramethylheptanedionato Tb0.5, Gd0.5 4-picoline-N-oxide
tris 2,2,6,6-tetramethylheptanedionato Tb0.5, Gd0.5 4-phenylpyridine
tris 2,2,6,6-tetramethylheptanedionato Tb0.5, Gd0.5 4-cyanopyridine
tris 2,2,6,6-tetramethylheptanedionato Tb0.5, Gd0.5 4-phenylpyridine-N-oxide
tris 2,2,6,6-tetramethylheptanedionato Tb0.5, Gd0.5 1-methylimidazole
tris 2,2,6,6-tetramethylheptanedionato Tb0.5, Gd0.5 triphenylphosphine oxide
tris 2,2,6,6-tetramethylheptanedionato Tb0.5, Gd0.5 2,2-bipyridyl
tris 2,2,6,6-tetramethylheptanedionato Tb0.5, Gd0.5 2,2-bipyridyl-N,N-dioxide
tris 2,2,6,6-tetramethylheptanedionato Tb0.5, Gd0.5 phenanthroline
tris 2,2,6,6-tetramethylheptanedionato Tb0.5, Gd0.5 bathocuproine
tris 2,2,6,6-tetramethylheptanedionato Tb0.5, Gd0.5 bathophenanthroline
tris 3-methylpentane-2,4-dionato Tb0.5, Gd0.5 dimethylaminopyridine
tris 3-methylpentane-2,4-dionato Tb0.5, Gd0.5 4-picoline-N-oxide
tris 3-methylpentane-2,4-dionato Tb0.5, Gd0.5 4-phenylpyridine
tris 3-methylpentane-2,4-dionato Tb0.5, Gd0.5 4-cyanopyridine
tris 3-methylpentane-2,4-dionato Tb0.5, Gd0.5 4-phenylpyridine-N-oxide
tris 3-methylpentane-2,4-dionato Tb0.5, Gd0.5 1-methylimidazole
tris 3-methylpentane-2,4-dionato Tb0.5, Gd0.5 triphenylphosphine oxide
tris 3-methylpentane-2,4-dionato Tb0.5, Gd0.5 2,2-bipyridyl
tris 3-methylpentane-2,4-dionato Tb0.5, Gd0.5 2,2-bipyridyl-N,N-dioxide
tris 3-methylpentane-2,4-dionato Tb0.5, Gd0.5 phenanthroline
tris 3-methylpentane-2,4-dionato Tb0.5, Gd0.5 bathocuproine
tris 3-methylpentane-2,4-dionato Tb0.5, Gd0.5 bathophenanthroline
tris 3-ethylpentane-2,4-dionato Tb0.5, Gd0.5 dimethylaminopyridine
tris 3-ethylpentane-2,4-dionato Tb0.5, Gd0.5 4-picoline-N-oxide
tris 3-ethylpentane-2,4-dionato Tb0.5, Gd0.5 4-phenylpyridine
tris 3-ethylpentane-2,4-dionato Tb0.5, Gd0.5 4-cyanopyridine
tris 3-ethylpentane-2,4-dionato Tb0.5, Gd0.5 4-phenylpyridine-N-oxide
tris 3-ethylpentane-2,4-dionato Tb0.5, Gd0.5 1-methylimidazole
tris 3-ethylpentane-2,4-dionato Tb0.5, Gd0.5 triphenylphosphine oxide
tris 3-ethylpentane-2,4-dionato Tb0.5, Gd0.5 2,2-bipyridyl
tris 3-ethylpentane-2,4-dionato Tb0.5, Gd0.5 2,2-bipyridyl-N,N-dioxide
tris 3-ethylpentane-2,4-dionato Tb0.5, Gd0.5 phenanthroline
tris 3-ethylpentane-2,4-dionato Tb0.5, Gd0.5 bathocuproine
tris 3-ethylpentane-2,4-dionato Tb0.5, Gd0.5 bathophenanthroline
tris pivaloyltrifluoroacetonato Tb0.5, Gd0.5 dimethylaminopyridine
tris pivaloyltrifluoroacetonato Tb0.5, Gd0.5 4-picoline-N-oxide
tris pivaloyltrifluoroacetonato Tb0.5, Gd0.5 4-phenylpyridine
tris pivaloyltrifluoroacetonato Tb0.5, Gd0.5 4-cyanopyridine
tris pivaloyltrifluoroacetonato Tb0.5, Gd0.5 4-phenylpyridine-N-oxide
tris pivaloyltrifluoroacetonato Tb0.5, Gd0.5 1-methylimidazole
tris pivaloyltrifluoroacetonato Tb0.5, Gd0.5 triphenylphosphine oxide
tris pivaloyltrifluoroacetonato Tb0.5, Gd0.5 2,2-bipyridyl
tris pivaloyltrifluoroacetonato Tb0.5, Gd0.5 2,2-bipyridyl-N,N-dioxide
tris pivaloyltrifluoroacetonato Tb0.5, Gd0.5 phenanthroline tris pivaloyltrifluoroacetonato Tb0.5, Gd0.5 bathocuproine
tris pivaloyltrifluoroacetonato Tb0.5, Gd0.5 bathophenanthroline
tris trifluoroacetylacetonato Tb0.5, Gd0.5 dimethylaminopyridine
tris trifluoroacetylacetonato Tb0.5, Gd0.5 4-picoline-N-oxide
tris trifluoroacetylacetonato Tb0.5, Gd0.5 4-phenylpyridine
tris trifluoroacetylacetonato Tb0.5, Gd0.5 4-cyanopyridine
tris trifluoroacetylacetonato Tb0.5, Gd0.5 4-phenylpyridine-N-oxide
tris trifluoroacetylacetonato Tb0.5, Gd0.5 1-methylimidazole
tris trifluoroacetylacetonato Tb0.5, Gd0.5 triphenylphosphine oxide
tris trifluoroacetylacetonato Tb0.5, Gd0.5 2,2-bipyridyl
tris trifluoroacetylacetonato Tb0.5, Gd0.5 2,2-bipyridyl-N,N-dioxide
tris trifluoroacetylacetonato Tb0.5, Gd0.5 phenanthroline
tris trifluoroacetylacetonato Tb0.5, Gd0.5 bathocuproine
tris trifluoroacetylacetonato Tb0.5, Gd0.5 bathophenanthroline
tris hexafluoroacetylacetonato Tb0.5, Gd0.5 dimethylaminopyridine
tris hexafluoroacetylacetonato Tb0.5, Gd0.5 4-picoline-N-oxide
tris hexafluoroacetylacetonato Tb0.5, Gd0.5 4-phenylpyridine
tris hexafluoroacetylacetonato Tb0.5, Gd0.5 4-cyanopyridine
tris hexafluoroacetylacetonato Tb0.5, Gd0.5 4-phenylpyridine-N-oxide
tris hexafluoroacetylacetonato Tb0.5, Gd0.5 1-methylimidazole
tris hexafluoroacetylacetonato Tb0.5, Gd0.5 triphenylphosphine oxide
tris hexafluoroacetylacetonato Tb0.5, Gd0.5 2,2-bipyridyl
tris hexafluoroacetylacetonato Tb0.5, Gd0.5 2,2-bipyridyl-N,N-dioxide
tris hexafluoroacetylacetonato Tb0.5, Gd0.5 phenanthroline
tris hexafluoroacetylacetonato Tb0.5, Gd0.5 bathocuproine
tris hexafluoroacetylacetonato Tb0.5, Gd0.5 bathophenanthroline
tris 6,6,7,7,8,8,8-heptafluoro-2,2-dimethyloctanedionato Tb0.5, Gd0.5 dimethylaminopyridine
tris 6,6,7,7,8,8,8-heptafluoro-2,2-dimethyloctanedionato Tb0.5, Gd0.5 4-picoline-N-oxide
tris 6,6,7,7,8,8,8-heptafluoro-2,2-dimethyloctanedionato Tb0.5, Gd0.5 4-phenylpyridine
tris 6,6,7,7,8,8,8-heptafluoro-2,2-dimethyloctanedionato Tb0.5, Gd0.5 4-cyanopyridine
tris 6,6,7,7,8,8,8-heptafluoro-2,2-dimethyloctanedionato Tb0.5, Gd0.5 4-phenylpyridine-N-oxide
tris 6,6,7,7,8,8,8-heptafluoro-2,2-dimethyloctanedionato Tb0.5, Gd0.5 1-methylimidazole
tris 6,6,7,7,8,8,8-heptafluoro-2,2-dimethyloctanedionato Tb0.5, Gd0.5 triphenylphosphine oxide
tris 6,6,7,7,8,8,8-heptafluoro-2,2-dimethyloctanedionato Tb0.5, Gd0.5 2,2-bipyridyl
tris 6,6,7,7,8,8,8-heptafluoro-2,2-dimethyloctanedionato Tb0.5, Gd0.5 2,2-bipyridyl-N,N-dioxide
tris 6,6,7,7,8,8,8-heptafluoro-2,2-dimethyloctanedionato Tb0.5, Gd0.5 phenanthroline
tris 6,6,7,7,8,8,8-heptafluoro-2,2-dimethyloctanedionato Tb0.5, Gd0.5 bathocuproine
tris 6,6,7,7,8,8,8-heptafluoro-2,2-dimethyloctanedionato Tb0.5, Gd0.5 bathophenanthroline
tris 1-phenyl-1,3-butanedionato Tb0.5, Gd0.5 dimethylaminopyridine
tris 1-phenyl-1,3-butanedionato Tb0.5, Gd0.5 4-picoline-N-oxide
tris 1-phenyl-1,3-butanedionato Tb0.5, Gd0.5 4-phenylpyridine
tris 1-phenyl-1,3-butanedionato Tb0.5, Gd0.5 4-cyanopyridine
tris 1-phenyl-1,3-butanedionato Tb0.5, Gd0.5 4-phenylpyridine-N-oxide
tris 1-phenyl-1,3-butanedionato Tb0.5, Gd0.5 1-methylimidazole
tris 1-phenyl-1,3-butanedionato Tb0.5, Gd0.5 triphenylphosphine oxide
tris 1-phenyl-1,3-butanedionato Tb0.5, Gd0.5 2,2-bipyridyl
tris 1-phenyl-1,3-butanedionato Tb0.5, Gd0.5 2,2-bipyridyl-N,N-dioxide
tris 1-phenyl-1,3-butanedionato Tb0.5, Gd0.5 phenanthroline
tris 1-phenyl-1,3-butanedionato Tb0.5, Gd0.5 bathocuproine
tris 1-phenyl-1,3-butanedionato Tb0.5, Gd0.5 bathophenanthroline
tris acetylacetonato Tb0.2, Gd0.8 dimethylaminopyridine
tris acetylacetonato Tb0.2, Gd0.8 4-picoline-N-oxide
tris acetylacetonato Tb0.2, Gd0.8 4-phenylpyridine
tris acetylacetonato Tb0.2, Gd0.8 4-cyanopyridine
tris acetylacetonato Tb0.2, Gd0.8 4-phenylpyridine-N-oxide
tris acetylacetonato Tb0.2, Gd0.8 1-methylimidazole
tris acetylacetonato Tb0.2, Gd0.8 triphenylphosphine oxide
tris acetylacetonato Tb0.2, Gd0.8 2,2-bipyridyl
tris acetylacetonato Tb0.2, Gd0.8 2,2-bipyridyl-N,N-dioxide
tris acetylacetonato Tb0.2, Gd0.8 phenanthroline
tris acetylacetonato Tb0.2, Gd0.8 bathocuproine
tris acetylacetonato Tb0.2, Gd0.8 bathophenanthroline
tris dibenzoylmethanato Tb0.2, Gd0.8 dimethylaminopyridine
tris dibenzoylmethanato Tb0.2, Gd0.8 4-picoline-N-oxide
tris dibenzoylmethanato Tb0.2, Gd0.8 4-phenylpyridine
tris dibenzoylmethanato Tb0.2, Gd0.8 4-cyanopyridine
tris dibenzoylmethanato Tb0.2, Gd0.8 4-phenylpyridine-N-oxide
tris dibenzoylmethanato Tb0.2, Gd0.8 1-methylimidazole
tris dibenzoylmethanato Tb0.2, Gd0.8 triphenylphosphine oxide
tris dibenzoylmethanato Tb0.2, Gd0.8 2,2-bipyridyl
tris dibenzoylmethanato Tb0.2, Gd0.8 2,2-bipyridyl-N,N-dioxide
tris dibenzoylmethanato Tb0.2, Gd0.8 phenanthroline
tris dibenzoylmethanato Tb0.2, Gd0.8 bathocuproine
tris dibenzoylmethanato Tb0.2, Gd0.8 bathophenanthroline
tris thenoyltrifluoroacetonato Tb0.2, Gd0.8 dimethylaminopyridine
tris thenoyltrifluoroacetonato Tb0.2, Gd0.8 4-picoline-N-oxide
tris thenoyltrifluoroacetonato Tb0.2, Gd0.8 4-phenylpyridine
tris thenoyltrifluoroacetonato Tb0.2, Gd0.8 4-cyanopyridine
tris thenoyltrifluoroacetonato Tb0.2, Gd0.8 4-phenylpyridine-N-oxide
tris thenoyltrifluoroacetonato Tb0.2, Gd0.8 1-methylimidazole
tris thenoyltrifluoroacetonato Tb0.2, Gd0.8 triphenylphosphine oxide
tris thenoyltrifluoroacetonato Tb0.2, Gd0.8 2,2-bipyridyl
tris thenoyltrifluoroacetonato Tb0.2, Gd0.8 2,2-bipyridyl-N,N-dioxide
tris thenoyltrifluoroacetonato Tb0.2, Gd0.8 phenanthroline tris thenoyltrifluoroacetonato Tb0.2, Gd0.8 bathocuproine
tris thenoyltrifluoroacetonato Tb0.2, Gd0.8 bathophenanthroline
tris 2,2,6,6-tetramethylheptanedionato Tb0.2, Gd0.8 dimethylaminopyridine
tris 2,2,6,6-tetramethylheptanedionato Tb0.2, Gd0.8 4-picoline-N-oxide
tris 2,2,6,6-tetramethylheptanedionato Tb0.2, Gd0.8 4-phenylpyridine
tris 2,2,6,6-tetramethylheptanedionato Tb0.2, Gd0.8 4-cyanopyridine
tris 2,2,6,6-tetramethylheptanedionato Tb0.2, Gd0.8 4-phenylpyridine-N-oxide
tris 2,2,6,6-tetramethylheptanedionato Tb0.2, Gd0.8 1-methylimidazole
tris 2,2,6,6-tetramethylheptanedionato Tb0.2, Gd0.8 triphenylphosphine oxide
tris 2,2,6,6-tetramethylheptanedionato Tb0.2, Gd0.8 2,2-bipyridyl
tris 2,2,6,6-tetramethylheptanedionato Tb0.2, Gd0.8 2,2-bipyridyl-N,N-dioxide
tris 2,2,6,6-tetramethylheptanedionato Tb0.2, Gd0.8 phenanthroline
tris 2,2,6,6-tetramethylheptanedionato Tb0.2, Gd0.8 bathocuproine
tris 2,2,6,6-tetramethylheptanedionato Tb0.2, Gd0.8 bathophenanthroline
tris 3-methylpentane-2,4-dionato Tb0.2, Gd0.8 dimethylaminopyridine
tris 3-methylpentane-2,4-dionato Tb0.2, Gd0.8 4-picoline-N-oxide
tris 3-methylpentane-2,4-dionato Tb0.2, Gd0.8 4-phenylpyridine
tris 3-methylpentane-2,4-dionato Tb0.2, Gd0.8 4-cyanopyridine
tris 3-methylpentane-2,4-dionato Tb0.2, Gd0.8 4-phenylpyridine-N-oxide
tris 3-methylpentane-2,4-dionato Tb0.2, Gd0.8 1-methylimidazole
tris 3-methylpentane-2,4-dionato Tb0.2, Gd0.8 triphenylphosphine oxide
tris 3-methylpentane-2,4-dionato Tb0.2, Gd0.8 2,2-bipyridyl
tris 3-methylpentane-2,4-dionato Tb0.2, Gd0.8 2,2-bipyridyl-N,N-dioxide
tris 3-methylpentane-2,4-dionato Tb0.2, Gd0.8 phenanthroline
tris 3-methylpentane-2,4-dionato Tb0.2, Gd0.8 bathocuproine
tris 3-methylpentane-2,4-dionato Tb0.2, Gd0.8 bathophenanthroline
tris 3-ethylpentane-2,4-dionato Tb0.2, Gd0.8 dimethylaminopyridine
tris 3-ethylpentane-2,4-dionato Tb0.2, Gd0.8 4-picoline-N-oxide
tris 3-ethylpentane-2,4-dionato Tb0.2, Gd0.8 4-phenylpyridine
tris 3-ethylpentane-2,4-dionato Tb0.2, Gd0.8 4-cyanopyridine
tris 3-ethylpentane-2,4-dionato Tb0.2, Gd0.8 4-phenylpyridine-N-oxide
tris 3-ethylpentane-2,4-dionato Tb0.2, Gd0.8 1-methylimidazole
tris 3-ethylpentane-2,4-dionato Tb0.2, Gd0.8 triphenylphosphine oxide
tris 3-ethylpentane-2,4-dionato Tb0.2, Gd0.8 2,2-bipyridyl
tris 3-ethylpentane-2,4-dionato Tb0.2, Gd0.8 2,2-bipyridyl-N,N-dioxide
tris 3-ethylpentane-2,4-dionato Tb0.2, Gd0.8 phenanthroline
tris 3-ethylpentane-2,4-dionato Tb0.2, Gd0.8 bathocuproine
tris 3-ethylpentane-2,4-dionato Tb0.2, Gd0.8 bathophenanthroline
tris pivaloyltrifluoroacetonato Tb0.2, Gd0.8 dimethylaminopyridine
tris pivaloyltrifluoroacetonato Tb0.2, Gd0.8 4-picoline-N-oxide
tris pivaloyltrifluoroacetonato Tb0.2, Gd0.8 4-phenylpyridine
tris pivaloyltrifluoroacetonato Tb0.2, Gd0.8 4-cyanopyridine
tris pivaloyltrifluoroacetonato Tb0.2, Gd0.8 4-phenylpyridine-N-oxide
tris pivaloyltrifluoroacetonato Tb0.2, Gd0.8 1-methylimidazole
tris pivaloyltrifluoroacetonato Tb0.2, Gd0.8 triphenylphosphine oxide
tris pivaloyltrifluoroacetonato Tb0.2, Gd0.8 2,2-bipyridyl
tris pivaloyltrifluoroacetonato Tb0.2, Gd0.8 2,2-bipyridyl-N,N-dioxide
tris pivaloyltrifluoroacetonato Tb0.2, Gd0.8 phenanthroline
tris pivaloyltrifluoroacetonato Tb0.2, Gd0.8 bathocuproine
tris pivaloyltrifluoroacetonato Tb0.2, Gd0.8 bathophenanthroline
tris trifluoroacetylacetonato Tb0.2, Gd0.8 dimethylaminopyridine
tris trifluoroacetylacetonato Tb0.2, Gd0.8 4-picoline-N-oxide
tris trifluoroacetylacetonato Tb0.2, Gd0.8 4-phenylpyridine
tris trifluoroacetylacetonato Tb0.2, Gd0.8 4-cyanopyridine
tris trifluoroacetylacetonato Tb0.2, Gd0.8 4-phenylpyridine-N-oxide
tris trifluoroacetylacetonato Tb0.2, Gd0.8 1-methylimidazole
tris trifluoroacetylacetonato Tb0.2, Gd0.8 triphenylphosphine oxide
tris trifluoroacetylacetonato Tb0.2, Gd0.8 2,2-bipyridyl
tris trifluoroacetylacetonato Tb0.2, Gd0.8 2,2-bipyridyl-N,N-dioxide
tris trifluoroacetylacetonato Tb0.2, Gd0.8 phenanthroline
tris trifluoroacetylacetonato Tb0.2, Gd0.8 bathocuproine
tris trifluoroacetylacetonato Tb0.2, Gd0.8 bathophenanthroline
tris hexafluoroacetylacetonato Tb0.2, Gd0.8 dimethylaminopyridine
tris hexafluoroacetylacetonato Tb0.2, Gd0.8 4-picoline-N-oxide
tris hexafluoroacetylacetonato Tb0.2, Gd0.8 4-phenylpyridine
tris hexafluoroacetylacetonato Tb0.2, Gd0.8 4-cyanopyridine
tris hexafluoroacetylacetonato Tb0.2, Gd0.8 4-phenylpyridine-N-oxide
tris hexafluoroacetylacetonato Tb0.2, Gd0.8 1-methylimidazole
tris hexafluoroacetylacetonato Tb0.2, Gd0.8 triphenylphosphine oxide
tris hexafluoroacetylacetonato Tb0.2, Gd0.8 2,2-bipyridyl
tris hexafluoroacetylacetonato Tb0.2, Gd0.8 2,2-bipyridyl-N,N-dioxide
tris hexafluoroacetylacetonato Tb0.2, Gd0.8 phenanthroline
tris hexafluoroacetylacetonato Tb0.2, Gd0.8 bathocuproine
tris hexafluoroacetylacetonato Tb0.2, Gd0.8 bathophenanthroline tris 6,6,7,7,8,8,8-heptafluoro-2,2-dimethyloctanedionato Tb0.2, Gd0.8 dimethylaminopyridine
tris 6,6,7,7,8,8,8-heptafluoro-2,2-dimethyloctanedionato Tb0.2, Gd0.8 4-picoline-N-oxide
tris 6,6,7,7,8,8,8-heptafluoro-2,2-dimethyloctanedionato Tb0.2, Gd0.8 4-phenylpyridine
tris 6,6,7,7,8,8,8-heptafluoro-2,2-dimethyloctanedionato Tb0.2, Gd0.8 4-cyanopyridine
tris 6,6,7,7,8,8,8-heptafluoro-2,2-dimethyloctanedionato Tb0.2, Gd0.8 4-phenylpyridine-N-oxide
tris 6,6,7,7,8,8,8-heptafluoro-2,2-dimethyloctanedionato Tb0.2, Gd0.8 1-methylimidazole
tris 6,6,7,7,8,8,8-heptafluoro-2,2-dimethyloctanedionato Tb0.2, Gd0.8 triphenylphosphine oxide
tris 6,6,7,7,8,8,8-heptafluoro-2,2-dimethyloctanedionato Tb0.2, Gd0.8 2,2-bipyridyl
tris 6,6,7,7,8,8,8-heptafluoro-2,2-dimethyloctanedionato Tb0.2, Gd0.8 2,2-bipyridyl-N,N-dioxide
tris 6,6,7,7,8,8,8-heptafluoro-2,2-dimethyloctanedionato Tb0.2, Gd0.8 phenanthroline
tris 6,6,7,7,8,8,8-heptafluoro-2,2-dimethyloctanedionato Tb0.2, Gd0.8 bathocuproine
tris 6,6,7,7,8,8,8-heptafluoro-2,2-dimethyloctanedionato Tb0.2, Gd0.8 bathophenanthroline
tris 1-phenyl-1,3-butanedionato Tb0.2, Gd0.8 dimethylaminopyridine
tris 1-phenyl-1,3-butanedionato Tb0.2, Gd0.8 4-picoline-N-oxide
tris 1-phenyl-1,3-butanedionato Tb0.2, Gd0.8 4-phenylpyridine
tris 1-phenyl-1,3-butanedionato Tb0.2, Gd0.8 4-cyanopyridine
tris 1-phenyl-1,3-butanedionato Tb0.2, Gd0.8 4-phenylpyridine-N-oxide
tris 1-phenyl-1,3-butanedionato Tb0.2, Gd0.8 1-methylimidazole
tris 1-phenyl-1,3-butanedionato Tb0.2, Gd0.8 triphenylphosphine oxide
tris 1-phenyl-1,3-butanedionato Tb0.2, Gd0.8 2,2-bipyridyl
tris 1-phenyl-1,3-butanedionato Tb0.2, Gd0.8 2,2-bipyridyl-N,N-dioxide
tris 1-phenyl-1,3-butanedionato Tb0.2, Gd0.8 phenanthroline
tris 1-phenyl-1,3-butanedionato Tb0.2, Gd0.8 bathocuproine
tris 1-phenyl-1,3-butanedionato Tb0.2, Gd0.8 bathophenanthroline
tris acetylacetonato Tb0.1, Gd0.9 dimethylaminopyridine
tris acetylacetonato Tb0.1, Gd0.9 4-picoline-N-oxide
tris acetylacetonato Tb0.1, Gd0.9 4-phenylpyridine
tris acetylacetonato Tb0.1, Gd0.9 4-cyanopyridine
tris acetylacetonato Tb0.1, Gd0.9 4-phenylpyridine-N-oxide
tris acetylacetonato Tb0.1, Gd0.9 1-methylimidazole
tris acetylacetonato Tb0.1, Gd0.9 triphenylphosphine oxide
tris acetylacetonato Tb0.1, Gd0.9 2,2-bipyridyl
tris acetylacetonato Tb0.1, Gd0.9 2,2-bipyridyl-N,N-dioxide
tris acetylacetonato Tb0.1, Gd0.9 phenanthroline
tris acetylacetonato Tb0.1, Gd0.9 bathocuproine
tris acetylacetonato Tb0.1, Gd0.9 bathophenanthroline
tris dibenzoylmethanato Tb0.1, Gd0.9 dimethylaminopyridine
tris dibenzoylmethanato Tb0.1, Gd0.9 4-picoline-N-oxide
tris dibenzoylmethanato Tb0.1, Gd0.9 4-phenylpyridine
tris dibenzoylmethanato Tb0.1, Gd0.9 4-cyanopyridine
tris dibenzoylmethanato Tb0.1, Gd0.9 4-phenylpyridine-N-oxide
tris dibenzoylmethanato Tb0.1, Gd0.9 1-methylimidazole
tris dibenzoylmethanato Tb0.1, Gd0.9 triphenylphosphine oxide
tris dibenzoylmethanato Tb0.1, Gd0.9 2,2-bipyridyl
tris dibenzoylmethanato Tb0.1, Gd0.9 2,2-bipyridyl-N,N-dioxide
tris dibenzoylmethanato Tb0.1, Gd0.9 phenanthroline
tris dibenzoylmethanato Tb0.1, Gd0.9 bathocuproine
tris dibenzoylmethanato Tb0.1, Gd0.9 bathophenanthroline
tris thenoyltrifluoroacetonato Tb0.1, Gd0.9 dimethylaminopyridine
tris thenoyltrifluoroacetonato Tb0.1, Gd0.9 4-picoline-N-oxide
tris thenoyltrifluoroacetonato Tb0.1, Gd0.9 4-phenylpyridine
tris thenoyltrifluoroacetonato Tb0.1, Gd0.9 4-cyanopyridine
tris thenoyltrifluoroacetonato Tb0.1, Gd0.9 4-phenylpyridine-N-oxide
tris thenoyltrifluoroacetonato Tb0.1, Gd0.9 1-methylimidazole
tris thenoyltrifluoroacetonato Tb0.1, Gd0.9 triphenylphosphine oxide
tris thenoyltrifluoroacetonato Tb0.1, Gd0.9 2,2-bipyridyl
tris thenoyltrifluoroacetonato Tb0.1, Gd0.9 2,2-bipyridyl-N,N-dioxide
tris thenoyltrifluoroacetonato Tb0.1, Gd0.9 phenanthroline
tris thenoyltrifluoroacetonato Tb0.1, Gd0.9 bathocuproine
tris thenoyltrifluoroacetonato Tb0.1, Gd0.9 bathophenanthroline
tris 2,2,6,6-tetramethylheptanedionato Tb0.1, Gd0.9 dimethylaminopyridine; brightness=9
tris 2,2,6,6-tetramethylheptanedionato Tb0.1, Gd0.9 4-picoline-N-oxide; brightness=4
tris 2,2,6,6-tetramethylheptanedionato Tb0.1, Gd0.9 4-phenylpyridine
tris 2,2,6,6-tetramethylheptanedionato Tb0.1, Gd0.9 4-cyanopyridine; brightness=2
tris 2,2,6,6-tetramethylheptanedionato Tb0.1, Gd0.9 4-phenylpyridine-N-oxide
tris 2,2,6,6-tetramethylheptanedionato Tb0.1, Gd0.9 1-methylimidazole
tris 2,2,6,6-tetramethylheptanedionato Tb0.1, Gd0.9 triphenylphosphine oxide; brightness=4
tris 2,2,6,6-tetramethylheptanedionato Tb0.1, Gd0.9 2,2-bipyridyl; brightness=6
tris 2,2,6,6-tetramethylheptanedionato Tb0.1, Gd0.9 2,2-bipyridyl-N,N-dioxide
tris 2,2,6,6-tetramethylheptanedionato Tb0.1, Gd0.9 phenanthroline
tris 2,2,6,6-tetramethylheptanedionato Tb0.1, Gd0.9 bathocuproine
tris 2,2,6,6-tetramethylheptanedionato Tb0.1, Gd0.9 bathophenanthroline
tris 3-methylpentane-2,4-dionato Tb0.1, Gd0.9 dimethylaminopyridine
tris 3-methylpentane-2,4-dionato Tb0.1, Gd0.9 4-picoline-N-oxide
tris 3-methylpentane-2,4-dionato Tb0.1, Gd0.9 4-phenylpyridine
tris 3-methylpentane-2,4-dionato Tb0.1, Gd0.9 4-cyanopyridine
tris 3-methylpentane-2,4-dionato Tb0.1, Gd0.9 4-phenylpyridine-N-oxide
tris 3-methylpentane-2,4-dionato Tb0.1, Gd0.9 1-methylimidazole
tris 3-methylpentane-2,4-dionato Tb0.1, Gd0.9 triphenylphosphine oxide tris 3-methylpentane-2,4-dionato Tb0.1, Gd0.9 2,2-bipyridyl
tris 3-methylpentane-2,4-dionato Tb0.1, Gd0.9 2,2-bipyridyl-N,N-dioxide
tris 3-methylpentane-2,4-dionato Tb0.1, Gd0.9 phenanthroline
tris 3-methylpentane-2,4-dionato Tb0.1, Gd0.9 bathocuproine
tris 3-methylpentane-2,4-dionato Tb0.1, Gd0.9 bathophenanthroline
tris 3-ethylpentane-2,4-dionato Tb0.1, Gd0.9 dimethylaminopyridine
tris 3-ethylpentane-2,4-dionato Tb0.1, Gd0.9 4-picoline-N-oxide
tris 3-ethylpentane-2,4-dionato Tb0.1, Gd0.9 4-phenylpyridine
tris 3-ethylpentane-2,4-dionato Tb0.1, Gd0.9 4-cyanopyridine
tris 3-ethylpentane-2,4-dionato Tb0.1, Gd0.9 4-phenylpyridine-N-oxide
tris 3-ethylpentane-2,4-dionato Tb0.1, Gd0.9 1-methylimidazole
tris 3-ethylpentane-2,4-dionato Tb0.1, Gd0.9 triphenylphosphine oxide
tris 3-ethylpentane-2,4-dionato Tb0.1, Gd0.9 2,2-bipyridyl
tris 3-ethylpentane-2,4-dionato Tb0.1, Gd0.9 2,2-bipyridyl-N,N-dioxide
tris 3-ethylpentane-2,4-dionato Tb0.1, Gd0.9 phenanthroline
tris 3-ethylpentane-2,4-dionato Tb0.1, Gd0.9 bathocuproine
tris 3-ethylpentane-2,4-dionato Tb0.1, Gd0.9 bathophenanthroline
tris pivaloyltrifluoroacetonato Tb0.1, Gd0.9 dimethylaminopyridine
tris pivaloyltrifluoroacetonato Tb0.1, Gd0.9 4-picoline-N-oxide
tris pivaloyltrifluoroacetonato Tb0.1, Gd0.9 4-phenylpyridine
tris pivaloyltrifluoroacetonato Tb0.1, Gd0.9 4-cyanopyridine
tris pivaloyltrifluoroacetonato Tb0.1, Gd0.9 4-phenylpyridine-N-oxide
tris pivaloyltrifluoroacetonato Tb0.1, Gd0.9 1-methylimidazole
tris pivaloyltrifluoroacetonato Tb0.1, Gd0.9 triphenylphosphine oxide
tris pivaloyltrifluoroacetonato Tb0.1, Gd0.9 2,2-bipyridyl
tris pivaloyltrifluoroacetonato Tb0.1, Gd0.9 2,2-bipyridyl-N,N-dioxide
tris pivaloyltrifluoroacetonato Tb0.1, Gd0.9 phenanthroline
tris pivaloyltrifluoroacetonato Tb0.1, Gd0.9 bathocuproine
tris pivaloyltrifluoroacetonato Tb0.1, Gd0.9 bathophenanthroline
tris trifluoroacetylacetonato Tb0.1, Gd0.9 dimethylaminopyridine
tris trifluoroacetylacetonato Tb0.1, Gd0.9 4-picoline-N-oxide
tris trifluoroacetylacetonato Tb0.1, Gd0.9 4-phenylpyridine
tris trifluoroacetylacetonato Tb0.1, Gd0.9 4-cyanopyridine
tris trifluoroacetylacetonato Tb0.1, Gd0.9 4-phenylpyridine-N-oxide
tris trifluoroacetylacetonato Tb0.1, Gd0.9 1-methylimidazole
tris trifluoroacetylacetonato Tb0.1, Gd0.9 triphenylphosphine oxide
tris trifluoroacetylacetonato Tb0.1, Gd0.9 2,2-bipyridyl
tris trifluoroacetylacetonato Tb0.1, Gd0.9 2,2-bipyridyl-N,N-dioxide
tris trifluoroacetylacetonato Tb0.1, Gd0.9 phenanthroline
tris trifluoroacetylacetonato Tb0.1, Gd0.9 bathocuproine
tris trifluoroacetylacetonato Tb0.1, Gd0.9 bathophenanthroline
tris hexafluoroacetylacetonato Tb0.1, Gd0.9 dimethylaminopyridine
tris hexafluoroacetylacetonato Tb0.1, Gd0.9 4-picoline-N-oxide
tris hexafluoroacetylacetonato Tb0.1, Gd0.9 4-phenylpyridine
tris hexafluoroacetylacetonato Tb0.1, Gd0.9 4-cyanopyridine
tris hexafluoroacetylacetonato Tb0.1, Gd0.9 4-phenylpyridine-N-oxide
tris hexafluoroacetylacetonato Tb0.1, Gd0.9 1-methylimidazole
tris hexafluoroacetylacetonato Tb0.1, Gd0.9 triphenylphosphine oxide
tris hexafluoroacetylacetonato Tb0.1, Gd0.9 2,2-bipyridyl
tris hexafluoroacetylacetonato Tb0.1, Gd0.9 2,2-bipyridyl-N,N-dioxide
tris hexafluoroacetylacetonato Tb0.1, Gd0.9 phenanthroline
tris hexafluoroacetylacetonato Tb0.1, Gd0.9 bathocuproine
tris hexafluoroacetylacetonato Tb0.1, Gd0.9 bathophenanthroline
tris 6,6,7,7,8,8,8-heptafluoro-2,2-dimethyloctanedionato Tb0.1, Gd0.9 dimethylaminopyridine
tris 6,6,7,7,8,8,8-heptafluoro-2,2-dimethyloctanedionato Tb0.1, Gd0.9 4-picoline-N-oxide
tris 6,6,7,7,8,8,8-heptafluoro-2,2-dimethyloctanedionato Tb0.1, Gd0.9 4-phenylpyridine
tris 6,6,7,7,8,8,8-heptafluoro-2,2-dimethyloctanedionato Tb0.1, Gd0.9 4-cyanopyridine
tris 6,6,7,7,8,8,8-heptafluoro-2,2-dimethyloctanedionato Tb0.1, Gd0.9 4-phenylpyridine-N-oxide
tris 6,6,7,7,8,8,8-heptafluoro-2,2-dimethyloctanedionato Tb0.1, Gd0.9 1-methylimidazole
tris 6,6,7,7,8,8,8-heptafluoro-2,2-dimethyloctanedionato Tb0.1, Gd0.9 triphenylphosphine oxide
tris 6,6,7,7,8,8,8-heptafluoro-2,2-dimethyloctanedionato Tb0.1, Gd0.9 2,2-bipyridyl
tris 6,6,7,7,8,8,8-heptafluoro-2,2-dimethyloctanedionato Tb0.1, Gd0.9 2,2-bipyridyl-N,N-dioxide
tris 6,6,7,7,8,8,8-heptafluoro-2,2-dimethyloctanedionato Tb0.1, Gd0.9 phenanthroline
tris 6,6,7,7,8,8,8-heptafluoro-2,2-dimethyloctanedionato Tb0.1, Gd0.9 bathocuproine
tris 6,6,7,7,8,8,8-heptafluoro-2,2-.dimethyloctanedionato Tb0.1, Gd0.9 bathophenanthroline
tris 1-phenyl-1,3-butanedionato Tb0.1, Gd0.9 dimethylaminopyridine
tris 1-phenyl-1,3-butanedionato Tb0.1, Gd0.9 4-picoline-N-oxide
tris 1-phenyl-1,3-butanedionato Tb0.1, Gd0.9 4-phenylpyridine
tris 1-phenyl-1,3-butanedionato Tb0.1, Gd0.9 4-cyanopyridine
tris 1-phenyl-1,3-butanedionato Tb0.1, Gd0.9 4-phenylpyridine-N-oxide
tris 1-phenyl-1,3-butanedionato Tb0.1, Gd0.9 1-methylimidazole
tris 1-phenyl-1,3-butanedionato Tb0.1, Gd0.9 triphenylphosphine oxide
tris 1-phenyl-1,3-butanedionato Tb0.1, Gd0.9 2,2-bipyridyl
tris 1-phenyl-1,3-butanedionato Tb0.1, Gd0.9 2,2-bipyridyl-N,N-dioxide tris 1-phenyl-1,3-butanedionato Tb0.1, Gd0.9 phenanthroline
tris 1-phenyl-1,3-butanedionato Tb0.1, Gd0.9 bathocuproine
tris 1-phenyl-1,3-butanedionato Tb0.1, Gd0.9 bathophenanthroline
tris acetylacetonato Tb0.01, Gd0.99 dimethylaminopyridine
tris acetylacetonato Tb0.01, Gd0.99 4-picoline-N-oxide
tris acetylacetonato Tb0.01, Gd0.99 4-phenylpyridine
tris acetylacetonato Tb0.01, Gd0.99 4-cyanopyridine
tris acetylacetonato Tb0.01, Gd0.99 4-phenylpyridine-N-oxide
tris acetylacetonato Tb0.01, Gd0.99 1-methylimidazole
tris acetylacetonato Tb0.01, Gd0.99 triphenylphosphine oxide
tris acetylacetonato Tb0.01, Gd0.99 2,2-bipyridyl
tris acetylacetonato Tb0.01, Gd0.99 2,2-bipyridyl-N,N-dioxide
tris acetylacetonato Tb0.01, Gd0.99 phenanthroline
tris acetylacetonato Tb0.01, Gd0.99 bathocuproine
tris acetylacetonato Tb0.01, Gd0.99 bathophenanthroline
tris dibenzoylmethanato Tb0.01, Gd0.99 dimethylaminopyridine
tris dibenzoylmethanato Tb0.01, Gd0.99 4-picoline-N-oxide
tris dibenzoylmethanato Tb0.01, Gd0.99 4-phenylpyridine
tris dibenzoylmethanato Tb0.01, Gd0.99 4-cyanopyridine
tris dibenzoylmethanato Tb0.01, Gd0.99 4-phenylpyridine-N-oxide
tris dibenzoylmethanato Tb0.01, Gd0.99 1-methylimidazole
tris dibenzoylmethanato Tb0.01, Gd0.99 triphenylphosphine oxide
tris dibenzoylmethanato Tb0.01, Gd0.99 2,2-bipyridyl
tris dibenzoylmethanato Tb0.01, Gd0.99 2,2-bipyridyl-N,N-dioxide
tris dibenzoylmethanato Tb0.01, Gd0.99 phenanthroline
tris dibenzoylmethanato Tb0.01, Gd0.99 bathocuproine
tris dibenzoylmethanato Tb0.01, Gd0.99 bathophenanthroline
tris thenoyltrifluoroacetonato Tb0.01, Gd0.99 dimethylaminopyridine
tris thenoyltrifluoroacetonato Tb0.01, Gd0.99 4-picoline-N-oxide
tris thenoyltrifluoroacetonato Tb0.01, Gd0.99 4-phenylpyridine
tris thenoyltrifluoroacetonato Tb0.01, Gd0.99 4-cyanopyridine
tris thenoyltrifluoroacetonato Tb0.01, Gd0.99 4-phenylpyridine-N-oxide
tris thenoyltrifluoroacetonato Tb0.01, Gd0.99 1-methylimidazole
tris thenoyltrifluoroacetonato Tb0.01, Gd0.99 triphenylphosphine oxide
tris thenoyltrifluoroacetonato Tb0.01, Gd0.99 2,2-bipyridyl
tris thenoyltrifluoroacetonato Tb0.01, Gd0.99 2,2-bipyridyl-N,N-dioxide
tris thenoyltrifluoroacetonato Tb0.01, Gd0.99 phenanthroline
tris thenoyltrifluoroacetonato Tb0.01, Gd0.99 bathocuproine
tris thenoyltrifluoroacetonato Tb0.01, Gd0.99 bathophenanthroline
tris 2,2,6,6-tetramethylheptanedionato Tb0.01, Gd0.99 dimethylaminopyridine
tris 2,2,6,6-tetramethylheptanedionato Tb0.01, Gd0.99 4-picoline-N-oxide
tris 2,2,6,6-tetramethylheptanedionato Tb0.01, Gd0.99 4-phenylpyridine
tris 2,2,6,6-tetramethylheptanedionato Tb0.01, Gd0.99 4-cyanopyridine
tris 2,2,6,6-tetramethylheptanedionato Tb0.01, Gd0.99 4-phenylpyridine-N-oxide
tris 2,2,6,6-tetramethylheptanedionato Tb0.01, Gd0.99 1-methylimidazole
tris 2,2,6,6-tetramethylheptanedionato Tb0.01, Gd0.99 triphenylphosphine oxide
tris 2,2,6,6-tetramethylheptanedionato Tb0.01, Gd0.99 2,2-bipyridyl
tris 2,2,6,6-tetramethylheptanedionato Tb0.01, Gd0.99 2,2-bipyridyl-N,N-dioxide
tris 2,2,6,6-tetramethylheptanedionato Tb0.01, Gd0.99 phenanthroline
tris 2,2,6,6-tetramethylheptanedionato Tb0.01, Gd0.99 bathocuproine
tris 2,2,6,6-tetramethylheptanedionato Tb0.01, Gd0.99 bathophenanthroline
tris 3-methylpentane-2,4-dionato Tb0.01, Gd0.99 dimethylaminopyridine
tris 3-methylpentane-2,4-dionato Tb0.01, Gd0.99 4-picoline-N-oxide
tris 3-methylpentane-2,4-dionato Tb0.01, Gd0.99 4-phenylpyridine
tris 3-methylpentane-2,4-dionato Tb0.01, Gd0.99 4-cyanopyridine
tris 3-methylpentane-2,4-dionato Tb0.01, Gd0.99 4-phenylpyridine-N-oxide
tris 3-methylpentane-2,4-dionato Tb0.01, Gd0.99 1-methylimidazole
tris 3-methylpentane-2,4-dionato Tb0.01, Gd0.99 triphenylphosphine oxide
tris 3-methylpentane-2,4-dionato Tb0.01, Gd0.99 2,2-bipyridyl
tris 3-methylpentane-2,4-dionato Tb0.01, Gd0.99 2,2-bipyridyl-N,N-dioxide
tris 3-methylpentane-2,4-dionato Tb0.01, Gd0.99 phenanthroline
tris 3-methylpentane-2,4-dionato Tb0.01, Gd0.99 bathocuproine
tris 3-methylpentane-2,4-dionato Tb0.01, Gd0.99 bathophenanthroline
tris 3-ethylpentane-2,4-dionato Tb0.01, Gd0.99 dimethylaminopyridine
tris 3-ethylpentane-2,4-dionato Tb0.01, Gd0.99 4-picoline-N-oxide
tris 3-ethylpentane-2,4-dionato Tb0.01, Gd0.99 4-phenylpyridine
tris 3-ethylpentane-2,4-dionato Tb0.01, Gd0.99 4-cyanopyridine
tris 3-ethylpentane-2,4-dionato Tb0.01, Gd0.99 4-phenylpyridine-N-oxide
tris 3-ethylpentane-2,4-dionato Tb0.01, Gd0.99 1-methylimidazole
tris 3-ethylpentane-2,4-dionato Tb0.01, Gd0.99 triphenylphosphine oxide
tris 3-ethylpentane-2,4-dionato Tb0.01, Gd0.99 2,2-bipyridyl
tris 3-ethylpentane-2,4-dionato Tb0.01, Gd0.99 2,2-bipyridyl-N,N-dioxide
tris 3-ethylpentane-2,4-dionato Tb0.01, Gd0.99 phenanthroline
tris 3-ethylpentane-2,4-dionato Tb0.01, Gd0.99 bathocuproine
tris 3-ethylpentane-2,4-dionato Tb0.01, Gd0.99 bathophenanthroline
tris pivaloyltrifluoroacetonato Tb0.01, Gd0.99 dimethylaminopyridine tris pivaloyltrifluoroacetonato Tb0.01, Gd0.99 4-picoline-N-oxide
tris pivaloyltrifluoroacetonato Tb0.01, Gd0.99 4-phenylpyridine
tris pivaloyltrifluoroacetonato Tb0.01, Gd0.99 4-cyanopyridine
tris pivaloyltrifluoroacetonato Tb0.01, Gd0.99 4-phenylpyridine-N-oxide
tris pivaloyltrifluoroacetonato Tb0.01, Gd0.99 1-methylimidazole
tris pivaloyltrifluoroacetonato Tb0.01, Gd0.99 triphenylphosphine oxide
tris pivaloyltrifluoroacetonato Tb0.01, Gd0.99 2,2-bipyridyl
tris pivaloyltrifluoroacetonato Tb0.01, Gd0.99 2,2-bipyridyl-N,N-dioxide
tris pivaloyltrifluoroacetonato Tb0.01, Gd0.99 phenanthroline
tris pivaloyltrifluoroacetonato Tb0.01, Gd0.99 bathocuproine
tris pivaloyltrifluoroacetonato Tb0.01, Gd0.99 bathophenanthroline
tris trifluoroacetylacetonato Tb0.01, Gd0.99 dimethylaminopyridine
tris trifluoroacetylacetonato Tb0.01, Gd0.99 4-picoline-N-oxide
tris trifluoroacetylacetonato Tb0.01, Gd0.99 4-phenylpyridine
tris trifluoroacetylacetonato Tb0.01, Gd0.99 4-cyanopyridine
tris trifluoroacetylacetonato Tb0.01, Gd0.99 4-phenylpyridine-N-oxide
tris trifluoroacetylacetonato Tb0.01, Gd0.99 1-methylimidazole
tris trifluoroacetylacetonato Tb0.01, Gd0.99 triphenylphosphine oxide
tris trifluoroacetylacetonato Tb0.01, Gd0.99 2,2-bipyridyl
tris trifluoroacetylacetonato Tb0.01, Gd0.99 2,2-bipyridyl-N,N-dioxide
tris trifluoroacetylacetonato Tb0.01, Gd0.99 phenanthroline
tris trifluoroacetylacetonato Tb0.01, Gd0.99 bathocuproine
tris trifluoroacetylacetonato Tb0.01, Gd0.99 bathophenanthroline
tris hexafluoroacetylacetonato Tb0.01, Gd0.99 dimethylaminopyridine
tris hexafluoroacetylacetonato Tb0.01, Gd0.99 4-picoline-N-oxide
tris hexafluoroacetylacetonato Tb0.01, Gd0.99 4-phenylpyridine
tris hexafluoroacetylacetonato Tb0.01, Gd0.99 4-cyanopyridine
tris hexafluoroacetylacetonato Tb0.01, Gd0.99 4-phenylpyridine-N-oxide
tris hexafluoroacetylacetonato Tb0.01, Gd0.99 1-methylimidazole
tris hexafluoroacetylacetonato Tb0.01, Gd0.99 triphenylphosphine oxide
tris hexafluoroacetylacetonato Tb0.01, Gd0.99 2,2-bipyridyl
tris hexafluoroacetylacetonato Tb0.01, Gd0.99 2,2-bipyridyl-N,N-dioxide
tris hexafluoroacetylacetonato Tb0.01, Gd0.99 phenanthroline
tris hexafluoroacetylacetonato Tb0.01, Gd0.99 bathocuproine
tris hexafluoroacetylacetonato Tb0.01, Gd0.99 bathophenanthroline
tris 6,6,7,7,8,8;8-heptafluoro-2,2-dimethyloctanedionato Tb0.01, Gd0.99 dimethylaminopyridine
tris 6,6,7,7,8,8,8-heptafluoro-2,2-dimethyloctanedionato Tb0.01, Gd0.99 4-picoline-N-oxide
tris 6,6,7,7,8,8,8-heptafluoro-2,2-dimethyloctanedionato Tb0.01, Gd0.99 4-phenylpyridine
tris 6,6,7,7,8,8,8-heptafluoro-2,2-dimethyloctanedionato Tb0.01, Gd0.99 4-cyanopyridine
tris 6,6,7,7,8,8,8-heptafluoro-2,2-dimethyloctanedionato Tb0.01, Gd0.99 4-phenylpyridine-N-oxide
tris 6,6,7,7,8,8,8-heptafluoro-2,2-dimethyloctanedionato Tb0.01, Gd0.99 1-methylimidazole
tris 6,6,7,7,8,8,8-heptafluoro-2,2-dimethyloctanedionato Tb0.01, Gd0.99 triphenylphosphine oxide
tris 6,6,7,7,8,8,8-heptafluoro-2,2-dimethyloctanedionato Tb0.01, Gd0.99 2,2-bipyridyl
tris 6,6,7,7,8,8,8-heptafluoro-2,2-dimethyloctanedionato Tb0.01, Gd0.99 2,2-bipyridyl-N,N-dioxide
tris 6,6,7,7,8,8,8-heptafluoro-2,2-dimethyloctanedionato Tb0.01, Gd0.99 phenanthroline
tris 6,6,7,7,8,8,8-heptafluoro-2,2-dimethyloctanedionato Tb0.01, Gd0.99 bathocuproine
tris 6,6,7,7,8,8,8-heptafluoro-2,2-dimethyloctanedionato Tb0.01, Gd0.99 bathophenanthroline
tris 1-phenyl-1,3-butanedionato Tb0.01, Gd0.99 dimethylaminopyridine
tris 1-phenyl-1,3-butanedionato Tb0.01, Gd0.99 4-picoline-N-oxide
tris 1-phenyl-1,3-butanedionato Tb0.01, Gd0.99 4-phenylpyridine
tris 1-phenyl-1,3-butanedionato Tb0.01, Gd0.99 4-cyanopyridine
tris 1-phenyl-1,3-butanedionato Tb0.01, Gd0.99 4-phenylpyridine-N-oxide
tris 1-phenyl-1,3-butanedionato Tb0.01, Gd0.99 1-methylimidazole
tris 1-phenyl-1,3-butanedionato Tb0.01, Gd0.99 triphenylphosphine oxide
tris 1-phenyl-1,3-butanedionato Tb0.01, Gd0.99 2,2-bipyridyl
tris 1-phenyl-1,3-butanedionato Tb0.01, Gd0.99 2,2-bipyridyl-N,N-dioxide
tris 1-phenyl-1,3-butanedionato Tb0.01, Gd0.99 phenanthroline
tris 1-phenyl-1,3-butanedionato Tb0.01, Gd0.99 bathocuproine
tris 1-phenyl-1,3-butanedionato Tb0.01, Gd0.99 bathophenanthroline
tris acetylacetonato Eu0.5, Gd0.5 dimethylaminopyridine
tris acetylacetonato Eu0.5, Gd0.5 4-picoline-N-oxide
tris acetylacetonato Eu0.5, Gd0.5 4-phenylpyridine
tris acetylacetonato Eu0.5, Gd0.5 4-cyanopyridine
tris acetylacetonato Eu0.5, Gd0.5 4-phenylpyridine-N-oxide
tris acetylacetonato Eu0.5, Gd0.5 1-methylimidazole
tris acetylacetonato Eu0.5, Gd0.5 triphenylphosphine oxide
tris acetylacetonato Eu0.5, Gd0.5 2,2-bipyridyl
tris acetylacetonato Eu0.5, Gd0.5 2,2-bipyridyl-N,N-dioxide
tris acetylacetonato Eu0.5, Gd0.5 phenanthroline
tris acetylacetonato Eu0.5, Gd0.5 bathocuproine
tris acetylacetonato Eu0.5, Gd0.5 bathophenanthroline
tris dibenzoylmethanato Eu0.5, Gd0.5 dimethylaminopyridine
tris dibenzoylmethanato Eu0.5, Gd0.5 4-picoline-N-oxide
tris dibenzoylmethanato Eu0.5, Gd0.5 4-phenylpyridine
tris dibenzoylmethanato Eu0.5, Gd0.5 4-cyanopyridine
tris dibenzoylmethanato Eu0.5, Gd0.5 4-phenylpyridine-N-oxide
tris dibenzoylmethanato Eu0.5, Gd0.5 1-methylimidazole tris dibenzoylmethanato Eu0.5, Gd0.5 triphenylphosphine oxide
tris dibenzoylmethanato Eu0.5, Gd0.5 2,2-bipyridyl
tris dibenzoylmethanato Eu0.5, Gd0.5 2,2-bipyridyl-N,N-dioxide
tris dibenzoylmethanato Eu0.5, Gd0.5 phenanthroline
tris dibenzoylmethanato Eu0.5, Gd0.5 bathocuproine
tris dibenzoylmethanato Eu0.5, Gd0.5 bathophenanthroline
tris thenoyltrifluoroacetonato Eu0.5, Gd0.5 dimethylaminopyridine
tris thenoyltrifluoroacetonato Eu0.5, Gd0.5 4-picoline-N-oxide
tris thenoyltrifluoroacetonato Eu0.5, Gd0.5 4-phenylpyridine
tris thenoyltrifluoroacetonato Eu0.5, Gd0.5 4-cyanopyridine
tris thenoyltrifluoroacetonato Eu0.5, Gd0.5 4-phenylpyridine-N-oxide
tris thenoyltrifluoroacetonato Eu0.5, Gd0.5 1-methylimidazole
tris thenoyltrifluoroacetonato Eu0.5, Gd0.5 triphenylphosphine oxide
tris thenoyltrifluoroacetonato Eu0.5, Gd0.5 2,2-bipyridyl
tris thenoyltrifluoroacetonato Eu0.5, Gd0.5 2,2-bipyridyl-N,N-dioxide
tris thenoyltrifluoroacetonato Eu0.5, Gd0.5 phenanthroline
tris thenoyltrifluoroacetonato Eu0.5, Gd0.5 bathocuproine
tris thenoyltrifluoroacetonato Eu0.5, Gd0.5 bathophenanthroline
tris 2,2,6,6-tetramethylheptanedionato Eu0.5, Gd0.5 dimethylaminopyridine
tris 2,2,6,6-tetramethylheptanedionato Eu0.5, Gd0.5 4-picoline-N-oxide
tris 2,2,6,6-tetramethylheptanedionato Eu0.5, Gd0.5 4-phenylpyridine
tris 2,2,6,6-tetramethylheptanedionato Eu0.5, Gd0.5 4-cyanopyridine
tris 2,2,6,6-tetramethylheptanedionato Eu0.5, Gd0.5 4-phenylpyridine-N-oxide
tris 2,2,6,6-tetramethylheptanedionato Eu0.5, Gd0.5 1-methylimidazole
tris 2,2,6,6-tetramethylheptanedionato Eu0.5, Gd0.5 triphenylphosphine oxide
tris 2,2,6,6-tetramethylheptanedionato Eu0.5, Gd0.5 2,2-bipyridyl
tris 2,2,6,6-tetramethylheptanedionato Eu0.5, Gd0.5 2,2-bipyridyl-N,N-dioxide
tris 2,2,6,6-tetramethylheptanedionato Eu0.5, Gd0.5 phenanthroline
tris 2,2,6,6-tetramethylheptanedionato Eu0.5, Gd0.5 bathocuproine
tris 2,2,6,6-tetramethylheptanedionato Eu0.5, Gd0.5 bathophenanthroline
tris 3-methylpentane-2,4-dionato Eu0.5, Gd0.5 dimethylaminopyridine
tris 3-methylpentane-2,4-dionato Eu0.5, Gd0.5 4-picoline-N-oxide
tris 3-methylpentane-2,4-dionato Eu0.5, Gd0.5 4-phenylpyridine
tris 3-methylpentane-2,4-dionato Eu0.5, Gd0.5 4-cyanopyridine
tris 3-methylpentane-2,4-dionato Eu0.5, Gd0.5 4-phenylpyridine-N-oxide
tris 3-methylpentane-2,4-dionato Eu0.5, Gd0.5 1-methylimidazole
tris 3-methylpentane-2,4-dionato Eu0.5, Gd0.5 triphenylphosphine oxide
tris 3-methylpentane-2,4-dionato Eu0.5, Gd0.5 2,2-bipyridyl
tris 3-methylpentane-2,4-dionato Eu0.5, Gd0.5 2,2-bipyridyl-N,N-dioxide
tris 3-methylpentane-2,4-dionato Eu0.5, Gd0.5 phenanthroline
tris 3-methylpentane-2,4-dionato Eu0.5, Gd0.5 bathocuproine
tris 3-methylpentane-2,4-dionato Eu0.5, Gd0.5 bathophenanthroline
tris 3-ethylpentane-2,4-dionato Eu0.5, Gd0.5 dimethylaminopyridine
tris 3-ethylpentane-2,4-dionato Eu0.5, Gd0.5 4-picoline-N-oxide
tris 3-ethylpentane-2,4-dionato Eu0.5, Gd0.5 4-phenylpyridine
tris 3-ethylpentane-2,4-dionato Eu0.5, Gd0.5 4-cyanopyridine
tris 3-ethylpentane-2,4-dionato Eu0.5, Gd0.5 4-phenylpyridine-N-oxide
tris 3-ethylpentane-2,4-dionato Eu0.5, Gd0.5 1-methylimidazole
tris 3-ethylpentane-2,4-dionato Eu0.5, Gd0.5 triphenylphosphine oxide
tris 3-ethylpentane-2,4-dionato Eu0.5, Gd0.5 2,2-bipyridyl
tris 3-ethylpentane-2,4-dionato Eu0.5, Gd0.5 2,2-bipyridyl-N,N-dioxide
tris 3-ethylpentane-2,4-dionato Eu0.5, Gd0.5 phenanthroline
tris 3-ethylpentane-2,4-dionato Eu0.5, Gd0.5 bathocuproine
tris 3-ethylpentane-2,4-dionato Eu0.5, Gd0.5 bathophenanthroline
tris pivaloyltrifluoroacetonato Eu0.5, Gd0.5 dimethylaminopyridine
tris pivaloyltrifluoroacetonato Eu0.5, Gd0.5 4-picoline-N-oxide
tris pivaloyltrifluoroacetonato Eu0.5, Gd0.5 4-phenylpyridine
tris pivaloyltrifluoroacetonato Eu0.5, Gd0.5 4-cyanopyridine
tris pivaloyltrifluoroacetonato Eu0.5, Gd0.5 4-phenylpyridine-N-oxide
tris pivaloyltrifluoroacetonato Eu0.5, Gd0.5 1-methylimidazole
tris pivaloyltrifluoroacetonato Eu0.5, Gd0.5 triphenylphosphine oxide
tris pivaloyltrifluoroacetonato Eu0.5, Gd0.5 2,2-bipyridyl
tris pivaloyltrifluoroacetonato Eu0.5, Gd0.5 2,2-bipyridyl-N,N-dioxide
tris pivaloyltrifluoroacetonato Eu0.5, Gd0.5 phenanthroline
tris pivaloyltrifluoroacetonato Eu0.5, Gd0.5 bathocuproine
tris pivaloyltrifluoroacetonato Eu0.5, Gd0.5 bathophenanthroline
tris trifluoroacetylacetonato Eu0.5, Gd0.5 dimethylaminopyridine
tris trifluoroacetylacetonato Eu0.5, Gd0.5 4-picoline-N-oxide
tris trifluoroacetylacetonato Eu0.5, Gd0.5 4-phenylpyridine
tris trifluoroacetylacetonato Eu0.5, Gd0.5 4-cyanopyridine
tris trifluoroacetylacetonato Eu0.5, Gd0.5 4-phenylpyridine-N-oxide
tris trifluoroacetylacetonato Eu0.5, Gd0.5 1-methylimidazole
tris trifluoroacetylacetonato Eu0.5, Gd0.5 triphenylphosphine oxide
tris trifluoroacetylacetonato Eu0.5, Gd0.5 2,2-bipyridyl tris trifluoroacetylacetonato Eu0.5, Gd0.5 2,2-bipyridyl-N,N-dioxide
tris trifluoroacetylacetonato Eu0.5, Gd0.5 phenanthroline
tris trifluoroacetylacetonato Eu0.5, Gd0.5 bathocuproine
tris trifluoroacetylacetonato Eu0.5, Gd0.5 bathophenanthroline
tris hexafluoroacetylacetonato Eu0.5, Gd0.5 dimethylaminopyridine
tris hexafluoroacetylacetonato Eu0.5, Gd0.5 4-picoline-N-oxide
tris hexafluoroacetylacetonato Eu0.5, Gd0.5 4-phenylpyridine
tris hexafluoroacetylacetonato Eu0.5, Gd0.5 4-cyanopyridine
tris hexafluoroacetylacetonato Eu0.5, Gd0.5 4-phenylpyridine-N-oxide
tris hexafluoroacetylacetonato Eu0.5, Gd0.5 1-methylimidazole
tris hexafluoroacetylacetonato Eu0.5, Gd0.5 triphenylphosphine oxide
tris hexafluoroacetylacetonato Eu0.5, Gd0.5 2,2-bipyridyl
tris hexafluoroacetylacetonato Eu0.5, Gd0.5 2,2-bipyridyl-N,N-dioxide
tris hexafluoroacetylacetonato Eu0.5, Gd0.5 phenanthroline
tris hexafluoroacetylacetonato Eu0.5, Gd0.5 bathocuproine
tris hexafluoroacetylacetonato Eu0.5, Gd0.5 bathophenanthroline
tris 6,6,7,7,8,8,8-heptafluoro-2,2-dimethyloctanedionato Eu0.5, Gd0.5 dimethylaminopyridine
tris 6,6,7,7,8,8,8-heptafluoro-2,2-dimethyloctanedionato Eu0.5, Gd0.5 4-picoline-N-oxide
tris 6,6,7,7,8,8,8-heptafluoro-2,2-dimethyloctanedionato Eu0.5, Gd0.5 4-phenylpyridine
tris 6,6,7,7,8,8,8-heptafluoro-2,2-dimethyloctanedionato Eu0.5, Gd0.5 4-cyanopyridine
tris 6,6,7,7,8,8,8-heptafluoro-2,2-dimethyloctanedionato Eu0.5, Gd0.5 4-phenylpyridine-N-oxide
tris 6,6,7,7,8,8,8-heptafluoro-2,2-dimethyloctanedionato Eu0.5, Gd0.5 1-methylimidazole
tris 6,6,7,7,8,8,8-heptafluoro-2,2-dimethyloctanedionato Eu0.5, Gd0.5 triphenylphosphine oxide
tris 6,6,7,7,8,8,8-heptafluoro-2,2-dimethyloctanedionato Eu0.5, Gd0.5 2,2-bipyridyl
tris 6,6,7,7,8,8,8-heptafluoro-2,2-dimethyloctanedionato Eu0.5, Gd0.5 2,2-bipyridyl-N,N-dioxide
tris 6,6,7,7,8,8,8-heptafluoro-2,2-dimethyloctanedionato Eu0.5, Gd0.5 phenanthroline
tris 6,6,7,7,8,8,8-heptafluoro-2,2-dimethyloctanedionato Eu0.5, Gd0.5 bathocuproine
tris 6,6,7,7,8,8,8-heptafluoro-2,2-dimethyloctanedionato Eu0.5, Gd0.5 bathophenanthroline
tris 1-phenyl-1,3-butanedionato Eu0.5, Gd0.5 dimethylaminopyridine
tris 1-phenyl-1,3-butanedionato Eu0.5, Gd0.5 4-picoline-N-oxide
tris 1-phenyl-1,3-butanedionato Eu0.5, Gd0.5 4-phenylpyridine
tris 1-phenyl-1,3-butanedionato Eu0.5, Gd0.5 4-cyanopyridine
tris 1-phenyl-1,3-butanedionato Eu0.5, Gd0.5 4-phenylpyridine-N-oxide
tris 1-phenyl-1,3-butanedionato Eu0.5, Gd0.5 1-methylimidazole
tris 1-phenyl-1,3-butanedionato Eu0.5, Gd0.5 triphenylphosphine oxide
tris 1-phenyl-1,3-butanedionato Eu0.5, Gd0.5 2,2-bipyridyl
tris 1-phenyl-1,3-butanedionato Eu0.5, Gd0.5 2,2-bipyridyl-N,N-dioxide
tris 1-phenyl-1,3-butanedionato Eu0.5, Gd0.5 phenanthroline
tris 1-phenyl-1,3-butanedionato Eu0.5, Gd0.5 bathocuproine
tris 1-phenyl-1,3-butanedionato Eu0.5, Gd0.5 bathophenanthroline
tris acetylacetonato Eu0.2, Gd0.8 dimethylaminopyridine
tris acetylacetonato Eu0.2, Gd0.8 4-picoline-N-oxide
tris acetylacetonato Eu0.2, Gd0.8 4-phenylpyridine
tris acetylacetonato Eu0.2, Gd0.8 4-cyanopyridine
tris acetylacetonato Eu0.2, Gd0.8 4-phenylpyridine-N-oxide
tris acetylacetonato Eu0.2, Gd0.8 1-methylimidazole
tris acetylacetonato Eu0.2, Gd0.8 triphenylphosphine oxide
tris acetylacetonato Eu0.2, Gd0.8 2,2-bipyridyl
tris acetylacetonato Eu0.2, Gd0.8 2,2-bipyridyl-N,N-dioxide
tris acetylacetonato Eu0.2, Gd0.8 phenanthroline
tris acetylacetonato Eu0.2, Gd0.8 bathocuproine
tris acetylacetonato Eu0.2, Gd0.8 bathophenanthroline
tris dibenzoylmethanato Eu0.2, Gd0.8 dimethylaminopyridine
tris dibenzoylmethanato Eu0.2, Gd0.8 4-picoline-N-oxide
tris dibenzoylmethanato Eu0.2, Gd0.8 4-phenylpyridine
tris dibenzoylmethanato Eu0.2, Gd0.8 4-cyanopyridine
tris dibenzoylmethanato Eu0.2, Gd0.8 4-phenylpyridine-N-oxide
tris dibenzoylmethanato Eu0.2, Gd0.8 1-methylimidazole
tris dibenzoylmethanato Eu0.2, Gd0.8 triphenylphosphine oxide
tris dibenzoylmethanato Eu0.2, Gd0.8 2,2-bipyridyl
tris dibenzoylmethanato Eu0.2, Gd0.8 2,2-bipyridyl-N,N-dioxide
tris dibenzoylmethanato Eu0.2, Gd0.8 phenanthroline
tris dibenzoylmethanato Eu0.2, Gd0.8 bathocuproine
tris dibenzoylmethanato Eu0.2, Gd0.8 bathophenanthroline
tris thenoyltrifluoroacetonato Eu0.2, Gd0.8 dimethylaminopyridine
tris thenoyltrifluoroacetonato Eu0.2, Gd0.8 4-picoline-N-oxide
tris thenoyltrifluoroacetonato Eu0.2, Gd0.8 4-phenylpyridine
tris thenoyltrifluoroacetonato Eu0.2, Gd0.8 4-cyanopyridine
tris thenoyltrifluoroacetonato Eu0.2, Gd0.8 4-phenylpyridine-N-oxide
tris thenoyltrifluoroacetonato Eu0.2, Gd0.8 1-methylimidazole
tris thenoyltrifluoroacetonato Eu0.2, Gd0.8 triphenylphosphine oxide
tris thenoyltrifluoroacetonato Eu0.2, Gd0.8 2,2-bipyridyl
tris thenoyltrifluoroacetonato Eu0.2, Gd0.8 2,2-bipyridyl-N,N-dioxide
tris thenoyltrifluoroacetonato Eu0.2, Gd0.8 phenanthroline
tris thenoyltrifluoroacetonato Eu0.2, Gd0.8 bathocuproine
tris thenoyltrifluoroacetonato Eu0.2, Gd0.8 bathophenanthroline
tris 2,2,6,6-tetramethylheptanedionato Eu0.2, Gd0.8 dimethylaminopyridine
tris 2,2,6,6-tetramethylheptanedionato Eu0.2, Gd0.8 4-picoline-N-oxide
tris 2,2,6,6-tetramethylheptanedionato Eu0.2, Gd0.8 4-phenylpyridine
tris 2,2,6,6-tetramethylheptanedionato Eu0.2, Gd0.8 4-cyanopyridine
tris 2,2,6,6-tetramethylheptanedionato Eu0.2, Gd0.8 4-phenylpyridine-N-oxide tris 2,2,6,6-tetramethylheptanedionato Eu0.2, Gd0.8 1-methylimidazole
tris 2,2,6,6-tetramethylheptanedionato Eu0.2, Gd0.8 triphenylphosphine oxide
tris 2,2,6,6-tetramethylheptanedionato Eu0.2, Gd0.8 2,2-bipyridyl
tris 2,2,6,6-tetramethylheptanedionato Eu0.2, Gd0.8 2,2-bipyridyl-N,N-dioxide
tris 2,2,6,6-tetramethylheptanedionato Eu0.2, Gd0.8 phenanthroline
tris 2,2,6,6-tetramethylheptanedionato Eu0.2, Gd0.8 bathocuproine
tris 2,2,6,6-tetramethylheptanedionato Eu0.2, Gd0.8 bathophenanthroline
tris 3-methylpentane-2,4-dionato Eu0.2, Gd0.8 dimethylaminopyridine
tris 3-methylpentane-2,4-dionato Eu0.2, Gd0.8 4-picoline-N-oxide
tris 3-methylpentane-2,4-dionato Eu0.2, Gd0.8 4-phenylpyridine
tris 3-methylpentane-2,4-dionato Eu0.2, Gd0.8 4-cyanopyridine
tris 3-methylpentane-2,4-dionato Eu0.2, Gd0.8 4-phenylpyridine-N-oxide
tris 3-methylpentane-2,4-dionato Eu0.2, Gd0.8 1-methylimidazole
tris 3-methylpentane-2,4-dionato Eu0.2, Gd0.8 triphenylphosphine oxide
tris 3-methylpentane-2,4-dionato Eu0.2, Gd0.8 2,2-bipyridyl
tris 3-methylpentane-2,4-dionato Eu0.2, Gd0.8 2,2-bipyridyl-N,N-dioxide
tris 3-methylpentane-2,4-dionato Eu0.2, Gd0.8 phenanthroline
tris 3-methylpentane-2,4-dionato Eu0.2, Gd0.8 bathocuproine
tris 3-methylpentane-2,4-dionato Eu0.2, Gd0.8 bathophenanthroline
tris 3-ethylpentane-2,4-dionato Eu0.2, Gd0.8 dimethylaminopyridine
tris 3-ethylpentane-2,4-dionato Eu0.2, Gd0.8 4-picoline-N-oxide
tris 3-ethylpentane-2,4-dionato Eu0.2, Gd0.8 4-phenylpyridine
tris 3-ethylpentane-2,4-dionato Eu0.2, Gd0.8 4-cyanopyridine
tris 3-ethylpentane-2,4-dionato Eu0.2, Gd0.8 4-phenylpyridine-N-oxide
tris 3-ethylpentane-2,4-dionato Eu0.2, Gd0.8 1-methylimidazole
tris 3-ethylpentane-2,4-dionato Eu0.2, Gd0.8 triphenylphosphine oxide
tris 3-ethylpentane-2,4-dionato Eu0.2, Gd0.8 2,2-bipyridyl
tris 3-ethylpentane-2,4-dionato Eu0.2, Gd0.8 2,2-bipyridyl-N,N-dioxide
tris 3-ethylpentane-2,4-dionato Eu0.2, Gd0.8 phenanthroline
tris 3-ethylpentane-2,4-dionato Eu0.2, Gd0.8 bathocuproine
tris 3-ethylpentane-2,4-dionato Eu0.2, Gd0.8 bathophenanthroline
tris pivaloyltrifluoroacetonato Eu0.2, Gd0.8 dimethylaminopyridine
tris pivaloyltrifluoroacetonato Eu0.2, Gd0.8 4-picoline-N-oxide
tris pivaloyltrifluoroacetonato Eu0.2, Gd0.8 4-phenylpyridine
tris pivaloyltrifluoroacetonato Eu0.2, Gd0.8 4-cyanopyridine
tris pivaloyltrifluoroacetonato Eu0.2, Gd0.8 4-phenylpyridine-N-oxide
tris pivaloyltrifluoroacetonato Eu0.2, Gd0.8 1-methylimidazole
tris pivaloyltrifluoroacetonato Eu0.2, Gd0.8 triphenylphosphine oxide
tris pivaloyltrifluoroacetonato Eu0.2, Gd0.8 2,2-bipyridyl
tris pivaloyltrifluoroacetonato Eu0.2, Gd0.8 2,2-bipyridyl-N,N-dioxide
tris pivaloyltrifluoroacetonato Eu0.2, Gd0.8 phenanthroline
tris pivaloyltrifluoroacetonato Eu0.2, Gd0.8 bathocuproine
tris pivaloyltrifluoroacetonato Eu0.2, Gd0.8 bathophenanthroline
tris trifluoroacetylacetonato Eu0.2, Gd0.8 dimethylaminopyridine
tris trifluoroacetylacetonato Eu0.2, Gd0.8 4-picoline-N-oxide
tris trifluoroacetylacetonato Eu0.2, Gd0.8 4-phenylpyridine
tris trifluoroacetylacetonato Eu0.2, Gd0.8 4-cyanopyridine
tris trifluoroacetylacetonato Eu0.2, Gd0.8 4-phenylpyridine-N-oxide
tris trifluoroacetylacetonato Eu0.2, Gd0.8 1-methylimidazole
tris trifluoroacetylacetonato Eu0.2, Gd0.8 triphenylphosphine oxide
tris trifluoroacetylacetonato Eu0.2, Gd0.8 2,2-bipyridyl
tris trifluoroacetylacetonato Eu0.2, Gd0.8 2,2-bipyridyl-N,N-dioxide
tris trifluoroacetylacetonato Eu0.2, Gd0.8 phenanthroline
tris trifluoroacetylacetonato Eu0.2, Gd0.8 bathocuproine
tris trifluoroacetylacetonato Eu0.2, Gd0.8 bathophenanthroline
tris hexafluoroacetylacetonato Eu0.2, Gd0.8 dimethylaminopyridine
tris hexafluoroacetylacetonato Eu0.2, Gd0.8 4-picoline-N-oxide
tris hexafluoroacetylacetonato Eu0.2, Gd0.8 4-phenylpyridine
tris hexafluoroacetylacetonato Eu0.2, Gd0.8 4-cyanopyridine
tris hexafluoroacetylacetonato Eu0.2, Gd0.8 4-phenylpyridine-N-oxide
tris hexafluoroacetylacetonato Eu0.2, Gd0.8 1-methylimidazole
tris hexafluoroacetylacetonato Eu0.2, Gd0.8 triphenylphosphine oxide
tris hexafluoroacetylacetonato Eu0.2, Gd0.8 2,2-bipyridyl
tris hexafluoroacetylacetonato Eu0.2, Gd0.8 2,2-bipyridyl-N,N-dioxide
tris hexafluoroacetylacetonato Eu0.2, Gd0.8 phenanthroline
tris hexafluoroacetylacetonato Eu0.2, Gd0.8 bathocuproine
tris hexafluoroacetylacetonato Eu0.2, Gd0.8 bathophenanthroline
tris 6,6,7,7,8,8,8-heptafluoro-2,2-dimethyloctanedionato Eu0.2, Gd0.8 dimethylaminopyridine
tris 6,6,7,7,8,8,8-heptafluoro-2,2-dimethyloctanedionato Eu0.2, Gd0.8 4-picoline-N-oxide
tris 6,6,7,7,8,8,8-heptafluoro-2,2-dimethyloctanedionato Eu0.2, Gd0.8 4-phenylpyridine
tris 6,6,7,7,8,8,8-heptafluoro-2,2-dimethyloctanedionato Eu0.2, Gd0.8 4-cyanopyridine
tris 6,6,7,7,8,8,8-heptafluoro-2,2-dimethyloctanedionato Eu0.2, Gd0.8 4-phenylpyridine-N-oxide
tris 6,6,7,7,8,8,8-heptafluoro-2,2-dimethyloctanedionato Eu0.2, Gd0.8 1-methylimidazole tris 6,6,7,7,8,8-heptafluoro-2,2-dimethyloctanedionato Eu0.2, Gd0.8 triphenylphosphine oxide
tris 6,6,7,7,8,8-heptafluoro-2,2-dimethyloctanedionato Eu0.2, Gd0.8 2,2-bipyridyl
tris 6,6,7,7,8,8-heptafluoro-2,2-dimethyloctanedionato Eu0.2, Gd0.8 2,2-bipyridyl-N,N-dioxide
tris 6,6,7,7,8,8-heptafluoro-2,2-dimethyloctanedionato Eu0.2, Gd0.8 phenanthroline
tris 6,6,7,7,8,8-heptafluoro-2,2-dimethyloctanedionato Eu0.2, Gd0.8 bathocuproine
tris 6,6,7,7,8,8-heptafluoro-2,2-dimethyloctanedionato Eu0.2, Gd0.8 bathophenanthroline
tris 1-phenyl-1,3-butanedionato Eu0.2, Gd0.8 dimethylaminopyridine
tris 1-phenyl-1,3-butanedionato Eu0.2, Gd0.8 4-picoline-N-oxide
tris 1-phenyl-1,3-butanedionato Eu0.2, Gd0.8 4-phenylpyridine
tris 1-phenyl-1,3-butanedionato Eu0.2, Gd0.8 4-cyanopyridine
tris 1-phenyl-1,3-butanedionato Eu0.2, Gd0.8 4-phenylpyridine-N-oxide
tris 1-phenyl-1,3-butanedionato Eu0.2, Gd0.8 1-methylimidazole
tris 1-phenyl-1,3-butanedionato Eu0.2, Gd0.8 triphenylphosphine oxide
tris 1-phenyl-1,3-butanedionato Eu0.2, Gd0.8 2,2-bipyridyl
tris 1-phenyl-1,3-butanedionato Eu0.2, Gd0.8 2,2-bipyridyl-N,N-dioxide
tris 1-phenyl-1,3-butanedionato Eu0.2, Gd0.8 phenanthroline
tris 1-phenyl-1,3-butanedionato Eu0.2, Gd0.8 bathocuproine
tris 1-phenyl-1,3-butanedionato Eu0.2, Gd0.8 bathophenanthroline
tris acetylacetonato Eu0.1, Gd0.9 dimethylaminopyridine
tris acetylacetonato Eu0.1, Gd0.9 4-picoline-N-oxide
tris acetylacetonato Eu0.1, Gd0.9 4-phenylpyridine
tris acetylacetonato Eu0.1, Gd0.9 4-cyanopyridine
tris acetylacetonato Eu0.1, Gd0.9 4-phenylpyridine-N-oxide
tris acetylacetonato Eu0.1, Gd0.9 1-methylimidazole
tris acetylacetonato Eu0.1, Gd0.9 triphenylphosphine oxide
tris acetylacetonato Eu0.1, Gd0.9 2,2-bipyridyl
tris acetylacetonato Eu0.1, Gd0.9 2,2-bipyridyl-N,N-dioxide
tris acetylacetonato Eu0.1, Gd0.9 phenanthroline
tris acetylacetonato Eu0.1, Gd0.9 bathocuproine
tris acetylacetonato Eu0.1, Gd0.9 bathophenanthroline
tris dibenzoylmethanato Eu0.1, Gd0.9 dimethylaminopyridine
tris dibenzoylmethanato Eu0.1, Gd0.9 4-picoline-N-oxide
tris dibenzoylmethanato Eu0.1, Gd0.9 4-phenylpyridine
tris dibenzoylmethanato Eu0.1, Gd0.9 4-cyanopyridine
tris dibenzoylmethanato Eu0.1, Gd0.9 4-phenylpyridine-N-oxide
tris dibenzoylmethanato Eu0.1, Gd0.9 1-methylimidazole
tris dibenzoylmethanato Eu0.1, Gd0.9 triphenylphosphine oxide
tris dibenzoylmethanato Eu0.1, Gd0.9 2,2-bipyridyl
tris dibenzoylmethanato Eu0.1, Gd0.9 2,2-bipyridyl-N,N-dioxide
tris dibenzoylmethanato Eu0.1, Gd0.9 phenanthroline
tris dibenzoylmethanato Eu0.1, Gd0.9 bathocuproine
tris dibenzoylmethanato Eu0.1, Gd0.9 bathophenanthroline
tris thenoyltrifluoroacetonato Eu0.1, Gd0.9 dimethylaminopyridine
tris thenoyltrifluoroacetonato Eu0.1, Gd0.9 4-picoline-N-oxide
tris thenoyltrifluoroacetonato Eu0.1, Gd0.9 4-phenylpyridine
tris thenoyltrifluoroacetonato Eu0.1, Gd0.9 4-cyanopyridine
tris thenoyltrifluoroacetonato Eu0.1, Gd0.9 4-phenylpyridine-N-oxide
tris thenoyltrifluoroacetonato Eu0.1, Gd0.9 1-methylimidazole
tris thenoyltrifluoroacetonato Eu0.1, Gd0.9 triphenylphosphine oxide
tris thenoyltrifluoroacetonato Eu0.1, Gd0.9 2,2-bipyridyl
tris thenoyltrifluoroacetonato Eu0.1, Gd0.9 2,2-bipyridyl-N,N-dioxide
tris thenoyltrifluoroacetonato Eu0.1, Gd0.9 phenanthroline
tris thenoyltrifluoroacetonato Eu0.1, Gd0.9 bathocuproine
tris thenoyltrifluoroacetonato Eu0.1, Gd0.9 bathophenanthroline
tris 2,2,6,6-tetramethylheptanedionato Eu0.1, Gd0.9 dimethylaminopyridine
tris 2,2,6,6-tetramethylheptanedionato Eu0.1, Gd0.9 4-picoline-N-oxide
tris 2,2,6,6-tetramethylheptanedionato Eu0.1, Gd0.9 4-phenylpyridine
tris 2,2,6,6-tetramethylheptanedionato Eu0.1, Gd0.9 4-cyanopyridine
tris 2,2,6,6-tetramethylheptanedionato Eu0.1, Gd0.9 4-phenylpyridine-N-oxide
tris 2,2,6,6-tetramethylheptanedionato Eu0.1, Gd0.9 1-methylimidazole
tris 2,2,6,6-tetramethylheptanedionato Eu0.1, Gd0.9 triphenylphosphine oxide
tris 2,2,6,6-tetramethylheptanedionato Eu0.1, Gd0.9 2,2-bipyridyl
tris 2,2,6,6-tetramethylheptanedionato Eu0.1, Gd0.9 2,2-bipyridyl-N,N-dioxide
tris 2,2,6,6-tetramethylheptanedionato Eu0.1, Gd0.9 phenanthroline
tris 2,2,6,6-tetramethylheptanedionato Eu0.1, Gd0.9 bathocuproine
tris 2,2,6,6-tetramethylheptanedionato Eu0.1, Gd0.9 bathophenanthroline
tris 3-methylpentane-2,4-dionato Eu0.1, Gd0.9 dimethylaminopyridine
tris 3-methylpentane-2,4-dionato Eu0.1, Gd0.9 4-picoline-N-oxide
tris 3-methylpentane-2,4-dionato Eu0.1, Gd0.9 4-phenylpyridine
tris 3-methylpentane-2,4-dionato Eu0.1, Gd0.9 4-cyanopyridine
tris 3-methylpentane-2,4-dionato Eu0.1, Gd0.9 4-phenylpyridine-N-oxide
tris 3-methylpentane-2,4-dionato Eu0.1, Gd0.9 1-methylimidazole
tris 3-methylpentane-2,4-dionato Eu0.1, Gd0.9 triphenylphosphine oxide
tris 3-methylpentane-2,4-dionato Eu0.1, Gd0.9 2,2-bipyridyl
tris 3-methylpentane-2,4-dionato Eu0.1, Gd0.9 2,2-bipyridyl-N,N-dioxide
tris 3-methylpentane-2,4-dionato Eu0.1, Gd0.9 phenanthroline
tris 3-methylpentane-2,4-dionato Eu0.1, Gd0.9 bathocuproine
tris 3-methylpentane-2,4-dionato Eu0.1, Gd0.9 bathophenanthroline
tris 3-ethylpentane-2,4-dionato Eu0.1, Gd0.9 dimethylaminopyridine tris 3-ethylpentane-2,4-dionato Eu0.1, Gd0.9 4-picoline-N-oxide
tris 3-ethylpentane-2,4-dionato Eu0.1, Gd0.9 4-phenylpyridine
tris 3-ethylpentane-2,4-dionato Eu0.1, Gd0.9 4-cyanopyridine
tris 3-ethylpentane-2,4-dionato Eu0.1, Gd0.9 4-phenylpyridine-N-oxide
tris 3-ethylpentane-2,4-dionato Eu0.1, Gd0.9 1-methylimidazole
tris 3-ethylpentane-2,4-dionato Eu0.1, Gd0.9 triphenylphosphine oxide
tris 3-ethylpentane-2,4-dionato Eu0.1, Gd0.9 2,2-bipyridyl
tris 3-ethylpentane-2,4-dionato Eu0.1, Gd0.9 2,2-bipyridyl-N,N-dioxide
tris 3-ethylpentane-2,4-dionato Eu0.1, Gd0.9 phenanthroline
tris 3-ethylpentane-2,4-dionato Eu0.1, Gd0.9 bathocuproine
tris 3-ethylpentane-2,4-dionato Eu0.1, Gd0.9 bathophenanthroline
tris pivaloyltrifluoroacetonato Eu0.1, Gd0.9 dimethylaminopyridine
tris pivaloyltrifluoroacetonato Eu0.1, Gd0.9 4-picoline-N-oxide
tris pivaloyltrifluoroacetonato Eu0.1, Gd0.9 4-phenylpyridine
tris pivaloyltrifluoroacetonato Eu0.1, Gd0.9 4-cyanopyridine
tris pivaloyltrifluoroacetonato Eu0.1, Gd0.9 4-phenylpyridine-N-oxide
tris pivaloyltrifluoroacetonato Eu0.1, Gd0.9 1-methylimidazole
tris pivaloyltrifluoroacetonato Eu0.1, Gd0.9 triphenylphosphine oxide
tris pivaloyltrifluoroacetonato Eu0.1, Gd0.9 2,2-bipyridyl
tris pivaloyltrifluoroacetonato Eu0.1, Gd0.9 2,2-bipyridyl-N,N-dioxide
tris pivaloyltrifluoroacetonato Eu0.1, Gd0.9 phenanthroline
tris pivaloyltrifluoroacetonato Eu0.1, Gd0.9 bathocuproine
tris pivaloyltrifluoroacetonato Eu0.1, Gd0.9 bathophenanthroline
tris trifluoroacetylacetonato Eu0.1, Gd0.9 dimethylaminopyridine
tris trifluoroacetylacetonato Eu0.1, Gd0.9 4-picoline-N-oxide
tris trifluoroacetylacetonato Eu0.1, Gd0.9 4-phenylpyridine
tris trifluoroacetylacetonato Eu0.1, Gd0.9 4-cyanopyridine
tris trifluoroacetylacetonato Eu0.1, Gd0.9 4-phenylpyridine-N-oxide
tris trifluoroacetylacetonato Eu0.1, Gd0.9 1-methylimidazole
tris trifluoroacetylacetonato Eu0.1, Gd0.9 triphenylphosphine oxide
tris trifluoroacetylacetonato Eu0.1, Gd0.9 2,2-bipyridyl
tris trifluoroacetylacetonato Eu0.1, Gd0.9 2,2-bipyridyl-N,N-dioxide
tris trifluoroacetylacetonato Eu0.1, Gd0.9 phenanthroline
tris trifluoroacetylacetonato Eu0.1, Gd0.9 bathocuproine
tris trifluoroacetylacetonato Eu0.1, Gd0.9 bathophenanthroline
tris hexafluoroacetylacetonato Eu0.1, Gd0.9 dimethylaminopyridine
tris hexafluoroacetylacetonato Eu0.1, Gd0.9 4-picoline-N-oxide
tris hexafluoroacetylacetonato Eu0.1, Gd0.9 4-phenylpyridine
tris hexafluoroacetylacetonato Eu0.1, Gd0.9 4-cyanopyridine
tris hexafluoroacetylacetonato Eu0.1, Gd0.9 4-phenylpyridine-N-oxide
tris hexafluoroacetylacetonato Eu0.1, Gd0.9 1-methylimidazole
tris hexafluoroacetylacetonato Eu0.1, Gd0.9 triphenylphosphine oxide
tris hexafluoroacetylacetonato Eu0.1, Gd0.9 2,2-bipyridyl
tris hexafluoroacetylacetonato Eu0.1, Gd0.9 2,2-bipyridyl-N,N-dioxide
tris hexafluoroacetylacetonato Eu0.1, Gd0.9 phenanthroline
tris hexafluoroacetylacetonato Eu0.1, Gd0.9 bathocuproine
tris hexafluoroacetylacetonato Eu0.1, Gd0.9 bathophenanthroline
tris 6,6,7,7,8,8,8-heptafluoro-2,2-dimethyloctanedionato Eu0.1, Gd0.9 dimethylaminopyridine
tris 6,6,7,7,8,8,8-heptafluoro-2,2-dimethyloctanedionato Eu0.1, Gd0.9 4-picoline-N-oxide
tris 6,6,7,7,8,8,8-heptafluoro-2,2-dimethyloctanedionato Eu0.1, Gd0.9 4-phenylpyridine
tris 6,6,7,7,8,8,8-heptafluoro-2,2-dimethyloctanedionato Eu0.1, Gd0.9 4-cyanopyridine
tris 6,6,7,7,8,8,8-heptafluoro-2,2-dimethyloctanedionato Eu0.1, Gd0.9 4-phenylpyridine-N-oxide
tris 6,6,7,7,8,8,8-heptafluoro-2,2-dimethyloctanedionato Eu0.1, Gd0.9 1-methylimidazole
tris 6,6,7,7,8,8,8-heptafluoro-2,2-dimethyloctanedionato Eu0.1, Gd0.9 triphenylphosphine oxide
tris 6,6,7,7,8,8,8-heptafluoro-2,2-dimethyloctanedionato Eu0.1, Gd0.9 2,2-bipyridyl
tris 6,6,7,7,8,8,8-heptafluoro-2,2-dimethyloctanedionato Eu0.1, Gd0.9 2,2-bipyridyl-N,N-dioxide
tris 6,6,7,7,8,8,8-heptafluoro-2,2-dimethyloctanedionato Eu0.1, Gd0.9 phenanthroline
tris 6,6,7,7,8,8,8-heptafluoro-2,2-dimethyloctanedionato Eu0.1, Gd0.9 bathocuproine
tris 6,6,7,7,8,8,8-heptafluoro-2,2-dimethyloctanedionato Eu0.1, Gd0.9 bathophenanthroline
tris 1-phenyl-1,3-butanedionato Eu0.1, Gd0.9 dimethylaminopyridine
tris 1-phenyl-1,3-butanedionato Eu0.1, Gd0.9 4-picoline-N-oxide
tris 1-phenyl-1,3-butanedionato Eu0.1, Gd0.9 4-phenylpyridine
tris 1-phenyl-1,3-butanedionato Eu0.1, Gd0.9 4-cyanopyridine
tris 1-phenyl-1,3-butanedionato Eu0.1, Gd0.9 4-phenylpyridine-N-oxide
tris 1-phenyl-1,3-butanedionato Eu0.1, Gd0.9 1-methylimidazole
tris 1-phenyl-1,3-butanedionato Eu0.1, Gd0.9 triphenylphosphine oxide
tris 1-phenyl-1,3-butanedionato Eu0.1, Gd0.9 2,2-bipyridyl
tris 1-phenyl-1,3-butanedionato Eu0.1, Gd0.9 2,2-bipyridyl-N,N-dioxide
tris 1-phenyl-1,3-butanedionato Eu0.1, Gd0.9 phenanthroline
tris 1-phenyl-1,3-butanedionato Eu0.1, Gd0.9 bathocuproine
tris 1-phenyl-1,3-butanedionato Eu0.1, Gd0.9 bathophenanthroline
tris acetylacetonato Eu0.01, Gd0.99 dimethylaminopyridine
tris acetylacetonato Eu0.01, Gd0.99 4-picoline-N-oxide
tris acetylacetonato Eu0.01, Gd0.99 4-phenylpyridine
tris acetylacetonato Eu0.01, Gd0.99 4-cyanopyridine tris acetylacetonato Eu0.01, Gd0.99 4-phenylpyridine-N-oxide
tris acetylacetonato Eu0.01, Gd0.99 1-methylimidazole
tris acetylacetonato Eu0.01, Gd0.99 triphenylphosphine oxide
tris acetylacetonato Eu0.01, Gd0.99 2,2-bipyridyl
tris acetylacetonato Eu0.01, Gd0.99 2,2-bipyridyl-N,N-dioxide
tris acetylacetonato Eu0.01, Gd0.99 phenanthroline
tris acetylacetonato Eu0.01, Gd0.99 bathocuproine
tris acetylacetonato Eu0.01, Gd0.99 bathophenanthroline
tris dibenzoylmethanato Eu0.01, Gd0.99 dimethylaminopyridine
tris dibenzoylmethanato Eu0.01, Gd0.99 4-picoline-N-oxide
tris dibenzoylmethanato Eu0.01, Gd0.99 4-phenylpyridine
tris dibenzoylmethanato Eu0.01, Gd0.99 4-cyanopyridine
tris dibenzoylmethanato Eu0.01, Gd0.99 4-phenylpyridine-N-oxide
tris dibenzoylmethanato Eu0.01, Gd0.99 1-methylimidazole
tris dibenzoylmethanato Eu0.01, Gd0.99 triphenylphosphine oxide
tris dibenzoylmethanato Eu0.01, Gd0.99 2,2-bipyridyl
tris dibenzoylmethanato Eu0.01, Gd0.99 2,2-bipyridyl-N,N-dioxide
tris dibenzoylmethanato Eu0.01, Gd0.99 phenanthroline
tris dibenzoylmethanato Eu0.01, Gd0.99 bathocuproine
tris dibenzoylmethanato Eu0.01, Gd0.99 bathophenanthroline
tris thenoyltrifluoroacetonato Eu0.01, Gd0.99 dimethylaminopyridine
tris thenoyltrifluoroacetonato Eu0.01, Gd0.99 4-picoline-N-oxide
tris thenoyltrifluoroacetonato Eu0.01, Gd0.99 4-phenylpyridine
tris thenoyltrifluoroacetonato Eu0.01, Gd0.99 4-cyanopyridine
tris thenoyltrifluoroacetonato Eu0.01, Gd0.99 4-phenylpyridine-N-oxide
tris thenoyltrifluoroacetonato Eu0.01, Gd0.99 1-methylimidazole
tris thenoyltrifluoroacetonato Eu0.01, Gd0.99 triphenylphosphine oxide
tris thenoyltrifluoroacetonato Eu0.01, Gd0.99 2,2-bipyridyl
tris thenoyltrifluoroacetonato Eu0.01, Gd0.99 2,2-bipyridyl-N,N-dioxide
tris thenoyltrifluoroacetonato Eu0.01, Gd0.99 phenanthroline
tris thenoyltrifluoroacetonato Eu0.01, Gd0.99 bathocuproine
tris thenoyltrifluoroacetonato Eu0.01, Gd0.99 bathophenanthroline
tris 2,2,6,6-tetramethylheptanedionato Eu0.01, Gd0.99 dimethylaminopyridine
tris 2,2,6,6-tetramethylheptanedionato Eu0.01, Gd0.99 4-picoline-N-oxide
tris 2,2,6,6-tetramethylheptanedionato Eu0.01, Gd0.99 4-phenylpyridine
tris 2,2,6,6-tetramethylheptanedionato Eu0.01, Gd0.99 4-cyanopyridine
tris 2,2,6,6-tetramethylheptanedionato Eu0.01, Gd0.99 4-phenylpyridine-N-oxide
tris 2,2,6,6-tetramethylheptanedionato Eu0.01, Gd0.99 1-methylimidazole
tris 2,2,6,6-tetramethylheptanedionato Eu0.01, Gd0.99 triphenylphosphine oxide
tris 2,2,6,6-tetramethylheptanedionato Eu0.01, Gd0.99 2,2-bipyridyl
tris 2,2,6,6-tetramethylheptanedionato Eu0.01, Gd0.99 2,2-bipyridyl-N,N-dioxide
tris 2,2,6,6-tetramethylheptanedionato Eu0.01, Gd0.99 phenanthroline
tris 2,2,6,6-tetramethylheptanedionato Eu0.01, Gd0.99 bathocuproine
tris 2,2,6,6-tetramethylheptanedionato Eu0.01, Gd0.99 bathophenanthroline
tris 3-methylpentane-2,4-dionato Eu0.01, Gd0.99 dimethylaminopyridine
tris 3-methylpentane-2,4-dionato Eu0.01, Gd0.99 4-picoline-N-oxide
tris 3-methylpentane-2,4-dionato Eu0.01, Gd0.99 4-phenylpyridine
tris 3-methylpentane-2,4-dionato Eu0.01, Gd0.99 4-cyanopyridine
tris 3-methylpentane-2,4-dionato Eu0.01, Gd0.99 4-phenylpyridine-N-oxide
tris 3-methylpentane-2,4-dionato Eu0.01, Gd0.99 1-methylimidazole
tris 3-methylpentane-2,4-dionato Eu0.01, Gd0.99 triphenylphosphine oxide
tris 3-methylpentane-2,4-dionato Eu0.01, Gd0.99 2,2-bipyridyl
tris 3-methylpentane-2,4-dionato Eu0.01, Gd0.99 2,2-bipyridyl-N,N-dioxide
tris 3-methylpentane-2,4-dionato Eu0.01, Gd0.99 phenanthroline
tris 3-methylpentane-2,4-dionato Eu0.01, Gd0.99 bathocuproine
tris 3-methylpentane-2,4-dionato Eu0.01, Gd0.99 bathophenanthroline
tris 3-ethylpentane-2,4-dionato Eu0.01, Gd0.99 dimethylaminopyridine
tris 3-ethylpentane-2,4-dionato Eu0.01, Gd0.99 4-picoline-N-oxide
tris 3-ethylpentane-2,4-dionato Eu0.01, Gd0.99 4-phenylpyridine
tris 3-ethylpentane-2,4-dionato Eu0.01, Gd0.99 4-cyanopyridine
tris 3-ethylpentane-2,4-dionato Eu0.01, Gd0.99 4-phenylpyridine-N-oxide
tris 3-ethylpentane-2,4-dionato Eu0.01, Gd0.99 1-methylimidazole
tris 3-ethylpentane-2,4-dionato Eu0.01, Gd0.99 triphenylphosphine oxide
tris 3-ethylpentane-2,4-dionato Eu0.01, Gd0.99 2,2-bipyridyl
tris 3-ethylpentane-2,4-dionato Eu0.01, Gd0.99 2,2-bipyridyl-N,N-dioxide
tris 3-ethylpentane-2,4-dionato Eu0.01, Gd0.99 phenanthroline
tris 3-ethylpentane-2,4-dionato Eu0.01, Gd0.99 bathocuproine
tris 3-ethylpentane-2,4-dionato Eu0.01, Gd0.99 bathophenanthroline
tris pivaloyltrifluoroacetonato Eu0.01, Gd0.99 dimethylaminopyridine
tris pivaloyltrifluoroacetonato Eu0.01, Gd0.99 4-picoline-N-oxide
tris pivaloyltrifluoroacetonato Eu0.01, Gd0.99 4-phenylpyridine
tris pivaloyltrifluoroacetonato Eu0.01, Gd0.99 4-cyanopyridine
tris pivaloyltrifluoroacetonato Eu0.01, Gd0.99 4-phenylpyridine-N-oxide tris pivaloyltrifluoroacetonato Eu0.01, Gd0.99 1-methylimidazole
tris pivaloyltrifluoroacetonato Eu0.01, Gd0.99 triphenylphosphine oxide
tris pivaloyltrifluoroacetonato Eu0.01, Gd0.99 2,2-bipyridyl
tris pivaloyltrifluoroacetonato Eu0.01, Gd0.99 2,2-bipyridyl-N,N-dioxide
tris pivaloyltrifluoroacetonato Eu0.01, Gd0.99 phenanthroline
tris pivaloyltrifluoroacetonato Eu0.01, Gd0.99 bathocuproine
tris pivaloyltrifluoroacetonato Eu0.01, Gd0.99 bathophenanthroline
tris trifluoroacetylacetonato Eu0.01, Gd0.99 dimethylaminopyridine
tris trifluoroacetylacetonato Eu0.01, Gd0.99 4-picoline-N-oxide
tris trifluoroacetylacetonato Eu0.01, Gd0.99 4-phenylpyridine
tris trifluoroacetylacetonato Eu0.01, Gd0.99 4-cyanopyridine
tris trifluoroacetylacetonato Eu0.01, Gd0.99 4-phenylpyridine-N-oxide
tris trifluoroacetylacetonato Eu0.01, Gd0.99 1-methylimidazole
tris trifluoroacetylacetonato Eu0.01, Gd0.99 triphenylphosphine oxide
tris trifluoroacetylacetonato Eu0.01, Gd0.99 2,2-bipyridyl
tris trifluoroacetylacetonato Eu0.01, Gd0.99 2,2-bipyridyl-N,N-dioxide
tris trifluoroacetylacetonato Eu0.01, Gd0.99 phenanthroline
tris trifluoroacetylacetonato Eu0.01, Gd0.99 bathocuproine
tris trifluoroacetylacetonato Eu0.01, Gd0.99 bathophenanthroline
tris hexafluoroacetylacetonato Eu0.01, Gd0.99 dimethylaminopyridine
tris hexafluoroacetylacetonato Eu0.01, Gd0.99 4-picoline-N-oxide
tris hexafluoroacetylacetonato Eu0.01, Gd0.99 4-phenylpyridine
tris hexafluoroacetylacetonato Eu0.01, Gd0.99 4-cyanopyridine
tris hexafluoroacetylacetonato Eu0.01, Gd0.99 4-phenylpyridine-N-oxide
tris hexafluoroacetylacetonato Eu0.01, Gd0.99 1-methylimidazole
tris hexafluoroacetylacetonato Eu0.01, Gd0.99 triphenylphosphine oxide
tris hexafluoroacetylacetonato Eu0.01, Gd0.99 2,2-bipyridyl
tris hexafluoroacetylacetonato Eu0.01, Gd0.99 2,2-bipyridyl-N,N-dioxide
tris hexafluoroacetylacetonato Eu0.01, Gd0.99 phenanthroline
tris hexafluoroacetylacetonato Eu0.01, Gd0.99 bathocuproine
tris hexafluoroacetylacetonato Eu0.01, Gd0.99 bathophenanthroline
tris 6,6,7,7,8,8,8-heptafluoro-2,2-dimethyloctanedionato Eu0.01, Gd0.99 dimethylaminopyridine
tris 6,6,7,7,8,8,8-heptafluoro-2,2-dimethyloctanedionato Eu0.01, Gd0.99 4-picoline-N-oxide
tris 6,6,7,7,8,8,8-heptafluoro-2,2-dimethyloctanedionato Eu0.01, Gd0.99 4-phenylpyridine
tris 6,6,7,7,8,8,8-heptafluoro-2,2-dimethyloctanedionato Eu0.01, Gd0.99 4-cyanopyridine
tris 6,6,7,7,8,8,8-heptafluoro-2,2-dimethyloctanedionato Eu0.01, Gd0.99 4-phenylpyridine-N-oxide
tris 6,6,7,7,8,8,8-heptafluoro-2,2-dimethyloctanedionato Eu0.01, Gd0.99 1-methylimidazole
tris 6,6,7,7,8,8,8-heptafluoro-2,2-dimethyloctanedionato Eu0.01, Gd0.99 triphenylphosphine oxide
tris 6,6,7,7,8,8,8-heptafluoro-2,2-dimethyloctanedionato Eu0.01, Gd0.99 2,2-bipyridyl
tris 6,6,7,7,8,8,8-heptafluoro-2,2-dimethyloctanedionato Eu0.01, Gd0.99 2,2-bipyridyl-N,N-dioxide
tris 6,6,7,7,8,8,8-heptafluoro-2,2-dimethyloctanedionato Eu0.01, Gd0.99 phenanthroline
tris 6,6,7,7,8,8,8-heptafluoro-2,2-dimethyloctanedionato Eu0.01, Gd0.99 bathocuproine
tris 6,6,7,7,8,8,8-heptafluoro-2,2-dimethyloctanedionato Eu0.01, Gd0.99 bathophenanthroline
tris 1-phenyl-1,3-butanedionato Eu0.01, Gd0.99 dimethylaminopyridine
tris 1-phenyl-1,3-butanedionato Eu0.01, Gd0.99 4-picoline-N-oxide
tris 1-phenyl-1,3-butanedionato Eu0.01, Gd0.99 4-phenylpyridine
tris 1-phenyl-1,3-butanedionato Eu0.01, Gd0.99 4-cyanopyridine
tris 1-phenyl-1,3-butanedionato Eu0.01, Gd0.99 4-phenylpyridine-N-oxide
tris 1-phenyl-1,3-butanedionato Eu0.01, Gd0.99 1-methylimidazole
tris 1-phenyl-1,3-butanedionato Eu0.01, Gd0.99 triphenylphosphine oxide
tris 1-phenyl-1,3-butanedionato Eu0.01, Gd0.99 2,2-bipyridyl
tris 1-phenyl-1,3-butanedionato Eu0.01, Gd0.99 2,2-bipyridyl-N,N-dioxide
tris 1-phenyl-1,3-butanedionato Eu0.01, Gd0.99 phenanthroline
tris 1-phenyl-1,3-butanedionato Eu0.01, Gd0.99 bathocuproine
tris 1-phenyl-1,3-butanedionato Eu0.01, Gd0.99 bathophenanthroline
tris acetylacetonato Eu0.5, Gd0.5 dimethylaminopyridine
tris acetylacetonato Eu0.5, Gd0.5 4-picoline-N-oxide
tris acetylacetonato Eu0.5, Gd0.5 4-phenylpyridine
tris acetylacetonato Eu0.5, Gd0.5 4-cyanopyridine
tris acetylacetonato Eu0.5, Gd0.5 4-phenylpyridine-N-oxide
tris acetylacetonato Eu0.5, Gd0.5 1-methylimidazole
tris acetylacetonato Eu0.5, Gd0.5 triphenylphosphine oxide
tris acetylacetonato Eu0.5, Gd0.5 2,2-bipyridyl
tris acetylacetonato Eu0.5, Gd0.5 2,2-bipyridyl-N,N-dioxide
tris acetylacetonato Eu0.5, Gd0.5 phenanthroline
tris acetylacetonato Eu0.5, Gd0.5 bathocuproine
tris acetylacetonato Eu0.5, Gd0.5 bathophenanthroline
tris dibenzoylmethanato Eu0.5, Gd0.5 dimethylaminopyridine
tris dibenzoylmethanato Eu0.5, Gd0.5 4-picoline-N-oxide
tris dibenzoylmethanato Eu0.5, Gd0.5 4-phenylpyridine
tris dibenzoylmethanato Eu0.5, Gd0.5 4-cyanopyridine
tris dibenzoylmethanato Eu0.5, Gd0.5 4-phenylpyridine-N-oxide
tris dibenzoylmethanato Eu0.5, Gd0.5 1-methylimidazole
tris dibenzoylmethanato Eu0.5, Gd0.5 triphenylphosphine oxide
tris dibenzoylmethanato Eu0.5, Gd0.5 2,2-bipyridyl
tris dibenzoylmethanato Eu0.5, Gd0.5 2,2-bipyridyl-N,N-dioxide
tris dibenzoylmethanato Eu0.5, Gd0.5 phenanthroline
tris dibenzoylmethanato Eu0.5, Gd0.5 bathocuproine
tris dibenzoylmethanato Eu0.5, Gd0.5 bathophenanthroline tris thenoyltrifluoroacetonato Eu0.5, Gd0.5 dimethylaminopyridine
tris thenoyltrifluoroacetonato Eu0.5, Gd0.5 4-picoline-N-oxide
tris thenoyltrifluoroacetonato Eu0.5, Gd0.5 4-phenylpyridine
tris thenoyltrifluoroacetonato Eu0.5, Gd0.5 4-cyanopyridine
tris thenoyltrifluoroacetonato Eu0.5, Gd0.5 4-phenylpyridine-N-oxide
tris thenoyltrifluoroacetonato Eu0.5, Gd0.5 1-methylimidazole
tris thenoyltrifluoroacetonato Eu0.5, Gd0.5 triphenylphosphine oxide
tris thenoyltrifluoroacetonato Eu0.5, Gd0.5 2,2-bipyridyl
tris thenoyltrifluoroacetonato Eu0.5, Gd0.5 2,2-bipyridyl-N,N-dioxide
tris thenoyltrifluoroacetonato Eu0.5, Gd0.5 phenanthroline
tris thenoyltrifluoroacetonato Eu0.5, Gd0.5 bathocuproine
tris thenoyltrifluoroacetonato Eu0.5, Gd0.5 bathophenanthroline
tris 2,2,6,6-tetramethylheptanedionato Eu0.5, Gd0.5 dimethylaminopyridine
tris 2,2,6,6-tetramethylheptanedionato Eu0.5, Gd0.5 4-picoline-N-oxide
tris 2,2,6,6-tetramethylheptanedionato Eu0.5, Gd0.5 4-phenylpyridine
tris 2,2,6,6-tetramethylheptanedionato Eu0.5, Gd0.5 4-cyanopyridine
tris 2,2,6,6-tetramethylheptanedionato Eu0.5, Gd0.5 4-phenylpyridine-N-oxide
tris 2,2,6,6-tetramethylheptanedionato Eu0.5, Gd0.5 1-methylimidazole
tris 2,2,6,6-tetramethylheptanedionato Eu0.5, Gd0.5 triphenylphosphine oxide
tris 2,2,6,6-tetramethylheptanedionato Eu0.5, Gd0.5 2,2-bipyridyl
tris 2,2,6,6-tetramethylheptanedionato Eu0.5, Gd0.5 2,2-bipyridyl-N,N-dioxide
tris 2,2,6,6-tetramethylheptanedionato Eu0.5, Gd0.5 phenanthroline
tris 2,2,6,6-tetramethylheptanedionato Eu0.5, Gd0.5 bathocuproine
tris 2,2,6,6-tetramethylheptanedionato Eu0.5, Gd0.5 bathophenanthroline
tris 3-methylpentane-2,4-dionato Eu0.5, Gd0.5 dimethylaminopyridine
tris 3-methylpentane-2,4-dionato Eu0.5, Gd0.5 4-picoline-N-oxide
tris 3-methylpentane-2,4-dionato Eu0.5, Gd0.5 4-phenylpyridine
tris 3-methylpentane-2,4-dionato Eu0.5, Gd0.5 4-cyanopyridine
tris 3-methylpentane-2,4-dionato Eu0.5, Gd0.5 4-phenylpyridine-N-oxide
tris 3-methylpentane-2,4-dionato Eu0.5, Gd0.5 1-methylimidazole
tris 3-methylpentane-2,4-dionato Eu0.5, Gd0.5 triphenylphosphine oxide
tris 3-methylpentane-2,4-dionato Eu0.5, Gd0.5 2,2-bipyridyl
tris 3-methylpentane-2,4-dionato Eu0.5, Gd0.5 2,2-bipyridyl-N,N-dioxide
tris 3-methylpentane-2,4-dionato Eu0.5, Gd0.5 phenanthroline
tris 3-methylpentane-2,4-dionato Eu0.5, Gd0.5 bathocuproine
tris 3-methylpentane-2,4-dionato Eu0.5, Gd0.5 bathophenanthroline
tris 3-ethylpentane-2,4-dionato Eu0.5, Gd0.5 dimethylaminopyridine
tris 3-ethylpentane-2,4-dionato Eu0.5, Gd0.5 4-picoline-N-oxide
tris 3-ethylpentane-2,4-dionato Eu0.5, Gd0.5 4-phenylpyridine
tris 3-ethylpentane-2,4-dionato Eu0.5, Gd0.5 4-cyanopyridine
tris 3-ethylpentane-2,4-dionato Eu0.5, Gd0.5 4-phenylpyridine-N-oxide
tris 3-ethylpentane-2,4-dionato Eu0.5, Gd0.5 1-methylimidazole
tris 3-ethylpentane-2,4-dionato Eu0.5, Gd0.5 triphenylphosphine oxide
tris 3-ethylpentane-2,4-dionato Eu0.5, Gd0.5 2,2-bipyridyl
tris 3-ethylpentane-2,4-dionato Eu0.5, Gd0.5 2,2-bipyridyl-N,N-dioxide
tris 3-ethylpentane-2,4-dionato Eu0.5, Gd0.5 phenanthroline
tris 3-ethylpentane-2,4-dionato Eu0.5, Gd0.5 bathocuproine
tris 3-ethylpentane-2,4-dionato Eu0.5, Gd0.5 bathophenanthroline
tris pivaloyltrifluoroacetonato Eu0.5, Gd0.5 dimethylaminopyridine
tris pivaloyltrifluoroacetonato Eu0.5, Gd0.5 4-picoline-N-oxide
tris pivaloyltrifluoroacetonato Eu0.5, Gd0.5 4-phenylpyridine
tris pivaloyltrifluoroacetonato Eu0.5, Gd0.5 4-cyanopyridine
tris pivaloyltrifluoroacetonato Eu0.5, Gd0.5 4-phenylpyridine-N-oxide
tris pivaloyltrifluoroacetonato Eu0.5, Gd0.5 1-methylimidazole
tris pivaloyltrifluoroacetonato Eu0.5, Gd0.5 triphenylphosphine oxide
tris pivaloyltrifluoroacetonato Eu0.5, Gd0.5 2,2-bipyridyl
tris pivaloyltrifluoroacetonato Eu0.5, Gd0.5 2,2-bipyridyl-N,N-dioxide
tris pivaloyltrifluoroacetonato Eu0.5, Gd0.5 phenanthroline
tris pivaloyltrifluoroacetonato Eu0.5, Gd0.5 bathocuproine
tris pivaloyltrifluoroacetonato Eu0.5, Gd0.5 bathophenanthroline
tris trifluoroacetylacetonato Eu0.5, Gd0.5 dimethylaminopyridine
tris trifluoroacetylacetonato Eu0.5, Gd0.5 4-picoline-N-oxide
tris trifluoroacetylacetonato Eu0.5, Gd0.5 4-phenylpyridine
tris trifluoroacetylacetonato Eu0.5, Gd0.5 4-cyanopyridine
tris trifluoroacetylacetonato Eu0.5, Gd0.5 4-phenylpyridine-N-oxide
tris trifluoroacetylacetonato Eu0.5, Gd0.5 1-methylimidazole
tris trifluoroacetylacetonato Eu0.5, Gd0.5 triphenylphosphine oxide
tris trifluoroacetylacetonato Eu0.5, Gd0.5 2,2-bipyridyl
tris trifluoroacetylacetonato Eu0.5, Gd0.5 2,2-bipyridyl-N,N-dioxide
tris trifluoroacetylacetonato Eu0.5, Gd0.5 phenanthroline
tris trifluoroacetylacetonato Eu0.5, Gd0.5 bathocuproine
tris trifluoroacetylacetonato Eu0.5, Gd0.5 bathophenanthroline
tris hexafluoroacetylacetonato Eu0.5, Gd0.5 dimethylaminopyridine tris hexafluoroacetylacetonato Eu0.5, Gd0.5 4-picoline-N-oxide
tris hexafluoroacetylacetonato Eu0.5, Gd0.5 4-phenylpyridine
tris hexafluoroacetylacetonato Eu0.5, Gd0.5 4-cyanopyridine
tris hexafluoroacetylacetonato Eu0.5, Gd0.5 4-phenylpyridine-N-oxide
tris hexafluoroacetylacetonato Eu0.5, Gd0.5 1-methylimidazole
tris hexafluoroacetylacetonato Eu0.5, Gd0.5 triphenylphosphine oxide
tris hexafluoroacetylacetonato Eu0.5, Gd0.5 2,2-bipyridyl
tris hexafluoroacetylacetonato Eu0.5, Gd0.5 2,2-bipyridyl-N,N-dioxide
tris hexafluoroacetylacetonato Eu0.5, Gd0.5 phenanthroline
tris hexafluoroacetylacetonato Eu0.5, Gd0.5 bathocuproine
tris hexafluoroacetylacetonato Eu0.5, Gd0.5 bathophenanthroline
tris 6,6,7,7,8,8,8-heptafluoro-2,2-dimethyloctanedionato Eu0.5, Gd0.5 dimethylaminopyridine
tris 6,6,7,7,8,8,8-heptafluoro-2,2-dimethyloctanedionato Eu0.5, Gd0.5 4-picoline-N-oxide
tris 6,6,7,7,8,8,8-heptafluoro-2,2-dimethyloctanedionato Eu0.5, Gd0.5 4-phenylpyridine
tris 6,6,7,7,8,8,8-heptafluoro-2,2-dimethyloctanedionato Eu0.5, Gd0.5 4-cyanopyridine
tris 6,6,7,7,8,8,8-heptafluoro-2,2-dimethyloctanedionato Eu0.5, Gd0.5 4-phenylpyridine-N-oxide
tris 6,6,7,7,8,8,8-heptafluoro-2,2-dimethyloctanedionato Eu0.5, Gd0.5 1-methylimidazole
tris 6,6,7,7,8,8,8-heptafluoro-2,2-dimethyloctanedionato Eu0.5, Gd0.5 triphenylphosphine oxide
tris 6,6,7,7,8,8,8-heptafluoro-2,2-dimethyloctanedionato Eu0.5, Gd0.5 2,2-bipyridyl
tris 6,6,7,7,8,8,8-heptafluoro-2,2-dimethyloctanedionato Eu0.5, Gd0.5 2,2-bipyridyl-N,N-dioxide
tris 6,6,7,7,8,8,8-heptafluoro-2,2-dimethyloctanedionato Eu0.5, Gd0.5 phenanthroline
tris 6,6,7,7,8,8,8-heptafluoro-2,2-dimethyloctanedionato Eu0.5, Gd0.5 bathocuproine
tris 6,6,7,7,8,8,8-heptafluoro-2,2-dimethyloctanedionato Eu0.5, Gd0.5 bathophenanthroline
tris 1-phenyl-1,3-butanedionato Eu0.5, Gd0.5 dimethylaminopyridine
tris 1-phenyl-1,3-butanedionato Eu0.5, Gd0.5 4-picoline-N-oxide
tris 1-phenyl-1,3-butanedionato Eu0.5, Gd0.5 4-phenylpyridine
tris 1-phenyl-1,3-butanedionato Eu0.5, Gd0.5 4-cyanopyridine
tris 1-phenyl-1,3-butanedionato Eu0.5, Gd0.5 4-phenylpyridine-N-oxide
tris 1-phenyl-1,3-butanedionato Eu0.5, Gd0.5 1-methylimidazole
tris 1-phenyl-1,3-butanedionato Eu0.5, Gd0.5 triphenylphosphine oxide
tris 1-phenyl-1,3-butanedionato Eu0.5, Gd0.5 2,2-bipyridyl
tris 1-phenyl-1,3-butanedionato Eu0.5, Gd0.5 2,2-bipyridyl-N,N-dioxide
tris 1-phenyl-1,3-butanedionato Eu0.5, Gd0.5 phenanthroline
tris 1-phenyl-1,3-butanedionato Eu0.5, Gd0.5 bathocuproine
tris 1-phenyl-1,3-butanedionato Eu0.5, Gd0.5 bathophenanthroline
tris acetylacetonato Eu0.2, Gd0.8 dimethylaminopyridine
tris acetylacetonato Eu0.2, Gd0.8 4-picoline-N-oxide
tris acetylacetonato Eu0.2, Gd0.8 4-phenylpyridine
tris acetylacetonato Eu0.2, Gd0.8 4-cyanopyridine
tris acetylacetonato Eu0.2, Gd0.8 4-phenylpyridine-N-oxide
tris acetylacetonato Eu0.2, Gd0.8 1-methylimidazole
tris acetylacetonato Eu0.2, Gd0.8 triphenylphosphine oxide
tris acetylacetonato Eu0.2, Gd0.8 2,2-bipyridyl
tris acetylacetonato Eu0.2, Gd0.8 2,2-bipyridyl-N,N-dioxide
tris acetylacetonato Eu0.2, Gd0.8 phenanthroline
tris acetylacetonato Eu0.2, Gd0.8 bathocuproine
tris acetylacetonato Eu0.2, Gd0.8 bathophenanthroline
tris dibenzoylmethanato Eu0.2, Gd0.8 dimethylaminopyridine
tris dibenzoylmethanato Eu0.2, Gd0.8 4-picoline-N-oxide
tris dibenzoylmethanato Eu0.2, Gd0.8 4-phenylpyridine
tris dibenzoylmethanato Eu0.2, Gd0.8 4-cyanopyridine
tris dibenzoylmethanato Eu0.2, Gd0.8 4-phenylpyridine-N-oxide
tris dibenzoylmethanato Eu0.2, Gd0.8 1-methylimidazole
tris dibenzoylmethanato Eu0.2, Gd0.8 triphenylphosphine oxide
tris dibenzoylmethanato Eu0.2, Gd0.8 2,2-bipyridyl
tris dibenzoylmethanato Eu0.2, Gd0.8 2,2-bipyridyl-N,N-dioxide
tris dibenzoylmethanato Eu0.2, Gd0.8 phenanthroline
tris dibenzoylmethanato Eu0.2, Gd0.8 bathocuproine
tris dibenzoylmethanato Eu0.2, Gd0.8 bathophenanthroline
tris thenoyltrifluoroacetonato Eu0.2, Gd0.8 dimethylaminopyridine
tris thenoyltrifluoroacetonato Eu0.2, Gd0.8 4-picoline-N-oxide
tris thenoyltrifluoroacetonato Eu0.2, Gd0.8 4-phenylpyridine
tris thenoyltrifluoroacetonato Eu0.2, Gd0.8 4-cyanopyridine
tris thenoyltrifluoroacetonato Eu0.2, Gd0.8 4-phenylpyridine-N-oxide
tris thenoyltrifluoroacetonato Eu0.2, Gd0.8 1-methylimidazole
tris thenoyltrifluoroacetonato Eu0.2, Gd0.8 triphenylphosphine oxide
tris thenoyltrifluoroacetonato Eu0.2, Gd0.8 2,2-bipyridyl
tris thenoyltrifluoroacetonato Eu0.2, Gd0.8 2,2-bipyridyl-N,N-dioxide
tris thenoyltrifluoroacetonato Eu0.2, Gd0.8 phenanthroline
tris thenoyltrifluoroacetonato Eu0.2, Gd0.8 bathocuproine
tris thenoyltrifluoroacetonato Eu0.2, Gd0.8 bathophenanthroline
tris 2,2,6,6-tetramethylheptanedionato Eu0.2, Gd0.8 dimethylaminopyridine
tris 2,2,6,6-tetramethylheptanedionato Eu0.2, Gd0.8 4-picoline-N-oxide
tris 2,2,6,6-tetramethylheptanedionato Eu0.2, Gd0.8 4-phenylpyridine
tris 2,2,6,6-tetramethylheptanedionato Eu0.2, Gd0.8 4-cyanopyridine
tris 2,2,6,6-tetramethylheptanedionato Eu0.2, Gd0.8 4-phenylpyridine-N-oxide
tris 2,2,6,6-tetramethylheptanedionato Eu0.2, Gd0.8 1-methylimidazole
tris 2,2,6,6-tetramethylheptanedionato Eu0.2, Gd0.8 triphenylphosphine oxide
tris 2,2,6,6-tetramethylheptanedionato Eu0.2, Gd0.8 2,2-bipyridyl
tris 2,2,6,6-tetramethylheptanedionato Eu0.2, Gd0.8 2,2-bipyridyl-N,N-dioxide
tris 2,2,6,6-tetramethylheptanedionato Eu0.2, Gd0.8 phenanthroline tris 2,2,6,6-tetramethylheptanedionato Eu0.2, Gd0.8 bathocuproine
tris 2,2,6,6-tetramethylheptanedionato Eu0.2, Gd0.8 bathophenanthroline
tris 3-methylpentane-2,4-dionato Eu0.2, Gd0.8 dimethylaminopyridine
tris 3-methylpentane-2,4-dionato Eu0.2, Gd0.8 4-picoline-N-oxide
tris 3-methylpentane-2,4-dionato Eu0.2, Gd0.8 4-phenylpyridine
tris 3-methylpentane-2,4-dionato Eu0.2, Gd0.8 4-cyanopyridine
tris 3-methylpentane-2,4-dionato Eu0.2, Gd0.8 4-phenylpyridine-N-oxide
tris 3-methylpentane-2,4-dionato Eu0.2, Gd0.8 1-methylimidazole
tris 3-methylpentane-2,4-dionato Eu0.2, Gd0.8 triphenylphosphine oxide
tris 3-methylpentane-2,4-dionato Eu0.2, Gd0.8 2,2-bipyridyl
tris 3-methylpentane-2,4-dionato Eu0.2, Gd0.8 2,2-bipyridyl-N,N-dioxide
tris 3-methylpentane-2,4-dionato Eu0.2, Gd0.8 phenanthroline
tris 3-methylpentane-2,4-dionato Eu0.2, Gd0.8 bathocuproine
tris 3-methylpentane-2,4-dionato Eu0.2, Gd0.8 bathophenanthroline
tris 3-ethylpentane-2,4-dionato Eu0.2, Gd0.8 dimethylaminopyridine
tris 3-ethylpentane-2,4-dionato Eu0.2, Gd0.8 4-picoline-N-oxide
tris 3-ethylpentane-2,4-dionato Eu0.2, Gd0.8 4-phenylpyridine
tris 3-ethylpentane-2,4-dionato Eu0.2, Gd0.8 4-cyanopyridine
tris 3-ethylpentane-2,4-dionato Eu0.2, Gd0.8 4-phenylpyridine-N-oxide
tris 3-ethylpentane-2,4-dionato Eu0.2, Gd0.8 1-methylimidazole
tris 3-ethylpentane-2,4-dionato Eu0.2, Gd0.8 triphenylphosphine oxide
tris 3-ethylpentane-2,4-dionato Eu0.2, Gd0.8 2,2-bipyridyl
tris 3-ethylpentane-2,4-dionato Eu0.2, Gd0.8 2,2-bipyridyl-N,N-dioxide
tris 3-ethylpentane-2,4-dionato Eu0.2, Gd0.8 phenanthroline
tris 3-ethylpentane-2,4-dionato Eu0.2, Gd0.8 bathocuproine
tris 3-ethylpentane-2,4-dionato Eu0.2, Gd0.8 bathophenanthroline
tris pivaloyltrifluoroacetonato Eu0.2, Gd0.8 dimethylaminopyridine
tris pivaloyltrifluoroacetonato Eu0.2, Gd0.8 4-picoline-N-oxide
tris pivaloyltrifluoroacetonato Eu0.2, Gd0.8 4-phenylpyridine
tris pivaloyltrifluoroacetonato Eu0.2, Gd0.8 4-cyanopyridine
tris pivaloyltrifluoroacetonato Eu0.2, Gd0.8 4-phenylpyridine-N-oxide
tris pivaloyltrifluoroacetonato Eu0.2, Gd0.8 1-methylimidazole
tris pivaloyltrifluoroacetonato Eu0.2, Gd0.8 triphenylphosphine oxide
tris pivaloyltrifluoroacetonato Eu0.2, Gd0.8 2,2-bipyridyl
tris pivaloyltrifluoroacetonato Eu0.2, Gd0.8 2,2-bipyridyl-N,N-dioxide
tris pivaloyltrifluoroacetonato Eu0.2, Gd0.8 phenanthroline
tris pivaloyltrifluoroacetonato Eu0.2, Gd0.8 bathocuproine
tris pivaloyltrifluoroacetonato Eu0.2, Gd0.8 bathophenanthroline
tris trifluoroacetylacetonato Eu0.2, Gd0.8 dimethylaminopyridine
tris trifluoroacetylacetonato Eu0.2, Gd0.8 4-picoline-N-oxide
tris trifluoroacetylacetonato Eu0.2, Gd0.8 4-phenylpyridine
tris trifluoroacetylacetonato Eu0.2, Gd0.8 4-cyanopyridine
tris trifluoroacetylacetonato Eu0.2, Gd0.8 4-phenylpyridine-N-oxide
tris trifluoroacetylacetonato Eu0.2, Gd0.8 1-methylimidazole
tris trifluoroacetylacetonato Eu0.2, Gd0.8 triphenylphosphine oxide
tris trifluoroacetylacetonato Eu0.2, Gd0.8 2,2-bipyridyl
tris trifluoroacetylacetonato Eu0.2, Gd0.8 2,2-bipyridyl-N,N-dioxide
tris trifluoroacetylacetonato Eu0.2, Gd0.8 phenanthroline
tris trifluoroacetylacetonato Eu0.2, Gd0.8 bathocuproine
tris trifluoroacetylacetonato Eu0.2, Gd0.8 bathophenanthroline
tris hexafluoroacetylacetonato Eu0.2, Gd0.8 dimethylaminopyridine
tris hexafluoroacetylacetonato Eu0.2, Gd0.8 4-picoline-N-oxide
tris hexafluoroacetylacetonato Eu0.2, Gd0.8 4-phenylpyridine
tris hexafluoroacetylacetonato Eu0.2, Gd0.8 4-cyanopyridine
tris hexafluoroacetylacetonato Eu0.2, Gd0.8 4-phenylpyridine-N-oxide
tris hexafluoroacetylacetonato Eu0.2, Gd0.8 1-methylimidazole
tris hexafluoroacetylacetonato Eu0.2, Gd0.8 triphenylphosphine oxide
tris hexafluoroacetylacetonato Eu0.2, Gd0.8 2,2-bipyridyl
tris hexafluoroacetylacetonato Eu0.2, Gd0.8 2,2-bipyridyl-N,N-dioxide
tris hexafluoroacetylacetonato Eu0.2, Gd0.8 phenanthroline
tris hexafluoroacetylacetonato Eu0.2, Gd0.8 bathocuproine
tris hexafluoroacetylacetonato Eu0.2, Gd0.8 bathophenanthroline
tris 6,6,7,7,8,8,8-heptafluoro-2,2-dimethyloctanedionato Eu0.2, Gd0.8 dimethylaminopyridine
tris 6,6,7,7,8,8,8-heptafluoro-2,2-dimethyloctanedionato Eu0.2, Gd0.8 4-picoline-N-oxide
tris 6,6,7,7,8,8,8-heptafluoro-2,2-dimethyloctanedionato Eu0.2, Gd0.8 4-phenylpyridine
tris 6,6,7,7,8,8,8-heptafluoro-2,2-dimethyloctanedionato Eu0.2, Gd0.8 4-cyanopyridine
tris 6,6,7,7,8,8,8-heptafluoro-2,2-dimethyloctanedionato Eu0.2, Gd0.8 4-phenylpyridine-N-oxide
tris 6,6,7,7,8,8,8-heptafluoro-2,2-dimethyloctanedionato Eu0.2, Gd0.8 1-methylimidazole
tris 6,6,7,7,8,8,8-heptafluoro-2,2-dimethyloctanedionato Eu0.2, Gd0.8 triphenylphosphine oxide
tris 6,6,7,7,8,8,8-heptafluoro-2,2-dimethyloctanedionato Eu0.2, Gd0.8 2,2-bipyridyl
tris 6,6,7,7,8,8,8-heptafluoro-2,2-dimethyloctanedionato Eu0.2, Gd0.8 2,2-bipyridyl-N,N-dioxide
tris 6,6,7,7,8,8,8-heptafluoro-2,2-dimethyloctanedionato Eu0.2, Gd0.8 phenanthroline
tris 6,6,7,7,8,8,8-heptafluoro-2,2-dimethyloctanedionato Eu0.2, Gd0.8 bathocuproine tris 6,6,7,7,8,8,8-heptafluoro-2,2-dimethyloctanedionato Eu0.2, Gd0.8 bathophenanthroline
tris 1-phenyl-1,3-butanedionato Eu0.2, Gd0.8 dimethylaminopyridine
tris 1-phenyl-1,3-butanedionato Eu0.2, Gd0.8 4-picoline-N-oxide
tris 1-phenyl-1,3-butanedionato Eu0.2, Gd0.8 4-phenylpyridine
tris 1-phenyl-1,3-butanedionato Eu0.2, Gd0.8 4-cyanopyridine
tris 1-phenyl-1,3-butanedionato Eu0.2, Gd0.8 4-phenylpyridine-N-oxide
tris 1-phenyl-1,3-butanedionato Eu0.2, Gd0.8 1-methylimidazole
tris 1-phenyl-1,3-butanedionato Eu0.2, Gd0.8 triphenylphosphine oxide
tris 1-phenyl-1,3-butanedionato Eu0.2, Gd0.8 2,2-bipyridyl
tris 1-phenyl-1,3-butanedionato Eu0.2, Gd0.8 2,2-bipyridyl-N,N-dioxide
tris 1-phenyl-1,3-butanedionato Eu0.2, Gd0.8 phenanthroline
tris 1-phenyl-1,3-butanedionato Eu0.2, Gd0.8 bathocuproine
tris 1-phenyl-1,3-butanedionato Eu0.2, Gd0.8 bathophenanthroline
tris acetylacetonato Eu0.1, Gd0.9 dimethylaminopyridine
tris acetylacetonato Eu0.1, Gd0.9 4-picoline-N-oxide
tris acetylacetonato Eu0.1, Gd0.9 4-phenylpyridine
tris acetylacetonato Eu0.1, Gd0.9 4-cyanopyridine
tris acetylacetonato Eu0.1, Gd0.9 4-phenylpyridine-N-oxide
tris acetylacetonato Eu0.1, Gd0.9 1-methylimidazole
tris acetylacetonato Eu0.1, Gd0.9 triphenylphosphine oxide
tris acetylacetonato Eu0.1, Gd0.9 2,2-bipyridyl
tris acetylacetonato Eu0.1, Gd0.9 2,2-bipyridyl-N,N-dioxide
tris acetylacetonato Eu0.1, Gd0.9 phenanthroline
tris acetylacetonato Eu0.1, Gd0.9 bathocuproine
tris acetylacetonato Eu0.1, Gd0.9 bathophenanthroline
tris dibenzoylmethanato Eu0.1, Gd0.9 dimethylaminopyridine
tris dibenzoylmethanato Eu0.1, Gd0.9 4-picoline-N-oxide
tris dibenzoylmethanato Eu0.1, Gd0.9 4-phenylpyridine
tris dibenzoylmethanato Eu0.1, Gd0.9 4-cyanopyridine
tris dibenzoylmethanato Eu0.1, Gd0.9 4-phenylpyridine-N-oxide
tris dibenzoylmethanato Eu0.1, Gd0.9 1-methylimidazole
tris dibenzoylmethanato Eu0.1, Gd0.9 triphenylphosphine oxide
tris dibenzoylmethanato Eu0.1, Gd0.9 2,2-bipyridyl
tris dibenzoylmethanato Eu0.1, Gd0.9 2,2-bipyridyl-N,N-dioxide
tris dibenzoylmethanato Eu0.1, Gd0.9 phenanthroline
tris dibenzoylmethanato Eu0.1, Gd0.9 bathocuproine
tris dibenzoylmethanato Eu0.1, Gd0.9 bathophenanthroline
tris thenoyltrifluoroacetonato Eu0.1, Gd0.9 dimethylaminopyridine
tris thenoyltrifluoroacetonato Eu0.1, Gd0.9 4-picoline-N-oxide
tris thenoyltrifluoroacetonato Eu0.1, Gd0.9 4-phenylpyridine
tris thenoyltrifluoroacetonato Eu0.1, Gd0.9 4-cyanopyridine
tris thenoyltrifluoroacetonato Eu0.1, Gd0.9 4-phenylpyridine-N-oxide
tris thenoyltrifluoroacetonato Eu0.1, Gd0.9 1-methylimidazole
tris thenoyltrifluoroacetonato Eu0.1, Gd0.9 triphenylphosphine oxide
tris thenoyltrifluoroacetonato Eu0.1, Gd0.9 2,2-bipyridyl
tris thenoyltrifluoroacetonato Eu0.1, Gd0.9 2,2-bipyridyl-N,N-dioxide
tris thenoyltrifluoroacetonato Eu0.1, Gd0.9 phenanthroline
tris thenoyltrifluoroacetonato Eu0.1, Gd0.9 bathocuproine
tris thenoyltrifluoroacetonato Eu0.1, Gd0.9 bathophenanthroline
tris 2,2,6,6-tetramethylheptanedionato Eu0.1, Gd0.9 dimethylaminopyridine
tris 2,2,6,6-tetramethylheptanedionato Eu0.1, Gd0.9 4-picoline-N-oxide
tris 2,2,6,6-tetramethylheptanedionato Eu0.1, Gd0.9 4-phenylpyridine
tris 2,2,6,6-tetramethylheptanedionato Eu0.1, Gd0.9 4-cyanopyridine
tris 2,2,6,6-tetramethylheptanedionato Eu0.1, Gd0.9 4-phenylpyridine-N-oxide
tris 2,2,6,6-tetramethylheptanedionato Eu0.1, Gd0.9 1-methylimidazole
tris 2,2,6,6-tetramethylheptanedionato Eu0.1, Gd0.9 triphenylphosphine oxide
tris 2,2,6,6-tetramethylheptanedionato Eu0.1, Gd0.9 2,2-bipyridyl
tris 2,2,6,6-tetramethylheptanedionato Eu0.1, Gd0.9 2,2-bipyridyl-N,N-dioxide
tris 2,2,6,6-tetramethylheptanedionato Eu0.1, Gd0.9 phenanthroline
tris 2,2,6,6-tetramethylheptanedionato Eu0.1, Gd0.9 bathocuproine
tris 2,2,6,6-tetramethylheptanedionato Eu0.1, Gd0.9 bathophenanthroline
tris 3-methylpentane-2,4-dionato Eu0.1, Gd0.9 dimethylaminopyridine
tris 3-methylpentane-2,4-dionato Eu0.1, Gd0.9 4-picoline-N-oxide
tris 3-methylpentane-2,4-dionato Eu0.1, Gd0.9 4-phenylpyridine
tris 3-methylpentane-2,4-dionato Eu0.1, Gd0.9 4-cyanopyridine
tris 3-methylpentane-2,4-dionato Eu0.1, Gd0.9 4-phenylpyridine-N-oxide
tris 3-methylpentane-2,4-dionato Eu0.1, Gd0.9 1-methylimidazole
tris 3-methylpentane-2,4-dionato Eu0.1, Gd0.9 triphenylphosphine oxide
tris 3-methylpentane-2,4-dionato Eu0.1, Gd0.9 2,2-bipyridyl
tris 3-methylpentane-2,4-dionato Eu0.1, Gd0.9 2,2-bipyridyl-N,N-dioxide
tris 3-methylpentane-2,4-dionato Eu0.1, Gd0.9 phenanthroline
tris 3-methylpentane-2,4-dionato Eu0.1, Gd0.9 bathocuproine
tris 3-methylpentane-2,4-dionato Eu0.1, Gd0.9 bathophenanthroline
tris 3-ethylpentane-2,4-dionato Eu0.1, Gd0.9 dimethylaminopyridine
tris 3-ethylpentane-2,4-dionato Eu0.1, Gd0.9 4-picoline-N-oxide
tris 3-ethylpentane-2,4-dionato Eu0.1, Gd0.9 4-phenylpyridine
tris 3-ethylpentane-2,4-dionato Eu0.1, Gd0.9 4-cyanopyridine
tris 3-ethylpentane-2,4-dionato Eu0.1, Gd0.9 4-phenylpyridine-N-oxide
tris 3-ethylpentane-2,4-dionato Eu0.1, Gd0.9 1-methylimidazole tris 3-ethylpentane-2,4-dionato Eu0.1, Gd0.9 triphenylphosphine oxide
tris 3-ethylpentane-2,4-dionato Eu0.1, Gd0.9 2,2-bipyridyl
tris 3-ethylpentane-2,4-dionato Eu0.1, Gd0.9 2,2-bipyridyl-N,N-dioxide
tris 3-ethylpentane-2,4-dionato Eu0.1, Gd0.9 phenanthroline
tris 3-ethylpentane-2,4-dionato Eu0.1, Gd0.9 bathocuproine
tris 3-ethylpentane-2,4-dionato Eu0.1i Gd0.9 bathophenanthroline
tris pivaloyltrifluoroacetonato Eu0.1, Gd0.9 dimethylaminopyridine
tris pivaloyltrifluoroacetonato Eu0.1, Gd0.9 4-picoline-N-oxide
tris pivaloyltrifluoroacetonato Eu0.1, Gd0.9 4-phenylpyridine
tris pivaloyltrifluoroacetonato Eu0.1, Gd0.9 4-cyanopyridine
tris pivaloyltrifluoroacetonato Eu0.1, Gd0.9 4-phenylpyridine-N-oxide
tris pivaloyltrifluoroacetonato Eu0.1, Gd0.9 1-methylimidazole
tris pivaloyltrifluoroacetonato Eu0.1, Gd0.9 triphenylphosphine oxide
tris pivaloyltrifluoroacetonato Eu0.1, Gd0.9 2,2-bipyridyl
tris pivaloyltrifluoroacetonato Eu0.1, Gd0.9 2,2-bipyridyl-N,N-dioxide
tris pivaloyltrifluoroacetonato Eu0.1, Gd0.9 phenanthroline
tris pivaloyltrifluoroacetonato Eu0.1, Gd0.9 bathocuproine
tris pivaloyltrifluoroacetonato Eu0.1, Gd0.9 bathophenanthroline
tris trifluoroacetylacetonato Eu0.1, Gd0.9 dimethylaminopyridine
tris trifluoroacetylacetonato Eu0.1, Gd0.9 4-picoline-N-oxide
tris trifluoroacetylacetonato Eu0.1, Gd0.9 4-phenylpyridine
tris trifluoroacetylacetonato Eu0.1, Gd0.9 4-cyanopyridine
tris trifluoroacetylacetonato Eu0.1, Gd0.9 4-phenylpyridine-N-oxide
tris trifluoroacetylacetonato Eu0.1, Gd0.9 1-methylimidazole
tris trifluoroacetylacetonato Eu0.1, Gd0.9 triphenylphosphine oxide
tris trifluoroacetylacetonato Eu0.1, Gd0.9 2,2-bipyridyl
tris trifluoroacetylacetonato Eu0.1, Gd0.9 2,2-bipyridyl-N,N-dioxide
tris trifluoroacetylacetonato Eu0.1, Gd0.9 phenanthroline
tris trifluoroacetylacetonato Eu0.1, Gd0.9 bathocuproine
tris trifluoroacetylacetonato Eu0.1, Gd0.9 bathophenanthroline
tris hexafluoroacetylacetonato Eu0.1, Gd0.9 dimethylaminopyridine
tris hexafluoroacetylacetonato Eu0.1, Gd0.9 4-picoline-N-oxide
tris hexafluoroacetylacetonato Eu0.1, Gd0.9 4-phenylpyridine
tris hexafluoroacetylacetonato Eu0.1, Gd0.9 4-cyanopyridine
tris hexafluoroacetylacetonato Eu0.1, Gd0.9 4-phenylpyridine-N-oxide
tris hexafluoroacetylacetonato Eu0.1, Gd0.9 1-methylimidazole
tris hexafluoroacetylacetonato Eu0.1, Gd0.9 triphenylphosphine oxide
tris hexafluoroacetylacetonato Eu0.1, Gd0.9 2,2-bipyridyl
tris hexafluoroacetylacetonato Eu0.1, Gd0.9 2,2-bipyridyl-N,N-dioxide
tris hexafluoroacetylacetonato Eu0.1, Gd0.9 phenanthroline
tris hexafluoroacetylacetonato Eu0.1, Gd0.9 bathocuproine
tris hexafluoroacetylacetonato Eu0.1, Gd0.9 bathophenanthroline
tris 6,6,7,7,8,8,8-heptafluoro-2,2-dimethyloctanedionato Eu0.1, Gd0.9 dimethylaminopyridine
tris 6,6,7,7,8,8,8-heptafluoro-2,2-dimethyloctanedionato Eu0.1, Gd0.9 4-picoline-N-oxide
tris 6,6,7,7,8,8,8-heptafluoro-2,2-dimethyloctanedionato Eu0.1, Gd0.9 4-phenylpyridine
tris 6,6,7,7,8,8,8-heptafluoro-2,2-dimethyloctanedionato Eu0.1, Gd0.9 4-cyanopyridine
tris 6,6,7,7,8,8,8-heptafluoro-2,2-dimethyloctanedionato Eu0.1, Gd0.9 4-phenylpyridine-N-oxide
tris 6,6,7,7,8,8,8-heptafluoro-2,2-dimethyloctanedionato Eu0.1, Gd0.9 1-methylimidazole
tris 6,6,7,7,8,8,8-heptafluoro-2,2-dimethyloctanedionato Eu0.1, Gd0.9 triphenylphosphine oxide
tris 6,6,7,7,8,8,8-heptafluoro-2,2-dimethyloctanedionato Eu0.1, Gd0.9 2,2-bipyridyl
tris 6,6,7,7,8,8,8-heptafluoro-2,2-dimethyloctanedionato Eu0.1, Gd0.9 2,2-bipyridyl-N,N-dioxide
tris 6,6,7,7,8,8,8-heptafluoro-2,2-dimethyloctanedionato Eu0.1, Gd0.9 phenanthroline
tris 6,6,7,7,8,8,8-heptafluoro-2,2-dimethyloctanedionato Eu0.1, Gd0.9 bathocuproine
tris 6,6,7,7,8,8,8-heptafluoro-2,2-dimethyloctanedionato Eu0.1, Gd0.9 bathophenanthroline
tris 1-phenyl-1,3-butanedionato Eu0.1, Gd0.9 dimethylaminopyridine
tris 1-phenyl-1,3-butanedionato Eu0.1, Gd0.9 4-picoline-N-oxide
tris 1-phenyl-1,3-butanedionato Eu0.1, Gd0.9 4-phenylpyridine
tris 1-phenyl-1,3-butanedionato Eu0.1, Gd0.9 4-cyanopyridine
tris 1-phenyl-1,3-butanedionato Eu0.1, Gd0.9 4-phenylpyridine-N-oxide
tris 1-phenyl-1,3-butanedionato Eu0.1, Gd0.9 1-methylimidazole
tris 1-phenyl-1,3-butanedionato Eu0.1, Gd0.9 triphenylphosphine oxide
tris 1-phenyl-1,3-butanedionato Eu0.1, Gd0.9 2,2-bipyridyl
tris 1-phenyl-1,3-butanedionato Eu0.1, Gd0.9 2,2-bipyridyl-N,N-dioxide
tris 1-phenyl-1,3-butanedionato Eu0.1, Gd0.9 phenanthroline
tris 1-phenyl-1,3-butanedionato Eu0.1, Gd0.9 bathocuproine
tris 1-phenyl-1,3-butanedionato Eu0.1, Gd0.9 bathophenanthroline
tris acetylacetonato Eu0.01, Gd0.99 dimethylaminopyridine
tris acetylacetonato Eu0.01, Gd0.99 4-picoline-N-oxide
tris acetylacetonato Eu0.01, Gd0.99 4-phenylpyridine
tris acetylacetonato Eu0.01, Gd0.99 4-cyanopyridine
tris acetylacetonato Eu0.01, Gd0.99 4-phenylpyridine-N-oxide
tris acetylacetonato Eu0.01, Gd0.99 1-methylimidazole
tris acetylacetonato Eu0.01, Gd0.99 triphenylphosphine oxide
tris acetylacetonato Eu0.01, Gd0.99 2,2-bipyridyl
tris acetylacetonato Eu0.01, Gd0.99 2,2-bipyridyl-N,N-dioxide
tris acetylacetonato Eu0.01, Gd0.99 phenanthroline
tris acetylacetonato Eu0.01, Gd0.99 bathocuproine
tris acetylacetonato Eu0.01, Gd0.99 bathophenanthroline tris dibenzoylmethanato Eu0.01, Gd0.99 dimethylaminopyridine
tris dibenzoylmethanato Eu0.01, Gd0.99 4-picoline-N-oxide
tris dibenzoylmethanato Eu0.01, Gd0.99 4-phenylpyridine
tris dibenzoylmethanato Eu0.01, Gd0.99 4-cyanopyridine
tris dibenzoylmethanato Eu0.01, Gd0.99 4-phenylpyridine-N-oxide
tris dibenzoylmethanato Eu0.01, Gd0.99 1-methylimidazole
tris dibenzoylmethanato Eu0.01, Gd0.99 triphenylphosphine oxide
tris dibenzoylmethanato Eu0.01, Gd0.99 2,2-bipyridyl
tris dibenzoylmethanato Eu0.01, Gd0.99 2,2-bipyridyl-N,N-dioxide
tris dibenzoylmethanato Eu0.01, Gd0.99 phenanthroline
tris dibenzoylmethanato Eu0.01, Gd0.99 bathocuproine
tris dibenzoylmethanato Eu0.01, Gd0.99 bathophenanthroline
tris thenoyltrifluoroacetonato Eu0.01, Gd0.99 dimethylaminopyridine
tris thenoyltrifluoroacetonato Eu0.01, Gd0.99 4-picoline-N-oxide
tris thenoyltrifluoroacetonato Eu0.01, Gd0.99 4-phenylpyridine
tris thenoyltrifluoroacetonato Eu0.01, Gd0.99 4-cyanopyridine
tris thenoyltrifluoroacetonato Eu0.01, Gd0.99 4-phenylpyridine-N-oxide
tris thenoyltrifluoroacetonato Eu0.01, Gd0.99 1-methylimidazole
tris thenoyltrifluoroacetonato Eu0.01, Gd0.99 triphenylphosphine oxide
tris thenoyltrifluoroacetonato Eu0.01, Gd0.99 2,2-bipyridyl
tris thenoyltrifluoroacetonato Eu0.01, Gd0.99 2,2-bipyridyl-N,N-dioxide
tris thenoyltrifluoroacetonato Eu0.01, Gd0.99 phenanthroline
tris thenoyltrifluoroacetonato Eu0.01, Gd0.99 bathocuproine
tris thenoyltrifluoroacetonato Eu0.01, Gd0.99 bathophenanthroline
tris 2,2,6,6-tetramethylheptanedionato Eu0.01, Gd0.99 dimethylaminopyridine
tris 2,2,6,6-tetramethylheptanedionato Eu0.01, Gd0.99 4-picoline-N-oxide
tris 2,2,6,6-tetramethylheptanedionato Eu0.01, Gd0.99 4-phenylpyridine
tris 2,2,6,6-tetramethylheptanedionato Eu0.01, Gd0.99 4-cyanopyridine
tris 2,2,6,6-tetramethylheptanedionato Eu0.01, Gd0.99 4-phenylpyridine-N-oxide
tris 2,2,6,6-tetramethylheptanedionato Eu0.01, Gd0.99 1-methylimidazole
tris 2,2,6,6-tetramethylheptanedionato Eu0.01, Gd0.99 triphenylphosphine oxide
tris 2,2,6,6-tetramethylheptanedionato Eu0.01, Gd0.99 2,2-bipyridyl
tris 2,2,6,6-tetramethylheptanedionato Eu0.01, Gd0.99 2,2-bipyridyl-N,N-dioxide
tris 2,2,6,6-tetramethylheptanedionato Eu0.01, Gd0.99 phenanthroline
tris 2,2,6,6-tetramethylheptanedionato Eu0.01, Gd0.99 bathocuproine
tris 2,2,6,6-tetramethylheptanedionato Eu0.01, Gd0.99 bathophenanthroline
tris 3-methylpentane-2,4-dionato Eu0.01, Gd0.99 dimethylaminopyridine
tris 3-methylpentane-2,4-dionato Eu0.01, Gd0.99 4-picoline-N-oxide
tris 3-methylpentane-2,4-dionato Eu0.01, Gd0.99 4-phenylpyridine
tris 3-methylpentane-2,4-dionato Eu0.01, Gd0.99 4-cyanopyridine
tris 3-methylpentane-2,4-dionato Eu0.01, Gd0.99 4-phenylpyridine-N-oxide
tris 3-methylpentane-2,4-dionato Eu0.01, Gd0.99 1-methylimidazole
tris 3-methylpentane-2,4-dionato Eu0.01, Gd0.99 triphenylphosphine oxide
tris 3-methylpentane-2,4-dionato Eu0.01, Gd0.99 2,2-bipyridyl
tris 3-methylpentane-2,4-dionato Eu0.01, Gd0.99 2,2-bipyridyl-N,N-dioxide
tris 3-methylpentane-2,4-dionato Eu0.01, Gd0.99 phenanthroline
tris 3-methylpentane-2,4-dionato Eu0.01, Gd0.99 bathocuproine
tris 3-methylpentane-2,4-dionato Eu0.01, Gd0.99 bathophenanthroline
tris 3-ethylpentane-2,4-dionato Eu0.01, Gd0.99 dimethylaminopyridine
tris 3-ethylpentane-2,4-dionato Eu0.01, Gd0.99 4-picoline-N-oxide
tris 3-ethylpentane-2,4-dionato Eu0.01, Gd0.99 4-phenylpyridine
tris 3-ethylpentane-2,4-dionato Eu0.01, Gd0.99 4-cyanopyridine
tris 3-ethylpentane-2,4-dionato Eu0.01, Gd0.99 4-phenylpyridine-N-oxide
tris 3-ethylpentane-2,4-dionato Eu0.01, Gd0.99 1-methylimidazole
tris 3-ethylpentane-2,4-dionato Eu0.01, Gd0.99 triphenylphosphine oxide
tris 3-ethylpentane-2,4-dionato Eu0.01, Gd0.99 2,2-bipyridyl
tris 3-ethylpentane-2,4-dionato Eu0.01, Gd0.99 2,2-bipyridyl-N,N-dioxide
tris 3-ethylpentane-2,4-dionato Eu0.01, Gd0.99 phenanthroline
tris 3-ethylpentane-2,4-dionato Eu0.01, Gd0.99 bathocuproine
tris 3-ethylpentane-2,4-dionato Eu0.01, Gd0.99 bathophenanthroline
tris pivaloyltrifluoroacetonato Eu0.01, Gd0.99 dimethylaminopyridine
tris pivaloyltrifluoroacetonato Eu0.01, Gd0.99 4-picoline-N-oxide
tris pivaloyltrifluoroacetonato Eu0.01, Gd0.99 4-phenylpyridine
tris pivaloyltrifluoroacetonato Eu0.01, Gd0.99 4-cyanopyridine
tris pivaloyltrifluoroacetonato Eu0.01, Gd0.99 4-phenylpyridine-N-oxide
tris pivaloyltrifluoroacetonato Eu0.01, Gd0.99 1-methylimidazole
tris pivaloyltrifluoroacetonato Eu0.01, Gd0.99 triphenylphosphine oxide
tris pivaloyltrifluoroacetonato Eu0.01, Gd0.99 2,2-bipyridyl
tris pivaloyltrifluoroacetonato Eu0.01, Gd0.99 2,2-bipyridyl-N,N-dioxide
tris pivaloyltrifluoroacetonato Eu0.01, Gd0.99 phenanthroline
tris pivaloyltrifluoroacetonato Eu0.01, Gd0.99 bathocuproine
tris pivaloyltrifluoroacetonato Eu0.01, Gd0.99 bathophenanthroline tris trifluoroacetylacetonato Eu0.01, Gd0.99 dimethylaminopyridine
tris trifluoroacetylacetonato Eu0.01, Gd0.99 4-picoline-N-oxide
tris trifluoroacetylacetonato Eu0.01, Gd0.99 4-phenylpyridine
tris trifluoroacetylacetonato Eu0.01, Gd0.99 4-cyanopyridine
tris trifluoroacetylacetonato Eu0.01, Gd0.99 4-phenylpyridine-N-oxide
tris trifluoroacetylacetonato Eu0.01, Gd0.99 1-methylimidazole
tris trifluoroacetylacetonato Eu0.01, Gd0.99 triphenylphosphine oxide
tris trifluoroacetylacetonato Eu0.01, Gd0.99 2,2-bipyridyl
tris trifluoroacetylacetonato Eu0.01, Gd0.99 2,2-bipyridyl-N,N-dioxide
tris trifluoroacetylacetonato Eu0.01, Gd0.99 phenanthroline
tris trifluoroacetylacetonato Eu0.01, Gd0.99 bathocuproine
tris trifluoroacetylacetonato Eu0.01, Gd0.99 bathophenanthroline
tris hexafluoroacetylacetonato Eu0.01, Gd0.99 dimethylaminopyridine
tris hexafluoroacetylacetonato Eu0.01, Gd0.99 4-picoline-N-oxide
tris hexafluoroacetylacetonato Eu0.01, Gd0.99 4-phenylpyridine
tris hexafluoroacetylacetonato Eu0.01, Gd0.99 4-cyanopyridine
tris hexafluoroacetylacetonato Eu0.01, Gd0.99 4-phenylpyridine-N-oxide
tris hexafluoroacetylacetonato Eu0.01, Gd0.99 1-methylimidazole
tris hexafluoroacetylacetonato Eu0.01, Gd0.99 triphenylphosphine oxide
tris hexafluoroacetylacetonato Eu0.01, Gd0.99 2,2-bipyridyl
tris hexafluoroacetylacetonato Eu0.01, Gd0.99 2,2-bipyridyl-N,N-dioxide
tris hexafluoroacetylacetonato Eu0.01, Gd0.99 phenanthroline
tris hexafluoroacetylacetonato Eu0.01, Gd0.99 bathocuproine
tris hexafluoroacetylacetonato Eu0.01, Gd0.99 bathophenanthroline
tris 6,6,7,7,8,8,8-heptafluoro-2,2-dimethyloctanedionato Eu0.01, Gd0.99 dimethylaminopyridine
tris 6,6,7,7,8,8,8-heptafluoro-2,2-dimethyloctanedionato Eu0.O0, Gd0.99 4-picoline-N-oxide
tris 6,6,7,7,8,8,8-heptafluoro-2,2-dimethyloctanedionato Eu0.01, Gd0.99 4-phenylpyridine
tris 6,6,7,7,8,8,8-heptafluoro-2,2-dimethyloctanedionato Eu0.01, Gd0.99 4-cyanopyridine
tris 6,6,7,7,8,8,8-heptafluoro-2,2-dimethyloctanedionato Eu0.01, Gd0.99 4-phenylpyridine-N-oxide
tris 6,6,7,7,8,8,8-heptafluoro-2,2-dimethyloctanedionato Eu0.01, Gd0.99 1-methylimidazole
tris 6,6,7,7,8,8,8-heptafluoro-2,2-dimethyloctanedionato Eu0.01, Gd0.99 triphenylphosphine oxide
tris 6,6,7,7,8,8,8-heptafluoro-2,2-dimethyloctanedionato Eu0.01, Gd0.99 2,2-bipyridyl
tris 6,6,7,7,8,8,8-heptafluoro-2,2-dimethyloctanedionato Eu0.01, Gd0.99 2,2-bipyridyl-N,N-dioxide
tris 6,6,7,7,8,8,8-heptafluoro-2,2-dimethyloctanedionato Eu0.01, Gd0.99 phenanthroline
tris 6,6,7,7,8,8,8-heptafluoro-2,2-dimethyloctanedionato Eu0.01, Gd0.99 bathocuproine
tris 6,6,7,7,8,8,8-heptafluoro-2,2-dimethyloctanedionato Eu0.01, Gd0.99 bathophenanthroline
tris 1-phenyl-1,3-butanedionato Eu0.01, Gd0.99 dimethylaminopyridine
tris 1-phenyl-1,3-butanedionato Eu0.01, Gd0.99 4-picoline-N-oxide
tris 1-phenyl-1,3-butanedionato Eu0.01, Gd0.99 4-phenylpyridine
tris 1-phenyl-1,3-butanedionato Eu0.01, Gd0.99 4-cyanopyridine
tris 1-phenyl-1,3-butanedionato Eu0.01, Gd0.99 4-phenylpyridine-N-oxide
tris 1-phenyl-1,3-butanedionato Eu0.01, Gd0.99 1-methylimidazole
tris 1-phenyl-1,3-butanedionato Eu0.01, Gd0.99 triphenylphosphine oxide
tris 1-phenyl-1,3-butanedionato Eu0.01, Gd0.99 2,2-bipyridyl
tris 1-phenyl-1,3-butanedionato Eu0.01, Gd0.99 2,2-bipyridyl-N,N-dioxide
tris 1-phenyl-1,3-butanedionato Eu0.01, Gd0.99 phenanthroline
tris 1-phenyl-1,3-butanedionato Eu0.01, Gd0.99 bathocuproine
tris 1-phenyl-1,3-butanedionato Eu0.01, Gd0.99 bathophenanthroline
tris acetylacetonato Sm0.5, Y0.5 dimethylaminopyridine
tris acetylacetonato Sm0.5, Y0.5 4-picoline-N-oxide
tris acetylacetonato Sm0.5, Y0.5 4-phenylpyridine
tris acetylacetonato Sm0.5, Y0.5 4-cyanopyridine
tris acetylacetonato Sm0.5, Y0.5 4-phenylpyridine-N-oxide
tris acetylacetonato Sm0.5, Y0.5 1-methylimidazole
tris acetylacetonato Sm0.5, Y0.5 triphenylphosphine oxide
tris acetylacetonato Sm0.5, Y0.5 2,2-bipyridyl
tris acetylacetonato Sm0.5, Y0.5 2,2-bipyridyl-N,N-dioxide
tris acetylacetonato Sm0.5, Y0.5 phenanthroline
tris acetylacetonato Sm0.5, Y0.5 bathocuproine
tris acetylacetonato Sm0.5, Y0.5 bathophenanthroline
tris dibenzoylmethanato Sm0.5, Y0.5 dimethylaminopyridine
tris dibenzoylmethanato Sm0.5, Y0.5 4-picoline-N-oxide
tris dibenzoylmethanato Sm0.5, Y0.5 4-phenylpyridine
tris dibenzoylmethanato Sm0.5, Y0.5 4-cyanopyridine
tris dibenzoylmethanato Sm0.5, Y0.5 4-phenylpyridine-N-oxide
tris dibenzoylmethanato Sm0.5, Y0.5 1-methylimidazole
tris dibenzoylmethanato Sm0.5, Y0.5 triphenylphosphine oxide
tris dibenzoylmethanato Sm0.5, Y0.5 2,2-bipyridyl
tris dibenzoylmethanato Sm0.5, Y0.5 2,2-bipyridyl-N,N-dioxide
tris dibenzoylmethanato Sm0.5, Y0.5 phenanthroline
tris dibenzoylmethanato Sm0.5, Y0.5 bathocuproine
tris dibenzoylmethanato Sm0.5, Y0.5 bathophenanthroline
tris thenoyltrifluoroacetonato Sm0.5, Y0.5 dimethylaminopyridine
tris thenoyltrifluoroacetonato Sm0.5, Y0.5 4-picoline-N-oxide
tris thenoyltrifluoroacetonato Sm0.5, Y0.5 4-phenylpyridine
tris thenoyltrifluoroacetonato Sm0.5, Y0.5 4-cyanopyridine
tris thenoyltrifluoroacetonato Sm0.5, Y0.5 4-phenylpyridine-N-oxide
tris thenoyltrifluoroacetonato Sm0.5, Y0.5 1-methylimidazole
tris thenoyltrifluoroacetonato Sm0.5, Y0.5 triphenylphosphine oxide
tris thenoyltrifluoroacetonato Sm0.5, Y0.5 2,2-bipyridyl tris thenoyltrifluoroacetonato Sm0.5, Y0.5 2,2-bipyridyl-N,N-dioxide
tris thenoyltrifluoroacetonato Sm0.5, Y0.5 phenanthroline
tris thenoyltrifluoroacetonato Sm0.5, Y0.5 bathocuproine
tris thenoyltrifluoroacetonato Sm0.5, Y0.5 bathophenanthroline
tris 2,2,6,6-tetramethylheptanedionato Sm0.5, Y0.5 dimethylaminopyridine
tris 2,2,6,6-tetramethylheptanedionato Sm0.5, Y0.5 4-picoline-N-oxide
tris 2,2,6,6-tetramethylheptanedionato Sm0.5, Y0.5 4-phenylpyridine
tris 2,2,6,6-tetramethylheptanedionato Sm0.5, Y0.5 4-cyanopyridine
tris 2,2,6,6-tetramethylheptanedionato Sm0.5, Y0.5 4-phenylpyridine-N-oxide
tris 2,2,6,6-tetramethylheptanedionato Sm0.5, Y0.5 1-methylimidazole
tris 2,2,6,6-tetramethylheptanedionato Sm0.5, Y0.5 triphenylphosphine oxide
tris 2,2,6,6-tetramethylheptanedionato Sm0.5, Y0.5 2,2-bipyridyl
tris 2,2,6,6-tetramethylheptanedionato Sm0.5, Y0.5 2,2-bipyridyl-N,N-dioxide
tris 2,2,6,6-tetramethylheptanedionato Sm0.5, Y0.5 phenanthroline
tris 2,2,6,6-tetramethylheptanedionato Sm0.5, Y0.5 bathocuproine
tris 2,2,6,6-tetramethylheptanedionato Sm0.5, Y0.5 bathophenanthroline
tris 3-methylpentane-2,4-dionato Sm0.5, Y0.5 dimethylaminopyridine
tris 3-methylpentane-2,4-dionato Sm0.5, Y0.5 4-picoline-N-oxide
tris 3-methylpentane-2,4-dionato Sm0.5, Y0.5 4-phenylpyridine
tris 3-methylpentane-2,4-dionato Sm0.5, Y0.5 4-cyanopyridine
tris 3-methylpentane-2,4-dionato Sm0.5, Y0.5 4-phenylpyridine-N-oxide
tris 3-methylpentane-2,4-dionato Sm0.5, Y0.5 1-methylimidazole
tris 3-methylpentane-2,4-dionato Sm0.5, Y0.5 triphenylphosphine oxide
tris 3-methylpentane-2,4-dionato Sm0.5, Y0.5 2,2-bipyridyl
tris 3-methylpentane-2,4-dionato Sm0.5, Y0.5 2,2-bipyridyl-N,N-dioxide
tris 3-methylpentane-2,4-dionato Sm0.5, Y0.5 phenanthroline
tris 3-methylpentane-2,4-dionato Sm0.5, Y0.5 bathocuproine
tris 3-methylpentane-2,4-dionato Sm0.5, Y0.5 bathophenanthroline
tris 3-ethylpentane-2,4-dionato Sm0.5, Y0.5 dimethylaminopyridine
tris 3-ethylpentane-2,4-dionato Sm0.5, Y0.5 4-picoline-N-oxide
tris 3-ethylpentane-2,4-dionato Sm0.5, Y0.5 4-phenylpyridine
tris 3-ethylpentane-2,4-dionato Sm0.5, Y0.5 4-cyanopyridine
tris 3-ethylpentane-2,4-dionato Sm0.5, Y0.5 4-phenylpyridine-N-oxide
tris 3-ethylpentane-2,4-dionato Sm0.5, Y0.5 1-methylimidazole
tris 3-ethylpentane-2,4-dionato Sm0.5, Y0.5 triphenylphosphine oxide
tris 3-ethylpentane-2,4-dionato Sm0.5, Y0.5 2,2-bipyridyl
tris 3-ethylpentane-2,4-dionato Sm0.5, Y0.5 2,2-bipyridyl-N,N-dioxide
tris 3-ethylpentane-2,4-dionato Sm0.5, Y0.5 phenanthroline
tris 3-ethylpentane-2,4-dionato Sm0.5, Y0.5 bathocuproine
tris 3-ethylpentane-2,4-dionato Sm0.5, Y0.5 bathophenanthroline
tris pivaloyltrifluoroacetonato Sm0.5, Y0.5 dimethylaminopyridine
tris pivaloyltrifluoroacetonato Sm0.5, Y0.5 4-picoline-N-oxide
tris pivaloyltrifluoroacetonato Sm0.5, Y0.5 4-phenylpyridine
tris pivaloyltrifluoroacetonato Sm0.5, Y0.5 4-cyanopyridine
tris pivaloyltrifluoroacetonato Sm0.5, Y0.5 4-phenylpyridine-N-oxide
tris pivaloyltrifluoroacetonato Sm0.5, Y0.5 1-methylimidazole
tris pivaloyltrifluoroacetonato Sm0.5, Y0.5 triphenylphosphine oxide
tris pivaloyltrifluoroacetonato Sm0.5, Y0.5 2,2-bipyridyl
tris pivaloyltrifluoroacetonato Sm0.5, Y0.5 2,2-bipyridyl-N,N-dioxide
tris pivaloyltrifluoroacetonato Sm0.5, Y0.5 phenanthroline
tris pivaloyltrifluoroacetonato Sm0.5, Y0.5 bathocuproine
tris pivaloyltrifluoroacetonato Sm0.5, Y0.5 bathophenanthroline
tris trifluoroacetylacetonato Sm0.5, Y0.5 dimethylaminopyridine
tris trifluoroacetylacetonato Sm0.5, Y0.5 4-picoline-N-oxide
tris trifluoroacetylacetonato Sm0.5, Y0.5 4-phenylpyridine
tris trifluoroacetylacetonato Sm0.5, Y0.5 4-cyanopyridine
tris trifluoroacetylacetonato Sm0.5, Y0.5 4-phenylpyridine-N-oxide
tris trifluoroacetylacetonato Sm0.5, Y0.5 1-methylimidazole
tris trifluoroacetylacetonato Sm0.5, Y0.5 triphenylphosphine oxide
tris trifluoroacetylacetonato Sm0.5, Y0.5 2,2-bipyridyl
tris trifluoroacetylacetonato Sm0.5, Y0.5 2,2-bipyridyl-N,N-dioxide
tris trifluoroacetylacetonato Sm0.5, Y0.5 phenanthroline
tris trifluoroacetylacetonato Sm0.5, Y0.5 bathocuproine
tris trifluoroacetylacetonato Sm0.5, Y0.5 bathophenanthroline
tris hexafluoroacetylacetonato Sm0.5, Y0.5 dimethylaminopyridine
tris hexafluoroacetylacetonato Sm0.5, Y0.5 4-picoline-N-oxide
tris hexafluoroacetylacetonato Sm0.5, Y0.5 4-phenylpyridine
tris hexafluoroacetylacetonato Sm0.5, Y0.5 4-cyanopyridine
tris hexafluoroacetylacetonato Sm0.5, Y0.5 4-phenylpyridine-N-oxide
tris hexafluoroacetylacetonato Sm0.5, Y0.5 1-methylimidazole
tris hexafluoroacetylacetonato Sm0.5, Y0.5 triphenylphosphine oxide
tris hexafluoroacetylacetonato Sm0.5, Y0.5 2,2-bipyridyl
tris hexafluoroacetylacetonato Sm0.5, Y0.5 2,2-bipyridyl-N,N-dioxide
tris hexafluoroacetylacetonato Sm0.5, Y0.5 phenanthroline
tris hexafluoroacetylacetonato Sm0.5, Y0.5 bathocuproine
tris hexafluoroacetylacetonato Sm0.5, Y0.5 bathophenanthroline
tris 6,6,7,7,8,8,8-heptafluoro-2,2-dimethyloctanedionato Sm0.5, Y0.5 dimethylaminopyridine tris 6,6,7,7,8,8-heptafluoro-2,2-dimethyloctanedionato Sm0.5, Y0.5 4-picoline-N-oxide
tris 6,6,7,7,8,8-heptafluoro-2,2-dimethyloctanedionato Sm0.5, Y0.5 4-phenylpyridine
tris 6,6,7,7,8,8-heptafluoro-2,2-dimethyloctanedionato Sm0.5, Y0.5 4-cyanopyridine
tris 6,6,7,7,8,8-heptafluoro-2,2-dimethyloctanedionato Sm0.5, Y0.5 4-phenylpyridine-N-oxide
tris 6,6,7,7,8,8-heptafluoro-2,2-dimethyloctanedionato Sm0.5, Y0.5 1-methylimidazole
tris 6,6,7,7,8,8-heptafluoro-2,2-dimethyloctanedionato Sm0.5, Y0.5 triphenylphosphine oxide
tris 6,6,7,7,8,8-heptafluoro-2,2-dimethyloctanedionato Sm0.5, Y0.5 2,2-bipyridyl
tris 6,6,7,7,8,8-heptafluoro-2,2-dimethyloctanedionato Sm0.5, Y0.5 2,2-bipyridyl-N,N-dioxide
tris 6,6,7,7,8,8-heptafluoro-2,2-dimethyloctanedionato Sm0.5, Y0.5 phenanthroline
tris 6,6,7,7,8,8-heptafluoro-2,2-dimethyloctanedionato Sm0.5, Y0.5 bathocuproine
tris 6,6,7,7,8,8-heptafluoro-2,2-dimethyloctanedionato Sm0.5, Y0.5 bathophenanthroline
tris 1-phenyl-1,3-butanedionato Sm0.5, Y0.5 dimethylaminopyridine
tris 1-phenyl-1,3-butanedionato Sm0.5, Y0.5 4-picoline-N-oxide
tris 1-phenyl-1,3-butanedionato Sm0.5, Y0.5 4-phenylpyridine
tris 1-phenyl-1,3-butanedionato Sm0.5, Y0.5 4-cyanopyridine
tris 1-phenyl-1,3-butanedionato Sm0.5, Y0.5 4-phenylpyridine-N-oxide
tris 1-phenyl-1,3-butanedionato Sm0.5, Y0.5 1-methylimidazole
tris 1-phenyl-1,3-butanedionato Sm0.5, Y0.5 triphenylphosphine oxide
tris 1-phenyl-1,3-butanedionato Sm0.5, Y0.5 2,2-bipyridyl
tris 1-phenyl-1,3-butanedionato Sm0.5, Y0.5 2,2-bipyridyl-N,N-dioxide
tris 1-phenyl-1,3-butanedionato Sm0.5, Y0.5 phenanthroline
tris 1-phenyl-1,3-butanedionato Sm0.5, Y0.5 bathocuproine
tris 1-phenyl-1,3-butanedionato Sm0.5, Y0.5 bathophenanthroline
tris acetylacetonato Sm0.2, Y0.8 dimethylaminopyridine
tris acetylacetonato Sm0.2, Y0.8 4-picoline-N-oxide
tris acetylacetonato Sm0.2, Y0.8 4-phenylpyridine
tris acetylacetonato Sm0.2, Y0.8 4-cyanopyridine
tris acetylacetonato Sm0.2, Y0.8 4-phenylpyridine-N-oxide
tris acetylacetonato Sm0.2, Y0.8 1-methylimidazole
tris acetylacetonato Sm0.2, Y0.8 triphenylphosphine oxide
tris acetylacetonato Sm0.2, Y0.8 2,2-bipyridyl
tris acetylacetonato Sm0.2, Y0.8 2,2-bipyridyl-N,N-dioxide
tris acetylacetonato Sm0.2, Y0.8 phenanthroline
tris acetylacetonato Sm0.2, Y0.8 bathocuproine
tris acetylacetonato Sm0.2, Y0.8 bathophenanthroline
tris dibenzoylmethanato Sm0.2, Y0.8 dimethylaminopyridine
tris dibenzoylmethanato Sm0.2, Y0.8 4-picoline-N-oxide
tris dibenzoylmethanato Sm0.2, Y0.8 4-phenylpyridine
tris dibenzoylmethanato Sm0.2, Y0.8 4-cyanopyridine
tris dibenzoylmethanato Sm0.2, Y0.8 4-phenylpyridine-N-oxide
tris dibenzoylmethanato Sm0.2, Y0.8 1-methylimidazole
tris dibenzoylmethanato Sm0.2, Y0.8 triphenylphosphine oxide
tris dibenzoylmethanato Sm0.2, Y0.8 2,2-bipyridyl
tris dibenzoylmethanato Sm0.2, Y0.8 2,2-bipyridyl-N,N-dioxide
tris dibenzoylmethanato Sm0.2, Y0.8 phenanthroline
tris dibenzoylmethanato Sm0.2, Y0.8 bathocuproine
tris dibenzoylmethanato Sm0.2, Y0.8 bathophenanthroline
tris thenoyltrifluoroacetonato Sm0.2, Y0.8 dimethylaminopyridine
tris thenoyltrifluoroacetonato Sm0.2, Y0.8 4-picoline-N-oxide
tris thenoyltrifluoroacetonato Sm0.2, Y0.8 4-phenylpyridine
tris thenoyltrifluoroacetonato Sm0.2, Y0.8 4-cyanopyridine
tris thenoyltrifluoroacetonato Sm0.2, Y0.8 4-phenylpyridine-N-oxide
tris thenoyltrifluoroacetonato Sm0.2, Y0.8 1-methylimidazole
tris thenoyltrifluoroacetonato Sm0.2, Y0.8 triphenylphosphine oxide
tris thenoyltrifluoroacetonato Sm0.2, Y0.8 2,2-bipyridyl
tris thenoyltrifluoroacetonato Sm0.2, Y0.8 2,2-bipyridyl-N,N-dioxide
tris thenoyltrifluoroacetonato Sm0.2, Y0.8 phenanthroline
tris thenoyltrifluoroacetonato Sm0.2, Y0.8 bathocuproine
tris thenoyltrifluoroacetonato Sm0.2, Y0.8 bathophenanthroline
tris 2,2,6,6-tetramethylheptanedionato Sm0.2, Y0.8 dimethylaminopyridine
tris 2,2,6,6-tetramethylheptanedionato Sm0.2, Y0.8 4-picoline-N-oxide
tris 2,2,6,6-tetramethylheptanedionato Sm0.2, Y0.8 4-phenylpyridine
tris 2,2,6,6-tetramethylheptanedionato Sm0.2, Y0.8 4-cyanopyridine
tris 2,2,6,6-tetramethylheptanedionato Sm0.2, Y0.8 4-phenylpyridine-N-oxide
tris 2,2,6,6-tetramethylheptanedionato Sm0.2, Y0.8 1-methylimidazole
tris 2,2,6,6-tetramethylheptanedionato Sm0.2, Y0.8 triphenylphosphine oxide
tris 2,2,6,6-tetramethylheptanedionato Sm0.2, Y0.8 2,2-bipyridyl
tris 2,2,6,6-tetramethylheptanedionato Sm0.2, Y0.8 2,2-bipyridyl-N,N-dioxide
tris 2,2,6,6-tetramethylheptanedionato Sm0.2, Y0.8 phenanthroline
tris 2,2,6,6-tetramethylheptanedionato Sm0.2, Y0.8 bathocuproine
tris 2,2,6,6-tetramethylheptanedionato Sm0.2, Y0.8 bathophenanthroline
tris 3-methylpentane-2,4-dionato Sm0.2, Y0.8 dimethylaminopyridine
tris 3-methylpentane-2,4-dionato Sm0.2, Y0.8 4-picoline-N-oxide
tris 3-methylpentane-2,4-dionato Sm0.2, Y0.8 4-phenylpyridine
tris 3-methylpentane-2,4-dionato Sm0.2, Y0.8 4-cyanopyridine
tris 3-methylpentane-2,4-dionato Sm0.2, Y0.8 4-phenylpyridine-N-oxide
tris 3-methylpentane-2,4-dionato Sm0.2, Y0.8 1-methylimidazole
tris 3-methylpentane-2,4-dionato Sm0.2, Y0.8 triphenylphosphine oxide
tris 3-methylpentane-2,4-dionato Sm0.2, Y0.8 2,2-bipyridyl
tris 3-methylpentane-2,4-dionato Sm0.2, Y0.8 2,2-bipyridyl-N,N-dioxide
tris 3-methylpentane-2,4-dionato Sm0.2, Y0.8 phenanthroline tris 3-methylpentane-2,4-dionato Sm0.2, Y0.8 bathocuproine
tris 3-methylpentane-2,4-dionato Sm0.2, Y0.8 bathophenanthroline
tris 3-ethylpentane-2,4-dionato Sm0.2, Y0.8 dimethylaminopyridine
tris 3-ethylpentane-2,4-dionato Sm0.2, Y0.8 4-picoline-N-oxide
tris 3-ethylpentane-2,4-dionato Sm0.2, Y0.8 4-phenylpyridine
tris 3-ethylpentane-2,4-dionato Sm0.2, Y0.8 4-cyanopyridine
tris 3-ethylpentane-2,4-dionato Sm0.2, Y0.8 4-phenylpyridine-N-oxide
tris 3-ethylpentane-2,4-dionato Sm0.2, Y0.8 1-methylimidazole
tris 3-ethylpentane-2,4-dionato Sm0.2, Y0.8 triphenylphosphine oxide
tris 3-ethylpentane-2,4-dionato Sm0.2, Y0.8 2,2-bipyridyl
tris 3-ethylpentane-2,4-dionato Sm0.2, Y0.8 2,2-bipyridyl-N,N-dioxide
tris 3-ethylpentane-2,4-dionato Sm0.2, Y0.8 phenanthroline
tris 3-ethylpentane-2,4-dionato Sm0.2, Y0.8 bathocuproine
tris 3-ethylpentane-2,4-dionato Sm0.2, Y0.8 bathophenanthroline
tris pivaloyltrifluoroacetonato Sm0.2, Y0.8 dimethylaminopyridine
tris pivaloyltrifluoroacetonato Sm0.2, Y0.8 4-picoline-N-oxide
tris pivaloyltrifluoroacetonato Sm0.2, Y0.8 4-phenylpyridine
tris pivaloyltrifluoroacetonato Sm0.2, Y0.8 4-cyanopyridine
tris pivaloyltrifluoroacetonato Sm0.2, Y0.8 4-phenylpyridine-N-oxide
tris pivaloyltrifluoroacetonato Sm0.2, Y0.8 1-methylimidazole
tris pivaloyltrifluoroacetonato Sm0.2, Y0.8 triphenylphosphine oxide
tris pivaloyltrifluoroacetonato Sm0.2, Y0.8 2,2-bipyridyl
tris pivaloyltrifluoroacetonato Sm0.2, Y0.8 2,2-bipyridyl-N,N-dioxide
tris pivaloyltrifluoroacetonato Sm0.2, Y0.8 phenanthroline
tris pivaloyltrifluoroacetonato Sm0.2, Y0.8 bathocuproine
tris pivaloyltrifluoroacetonato Sm0.2, Y0.8 bathophenanthroline
tris trifluoroacetylacetonato Sm0.2, Y0.8 dimethylaminopyridine
tris trifluoroacetylacetonato Sm0.2, Y0.8 4-picoline-N-oxide
tris trifluoroacetylacetonato Sm0.2, Y0.8 4-phenylpyridine
tris trifluoroacetylacetonato Sm0.2, Y0.8 4-cyanopyridine
tris trifluoroacetylacetonato Sm0.2, Y0.8 4-phenylpyridine-N-oxide
tris trifluoroacetylacetonato Sm0.2, Y0.8 1-methylimidazole
tris trifluoroacetylacetonato Sm0.2, Y0.8 triphenylphosphine oxide
tris trifluoroacetylacetonato Sm0.2, Y0.8 2,2-bipyridyl
tris trifluoroacetylacetonato Sm0.2, Y0.8 2,2-bipyridyl-N,N-dioxide
tris trifluoroacetylacetonato Sm0.2, Y0.8 phenanthroline
tris trifluoroacetylacetonato Sm0.2, Y0.8 bathocuproine
tris trifluoroacetylacetonato Sm0.2, Y0.8 bathophenanthroline
tris hexafluoroacetylacetonato Sm0.2, Y0.8 dimethylaminopyridine
tris hexafluoroacetylacetonato Sm0.2, Y0.8 4-picoline-N-oxide
tris hexafluoroacetylacetonato Sm0.2, Y0.8 4-phenylpyridine
tris hexafluoroacetylacetonato Sm0.2, Y0.8 4-cyanopyridine
tris hexafluoroacetylacetonato Sm0.2, Y0.8 4-phenylpyridine-N-oxide
tris hexafluoroacetylacetonato Sm0.2, Y0.8 1-methylimidazole
tris hexafluoroacetylacetonato Sm0.2, Y0.8 triphenylphosphine oxide
tris hexafluoroacetylacetonato Sm0.2, Y0.8 2,2-bipyridyl
tris hexafluoroacetylacetonato Sm0.2, Y0.8 2,2-bipyridyl-N,N-dioxide
tris hexafluoroacetylacetonato Sm0.2, Y0.8 phenanthroline
tris hexafluoroacetylacetonato Sm0.2, Y0.8 bathocuproine
tris hexafluoroacetylacetonato Sm0.2, Y0.8 bathophenanthroline
tris 6,6,7,7,8,8,8-heptafluoro-2,2-dimethyloctanedionato Sm0.2, Y0.8 dimethylaminopyridine
tris 6,6,7,7,8,8,8-heptafluoro-2,2-dimethyloctanedionato Sm0.2, Y0.8 4-picoline-N-oxide
tris 6,6,7,7,8,8,8-heptafluoro-2,2-dimethyloctanedionato Sm0.2, Y0.8 4-phenylpyridine
tris 6,6,7,7,8,8,8-heptafluoro-2,2-dimethyloctanedionato Sm0.2, Y0.8 4-cyanopyridine
tris 6,6,7,7,8,8,8-heptafluoro-2,2-dimethyloctanedionato Sm0.2, Y0.8 4-phenylpyridine-N-oxide
tris 6,6,7,7,8,8,8-heptafluoro-2,2-dimethyloctanedionato Sm0.2, Y0.8 1-methylimidazole
tris 6,6,7,7,8,8,8-heptafluoro-2,2-dimethyloctanedionato Sm0.2, Y0.8 triphenylphosphine oxide
tris 6,6,7,7,8,8,8-heptafluoro-2,2-dimethyloctanedionato Sm0.2, Y0.8 2,2-bipyridyl
tris 6,6,7,7,8,8,8-heptafluoro-2,2-dimethyloctanedionato Sm0.2, Y0.8 2,2-bipyridyl-N,N-dioxide
tris 6,6,7,7,8,8,8-heptafluoro-2,2-dimethyloctanedionato Sm0.2, Y0.8 phenanthroline
tris 6,6,7,7,8,8,8-heptafluoro-2,2-dimethyloctanedionato Sm0.2, Y0.8 bathocuproine
tris 6,6,7,7,8,8,8-heptafluoro-2,2-dimethyloctanedionato Sm0.2, Y0.8 bathophenanthroline
tris 1-phenyl-1,3-butanedionato Sm0.2, Y0.8 dimethylaminopyridine
tris 1-phenyl-1,3-butanedionato Sm0.2, Y0.8 4-picoline-N-oxide
tris 1-phenyl-1,3-butanedionato Sm0.2, Y0.8 4-phenylpyridine
tris 1-phenyl-1,3-butanedionato Sm0.2, Y0.8 4-cyanopyridine
tris 1-phenyl-1,3-butanedionato Sm0.2, Y0.8 4-phenylpyridine-N-oxide
tris 1-phenyl-1,3-butanedionato Sm0.2, Y0.8 1-methylimidazole
tris 1-phenyl-1,3-butanedionato Sm0.2, Y0.8 triphenylphosphine oxide
tris 1-phenyl-1,3-butanedionato Sm0.2, Y0.8 2,2-bipyridyl
tris 1-phenyl-1,3-butanedionato Sm0.2, Y0.8 2,2-bipyridyl-N,N-dioxide
tris 1-phenyl-1,3-butanedionato Sm0.2, Y0.8 phenanthroline
tris 1-phenyl-1,3-butanedionato Sm0.2, Y0.8 bathocuproine
tris 1-phenyl-1,3-butanedionato Sm0.2, Y0.8 bathophenanthroline
tris acetylacetonato Sm0.1, Y0.9 dimethylaminopyridine
tris acetylacetonato Sm0.1, Y0.9 4-picoline-N-oxide
tris acetylacetonato Sm0.1, Y0.9 4-phenylpyridine
tris acetylacetonato Sm0.1, Y0.9 4-cyanopyridine
tris acetylacetonato Sm0.1, Y0.9 4-phenylpyridine-N-oxide
tris acetylacetonato Sm0.1, Y0.9 1-methylimidazole tris acetylacetonato Sm0.1, Y0.9 triphenylphosphine oxide
tris acetylacetonato Sm0.1, Y0.9 2,2-bipyridyl
tris acetylacetonato Sm0.1, Y0.9 2,2-bipyridyl-N,N-dioxide
tris acetylacetonato Sm0.1, Y0.9 phenanthroline
tris acetylacetonato Sm0.1, Y0.9 bathocuproine
tris acetylacetonato Sm0.1, Y0.9 bathophenanthroline
tris dibenzoylmethanato Sm0.1, Y0.9 dimethylaminopyridine
tris dibenzoylmethanato Sm0.1, Y0.9 4-picoline-N-oxide
tris dibenzoylmethanato Sm0.1, Y0.9 4-phenylpyridine
tris dibenzoylmethanato Sm0.1, Y0.9 4-cyanopyridine
tris dibenzoylmethanato Sm0.1, Y0.9 4-phenylpyridine-N-oxide
tris dibenzoylmethanato Sm0.1, Y0.9 1-methylimidazole
tris dibenzoylmethanato Sm0.1, Y0.9 triphenylphosphine oxide
tris dibenzoylmethanato Sm0.1, Y0.9 2,2-bipyridyl
tris dibenzoylmethanato Sm0.1, Y0.9 2,2-bipyridyl-N,N-dioxide
tris dibenzoylmethanato Sm0.1, Y0.9 phenanthroline
tris dibenzoylmethanato Sm0.1, Y0.9 bathocuproine
tris dibenzoylmethanato Sm0.1, Y0.9 bathophenanthroline
tris thenoyltrifluoroacetonato Sm0.1, Y0.9 dimethylaminopyridine
tris thenoyltrifluoroacetonato Sm0.1, Y0.9 4-picoline-N-oxide
tris thenoyltrifluoroacetonato Sm0.1, Y0.9 4-phenylpyridine
tris thenoyltrifluoroacetonato Sm0.1, Y0.9 4-cyanopyridine
tris thenoyltrifluoroacetonato Sm0.1, Y0.9 4-phenylpyridine-N-oxide
tris thenoyltrifluoroacetonato Sm0.1, Y0.9 1-methylimidazole
tris thenoyltrifluoroacetonato Sm0.1, Y0.9 triphenylphosphine oxide
tris thenoyltrifluoroacetonato Sm0.1, Y0.9 2,2-bipyridyl
tris thenoyltrifluoroacetonato Sm0.1, Y0.9 2,2-bipyridyl-N,N-dioxide
tris thenoyltrifluoroacetonato Sm0.1, Y0.9 phenanthroline
tris thenoyltrifluoroacetonato Sm0.1, Y0.9 bathocuproine
tris thenoyltrifluoroacetonato Sm0.1, Y0.9 bathophenanthroline
tris 2,2,6,6-tetramethylheptanedionato Sm0.1, Y0.9 dimethylaminopyridine
tris 2,2,6,6-tetramethylheptanedionato Sm0.1, Y0.9 4-picoline-N-oxide
tris 2,2,6,6-tetramethylheptanedionato Sm0.1, Y0.9 4-phenylpyridine
tris 2,2,6,6-tetramethylheptanedionato Sm0.1, Y0.9 4-cyanopyridine
tris 2,2,6,6-tetramethylheptanedionato Sm0.1, Y0.9 4-phenylpyridine-N-oxide
tris 2,2,6,6-tetramethylheptanedionato Sm0.1, Y0.9 1-methylimidazole
tris 2,2,6,6-tetramethylheptanedionato Sm0.1, Y0.9 triphenylphosphine oxide
tris 2,2,6,6-tetramethylheptanedionato Sm0.1, Y0.9 2,2-bipyridyl
tris 2,2,6,6-tetramethylheptanedionato Sm0.1, Y0.9 2,2-bipyridyl-N,N-dioxide
tris 2,2,6,6-tetramethylheptanedionato Sm0.1, Y0.9 phenanthroline
tris 2,2,6,6-tetramethylheptanedionato Sm0.1, Y0.9 bathocuproine
tris 2,2,6,6-tetramethylheptanedionato Sm0.1, Y0.9 bathophenanthroline
tris 3-methylpentane-2,4-dionato Sm0.1, Y0.9 dimethylaminopyridine
tris 3-methylpentane-2,4-dionato Sm0.1, Y0.9 4-picoline-N-oxide
tris 3-methylpentane-2,4-dionato Sm0.1, Y0.9 4-phenylpyridine
tris 3-methylpentane-2,4-dionato Sm0.1, Y0.9 4-cyanopyridine
tris 3-methylpentane-2,4-dionato Sm0.1, Y0.9 4-phenylpyridine-N-oxide
tris 3-methylpentane-2,4-dionato Sm0.1, Y0.9 1-methylimidazole
tris 3-methylpentane-2,4-dionato Sm0.1, Y0.9 triphenylphosphine oxide
tris 3-methylpentane-2,4-dionato Sm0.1, Y0.9 2,2-bipyridyl
tris 3-methylpentane-2,4-dionato Sm0.1, Y0.9 2,2-bipyridyl-N,N-dioxide
tris 3-methylpentane-2,4-dionato Sm0.1, Y0.9 phenanthroline
tris 3-methylpentane-2,4-dionato Sm0.1, Y0.9 bathocuproine
tris 3-methylpentane-2,4-dionato Sm0.1, Y0.9 bathophenanthroline
tris 3-ethylpentane-2,4-dionato Sm0.1, Y0.9 dimethylaminopyridine
tris 3-ethylpentane-2,4-dionato Sm0.1, Y0.9 4-picoline-N-oxide
tris 3-ethylpentane-2,4-dionato Sm0.1, Y0.9 4-phenylpyridine
tris 3-ethylpentane-2,4-dionato Sm0.1, Y0.9 4-cyanopyridine
tris 3-ethylpentane-2,4-dionato Sm0.1, Y0.9 4-phenylpyridine-N-oxide
tris 3-ethylpentane-2,4-dionato Sm0.1, Y0.9 1-methylimidazole
tris 3-ethylpentane-2,4-dionato Sm0.1, Y0.9 triphenylphosphine oxide
tris 3-ethylpentane-2,4-dionato Sm0.1, Y0.9 2,2-bipyridyl
tris 3-ethylpentane-2,4-dionato Sm0.1, Y0.9 2,2-bipyridyl-N,N-dioxide
tris 3-ethylpentane-2,4-dionato Sm0.1, Y0.9 phenanthroline
tris 3-ethylpentane-2,4-dionato Sm0.1, Y0.9 bathocuproine
tris 3-ethylpentane-2,4-dionato Sm0.1, Y0.9 bathophenanthroline
tris pivaloyltrifluoroacetonato Sm0.1, Y0.9 dimethylaminopyridine
tris pivaloyltrifluoroacetonato Sm0.1, Y0.9 4-picoline-N-oxide
tris pivaloyltrifluoroacetonato Sm0.1, Y0.9 4-phenylpyridine
tris pivaloyltrifluoroacetonato Sm0.1, Y0.9 4-cyanopyridine
tris pivaloyltrifluoroacetonato Sm0.1, Y0.9 4-phenylpyridine-N-oxide
tris pivaloyltrifluoroacetonato Sm0.1, Y0.9 1-methylimidazole
tris pivaloyltrifluoroacetonato Sm0.1, Y0.9 triphenylphosphine oxide
tris pivaloyltrifluoroacetonato Sm0.1, Y0.9 2,2-bipyridyl
tris pivaloyltrifluoroacetonato Sm0.1, Y0.9 2,2-bipyridyl-N,N-dioxide
tris pivaloyltrifluoroacetonato Sm0.1, Y0.9 phenanthroline
tris pivaloyltrifluoroacetonato Sm0.1, Y0.9 bathocuproine
tris pivaloyltrifluoroacetonato Sm0.1, Y0.9 bathophenanthroline
tris trifluoroacetylacetonato Sm0.1, Y0.9 dimethylaminopyridine
tris trifluoroacetylacetonato Sm0.1, Y0.9 4-picoline-N-oxide
tris trifluoroacetylacetonato Sm0.1, Y0.9 4-phenylpyridine tris trifluoroacetylacetonato Sm0.1, Y0.9 4-cyanopyridine
tris trifluoroacetylacetonato Sm0.1, Y0.9 4-phenylpyridine-N-oxide
tris trifluoroacetylacetonato Sm0.1, Y0.9 1-methylimidazole
tris trifluoroacetylacetonato Sm0.1, Y0.9 triphenylphosphine oxide
tris trifluoroacetylacetonato Sm0.1, Y0.9 2,2-bipyridyl
tris trifluoroacetylacetonato Sm0.1, Y0.9 2,2-bipyridyl-N,N-dioxide
tris trifluoroacetylacetonato Sm0.1, Y0.9 phenanthroline
tris trifluoroacetylacetonato Sm0.1, Y0.9 bathocuproine
tris trifluoroacetylacetonato Sm0.1, Y0.9 bathophenanthroline
tris hexafluoroacetylacetonato Sm0.1, Y0.9 dimethylaminopyridine
tris hexafluoroacetylacetonato Sm0.1, Y0.9 4-picoline-N-oxide
tris hexafluoroacetylacetonato Sm0.1, Y0.9 4-phenylpyridine
tris hexafluoroacetylacetonato Sm0.1, Y0.9 4-cyanopyridine
tris hexafluoroacetylacetonato Sm0.1, Y0.9 4-phenylpyridine-N-oxide
tris hexafluoroacetylacetonato Sm0.1, Y0.9 1-methylimidazole
tris hexafluoroacetylacetonato Sm0.1, Y0.9 triphenylphosphine oxide
tris hexafluoroacetylacetonato Sm0.1, Y0.9 2,2-bipyridyl
tris hexafluoroacetylacetonato Sm0.1, Y0.9 2,2-bipyridyl-N,N-dioxide
tris hexafluoroacetylacetonato Sm0.1, Y0.9 phenanthroline
tris hexafluoroacetylacetonato Sm0.1, Y0.9 bathocuproine
tris hexafluoroacetylacetonato Sm0.1, Y0.9 bathophenanthroline
tris 6,6,7,7,8,8,8-heptafluoro-2,2-dimethyloctanedionato Sm0.1, Y0.9 dimethylaminopyridine
tris 6,6,7,7,8,8,8-heptafluoro-2,2-dimethyloctanedionato Sm0.1, Y0.9 4-picoline-N-oxide
tris 6,6,7,7,8,8,8-heptafluoro-2,2-dimethyloctanedionato Sm0.1, Y0.9 4-phenylpyridine
tris 6,6,7,7,8,8,8-heptafluoro-2,2-dimethyloctanedionato Sm0.1, Y0.9 4-cyanopyridine
tris 6,6,7,7,8,8,8-heptafluoro-2,2-dimethyloctanedionato Sm0.1, Y0.9 4-phenylpyridine-N-oxide
tris 6,6,7,7,8,8,8-heptafluoro-2,2-dimethyloctanedionato Sm0.1, Y0.9 1-methylimidazole
tris 6,6,7,7,8,8,8-heptafluoro-2,2-dimethyloctanedionato Sm0.1, Y0.9 triphenylphosphine oxide
tris 6,6,7,7,8,8,8-heptafluoro-2,2-dimethyloctanedionato Sm0.1, Y0.9 2,2-bipyridyl
tris 6,6,7,7,8,8,8-heptafluoro-2,2-dimethyloctanedionato Sm0.1, Y0.9 2,2-bipyridyl-N,N-dioxide
tris 6,6,7,7,8,8,8-heptafluoro-2,2-dimethyloctanedionato Sm0.1, Y0.9 phenanthroline
tris 6,6,7,7,8,8,8-heptafluoro-2,2-dimethyloctanedionato Sm0.1, Y0.9 bathocuproine
tris 6,6,7,7,8,8,8-heptafluoro-2,2-dimethyloctanedionato Sm0.1, Y0.9 bathophenanthroline
tris 1-phenyl-1,3-butanedionato Sm0.1, Y0.9 dimethylaminopyridine
tris 1-phenyl-1,3-butanedionato Sm0.1, Y0.9 4-picoline-N-oxide
tris 1-phenyl-1,3-butanedionato Sm0.1, Y0.9 4-phenylpyridine
tris 1-phenyl-1,3-butanedionato Sm0.1, Y0.9 4-cyanopyridine
tris 1-phenyl-1,3-butanedionato Sm0.1, Y0.9 4-phenylpyridine-N-oxide
tris 1-phenyl-1,3-butanedionato Sm0.1, Y0.9 1-methylimidazole
tris 1-phenyl-1,3-butanedionato Sm0.1, Y0.9 triphenylphosphine oxide
tris 1-phenyl-1,3-butanedionato Sm0.1, Y0.9 2,2-bipyridyl
tris 1-phenyl-1,3-butanedionato Sm0.1, Y0.9 2,2-bipyridyl-N,N-dioxide
tris 1-phenyl-1,3-butanedionato Sm0.1, Y0.9 phenanthroline
tris 1-phenyl-1,3-butanedionato Sm0.1, Y0.9 bathocuproine
tris 1-phenyl-1,3-butanedionato Sm0.1, Y0.9 bathophenanthroline
tris acetylacetonato Sm0.01, Y0.99 dimethylaminopyridine
tris acetylacetonato Sm0.01, Y0.99 4-picoline-N-oxide
tris acetylacetonato Sm0.01, Y0.99 4-phenylpyridine
tris acetylacetonato Sm0.01, Y0.99 4-cyanopyridine
tris acetylacetonato Sm0.01, Y0.99 4-phenylpyridine-N-oxide
tris acetylacetonato Sm0.01, Y0.99 1-methylimidazole
tris acetylacetonato Sm0.01, Y0.99 triphenylphosphine oxide
tris acetylacetonato Sm0.01, Y0.99 2,2-bipyridyl
tris acetylacetonato Sm0.01, Y0.99 2,2-bipyridyl-N,N-dioxide
tris acetylacetonato Sm0.01, Y0.99 phenanthroline
tris acetylacetonato Sm0.01, Y0.99 bathocuproine
tris acetylacetonato Sm0.01, Y0.99 bathophenanthroline
tris dibenzoylmethanato Sm0.01, Y0.99 dimethylaminopyridine
tris dibenzoylmethanato Sm0.01, Y0.99 4-picoline-N-oxide
tris dibenzoylmethanato Sm0.01, Y0.99 4-phenylpyridine
tris dibenzoylmethanato Sm0.01, Y0.99 4-cyanopyridine
tris dibenzoylmethanato Sm0.01, Y0.99 4-phenylpyridine-N-oxide
tris dibenzoylmethanato Sm0.01, Y0.99 1-methylimidazole
tris dibenzoylmethanato Sm0.01, Y0.99 triphenylphosphine oxide
tris dibenzoylmethanato Sm0.01, Y0.99 2,2-bipyridyl
tris dibenzoylmethanato Sm0.01, Y0.99 2,2-bipyridyl-N,N-dioxide
tris dibenzoylmethanato Sm0.01, Y0.99 phenanthroline
tris dibenzoylmethanato Sm0.01, Y0.99 bathocuproine
tris dibenzoylmethanato Sm0.01, Y0.99 bathophenanthroline
tris thenoyltrifluoroacetonato Sm0.01, Y0.99 dimethylaminopyridine
tris thenoyltrifluoroacetonato Sm0.01, Y0.99 4-picoline-N-oxide
tris thenoyltrifluoroacetonato Sm0.01, Y0.99 4-phenylpyridine
tris thenoyltrifluoroacetonato Sm0.01, Y0.99 4-cyanopyridine
tris thenoyltrifluoroacetonato Sm0.01, Y0.99 4-phenylpyridine-N-oxide
tris thenoyltrifluoroacetonato Sm0.01, Y0.99 1-methylimidazole
tris thenoyltrifluoroacetonato Sm0.01, Y0.99 triphenylphosphine oxide
tris thenoyltrifluoroacetonato Sm0.01, Y0.99 2,2-bipyridyl
tris thenoyltrifluoroacetonato Sm0.01, Y0.99 2,2-bipyridyl-N,N-dioxide
tris thenoyltrifluoroacetonato Sm0.01, Y0.99 phenanthroline
tris thenoyltrifluoroacetonato Sm0.01, Y0.99 bathocuproine
tris thenoyltrifluoroacetonato Sm0.01, Y0.99 bathophenanthroline
tris 2,2,6,6-tetramethylheptanedionato Sm0.01, Y0.99 dimethylaminopyridine tris 2,2,6,6-tetramethylheptanedionato Sm0.01, Y0.99 4-picoline-N-oxide
tris 2,2,6,6-tetramethylheptanedionato Sm0.01, Y0.99 4-phenylpyridine
tris 2,2,6,6-tetramethylheptanedionato Sm0.01, Y0.99 4-cyanopyridine
tris 2,2,6,6-tetramethylheptanedionato Sm0.01, Y0.99 4-phenylpyridine-N-oxide
tris 2,2,6,6-tetramethylheptanedionato Sm0.01, Y0.99 1-methylimidazole
tris 2,2,6,6-tetramethylheptanedionato Sm0.01, Y0.99 triphenylphosphine oxide
tris 2,2,6,6-tetramethylheptanedionato Sm0.01, Y0.99 2,2-bipyridyl
tris 2,2,6,6-tetramethylheptanedionato Sm0.01, Y0.99 2,2-bipyridyl-N,N-dioxide
tris 2,2,6,6-tetramethylheptanedionato Sm0.01, Y0.99 phenanthroline
tris 2,2,6,6-tetramethylheptanedionato Sm0.01, Y0.99 bathocuproine
tris 2,2,6,6-tetramethylheptanedionato Sm0.01, Y0.99 bathophenanthroline
tris 3-methylpentane-2,4-dionato Sm0.01, Y0.99 dimethylaminopyridine
tris 3-methylpentane-2,4-dionato Sm0.01, Y0.99 4-picoline-N-oxide
tris 3-methylpentane-2,4-dionato Sm0.01, Y0.99 4-phenylpyridine
tris 3-methylpentane-2,4-dionato Sm0.01, Y0.99 4-cyanopyridine
tris 3-methylpentane-2,4-dionato Sm0.01, Y0.99 4-phenylpyridine-N-oxide
tris 3-methylpentane-2,4-dionato Sm0.01, Y0.99 1-methylimidazole
tris 3-methylpentane-2,4-dionato Sm0.01, Y0.99 triphenylphosphine oxide
tris 3-methylpentane-2,4-dionato Sm0.01, Y0.99 2,2-bipyridyl
tris 3-methylpentane-2,4-dionato Sm0.01, Y0.99 2,2-bipyridyl-N,N-dioxide
tris 3-methylpentane-2,4-dionato Sm0.01, Y0.99 phenanthroline
tris 3-methylpentane-2,4-dionato Sm0.01, Y0.99 bathocuproine
tris 3-methylpentane-2,4-dionato Sm0.01, Y0.99 bathophenanthroline
tris 3-ethylpentane-2,4-dionato Sm0.01, Y0.99 dimethylaminopyridine
tris 3-ethylpentane-2,4-dionato Sm0.01, Y0.99 4-picoline-N-oxide
tris 3-ethylpentane-2,4-dionato Sm0.01, Y0.99 4-phenylpyridine
tris 3-ethylpentane-2,4-dionato Sm0.01, Y0.99 4-cyanopyridine
tris 3-ethylpentane-2,4-dionato Sm0.01, Y0.99 4-phenylpyridine-N-oxide
tris 3-ethylpentane-2,4-dionato Sm0.01, Y0.99 1-methylimidazole
tris 3-ethylpentane-2,4-dionato Sm0.01, Y0.99 triphenylphosphine oxide
tris 3-ethylpentane-2,4-dionato Sm0.01, Y0.99 2,2-bipyridyl
tris 3-ethylpentane-2,4-dionato Sm0.01, Y0.99 2,2-bipyridyl-N,N-dioxide
tris 3-ethylpentane-2,4-dionato Sm0.01, Y0.99 phenanthroline
tris 3-ethylpentane-2,4-dionato Sm0.01, Y0.99 bathocuproine
tris 3-ethylpentane-2,4-dionato Sm0.01, Y0.99 bathophenanthroline
tris pivaloyltrifluoroacetonato Sm0.01, Y0.99 dimethylaminopyridine
tris pivaloyltrifluoroacetonato Sm0.01, Y0.99 4-picoline-N-oxide
tris pivaloyltrifluoroacetonato Sm0.01, Y0.99 4-phenylpyridine
tris pivaloyltrifluoroacetonato Sm0.01, Y0.99 4-cyanopyridine
tris pivaloyltrifluoroacetonato Sm0.01, Y0.99 4-phenylpyridine-N-oxide
tris pivaloyltrifluoroacetonato Sm0.01, Y0.99 1-methylimidazole
tris pivaloyltrifluoroacetonato Sm0.01, Y0.99 triphenylphosphine oxide
tris pivaloyltrifluoroacetonato Sm0.01, Y0.99 2,2-bipyridyl
tris pivaloyltrifluoroacetonato Sm0.01, Y0.99 2,2-bipyridyl-N,N-dioxide
tris pivaloyltrifluoroacetonato Sm0.01, Y0.99 phenanthroline
tris pivaloyltrifluoroacetonato Sm0.01, Y0.99 bathocuproine
tris pivaloyltrifluoroacetonato Sm0.01, Y0.99 bathophenanthroline
tris trifluoroacetylacetonato Sm0.01, Y0.99 dimethylaminopyridine
tris trifluoroacetylacetonato Sm0.01, Y0.99 4-picoline-N-oxide
tris trifluoroacetylacetonato Sm0.01, Y0.99 4-phenylpyridine
tris trifluoroacetylacetonato Sm0.01, Y0.99 4-cyanopyridine
tris trifluoroacetylacetonato Sm0.01, Y0.99 4-phenylpyridine-N-oxide
tris trifluoroacetylacetonato Sm0.01, Y0.99 1-methylimidazole
tris trifluoroacetylacetonato Sm0.01, Y0.99 triphenylphosphine oxide
tris trifluoroacetylacetonato Sm0.01, Y0.99 2,2-bipyridyl
tris trifluoroacetylacetonato Sm0.01, Y0.99 2,2-bipyridyl-N,N-dioxide
tris trifluoroacetylacetonato Sm0.01, Y0.99 phenanthroline
tris trifluoroacetylacetonato Sm0.01, Y0.99 bathocuproine
tris trifluoroacetylacetonato Sm0.01, Y0.99 bathophenanthroline
tris hexafluoroacetylacetonato Sm0.01, Y0.99 dimethylaminopyridine
tris hexafluoroacetylacetonato Sm0.01, Y0.99 4-picoline-N-oxide
tris hexafluoroacetylacetonato Sm0.01, Y0.99 4-phenylpyridine
tris hexafluoroacetylacetonato Sm0.01, Y0.99 4-cyanopyridine
tris hexafluoroacetylacetonato Sm0.01, Y0.99 4-phenylpyridine-N-oxide
tris hexafluoroacetylacetonato Sm0.01, Y0.99 1-methylimidazole
tris hexafluoroacetylacetonato Sm0.01, Y0.99 triphenylphosphine oxide
tris hexafluoroacetylacetonato Sm0.01, Y0.99 2,2-bipyridyl
tris hexafluoroacetylacetonato Sm0.01, Y0.99 2,2-bipyridyl-N,N-dioxide
tris hexafluoroacetylacetonato Sm0.01, Y0.99 phenanthroline
tris hexafluoroacetylacetonato Sm0.01, Y0.99 bathocuproine
tris hexafluoroacetylacetonato Sm0.01, Y0.99 bathophenanthroline tris 6,6,7,7,8,8-heptafluoro-2,2-dimethyloctanedionato Sm0.01, Y0.99 dimethylaminopyridine
tris 6,6,7,7,8,8-heptafluoro-2,2-dimethyloctanedionato Sm0.01, Y0.99 4-picoline-N-oxide
tris 6,6,7,7,8,8-heptafluoro-2,2-dimethyloctanedionato Sm0.01, Y0.99 4-phenylpyridine
tris 6,6,7,7,8,8-heptafluoro-2,2-dimethyloctanedionato Sm0.01, Y0.99 4-cyanopyridine
tris 6,6,7,7,8,8-heptafluoro-2,2-dimethyloctanedionato Sm0.01, Y0.99 4-phenylpyridine-N-oxide
tris 6,6,7,7,8,8-heptafluoro-2,2-dimethyloctanedionato Sm0.01, Y0.99 1-methylimidazole
tris 6,6,7,7,8,8-heptafluoro-2,2-dimethyloctanedionato Sm0.01, Y0.99 triphenylphosphine oxide
tris 6,6,7,7,8,8-heptafluoro-2,2-dimethyloctanedionato Sm0.01, Y0.99 2,2-bipyridyl
tris 6,6,7,7,8,8-heptafluoro-2,2-dimethyloctanedionato Sm0.01, Y0.99 2,2-bipyridyl-N,N-dioxide
tris 6,6,7,7,8,8-heptafluoro-2,2-dimethyloctanedionato Sm0.01, Y0.99 phenanthroline
tris 6,6,7,7,8,8-heptafluoro-2,2-dimethyloctanedionato Sm0.01, Y0.99 bathocuproine
tris 6,6,7,7,8,8-heptafluoro-2,2-dimethyloctanedionato Sm0.01, Y0.99 bathophenanthroline
tris 1-phenyl-1,3-butanedionato Sm0.01, Y0.99 dimethylaminopyridine
tris 1-phenyl-1,3-butanedionato Sm0.01, Y0.99 4-picoline-N-oxide
tris 1-phenyl-1,3-butanedionato Sm0.01, Y0.99 4-phenylpyridine
tris 1-phenyl-1,3-butanedionato Sm0.01, Y0.99 4-cyanopyridine
tris 1-phenyl-1,3-butanedionato Sm0.01, Y0.99 4-phenylpyridine-N-oxide
tris 1-phenyl-1,3-butanedionato Sm0.01, Y0.99 1-methylimidazole
tris 1-phenyl-1,3-butanedionato Sm0.01, Y0.99 triphenylphosphine oxide
tris 1-phenyl-1,3-butanedionato Sm0.01, Y0.99 2,2-bipyridyl
tris 1-phenyl-1,3-butanedionato Sm0.01, Y0.99 2,2-bipyridyl-N,N-dioxide
tris 1-phenyl-1,3-butanedionato Sm0.01, Y0.99 phenanthroline
tris 1-phenyl-1,3-butanedionato Sm0.01, Y0.99 bathocuproine
tris 1-phenyl-1,3-butanedionato Sm0.01, Y0.99 bathophenanthroline
tris acetylacetonato Dy0.5, Y0.5 dimethylaminopyridine
tris acetylacetonato Dy0.5, Y0.5 4-picoline-N-oxide
tris acetylacetonato Dy0.5, Y0.5 4-phenylpyridine
tris acetylacetonato Dy0.5, Y0.5 4-cyanopyridine
tris acetylacetonato Dy0.5, Y0.5 4-phenylpyridine-N-oxide
tris acetylacetonato Dy0.5, Y0.5 1-methylimidazole
tris acetylacetonato Dy0.5, Y0.5 triphenylphosphine oxide
tris acetylacetonato Dy0.5, Y0.5 2,2-bipyridyl
tris acetylacetonato Dy0.5, Y0.5 2,2-bipyridyl-N,N-dioxide
tris acetylacetonato Dy0.5, Y0.5 phenanthroline
tris acetylacetonato Dy0.5, Y0.5 bathocuproine
tris acetylacetonato Dy0.5, Y0.5 bathophenanthroline
tris dibenzoylmethanato Dy0.5, Y0.5 dimethylaminopyridine
tris dibenzoylmethanato Dy0.5, Y0.5 4-picoline-N-oxide
tris dibenzoylmethanato Dy0.5, Y0.5 4-phenylpyridine
tris dibenzoylmethanato Dy0.5, Y0.5 4-cyanopyridine
tris dibenzoylmethanato Dy0.5, Y0.5 4-phenylpyridine-N-oxide
tris dibenzoylmethanato Dy0.5, Y0.5 1-methylimidazole
tris dibenzoylmethanato Dy0.5, Y0.5 triphenylphosphine oxide
tris dibenzoylmethanato Dy0.5, Y0.5 2,2-bipyridyl
tris dibenzoylmethanato Dy0.5, Y0.5 2,2-bipyridyl-N,N-dioxide
tris dibenzoylmethanato Dy0.5, Y0.5 phenanthroline
tris dibenzoylmethanato Dy0.5, Y0.5 bathocuproine
tris dibenzoylmethanato Dy0.5, Y0.5 bathophenanthroline
tris thenoyltrifluoroacetonato Dy0.5, Y0.5 dimethylaminopyridine
tris thenoyltrifluoroacetonato Dy0.5, Y0.5 4-picoline-N-oxide
tris thenoyltrifluoroacetonato Dy0.5, Y0.5 4-phenylpyridine
tris thenoyltrifluoroacetonato Dy0.5, Y0.5 4-cyanopyridine
tris thenoyltrifluoroacetonato Dy0.5, Y0.5 4-phenylpyridine-N-oxide
tris thenoyltrifluoroacetonato Dy0.5, Y0.5 1-methylimidazole
tris thenoyltrifluoroacetonato Dy0.5, Y0.5 triphenylphosphine oxide
tris thenoyltrifluoroacetonato Dy0.5, Y0.5 2,2-bipyridyl
tris thenoyltrifluoroacetonato Dy0.5, Y0.5 2,2-bipyridyl-N,N-dioxide
tris thenoyltrifluoroacetonato Dy0.5, Y0.5 phenanthroline
tris thenoyltrifluoroacetonato Dy0.5, Y0.5 bathocuproine
tris thenoyltrifluoroacetonato Dy0.5, Y0.5 bathophenanthroline
tris 2,2,6,6-tetramethylheptanedionato Dy0.5, Y0.5 dimethylaminopyridine
tris 2,2,6,6-tetramethylheptanedionato Dy0.5, Y0.5 4-picoline-N-oxide
tris 2,2,6,6-tetramethylheptanedionato Dy0.5, Y0.5 4-phenylpyridine
tris 2,2,6,6-tetramethylheptanedionato Dy0.5, Y0.5 4-cyanopyridine
tris 2,2,6,6-tetramethylheptanedionato Dy0.5, Y0.5 4-phenylpyridine-N-oxide
tris 2,2,6,6-tetramethylheptanedionato Dy0.5, Y0.5 1-methylimidazole
tris 2,2,6,6-tetramethylheptanedionato Dy0.5, Y0.5 triphenylphosphine oxide
tris 2,2,6,6-tetramethylheptanedionato Dy0.5, Y0.5 2,2-bipyridyl
tris 2,2,6,6-tetramethylheptanedionato Dy0.5, Y0.5 2,2-bipyridyl-N,N-dioxide
tris 2,2,6,6-tetramethylheptanedionato Dy0.5, Y0.5 phenanthroline
tris 2,2,6,6-tetramethylheptanedionato Dy0.5, Y0.5 bathocuproine
tris 2,2,6,6-tetramethylheptanedionato Dy0.5, Y0.5 bathophenanthroline
tris 3-methylpentane-2,4-dionato Dy0.5, Y0.5 dimethylaminopyridine
tris 3-methylpentane-2,4-dionato Dy0.5, Y0.5 4-picoline-N-oxide
tris 3-methylpentane-2,4-dionato Dy0.5, Y0.5 4-phenylpyridine
tris 3-methylpentane-2,4-dionato Dy0.5, Y0.5 4-cyanopyridine
tris 3-methylpentane-2,4-dionato Dy0.5, Y0.5 4-phenylpyridine-N-oxide
tris 3-methylpentane-2,4-dionato Dy0.5, Y0.5 1-methylimidazole
tris 3-methylpentane-2,4-dionato Dy0.5, Y0.5 triphenylphosphine oxide
tris 3-methylpentane-2,4-dionato Dy0.5, Y0.5 2,2-bipyridyl tris 3-methylpentane-2,4-dionato Dy0.5, Y0.5 2,2-bipyridyl-N,N-dioxide
tris 3-methylpentane-2,4-dionato Dy0.5, Y0.5 phenanthroline
tris 3-methylpentane-2,4-dionato Dy0.5, Y0.5 bathocuproine
tris 3-methylpentane-2,4-dionato Dy0.5, Y0.5 bathophenanthroline
tris 3-ethylpentane-2,4-dionato Dy0.5, Y0.5 dimethylaminopyridine
tris 3-ethylpentane-2,4-dionato Dy0.5, Y0.5 4-picoline-N-oxide
tris 3-ethylpentane-2,4-dionato Dy0.5, Y0.5 4-phenylpyridine
tris 3-ethylpentane-2,4-dionato Dy0.5, Y0.5 4-cyanopyridine
tris 3-ethylpentane-2,4-dionato Dy0.5, Y0.5 4-phenylpyridine-N-oxide
tris 3-ethylpentane-2,4-dionato Dy0.5, Y0.5 1-methylimidazole
tris 3-ethylpentane-2,4-dionato Dy0.5, Y0.5 triphenylphosphine oxide
tris 3-ethylpentane-2,4-dionato Dy0.5, Y0.5 2,2-bipyridyl
tris 3-ethylpentane-2,4-dionato Dy0.5, Y0.5 2,2-bipyridyl-N,N-dioxide
tris 3-ethylpentane-2,4-dionato Dy0.5, Y0.5 phenanthroline
tris 3-ethylpentane-2,4-dionato Dy0.5, Y0.5 bathocuproine
tris 3-ethylpentane-2,4-dionato Dy0.5, Y0.5 bathophenanthroline
tris pivaloyltrifluoroacetonato Dy0.5, Y0.5 dimethylaminopyridine
tris pivaloyltrifluoroacetonato Dy0.5, Y0.5 4-picoline-N-oxide
tris pivaloyltrifluoroacetonato Dy0.5, Y0.5 4-phenylpyridine
tris pivaloyltrifluoroacetonato Dy0.5, Y0.5 4-cyanopyridine
tris pivaloyltrifluoroacetonato Dy0.5, Y0.5 4-phenylpyridine-N-oxide
tris pivaloyltrifluoroacetonato Dy0.5, Y0.5 1-methylimidazole
tris pivaloyltrifluoroacetonato Dy0.5, Y0.5 triphenylphosphine oxide
tris pivaloyltrifluoroacetonato Dy0.5, Y0.5 2,2-bipyridyl
tris pivaloyltrifluoroacetonato Dy0.5, Y0.5 2,2-bipyridyl-N,N-dioxide
tris pivaloyltrifluoroacetonato Dy0.5, Y0.5 phenanthroline
tris pivaloyltrifluoroacetonato Dy0.5, Y0.5 bathocuproine
tris pivaloyltrifluoroacetonato Dy0.5, Y0.5 bathophenanthroline
tris trifluoroacetylacetonato Dy0.5, Y0.5 dimethylaminopyridine
tris trifluoroacetylacetonato Dy0.5, Y0.5 4-picoline-N-oxide
tris trifluoroacetylacetonato Dy0.5, Y0.5 4-phenylpyridine
tris trifluoroacetylacetonato Dy0.5, Y0.5 4-cyanopyridine
tris trifluoroacetylacetonato Dy0.5, Y0.5 4-phenylpyridine-N-oxide
tris trifluoroacetylacetonato Dy0.5, Y0.5 1-methylimidazole
tris trifluoroacetylacetonato Dy0.5, Y0.5 triphenylphosphine oxide
tris trifluoroacetylacetonato Dy0.5, Y0.5 2,2-bipyridyl
tris trifluoroacetylacetonato Dy0.5, Y0.5 2,2-bipyridyl-N,N-dioxide
tris trifluoroacetylacetonato Dy0.5, Y0.5 phenanthroline
tris trifluoroacetylacetonato Dy0.5, Y0.5 bathocuproine
tris trifluoroacetylacetonato Dy0.5, Y0.5 bathophenanthroline
tris hexafluoroacetylacetonato Dy0.5, Y0.5 dimethylaminopyridine
tris hexafluoroacetylacetonato Dy0.5, Y0.5 4-picoline-N-oxide
tris hexafluoroacetylacetonato Dy0.5, Y0.5 4-phenylpyridine
tris hexafluoroacetylacetonato Dy0.5, Y0.5 4-cyanopyridine
tris hexafluoroacetylacetonato Dy0.5, Y0.5 4-phenylpyridine-N-oxide
tris hexafluoroacetylacetonato Dy0.5, Y0.5 1-methylimidazole
tris hexafluoroacetylacetonato Dy0.5, Y0.5 triphenylphosphine oxide
tris hexafluoroacetylacetonato Dy0.5, Y0.5 2,2-bipyridyl
tris hexafluoroacetylacetonato Dy0.5, Y0.5 2,2-bipyridyl-N,N-dioxide
tris hexafluoroacetylacetonato Dy0.5, Y0.5 phenanthroline
tris hexafluoroacetylacetonato Dy0.5, Y0.5 bathocuproine
tris hexafluoroacetylacetonato Dy0.5, Y0.5 bathophenanthroline
tris 6,6,7,7,8,8,8-heptafluoro-2,2-dimethyloctanedionato Dy0.5, Y0.5 dimethylaminopyridine
tris 6,6,7,7,8,8,8-heptafluoro-2,2-dimethyloctanedionato Dy0.5, Y0.5 4-picoline-N-oxide
tris 6,6,7,7,8,8,8-heptafluoro-2,2-dimethyloctanedionato Dy0.5, Y0.5 4-phenylpyridine
tris 6,6,7,7,8,8,8-heptafluoro-2,2-dimethyloctanedionato Dy0.5, Y0.5 4-cyanopyridine
tris 6,6,7,7,8,8,8-heptafluoro-2,2-dimethyloctanedionato Dy0.5, Y0.5 4-phenylpyridine-N-oxide
tris 6,6,7,7,8,8,8-heptafluoro-2,2-dimethyloctanedionato Dy0.5, Y0.5 1-methylimidazole
tris 6,6,7,7,8,8,8-heptafluoro-2,2-dimethyloctanedionato Dy0.5, Y0.5 triphenylphosphine oxide
tris 6,6,7,7,8,8,8-heptafluoro-2,2-dimethyloctanedionato Dy0.5, Y0.5 2,2-bipyridyl
tris 6,6,7,7,8,8,8-heptafluoro-2,2-dimethyloctanedionato Dy0.5, Y0.5 2,2-bipyridyl-N,N-dioxide
tris 6,6,7,7,8,8,8-heptafluoro-2,2-dimethyloctanedionato Dy0.5, Y0.5 phenanthroline
tris 6,6,7,7,8,8,8-heptafluoro-2,2-dimethyloctanedionato Dy0.5, Y0.5 bathocuproine
tris 6,6,7,7,8,8,8-heptafluoro-2,2-dimethyloctanedionato Dy0.5, Y0.5 bathophenanthroline
tris 1-phenyl-1,3-butanedionato Dy0.5, Y0.5 dimethylaminopyridine
tris 1-phenyl-1,3-butanedionato Dy0.5, Y0.5 4-picoline-N-oxide
tris 1-phenyl-1,3-butanedionato Dy0.5, Y0.5 4-phenylpyridine
tris 1-phenyl-1,3-butanedionato Dy0.5, Y0.5 4-cyanopyridine
tris 1-phenyl-1,3-butanedionato Dy0.5, Y0.5 4-phenylpyridine-N-oxide
tris 1-phenyl-1,3-butanedionato Dy0.5, Y0.5 1-methylimidazole
tris 1-phenyl-1,3-butanedionato Dy0.5, Y0.5 triphenylphosphine oxide
tris 1-phenyl-1,3-butanedionato Dy0.5, Y0.5 2,2-bipyridyl
tris 1-phenyl-1,3-butanedionato Dy0.5, Y0.5 2,2-bipyridyl-N,N-dioxide
tris 1-phenyl-1,3-butanedionato Dy0.5, Y0.5 phenanthroline
tris 1-phenyl-1,3-butanedionato Dy0.5, Y0.5 bathocuproine
tris 1-phenyl-1,3-butanedionato Dy0.5, Y0.5 bathophenanthroline
tris acetylacetonato Dy0.2, Y0.8 dimethylaminopyridine
tris acetylacetonato Dy0.2, Y0.8 4-picoline-N-oxide tris acetylacetonato Dy0.2, Y0.8 4-phenylpyridine
tris acetylacetonato Dy0.2, Y0.8 4-cyanopyridine
tris acetylacetonato Dy0.2, Y0.8 4-phenylpyridine-N-oxide
tris acetylacetonato Dy0.2, Y0.8 1-methylimidazole
tris acetylacetonato Dy0.2, Y0.8 triphenylphosphine oxide
tris acetylacetonato Dy0.2, Y0.8 2,2-bipyridyl
tris acetylacetonato Dy0.2, Y0.8 2,2-bipyridyl-N,N-dioxide
tris acetylacetonato Dy0.2, Y0.8 phenanthroline
tris acetylacetonato Dy0.2, Y0.8 bathocuproine
tris acetylacetonato Dy0.2, Y0.8 bathophenanthroline
tris dibenzoylmethanato Dy0.2, Y0.8 dimethylaminopyridine
tris dibenzoylmethanato Dy0.2, Y0.8 4-picoline-N-oxide
tris dibenzoylmethanato Dy0.2, Y0.8 4-phenylpyridine
tris dibenzoylmethanato Dy0.2, Y0.8 4-cyanopyridine
tris dibenzoylmethanato Dy0.2, Y0.8 4-phenylpyridine-N-oxide
tris dibenzoylmethanato Dy0.2, Y0.8 1-methylimidazole
tris dibenzoylmethanato Dy0.2, Y0.8 triphenylphosphine oxide
tris dibenzoylmethanato Dy0.2, Y0.8 2,2-bipyridyl
tris dibenzoylmethanato Dy0.2, Y0.8 2,2-bipyridyl-N,N-dioxide
tris dibenzoylmethanato Dy0.2, Y0.8 phenanthroline
tris dibenzoylmethanato Dy0.2, Y0.8 bathocuproine
tris dibenzoylmethanato Dy0.2, Y0.8 bathophenanthroline
tris thenoyltrifluoroacetonato Dy0.2, Y0.8 dimethylaminopyridine
tris thenoyltrifluoroacetonato Dy0.2, Y0.8 4-picoline-N-oxide
tris thenoyltrifluoroacetonato Dy0.2, Y0.8 4-phenylpyridine
tris thenoyltrifluoroacetonato Dy0.2, Y0.8 4-cyanopyridine
tris thenoyltrifluoroacetonato Dy0.2, Y0.8 4-phenylpyridine-N-oxide
tris thenoyltrifluoroacetonato Dy0.2, Y0.8 1-methylimidazole
tris thenoyltrifluoroacetonato Dy0.2, Y0.8 triphenylphosphine oxide
tris thenoyltrifluoroacetonato Dy0.2, Y0.8 2,2-bipyridyl
tris thenoyltrifluoroacetonato Dy0.2, Y0.8 2,2-bipyridyl-N,N-dioxide
tris thenoyltrifluoroacetonato Dy0.2, Y0.8 phenanthroline
tris thenoyltrifluoroacetonato Dy0.2, Y0.8 bathocuproine
tris thenoyltrifluoroacetonato Dy0.2, Y0.8 bathophenanthroline
tris 2,2,6,6-tetramethylheptanedionato Dy0.2, Y0.8 dimethylaminopyridine
tris 2,2,6,6-tetramethylheptanedionato Dy0.2, Y0.8 4-picoline-N-oxide
tris 2,2,6,6-tetramethylheptanedionato Dy0.2, Y0.8 4-phenylpyridine
tris 2,2,6,6-tetramethylheptanedionato Dy0.2, Y0.8 4-cyanopyridine
tris 2,2,6,6-tetramethylheptanedionato Dy0.2, Y0.8 4-phenylpyridine-N-oxide
tris 2,2,6,6-tetramethylheptanedionato Dy0.2, Y0.8 1-methylimidazole
tris 2,2,6,6-tetramethylheptanedionato Dy0.2, Y0.8 triphenylphosphine oxide
tris 2,2,6,6-tetramethylheptanedionato Dy0.2, Y0.8 2,2-bipyridyl
tris 2,2,6,6-tetramethylheptanedionato Dy0.2, Y0.8 2,2-bipyridyl-N,N-dioxide
tris 2,2,6,6-tetramethylheptanedionato Dy0.2, Y0.8 phenanthroline
tris 2,2,6,6-tetramethylheptanedionato Dy0.2, Y0.8 bathocuproine
tris 2,2,6,6-tetramethylheptanedionato Dy0.2, Y0.8 bathophenanthroline
tris 3-methylpentane-2,4-dionato Dy0.2, Y0.8 dimethylaminopyridine
tris 3-methylpentane-2,4-dionato Dy0.2, Y0.8 4-picoline-N-oxide
tris 3-methylpentane-2,4-dionato Dy0.2, Y0.8 4-phenylpyridine
tris 3-methylpentane-2,4-dionato Dy0.2, Y0.8 4-cyanopyridine
tris 3-methylpentane-2,4-dionato Dy0.2, Y0.8 4-phenylpyridine-N-oxide
tris 3-methylpentane-2,4-dionato Dy0.2, Y0.8 1-methylimidazole
tris 3-methylpentane-2,4-dionato Dy0.2, Y0.8 triphenylphosphine oxide
tris 3-methylpentane-2,4-dionato Dy0.2, Y0.8 2,2-bipyridyl
tris 3-methylpentane-2,4-dionato Dy0.2, Y0.8 2,2-bipyridyl-N,N-dioxide
tris 3-methylpentane-2,4-dionato Dy0.2, Y0.8 phenanthroline
tris 3-methylpentane-2,4-dionato Dy0.2, Y0.8 bathocuproine
tris 3-methylpentane-2,4-dionato Dy0.2, Y0.8 bathophenanthroline
tris 3-ethylpentane-2,4-dionato Dy0.2, Y0.8 dimethylaminopyridine
tris 3-ethylpentane-2,4-dionato Dy0.2, Y0.8 4-picoline-N-oxide
tris 3-ethylpentane-2,4-dionato Dy0.2, Y0.8 4-phenylpyridine
tris 3-ethylpentane-2,4-dionato Dy0.2, Y0.8 4-cyanopyridine
tris 3-ethylpentane-2,4-dionato Dy0.2, Y0.8 4-phenylpyridine-N-oxide
tris 3-ethylpentane-2,4-dionato Dy0.2, Y0.8 1-methylimidazole
tris 3-ethylpentane-2,4-dionato Dy0.2, Y0.8 triphenylphosphine oxide
tris 3-ethylpentane-2,4-dionato Dy0.2, Y0.8 2,2-bipyridyl
tris 3-ethylpentane-2,4-dionato Dy0.2, Y0.8 2,2-bipyridyl-N,N-dioxide
tris 3-ethylpentane-2,4-dionato Dy0.2, Y0.8 phenanthroline
tris 3-ethylpentane-2,4-dionato Dy0.2, Y0.8 bathocuproine
tris 3-ethylpentane-2,4-dionato Dy0.2, Y0.8 bathophenanthroline
tris pivaloyltrifluoroacetonato Dy0.2, Y0.8 dimethylaminopyridine
tris pivaloyltrifluoroacetonato Dy0.2, Y0.8 4-picoline-N-oxide
tris pivaloyltrifluoroacetonato Dy0.2, Y0.8 4-phenylpyridine
tris pivaloyltrifluoroacetonato Dy0.2, Y0.8 4-cyanopyridine
tris pivaloyltrifluoroacetonato Dy0.2, Y0.8 4-phenylpyridine-N-oxide
tris pivaloyltrifluoroacetonato Dy0.2, Y0.8 1-methylimidazole
tris pivaloyltrifluoroacetonato Dy0.2, Y0.8 triphenylphosphine oxide
tris pivaloyltrifluoroacetonato Dy0.2, Y0.8 2,2-bipyridyl
tris pivaloyltrifluoroacetonato Dy0.2, Y0.8 2,2-bipyridyl-N,N-dioxide
tris pivaloyltrifluoroacetonato Dy0.2, Y0.8 phenanthroline
tris pivaloyltrifluoroacetonato Dy0.2, Y0.8 bathocuproine
tris pivaloyltrifluoroacetonato Dy0.2, Y0.8 bathophenanthroline tris trifluoroacetylacetonato Dy0.2, Y0.8 dimethylaminopyridine
tris trifluoroacetylacetonato Dy0.2, Y0.8 4-picoline-N-oxide
tris trifluoroacetylacetonato Dy0.2, Y0.8 4-phenylpyridine
tris trifluoroacetylacetonato Dy0.2, Y0.8 4-cyanopyridine
tris trifluoroacetylacetonato Dy0.2, Y0.8 4-phenylpyridine-N-oxide
tris trifluoroacetylacetonato Dy0.2, Y0.8 1-methylimidazole
tris trifluoroacetylacetonato Dy0.2, Y0.8 triphenylphosphine oxide
tris trifluoroacetylacetonato Dy0.2, Y0.8 2,2-bipyridyl
tris trifluoroacetylacetonato Dy0.2, Y0.8 2,2-bipyridyl-N,N-dioxide
tris trifluoroacetylacetonato Dy0.2, Y0.8 phenanthroline
tris trifluoroacetylacetonato Dy0.2, Y0.8 bathocuproine
tris trifluoroacetylacetonato Dy0.2, Y0.8 bathophenanthroline
tris hexafluoroacetylacetonato Dy0.2, Y0.8 dimethylaminopyridine
tris hexafluoroacetylacetonato Dy0.2, Y0.8 4-picoline-N-oxide
tris hexafluoroacetylacetonato Dy0.2, Y0.8 4-phenylpyridine
tris hexafluoroacetylacetonato Dy0.2, Y0.8 4-cyanopyridine
tris hexafluoroacetylacetonato Dy0.2, Y0.8 4-phenylpyridine-N-oxide
tris hexafluoroacetylacetonato Dy0.2, Y0.8 1-methylimidazole
tris hexafluoroacetylacetonato Dy0.2, Y0.8 triphenylphosphine oxide
tris hexafluoroacetylacetonato Dy0.2, Y0.8 2,2-bipyridyl
tris hexafluoroacetylacetonato Dy0.2, Y0.8 2,2-bipyridyl-N,N-dioxide
tris hexafluoroacetylacetonato Dy0.2, Y0.8 phenanthroline
tris hexafluoroacetylacetonato Dy0.2, Y0.8 bathocuproine
tris hexafluoroacetylacetonato Dy0.2, Y0.8 bathophenanthroline
tris 6,6,7,7,8,8,8-heptafluoro-2,2-dimethyloctanedionato Dy0.2, Y0.8 dimethylaminopyridine
tris 6,6,7,7,8,8,8-heptafluoro-2,2-dimethyloctanedionato Dy0.2, Y0.8 4-picoline-N-oxide
tris 6,6,7,7,8,8,8-heptafluoro-2,2-dimethyloctanedionato Dy0.2, Y0.8 4-phenylpyridine
tris 6,6,7,7,8,8,8-heptafluoro-2,2-dimethyloctanedionato Dy0.2, Y0.8 4-cyanopyridine
tris 6,6,7,7,8,8,8-heptafluoro-2,2-dimethyloctanedionato Dy0.2, Y0.8 4-phenylpyridine-N-oxide
tris 6,6,7,7,8,8,8-heptafluoro-2,2-dimethyloctanedionato Dy0.2, Y0.8 1-methylimidazole
tris 6,6,7,7,8,8,8-heptafluoro-2,2-dimethyloctanedionato Dy0.2, Y0.8 triphenylphosphine oxide
tris 6,6,7,7,8,8,8-heptafluoro-2,2-dimethyloctanedionato Dy0.2, Y0.8 2,2-bipyridyl
tris 6,6,7,7,8,8,8-heptafluoro-2,2-dimethyloctanedionato Dy0.2, Y0.8 2,2-bipyridyl-N,N-dioxide
tris 6,6,7,7,8,8,8-heptafluoro-2,2-dimethyloctanedionato Dy0.2, Y0.8 phenanthroline
tris 6,6,7,7,8,8,8-heptafluoro-2,2-dimethyloctanedionato Dy0.2, Y0.8 bathocuproine
tris 6,6,7,7,8,8,8-heptafluoro-2,2-dimethyloctanedionato Dy0.2, Y0.8 bathophenanthroline
tris 1-phenyl-1,3-butanedionato Dy0.2, Y0.8 dimethylaminopyridine
tris 1-phenyl-1,3-butanedionato Dy0.2, Y0.8 4-picoline-N-oxide
tris 1-phenyl-1,3-butanedionato Dy0.2, Y0.8 4-phenylpyridine
tris 1-phenyl-1,3-butanedionato Dy0.2, Y0.8 4-cyanopyridine
tris 1-phenyl-1,3-butanedionato Dy0.2, Y0.8 4-phenylpyridine-N-oxide
tris 1-phenyl-1,3-butanedionato Dy0.2, Y0.8 1-methylimidazole
tris 1-phenyl-1,3-butanedionato Dy0.2, Y0.8 triphenylphosphine oxide
tris 1-phenyl-1,3-butanedionato Dy0.2, Y0.8 2,2-bipyridyl
tris 1-phenyl-1,3-butanedionato Dy0.2, Y0.8 2,2-bipyridyl-N,N-dioxide
tris 1-phenyl-1,3-butanedionato Dy0.2, Y0.8 phenanthroline
tris 1-phenyl-1,3-butanedionato Dy0.2, Y0.8 bathocuproine
tris 1-phenyl-1,3-butanedionato Dy0.2, Y0.8 bathophenanthroline
tris acetylacetonato Dy0.1, Y0.9 dimethylaminopyridine
tris acetylacetonato Dy0.1, Y0.9 4-picoline-N-oxide
tris acetylacetonato Dy0.1, Y0.9 4-phenylpyridine
tris acetylacetonato Dy0.1, Y0.9 4-cyanopyridine
tris acetylacetonato Dy0.1, Y0.9 4-phenylpyridine-N-oxide
tris acetylacetonato Dy0.1, Y0.9 1-methylimidazole
tris acetylacetonato Dy0.1, Y0.9 triphenylphosphine oxide
tris acetylacetonato Dy0.1, Y0.9 2,2-bipyridyl
tris acetylacetonato Dy0.1, Y0.9 2,2-bipyridyl-N,N-dioxide
tris acetylacetonato Dy0.1, Y0.9 phenanthroline
tris acetylacetonato Dy0.1, Y0.9 bathocuproine
tris acetylacetonato Dy0.1, Y0.9 bathophenanthroline
tris dibenzoylmethanato Dy0.1, Y0.9 dimethylaminopyridine
tris dibenzoylmethanato Dy0.1, Y0.9 4-picoline-N-oxide
tris dibenzoylmethanato Dy0.1, Y0.9 4-phenylpyridine
tris dibenzoylmethanato Dy0.1, Y0.9 4-cyanopyridine
tris dibenzoylmethanato Dy0.1, Y0.9 4-phenylpyridine-N-oxide
tris dibenzoylmethanato Dy0.1, Y0.9 1-methylimidazole
tris dibenzoylmethanato Dy0.1, Y0.9 triphenylphosphine oxide
tris dibenzoylmethanato Dy0.1, Y0.9 2,2-bipyridyl
tris dibenzoylmethanato Dy0.1, Y0.9 2,2-bipyridyl-N,N-dioxide
tris dibenzoylmethanato Dy0.1, Y0.9 phenanthroline
tris dibenzoylmethanato Dy0.1, Y0.9 bathocuproine
tris dibenzoylmethanato Dy0.1, Y0.9 bathophenanthroline
tris thenoyltrifluoroacetonato Dy0.1, Y0.9 dimethylaminopyridine
tris thenoyltrifluoroacetonato Dy0.1, Y0.9 4-picoline-N-oxide
tris thenoyltrifluoroacetonato Dy0.1, Y0.9 4-phenylpyridine
tris thenoyltrifluoroacetonato Dy0.1, Y0.9 4-cyanopyridine
tris thenoyltrifluoroacetonato Dy0.1, Y0.9 4-phenylpyridine-N-oxide
tris thenoyltrifluoroacetonato Dy0.1, Y0.9 1-methylimidazole
tris thenoyltrifluoroacetonato Dy0.1, Y0.9 triphenylphosphine oxide
tris thenoyltrifluoroacetonato Dy0.1, Y0.9 2,2-bipyridyl
tris thenoyltrifluoroacetonato Dy0.1, Y0.9 2,2-bipyridyl-N,N-dioxide
tris thenoyltrifluoroacetonato Dy0.1, Y0.9 phenanthroline
tris thenoyltrifluoroacetonato Dy0.1, Y0.9 bathocuproine
tris thenoyltrifluoroacetonato Dy0.1, Y0.9 bathophenanthroline
tris 2,2,6,6-tetramethylheptanedionato Dy0.1, Y0.9 dimethylaminopyridine
tris 2,2,6,6-tetramethylheptanedionato Dy0.1, Y0.9 4-picoline-N-oxide tris 2,2,6,6-tetramethylheptanedionato Dy0.1, Y0.9 4-phenylpyridine
tris 2,2,6,6-tetramethylheptanedionato Dy0.1, Y0.9 4-cyanopyridine
tris 2,2,6,6-tetramethylheptanedionato Dy0.1, Y0.9 4-phenylpyridine-N-oxide
tris 2,2,6,6-tetramethylheptanedionato Dy0.1, Y0.9 1-methylimidazole
tris 2,2,6,6-tetramethylheptanedionato Dy0.1, Y0.9 triphenylphosphine oxide
tris 2,2,6,6-tetramethylheptanedionato Dy0.1, Y0.9 2,2-bipyridyl
tris 2,2,6,6-tetramethylheptanedionato Dy0.1, Y0.9 2,2-bipyridyl-N,N-dioxide
tris 2,2,6,6-tetramethylheptanedionato Dy0.1, Y0.9 phenanthroline
tris 2,2,6,6-tetramethylheptanedionato Dy0.1, Y0.9 bathocuproine
tris 2,2,6,6-tetramethylheptanedionato Dy0.1, Y0.9 bathophenanthroline
tris 3-methylpentane-2,4-dionato Dy0.1, Y0.9 dimethylaminopyridine
tris 3-methylpentane-2,4-dionato Dy0.1, Y0.9 4-picoline-N-oxide
tris 3-methylpentane-2,4-dionato Dy0.1, Y0.9 4-phenylpyridine
tris 3-methylpentane-2,4-dionato Dy0.1, Y0.9 4-cyanopyridine
tris 3-methylpentane-2,4-dionato Dy0.1, Y0.9 4-phenylpyridine-N-oxide
tris 3-methylpentane-2,4-dionato Dy0.1, Y0.9 1-methylimidazole
tris 3-methylpentane-2,4-dionato Dy0.1, Y0.9 triphenylphosphine oxide
tris 3-methylpentane-2,4-dionato Dy0.1, Y0.9 2,2-bipyridyl
tris 3-methylpentane-2,4-dionato Dy0.1, Y0.9 2,2-bipyridyl-N,N-dioxide
tris 3-methylpentane-2,4-dionato Dy0.1, Y0.9 phenanthroline
tris 3-methylpentane-2,4-dionato Dy0.1, Y0.9 bathocuproine
tris 3-methylpentane-2,4-dionato Dy0.1, Y0.9 bathophenanthroline
tris 3-ethylpentane-2,4-dionato Dy0.1, Y0.9 dimethylaminopyridine
tris 3-ethylpentane-2,4-dionato Dy0.1, Y0.9 4-picoline-N-oxide
tris 3-ethylpentane-2,4-dionato Dy0.1, Y0.9 4-phenylpyridine
tris 3-ethylpentane-2,4-dionato Dy0.1, Y0.9 4-cyanopyridine
tris 3-ethylpentane-2,4-dionato Dy0.1, Y0.9 4-phenylpyridine-N-oxide
tris 3-ethylpentane-2,4-dionato Dy0.1, Y0.9 1-methylimidazole
tris 3-ethylpentane-2,4-dionato Dy0.1, Y0.9 triphenylphosphine oxide
tris 3-ethylpentane-2,4-dionato Dy0.1, Y0.9 2,2-bipyridyl
tris 3-ethylpentane-2,4-dionato Dy0.1, Y0.9 2,2-bipyridyl-N,N-dioxide
tris 3-ethylpentane-2,4-dionato Dy0.1, Y0.9 phenanthroline
tris 3-ethylpentane-2,4-dionato Dy0.1, Y0.9 bathocuproine
tris 3-ethylpentane-2,4-dionato Dy0.1, Y0.9 bathophenanthroline
tris pivaloyltrifluoroacetonato Dy0.1, Y0.9 dimethylaminopyridine
tris pivaloyltrifluoroacetonato Dy0.1, Y0.9 4-picoline-N-oxide
tris pivaloyltrifluoroacetonato Dy0.1, Y0.9 4-phenylpyridine
tris pivaloyltrifluoroacetonato Dy0.1, Y0.9 4-cyanopyridine
tris pivaloyltrifluoroacetonato Dy0.1, Y0.9 4-phenylpyridine-N-oxide
tris pivaloyltrifluoroacetonato Dy0.1, Y0.9 1-methylimidazole
tris pivaloyltrifluoroacetonato Dy0.1, Y0.9 triphenylphosphine oxide
tris pivaloyltrifluoroacetonato Dy0.1, Y0.9 2,2-bipyridyl
tris pivaloyltrifluoroacetonato Dy0.1, Y0.9 2,2-bipyridyl-N,N-dioxide
tris pivaloyltrifluoroacetonato Dy0.1, Y0.9 phenanthroline
tris pivaloyltrifluoroacetonato Dy0.1, Y0.9 bathocuproine
tris pivaloyltrifluoroacetonato Dy0.1, Y0.9 bathophenanthroline
tris trifluoroacetylacetonato Dy0.1, Y0.9 dimethylaminopyridine
tris trifluoroacetylacetonato Dy0.1, Y0.9 4-picoline-N-oxide
tris trifluoroacetylacetonato Dy0.1, Y0.9 4-phenylpyridine
tris trifluoroacetylacetonato Dy0.1, Y0.9 4-cyanopyridine
tris trifluoroacetylacetonato Dy0.1, Y0.9 4-phenylpyridine-N-oxide
tris trifluoroacetylacetonato Dy0.1, Y0.9 1-methylimidazole
tris trifluoroacetylacetonato Dy0.1, Y0.9 triphenylphosphine oxide
tris trifluoroacetylacetonato Dy0.1, Y0.9 2,2-bipyridyl
tris trifluoroacetylacetonato Dy0.1, Y0.9 2,2-bipyridyl-N,N-dioxide
tris trifluoroacetylacetonato Dy0.1, Y0.9 phenanthroline
tris trifluoroacetylacetonato Dy0.1, Y0.9 bathocuproine
tris trifluoroacetylacetonato Dy0.1, Y0.9 bathophenanthroline
tris hexafluoroacetylacetonato Dy0.1, Y0.9 dimethylaminopyridine
tris hexafluoroacetylacetonato Dy0.1, Y0.9 4-picoline-N-oxide
tris hexafluoroacetylacetonato Dy0.1, Y0.9 4-phenylpyridine
tris hexafluoroacetylacetonato Dy0.1, Y0.9 4-cyanopyridine
tris hexafluoroacetylacetonato Dy0.1, Y0.9 4-phenylpyridine-N-oxide
tris hexafluoroacetylacetonato Dy0.1, Y0.9 1-methylimidazole
tris hexafluoroacetylacetonato Dy0.1, Y0.9 triphenylphosphine oxide
tris hexafluoroacetylacetonato Dy0.1, Y0.9 2,2-bipyridyl
tris hexafluoroacetylacetonato Dy0.1, Y0.9 2,2-bipyridyl-N,N-dioxide
tris hexafluoroacetylacetonato Dy0.1, Y0.9 phenanthroline
tris hexafluoroacetylacetonato Dy0.1, Y0.9 bathocuproine
tris hexafluoroacetylacetonato Dy0.1, Y0.9 bathophenanthroline
tris 6,6,7,7,8,8,8-heptafluoro-2,2-dimethyloctanedionato Dy0.1, Y0.9 dimethylaminopyridine
tris 6,6,7,7,8,8,8-heptafluoro-2,2-dimethyloctanedionato Dy0.1, Y0.9 4-picoline-N-oxide
tris 6,6,7,7,8,8,8-heptafluoro-2,2-dimethyloctanedionato Dy0.1, Y0.9 4-phenylpyridine
tris 6,6,7,7,8,8,8-heptafluoro-2,2-dimethyloctanedionato Dy0.1, Y0.9 4-cyanopyridine
tris 6,6,7,7,8,8,8-heptafluoro-2,2-dimethyloctanedionato Dy0.1, Y0.9 4-phenylpyridine-N-oxide
tris 6,6,7,7,8,8,8-heptafluoro-2,2-dimethyloctanedionato Dy0.1, Y0.9 1-methylimidazole tris 6,6,7,7,8,8-heptafluoro-2,2-dimethyloctanedionato Dy0.1, Y0.9 triphenylphosphine oxide
tris 6,6,7,7,8,8-heptafluoro-2,2-dimethyloctanedionato Dy0.1, Y0.9 2,2-bipyridyl
tris 6,6,7,7,8,8-heptafluoro-2,2-dimethyloctanedionato Dy0.1, Y0.9 2,2-bipyridyl-N,N-dioxide
tris 6,6,7,7,8,8-heptafluoro-2,2-dimethyloctanedionato Dy0.1, Y0.9 phenanthroline
tris 6,6,7,7,8,8-heptafluoro-2,2-dimethyloctanedionato Dy0.1, Y0.9 bathocuproine
tris 6,6,7,7,8,8-heptafluoro-2,2-dimethyloctanedionato Dy0.1, Y0.9 bathophenanthroline
tris 1-phenyl-1,3-butanedionato Dy0.1, Y0.9 dimethylaminopyridine
tris 1-phenyl-1,3-butanedionato Dy0.1, Y0.9 4-picoline-N-oxide
tris 1-phenyl-1,3-butanedionato Dy0.1, Y0.9 4-phenylpyridine
tris 1-phenyl-1,3-butanedionato Dy0.1, Y0.9 4-cyanopyridine
tris 1-phenyl-1,3-butanedionato Dy0.1, Y0.9 4-phenylpyridine-N-oxide
tris 1-phenyl-1,3-butanedionato Dy0.1, Y0.9 1-methylimidazole
tris 1-phenyl-1,3-butanedionato Dy0.1, Y0.9 triphenylphosphine oxide
tris 1-phenyl-1,3-butanedionato Dy0.1, Y0.9 2,2-bipyridyl
tris 1-phenyl-1,3-butanedionato Dy0.1, Y0.9 2,2-bipyridyl-N,N-dioxide
tris 1-phenyl-1,3-butanedionato Dy0.1, Y0.9 phenanthroline
tris 1-phenyl-1,3-butanedionato Dy0.1, Y0.9 bathocuproine
tris 1-phenyl-1,3-butanedionato Dy0.1, Y0.9 bathophenanthroline
tris acetylacetonato Dy0.01, Y0.99 dimethylaminopyridine
tris acetylacetonato Dy0.01, Y0.99 4-picoline-N-oxide
tris acetylacetonato Dy0.01, Y0.99 4-phenylpyridine
tris acetylacetonato Dy0.01, Y0.99 4-cyanopyridine
tris acetylacetonato Dy0.01, Y0.99 4-phenylpyridine-N-oxide
tris acetylacetonato Dy0.01, Y0.99 1-methylimidazole
tris acetylacetonato Dy0.01, Y0.99 triphenylphosphine oxide
tris acetylacetonato Dy0.01, Y0.99 2,2-bipyridyl
tris acetylacetonato Dy0.01, Y0.99 2,2-bipyridyl-N,N-dioxide
tris acetylacetonato Dy0.01, Y0.99 phenanthroline
tris acetylacetonato Dy0.01, Y0.99 bathocuproine
tris acetylacetonato Dy0.01, Y0.99 bathophenanthroline
tris dibenzoylmethanato Dy0.01, Y0.99 dimethylaminopyridine
tris dibenzoylmethanato Dy0.01, Y0.99 4-picoline-N-oxide
tris dibenzoylmethanato Dy0.01, Y0.99 4-phenylpyridine
tris dibenzoylmethanato Dy0.01, Y0.99 4-cyanopyridine
tris dibenzoylmethanato Dy0.01, Y0.99 4-phenylpyridine-N-oxide
tris dibenzoylmethanato Dy0.01, Y0.99 1-methylimidazole
tris dibenzoylmethanato Dy0.01, Y0.99 triphenylphosphine oxide
tris dibenzoylmethanato Dy0.01, Y0.99 2,2-bipyridyl
tris dibenzoylmethanato Dy0.01, Y0.99 2,2-bipyridyl-N,N-dioxide
tris dibenzoylmethanato Dy0.01, Y0.99 phenanthroline
tris dibenzoylmethanato Dy0.01, Y0.99 bathocuproine
tris dibenzoylmethanato Dy0.01, Y0.99 bathophenanthroline
tris thenoyltrifluoroacetonato Dy0.01, Y0.99 dimethylaminopyridine
tris thenoyltrifluoroacetonato Dy0.01, Y0.99 4-picoline-N-oxide
tris thenoyltrifluoroacetonato Dy0.01, Y0.99 4-phenylpyridine
tris thenoyltrifluoroacetonato Dy0.01, Y0.99 4-cyanopyridine
tris thenoyltrifluoroacetonato Dy0.01, Y0.99 4-phenylpyridine-N-oxide
tris thenoyltrifluoroacetonato Dy0.01, Y0.99 1-methylimidazole
tris thenoyltrifluoroacetonato Dy0.01, Y0.99 triphenylphosphine oxide
tris thenoyltrifluoroacetonato Dy0.01, Y0.99 2,2-bipyridyl
tris thenoyltrifluoroacetonato Dy0.01, Y0.99 2,2-bipyridyl-N,N-dioxide
tris thenoyltrifluoroacetonato Dy0.01, Y0.99 phenanthroline
tris thenoyltrifluoroacetonato Dy0.01, Y0.99 bathocuproine
tris thenoyltrifluoroacetonato Dy0.01, Y0.99 bathophenanthroline
tris 2,2,6,6-tetramethylheptanedionato Dy0.01, Y0.99 dimethylaminopyridine
tris 2,2,6,6-tetramethylheptanedionato Dy0.01, Y0.99 4-picoline-N-oxide
tris 2,2,6,6-tetramethylheptanedionato Dy0.01, Y0.99 4-phenylpyridine
tris 2,2,6,6-tetramethylheptanedionato Dy0.01, Y0.99 4-cyanopyridine
tris 2,2,6,6-tetramethylheptanedionato Dy0.01, Y0.99 4-phenylpyridine-N-oxide
tris 2,2,6,6-tetramethylheptanedionato Dy0.01, Y0.99 1-methylimidazole
tris 2,2,6,6-tetramethylheptanedionato Dy0.01, Y0.99 triphenylphosphine oxide
tris 2,2,6,6-tetramethylheptanedionato Dy0.01, Y0.99 2,2-bipyridyl
tris 2,2,6,6-tetramethylheptanedionato Dy0.01, Y0.99 2,2-bipyridyl-N,N-dioxide
tris 2,2,6,6-tetramethylheptanedionato Dy0.01, Y0.99 phenanthroline
tris 2,2,6,6-tetramethylheptanedionato Dy0.01, Y0.99 bathocuproine
tris 2,2,6,6-tetramethylheptanedionato Dy0.01, Y0.99 bathophenanthroline
tris 3-methylpentane-2,4-dionato Dy0.01, Y0.99 dimethylaminopyridine
tris 3-methylpentane-2,4-dionato Dy0.01, Y0.99 4-picoline-N-oxide
tris 3-methylpentane-2,4-dionato Dy0.01, Y0.99 4-phenylpyridine
tris 3-methylpentane-2,4-dionato Dy0.01, Y0.99 4-cyanopyridine
tris 3-methylpentane-2,4-dionato Dy0.01, Y0.99 4-phenylpyridine-N-oxide
tris 3-methylpentane-2,4-dionato Dy0.01, Y0.99 1-methylimidazole
tris 3-methylpentane-2,4-dionato Dy0.01, Y0.99 triphenylphosphine oxide
tris 3-methylpentane-2,4-dionato Dy0.01, Y0.99 2,2-bipyridyl
tris 3-methylpentane-2,4-dionato Dy0.01, Y0.99 2,2-bipyridyl-N,N-dioxide
tris 3-methylpentane-2,4-dionato Dy0.01, Y0.99 phenanthroline
tris 3-methylpentane-2,4-dionato Dy0.01, Y0.99 bathocuproine
tris 3-methylpentane-2,4-dionato Dy0.01, Y0.99 bathophenanthroline tris 3-ethylpentane-2,4-dionato Dy0.01, Y0.99 dimethylaminopyridine
tris 3-ethylpentane-2,4-dionato Dy0.01, Y0.99 4-picoline-N-oxide
tris 3-ethylpentane-2,4-dionato Dy0.01, Y0.99 4-phenylpyridine
tris 3-ethylpentane-2,4-dionato Dy0.01, Y0.99 4-cyanopyridine
tris 3-ethylpentane-2,4-dionato Dy0.01, Y0.99 4-phenylpyridine-N-oxide
tris 3-ethylpentane-2,4-dionato Dy0.01, Y0.99 1-methylimidazole
tris 3-ethylpentane-2,4-dionato Dy0.01, Y0.99 triphenylphosphine oxide
tris 3-ethylpentane-2,4-dionato Dy0.01, Y0.99 2,2-bipyridyl
tris 3-ethylpentane-2,4-dionato Dy0.01, Y0.99 2,2-bipyridyl-N,N-dioxide
tris 3-ethylpentane-2,4-dionato Dy0.01, Y0.99 phenanthroline
tris 3-ethylpentane-2,4-dionato Dy0.01, Y0.99 bathocuproine
tris 3-ethylpentane-2,4-dionato Dy0.01, Y0.99 bathophenanthroline
tris pivaloyltrifluoroacetonato Dy0.01, Y0.99 dimethylaminopyridine
tris pivaloyltrifluoroacetonato Dy0.01, Y0.99 4-picoline-N-oxide
tris pivaloyltrifluoroacetonato Dy0.01, Y0.99 4-phenylpyridine
tris pivaloyltrifluoroacetonato Dy0.01, Y0.99 4-cyanopyridine
tris pivaloyltrifluoroacetonato Dy0.01, Y0.99 4-phenylpyridine-N-oxide
tris pivaloyltrifluoroacetonato Dy0.01, Y0.99 1-methylimidazole
tris pivaloyltrifluoroacetonato Dy0.01, Y0.99 triphenylphosphine oxide
tris pivaloyltrifluoroacetonato Dy0.01, Y0.99 2,2-bipyridyl
tris pivaloyltrifluoroacetonato Dy0.01, Y0.99 2,2-bipyridyl-N,N-dioxide
tris pivaloyltrifluoroacetonato Dy0.01, Y0.99 phenanthroline
tris pivaloyltrifluoroacetonato Dy0.01, Y0.99 bathocuproine
tris pivaloyltrifluoroacetonato Dy0.01, Y0.99 bathophenanthroline
tris trifluoroacetylacetonato Dy0.01, Y0.99 dimethylaminopyridine
tris trifluoroacetylacetonato Dy0.01, Y0.99 4-picoline-N-oxide
tris trifluoroacetylacetonato Dy0.01, Y0.99 4-phenylpyridine
tris trifluoroacetylacetonato Dy0.01, Y0.99 4-cyanopyridine
tris trifluoroacetylacetonato Dy0.01, Y0.99 4-phenylpyridine-N-oxide
tris trifluoroacetylacetonato Dy0.01, Y0.99 1-methylimidazole
tris trifluoroacetylacetonato Dy0.01, Y0.99 triphenylphosphine oxide
tris trifluoroacetylacetonato Dy0.01, Y0.99 2,2-bipyridyl
tris trifluoroacetylacetonato Dy0.01, Y0.99 2,2-bipyridyl-N,N-dioxide
tris trifluoroacetylacetonato Dy0.01, Y0.99 phenanthroline
tris trifluoroacetylacetonato Dy0.01, Y0.99 bathocuproine
tris trifluoroacetylacetonato Dy0.01, Y0.99 bathophenanthroline
tris hexafluoroacetylacetonato Dy0.01, Y0.99 dimethylaminopyridine
tris hexafluoroacetylacetonato Dy0.01, Y0.99 4-picoline-N-oxide
tris hexafluoroacetylacetonato Dy0.01, Y0.99 4-phenylpyridine
tris hexafluoroacetylacetonato Dy0.01, Y0.99 4-cyanopyridine
tris hexafluoroacetylacetonato Dy0.01, Y0.99 4-phenylpyridine-N-oxide
tris hexafluoroacetylacetonato Dy0.01, Y0.99 1-methylimidazole
tris hexafluoroacetylacetonato Dy0.01, Y0.99 triphenylphosphine oxide
tris hexafluoroacetylacetonato Dy0.01, Y0.99 2,2-bipyridyl
tris hexafluoroacetylacetonato Dy0.01, Y0.99 2,2-bipyridyl-N,N-dioxide
tris hexafluoroacetylacetonato Dy0.01, Y0.99 phenanthroline
tris hexafluoroacetylacetonato Dy0.01, Y0.99 bathocuproine
tris hexafluoroacetylacetonato Dy0.01, Y0.99 bathophenanthroline
tris 6,6,7,7,8,8,8-heptafluoro-2,2-dimethyloctanedionato Dy0.01, Y0.99 dimethylaminopyridine
tris 6,6,7,7,8,8,8-heptafluoro-2,2-dimethyloctanedionato Dy0.01, Y0.99 4-picoline-N-oxide
tris 6,6,7,7,8,8,8-heptafluoro-2,2-dimethyloctanedionato Dy0.01, Y0.99 4-phenylpyridine
tris 6,6,7,7,8,8,8-heptafluoro-2,2-dimethyloctanedionato Dy0.01, Y0.99 4-cyanopyridine
tris 6,6,7,7,8,8,8-heptafluoro-2,2-dimethyloctanedionato Dy0.01, Y0.99 4-phenylpyridine-N-oxide
tris 6,6,7,7,8,8,8-heptafluoro-2,2-dimethyloctanedionato Dy0.01, Y0.99 1-methylimidazole
tris 6,6,7,7,8,8,8-heptafluoro-2,2-dimethyloctanedionato Dy0.01, Y0.99 triphenylphosphine oxide
tris 6,6,7,7,8,8,8-heptafluoro-2,2-dimethyloctanedionato Dy0.01, Y0.99 2,2-bipyridyl
tris 6,6,7,7,8,8,8-heptafluoro-2,2-dimethyloctanedionato Dy0.01, Y0.99 2,2-bipyridyl-N,N-dioxide
tris 6,6,7,7,8,8,8-heptafluoro-2,2-dimethyloctanedionato Dy0.01, Y0.99 phenanthroline
tris 6,6,7,7,8,8,8-heptafluoro-2,2-dimethyloctanedionato Dy0.01, Y0.99 bathocuproine
tris 6,6,7,7,8,8,8-heptafluoro-2,2-dimethyloctanedionato Dy0.01, Y0.99 bathophenanthroline
tris 1-phenyl-1,3-butanedionato Dy0.01, Y0.99 dimethylaminopyridine
tris 1-phenyl-1,3-butanedionato Dy0.01, Y0.99 4-picoline-N-oxide
tris 1-phenyl-1,3-butanedionato Dy0.01, Y0.99 4-phenylpyridine
tris 1-phenyl-1,3-butanedionato Dy0.01, Y0.99 4-cyanopyridine
tris 1-phenyl-1,3-butanedionato Dy0.01, Y0.99 4-phenylpyridine-N-oxide
tris 1-phenyl-1,3-butanedionato Dy0.01, Y0.99 1-methylimidazole
tris 1-phenyl-1,3-butanedionato Dy0.01, Y0.99 triphenylphosphine oxide
tris 1-phenyl-1,3-butanedionato Dy0.01, Y0.99 2,2-bipyridyl
tris 1-phenyl-1,3-butanedionato Dy0.01, Y0.99 2,2-bipyridyl-N,N-dioxide
tris 1-phenyl-1,3-butanedionato Dy0.01, Y0.99 phenanthroline
tris 1-phenyl-1,3-butanedionato Dy0.01, Y0.99 bathocuproine tris 1-phenyl-1,3-butanedionato Dy0.01, Y0.99 bathophenanthroline
tris acetylacetonato Dy0.5, Y0.5 dimethylaminopyridine
tris acetylacetonato Dy0.5, Y0.5 4-picoline-N-oxide
tris acetylacetonato Dy0.5, Y0.5 4-phenylpyridine
tris acetylacetonato Dy0.5, Y0.5 4-cyanopyridine
tris acetylacetonato Dy0.5, Y0.5 4-phenylpyridine-N-oxide
tris acetylacetonato Dy0.5, Y0.5 1-methylimidazole
tris acetylacetonato Dy0.5, Y0.5 triphenylphosphine oxide
tris acetylacetonato Dy0.5, Y0.5 2,2-bipyridyl
tris acetylacetonato Dy0.5, Y0.5 2,2-bipyridyl-N,N-dioxide
tris acetylacetonato Dy0.5, Y0.5 phenanthroline
tris acetylacetonato Dy0.5, Y0.5 bathocuproine
tris acetylacetonato Dy0.5, Y0.5 bathophenanthroline
tris dibenzoylmethanato Dy0.5, Y0.5 dimethylaminopyridine
tris dibenzoylmethanato Dy0.5, Y0.5 4-picoline-N-oxide
tris dibenzoylmethanato Dy0.5, Y0.5 4-phenylpyridine
tris dibenzoylmethanato Dy0.5, Y0.5 4-cyanopyridine
tris dibenzoylmethanato Dy0.5, Y0.5 4-phenylpyridine-N-oxide
tris dibenzoylmethanato Dy0.5, Y0.5 1-methylimidazole
tris dibenzoylmethanato Dy0.5, Y0.5 triphenylphosphine oxide
tris dibenzoylmethanato Dy0.5, Y0.5 2,2-bipyridyl
tris dibenzoylmethanato Dy0.5, Y0.5 2,2-bipyridyl-N,N-dioxide
tris dibenzoylmethanato Dy0.5, Y0.5 phenanthroline
tris dibenzoylmethanato Dy0.5, Y0.5 bathocuproine
tris dibenzoylmethanato Dy0.5, Y0.5 bathophenanthroline
tris thenoyltrifluoroacetonato Dy0.5, Y0.5 dimethylaminopyridine
tris thenoyltrifluoroacetonato Dy0.5, Y0.5 4-picoline-N-oxide
tris thenoyltrifluoroacetonato Dy0.5, Y0.5 4-phenylpyridine
tris thenoyltrifluoroacetonato Dy0.5, Y0.5 4-cyanopyridine
tris thenoyltrifluoroacetonato Dy0.5, Y0.5 4-phenylpyridine-N-oxide
tris thenoyltrifluoroacetonato Dy0.5, Y0.5 1-methylimidazole
tris thenoyltrifluoroacetonato Dy0.5, Y0.5 triphenylphosphine oxide
tris thenoyltrifluoroacetonato Dy0.5, Y0.5 2,2-bipyridyl
tris thenoyltrifluoroacetonato Dy0.5, Y0.5 2,2-bipyridyl-N,N-dioxide
tris thenoyltrifluoroacetonato Dy0.5, Y0.5 phenanthroline
tris thenoyltrifluoroacetonato Dy0.5, Y0.5 bathocuproine
tris thenoyltrifluoroacetonato Dy0.5, Y0.5 bathophenanthroline
tris 2,2,6,6-tetramethylheptanedionato Dy0.5, Y0.5 dimethylaminopyridine
tris 2,2,6,6-tetramethylheptanedionato Dy0.5, Y0.5 4-picoline-N-oxide
tris 2,2,6,6-tetramethylheptanedionato Dy0.5, Y0.5 4-phenylpyridine
tris 2,2,6,6-tetramethylheptanedionato Dy0.5, Y0.5 4-cyanopyridine
tris 2,2,6,6-tetramethylheptanedionato Dy0.5, Y0.5 4-phenylpyridine-N-oxide
tris 2,2,6,6-tetramethylheptanedionato Dy0.5, Y0.5 1-methylimidazole
tris 2,2,6,6-tetramethylheptanedionato Dy0.5, Y0.5 triphenylphosphine oxide
tris 2,2,6,6-tetramethylheptanedionato Dy0.5, Y0.5 2,2-bipyridyl
tris 2,2,6,6-tetramethylheptanedionato Dy0.5, Y0.5 2,2-bipyridyl-N,N-dioxide
tris 2,2,6,6-tetramethylheptanedionato Dy0.5, Y0.5 phenanthroline
tris 2,2,6,6-tetramethylheptanedionato Dy0.5, Y0.5 bathocuproine
tris 2,2,6,6-tetramethylheptanedionato Dy0.5, Y0.5 bathophenanthroline
tris 3-methylpentane-2,4-dionato Dy0.5, Y0.5 dimethylaminopyridine
tris 3-methylpentane-2,4-dionato Dy0.5, Y0.5 4-picoline-N-oxide
tris 3-methylpentane-2,4-dionato Dy0.5, Y0.5 4-phenylpyridine
tris 3-methylpentane-2,4-dionato Dy0.5, Y0.5 4-cyanopyridine
tris 3-methylpentane-2,4-dionato Dy0.5, Y0.5 4-phenylpyridine-N-oxide
tris 3-methylpentane-2,4-dionato Dy0.5, Y0.5 1-methylimidazole
tris 3-methylpentane-2,4-dionato Dy0.5, Y0.5 triphenylphosphine oxide
tris 3-methylpentane-2,4-dionato Dy0.5, Y0.5 2,2-bipyridyl
tris 3-methylpentane-2,4-dionato Dy0.5, Y0.5 2,2-bipyridyl-N,N-dioxide
tris 3-methylpentane-2,4-dionato Dy0.5, Y0.5 phenanthroline
tris 3-methylpentane-2,4-dionato Dy0.5, Y0.5 bathocuproine
tris 3-methylpentane-2,4-dionato Dy0.5, Y0.5 bathophenanthroline
tris 3-ethylpentane-2,4-dionato Dy0.5, Y0.5 dimethylaminopyridine
tris 3-ethylpentane-2,4-dionato Dy0.5, Y0.5 4-picoline-N-oxide
tris 3-ethylpentane-2,4-dionato Dy0.5, Y0.5 4-phenylpyridine
tris 3-ethylpentane-2,4-dionato Dy0.5, Y0.5 4-cyanopyridine
tris 3-ethylpentane-2,4-dionato Dy0.5, Y0.5 4-phenylpyridine-N-oxide
tris 3-ethylpentane-2,4-dionato Dy0.5, Y0.5 1-methylimidazole
tris 3-ethylpentane-2,4-dionato Dy0.5, Y0.5 triphenylphosphine oxide
tris 3-ethylpentane-2,4-dionato Dy0.5, Y0.5 2,2-bipyridyl
tris 3-ethylpentane-2,4-dionato Dy0.5, Y0.5 2,2-bipyridyl-N,N-dioxide
tris 3-ethylpentane-2,4-dionato Dy0.5, Y0.5 phenanthroline
tris 3-ethylpentane-2,4-dionato Dy0.5, Y0.5 bathocuproine
tris 3-ethylpentane-2,4-dionato Dy0.5, Y0.5 bathophenanthroline
tris pivaloyltrifluoroacetonato Dy0.5, Y0.5 dimethylaminopyridine
tris pivaloyltrifluoroacetonato Dy0.5, Y0.5 4-picoline-N-oxide
tris pivaloyltrifluoroacetonato Dy0.5, Y0.5 4-phenylpyridine
tris pivaloyltrifluoroacetonato Dy0.5, Y0.5 4-cyanopyridine
tris pivaloyltrifluoroacetonato Dy0.5, Y0.5 4-phenylpyridine-N-oxide
tris pivaloyltrifluoroacetonato Dy0.5, Y0.5 1-methylimidazole
tris pivaloyltrifluoroacetonato Dy0.5, Y0.5 triphenylphosphine oxide
tris pivaloyltrifluoroacetonato Dy0.5, Y0.5 2,2-bipyridyl
tris pivaloyltrifluoroacetonato Dy0.5, Y0.5 2,2-bipyridyl-N,N-dioxide
tris pivaloyltrifluoroacetonato Dy0.5, Y0.5 phenanthroline tris pivaloyltrifluoroacetonato Dy0.5, Y0.5 bathocuproine
tris pivaloyltrifluoroacetonato Dy0.5, Y0.5 bathophenanthroline
tris trifluoroacetylacetonato Dy0.5, Y0.5 dimethylaminopyridine
tris trifluoroacetylacetonato Dy0.5, Y0.5 4-picoline-N-oxide
tris trifluoroacetylacetonato Dy0.5, Y0.5 4-phenylpyridine
tris trifluoroacetylacetonato Dy0.5, Y0.5 4-cyanopyridine
tris trifluoroacetylacetonato Dy0.5, Y0.5 4-phenylpyridine-N-oxide
tris trifluoroacetylacetonato Dy0.5, Y0.5 1-methylimidazole
tris trifluoroacetylacetonato Dy0.5, Y0.5 triphenylphosphine oxide
tris trifluoroacetylacetonato Dy0.5, Y0.5 2,2-bipyridyl
tris trifluoroacetylacetonato Dy0.5, Y0.5 2,2-bipyridyl-N,N-dioxide
tris trifluoroacetylacetonato Dy0.5, Y0.5 phenanthroline
tris trifluoroacetylacetonato Dy0.5, Y0.5 bathocuproine
tris trifluoroacetylacetonato Dy0.5, Y0.5 bathophenanthroline
tris hexafluoroacetylacetonato Dy0.5, Y0.5 dimethylaminopyridine
tris hexafluoroacetylacetonato Dy0.5, Y0.5 4-picoline-N-oxide
tris hexafluoroacetylacetonato Dy0.5, Y0.5 4-phenylpyridine
tris hexafluoroacetylacetonato Dy0.5, Y0.5 4-cyanopyridine
tris hexafluoroacetylacetonato Dy0.5, Y0.5 4-phenylpyridine-N-oxide
tris hexafluoroacetylacetonato Dy0.5, Y0.5 1-methylimidazole
tris hexafluoroacetylacetonato Dy0.5, Y0.5 triphenylphosphine oxide
tris hexafluoroacetylacetonato Dy0.5, Y0.5 2,2-bipyridyl
tris hexafluoroacetylacetonato Dy0.5, Y0.5 2,2-bipyridyl-N,N-dioxide
tris hexafluoroacetylacetonato Dy0.5, Y0.5 phenanthroline
tris hexafluoroacetylacetonato Dy0.5, Y0.5 bathocuproine
tris hexafluoroacetylacetonato Dy0.5, Y0.5 bathophenanthroline
tris 6,6,7,7,8,8,8-heptafluoro-2,2-dimethyloctanedionato Dy0.5, Y0.5 dimethylaminopyridine
tris 6,6,7,7,8,8,8-heptafluoro-2,2-dimethyloctanedionato Dy0.5, Y0.5 4-picoline-N-oxide
tris 6,6,7,7,8,8,8-heptafluoro-2,2-dimethyloctanedionato Dy0.5, Y0.5 4-phenylpyridine
tris 6,6,7,7,8,8,8-heptafluoro-2,2-dimethyloctanedionato Dy0.5, Y0.5 4-cyanopyridine
tris 6,6,7,7,8,8,8-heptafluoro-2,2-dimethyloctanedionato Dy0.5, Y0.5 4-phenylpyridine-N-oxide
tris 6,6,7,7,8,8,8-heptafluoro-2,2-dimethyloctanedionato Dy0.5, Y0.5 1-methylimidazole
tris 6,6,7,7,8,8,8-heptafluoro-2,2-dimethyloctanedionato Dy0.5, Y0.5 triphenylphosphine oxide
tris 6,6,7,7,8,8,8-heptafluoro-2,2-dimethyloctanedionato Dy0.5, Y0.5 2,2-bipyridyl
tris 6,6,7,7,8,8,8-heptafluoro-2,2-dimethyloctanedionato Dy0.5, Y0.5 2,2-bipyridyl-N,N-dioxide
tris 6,6,7,7,8,8,8-heptafluoro-2,2-dimethyloctanedionato Dy0.5, Y0.5 phenanthroline
tris 6,6,7,7,8,8,8-heptafluoro-2,2-dimethyloctanedionato Dy0.5, Y0.5 bathocuproine
tris 6,6,7,7,8,8,8-heptafluoro-2,2-dimethyloctanedionato Dy0.5, Y0.5 bathophenanthroline
tris 1-phenyl-1,3-butanedionato Dy0.5, Y0.5 dimethylaminopyridine
tris 1-phenyl-1,3-butanedionato Dy0.5, Y0.5 4-picoline-N-oxide
tris 1-phenyl-1,3-butanedionato Dy0.5, Y0.5 4-phenylpyridine
tris 1-phenyl-1,3-butanedionato Dy0.5, Y0.5 4-cyanopyridine
tris 1-phenyl-1,3-butanedionato Dy0.5, Y0.5 4-phenylpyridine-N-oxide
tris 1-phenyl-1,3-butanedionato Dy0.5, Y0.5 1-methylimidazole
tris 1-phenyl-1,3-butanedionato Dy0.5, Y0.5 triphenylphosphine oxide
tris 1-phenyl-1,3-butanedionato Dy0.5, Y0.5 2,2-bipyridyl
tris 1-phenyl-1,3-butanedionato Dy0.5, Y0.5 2,2-bipyridyl-N,N-dioxide
tris 1-phenyl-1,3-butanedionato Dy0.5, Y0.5 phenanthroline
tris 1-phenyl-1,3-butanedionato Dy0.5, Y0.5 bathocuproine
tris 1-phenyl-1,3-butanedionato Dy0.5, Y0.5 bathophenanthroline
tris acetylacetonato Dy0.2, Y0.8 dimethylaminopyridine
tris acetylacetonato Dy0.2, Y0.8 4-picoline-N-oxide
tris acetylacetonato Dy0.2, Y0.8 4-phenylpyridine
tris acetylacetonato Dy0.2, Y0.8 4-cyanopyridine
tris acetylacetonato Dy0.2, Y0.8 4-phenylpyridine-N-oxide
tris acetylacetonato Dy0.2, Y0.8 1-methylimidazole
tris acetylacetonato Dy0.2, Y0.8 triphenylphosphine oxide
tris acetylacetonato Dy0.2, Y0.8 2,2-bipyridyl
tris acetylacetonato Dy0.2, Y0.8 2,2-bipyridyl-N,N-dioxide
tris acetylacetonato Dy0.2, Y0.8 phenanthroline
tris acetylacetonato Dy0.2, Y0.8 bathocuproine
tris acetylacetonato Dy0.2, Y0.8 bathophenanthroline
tris dibenzoylmethanato Dy0.2, Y0.8 dimethylaminopyridine
tris dibenzoylmethanato Dy0.2, Y0.8 4-picoline-N-oxide
tris dibenzoylmethanato Dy0.2, Y0.8 4-phenylpyridine
tris dibenzoylmethanato Dy0.2, Y0.8 4-cyanopyridine
tris dibenzoylmethanato Dy0.2, Y0.8 4-phenylpyridine-N-oxide
tris dibenzoylmethanato Dy0.2, Y0.8 1-methylimidazole
tris dibenzoylmethanato Dy0.2, Y0.8 triphenylphosphine oxide
tris dibenzoylmethanato Dy0.2, Y0.8 2,2-bipyridyl
tris dibenzoylmethanato Dy0.2, Y0.8 2,2-bipyridyl-N,N-dioxide
tris dibenzoylmethanato Dy0.2, Y0.8 phenanthroline
tris dibenzoylmethanato Dy0.2, Y0.8 bathocuproine
tris dibenzoylmethanato Dy0.2, Y0.8 bathophenanthroline
tris thenoyltrifluoroacetonato Dy0.2, Y0.8 dimethylaminopyridine
tris thenoyltrifluoroacetonato Dy0.2, Y0.8 4-picoline-N-oxide
tris thenoyltrifluoroacetonato Dy0.2, Y0.8 4-phenylpyridine
tris thenoyltrifluoroacetonato Dy0.2, Y0.8 4-cyanopyridine
tris thenoyltrifluoroacetonato Dy0.2, Y0.8 4-phenylpyridine-N-oxide
tris thenoyltrifluoroacetonato Dy0.2, Y0.8 1-methylimidazole
tris thenoyltrifluoroacetonato Dy0.2, Y0.8 triphenylphosphine oxide
tris thenoyltrifluoroacetonato Dy0.2, Y0.8 2,2-bipyridyl
tris thenoyltrifluoroacetonato Dy0.2, Y0.8 2,2-bipyridyl-N,N-dioxide
tris thenoyltrifluoroacetonato Dy0.2, Y0.8 phenanthroline
tris thenoyltrifluoroacetonato Dy0.2, Y0.8 bathocuproine
tris thenoyltrifluoroacetonato Dy0.2, Y0.8 bathophenanthroline tris 2,2,6,6-tetramethylheptanedionato Dy0.2, Y0.8 dimethylaminopyridine
tris 2,2,6,6-tetramethylheptanedionato Dy0.2, Y0.8 4-picoline-N-oxide
tris 2,2,6,6-tetramethylheptanedionato Dy0.2, Y0.8 4-phenylpyridine
tris 2,2,6,6-tetramethylheptanedionato Dy0.2, Y0.8 4-cyanopyridine
tris 2,2,6,6-tetramethylheptanedionato Dy0.2, Y0.8 4-phenylpyridine-N-oxide
tris 2,2,6,6-tetramethylheptanedionato Dy0.2, Y0.8 1-methylimidazole
tris 2,2,6,6-tetramethylheptanedionato Dy0.2, Y0.8 triphenylphosphine oxide
tris 2,2,6,6-tetramethylheptanedionato Dy0.2, Y0.8 2,2-bipyridyl
tris 2,2,6,6-tetramethylheptanedionato Dy0.2, Y0.8 2,2-bipyridyl-N,N-dioxide
tris 2,2,6,6-tetramethylheptanedionato Dy0.2, Y0.8 phenanthroline
tris 2,2,6,6-tetramethylheptanedionato Dy0.2, Y0.8 bathocuproine
tris 2,2,6,6-tetramethylheptanedionato Dy0.2, Y0.8 bathophenanthroline
tris 3-methylpentane-2,4-dionato Dy0.2, Y0.8 dimethylaminopyridine
tris 3-methylpentane-2,4-dionato Dy0.2, Y0.8 4-picoline-N-oxide
tris 3-methylpentane-2,4-dionato Dy0.2, Y0.8 4-phenylpyridine
tris 3-methylpentane-2,4-dionato Dy0.2, Y0.8 4-cyanopyridine
tris 3-methylpentane-2,4-dionato Dy0.2, Y0.8 4-phenylpyridine-N-oxide
tris 3-methylpentane-2,4-dionato Dy0.2, Y0.8 1-methylimidazole
tris 3-methylpentane-2,4-dionato Dy0.2, Y0.8 triphenylphosphine oxide
tris 3-methylpentane-2,4-dionato Dy0.2, Y0.8 2,2-bipyridyl
tris 3-methylpentane-2,4-dionato Dy0.2, Y0.8 2,2-bipyridyl-N,N-dioxide
tris 3-methylpentane-2,4-dionato Dy0.2, Y0.8 phenanthroline
tris 3-methylpentane-2,4-dionato Dy0.2, Y0.8 bathocuproine
tris 3-methylpentane-2,4-dionato Dy0.2, Y0.8 bathophenanthroline
tris 3-ethylpentane-2,4-dionato Dy0.2, Y0.8 dimethylaminopyridine
tris 3-ethylpentane-2,4-dionato Dy0.2, Y0.8 4-picoline-N-oxide
tris 3-ethylpentane-2,4-dionato Dy0.2, Y0.8 4-phenylpyridine
tris 3-ethylpentane-2,4-dionato Dy0.2, Y0.8 4-cyanopyridine
tris 3-ethylpentane-2,4-dionato Dy0.2, Y0.8 4-phenylpyridine-N-oxide
tris 3-ethylpentane-2,4-dionato Dy0.2, Y0.8 1-methylimidazole
tris 3-ethylpentane-2,4-dionato Dy0.2, Y0.8 triphenylphosphine oxide
tris 3-ethylpentane-2,4-dionato Dy0.2, Y0.8 2,2-bipyridyl
tris 3-ethylpentane-2,4-dionato Dy0.2, Y0.8 2,2-bipyridyl-N,N-dioxide
tris 3-ethylpentane-2,4-dionato Dy0.2, Y0.8 phenanthroline
tris 3-ethylpentane-2,4-dionato Dy0.2, Y0.8 bathocuproine
tris 3-ethylpentane-2,4-dionato Dy0.2, Y0.8 bathophenanthroline
tris pivaloyltrifluoroacetonato Dy0.2, Y0.8 dimethylaminopyridine
tris pivaloyltrifluoroacetonato Dy0.2, Y0.8 4-picoline-N-oxide
tris pivaloyltrifluoroacetonato Dy0.2, Y0.8 4-phenylpyridine
tris pivaloyltrifluoroacetonato Dy0.2, Y0.8 4-cyanopyridine
tris pivaloyltrifluoroacetonato Dy0.2, Y0.8 4-phenylpyridine-N-oxide
tris pivaloyltrifluoroacetonato Dy0.2, Y0.8 1-methylimidazole
tris pivaloyltrifluoroacetonato Dy0.2, Y0.8 triphenylphosphine oxide
tris pivaloyltrifluoroacetonato Dy0.2, Y0.8 2,2-bipyridyl
tris pivaloyltrifluoroacetonato Dy0.2, Y0.8 2,2-bipyridyl-N,N-dioxide
tris pivaloyltrifluoroacetonato Dy0.2, Y0.8 phenanthroline
tris pivaloyltrifluoroacetonato Dy0.2, Y0.8 bathocuproine
tris pivaloyltrifluoroacetonato Dy0.2, Y0.8 bathophenanthroline
tris trifluoroacetylacetonato Dy0.2, Y0.8 dimethylaminopyridine
tris trifluoroacetylacetonato Dy0.2, Y0.8 4-picoline-N-oxide
tris trifluoroacetylacetonato Dy0.2, Y0.8 4-phenylpyridine
tris trifluoroacetylacetonato Dy0.2, Y0.8 4-cyanopyridine
tris trifluoroacetylacetonato Dy0.2, Y0.8 4-phenylpyridine-N-oxide
tris trifluoroacetylacetonato Dy0.2, Y0.8 1-methylimidazole
tris trifluoroacetylacetonato Dy0.2, Y0.8 triphenylphosphine oxide
tris trifluoroacetylacetonato Dy0.2, Y0.8 2,2-bipyridyl
tris trifluoroacetylacetonato Dy0.2, Y0.8 2,2-bipyridyl-N,N-dioxide
tris trifluoroacetylacetonato Dy0.2, Y0.8 phenanthroline
tris trifluoroacetylacetonato Dy0.2, Y0.8 bathocuproine
tris trifluoroacetylacetonato Dy0.2, Y0.8 bathophenanthroline
tris hexafluoroacetylacetonato Dy0.2, Y0.8 dimethylaminopyridine
tris hexafluoroacetylacetonato Dy0.2, Y0.8 4-picoline-N-oxide
tris hexafluoroacetylacetonato Dy0.2, Y0.8 4-phenylpyridine
tris hexafluoroacetylacetonato Dy0.2, Y0.8 4-cyanopyridine
tris hexafluoroacetylacetonato Dy0.2, Y0.8 4-phenylpyridine-N-oxide
tris hexafluoroacetylacetonato Dy0.2, Y0.8 1-methylimidazole
tris hexafluoroacetylacetonato Dy0.2, Y0.8 triphenylphosphine oxide
tris hexafluoroacetylacetonato Dy0.2, Y0.8 2,2-bipyridyl
tris hexafluoroacetylacetonato Dy0.2, Y0.8 2,2-bipyridyl-N,N-dioxide
tris hexafluoroacetylacetonato Dy0.2, Y0.8 phenanthroline
tris hexafluoroacetylacetonato Dy0.2, Y0.8 bathocuproine
tris hexafluoroacetylacetonato Dy0.2, Y0.8 bathophenanthroline
tris 6,6,7,7,8,8,8-heptafluoro-2,2-dimethyloctanedionato Dy0.2, Y0.8 dimethylaminopyridine
tris 6,6,7,7,8,8,8-heptafluoro-2,2-dimethyloctanedionato Dy0.2, Y0.8 4-picoline-N-oxide
tris 6,6,7,7,8,8,8-heptafluoro-2,2-dimethyloctanedionato Dy0.2, Y0.8 4-phenylpyridine
tris 6,6,7,7,8,8,8-heptafluoro-2,2-dimethyloctanedionato Dy0.2, Y0.8 4-cyanopyridine tris 6,6,7,7,8,8,8-heptafluoro-2,2-dimethyloctanedionato Dy0.2, Y0.8 4-phenylpyridine-N-oxide
tris 6,6,7,7,8,8,8-heptafluoro-2,2-dimethyloctanedionato Dy0.2, Y0.8 1-methylimidazole
tris 6,6,7,7,8,8,8-heptafluoro-2,2-dimethyloctanedionato Dy0.2, Y0.8 triphenylphosphine oxide
tris 6,6,7,7,8,8,8-heptafluoro-2,2-dimethyloctanedionato Dy0.2, Y0.8 2,2-bipyridyl
tris 6,6,7,7,8,8,8-heptafluoro-2,2-dimethyloctanedionato Dy0.2, Y0.8 2,2-bipyridyl-N,N-dioxide
tris 6,6,7,7,8,8,8-heptafluoro-2,2-dimethyloctanedionato Dy0.2, Y0.8 phenanthroline
tris 6,6,7,7,8,8,8-heptafluoro-2,2-dimethyloctanedionato Dy0.2, Y0.8 bathocuproine
tris 6,6,7,7,8,8,8-heptafluoro-2,2-dimethyloctanedionato Dy0.2, Y0.8 bathophenanthroline
tris 1-phenyl-1,3-butanedionato Dy0.2, Y0.8 dimethylaminopyridine
tris 1-phenyl-1,3-butanedionato Dy0.2, Y0.8 4-picoline-N-oxide
tris 1-phenyl-1,3-butanedionato Dy0.2, Y0.8 4-phenylpyridine
tris 1-phenyl-1,3-butanedionato Dy0.2, Y0.8 4-cyanopyridine
tris 1-phenyl-1,3-butanedionato Dy0.2, Y0.8 4-phenylpyridine-N-oxide
tris 1-phenyl-1,3-butanedionato Dy0.2, Y0.8 1-methylimidazole
tris 1-phenyl-1,3-butanedionato Dy0.2, Y0.8 triphenylphosphine oxide
tris 1-phenyl-1,3-butanedionato Dy0.2, Y0.8 2,2-bipyridyl
tris 1-phenyl-1,3-butanedionato Dy0.2, Y0.8 2,2-bipyridyl-N,N-dioxide
tris 1-phenyl-1,3-butanedionato Dy0.2, Y0.8 phenanthroline
tris 1-phenyl-1,3-butanedionato Dy0.2, Y0.8 bathocuproine
tris 1-phenyl-1,3-butanedionato Dy0.2, Y0.8 bathophenanthroline
tris acetylacetonato Dy0.1, Y0.9 dimethylaminopyridine
tris acetylacetonato Dy0.1, Y0.9 4-picoline-N-oxide
tris acetylacetonato Dy0.1, Y0.9 4-phenylpyridine
tris acetylacetonato Dy0.1, Y0.9 4-cyanopyridine
tris acetylacetonato Dy0.1, Y0.9 4-phenylpyridine-N-oxide
tris acetylacetonato Dy0.1, Y0.9 1-methylimidazole
tris acetylacetonato Dy0.1, Y0.9 triphenylphosphine oxide
tris acetylacetonato Dy0.1, Y0.9 2,2-bipyridyl
tris acetylacetonato Dy0.1, Y0.9 2,2-bipyridyl-N,N-dioxide
tris acetylacetonato Dy0.1, Y0.9 phenanthroline
tris acetylacetonato Dy0.1, Y0.9 bathocuproine
tris acetylacetonato Dy0.1, Y0.9 bathophenanthroline
tris dibenzoylmethanato Dy0.1, Y0.9 dimethylaminopyridine
tris dibenzoylmethanato Dy0.1, Y0.9 4-picoline-N-oxide
tris dibenzoylmethanato Dy0.1, Y0.9 4-phenylpyridine
tris dibenzoylmethanato Dy0.1, Y0.9 4-cyanopyridine
tris dibenzoylmethanato Dy0.1, Y0.9 4-phenylpyridine-N-oxide
tris dibenzoylmethanato Dy0.1, Y0.9 1-methylimidazole
tris dibenzoylmethanato Dy0.1, Y0.9 triphenylphosphine oxide
tris dibenzoylmethanato Dy0.1, Y0.9 2,2-bipyridyl
tris dibenzoylmethanato Dy0.1, Y0.9 2,2-bipyridyl-N,N-dioxide
tris dibenzoylmethanato Dy0.1, Y0.9 phenanthroline
tris dibenzoylmethanato Dy0.1, Y0.9 bathocuproine
tris dibenzoylmethanato Dy0.1, Y0.9 bathophenanthroline
tris thenoyltrifluoroacetonato Dy0.1, Y0.9 dimethylaminopyridine
tris thenoyltrifluoroacetonato Dy0.1, Y0.9 4-picoline-N-oxide
tris thenoyltrifluoroacetonato Dy0.1, Y0.9 4-phenylpyridine
tris thenoyltrifluoroacetonato Dy0.1, Y0.9 4-cyanopyridine
tris thenoyltrifluoroacetonato Dy0.1, Y0.9 4-phenylpyridine-N-oxide
tris thenoyltrifluoroacetonato Dy0.1, Y0.9 1-methylimidazole
tris thenoyltrifluoroacetonato Dy0.1, Y0.9 triphenylphosphine oxide
tris thenoyltrifluoroacetonato Dy0.1, Y0.9 2,2-bipyridyl
tris thenoyltrifluoroacetonato Dy0.1, Y0.9 2,2-bipyridyl-N,N-dioxide
tris thenoyltrifluoroacetonato Dy0.1, Y0.9 phenanthroline
tris thenoyltrifluoroacetonato Dy0.1, Y0.9 bathocuproine
tris thenoyltrifluoroacetonato Dy0.1, Y0.9 bathophenanthroline
tris 2,2,6,6-tetramethylheptanedionato Dy0.1, Y0.9 dimethylaminopyridine
tris 2,2,6,6-tetramethylheptanedionato Dy0.1, Y0.9 4-picoline-N-oxide
tris 2,2,6,6-tetramethylheptanedionato Dy0.1, Y0.9 4-phenylpyridine
tris 2,2,6,6-tetramethylheptanedionato Dy0.1, Y0.9 4-cyanopyridine
tris 2,2,6,6-tetramethylheptanedionato Dy0.1, Y0.9 4-phenylpyridine-N-oxide
tris 2,2,6,6-tetramethylheptanedionato Dy0.1, Y0.9 1-methylimidazole
tris 2,2,6,6-tetramethylheptanedionato Dy0.1, Y0.9 triphenylphosphine oxide
tris 2,2,6,6-tetramethylheptanedionato Dy0.1, Y0.9 2,2-bipyridyl
tris 2,2,6,6-tetramethylheptanedionato Dy0.1, Y0.9 2,2-bipyridyl-N,N-dioxide
tris 2,2,6,6-tetramethylheptanedionato Dy0.1, Y0.9 phenanthroline
tris 2,2,6,6-tetramethylheptanedionato Dy0.1, Y0.9 bathocuproine
tris 2,2,6,6-tetramethylheptanedionato Dy0.1, Y0.9 bathophenanthroline
tris 3-methylpentane-2,4-dionato Dy0.1, Y0.9 dimethylaminopyridine
tris 3-methylpentane-2,4-dionato Dy0.1, Y0.9 4-picoline-N-oxide
tris 3-methylpentane-2,4-dionato Dy0.1, Y0.9 4-phenylpyridine
tris 3-methylpentane-2,4-dionato Dy0.1, Y0.9 4-cyanopyridine
tris 3-methylpentane-2,4-dionato Dy0.1, Y0.9 4-phenylpyridine-N-oxide
tris 3-methylpentane-2,4-dionato Dy0.1, Y0.9 1-methylimidazole
tris 3-methylpentane-2,4-dionato Dy0.1, Y0.9 triphenylphosphine oxide
tris 3-methylpentane-2,4-dionato Dy0.1, Y0.9 2,2-bipyridyl
tris 3-methylpentane-2,4-dionato Dy0.1, Y0.9 2,2-bipyridyl-N,N-dioxide
tris 3-methylpentane-2,4-dionato Dy0.1, Y0.9 phenanthroline
tris 3-methylpentane-2,4-dionato Dy0.1, Y0.9 bathocuproine
tris 3-methylpentane-2,4-dionato Dy0.1, Y0.9 bathophenanthroline
tris 3-ethylpentane-2,4-dionato Dy0.1, Y0.9 dimethylaminopyridine tris 3-ethylpentane-2,4-dionato Dy0.1, Y0.9 4-picoline-N-oxide
tris 3-ethylpentane-2,4-dionato Dy0.1, Y0.9 4-phenylpyridine
tris 3-ethylpentane-2,4-dionato Dy0.1, Y0.9 4-cyanopyridine
tris 3-ethylpentane-2,4-dionato Dy0.1, Y0.9 4-phenylpyridine-N-oxide
tris 3-ethylpentane-2,4-dionato Dy0.1, Y0.9 1-methylimidazole
tris 3-ethylpentane-2,4-dionato Dy0.1, Y0.9 triphenylphosphine oxide
tris 3-ethylpentane-2,4-dionato Dy0.1, Y0.9 2,2-bipyridyl
tris 3-ethylpentane-2,4-dionato Dy0.1, Y0.9 2,2-bipyridyl-N,N-dioxide
tris 3-ethylpentane-2,4-dionato Dy0.1, Y0.9 phenanthroline
tris 3-ethylpentane-2,4-dionato Dy0.1, Y0.9 bathocuproine
tris 3-ethylpentane-2,4-dionato Dy0.1, Y0.9 bathophenanthroline
tris pivaloyltrifluoroacetonato Dy0.1, Y0.9 dimethylaminopyridine
tris pivaloyltrifluoroacetonato Dy0.1, Y0.9 4-picoline-N-oxide
tris pivaloyltrifluoroacetonato Dy0.1, Y0.9 4-phenylpyridine
tris pivaloyltrifluoroacetonato Dy0.1, Y0.9 4-cyanopyridine
tris pivaloyltrifluoroacetonato Dy0.1, Y0.9 4-phenylpyridine-N-oxide
tris pivaloyltrifluoroacetonato Dy0.1, Y0.9 1-methylimidazole
tris pivaloyltrifluoroacetonato Dy0.1, Y0.9 triphenylphosphine oxide
tris pivaloyltrifluoroacetonato Dy0.1, Y0.9 2,2-bipyridyl
tris pivaloyltrifluoroacetonato Dy0.1, Y0.9 2,2-bipyridyl-N,N-dioxide
tris pivaloyltrifluoroacetonato Dy0.1, Y0.9 phenanthroline
tris pivaloyltrifluoroacetonato Dy0.1, Y0.9 bathocuproine
tris pivaloyltrifluoroacetonato Dy0.1, Y0.9 bathophenanthroline
tris trifluoroacetylacetonato Dy0.1, Y0.9 dimethylaminopyridine
tris trifluoroacetylacetonato Dy0.1, Y0.9 4-picoline-N-oxide
tris trifluoroacetylacetonato Dy0.1, Y0.9 4-phenylpyridine
tris trifluoroacetylacetonato Dy0.1, Y0.9 4-cyanopyridine
tris trifluoroacetylacetonato Dy0.1, Y0.9 4-phenylpyridine-N-oxide
tris trifluoroacetylacetonato Dy0.1, Y0.9 1-methylimidazole
tris trifluoroacetylacetonato Dy0.1, Y0.9 triphenylphosphine oxide
tris trifluoroacetylacetonato Dy0.1, Y0.9 2,2-bipyridyl
tris trifluoroacetylacetonato Dy0.1, Y0.9 2,2-bipyridyl-N,N-dioxide
tris trifluoroacetylacetonato Dy0.1, Y0.9 phenanthroline
tris trifluoroacetylacetonato Dy0.1, Y0.9 bathocuproine
tris trifluoroacetylacetonato Dy0.1, Y0.9 bathophenanthroline
tris hexafluoroacetylacetonato Dy0.1, Y0.9 dimethylaminopyridine
tris hexafluoroacetylacetonato Dy0.1, Y0.9 4-picoline-N-oxide
tris hexafluoroacetylacetonato Dy0.1, Y0.9 4-phenylpyridine
tris hexafluoroacetylacetonato Dy0.1, Y0.9 4-cyanopyridine
tris hexafluoroacetylacetonato Dy0.1, Y0.9 4-phenylpyridine-N-oxide
tris hexafluoroacetylacetonato Dy0.1, Y0.9 1-methylimidazole
tris hexafluoroacetylacetonato Dy0.1, Y0.9 triphenylphosphine oxide
tris hexafluoroacetylacetonato Dy0.1, Y0.9 2,2-bipyridyl
tris hexafluoroacetylacetonato Dy0.1, Y0.9 2,2-bipyridyl-N,N-dioxide
tris hexafluoroacetylacetonato Dy0.1, Y0.9 phenanthroline
tris hexafluoroacetylacetonato Dy0.1, Y0.9 bathocuproine
tris hexafluoroacetylacetonato Dy0.1, Y0.9 bathophenanthroline
tris 6,6,7,7,8,8-heptafluoro-2,2-dimethyloctanedionato Dy0.1, Y0.9 dimethylaminopyridine
tris 6,6,7,7,8,8-heptafluoro-2,2-dimethyloctanedionato Dy0.1, Y0.9 4-picoline-N-oxide
tris 6,6,7,7,8,8-heptafluoro-2,2-dimethyloctanedionato Dy0.1, Y0.9 4-phenylpyridine
tris 6,6,7,7,8,8-heptafluoro-2,2-dimethyloctanedionato Dy0.1, Y0.9 4-cyanopyridine
tris 6,6,7,7,8,8-heptafluoro-2,2-dimethyloctanedionato Dy0.1, Y0.9 4-phenylpyridine-N-oxide
tris 6,6,7,7,8,8-heptafluoro-2,2-dimethyloctanedionato Dy0.1, Y0.9 1-methylimidazole
tris 6,6,7,7,8,8-heptafluoro-2,2-dimethyloctanedionato Dy0.1, Y0.9 triphenylphosphine oxide
tris 6,6,7,7,8,8-heptafluoro-2,2-dimethyloctanedionato Dy0.1, Y0.9 2,2-bipyridyl
tris 6,6,7,7,8,8-heptafluoro-2,2-dimethyloctanedionato Dy0.1, Y0.9 2,2-bipyridyl-N,N-dioxide
tris 6,6,7,7,8,8-heptafluoro-2,2-dimethyloctanedionato Dy0.1, Y0.9 phenanthroline
tris 6,6,7,7,8,8-heptafluoro-2,2-dimethyloctanedionato Dy0.1, Y0.9 bathocuproine
tris 6,6,7,7,8,8-heptafluoro-2,2-dimethyloctanedionato Dy0.1, Y0.9 bathophenanthroline
tris 1-phenyl-1,3-butanedionato Dy0.1, Y0.9 dimethylaminopyridine
tris 1-phenyl-1,3-butanedionato Dy0.1, Y0.9 4-picoline-N-oxide
tris 1-phenyl-1,3-butanedionato Dy0.1, Y0.9 4-phenylpyridine
tris 1-phenyl-1,3-butanedionato Dy0.1, Y0.9 4-cyanopyridine
tris 1-phenyl-1,3-butanedionato Dy0.1, Y0.9 4-phenylpyridine-N-oxide
tris 1-phenyl-1,3-butanedionato Dy0.1, Y0.9 1-methylimidazole
tris 1-phenyl-1,3-butanedionato Dy0.1, Y0.9 triphenylphosphine oxide
tris 1-phenyl-1,3-butanedionato Dy0.1, Y0.9 2,2-bipyridyl
tris 1-phenyl-1,3-butanedionato Dy0.1, Y0.9 2,2-bipyridyl-N,N-dioxide
tris 1-phenyl-1,3-butanedionato Dy0.1, Y0.9 phenanthroline
tris 1-phenyl-1,3-butanedionato Dy0.1, Y0.9 bathocuproine
tris 1-phenyl-1,3-butanedionato Dy0.1, Y0.9 bathophenanthroline
tris acetylacetonato Dy0.01, Y0.99 dimethylaminopyridine
tris acetylacetonato Dy0.01, Y0.99 4-picoline-N-oxide
tris acetylacetonato Dy0.01, Y0.99 4-phenylpyridine
tris acetylacetonato Dy0.01, Y0.99 4-cyanopyridine
tris acetylacetonato Dy0.01, Y0.99 4-phenylpyridine-N-oxide
tris acetylacetonato Dy0.01, Y0.99 1-methylimidazole
tris acetylacetonato Dy0.01, Y0.99 triphenylphosphine oxide
tris acetylacetonato Dy0.01, Y0.99 2,2-bipyridyl
tris acetylacetonato Dy0.01, Y0.99 2,2-bipyridyl-N,N-dioxide
tris acetylacetonato Dy0.01, Y0.99 phenanthroline tris acetylacetonato Dy0.01, Y0.99 bathocuproine
tris acetylacetonato Dy0.01, Y0.99 bathophenanthroline
tris dibenzoylmethanato Dy0.01, Y0.99 dimethylaminopyridine
tris dibenzoylmethanato Dy0.01, Y0.99 4-picoline-N-oxide
tris dibenzoylmethanato Dy0.01, Y0.99 4-phenylpyridine
tris dibenzoylmethanato Dy0.01, Y0.99 4-cyanopyridine
tris dibenzoylmethanato Dy0.01, Y0.99 4-phenylpyridine-N-oxide
tris dibenzoylmethanato Dy0.01, Y0.99 1-methylimidazole
tris dibenzoylmethanato Dy0.01, Y0.99 triphenylphosphine oxide
tris dibenzoylmethanato Dy0.01, Y0.99 2,2-bipyridyl
tris dibenzoylmethanato Dy0.01, Y0.99 2,2-bipyridyl-N,N-dioxide
tris dibenzoylmethanato Dy0.01, Y0.99 phenanthroline
tris dibenzoylmethanato Dy0.01, Y0.99 bathocuproine
tris dibenzoylmethanato Dy0.01, Y0.99 bathophenanthroline
tris thenoyltrifluoroacetonato Dy0.01, Y0.99 dimethylaminopyridine
tris thenoyltrifluoroacetonato Dy0.01, Y0.99 4-picoline-N-oxide
tris thenoyltrifluoroacetonato Dy0.01, Y0.99 4-phenylpyridine
tris thenoyltrifluoroacetonato Dy0.01, Y0.99 4-cyanopyridine
tris thenoyltrifluoroacetonato Dy0.01, Y0.99 4-phenylpyridine-N-oxide
tris thenoyltrifluoroacetonato Dy0.01, Y0.99 1-methylimidazole
tris thenoyltrifluoroacetonato Dy0.01, Y0.99 triphenylphosphine oxide
tris thenoyltrifluoroacetonato Dy0.01, Y0.99 2,2-bipyridyl
tris thenoyltrifluoroacetonato Dy0.01, Y0.99 2,2-bipyridyl-N,N-dioxide
tris thenoyltrifluoroacetonato Dy0.01, Y0.99 phenanthroline
tris thenoyltrifluoroacetonato Dy0.01, Y0.99 bathocuproine
tris thenoyltrifluoroacetonato Dy0.01, Y0.99 bathophenanthroline
tris 2,2,6,6-tetramethylheptanedionato Dy0.01, Y0.99 dimethylaminopyridine
tris 2,2,6,6-tetramethylheptanedionato Dy0.01, Y0.99 4-picoline-N-oxide
tris 2,2,6,6-tetramethylheptanedionato Dy0.01, Y0.99 4-phenylpyridine
tris 2,2,6,6-tetramethylheptanedionato Dy0.01, Y0.99 4-cyanopyridine
tris 2,2,6,6-tetramethylheptanedionato Dy0.01, Y0.99 4-phenylpyridine-N-oxide
tris 2,2,6,6-tetramethylheptanedionato Dy0.01, Y0.99 1-methylimidazole
tris 2,2,6,6-tetramethylheptanedionato Dy0.01, Y0.99 triphenylphosphine oxide
tris 2,2,6,6-tetramethylheptanedionato Dy0.01, Y0.99 2,2-bipyridyl
tris 2,2,6,6-tetramethylheptanedionato Dy0.01, Y0.99 2,2-bipyridyl-N,N-dioxide
tris 2,2,6,6-tetramethylheptanedionato Dy0.01, Y0.99 phenanthroline
tris 2,2,6,6-tetramethylheptanedionato Dy0.01, Y0.99 bathocuproine
tris 2,2,6,6-tetramethylheptanedionato Dy0.01, Y0.99 bathophenanthroline
tris 3-methylpentane-2,4-dionato Dy0.01, Y0.99 dimethylaminopyridine
tris 3-methylpentane-2,4-dionato Dy0.01, Y0.99 4-picoline-N-oxide
tris 3-methylpentane-2,4-dionato Dy0.01, Y0.99 4-phenylpyridine
tris 3-methylpentane-2,4-dionato Dy0.01, Y0.99 4-cyanopyridine
tris 3-methylpentane-2,4-dionato Dy0.01, Y0.99 4-phenylpyridine-N-oxide
tris 3-methylpentane-2,4-dionato Dy0.01, Y0.99 1-methylimidazole
tris 3-methylpentane-2,4-dionato Dy0.01, Y0.99 triphenylphosphine oxide
tris 3-methylpentane-2,4-dionato Dy0.01, Y0.99 2,2-bipyridyl
tris 3-methylpentane-2,4-dionato Dy0.01, Y0.99 2,2-bipyridyl-N,N-dioxide
tris 3-methylpentane-2,4-dionato Dy0.01, Y0.99 phenanthroline
tris 3-methylpentane-2,4-dionato Dy0.01, Y0.99 bathocuproine
tris 3-methylpentane-2,4-dionato Dy0.01, Y0.99 bathophenanthroline
tris 3-ethylpentane-2,4-dionato Dy0.01, Y0.99 dimethylaminopyridine
tris 3-ethylpentane-2,4-dionato Dy0.01, Y0.99 4-picoline-N-oxide
tris 3-ethylpentane-2,4-dionato Dy0.01, Y0.99 4-phenylpyridine
tris 3-ethylpentane-2,4-dionato Dy0.01, Y0.99 4-cyanopyridine
tris 3-ethylpentane-2,4-dionato Dy0.01, Y0.99 4-phenylpyridine-N-oxide
tris 3-ethylpentane-2,4-dionato Dy0.01, Y0.99 1-methylimidazole
tris 3-ethylpentane-2,4-dionato Dy0.01, Y0.99 triphenylphosphine oxide
tris 3-ethylpentane-2,4-dionato Dy0.01, Y0.99 2,2-bipyridyl
tris 3-ethylpentane-2,4-dionato Dy0.01, Y0.99 2,2-bipyridyl-N,N-dioxide
tris 3-ethylpentane-2,4-dionato Dy0.01, Y0.99 phenanthroline
tris 3-ethylpentane-2,4-dionato Dy0.01, Y0.99 bathocuproine
tris 3-ethylpentane-2,4-dionato Dy0.01, Y0.99 bathophenanthroline
tris pivaloyltrifluoroacetonato Dy0.01, Y0.99 dimethylaminopyridine
tris pivaloyltrifluoroacetonato Dy0.01, Y0.99 4-picoline-N-oxide
tris pivaloyltrifluoroacetonato Dy0.01, Y0.99 4-phenylpyridine
tris pivaloyltrifluoroacetonato Dy0.01, Y0.99 4-cyanopyridine
tris pivaloyltrifluoroacetonato Dy0.01, Y0.99 4-phenylpyridine-N-oxide
tris pivaloyltrifluoroacetonato Dy0.01, Y0.99 1-methylimidazole
tris pivaloyltrifluoroacetonato Dy0.01, Y0.99 triphenylphosphine oxide
tris pivaloyltrifluoroacetonato Dy0.01, Y0.99 2,2-bipyridyl
tris pivaloyltrifluoroacetonato Dy0.01, Y0.99 2,2-bipyridyl-N,N-dioxide
tris pivaloyltrifluoroacetonato Dy0.01, Y0.99 phenanthroline
tris pivaloyltrifluoroacetonato Dy0.01, Y0.99 bathocuproine
tris pivaloyltrifluoroacetonato Dy0.01, Y0.99 bathophenanthroline tris trifluoroacetylacetonato Dy0.01, Y0.99 dimethylaminopyridine
tris trifluoroacetylacetonato Dy0.01, Y0.99 4-picoline-N-oxide
tris trifluoroacetylacetonato Dy0.01, Y0.99 4-phenylpyridine
tris trifluoroacetylacetonato Dy0.01, Y0.99 4-cyanopyridine
tris trifluoroacetylacetonato Dy0.01, Y0.99 4-phenylpyridine-N-oxide
tris trifluoroacetylacetonato Dy0.01, Y0.99 1-methylimidazole
tris trifluoroacetylacetonato Dy0.01, Y0.99 triphenylphosphine oxide
tris trifluoroacetylacetonato Dy0.01, Y0.99 2,2-bipyridyl
tris trifluoroacetylacetonato Dy0.01, Y0.99 2,2-bipyridyl-N,N-dioxide
tris trifluoroacetylacetonato Dy0.01, Y0.99 phenanthroline
tris trifluoroacetylacetonato Dy0.01, Y0.99 bathocuproine
tris trifluoroacetylacetonato Dy0.01, Y0.99 bathophenanthroline
tris hexafluoroacetylacetonato Dy0.01, Y0.99 dimethylaminopyridine
tris hexafluoroacetylacetonato Dy0.01, Y0.99 4-picoline-N-oxide
tris hexafluoroacetylacetonato Dy0.01, Y0.99 4-phenylpyridine
tris hexafluoroacetylacetonato Dy0.01, Y0.99 4-cyanopyridine
tris hexafluoroacetylacetonato Dy0.01, Y0.99 4-phenylpyridine-N-oxide
tris hexafluoroacetylacetonato Dy0.01, Y0.99 1-methylimidazole
tris hexafluoroacetylacetonato Dy0.01, Y0.99 triphenylphosphine oxide
tris hexafluoroacetylacetonato Dy0.01, Y0.99 2,2-bipyridyl
tris hexafluoroacetylacetonato Dy0.01, Y0.99 2,2-bipyridyl-N,N-dioxide
tris hexafluoroacetylacetonato Dy0.01Y0.99 phenanthroline
tris hexafluoroacetylacetonato Dy0.01, Y0.99 bathocuproine
tris hexafluoroacetylacetonato Dy0.01, Y0.99 bathophenanthroline
tris 6,6,7,7,8,8,8-heptafluoro-2,2-dimethyloctanedionato Dy0.01, Y0.99 dimethylaminopyridine
tris 6,6,7,7,8,8,8-heptafluoro-2,2-dimethyloctanedionato Dy0.01, Y0.99 4-picoline-N-oxide
tris 6,6,7,7,8,8,8-heptafluoro-2,2-dimethyloctanedionato Dy0.01, Y0.99 4-phenylpyridine
tris 6,6,7,7,8,8,8-heptafluoro-2,2-dimethyloctanedionato Dy0.01, Y0.99 4-cyanopyridine
tris 6,6,7,7,8,8,8-heptafluoro-2,2-dimethyloctanedionato Dy0.01, Y0.99 4-phenylpyridine-N-oxide
tris 6,6,7,7,8,8,8-heptafluoro-2,2-dimethyloctanedionato Dy0.01, Y0.99 1-methylimidazole
tris 6,6,7,7,8,8,8-heptafluoro-2,2-dimethyloctanedionato Dy0.01, Y0.99 triphenylphosphine oxide
tris 6,6,7,7,8,8,8-heptafluoro-2,2-dimethyloctanedionato Dy0.01, Y0.99 2,2-bipyridyl
tris 6,6,7,7,8,8,8-heptafluoro-2,2-dimethyloctanedionato Dy0.01, Y0.99 2,2-bipyridyl-N,N-dioxide
tris 6,6,7,7,8,8,8-heptafluoro-2,2-dimethyloctanedionato Dy0.01, Y0.99 phenanthroline
tris 6,6,7,7,8,8,8-heptafluoro-2,2-dimethyloctanedionato Dy0.01, Y0.99 bathocuproine
tris 6,6,7,7,8,8,8-heptafluoro-2,2-dimethyloctanedionato Dy0.01, Y0.99 bathophenanthroline
tris 1-phenyl-1,3-butanedionato Dy0.01, Y0.99 dimethylaminopyridine
tris 1-phenyl-1,3-butanedionato Dy0.01, Y0.99 4-picoline-N-oxide
tris 1-phenyl-1,3-butanedionato Dy0.01, Y0.99 4-phenylpyridine
tris 1-phenyl-1,3-butanedionato Dy0.01, Y0.99 4-cyanopyridine
tris 1-phenyl-1,3-butanedionato Dy0.01, Y0.99 4-phenylpyridine-N-oxide
tris 1-phenyl-1,3-butanedionato Dy0.01, Y0.99 1-methylimidazole
tris 1-phenyl-1,3-butanedionato Dy0.01, Y0.99 triphenylphosphine oxide
tris 1-phenyl-1,3-butanedionato Dy0.01, Y0.99 2,2-bipyridyl
tris 1-phenyl-1,3-butanedionato Dy0.01, Y0.99 2,2-bipyridyl-N,N-dioxide
tris 1-phenyl-1,3-butanedionato Dy0.01, Y0.99 phenanthroline
tris 1-phenyl-1,3-butanedionato Dy0.01, Y0.99 bathocuproine
tris 1-phenyl-1,3-butanedionato Dy0.01, Y0.99 bathophenanthroline
tris acetylacetonato Sm0.5, La0.5 dimethylaminopyridine
tris acetylacetonato Sm0.5, La0.5 4-picoline-N-oxide
tris acetylacetonato Sm0.5, La0.5 4-phenylpyridine
tris acetylacetonato Sm0.5, La0.5 4-cyanopyridine
tris acetylacetonato Sm0.5, La0.5 4-phenylpyridine-N-oxide
tris acetylacetonato Sm0.5, La0.5 1-methylimidazole
tris acetylacetonato Sm0.5, La0.5 triphenyiphosphine oxide
tris acetylacetonato Sm0.5, La0.5 2,2-bipyridyl
tris acetylacetonato Sm0.5, La0.5 2,2-bipyridyl-N,N-dioxide
tris acetylacetonato Sm0.5, La0.5 phenanthroline
tris acetylacetonato Sm0.5, La0.5 bathocuproine
tris acetylacetonato Sm0.5, La0.5 bathophenanthroline
tris dibenzoylmethanato Sm0.5, La0.5 dimethylaminopyridine
tris dibenzoylmethanato Sm0.5, La0.5 4-picoline-N-oxide
tris dibenzoylmethanato Sm0.5, La0.5 4-phenylpyridine
tris dibenzoylmethanato Sm0.5, La0.5 4-cyanopyridine
tris dibenzoylmethanato Sm0.5, La0.5 4-phenylpyridine-N-oxide
tris dibenzoylmethanato Sm0.5, La0.5 1-methylimidazole
tris dibenzoylmethanato Sm0.5, La0.5 triphenylphosphine oxide
tris dibenzoylmethanato Sm0.5, La0.5 2,2-bipyridyl
tris dibenzoylmethanato Sm0.5, La0.5 2,2-bipyridyl-N,N-dioxide
tris dibenzoylmethanato Sm0.5, La0.5 phenanthroline
tris dibenzoylmethanato Sm0.5, La0.5 bathocuproine
tris dibenzoylmethanato Sm0.5, La0.5 bathophenanthroline
tris thenoyltrifluoroacetonato Sm0.5, La0.5 dimethylaminopyridine
tris thenoyltrifluoroacetonato Sm0.5, La0.5 4-picoline-N-oxide
tris thenoyltrifluoroacetonato Sm0.5, La0.5 4-phenylpyridine
tris thenoyltrifluoroacetonato Sm0.5, La0.5 4-cyanopyridine
tris thenoyltrifluoroacetonato Sm0.5, La0.5 4-phenylpyridine-N-oxide
tris thenoyltrifluoroacetonato Sm0.5, La0.5 1-methylimidazole
tris thenoyltrifluoroacetonato Sm0.5, La0.5 triphenylphosphine oxide
tris thenoyltrifluoroacetonato Sm0.5, La0.5 2,2-bipyridyl
tris thenoyltrifluoroacetonato Sm0.5, La0.5 2,2-bipyridyl-N,N-dioxide tris thenoyltrifluoroacetonato Sm0.5, La0.5 phenanthroline
tris thenoyltrifluoroacetonato Sm0.5, La0.5 bathocuproine
tris thenoyltrifluoroacetonato Sm0.5, La0.5 bathophenanthroline
tris 2,2,6,6-tetramethylheptanedionato Sm0.5, La0.5 dimethylaminopyridine
tris 2,2,6,6-tetramethylheptanedionato Sm0.5, La0.5 4-picoline-N-oxide
tris 2,2,6,6-tetramethylheptanedionato Sm0.5, La0.5 4-phenylpyridine
tris 2,2,6,6-tetramethylheptanedionato Sm0.5, La0.5 4-cyanopyridine
tris 2,2,6,6-tetramethylheptanedionato Sm0.5, La0.5 4-phenylpyridine-N-oxide
tris 2,2,6,6-tetramethylheptanedionato Sm0.5, La0.5 1-methylimidazole
tris 2,2,6,6-tetramethylheptanedionato Sm0.5, La0.5 triphenylphosphine oxide
tris 2,2,6,6-tetramethylheptanedionato Sm0.5, La0.5 2,2-bipyridyl
tris 2,2,6,6-tetramethylheptanedionato Sm0.5, La0.5 2,2-bipyridyl-N,N-dioxide
tris 2,2,6,6-tetramethylheptanedionato Sm0.5, La0.5 phenanthroline
tris 2,2,6,6-tetramethylheptanedionato Sm0.5, La0.5 bathocuproine
tris 2,2,6,6-tetramethylheptanedionato Sm0.5, La0.5 bathophenanthroline
tris 3-methylpentane-2,4-dionato Sm0.5, La0.5 dimethylaminopyridine
tris 3-methylpentane-2,4-dionato Sm0.5, La0.5 4-picoline-N-oxide
tris 3-methylpentane-2,4-dionato Sm0.5, La0.5 4-phenylpyridine
tris 3-methylpentane-2,4-dionato Sm0.5, La0.5 4-cyanopyridine
tris 3-methylpentane-2,4-dionato Sm0.5, La0.5 4-phenylpyridine-N-oxide
tris 3-methylpentane-2,4-dionato Sm0.5, La0.5 1-methylimidazole
tris 3-methylpentane-2,4-dionato Sm0.5, La0.5 triphenylphosphine oxide
tris 3-methylpentane-2,4-dionato Sm0.5, La0.5 2,2-bipyridyl
tris 3-methylpentane-2,4-dionato Sm0.5, La0.5 2,2-bipyridyl-N,N-dioxide
tris 3-methylpentane-2,4-dionato Sm0.5, La0.5 phenanthroline
tris 3-methylpentane-2,4-dionato Sm0.5, La0.5 bathocuproine
tris 3-methylpentane-2,4-dionato Sm0.5, La0.5 bathophenanthroline
tris 3-ethylpentane-2,4-dionato Sm0.5, La0.5 dimethylaminopyridine
tris 3-ethylpentane-2,4-dionato Sm0.5, La0.5 4-picoline-N-oxide
tris 3-ethylpentane-2,4-dionato Sm0.5, La0.5 4-phenylpyridine
tris 3-ethylpentane-2,4-dionato Sm0.5, La0.5 4-cyanopyridine
tris 3-ethylpentane-2,4-dionato Sm0.5, La0.5 4-phenylpyridine-N-oxide
tris 3-ethylpentane-2,4-dionato Sm0.5, La0.5 1-methylimidazole
tris 3-ethylpentane-2,4-dionato Sm0.5, La0.5 triphenylphosphine oxide
tris 3-ethylpentane-2,4-dionato Sm0.5, La0.5 2,2-bipyridyl
tris 3-ethylpentane-2,4-dionato Sm0.5, La0.5 2,2-bipyridyl-N,N-dioxide
tris 3-ethylpentane-2,4-dionato Sm0.5, La0.5 phenanthroline
tris 3-ethylpentane-2,4-dionato Sm0.5, La0.5 bathocuproine
tris 3-ethylpentane-2,4-dionato Sm0.5, La0.5 bathophenanthroline
tris pivaloyltrifluoroacetonato Sm0.5, La0.5 dimethylaminopyridine
tris pivaloyltrifluoroacetonato Sm0.5, La0.5 4-picoline-N-oxide
tris pivaloyltrifluoroacetonato Sm0.5, La0.5 4-phenylpyridine
tris pivaloyltrifluoroacetonato Sm0.5, La0.5 4-cyanopyridine
tris pivaloyltrifluoroacetonato Sm0.5, La0.5 4-phenylpyridine-N-oxide
tris pivaloyltrifluoroacetonato Sm0.5, La0.5 1-methylimidazole
tris pivaloyltrifluoroacetonato Sm0.5, La0.5 triphenylphosphine oxide
tris pivaloyltrifluoroacetonato Sm0.5, La0.5 2,2-bipyridyl
tris pivaloyltrifluoroacetonato Sm0.5, La0.5 2,2-bipyridyl-N,N-dioxide
tris pivaloyltrifluoroacetonato Sm0.5, La0.5 phenanthroline
tris pivaloyltrifluoroacetonato Sm0.5, La0.5 bathocuproine
tris pivaloyltrifluoroacetonato Sm0.5, La0.5 bathophenanthroline
tris trifluoroacetylacetonato Sm0.5, La0.5 dimethylaminopyridine
tris trifluoroacetylacetonato Sm0.5, La0.5 4-picoline-N-oxide
tris trifluoroacetylacetonato Sm0.5, La0.5 4-phenylpyridine
tris trifluoroacetylacetonato Sm0.5, La0.5 4-cyanopyridine
tris trifluoroacetylacetonato Sm0.5, La0.5 4-phenylpyridine-N-oxide
tris trifluoroacetylacetonato Sm0.5, La0.5 1-methylimidazole
tris trifluoroacetylacetonato Sm0.5, La0.5 triphenylphosphine oxide
tris trifluoroacetylacetonato Sm0.5, La0.5 2,2-bipyridyl
tris trifluoroacetylacetonato Sm0.5, La0.5 2,2-bipyridyl-N,N-dioxide
tris trifluoroacetylacetonato Sm0.5, La0.5 phenanthroline
tris trifluoroacetylacetonato Sm0.5, La0.5 bathocuproine
tris trifluoroacetylacetonato Sm0.5, La0.5 bathophenanthroline
tris hexafluoroacetylacetonato Sm0.5, La0.5 dimethylaminopyridine
tris hexafluoroacetylacetonato Sm0.5, La0.5 4-picoline-N-oxide
tris hexafluoroacetylacetonato Sm0.5, La0.5 4-phenylpyridine
tris hexafluoroacetylacetonato Sm0.5, La0.5 4-cyanopyridine
tris hexafluoroacetylacetonato Sm0.5, La0.5 4-phenylpyridine-N-oxide
tris hexafluoroacetylacetonato Sm0.5, La0.5 1-methylimidazole
tris hexafluoroacetylacetonato Sm0.5, La0.5 triphenylphosphine oxide
tris hexafluoroacetylacetonato Sm0.5, La0.5 2,2-bipyridyl
tris hexafluoroacetylacetonato Sm0.5, La0.5 2,2-bipyridyl-N,N-dioxide
tris hexafluoroacetylacetonato Sm0.5, La0.5 phenanthroline
tris hexafluoroacetylacetonato Sm0.5, La0.5 bathocuproine tris hexafluoroacetylacetonato Sm0.5, La0.5 bathophenanthroline
tris 6,6,7,7,8,8,8-heptafluoro-2,2-dimethyloctanedionato Sm0.5, La0.5 dimethylaminopyridine
tris 6,6,7,7,8,8,8-heptafluoro-2,2-dimethyloctanedionato Sm0.5, La0.5 4-picoline-N-oxide
tris 6,6,7,7,8,8,8-heptafluoro-2,2-dimethyloctanedionato Sm0.5, La0.5 4-phenylpyridine
tris 6,6,7,7,8,8,8-heptafluoro-2,2-dimethyloctanedionato Sm0.5, La0.5 4-cyanopyridine
tris 6,6,7,7,8,8,8-heptafluoro-2,2-dimethyloctanedionato Sm0.5, La0.5 4-phenylpyridine-N-oxide
tris 6,6,7,7,8,8,8-heptafluoro-2,2-dimethyloctanedionato Sm0.5, La0.5 1-methylimidazole
tris 6,6,7,7,8,8,8-heptafluoro-2,2-dimethyloctanedionato Sm0.5, La0.5 triphenylphosphine oxide
tris 6,6,7,7,8,8,8-heptafluoro-2,2-dimethyloctanedionato Sm0.5, La0.5 2,2-bipyridyl
tris 6,6,7,7,8,8,8-heptafluoro-2,2-dimethyloctanedionato Sm0.5, La0.5 2,2-bipyridyl-N,N-dioxide
tris 6,6,7,7,8,8,8-heptafluoro-2,2-dimethyloctanedionato Sm0.5, La0.5 phenanthroline
tris 6,6,7,7,8,8,8-heptafluoro-2,2-dimethyloctanedionato Sm0.5, La0.5 bathocuproine
tris 6,6,7,7,8,8,8-heptafluoro-2,2-dimethyloctanedionato Sm0.5, La0.5 bathophenanthroline
tris 1-phenyl-1,3-butanedionato Sm0.5, La0.5 dimethylaminopyridine
tris 1-phenyl-1,3-butanedionato Sm0.5, La0.5 4-picoline-N-oxide
tris 1-phenyl-1,3-butanedionato Sm0.5, La0.5 4-phenylpyridine
tris 1-phenyl-1,3-butanedionato Sm0.5, La0.5 4-cyanopyridine
tris 1-phenyl-1,3-butanedionato Sm0.5, La0.5 4-phenylpyridine-N-oxide
tris 1-phenyl-1,3-butanedionato Sm0.5, La0.5 1-methylimidazole
tris 1-phenyl-1,3-butanedionato Sm0.5, La0.5 triphenylphosphine oxide
tris 1-phenyl-1,3-butanedionato Sm0.5, La0.5 2,2-bipyridyl
tris 1-phenyl-1,3-butanedionato Sm0.5, La0.5 2,2-bipyridyl-N,N-dioxide
tris 1-phenyl-1,3-butanedionato Sm0.5, La0.5 phenanthroline
tris 1-phenyl-1,3-butanedionato Sm0.5, La0.5 bathocuproine
tris 1-phenyl-1,3-butanedionato Sm0.5, La0.5 bathophenanthroline
tris acetylacetonato Sm0.2, La0.8 dimethylaminopyridine
tris acetylacetonato Sm0.2, La0.8 4-picoline-N-oxide
tris acetylacetonato Sm0.2, La0.8 4-phenylpyridine
tris acetylacetonato Sm0.2, La0.8 4-cyanopyridine
tris acetylacetonato Sm0.2, La0.8 4-phenylpyridine-N-oxide
tris acetylacetonato Sm0.2, La0.8 1-methylimidazole
tris acetylacetonato Sm0.2, La0.8 triphenylphosphine oxide
tris acetylacetonato Sm0.2, La0.8 2,2-bipyridyl
tris acetylacetonato Sm0.2, La0.8 2,2-bipyridyl-N,N-dioxide
tris acetylacetonato Sm0.2, La0.8 phenanthroline
tris acetylacetonato Sm0.2, La0.8 bathocuproine
tris acetylacetonato Sm0.2, La0.8 bathophenanthroline
tris dibenzoylmethanato Sm0.2, La0.8 dimethylaminopyridine
tris dibenzoylmethanato Sm0.2, La0.8 4-picoline-N-oxide
tris dibenzoylmethanato Sm0.2, La0.8 4-phenylpyridine
tris dibenzoylmethanato Sm0.2, La0.8 4-cyanopyridine
tris dibenzoylmethanato Sm0.2, La0.8 4-phenylpyridine-N-oxide
tris dibenzoylmethanato Sm0.2, La0.8 1-methylimidazole
tris dibenzoylmethanato Sm0.2, La0.8 triphenylphosphine oxide
tris dibenzoylmethanato Sm0.2, La0.8 2,2-bipyridyl
tris dibenzoylmethanato Sm0.2, La0.8 2,2-bipyridyl-N,N-dioxide
tris dibenzoylmethanato Sm0.2, La0.8 phenanthroline
tris dibenzoylmethanato Sm0.2, La0.8 bathocuproine
tris dibenzoylmethanato Sm0.2, La0.8 bathophenanthroline
tris thenoyltrifluoroacetonato Sm0.2, La0.8 dimethylaminopyridine
tris thenoyltrifluoroacetonato Sm0.2, La0.8 4-picoline-N-oxide
tris thenoyltrifluoroacetonato Sm0.2, La0.8 4-phenylpyridine
tris thenoyltrifluoroacetonato Sm0.2, La0.8 4-cyanopyridine
tris thenoyltrifluoroacetonato Sm0.2, La0.8 4-phenylpyridine-N-oxide
tris thenoyltrifluoroacetonato Sm0.2, La0.8 1-methylimidazole
tris thenoyltrifluoroacetonato Sm0.2, La0.8 triphenylphosphine oxide
tris thenoyltrifluoroacetonato Sm0.2, La0.8 2,2-bipyridyl
tris thenoyltrifluoroacetonato Sm0.2, La0.8 2,2-bipyridyl-N,N-dioxide
tris thenoyltrifluoroacetonato Sm0.2, La0.8 phenanthroline
tris thenoyltrifluoroacetonato Sm0.2, La0.8 bathocuproine
tris thenoyltrifluoroacetonato Sm0.2, La0.8 bathophenanthroline
tris 2,2,6,6-tetramethylheptanedionato Sm0.2, La0.8 dimethylaminopyridine
tris 2,2,6,6-tetramethylheptanedionato Sm0.2, La0.8 4-picoline-N-oxide
tris 2,2,6,6-tetramethylheptanedionato Sm0.2, La0.8 4-phenylpyridine
tris 2,2,6,6-tetramethylheptanedionato Sm0.2, La0.8 4-cyanopyridine
tris 2,2,6,6-tetramethylheptanedionato Sm0.2, La0.8 4-phenylpyridine-N-oxide
tris 2,2,6,6-tetramethylheptanedionato Sm0.2, La0.8 1-methylimidazole
tris 2,2,6,6-tetramethylheptanedionato Sm0.2, La0.8 triphenylphosphine oxide
tris 2,2,6,6-tetramethylheptanedionato Sm0.2, La0.8 2,2-bipyridyl
tris 2,2,6,6-tetramethylheptanedionato Sm0.2, La0.8 2,2-bipyridyl-N,N-dioxide
tris 2,2,6,6-tetramethylheptanedionato Sm0.2, La0.8 phenanthroline
tris 2,2,6,6-tetramethylheptanedionato Sm0.2, La0.8 bathocuproine
tris 2,2,6,6-tetramethylheptanedionato Sm0.2, La0.8 bathophenanthroline
tris 3-methylpentane-2,4-dionato Sm0.2, La0.8 dimethylaminopyridine
tris 3-methylpentane-2,4-dionato Sm0.2, La0.8 4-picoline-N-oxide
tris 3-methylpentane-2,4-dionato Sm0.2, La0.8 4-phenylpyridine
tris 3-methylpentane-2,4-dionato Sm0.2, La0.8 4-cyanopyridine
tris 3-methylpentane-2,4-dionato Sm0.2, La0.8 4-phenylpyridine-N-oxide
tris 3-methylpentane-2,4-dionato Sm0.2, La0.8 1-methylimidazole tris 3-methylpentane-2,4-dionato Sm0.2, La0.8 triphenylphosphine oxide
tris 3-methylpentane-2,4-dionato Sm0.2, La0.8 2,2-bipyridyl
tris 3-methylpentane-2,4-dionato Sm0.2, La0.8 2,2-bipyridyl-N,N-dioxide
tris 3-methylpentane-2,4-dionato Sm0.2, La0.8 phenanthroline
tris 3-methylpentane-2,4-dionato Sm0.2, La0.8 bathocuproine
tris 3-methylpentane-2,4-dionato Sm0.2, La0.8 bathophenanthroline
tris 3-ethylpentane-2,4-dionato Sm0.2, La0.8 dimethylaminopyridine
tris 3-ethylpentane-2,4-dionato Sm0.2, La0.8 4-picoline-N-oxide
tris 3-ethylpentane-2,4-dionato Sm0.2, La0.8 4-phenylpyridine
tris 3-ethylpentane-2,4-dionato Sm0.2, La0.8 4-cyanopyridine
tris 3-ethylpentane-2,4-dionato Sm0.2, La0.8 4-phenylpyridine-N-oxide
tris 3-ethylpentane-2,4-dionato Sm0.2, La0.8 1-methylimidazole
tris 3-ethylpentane-2,4-dionato Sm0.2, La0.8 triphenylphosphine oxide
tris 3-ethylpentane-2,4-dionato Sm0.2, La0.8 2,2-bipyridyl
tris 3-ethylpentane-2,4-dionato Sm0.2, La0.8 2,2-bipyridyl-N,N-dioxide
tris 3-ethylpentane-2,4-dionato Sm0.2, La0.8 phenanthroline
tris 3-ethylpentane-2,4-dionato Sm0.2, La0.8 bathocuproine
tris 3-ethylpentane-2,4-dionato Sm0.2, La0.8 bathophenanthroline
tris pivaloyltrifluoroacetonato Sm0.2, La0.8 dimethylaminopyridine
tris pivaloyltrifluoroacetonato Sm0.2, La0.8 4-picoline-N-oxide
tris pivaloyltrifluoroacetonato Sm0.2, La0.8 4-phenylpyridine
tris pivaloyltrifluoroacetonato Sm0.2, La0.8 4-cyanopyridine
tris pivaloyltrifluoroacetonato Sm0.2, La0.8 4-phenylpyridine-N-oxide
tris pivaloyltrifluoroacetonato Sm0.2, La0.8 1-methylimidazole
tris pivaloyltrifluoroacetonato Sm0.2, La0.8 triphenylphosphine oxide
tris pivaloyltrifluoroacetonato Sm0.2, La0.8 2,2-bipyridyl
tris pivaloyltrifluoroacetonato Sm0.2, La0.8 2,2-bipyridyl-N,N-dioxide
tris pivaloyltrifluoroacetonato Sm0.2, La0.8 phenanthroline
tris pivaloyltrifluoroacetonato Sm0.2, La0.8 bathocuproine
tris pivaloyltrifluoroacetonato Sm0.2, La0.8 bathophenanthroline
tris trifluoroacetylacetonato Sm0.2, La0.8 dimethylaminopyridine
tris trifluoroacetylacetonato Sm0.2, La0.8 4-picoline-N-oxide
tris trifluoroacetylacetonato Sm0.2, La0.8 4-phenylpyridine
tris trifluoroacetylacetonato Sm0.2, La0.8 4-cyanopyridine
tris trifluoroacetylacetonato Sm0.2, La0.8 4-phenylpyridine-N-oxide
tris trifluoroacetylacetonato Sm0.2, La0.8 1-methylimidazole
tris trifluoroacetylacetonato Sm0.2, La0.8 triphenylphosphine oxide
tris trifluoroacetylacetonato Sm0.2, La0.8 2,2-bipyridyl
tris trifluoroacetylacetonato Sm0.2, La0.8 2,2-bipyridyl-N,N-dioxide
tris trifluoroacetylacetonato Sm0.2, La0.8 phenanthroline
tris trifluoroacetylacetonato Sm0.2, La0.8 bathocuproine
tris trifluoroacetylacetonato Sm0.2, La0.8 bathophenanthroline
tris hexafluoroacetylacetonato Sm0.2, La0.8 dimethylaminopyridine
tris hexafluoroacetylacetonato Sm0.2, La0.8 4-picoline-N-oxide
tris hexafluoroacetylacetonato Sm0.2, La0.8 4-phenylpyridine
tris hexafluoroacetylacetonato Sm0.2, La0.8 4-cyanopyridine
tris hexafluoroacetylacetonato Sm0.2, La0.8 4-phenylpyridine-N-oxide
tris hexafluoroacetylacetonato Sm0.2, La0.8 1-methylimidazole
tris hexafluoroacetylacetonato Sm0.2, La0.8 triphenylphosphine oxide
tris hexafluoroacetylacetonato Sm0.2, La0.8 2,2-bipyridyl
tris hexafluoroacetylacetonato Sm0.2, La0.8 2,2-bipyridyl-N,N-dioxide
tris hexafluoroacetylacetonato Sm0.2, La0.8 phenanthroline
tris hexafluoroacetylacetonato Sm0.2, La0.8 bathocuproine
tris hexafluoroacetylacetonato Sm0.2, La0.8 bathophenanthroline
tris 6,6,7,7,8,8,8-heptafluoro-2,2-dimethyloctanedionato Sm0.2, La0.8 dimethylaminopyridine
tris 6,6,7,7,8,8,8-heptafluoro-2,2-dimethyloctanedionato Sm0.2, La0.8 4-picoline-N-oxide
tris 6,6,7,7,8,8,8-heptafluoro-2,2-dimethyloctanedionato Sm0.2, La0.8 4-phenylpyridine
tris 6,6,7,7,8,8,8-heptafluoro-2,2-dimethyloctanedionato Sm0.2, La0.8 4-cyanopyridine
tris 6,6,7,7,8,8,8-heptafluoro-2,2-dimethyloctanedionato Sm0.2, La0.8 4-phenylpyridine-N-oxide
tris 6,6,7,7,8,8,8-heptafluoro-2,2-dimethyloctanedionato Sm0.2, La0.8 1-methylimidazole
tris 6,6,7,7,8,8,8-heptafluoro-2,2-dimethyloctanedionato Sm0.2, La0.8 triphenylphosphine oxide
tris 6,6,7,7,8,8,8-heptafluoro-2,2-dimethyloctanedionato Sm0.2, La0.8 2,2-bipyridyl
tris 6,6,7,7,8,8,8-heptafluoro-2,2-dimethyloctanedionato Sm0.2, La0.8 2,2-bipyridyl-N,N-dioxide
tris 6,6,7,7,8,8,8-heptafluoro-2,2-dimethyloctanedionato Sm0.2, La0.8 phenanthroline
tris 6,6,7,7,8,8,8-heptafluoro-2,2-dimethyloctanedionato Sm0.2, La0.8 bathocuproine
tris 6,6,7,7,8,8,8-heptafluoro-2,2-dimethyloctanedionato Sm0.2, La0.8 bathophenanthroline
tris 1-phenyl-1,3-butanedionato Sm0.2, La0.8 dimethylaminopyridine
tris 1-phenyl-1,3-butanedionato Sm0.2, La0.8 4-picoline-N-oxide
tris 1-phenyl-1,3-butanedionato Sm0.2, La0.8 4-phenylpyridine
tris 1-phenyl-1,3-butanedionato Sm0.2, La0.8 4-cyanopyridine
tris 1-phenyl-1,3-butanedionato Sm0.2, La0.8 4-phenylpyridine-N-oxide
tris 1-phenyl-1,3-butanedionato Sm0.2, La0.8 1-methylimidazole
tris 1-phenyl-1,3-butanedionato Sm0.2, La0.8 triphenylphosphine oxide
tris 1-phenyl-1,3-butanedionato Sm0.2, La0.8 2,2-bipyridyl tris 1-phenyl-1,3-butanedionato Sm0.2, La0.8 2,2-bipyridyl-N,N-dioxide
tris 1-phenyl-1,3-butanedionato Sm0.2, La0.8 phenanthroline
tris 1-phenyl-1,3-butanedionato Sm0.2, La0.8 bathocuproine
tris 1-phenyl-1,3-butanedionato Sm0.2, La0.8 bathophenanthroline
tris acetylacetonato Sm0.1, La0.9 dimethylaminopyridine
tris acetylacetonato Sm0.1, La0.9 4-picoline-N-oxide
tris acetylacetonato Sm0.1, La0.9 4-phenylpyridine
tris acetylacetonato Sm0.1, La0.9 4-cyanopyridine
tris acetylacetonato Sm0.1, La0.9 4-phenylpyridine-N-oxide
tris acetylacetonato Sm0.1, La0.9 1-methylimidazole
tris acetylacetonato Sm0.1, La0.9 triphenylphosphine oxide
tris acetylacetonato Sm0.1, La0.9 2,2-bipyridyl
tris acetylacetonato Sm0.1, La0.9 2,2-bipyridyl-N,N-dioxide
tris acetylacetonato Sm0.1, La0.9 phenanthroline
tris acetylacetonato Sm0.1, La0.9 bathocuproine
tris acetylacetonato Sm0.1, La0.9 bathophenanthroline
tris dibenzoylmethanato Sm0.1, La0.9 dimethylaminopyridine
tris dibenzoylmethanato Sm0.1, La0.9 4-picoline-N-oxide
tris dibenzoylmethanato Sm0.1, La0.9 4-phenylpyridine
tris dibenzoylmethanato Sm0.1, La0.9 4-cyanopyridine
tris dibenzoylmethanato Sm0.1, La0.9 4-phenylpyridine-N-oxide
tris dibenzoylmethanato Sm0.1, La0.9 1-methylimidazole
tris dibenzoylmethanato Sm0.1, La0.9 triphenylphosphine oxide
tris dibenzoylmethanato Sm0.1, La0.9 2,2-bipyridyl
tris dibenzoylmethanato Sm0.1, La0.9 2,2-bipyridyl-N,N-dioxide
tris dibenzoylmethanato Sm0.1, La0.9 phenanthroline
tris dibenzoylmethanato Sm0.1, La0.9 bathocuproine
tris dibenzoylmethanato Sm0.1, La0.9 bathophenanthroline
tris thenoyltrifluoroacetonato Sm0.1, La0.9 dimethylaminopyridine
tris thenoyltrifluoroacetonato Sm0.1, La0.9 4-picoline-N-oxide
tris thenoyltrifluoroacetonato Sm0.1, La0.9 4-phenylpyridine
tris thenoyltrifluoroacetonato Sm0.1, La0.9 4-cyanopyridine
tris thenoyltrifluoroacetonato Sm0.1, La0.9 4-phenylpyridine-N-oxide
tris thenoyltrifluoroacetonato Sm0.1, La0.9 1-methylimidazole
tris thenoyltrifluoroacetonato Sm0.1, La0.9 triphenylphosphine oxide
tris thenoyltrifluoroacetonato Sm0.1, La0.9 2,2-bipyridyl
tris thenoyltrifluoroacetonato Sm0.1, La0.9 2,2-bipyridyl-N,N-dioxide
tris thenoyltrifluoroacetonato Sm0.1, La0.9 phenanthroline
tris thenoyltrifluoroacetonato Sm0.1, La0.9 bathocuproine
tris thenoyltrifluoroacetonato Sm0.1, La0.9 bathophenanthroline
tris 2,2,6,6-tetramethylheptanedionato Sm0.1, La0.9 dimethylaminopyridine
tris 2,2,6,6-tetramethylheptanedionato Sm0.1, La0.9 4-picoline-N-oxide
tris 2,2,6,6-tetramethylheptanedionato Sm0.1, La0.9 4-phenylpyridine
tris 2,2,6,6-tetramethylheptanedionato Sm0.1, La0.9 4-cyanopyridine
tris 2,2,6,6-tetramethylheptanedionato Sm0.1, La0.9 4-phenylpyridine-N-oxide
tris 2,2,6,6-tetramethylheptanedionato Sm0.1, La0.9 1-methylimidazole
tris 2,2,6,6-tetramethylheptanedionato Sm0.1, La0.9 triphenylphosphine oxide
tris 2,2,6,6-tetramethylheptanedionato Sm0.1, La0.9 2,2-bipyridyl
tris 2,2,6,6-tetramethylheptanedionato Sm0.1, La0.9 2,2-bipyridyl-N,N-dioxide
tris 2,2,6,6-tetramethylheptanedionato Sm0.1, La0.9 phenanthroline
tris 2,2,6,6-tetramethylheptanedionato Sm0.1, La0.9 bathocuproine
tris 2,2,6,6-tetramethylheptanedionato Sm0.1, La0.9 bathophenanthroline
tris 3-methylpentane-2,4-dionato Sm0.1, La0.9 dimethylaminopyridine
tris 3-methylpentane-2,4-dionato Sm0.1, La0.9 4-picoline-N-oxide
tris 3-methylpentane-2,4-dionato Sm0.1, La0.9 4-phenylpyridine
tris 3-methylpentane-2,4-dionato Sm0.1, La0.9 4-cyanopyridine
tris 3-methylpentane-2,4-dionato Sm0.1, La0.9 4-phenylpyridine-N-oxide
tris 3-methylpentane-2,4-dionato Sm0.1, La0.9 1-methylimidazole
tris 3-methylpentane-2,4-dionato Sm0.1, La0.9 triphenylphosphine oxide
tris 3-methylpentane-2,4-dionato Sm0.1, La0.9 2,2-bipyridyl
tris 3-methylpentane-2,4-dionato Sm0.1, La0.9 2,2-bipyridyl-N,N-dioxide
tris 3-methylpentane-2,4-dionato Sm0.1, La0.9 phenanthroline
tris 3-methylpentane-2,4-dionato Sm0.1, La0.9 bathocuproine
tris 3-methylpentane-2,4-dionato Sm0.1, La0.9 bathophenanthroline
tris 3-ethylpentane-2,4-dionato Sm0.1, La0.9 dimethylaminopyridine
tris 3-ethylpentane-2,4-dionato Sm0.1, La0.9 4-picoline-N-oxide
tris 3-ethylpentane-2,4-dionato Sm0.1, La0.9 4-phenylpyridine
tris 3-ethylpentane-2,4-dionato Sm0.1, La0.9 4-cyanopyridine
tris 3-ethylpentane-2,4-dionato Sm0.1, La0.9 4-phenylpyridine-N-oxide
tris 3-ethylpentane-2,4-dionato Sm0.1, La0.9 1-methylimidazole
tris 3-ethylpentane-2,4-dionato Sm0.1, La0.9 triphenylphosphine oxide
tris 3-ethylpentane-2,4-dionato Sm0.1, La0.9 2,2-bipyridyl
tris 3-ethylpentane-2,4-dionato Sm0.1, La0.9 2,2-bipyridyl-N,N-dioxide
tris 3-ethylpentane-2,4-dionato Sm0.1, La0.9 phenanthroline
tris 3-ethylpentane-2,4-dionato Sm0.1, La0.9 bathocuproine
tris 3-ethylpentane-2,4-dionato Sm0.1, La0.9 bathophenanthroline
tris pivaloyltrifluoroacetonato Sm0.1, La0.9 dimethylaminopyridine
tris pivaloyltrifluoroacetonato Sm0.1, La0.9 4-picoline-N-oxide
tris pivaloyltrifluoroacetonato Sm0.1, La0.9 4-phenylpyridine tris pivaloyltrifluoroacetonato Sm0.1, La0.9 4-cyanopyridine
tris pivaloyltrifluoroacetonato Sm0.1, La0.9 4-phenylpyridine-N-oxide
tris pivaloyltrifluoroacetonato Sm0.1, La0.9 1-methylimidazole
tris pivaloyltrifluoroacetonato Sm0.1, La0.9 triphenylphosphine oxide
tris pivaloyltrifluoroacetonato Sm0.1, La0.9 2,2-bipyridyl
tris pivaloyltrifluoroacetonato Sm0.1, La0.9 2,2-bipyridyl-N,N-dioxide
tris pivaloyltrifluoroacetonato Sm0.1, La0.9 phenanthroline
tris pivaloyltrifluoroacetonato Sm0.1, La0.9 bathocuproine
tris pivaloyltrifluoroacetonato Sm0.1, La0.9 bathophenanthroline
tris trifluoroacetylacetonato Sm0.1, La0.9 dimethylaminopyridine
tris trifluoroacetylacetonato Sm0.1, La0.9 4-picoline-N-oxide
tris trifluoroacetylacetonato Sm0.1, La0.9 4-phenylpyridine
tris trifluoroacetylacetonato Sm0.1, La0.9 4-cyanopyridine
tris trifluoroacetylacetonato Sm0.1, La0.9 4-phenylpyridine-N-oxide
tris trifluoroacetylacetonato Sm0.1, La0.9 1-methylimidazole
tris trifluoroacetylacetonato Sm0.1, La0.9 triphenylphosphine oxide
tris trifluoroacetylacetonato Sm0.1, La0.9 2,2-bipyridyl
tris trifluoroacetylacetonato Sm0.1, La0.9 2,2-bipyridyl-N,N-dioxide
tris trifluoroacetylacetonato Sm0.1, La0.9 phenanthroline
tris trifluoroacetylacetonato Sm0.1, La0.9 bathocuproine
tris trifluoroacetylacetonato Sm0.1, La0.9 bathophenanthroline
tris hexafluoroacetylacetonato Sm0.1, La0.9 dimethylaminopyridine
tris hexafluoroacetylacetonato Sm0.1, La0.9 4-picoline-N-oxide
tris hexafluoroacetylacetonato Sm0.1, La0.9 4-phenylpyridine
tris hexafluoroacetylacetonato Sm0.1, La0.9 4-cyanopyridine
tris hexafluoroacetylacetonato Sm0.1, La0.9 4-phenylpyridine-N-oxide
tris hexafluoroacetylacetonato Sm0.1, La0.9 1-methylimidazole
tris hexafluoroacetylacetonato Sm0.1, La0.9 triphenylphosphine oxide
tris hexafluoroacetylacetonato Sm0.1, La0.9 2,2-bipyridyl
tris hexafluoroacetylacetonato Sm0.1, La0.9 2,2-bipyridyl-N,N-dioxide
tris hexafluoroacetylacetonato Sm0.1, La0.9 phenanthroline
tris hexafluoroacetylacetonato Sm0.1, La0.9 bathocuproine
tris hexafluoroacetylacetonato Sm0.1, La0.9 bathophenanthroline
tris 6,6,7,7,8,8,8-heptafluoro-2,2-dimethyloctanedionato Sm0.1, La0.9 dimethylaminopyridine
tris 6,6,7,7,8,8,8-heptafluoro-2,2-dimethyloctanedionato Sm0.1, La0.9 4-picoline-N-oxide
tris 6,6,7,7,8,8,8-heptafluoro-2,2-dimethyloctanedionato Sm0.1, La0.9 4-phenylpyridine
tris 6,6,7,7,8,8,8-heptafluoro-2,2-dimethyloctanedionato Sm0.1, La0.9 4-cyanopyridine
tris 6,6,7,7,8,8,8-heptafluoro-2,2-dimethyloctanedionato Sm0.1, La0.9 4-phenylpyridine-N-oxide
tris 6,6,7,7,8,8,8-heptafluoro-2,2-dimethyloctanedionato Sm0.1, La0.9 1-methylimidazole
tris 6,6,7,7,8,8,8-heptafluoro-2,2-dimethyloctanedionato Sm0.1, La0.9 triphenylphosphine oxide
tris 6,6,7,7,8,8,8-heptafluoro-2,2-dimethyloctanedionato Sm0.1, La0.9 2,2-bipyridyl
tris 6,6,7,7,8,8,8-heptafluoro-2,2-dimethyloctanedionato Sm0.1, La0.9 2,2-bipyridyl-N,N-dioxide
tris 6,6,7,7,8,8,8-heptafluoro-2,2-dimethyloctanedionato Sm0.1, La0.9 phenanthroline
tris 6,6,7,7,8,8,8-heptafluoro-2,2-dimethyloctanedionato Sm0.1, La0.9 bathocuproine
tris 6,6,7,7,8,8,8-heptafluoro-2,2-dimethyloctanedionato Sm0.1, La0.9 bathophenanthroline
tris 1-phenyl-1,3-butanedionato Sm0.1, La0.9 dimethylaminopyridine
tris 1-phenyl-1,3-butanedionato Sm0.1, La0.9 4-picoline-N-oxide
tris 1-phenyl-1,3-butanedionato Sm0.1, La0.9 4-phenylpyridine
tris 1-phenyl-1,3-butanedionato Sm0.1, La0.9 4-cyanopyridine
tris 1-phenyl-1,3-butanedionato Sm0.1, La0.9 4-phenylpyridine-N-oxide
tris 1-phenyl-1,3-butanedionato Sm0.1, La0.9 1-methylimidazole
tris 1-phenyl-1,3-butanedionato Sm0.1, La0.9 triphenylphosphine oxide
tris 1-phenyl-1,3-butanedionato Sm0.1, La0.9 2,2-bipyridyl
tris 1-phenyl-1,3-butanedionato Sm0.1, La0.9 2,2-bipyridyl-N,N-dioxide
tris 1-phenyl-1,3-butanedionato Sm0.1, La0.9 phenanthroline
tris 1-phenyl-1,3-butanedionato Sm0.1, La0.9 bathocuproine
tris 1-phenyl-1,3-butanedionato Sm0.1, La0.9 bathophenanthroline
tris acetylacetonato Sm0.01, La0.99 dimethylaminopyridine
tris acetylacetonato Sm0.01, La0.99 4-picoline-N-oxide
tris acetylacetonato Sm0.01, La0.99 4-phenylpyridine
tris acetylacetonato Sm0.01, La0.99 4-cyanopyridine
tris acetylacetonato Sm0.01, La0.99 4-phenylpyridine-N-oxide
tris acetylacetonato Sm0.01, La0.99 1-methylimidazole
tris acetylacetonato Sm0.01, La0.99 triphenylphosphine oxide
tris acetylacetonato Sm0.01, La0.99 2,2-bipyridyl
tris acetylacetonato Sm0.01, La0.99 2,2-bipyridyl-N,N-dioxide
tris acetylacetonato Sm0.01, La0.99 phenanthroline
tris acetylacetonato Sm0.01, La0.99 bathocuproine
tris acetylacetonato Sm0.01, La0.99 bathophenanthroline
tris dibenzoylmethanato Sm0.01, La0.99 dimethylaminopyridine
tris dibenzoylmethanato Sm0.01, La0.99 4-picoline-N-oxide
tris dibenzoylmethanato Sm0.01, La0.99 4-phenylpyridine
tris dibenzoylmethanato Sm0.01, La0.99 4-cyanopyridine
tris dibenzoylmethanato Sm0.01, La0.99 4-phenylpyridine-N-oxide
tris dibenzoylmethanato Sm0.01, La0.99 1-methylimidazole
tris dibenzoylmethanato Sm0.01, La0.99 triphenylphosphine oxide
tris dibenzoylmethanato Sm0.01, La0.99 2,2-bipyridyl
tris dibenzoylmethanato Sm0.01, La0.99 2,2-bipyridyl-N,N-dioxide
tris dibenzoylmethanato Sm0.01, La0.99 phenanthroline
tris dibenzoylmethanato Sm0.01, La0.99 bathocuproine
tris dibenzoylmethanato Sm0.01, La0.99 bathophenanthroline tris thenoyltrifluoroacetonato Sm0.01, La0.99 dimethylaminopyridine
tris thenoyltrifluoroacetonato Sm0.01, La0.99 4-picoline-N-oxide
tris thenoyltrifluoroacetonato Sm0.01, La0.99 4-phenylpyridine
tris thenoyltrifluoroacetonato Sm0.01, La0.99 4-cyanopyridine
tris thenoyltrifluoroacetonato Sm0.01, La0.99 4-phenylpyridine-N-oxide
tris thenoyltrifluoroacetonato Sm0.01, La0.99 1-methylimidazole
tris thenoyltrifluoroacetonato Sm0.01, La0.99 triphenylphosphine oxide
tris thenoyltrifluoroacetonato Sm0.01, La0.99 2,2-bipyridyl
tris thenoyltrifluoroacetonato Sm0.01, La0.99 2,2-bipyridyl-N,N-dioxide
tris thenoyltrifluoroacetonato Sm0.01, La0.99 phenanthroline
tris thenoyltrifluoroacetonato Sm0.01, La0.99 bathocuproine
tris thenoyltrifluoroacetonato Sm0.01, La0.99 bathophenanthroline
tris 2,2,6,6-tetramethylheptanedionato Sm0.01, La0.99 dimethylaminopyridine
tris 2,2,6,6-tetramethylheptanedionato Sm0.01, La0.99 4-picoline-N-oxide
tris 2,2,6,6-tetramethylheptanedionato Sm0.01, La0.99 4-phenylpyridine
tris 2,2,6,6-tetramethylheptanedionato Sm0.01, La0.99 4-cyanopyridine
tris 2,2,6,6-tetramethylheptanedionato Sm0.01, La0.99 4-phenylpyridine-N-oxide
tris 2,2,6,6-tetramethylheptanedionato Sm0.01, La0.99 1-methylimidazole
tris 2,2,6,6-tetramethylheptanedionato Sm0.01, La0.99 triphenylphosphine oxide
tris 2,2,6,6-tetramethylheptanedionato Sm0.01, La0.99 2,2-bipyridyl
tris 2,2,6,6-tetramethylheptanedionato Sm0.01, La0.99 2,2-bipyridyl-N,N-dioxide
tris 2,2,6,6-tetramethylheptanedionato Sm0.01, La0.99 phenanthroline
tris 2,2,6,6-tetramethylheptanedionato Sm0.01, La0.99 bathocuproine
tris 2,2,6,6-tetramethylheptanedionato Sm0.01, La0.99 bathophenanthroline
tris 3-methylpentane-2,4-dionato Sm0.01, La0.99 dimethylaminopyridine
tris 3-methylpentane-2,4-dionato Sm0.01, La0.99 4-picoline-N-oxide
tris 3-methylpentane-2,4-dionato Sm0.01, La0.99 4-phenylpyridine
tris 3-methylpentane-2,4-dionato Sm0.01, La0.99 4-cyanopyridine
tris 3-methylpentane-2,4-dionato Sm0.01, La0.99 4-phenylpyridine-N-oxide
tris 3-methylpentane-2,4-dionato Sm0.01, La0.99 1-methylimidazole
tris 3-methylpentane-2,4-dionato Sm0.01, La0.99 triphenylphosphine oxide
tris 3-methylpentane-2,4-dionato Sm0.01, La0.99 2,2-bipyridyl
tris 3-methylpentane-2,4-dionato Sm0.01, La0.99 2,2-bipyridyl-N,N-dioxide
tris 3-methylpentane-2,4-dionato Sm0.01, La0.99 phenanthroline
tris 3-methylpentane-2,4-dionato Sm0.01, La0.99 bathocuproine
tris 3-methylpentane-2,4-dionato Sm0.01, La0.99 bathophenanthroline
tris 3-ethylpentane-2,4-dionato Sm0.01, La0.99 dimethylaminopyridine
tris 3-ethylpentane-2,4-dionato Sm0.01, La0.99 4-picoline-N-oxide
tris 3-ethylpentane-2,4-dionato Sm0.01, La0.99 4-phenylpyridine
tris 3-ethylpentane-2,4-dionato Sm0.01, La0.99 4-cyanopyridine
tris 3-ethylpentane-2,4-dionato Sm0.01, La0.99 4-phenylpyridine-N-oxide
tris 3-ethylpentane-2,4-dionato Sm0.01, La0.99 1-methylimidazole
tris 3-ethylpentane-2,4-dionato Sm0.01, La0.99 triphenylphosphine oxide
tris 3-ethylpentane-2,4-dionato Sm0.01, La0.99 2,2-bipyridyl
tris 3-ethylpentane-2,4-dionato Sm0.01, La0.99 2,2-bipyridyl-N,N-dioxide
tris 3-ethylpentane-2,4-dionato Sm0.01, La0.99 phenanthroline
tris 3-ethylpentane-2,4-dionato Sm0.01, La0.99 bathocuproine
tris 3-ethylpentane-2,4-dionato Sm0.01, La0.99 bathophenanthroline
tris pivaloyltrifluoroacetonato Sm0.01, La0.99 dimethylaminopyridine
tris pivaloyltrifluoroacetonato Sm0.01, La0.99 4-picoline-N-oxide
tris pivaloyltrifluoroacetonato Sm0.01, La0.99 4-phenylpyridine
tris pivaloyltrifluoroacetonato Sm0.01, La0.99 4-cyanopyridine
tris pivaloyltrifluoroacetonato Sm0.01, La0.99 4-phenylpyridine-N-oxide
tris pivaloyltrifluoroacetonato Sm0.01, La0.99 1-methylimidazole
tris pivaloyltrifluoroacetonato Sm0.01, La0.99 triphenylphosphine oxide
tris pivaloyltrifluoroacetonato Sm0.01, La0.99 2,2-bipyridyl
tris pivaloyltrifluoroacetonato Sm0.01, La0.99 2,2-bipyridyl-N,N-dioxide
tris pivaloyltrifluoroacetonato Sm0.01, La0.99 phenanthroline
tris pivaloyltrifluoroacetonato Sm0.01, La0.99 bathocuproine
tris pivaloyltrifluoroacetonato Sm0.01, La0.99 bathophenanthroline
tris trifluoroacetylacetonato Sm0.01, La0.99 dimethylaminopyridine
tris trifluoroacetylacetonato Sm0.01, La0.99 4-picoline-N-oxide
tris trifluoroacetylacetonato Sm0.01, La0.99 4-phenylpyridine
tris trifluoroacetylacetonato Sm0.01, La0.99 4-cyanopyridine
tris trifluoroacetylacetonato Sm0.01, La0.99 4-phenylpyridine-N-oxide
tris trifluoroacetylacetonato Sm0.01, La0.99 1-methylimidazole
tris trifluoroacetylacetonato Sm0.01, La0.99 triphenylphosphine oxide
tris trifluoroacetylacetonato Sm0.01, La0.99 2,2-bipyridyl tris trifluoroacetylacetonato Sm0.01, La0.99 2,2-bipyridyl-N,N-dioxide
tris trifluoroacetylacetonato Sm0.01, La0.99 phenanthroline
tris trifluoroacetylacetonato Sm0.01, La0.99 bathocuproine
tris trifluoroacetylacetonato Sm0.01, La0.99 bathophenanthroline
tris hexafluoroacetylacetonato Sm0.01, La0.99 dimethylaminopyridine
tris hexafluoroacetylacetonato Sm0.01, La0.99 4-picoline-N-oxide
tris hexafluoroacetylacetonato Sm0.01, La0.99 4-phenylpyridine
tris hexafluoroacetylacetonato Sm0.01, La0.99 4-cyanopyridine
tris hexafluoroacetylacetonato Sm0.01, La0.99 4-phenylpyridine-N-oxide
tris hexafluoroacetylacetonato Sm0.01, La0.99 1-methylimidazole
tris hexafluoroacetylacetonato Sm0.01, La0.99 triphenylphosphine oxide
tris hexafluoroacetylacetonato Sm0.01, La0.99 2,2-bipyridyl
tris hexafluoroacetylacetonato Sm0.01, La0.99 2,2-bipyridyl-N,N-dioxide
tris hexafluoroacetylacetonato Sm0.01, La0.99 phenanthroline
tris hexafluoroacetylacetonato Sm0.01, La0.99 bathocuproine
tris hexafluoroacetylacetonato Sm0.01, La0.99 bathophenanthroline
tris 6,6,7,7,8,8,8-heptafluoro-2,2-dimethyloctanedionato Sm0.01, La0.99 dimethylaminopyridine
tris 6,6,7,7,8,8,8-heptafluoro-2,2-dimethyloctanedionato Sm0.01, La0.99 4-picoline-N-oxide
tris 6,6,7,7,8,8,8-heptafluoro-2,2-dimethyloctanedionato Sm0.01, La0.99 4-phenylpyridine
tris 6,6,7,7,8,8,8-heptafluoro-2,2-dimethyloctanedionato Sm0.01, La0.99 4-cyanopyridine
tris 6,6,7,7,8,8,8-heptafluoro-2,2-dimethyloctanedionato Sm0.01, La0.99 4-phenylpyridine-N-oxide
tris 6,6,7,7,8,8,8-heptafluoro-2,2-dimethyloctanedionato Sm0.01, La0.99 1-methylimidazole
tris 6,6,7,7,8,8,8-heptafluoro-2,2-dimethyloctanedionato Sm0.01, La0.99 triphenylphosphine oxide
tris 6,6,7,7,8,8,8-heptafluoro-2,2-dimethyloctanedionato Sm0.01, La0.99 2,2-bipyridyl
tris 6,6,7,7,8,8,8-heptafluoro-2,2-dimethyloctanedionato Sm0.01, La0.99 2,2-bipyridyl-N,N-dioxide
tris 6,6,7,7,8,8,8-heptafluoro-2,2-dimethyloctanedionato Sm0.01, La0.99 phenanthroline
tris 6,6,7,7,8,8,8-heptafluoro-2,2-dimethyloctanedionato Sm0.01, La0.99 bathocuproine
tris 6,6,7,7,8,8,8-heptafluoro-2,2-dimethyloctanedionato Sm0.01, La0.99 bathophenanthroline
tris 1-phenyl-1,3-butanedionato Sm0.01, La0.99 dimethylaminopyridine
tris 1-phenyl-1,3-butanedionato Sm0.01, La0.99 4-picoline-N-oxide
tris 1-phenyl-1,3-butanedionato Sm0.01, La0.99 4-phenylpyridine
tris 1-phenyl-1,3-butanedionato Sm0.01, La0.99 4-cyanopyridine
tris 1-phenyl-1,3-butanedionato Sm0.01, La0.99 4-phenylpyridine-N-oxide
tris 1-phenyl-1,3-butanedionato Sm0.01, La0.99 1-methylimidazole
tris 1-phenyl-1,3-butanedionato Sm0.01, La0.99 triphenylphosphine oxide
tris 1-phenyl-1,3-butanedionato Sm0.01, La0.99 2,2-bipyridyl
tris 1-phenyl-1,3-butanedionato Sm0.01, La0.99 2,2-bipyridyl-N,N-dioxide
tris 1-phenyl-1,3-butanedionato Sm0.01, La0.99 phenanthroline
tris 1-phenyl-1,3-butanedionato Sm0.01, La0.99 bathocuproine
tris 1-phenyl-1,3-butanedionato Sm0.01, La0.99 bathophenanthroline
tris acetylacetonato Dy0.5, La0.5 dimethylaminopyridine
tris acetylacetonato Dy0.5, La0.5 4-picoline-N-oxide
tris acetylacetonato Dy0.5, La0.5 4-phenylpyridine
tris acetylacetonato Dy0.5, La0.5 4-cyanopyridine
tris acetylacetonato Dy0.5, La0.5 4-phenylpyridine-N-oxide
tris acetylacetonato Dy0.5, La0.5 1-methylimidazole
tris acetylacetonato Dy0.5, La0.5 triphenylphosphine oxide
tris acetylacetonato Dy0.5, La0.5 2,2-bipyridyl
tris acetylacetonato Dy0.5, La0.5 2,2-bipyridyl-N,N-dioxide
tris acetylacetonato Dy0.5, La0.5 phenanthroline
tris acetylacetonato Dy0.5, La0.5 bathocuproine
tris acetylacetonato Dy0.5, La0.5 bathophenanthroline
tris dibenzoylmethanato Dy0.5, La0.5 dimethylaminopyridine
tris dibenzoylmethanato Dy0.5, La0.5 4-picoline-N-oxide
tris dibenzoylmethanato Dy0.5, La0.5 4-phenylpyridine
tris dibenzoylmethanato Dy0.5, La0.5 4-cyanopyridine
tris dibenzoylmethanato Dy0.5, La0.5 4-phenylpyridine-N-oxide
tris dibenzoylmethanato Dy0.5, La0.5 1-methylimidazole
tris dibenzoylmethanato Dy0.5, La0.5 triphenylphosphine oxide
tris dibenzoylmethanato Dy0.5, La0.5 2,2-bipyridyl
tris dibenzoylmethanato Dy0.5, La0.5 2,2-bipyridyl-N,N-dioxide
tris dibenzoylmethanato Dy0.5, La0.5 phenanthroline
tris dibenzoylmethanato Dy0.5, La0.5 bathocuproine
tris dibenzoylmethanato Dy0.5, La0.5 bathophenanthroline
tris thenoyltrifluoroacetonato Dy0.5, La0.5 dimethylaminopyridine
tris thenoyltrifluoroacetonato Dy0.5, La0.5 4-picoline-N-oxide
tris thenoyltrifluoroacetonato Dy0.5, La0.5 4-phenylpyridine
tris thenoyltrifluoroacetonato Dy0.5, La0.5 4-cyanopyridine
tris thenoyltrifluoroacetonato Dy0.5, La0.5 4-phenylpyridine-N-oxide
tris thenoyltrifluoroacetonato Dy0.5, La0.5 1-methylimidazole
tris thenoyltrifluoroacetonato Dy0.5, La0.5 triphenylphosphine oxide
tris thenoyltrifluoroacetonato Dy0.5, La0.5 2,2-bipyridyl
tris thenoyltrifluoroacetonato Dy0.5, La0.5 2,2-bipyridyl-N,N-dioxide
tris thenoyltrifluoroacetonato Dy0.5, La0.5 phenanthroline
tris thenoyltrifluoroacetonato Dy0.5, La0.5 bathocuproine
tris thenoyltrifluoroacetonato Dy0.5, La0.5 bathophenanthroline
tris 2,2,6,6-tetramethylheptanedionato Dy0.5, La0.5 dimethylaminopyridine
tris 2,2,6,6-tetramethylheptanedionato Dy0.5, La0.5 4-picoline-N-oxide
tris 2,2,6,6-tetramethylheptanedionato Dy0.5, La0.5 4-phenylpyridine
tris 2,2,6,6-tetramethylheptanedionato Dy0.5, La0.5 4-cyanopyridine tris 2,2,6,6-tetramethylheptanedionato Dy0.5, La0.5 4-phenylpyridine-N-oxide
tris 2,2,6,6-tetramethylheptanedionato Dy0.5, La0.5 1-methylimidazole
tris 2,2,6,6-tetramethylheptanedionato Dy0.5, La0.5 triphenylphosphine oxide
tris 2,2,6,6-tetramethylheptanedionato Dy0.5, La0.5 2,2-bipyridyl
tris 2,2,6,6-tetramethylheptanedionato Dy0.5, La0.5 2,2-bipyridyl-N,N-dioxide
tris 2,2,6,6-tetramethylheptanedionato Dy0.5, La0.5 phenanthroline
tris 2,2,6,6-tetramethylheptanedionato Dy0.5, La0.5 bathocuproine
tris 2,2,6,6-tetramethylheptanedionato Dy0.5, La0.5 bathophenanthroline
tris 3-methylpentane-2,4-dionato Dy0.5, La0.5 dimethylaminopyridine
tris 3-methylpentane-2,4-dionato Dy0.5, La0.5 4-picoline-N-oxide
tris 3-methylpentane-2,4-dionato Dy0.5, La0.5 4-phenylpyridine
tris 3-methylpentane-2,4-dionato Dy0.5, La0.5 4-cyanopyridine
tris 3-methylpentane-2,4-dionato Dy0.5, La0.5 4-phenylpyridine-N-oxide
tris 3-methylpentane-2,4-dionato Dy0.5, La0.5 1-methylimidazole
tris 3-methylpentane-2,4-dionato Dy0.5, La0.5 triphenylphosphine oxide
tris 3-methylpentane-2,4-dionato Dy0.5, La0.5 2,2-bipyridyl
tris 3-methylpentane-2,4-dionato Dy0.5, La0.5 2,2-bipyridyl-N,N-dioxide
tris 3-methylpentane-2,4-dionato Dy0.5, La0.5 phenanthroline
tris 3-methylpentane-2,4-dionato Dy0.5, La0.5 bathocuproine
tris 3-methylpentane-2,4-dionato Dy0.5, La0.5 bathophenanthroline
tris 3-ethylpentane-2,4-dionato Dy0.5, La0.5 dimethylaminopyridine
tris 3-ethylpentane-2,4-dionato Dy0.5, La0.5 4-picoline-N-oxide
tris 3-ethylpentane-2,4-dionato Dy0.5, La0.5 4-phenylpyridine
tris 3-ethylpentane-2,4-dionato Dy0.5, La0.5 4-cyanopyridine
tris 3-ethylpentane-2,4-dionato Dy0.5, La0.5 4-phenylpyridine-N-oxide
tris 3-ethylpentane-2,4-dionato Dy0.5, La0.5 1-methylimidazole
tris 3-ethylpentane-2,4-dionato Dy0.5, La0.5 triphenylphosphine oxide
tris 3-ethylpentane-2,4-dionato Dy0.5, La0.5 2,2-bipyridyl
tris 3-ethylpentane-2,4-dionato Dy0.5, La0.5 2,2-bipyridyl-N,N-dioxide
tris 3-ethylpentane-2,4-dionato Dy0.5, La0.5 phenanthroline
tris 3-ethylpentane-2,4-dionato Dy0.5, La0.5 bathocuproine
tris 3-ethylpentane-2,4-dionato Dy0.5, La0.5 bathophenanthroline
tris pivaloyltrifluoroacetonato Dy0.5, La0.5 dimethylaminopyridine
tris pivaloyltrifluoroacetonato Dy0.5, La0.5 4-picoline-N-oxide
tris pivaloyltrifluoroacetonato Dy0.5, La0.5 4-phenylpyridine
tris pivaloyltrifluoroacetonato Dy0.5, La0.5 4-cyanopyridine
tris pivaloyltrifluoroacetonato Dy0.5, La0.5 4-phenylpyridine-N-oxide
tris pivaloyltrifluoroacetonato Dy0.5, La0.5 1-methylimidazole
tris pivaloyltrifluoroacetonato Dy0.5, La0.5 triphenylphosphine oxide
tris pivaloyltrifluoroacetonato Dy0.5, La0.5 2,2-bipyridyl
tris pivaloyltrifluoroacetonato Dy0.5, La0.5 2,2-bipyridyl-N,N-dioxide
tris pivaloyltrifluoroacetonato Dy0.5, La0.5 phenanthroline
tris pivaloyltrifluoroacetonato Dy0.5, La0.5 bathocuproine
tris pivaloyltrifluoroacetonato Dy0.5, La0.5 bathophenanthroline
tris trifluoroacetylacetonato Dy0.5, La0.5 dimethylaminopyridine
tris trifluoroacetylacetonato Dy0.5, La0.5 4-picoline-N-oxide
tris trifluoroacetylacetonato Dy0.5, La0.5 4-phenylpyridine
tris trifluoroacetylacetonato Dy0.5, La0.5 4-cyanopyridine
tris trifluoroacetylacetonato Dy0.5, La0.5 4-phenylpyridine-N-oxide
tris trifluoroacetylacetonato Dy0.5, La0.5 1-methylimidazole
tris trifluoroacetylacetonato Dy0.5, La0.5 triphenylphosphine oxide
tris trifluoroacetylacetonato Dy0.5, La0.5 2,2-bipyridyl
tris trifluoroacetylacetonato Dy0.5, La0.5 2,2-bipyridyl-N,N-dioxide
tris trifluoroacetylacetonato Dy0.5, La0.5 phenanthroline
tris trifluoroacetylacetonato Dy0.5, La0.5 bathocuproine
tris trifluoroacetylacetonato Dy0.5, La0.5 bathophenanthroline
tris hexafluoroacetylacetonato Dy0.5, La0.5 dimethylaminopyridine
tris hexafluoroacetylacetonato Dy0.5, La0.5 4-picoline-N-oxide
tris hexafluoroacetylacetonato Dy0.5, La0.5 4-phenylpyridine
tris hexafluoroacetylacetonato Dy0.5, La0.5 4-cyanopyridine
tris hexafluoroacetylacetonato Dy0.5, La0.5 4-phenylpyridine-N-oxide
tris hexafluoroacetylacetonato Dy0.5, La0.5 1-methylimidazole
tris hexafluoroacetylacetonato Dy0.5, La0.5 triphenylphosphine oxide
tris hexafluoroacetylacetonato Dy0.5, La0.5 2,2-bipyridyl
tris hexafluoroacetylacetonato Dy0.5, La0.5 2,2-bipyridyl-N,N-dioxide
tris hexafluoroacetylacetonato Dy0.5, La0.5 phenanthroline
tris hexafluoroacetylacetonato Dy0.5, La0.5 bathocuproine
tris hexafluoroacetylacetonato Dy0.5, La0.5 bathophenanthroline
tris 6,6,7,7,8,8,8-heptafluoro-2,2-dimethyloctanedionato Dy0.5, La0.5 dimethylaminopyridine
tris 6,6,7,7,8,8,8-heptafluoro-2,2-dimethyloctanedionato Dy0.5, La0.5 4-picoline-N-oxide
tris 6,6,7,7,8,8,8-heptafluoro-2,2-dimethyloctanedionato Dy0.5, La0.5 4-phenylpyridine
tris 6,6,7,7,8,8,8-heptafluoro-2,2-dimethyloctanedionato Dy0.5, La0.5 4-cyanopyridine
tris 6,6,7,7,8,8,8-heptafluoro-2,2-dimethyloctanedionato Dy0.5, La0.5 4-phenylpyridine-N-oxide
tris 6,6,7,7,8,8,8-heptafluoro-2,2-dimethyloctanedionato Dy0.5, La0.5 1-methylimidazole tris 6,6,7,7,8,8,8-heptafluoro-2,2-dimethyloctanedionato Dy0.5, La0.5 triphenylphosphine oxide
tris 6,6,7,7,8,8,8-heptafluoro-2,2-dimethyloctanedionato Dy0.5, La0.5 2,2-bipyridyl
tris 6,6,7,7,8,8,8-heptafluoro-2,2-dimethyloctanedionato Dy0.5, La0.5 2,2-bipyridyl-N,N-dioxide
tris 6,6,7,7,8,8,8-heptafluoro-2,2-dimethyloctanedionato Dy0.5, La0.5 phenanthroline
tris 6,6,7,7,8,8,8-heptafluoro-2,2-dimethyloctanedionato Dy0.5, La0.5 bathocuproine
tris 6,6,7,7,8,8,8-heptafluoro-2,2-dimethyloctanedionato Dy0.5, La0.5 bathophenanthroline
tris 1-phenyl-1,3-butanedionato Dy0.5, La0.5 dimethylaminopyridine
tris 1-phenyl-1,3-butanedionato Dy0.5, La0.5 4-picoline-N-oxide
tris 1-phenyl-1,3-butanedionato Dy0.5, La0.5 4-phenylpyridine
tris 1-phenyl-1,3-butanedionato Dy0.5, La0.5 4-cyanopyridine
tris 1-phenyl-1,3-butanedionato Dy0.5, La0.5 4-phenylpyridine-N-oxide
tris 1-phenyl-1,3-butanedionato Dy0.5, La0.5 1-methylimidazole
tris 1-phenyl-1,3-butanedionato Dy0.5, La0.5 triphenylphosphine oxide
tris 1-phenyl-1,3-butanedionato Dy0.5, La0.5 2,2-bipyridyl
tris 1-phenyl-1,3-butanedionato Dy0.5, La0.5 2,2-bipyridyl-N,N-dioxide
tris 1-phenyl-1,3-butanedionato Dy0.5, La0.5 phenanthroline
tris 1-phenyl-1,3-butanedionato Dy0.5, La0.5 bathocuproine
tris 1-phenyl-1,3-butanedionato Dy0.5, La0.5 bathophenanthroline
tris acetylacetonato Dy0.2, La0.8 dimethylaminopyridine
tris acetylacetonato Dy0.2, La0.8 4-picoline-N-oxide
tris acetylacetonato Dy0.2, La0.8 4-phenylpyridine
tris acetylacetonato Dy0.2, La0.8 4-cyanopyridine
tris acetylacetonato Dy0.2, La0.8 4-phenylpyridine-N-oxide
tris acetylacetonato Dy0.2, La0.8 1-methylimidazole
tris acetylacetonato Dy0.2, La0.8 triphenylphosphine oxide
tris acetylacetonato Dy0.2, La0.8 2,2-bipyridyl
tris acetylacetonato Dy0.2, La0.8 2,2-bipyridyl-N,N-dioxide
tris acetylacetonato Dy0.2, La0.8 phenanthroline
tris acetylacetonato Dy0.2, La0.8 bathocuproine
tris acetylacetonato Dy0.2, La0.8 bathophenanthroline
tris dibenzoylmethanato Dy0.2, La0.8 dimethylaminopyridine
tris dibenzoylmethanato Dy0.2, La0.8 4-picoline-N-oxide
tris dibenzoylmethanato Dy0.2, La0.8 4-phenylpyridine
tris dibenzoylmethanato Dy0.2, La0.8 4-cyanopyridine
tris dibenzoylmethanato Dy0.2, La0.8 4-phenylpyridine-N-oxide
tris dibenzoylmethanato Dy0.2, La0.8 1-methylimidazole
tris dibenzoylmethanato Dy0.2, La0.8 triphenylphosphine oxide
tris dibenzoylmethanato Dy0.2, La0.8 2,2-bipyridyl
tris dibenzoylmethanato Dy0.2, La0.8 2,2-bipyridyl-N,N-dioxide
tris dibenzoylmethanato Dy0.2, La0.8 phenanthroline
tris dibenzoylmethanato Dy0.2, La0.8 bathocuproine
tris dibenzoylmethanato Dy0.2, La0.8 bathophenanthroline
tris thenoyltrifluoroacetonato Dy0.2, La0.8 dimethylaminopyridine
tris thenoyltrifluoroacetonato Dy0.2, La0.8 4-picoline-N-oxide
tris thenoyltrifluoroacetonato Dy0.2, La0.8 4-phenylpyridine
tris thenoyltrifluoroacetonato Dy0.2, La0.8 4-cyanopyridine
tris thenoyltrifluoroacetonato Dy0.2, La0.8 4-phenylpyridine-N-oxide
tris thenoyltrifluoroacetonato Dy0.2, La0.8 1-methylimidazole
tris thenoyltrifluoroacetonato Dy0.2, La0.8 triphenylphosphine oxide
tris thenoyltrifluoroacetonato Dy0.2, La0.8 2,2-bipyridyl
tris thenoyltrifluoroacetonato Dy0.2, La0.8 2,2-bipyridyl-N,N-dioxide
tris thenoyltrifluoroacetonato Dy0.2, La0.8 phenanthroline
tris thenoyltrifluoroacetonato Dy0.2, La0.8 bathocuproine
tris thenoyltrifluoroacetonato Dy0.2, La0.8 bathophenanthroline
tris 2,2,6,6-tetramethylheptanedionato Dy0.2, La0.8 dimethylaminopyridine
tris 2,2,6,6-tetramethylheptanedionato Dy0.2, La0.8 4-picoline-N-oxide
tris 2,2,6,6-tetramethylheptanedionato Dy0.2, La0.8 4-phenylpyridine
tris 2,2,6,6-tetramethylheptanedionato Dy0.2, La0.8 4-cyanopyridine
tris 2,2,6,6-tetramethylheptanedionato Dy0.2, La0.8 4-phenylpyridine-N-oxide
tris 2,2,6,6-tetramethylheptanedionato Dy0.2, La0.8 1-methylimidazole
tris 2,2,6,6-tetramethylheptanedionato Dy0.2, La0.8 triphenyiphosphine oxide
tris 2,2,6,6-tetramethylheptanedionato Dy0.2, La0.8 2,2-bipyridyl
tris 2,2,6,6-tetramethylheptanedionato Dy0.2, La0.8 2,2-bipyridyl-N,N-dioxide
tris 2,2,6,6-tetramethylheptanedionato Dy0.2, La0.8 phenanthroline
tris 2,2,6,6-tetramethylheptanedionato Dy0.2, La0.8 bathocuproine
tris 2,2,6,6-tetramethylheptanedionato Dy0.2, La0.8 bathophenanthroline
tris 3-methylpentane-2,4-dionato Dy0.2, La0.8 dimethylaminopyridine
tris 3-methylpentane-2,4-dionato Dy0.2, La0.8 4-picoline-N-oxide
tris 3-methylpentane-2,4-dionato Dy0.2, La0.8 4-phenylpyridine
tris 3-methylpentane-2,4-dionato Dy0.2, La0.8 4-cyanopyridine
tris 3-methylpentane-2,4-dionato Dy0.2, La0.8 4-phenylpyridine-N-oxide
tris 3-methylpentane-2,4-dionato Dy0.2, La0.8 1-methylimidazole
tris 3-methylpentane-2,4-dionato Dy0.2, La0.8 triphenylphosphine oxide
tris 3-methylpentane-2,4-dionato Dy0.2, La0.8 2,2-bipyridyl
tris 3-methylpentane-2,4-dionato Dy0.2, La0.8 2,2-bipyridyl-N,N-dioxide
tris 3-methylpentane-2,4-dionato Dy0.2, La0.8 phenanthroline
tris 3-methylpentane-2,4-dionato Dy0.2, La0.8 bathocuproine
tris 3-methylpentane-2,4-dionato Dy0.2, La0.8 bathophenanthroline
tris 3-ethylpentane-2,4-dionato Dy0.2, La0.8 dimethylaminopyridine
tris 3-ethylpentane-2,4-dionato Dy0.2, La0.8 4-picoline-N-oxide tris 3-ethylpentane-2,4-dionato Dy0.2, La0.8 4-phenylpyridine
tris 3-ethylpentane-2,4-dionato Dy0.2, La0.8 4-cyanopyridine
tris 3-ethylpentane-2,4-dionato Dy0.2, La0.8 4-phenylpyridine-N-oxide
tris 3-ethylpentane-2,4-dionato Dy0.2, La0.8 1-methylimidazole
tris 3-ethylpentane-2,4-dionato Dy0.2, La0.8 triphenylphosphine oxide
tris 3-ethylpentane-2,4-dionato Dy0.2, La0.8 2,2-bipyridyl
tris 3-ethylpentane-2,4-dionato Dy0.2, La0.8 2,2-bipyridyl-N,N-dioxide
tris 3-ethylpentane-2,4-dionato Dy0.2, La0.8 phenanthroline
tris 3-ethylpentane-2,4-dionato Dy0.2, La0.8 bathocuproine
tris 3-ethylpentane-2,4-dionato Dy0.2, La0.8 bathophenanthroline
tris pivaloyltrifluoroacetonato Dy0.2, La0.8 dimethylaminopyridine
tris pivaloyltrifluoroacetonato Dy0.2, La0.8 4-picoline-N-oxide
tris pivaloyltrifluoroacetonato Dy0.2, La0.8 4-phenylpyridine
tris pivaloyltrifluoroacetonato Dy0.2, La0.8 4-cyanopyridine
tris pivaloyltrifluoroacetonato Dy0.2, La0.8 4-phenylpyridine-N-oxide
tris pivaloyltrifluoroacetonato Dy0.2, La0.8 1-methylimidazole
tris pivaloyltrifluoroacetonato Dy0.2, La0.8 triphenylphosphine oxide
tris pivaloyltrifluoroacetonato Dy0.2, La0.8 2,2-bipyridyl
tris pivaloyltrifluoroacetonato Dy0.2, La0.8 2,2-bipyridyl-N,N-dioxide
tris pivaloyltrifluoroacetonato Dy0.2, La0.8 phenanthroline
tris pivaloyltrifluoroacetonato Dy0.2, La0.8 bathocuproine
tris pivaloyltrifluoroacetonato Dy0.2, La0.8 bathophenanthroline
tris trifluoroacetylacetonato Dy0.2, La0.8 dimethylaminopyridine
tris trifluoroacetylacetonato Dy0.2, La0.8 4-picoline-N-oxide
tris trifluoroacetylacetonato Dy0.2, La0.8 4-phenylpyridine
tris trifluoroacetylacetonato Dy0.2, La0.8 4-cyanopyridine
tris trifluoroacetylacetonato Dy0.2, La0.8 4-phenylpyridine-N-oxide
tris trifluoroacetylacetonato Dy0.2, La0.8 1-methylimidazole
tris trifluoroacetylacetonato Dy0.2, La0.8 triphenylphosphine oxide
tris trifluoroacetylacetonato Dy0.2, La0.8 2,2-bipyridyl
tris trifluoroacetylacetonato Dy0.2, La0.8 2,2-bipyridyl-N,N-dioxide
tris trifluoroacetylacetonato Dy0.2, La0.8 phenanthroline
tris trifluoroacetylacetonato Dy0.2, La0.8 bathocuproine
tris trifluoroacetylacetonato Dy0.2, La0.8 bathophenanthroline
tris hexafluoroacetylacetonato Dy0.2, La0.8 dimethylaminopyridine
tris hexafluoroacetylacetonato Dy0.2, La0.8 4-picoline-N-oxide
tris hexafluoroacetylacetonato Dy0.2, La0.8 4-phenylpyridine
tris hexafluoroacetylacetonato Dy0.2, La0.8 4-cyanopyridine
tris hexafluoroacetylacetonato Dy0.2, La0.8 4-phenylpyridine-N-oxide
tris hexafluoroacetylacetonato Dy0.2, La0.8 1-methylimidazole
tris hexafluoroacetylacetonato Dy0.2, La0.8 triphenylphosphine oxide
tris hexafluoroacetylacetonato Dy0.2, La0.8 2,2-bipyridyl
tris hexafluoroacetylacetonato Dy0.2, La0.8 2,2-bipyridyl-N,N-dioxide
tris hexafluoroacetylacetonato Dy0.2, La0.8 phenanthroline
tris hexafluoroacetylacetonato Dy0.2, La0.8 bathocuproine
tris hexafluoroacetylacetonato Dy0.2, La0.8 bathophenanthroline
tris 6,6,7,7,8,8,8-heptafluoro-2,2-dimethyloctanedionato Dy0.2, La0.8 dimethylaminopyridine
tris 6,6,7,7,8,8,8-heptafluoro-2,2-dimethyloctanedionato Dy0.2, La0.8 4-picoline-N-oxide
tris 6,6,7,7,8,8,8-heptafluoro-2,2-dimethyloctanedionato Dy0.2, La0.8 4-phenylpyridine
tris 6,6,7,7,8,8,8-heptafluoro-2,2-dimethyloctanedionato Dy0.2, La0.8 4-cyanopyridine
tris 6,6,7,7,8,8,8-heptafluoro-2,2-dimethyloctanedionato Dy0.2, La0.8 4-phenylpyridine-N-oxide
tris 6,6,7,7,8,8,8-heptafluoro-2,2-dimethyloctanedionato Dy0.2, La0.8 1-methylimidazole
tris 6,6,7,7,8,8,8-heptafluoro-2,2-dimethyloctanedionato Dy0.2, La0.8 triphenylphosphine oxide
tris 6,6,7,7,8,8,8-heptafluoro-2,2-dimethyloctanedionato Dy0.2, La0.8 2,2-bipyridyl
tris 6,6,7,7,8,8,8-heptafluoro-2,2-dimethyloctanedionato Dy0.2, La0.8 2,2-bipyridyl-N,N-dioxide
tris 6,6,7,7,8,8,8-heptafluoro-2,2-dimethyloctanedionato Dy0.2, La0.8 phenanthroline
tris 6,6,7,7,8,8,8-heptafluoro-2,2-dimethyloctanedionato Dy0.2, La0.8 bathocuproine
tris 6,6,7,7,8,8,8-heptafluoro-2,2-dimethyloctanedionato Dy0.2, La0.8 bathophenanthroline
tris 1-phenyl-1,3-butanedionato Dy0.2, La0.8 dimethylaminopyridine
tris 1-phenyl-1,3-butanedionato Dy0.2, La0.8 4-picoline-N-oxide
tris 1-phenyl-1,3-butanedionato Dy0.2, La0.8 4-phenylpyridine
tris 1-phenyl-1,3-butanedionato Dy0.2, La0.8 4-cyanopyridine
tris 1-phenyl-1,3-butanedionato Dy0.2, La0.8 4-phenylpyridine-N-oxide
tris 1-phenyl-1,3-butanedionato Dy0.2, La0.8 1-methylimidazole
tris 1-phenyl-1,3-butanedionato Dy0.2, La0.8 triphenylphosphine oxide
tris 1-phenyl-1,3-butanedionato Dy0.2, La0.8 2,2-bipyridyl
tris 1-phenyl-1,3-butanedionato Dy0.2, La0.8 2,2-bipyridyl-N,N-dioxide
tris 1-phenyl-1,3-butanedionato Dy0.2, La0.8 phenanthroline
tris 1-phenyl-1,3-butanedionato Dy0.2, La0.8 bathocuproine
tris 1-phenyl-1,3-butanedionato Dy0.2, La0.8 bathophenanthroline
tris acetylacetonato Dy0.1, La0.9 dimethylaminopyridine
tris acetylacetonato Dy0.1, La0.9 4-picoline-N-oxide
tris acetylacetonato Dy0.1, La0.9 4-phenylpyridine
tris acetylacetonato Dy0.1, La0.9 4-cyanopyridine
tris acetylacetonato Dy0.1, La0.9 4-phenylpyridine-N-oxide
tris acetylacetonato Dy0.1, La0.9 1-methylimidazole
tris acetylacetonato Dy0.1, La0.9 triphenylphosphine oxide
tris acetylacetonato Dy0.1, La0.9 2,2-bipyridyl
tris acetylacetonato Dy0.1, La0.9 2,2-bipyridyl-N,N-dioxide
tris acetylacetonato Dy0.1, La0.9 phenanthroline tris acetylacetonato Dy0.1, La0.9 bathocuproine
tris acetylacetonato Dy0.1, La0.9 bathophenanthroline
tris dibenzoylmethanato Dy0.1, La0.9 dimethylaminopyridine
tris dibenzoylmethanato Dy0.1, La0.9 4-picoline-N-oxide
tris dibenzoylmethanato Dy0.1, La0.9 4-phenylpyridine
tris dibenzoylmethanato Dy0.1, La0.9 4-cyanopyridine
tris dibenzoylmethanato Dy0.1, La0.9 4-phenylpyridine-N-oxide
tris dibenzoylmethanato Dy0.1, La0.9 1-methylimidazole
tris dibenzoylmethanato Dy0.1, La0.9 triphenylphosphine oxide
tris dibenzoylmethanato Dy0.1, La0.9 2,2-bipyridyl
tris dibenzoylmethanato Dy0.1, La0.9 2,2-bipyridyl-N,N-dioxide
tris dibenzoylmethanato Dy0.1, La0.9 phenanthroline
tris dibenzoylmethanato Dy0.1, La0.9 bathocuproine
tris dibenzoylmethanato Dy0.1, La0.9 bathophenanthroline
tris thenoyltrifluoroacetonato Dy0.1, La0.9 dimethylaminopyridine
tris thenoyltrifluoroacetonato Dy0.1, La0.9 4-picoline-N-oxide
tris thenoyltrifluoroacetonato Dy0.1, La0.9 4-phenylpyridine
tris thenoyltrifluoroacetonato Dy0.1, La0.9 4-cyanopyridine
tris thenoyltrifluoroacetonato Dy0.1, La0.9 4-phenylpyridine-N-oxide
tris thenoyltrifluoroacetonato Dy0.1, La0.9 1-methylimidazole
tris thenoyltrifluoroacetonato Dy0.1, La0.9 triphenylphosphine oxide
tris thenoyltrifluoroacetonato Dy0.1, La0.9 2,2-bipyridyl
tris thenoyltrifluoroacetonato Dy0.1, La0.9 2,2-bipyridyl-N,N-dioxide
tris thenoyltrifluoroacetonato Dy0.1, La0.9 phenanthroline
tris thenoyltrifluoroacetonato Dy0.1, La0.9 bathocuproine
tris thenoyltrifluoroacetonato Dy0.1, La0.9 bathophenanthroline
tris 2,2,6,6-tetramethylheptanedionato Dy0.1, La0.9 dimethylaminopyridine
tris 2,2,6,6-tetramethylheptanedionato Dy0.1, La0.9 4-picoline-N-oxide
tris 2,2,6,6-tetramethylheptanedionato Dy0.1, La0.9 4-phenylpyridine
tris 2,2,6,6-tetramethylheptanedionato Dy0.1, La0.9 4-cyanopyridine
tris 2,2,6,6-tetramethylheptanedionato Dy0.1, La0.9 4-phenylpyridine-N-oxide
tris 2,2,6,6-tetramethylheptanedionato Dy0.1, La0.9 1-methylimidazole
tris 2,2,6,6-tetramethylheptanedionato Dy0.1, La0.9 triphenylphosphine oxide
tris 2,2,6,6-tetramethylheptanedionato Dy0.1, La0.9 2,2-bipyridyl
tris 2,2,6,6-tetramethylheptanedionato Dy0.1, La0.9 2,2-bipyridyl-N,N-dioxide
tris 2,2,6,6-tetramethylheptanedionato Dy0.1, La0.9 phenanthroline
tris 2,2,6,6-tetramethylheptanedionato Dy0.1, La0.9 bathocuproine
tris 2,2,6,6-tetramethylheptanedionato Dy0.1, La0.9 bathophenanthroline
tris 3-methylpentane-2,4-dionato Dy0.1, La0.9 dimethylaminopyridine
tris 3-methylpentane-2,4-dionato Dy0.1, La0.9 4-picoline-N-oxide
tris 3-methylpentane-2,4-dionato Dy0.1, La0.9 4-phenylpyridine
tris 3-methylpentane-2,4-dionato Dy0.1, La0.9 4-cyanopyridine
tris 3-methylpentane-2,4-dionato Dy0.1, La0.9 4-phenylpyridine-N-oxide
tris 3-methylpentane-2,4-dionato Dy0.1, La0.9 1-methylimidazole
tris 3-methylpentane-2,4-dionato Dy0.1, La0.9 triphenylphosphine oxide
tris 3-methylpentane-2,4-dionato Dy0.1, La0.9 2,2-bipyridyl
tris 3-methylpentane-2,4-dionato Dy0.1, La0.9 2,2-bipyridyl-N,N-dioxide
tris 3-methylpentane-2,4-dionato Dy0.1, La0.9 phenanthroline
tris 3-methylpentane-2,4-dionato Dy0.1, La0.9 bathocuproine
tris 3-methylpentane-2,4-dionato Dy0.1, La0.9 bathophenanthroline
tris 3-ethylpentane-2,4-dionato Dy0.1, La0.9 dimethylaminopyridine
tris 3-ethylpentane-2,4-dionato Dy0.1, La0.9 4-picoline-N-oxide
tris 3-ethylpentane-2,4-dionato Dy0.1, La0.9 4-phenylpyridine
tris 3-ethylpentane-2,4-dionato Dy0.1, La0.9 4-cyanopyridine
tris 3-ethylpentane-2,4-dionato Dy0.1, La0.9 4-phenylpyridine-N-oxide
tris 3-ethylpentane-2,4-dionato Dy0.1, La0.9 1-methylimidazole
tris 3-ethylpentane-2,4-dionato Dy0.1, La0.9 triphenylphosphine oxide
tris 3-ethylpentane-2,4-dionato Dy0.1, La0.9 2,2-bipyridyl
tris 3-ethylpentane-2,4-dionato Dy0.1, La0.9 2,2-bipyridyl-N,N-dioxide
tris 3-ethylpentane-2,4-dionato Dy0.1, La0.9 phenanthroline
tris 3-ethylpentane-2,4-dionato Dy0.1, La0.9 bathocuproine
tris 3-ethylpentane-2,4-dionato Dy0.1, La0.9 bathophenanthroline
tris pivaloyltrifluoroacetonato Dy0.1, La0.9 dimethylaminopyridine
tris pivaloyltrifluoroacetonato Dy0.1, La0.9 4-picoline-N-oxide
tris pivaloyltrifluoroacetonato Dy0.1, La0.9 4-phenylpyridine
tris pivaloyltrifluoroacetonato Dy0.1, La0.9 4-cyanopyridine
tris pivaloyltrifluoroacetonato Dy0.1, La0.9 4-phenylpyridine-N-oxide
tris pivaloyltrifluoroacetonato Dy0.1, La0.9 1-methylimidazole
tris pivaloyltrifluoroacetonato Dy0.1, La0.9 triphenylphosphine oxide
tris pivaloyltrifluoroacetonato Dy0.1, La0.9 2,2-bipyridyl
tris pivaloyltrifluoroacetonato Dy0.1, La0.9 2,2-bipyridyl-N,N-dioxide
tris pivaloyltrifluoroacetonato Dy0.1, La0.9 phenanthroline
tris pivaloyltrifluoroacetonato Dy0.1, La0.9 bathocuproine
tris pivaloyltrifluoroacetonato Dy0.1, La0.9 bathophenanthroline
tris trifluoroacetylacetonato Dy0.1, La0.9 dimethylaminopyridine
tris trifluoroacetylacetonato Dy0.1, La0.9 4-picoline-N-oxide
tris trifluoroacetylacetonato Dy0.1, La0.9 4-phenylpyridine
tris trifluoroacetylacetonato Dy0.1, La0.9 4-cyanopyridine tris trifluoroacetylacetonato Dy0.1, La0.9 4-phenylpyridine-N-oxide
tris trifluoroacetylacetonato Dy0.1, La0.9 1-methylimidazole
tris trifluoroacetylacetonato Dy0.1, La0.9 triphenylphosphine oxide
tris trifluoroacetylacetonato Dy0.1, La0.9 2,2-bipyridyl
tris trifluoroacetylacetonato Dy0.1, La0.9 2,2-bipyridyl-N,N-dioxide
tris trifluoroacetylacetonato Dy0.1, La0.9 phenanthroline
tris trifluoroacetylacetonato Dy0.1, La0.9 bathocuproine
tris trifluoroacetylacetonato Dy0.1, La0.9 bathophenanthroline
tris hexafluoroacetylacetonato Dy0.1, La0.9 dimethylaminopyridine
tris hexafluoroacetylacetonato Dy0.1, La0.9 4-picoline-N-oxide
tris hexafluoroacetylacetonato Dy0.1, La0.9 4-phenylpyridine
tris hexafluoroacetylacetonato Dy0.1, La0.9 4-cyanopyridine
tris hexafluoroacetylacetonato Dy0.1, La0.9 4-phenylpyridine-N-oxide
tris hexafluoroacetylacetonato Dy0.1, La0.9 1-methylimidazole
tris hexafluoroacetylacetonato Dy0.1, La0.9 triphenylphosphine oxide
tris hexafluoroacetylacetonato Dy0.1, La0.9 2,2-bipyridyl
tris hexafluoroacetylacetonato Dy0.1, La0.9 2,2-bipyridyl-N,N-dioxide
tris hexafluoroacetylacetonato Dy0.1, La0.9 phenanthroline
tris hexafluoroacetylacetonato Dy0.1, La0.9 bathocuproine
tris hexafluoroacetylacetonato Dy0.1, La0.9 bathophenanthroline
tris 6,6,7,7,8,8,8-heptafluoro-2,2-dimethyloctanedionato Dy0.1, La0.9 dimethylaminopyridine
tris 6,6,7,7,8,8,8-heptafluoro-2,2-dimethyloctanedionato Dy0.1, La0.9 4-picoline-N-oxide
tris 6,6,7,7,8,8,8-heptafluoro-2,2-dimethyloctanedionato Dy0.1, La0.9 4-phenylpyridine
tris 6,6,7,7,8,8,8-heptafluoro-2,2-dimethyloctanedionato Dy0.1, La0.9 4-cyanopyridine
tris 6,6,7,7,8,8,8-heptafluoro-2,2-dimethyloctanedionato Dy0.1, La0.9 4-phenylpyridine-N-oxide
tris 6,6,7,7,8,8,8-heptafluoro-2,2-dimethyloctanedionato Dy0.1, La0.9 1-methylimidazole
tris 6,6,7,7,8,8,8-heptafluoro-2,2-dimethyloctanedionato Dy0.1, La0.9 triphenylphosphine oxide
tris 6,6,7,7,8,8,8-heptafluoro-2,2-dimethyloctanedionato Dy0.1, La0.9 2,2-bipyridyl
tris 6,6,7,7,8,8,8-heptafluoro-2,2-dimethyloctanedionato Dy0.1, La0.9 2,2-bipyridyl-N,N-dioxide
tris 6,6,7,7,8,8,8-heptafluoro-2,2-dimethyloctanedionato Dy0.1, La0.9 phenanthroline
tris 6,6,7,7,8,8,8-heptafluoro-2,2-dimethyloctanedionato Dy0.1, La0.9 bathocuproine
tris 6,6,7,7,8,8,8-heptafluoro-2,2-dimethyloctanedionato Dy0.1, La0.9 bathophenanthroline
tris 1-phenyl-1,3-butanedionato Dy0.1, La0.9 dimethylaminopyridine
tris 1-phenyl-1,3-butanedionato Dy0.1, La0.9 4-picoline-N-oxide
tris 1-phenyl-1,3-butanedionato Dy0.1, La0.9 4-phenylpyridine
tris 1-phenyl-1,3-butanedionato Dy0.1, La0.9 4-cyanopyridine
tris 1-phenyl-1,3-butanedionato Dy0.1, La0.9 4-phenylpyridine-N-oxide
tris 1-phenyl-1,3-butanedionato Dy0.1, La0.9 1-methylimidazole
tris 1-phenyl-1,3-butanedionato Dy0.1, La0.9 triphenylphosphine oxide
tris 1-phenyl-1,3-butanedionato Dy0.1, La0.9 2,2-bipyridyl
tris 1-phenyl-1,3-butanedionato Dy0.1, La0.9 2,2-bipyridyl-N,N-dioxide
tris 1-phenyl-1,3-butanedionato Dy0.1, La0.9 phenanthroline
tris 1-phenyl-1,3-butanedionato Dy0.1, La0.9 bathocuproine
tris 1-phenyl-1,3-butanedionato Dy0.1, La0.9 bathophenanthroline
tris acetylacetonato Dy0.01, La0.99 dimethylaminopyridine
tris acetylacetonato Dy0.01, La0.99 4-picoline-N-oxide
tris acetylacetonato Dy0.01, La0.99 4-phenylpyridine
tris acetylacetonato Dy0.01, La0.99 4-cyanopyridine
tris acetylacetonato Dy0.01, La0.99 4-phenylpyridine-N-oxide
tris acetylacetonato Dy0.01, La0.99 1-methylimidazole
tris acetylacetonato Dy0.01, La0.99 triphenylphosphine oxide
tris acetylacetonato Dy0.01, La0.99 2,2-bipyridyl
tris acetylacetonato Dy0.01, La0.99 2,2-bipyridyl-N,N-dioxide
tris acetylacetonato Dy0.01, La0.99 phenanthroline
tris acetylacetonato Dy0.01, La0.99 bathocuproine
tris acetylacetonato Dy0.01, La0.99 bathophenanthroline
tris dibenzoylmethanato Dy0.01, La0.99 dimethylaminopyridine
tris dibenzoylmethanato Dy0.01, La0.99 4-picoline-N-oxide
tris dibenzoylmethanato Dy0.01, La0.99 4-phenylpyridine
tris dibenzoylmethanato Dy0.01, La0.99 4-cyanopyridine
tris dibenzoylmethanato Dy0.01, La0.99 4-phenylpyridine-N-oxide
tris dibenzoylmethanato Dy0.01, La0.99 1-methylimidazole
tris dibenzoylmethanato Dy0.01, La0.99 triphenylphosphine oxide
tris dibenzoylmethanato Dy0.01, La0.99 2,2-bipyridyl
tris dibenzoylmethanato Dy0.01, La0.99 2,2-bipyridyl-N,N-dioxide
tris dibenzoylmethanato Dy0.01, La0.99 phenanthroline
tris dibenzoylmethanato Dy0.01, La0.99 bathocuproine
tris dibenzoylmethanato Dy0.01, La0.99 bathophenanthroline
tris thenoyltrifluoroacetonato Dy0.01, La0.99 dimethylaminopyridine
tris thenoyltrifluoroacetonato Dy0.01, La0.99 4-picoline-N-oxide
tris thenoyltrifluoroacetonato Dy0.01, La0.99 4-phenylpyridine
tris thenoyltrifluoroacetonato Dy0.01, La0.99 4-cyanopyridine
tris thenoyltrifluoroacetonato Dy0.01, La0.99 4-phenylpyridine-N-oxide
tris thenoyltrifluoroacetonato Dy0.01, La0.99 1-methylimidazole
tris thenoyltrifluoroacetonato Dy0.01, La0.99 triphenylphosphine oxide
tris thenoyltrifluoroacetonato Dy0.01, La0.99 2,2-bipyridyl
tris thenoyltrifluoroacetonato Dy0.01, La0.99 2,2-bipyridyl-N,N-dioxide
tris thenoyltrifluoroacetonato Dy0.01, La0.99 phenanthroline
tris thenoyltrifluoroacetonato Dy0.01, La0.99 bathocuproine tris thenoyltrifluoroacetonato Dy0.01, La0.99 bathophenanthroline
tris 2,2,6,6-tetramethylheptanedionato Dy0.01, La0.99 dimethylaminopyridine
tris 2,2,6,6-tetramethylheptanedionato Dy0.01, La0.99 4-picoline-N-oxide
tris 2,2,6,6-tetramethylheptanedionato Dy0.01, La0.99 4-phenylpyridine
tris 2,2,6,6-tetramethylheptanedionato Dy0.01, La0.99 4-cyanopyridine
tris 2,2,6,6-tetramethylheptanedionato Dy0.01, La0.99 4-phenylpyridine-N-oxide
tris 2,2,6,6-tetramethylheptanedionato Dy0.01, La0.99 1-methylimidazole
tris 2,2,6,6-tetramethylheptanedionato Dy0.01, La0.99 triphenylphosphine oxide
tris 2,2,6,6-tetramethylheptanedionato Dy0.01, La0.99 2,2-bipyridyl
tris 2,2,6,6-tetramethylheptanedionato Dy0.01, La0.99 2,2-bipyridyl-N,N-dioxide
tris 2,2,6,6-tetramethylheptanedionato Dy0.01, La0.99 phenanthroline
tris 2,2,6,6-tetramethylheptanedionato Dy0.01, La0.99 bathocuproine
tris 2,2,6,6-tetramethylheptanedionato Dy0.01, La0.99 bathophenanthroline
tris 3-methylpentane-2,4-dionato Dy0.01, La0.99 dimethylaminopyridine
tris 3-methylpentane-2,4-dionato Dy0.01, La0.99 4-picoline-N-oxide
tris 3-methylpentane-2,4-dionato Dy0.01, La0.99 4-phenylpyridine
tris 3-methylpentane-2,4-dionato Dy0.01, La0.99 4-cyanopyridine
tris 3-methylpentane-2,4-dionato Dy0.01, La0.99 4-phenylpyridine-N-oxide
tris 3-methylpentane-2,4-dionato Dy0.01, La0.99 1-methylimidazole
tris 3-methylpentane-2,4-dionato Dy0.01, La0.99 triphenylphosphine oxide
tris 3-methylpentane-2,4-dionato Dy0.01, La0.99 2,2-bipyridyl
tris 3-methylpentane-2,4-dionato Dy0.01, La0.99 2,2-bipyridyl-N,N-dioxide
tris 3-methylpentane-2,4-dionato Dy0.01, La0.99 phenanthroline
tris 3-methylpentane-2,4-dionato Dy0.01, La0.99 bathocuproine
tris 3-methylpentane-2,4-dionato Dy0.01, La0.99 bathophenanthroline
tris 3-ethylpentane-2,4-dionato Dy0.01, La0.99 dimethylaminopyridine
tris 3-ethylpentane-2,4-dionato Dy0.01, La0.99 4-picoline-N-oxide
tris 3-ethylpentane-2,4-dionato Dy0.01, La0.99 4-phenylpyridine
tris 3-ethylpentane-2,4-dionato Dy0.01, La0.99 4-cyanopyridine
tris 3-ethylpentane-2,4-dionato Dy0.01, La0.99 4-phenylpyridine-N-oxide
tris 3-ethylpentane-2,4-dionato Dy0.01, La0.99 1-methylimidazole
tris 3-ethylpentane-2,4-dionato Dy0.01, La0.99 triphenylphosphine oxide
tris 3-ethylpentane-2,4-dionato Dy0.01, La0.99 2,2-bipyridyl
tris 3-ethylpentane-2,4-dionato Dy0.01, La0.99 2,2-bipyridyl-N,N-dioxide
tris 3-ethylpentane-2,4-dionato Dy0.01, La0.99 phenanthroline
tris 3-ethylpentane-2,4-dionato Dy0.01, La0.99 bathocuproine
tris 3-ethylpentane-2,4-dionato Dy0.01, La0.99 bathophenanthroline
tris pivaloyltrifluoroacetonato Dy0.01, La0.99 dimethylaminopyridine
tris pivaloyltrifluoroacetonato Dy0.01, La0.99 4-picoline-N-oxide
tris pivaloyltrifluoroacetonato Dy0.01, La0.99 4-phenylpyridine
tris pivaloyltrifluoroacetonato Dy0.01, La0.99 4-cyanopyridine
tris pivaloyltrifluoroacetonato Dy0.01, La0.99 4-phenylpyridine-N-oxide
tris pivaloyltrifluoroacetonato Dy0.01, La0.99 1-methylimidazole
tris pivaloyltrifluoroacetonato Dy0.01, La0.99 triphenylphosphine oxide
tris pivaloyltrifluoroacetonato Dy0.01, La0.99 2,2-bipyridyl
tris pivaloyltrifluoroacetonato Dy0.01, La0.99 2,2-bipyridyl-N,N-dioxide
tris pivaloyltrifluoroacetonato Dy0.01, La0.99 phenanthroline
tris pivaloyltrifluoroacetonato Dy0.01, La0.99 bathocuproine
tris pivaloyltrifluoroacetonato Dy0.01, La0.99 bathophenanthroline
tris trifluoroacetylacetonato Dy0.01, La0.99 dimethylaminopyridine
tris trifluoroacetylacetonato Dy0.01, La0.99 4-picoline-N-oxide
tris trifluoroacetylacetonato Dy0.01, La0.99 4-phenylpyridine
tris trifluoroacetylacetonato Dy0.01, La0.99 4-cyanopyridine
tris trifluoroacetylacetonato Dy0.01, La0.99 4-phenylpyridine-N-oxide
tris trifluoroacetylacetonato Dy0.01, La0.99 1-methylimidazole
tris trifluoroacetylacetonato Dy0.01, La0.99 triphenylphosphine oxide
tris trifluoroacetylacetonato Dy0.01, La0.99 2,2-bipyridyl
tris trifluoroacetylacetonato Dy0.01, La0.99 2,2-bipyridyl-N,N-dioxide
tris trifluoroacetylacetonato Dy0.01, La0.99 phenanthroline
tris trifluoroacetylacetonato Dy0.01, La0.99 bathocuproine
tris trifluoroacetylacetonato Dy0.01, La0.99 bathophenanthroline
tris hexafluoroacetylacetonato Dy0.01, La0.99 dimethylaminopyridine
tris hexafluoroacetylacetonato Dy0.01, La0.99 4-picoline-N-oxide
tris hexafluoroacetylacetonato Dy0.01, La0.99 4-phenylpyridine
tris hexafluoroacetylacetonato Dy0.01, La0.99 4-cyanopyridine
tris hexafluoroacetylacetonato Dy0.01, La0.99 4-phenylpyridine-N-oxide
tris hexafluoroacetylacetonato Dy0.01, La0.99 1-methylimidazole
tris hexafluoroacetylacetonato Dy0.01, La0.99 triphenylphosphine oxide
tris hexafluoroacetylacetonato Dy0.01, La0.99 2,2-bipyridyl tris hexafluoroacetylacetonato Dy0.01, La0.99 2,2-bipyridyl-N,N-dioxide
tris hexafluoroacetylacetonato Dy0.01, La0.99 phenanthroline
tris hexafluoroacetylacetonato Dy0.01, La0.99 bathocuproine
tris hexafluoroacetylacetonato Dy0.01, La0.99 bathophenanthroline
tris 6,6,7,7,8,8,8-heptafluoro-2,2-dimethyloctanedionato Dy0.01, La0.99 dimethylaminopyridine
tris 6,6,7,7,8,8,8-heptafluoro-2,2-dimethyloctanedionato Dy0.01, La0.99 4-picoline-N-oxide
tris 6,6,7,7,8,8,8-heptafluoro-2,2-dimethyloctanedionato Dy0.01, La0.99 4-phenylpyridine
tris 6,6,7,7,8,8,8-heptafluoro-2,2-dimethyloctanedionato Dy0.01, La0.99 4-cyanopyridine
tris 6,6,7,7,8,8,8-heptafluoro-2,2-dimethyloctanedionato Dy0.01, La0.99 4-phenylpyridine-N-oxide
tris 6,6,7,7,8,8,8-heptafluoro-2,2-dimethyloctanedionato Dy0.01, La0.99 1-methylimidazole
tris 6,6,7,7,8,8,8-heptafluoro-2,2-dimethyloctanedionato Dy0.01, La0.99 triphenylphosphine oxide
tris 6,6,7,7,8,8,8-heptafluoro-2,2-dimethyloctanedionato Dy0.01, La0.99 2,2-bipyridyl
tris 6,6,7,7,8,8,8-heptafluoro-2,2-dimethyloctanedionato Dy0.01, La0.99 2,2-bipyridyl-N,N-dioxide
tris 6,6,7,7,8,8,8-heptafluoro-2,2-dimethyloctanedionato Dy0.01, La0.99 phenanthroline
tris 6,6,7,7,8,8,8-heptafluoro-2,2-dimethyloctanedionato Dy0.01, La0.99 bathocuproine
tris 6,6,7,7,8,8,8-heptafluoro-2,2-dimethyloctanedionato Dy0.01, La0.99 bathophenanthroline
tris 1-phenyl-1,3-butanedionato Dy0.01, La0.99 dimethylaminopyridine
tris 1-phenyl-1,3-butanedionato Dy0.01, La0.99 4-picoline-N-oxide
tris 1-phenyl-1,3-butanedionato Dy0.01, La0.99 4-phenylpyridine
tris 1-phenyl-1,3-butanedionato Dy0.01, La0.99 4-cyanopyridine
tris 1-phenyl-1,3-butanedionato Dy0.01, La0.99 4-phenylpyridine-N-oxide
tris 1-phenyl-1,3-butanedionato Dy0.01, La0.99 1-methylimidazole
tris 1-phenyl-1,3-butanedionato Dy0.01, La0.99 triphenylphosphine oxide
tris 1-phenyl-1,3-butanedionato Dy0.01, La0.99 2,2-bipyridyl
tris 1-phenyl-1,3-butanedionato Dy0.01, La0.99 2,2-bipyridyl-N,N-dioxide
tris 1-phenyl-1,3-butanedionato Dy0.01, La0.99 phenanthroline
tris 1-phenyl-1,3-butanedionato Dy0.01, La0.99 bathocuproine
tris 1-phenyl-1,3-butanedionato Dy0.01, La0.99 bathophenanthroline
tris acetylacetonato Dy0.5, La0.5 dimethylaminopyridine
tris acetylacetonato Dy0.5, La0.5 4-picoline-N-oxide
tris acetylacetonato Dy0.5, La0.5 4-phenylpyridine
tris acetylacetonato Dy0.5, La0.5 4-cyanopyridine
tris acetylacetonato Dy0.5, La0.5 4-phenylpyridine-N-oxide
tris acetylacetonato Dy0.5, La0.5 1-methylimidazole
tris acetylacetonato Dy0.5, La0.5 triphenylphosphine oxide
tris acetylacetonato Dy0.5, La0.5 2,2-bipyridyl
tris acetylacetonato Dy0.5, La0.5 2,2-bipyridyl-N,N-dioxide
tris acetylacetonato Dy0.5, La0.5 phenanthroline
tris acetylacetonato Dy0.5, La0.5 bathocuproine
tris acetylacetonato Dy0.5, La0.5 bathophenanthroline
tris dibenzoylmethanato Dy0.5, La0.5 dimethylaminopyridine
tris dibenzoylmethanato Dy0.5, La0.5 4-picoline-N-oxide
tris dibenzoylmethanato Dy0.5, La0.5 4-phenylpyridine
tris dibenzoylmethanato Dy0.5, La0.5 4-cyanopyridine
tris dibenzoylmethanato Dy0.5, La0.5 4-phenylpyridine-N-oxide
tris dibenzoylmethanato Dy0.5, La0.5 1-methylimidazole
tris dibenzoylmethanato Dy0.5, La0.5 triphenylphosphine oxide
tris dibenzoylmethanato Dy0.5, La0.5 2,2-bipyridyl
tris dibenzoylmethanato Dy0.5, La0.5 2,2-bipyridyl-N,N-dioxide
tris dibenzoylmethanato Dy0.5, La0.5 phenanthroline
tris dibenzoylmethanato Dy0.5, La0.5 bathocuproine
tris dibenzoylmethanato Dy0.5, La0.5 bathophenanthroline
tris thenoyltrifluoroacetonato Dy0.5, La0.5 dimethylaminopyridine
tris thenoyltrifluoroacetonato Dy0.5, La0.5 4-picoline-N-oxide
tris thenoyltrifluoroacetonato Dy0.5, La0.5 4-phenylpyridine
tris thenoyltrifluoroacetonato Dy0.5, La0.5 4-cyanopyridine
tris thenoyltrifluoroacetonato Dy0.5, La0.5 4-phenylpyridine-N-oxide
tris thenoyltrifluoroacetonato Dy0.5, La0.5 1-methylimidazole
tris thenoyltrifluoroacetonato Dy0.5, La0.5 triphenylphosphine oxide
tris thenoyltrifluoroacetonato Dy0.5, La0.5 2,2-bipyridyl
tris thenoyltrifluoroacetonato Dy0.5, La0.5 2,2-bipyridyl-N,N-dioxide
tris thenoyltrifluoroacetonato Dy0.5, La0.5 phenanthroline
tris thenoyltrifluoroacetonato Dy0.5, La0.5 bathocuproine
tris thenoyltrifluoroacetonato Dy0.5, La0.5 bathophenanthroline
tris 2,2,6,6-tetramethylheptanedionato Dy0.5, La0.5 dimethylaminopyridine
tris 2,2,6,6-tetramethylheptanedionato Dy0.5, La0.5 4-picoline-N-oxide
tris 2,2,6,6-tetramethylheptanedionato Dy0.5, La0.5 4-phenylpyridine
tris 2,2,6,6-tetramethylheptanedionato Dy0.5, La0.5 4-cyanopyridine
tris 2,2,6,6-tetramethylheptanedionato Dy0.5, La0.5 4-phenylpyridine-N-oxide
tris 2,2,6,6-tetramethylheptanedionato Dy0.5, La0.5 1-methylimidazole
tris 2,2,6,6-tetramethylheptanedionato Dy0.5, La0.5 triphenylphosphine oxide
tris 2,2,6,6-tetramethylheptanedionato Dy0.5, La0.5 2,2-bipyridyl
tris 2,2,6,6-tetramethylheptanedionato Dy0.5, La0.5 2,2-bipyridyl-N,N-dioxide
tris 2,2,6,6-tetramethylheptanedionato Dy0.5, La0.5 phenanthroline
tris 2,2,6,6-tetramethylheptanedionato Dy0.5, La0.5 bathocuproine
tris 2,2,6,6-tetramethylheptanedionato Dy0.5, La0.5 bathophenanthroline
tris 3-methylpentane-2,4-dionato Dy0.5, La0.5 dimethylaminopyridine
tris 3-methylpentane-2,4-dionato Dy0.5, La0.5 4-picoline-N-oxide
tris 3-methylpentane-2,4-dionato Dy0.5, La0.5 4-phenylpyridine tris 3-methylpentane-2,4-dionato Dy0.5, La0.5 4-cyanopyridine
tris 3-methylpentane-2,4-dionato Dy0.5, La0.5 4-phenylpyridine-N-oxide
tris 3-methylpentane-2,4-dionato Dy0.5, La0.5 1-methylimidazole
tris 3-methylpentane-2,4-dionato Dy0.5, La0.5 triphenylphosphine oxide
tris 3-methylpentane-2,4-dionato Dy0.5, La0.5 2,2-bipyridyl
tris 3-methylpentane-2,4-dionato Dy0.5, La0.5 2,2-bipyridyl-N,N-dioxide
tris 3-methylpentane-2,4-dionato Dy0.5, La0.5 phenanthroline
tris 3-methylpentane-2,4-dionato Dy0.5, La0.5 bathocuproine
tris 3-methylpentane-2,4-dionato Dy0.5, La0.5 bathophenanthroline
tris 3-ethylpentane-2,4-dionato Dy0.5, La0.5 dimethylaminopyridine
tris 3-ethylpentane-2,4-dionato Dy0.5, La0.5 4-picoline-N-oxide
tris 3-ethylpentane-2,4-dionato Dy0.5, La0.5 4-phenylpyridine
tris 3-ethylpentane-2,4-dionato Dy0.5, La0.5 4-cyanopyridine
tris 3-ethylpentane-2,4-dionato Dy0.5, La0.5 4-phenylpyridine-N-oxide
tris 3-ethylpentane-2,4-dionato Dy0.5, La0.5 1-methylimidazole
tris 3-ethylpentane-2,4-dionato Dy0.5, La0.5 triphenylphosphine oxide
tris 3-ethylpentane-2,4-dionato Dy0.5, La0.5 2,2-bipyridyl
tris 3-ethylpentane-2,4-dionato Dy0.5, La0.5 2,2-bipyridyl-N,N-dioxide
tris 3-ethylpentane-2,4-dionato Dy0.5, La0.5 phenanthroline
tris 3-ethylpentane-2,4-dionato Dy0.5, La0.5 bathocuproine
tris 3-ethylpentane-2,4-dionato Dy0.5, La0.5 bathophenanthroline
tris pivaloyltrifluoroacetonato Dy0.5, La0.5 dimethylaminopyridine
tris pivaloyltrifluoroacetonato Dy0.5, La0.5 4-picoline-N-oxide
tris pivaloyltrifluoroacetonato Dy0.5, La0.5 4-phenylpyridine
tris pivaloyltrifluoroacetonato Dy0.5, La0.5 4-cyanopyridine
tris pivaloyltrifluoroacetonato Dy0.5, La0.5 4-phenylpyridine-N-oxide
tris pivaloyltrifluoroacetonato Dy0.5, La0.5 1-methylimidazole
tris pivaloyltrifluoroacetonato Dy0.5, La0.5 triphenylphosphine oxide
tris pivaloyltrifluoroacetonato Dy0.5, La0.5 2,2-bipyridyl
tris pivaloyltrifluoroacetonato Dy0.5, La0.5 2,2-bipyridyl-N,N-dioxide
tris pivaloyltrifluoroacetonato Dy0.5, La0.5 phenanthroline
tris pivaloyltrifluoroacetonato Dy0.5, La0.5 bathocuproine
tris pivaloyltrifluoroacetonato Dy0.5, La0.5 bathophenanthroline
tris trifluoroacetylacetonato Dy0.5, La0.5 dimethylaminopyridine
tris trifluoroacetylacetonato Dy0.5, La0.5 4-picoline-N-oxide
tris trifluoroacetylacetonato Dy0.5, La0.5 4-phenylpyridine
tris trifluoroacetylacetonato Dy0.5, La0.5 4-cyanopyridine
tris trifluoroacetylacetonato Dy0.5, La0.5 4-phenylpyridine-N-oxide
tris trifluoroacetylacetonato Dy0.5, La0.5 1-methylimidazole
tris trifluoroacetylacetonato Dy0.5, La0.5 triphenylphosphine oxide
tris trifluoroacetylacetonato Dy0.5, La0.5 2,2-bipyridyl
tris trifluoroacetylacetonato Dy0.5, La0.5 2,2-bipyridyl-N,N-dioxide
tris trifluoroacetylacetonato Dy0.5, La0.5 phenanthroline
tris trifluoroacetylacetonato Dy0.5, La0.5 bathocuproine
tris trifluoroacetylacetonato Dy0.5, La0.5 bathophenanthroline
tris hexafluoroacetylacetonato Dy0.5, La0.5 dimethylaminopyridine
tris hexafluoroacetylacetonato Dy0.5, La0.5 4-picoline-N-oxide
tris hexafluoroacetylacetonato Dy0.5, La0.5 4-phenylpyridine
tris hexafluoroacetylacetonato Dy0.5, La0.5 4-cyanopyridine
tris hexafluoroacetylacetonato Dy0.5, La0.5 4-phenylpyridine-N-oxide
tris hexafluoroacetylacetonato Dy0.5, La0.5 1-methylimidazole
tris hexafluoroacetylacetonato Dy0.5, La0.5 triphenylphosphine oxide
tris hexafluoroacetylacetonato Dy0.5, La0.5 2,2-bipyridyl
tris hexafluoroacetylacetonato Dy0.5, La0.5 2,2-bipyridyl-N,N-dioxide
tris hexafluoroacetylacetonato Dy0.5, La0.5 phenanthroline
tris hexafluoroacetylacetonato Dy0.5, La0.5 bathocuproine
tris hexafluoroacetylacetonato Dy0.5, La0.5 bathophenanthroline
tris 6,6,7,7,8,8,8-heptafluoro-2,2-dimethyloctanedionato Dy0.5, La0.5 dimethylaminopyridine
tris 6,6,7,7,8,8,8-heptafluoro-2,2-dimethyloctanedionato Dy0.5, La0.5 4-picoline-N-oxide
tris 6,6,7,7,8,8,8-heptafluoro-2,2-dimethyloctanedionato Dy0.5, La0.5 4-phenylpyridine
tris 6,6,7,7,8,8,8-heptafluoro-2,2-dimethyloctanedionato Dy0.5, La0.5 4-cyanopyridine
tris 6,6,7,7,8,8,8-heptafluoro-2,2-dimethyloctanedionato Dy0.5, La0.5 4-phenylpyridine-N-oxide
tris 6,6,7,7,8,8,8-heptafluoro-2,2-dimethyloctanedionato Dy0.5, La0.5 1-methylimidazole
tris 6,6,7,7,8,8,8-heptafluoro-2,2-dimethyloctanedionato Dy0.5, La0.5 triphenylphosphine oxide
tris 6,6,7,7,8,8,8-heptafluoro-2,2-dimethyloctanedionato Dy0.5, La0.5 2,2-bipyridyl
tris 6,6,7,7,8,8,8-heptafluoro-2,2-dimethyloctanedionato Dy0.5, La0.5 2,2-bipyridyl-N,N-dioxide
tris 6,6,7,7,8,8,8-heptafluoro-2,2-dimethyloctanedionato Dy0.5, La0.5 phenanthroline
tris 6,6,7,7,8,8,8-heptafluoro-2,2-dimethyloctanedionato Dy0.5, La0.5 bathocuproine
tris 6,6,7,7,8,8,8-heptafluoro-2,2-dimethyloctanedionato Dy0.5, La0.5 bathophenanthroline
tris 1-phenyl-1,3-butanedionato Dy0.5, La0.5 dimethylaminopyridine
tris 1-phenyl-1,3-butanedionato Dy0.5, La0.5 4-picoline-N-oxide
tris 1-phenyl-1,3-butanedionato Dy0.5, La0.5 4-phenylpyridine
tris 1-phenyl-1,3-butanedionato Dy0.5, La0.5 4-cyanopyridine
tris 1-phenyl-1,3-butanedionato Dy0.5, La0.5 4-phenylpyridine-N-oxide tris 1-phenyl-1,3-butanedionato Dy0.5, La0.5 1-methylimidazole
tris 1-phenyl-1,3-butanedionato Dy0.5, La0.5 triphenylphosphine oxide
tris 1-phenyl-1,3-butanedionato Dy0.5, La0.5 2,2-bipyridyl
tris 1-phenyl-1,3-butanedionato Dy0.5, La0.5 2,2-bipyridyl-N,N-dioxide
tris 1-phenyl-1,3-butanedionato Dy0.5, La0.5 phenanthroline
tris 1-phenyl-1,3-butanedionato Dy0.5, La0.5 bathocuproine
tris 1-phenyl-1,3-butanedionato Dy0.5, La0.5 bathophenanthroline
tris acetylacetonato Dy0.2, La0.8 dimethylaminopyridine
tris acetylacetonato Dy0.2, La0.8 4-picoline-N-oxide
tris acetylacetonato Dy0.2, La0.8 4-phenylpyridine
tris acetylacetonato Dy0.2, La0.8 4-cyanopyridine
tris acetylacetonato Dy0.2, La0.8 4-phenylpyridine-N-oxide
tris acetylacetonato Dy0.2, La0.8 1-methylimidazole
tris acetylacetonato Dy0.2, La0.8 triphenylphosphine oxide
tris acetylacetonato Dy0.2, La0.8 2,2-bipyridyl
tris acetylacetonato Dy0.2, La0.8 2,2-bipyridyl-N,N-dioxide
tris acetylacetonato Dy0.2, La0.8 phenanthroline
tris acetylacetonato Dy0.2, La0.8 bathocuproine
tris acetylacetonato Dy0.2, La0.8 bathophenanthroline
tris dibenzoylmethanato Dy0.2, La0.8 dimethylaminopyridine
tris dibenzoylmethanato Dy0.2, La0.8 4-picoline-N-oxide
tris dibenzoylmethanato Dy0.2, La0.8 4-phenylpyridine
tris dibenzoylmethanato Dy0.2, La0.8 4-cyanopyridine
tris dibenzoylmethanato Dy0.2, La0.8 4-phenylpyridine-N-oxide
tris dibenzoylmethanato Dy0.2, La0.8 1-methylimidazole
tris dibenzoylmethanato Dy0.2, La0.8 triphenylphosphine oxide
tris dibenzoylmethanato Dy0.2, La0.8 2,2-bipyridyl
tris dibenzoylmethanato Dy0.2, La0.8 2,2-bipyridyl-N,N-dioxide
tris dibenzoylmethanato Dy0.2, La0.8 phenanthroline
tris dibenzoylmethanato Dy0.2, La0.8 bathocuproine
tris dibenzoylmethanato Dy0.2, La0.8 bathophenanthroline
tris thenoyltrifluoroacetonato Dy0.2, La0.8 dimethylaminopyridine
tris thenoyltrifluoroacetonato Dy0.2, La0.8 4-picoline-N-oxide
tris thenoyltrifluoroacetonato Dy0.2, La0.8 4-phenylpyridine
tris thenoyltrifluoroacetonato Dy0.2, La0.8 4-cyanopyridine
tris thenoyltrifluoroacetonato Dy0.2, La0.8 4-phenylpyridine-N-oxide
tris thenoyltrifluoroacetonato Dy0.2, La0.8 1-methylimidazole
tris thenoyltrifluoroacetonato Dy0.2, La0.8 triphenylphosphine oxide
tris thenoyltrifluoroacetonato Dy0.2, La0.8 2,2-bipyridyl
tris thenoyltrifluoroacetonato Dy0.2, La0.8 2,2-bipyridyl-N,N-dioxide
tris thenoyltrifluoroacetonato Dy0.2, La0.8 phenanthroline
tris thenoyltrifluoroacetonato Dy0.2, La0.8 bathocuproine
tris thenoyltrifluoroacetonato Dy0.2, La0.8 bathophenanthroline
tris 2,2,6,6-tetramethylheptanedionato Dy0.2, La0.8 dimethylaminopyridine
tris 2,2,6,6-tetramethylheptanedionato Dy0.2, La0.8 4-picoline-N-oxide
tris 2,2,6,6-tetramethylheptanedionato Dy0.2, La0.8 4-phenylpyridine
tris 2,2,6,6-tetramethylheptanedionato Dy0.2, La0.8 4-cyanopyridine
tris 2,2,6,6-tetramethylheptanedionato Dy0.2, La0.8 4-phenylpyridine-N-oxide
tris 2,2,6,6-tetramethylheptanedionato Dy0.2, La0.8 1-methylimidazole
tris 2,2,6,6-tetramethylheptanedionato Dy0.2, La0.8 triphenylphosphine oxide
tris 2,2,6,6-tetramethylheptanedionato Dy0.2, La0.8 2,2-bipyridyl
tris 2,2,6,6-tetramethylheptanedionato Dy0.2, La0.8 2,2-bipyridyl-N,N-dioxide
tris 2,2,6,6-tetramethylheptanedionato Dy0.2, La0.8 phenanthroline
tris 2,2,6,6-tetramethylheptanedionato Dy0.2, La0.8 bathocuproine
tris 2,2,6,6-tetramethylheptanedionato Dy0.2, La0.8 bathophenanthroline
tris 3-methylpentane-2,4-dionato Dy0.2, La0.8 dimethylaminopyridine
tris 3-methylpentane-2,4-dionato Dy0.2, La0.8 4-picoline-N-oxide
tris 3-methylpentane-2,4-dionato Dy0.2, La0.8 4-phenylpyridine
tris 3-methylpentane-2,4-dionato Dy0.2, La0.8 4-cyanopyridine
tris 3-methylpentane-2,4-dionato Dy0.2, La0.8 4-phenylpyridine-N-oxide
tris 3-methylpentane-2,4-dionato Dy0.2, La0.8 1-methylimidazole
tris 3-methylpentane-2,4-dionato Dy0.2, La0.8 triphenylphosphine oxide
tris 3-methylpentane-2,4-dionato Dy0.2, La0.8 2,2-bipyridyl
tris 3-methylpentane-2,4-dionato Dy0.2, La0.8 2,2-bipyridyl-N,N-dioxide
tris 3-methylpentane-2,4-dionato Dy0.2, La0.8 phenanthroline
tris 3-methylpentane-2,4-dionato Dy0.2, La0.8 bathocuproine
tris 3-methylpentane-2,4-dionato Dy0.2, La0.8 bathophenanthroline
tris 3-ethylpentane-2,4-dionato Dy0.2, La0.8 dimethylaminopyridine
tris 3-ethylpentane-2,4-dionato Dy0.2, La0.8 4-picoline-N-oxide
tris 3-ethylpentane-2,4-dionato Dy0.2, La0.8 4-phenylpyridine
tris 3-ethylpentane-2,4-dionato Dy0.2, La0.8 4-cyanopyridine
tris 3-ethylpentane-2,4-dionato Dy0.2, La0.8 4-phenylpyridine-N-oxide
tris 3-ethylpentane-2,4-dionato Dy0.2, La0.8 1-methylimidazole
tris 3-ethylpentane-2,4-dionato Dy0.2, La0.8 triphenylphosphine oxide
tris 3-ethylpentane-2,4-dionato Dy0.2, La0.8 2,2-bipyridyl
tris 3-ethylpentane-2,4-dionato Dy0.2, La0.8 2,2-bipyridyl-N,N-dioxide
tris 3-ethylpentane-2,4-dionato Dy0.2, La0.8 phenanthroline
tris 3-ethylpentane-2,4-dionato Dy0.2, La0.8 bathocuproine
tris 3-ethylpentane-2,4-dionato Dy0.2, La0.8 bathophenanthroline
tris pivaloyltrifluoroacetonato Dy0.2, La0.8 dimethylaminopyridine
tris pivaloyltrifluoroacetonato Dy0.2, La0.8 4-picoline-N-oxide tris pivaloyltrifluoroacetonato Dy0.2, La0.8 4-phenylpyridine
tris pivaloyltrifluoroacetonato Dy0.2, La0.8 4-cyanopyridine
tris pivaloyltrifluoroacetonato Dy0.2, La0.8 4-phenylpyridine-N-oxide
tris pivaloyltrifluoroacetonato Dy0.2, La0.8 1-methylimidazole
tris pivaloyltrifluoroacetonato Dy0.2, La0.8 triphenylphosphine oxide
tris pivaloyltrifluoroacetonato Dy0.2, La0.8 2,2-bipyridyl
tris pivaloyltrifluoroacetonato Dy0.2, La0.8 2,2-bipyridyl-N,N-dioxide
tris pivaloyltrifluoroacetonato Dy0.2, La0.8 phenanthroline
tris pivaloyltrifluoroacetonato Dy0.2, La0.8 bathocuproine
tris pivaloyltrifluoroacetonato Dy0.2, La0.8 bathophenanthroline
tris trifluoroacetylacetonato Dy0.2, La0.8 dimethylaminopyridine
tris trifluoroacetylacetonato Dy0.2, La0.8 4-picoline-N-oxide
tris trifluoroacetylacetonato Dy0.2, La0.8 4-phenylpyridine
tris trifluoroacetylacetonato Dy0.2, La0.8 4-cyanopyridine
tris trifluoroacetylacetonato Dy0.2, La0.8 4-phenylpyridine-N-oxide
tris trifluoroacetylacetonato Dy0.2, La0.8 1-methylimidazole
tris trifluoroacetylacetonato Dy0.2, La0.8 triphenylphosphine oxide
tris trifluoroacetylacetonato Dy0.2, La0.8 2,2-bipyridyl
tris trifluoroacetylacetonato Dy0.2, La0.8 2,2-bipyridyl-N,N-dioxide
tris trifluoroacetylacetonato Dy0.2, La0.8 phenanthroline
tris trifluoroacetylacetonato Dy0.2, La0.8 bathocuproine
tris trifluoroacetylacetonato Dy0.2, La0.8 bathophenanthroline
tris hexafluoroacetylacetonato Dy0.2, La0.8 dimethylaminopyridine
tris hexafluoroacetylacetonato Dy0.2, La0.8 4-picoline-N-oxide
tris hexafluoroacetylacetonato Dy0.2, La0.8 4-phenylpyridine
tris hexafluoroacetylacetonato Dy0.2, La0.8 4-cyanopyridine
tris hexafluoroacetylacetonato Dy0.2, La0.8 4-phenylpyridine-N-oxide
tris hexafluoroacetylacetonato Dy0.2, La0.8 1-methylimidazole
tris hexafluoroacetylacetonato Dy0.2, La0.8 triphenylphosphine oxide
tris hexafluoroacetylacetonato Dy0.2, La0.8 2,2-bipyridyl
tris hexafluoroacetylacetonato Dy0.2, La0.8 2,2-bipyridyl-N,N-dioxide
tris hexafluoroacetylacetonato Dy0.2, La0.8 phenanthroline
tris hexafluoroacetylacetonato Dy0.2, La0.8 bathocuproine
tris hexafluoroacetylacetonato Dy0.2, La0.8 bathophenanthroline
tris 6,6,7,7,8,8,8-heptafluoro-2,2-dimethyloctanedionato Dy0.2, La0.8 dimethylaminopyridine
tris 6,6,7,7,8,8,8-heptafluoro-2,2-dimethyloctanedionato Dy0.2, La0.8 4-picoline-N-oxide
tris 6,6,7,7,8,8,8-heptafluoro-2,2-dimethyloctanedionato Dy0.2, La0.8 4-phenylpyridine
tris 6,6,7,7,8,8,8-heptafluoro-2,2-dimethyloctanedionato Dy0.2, La0.8 4-cyanopyridine
tris 6,6,7,7,8,8,8-heptafluoro-2,2-dimethyloctanedionato Dy0.2, La0.8 4-phenylpyridine-N-oxide
tris 6,6,7,7,8,8,8-heptafluoro-2,2-dimethyloctanedionato Dy0.2, La0.8 1-methylimidazole
tris 6,6,7,7,8,8,8-heptafluoro-2,2-dimethyloctanedionato Dy0.2, La0.8 triphenylphosphine oxide
tris 6,6,7,7,8,8,8-heptafluoro-2,2-dimethyloctanedionato Dy0.2, La0.8 2,2-bipyridyl
tris 6,6,7,7,8,8,8-heptafluoro-2,2-dimethyloctanedionato Dy0.2, La0.8 2,2-bipyridyl-N,N-dioxide
tris 6,6,7,7,8,8,8-heptafluoro-2,2-dimethyloctanedionato Dy0.2, La0.8 phenanthroline
tris 6,6,7,7,8,8,8-heptafluoro-2,2-dimethyloctanedionato Dy0.2, La0.8 bathocuproine
tris 6,6,7,7,8,8,8-heptafluoro-2,2-dimethyloctanedionato Dy0.2, La0.8 bathophenanthroline
tris 1-phenyl-1,3-butanedionato Dy0.2, La0.8 dimethylaminopyridine
tris 1-phenyl-1,3-butanedionato Dy0.2, La0.8 4-picoline-N-oxide
tris 1-phenyl-1,3-butanedionato Dy0.2, La0.8 4-phenylpyridine
tris 1-phenyl-1,3-butanedionato Dy0.2, La0.8 4-cyanopyridine
tris 1-phenyl-1,3-butanedionato Dy0.2, La0.8 4-phenylpyridine-N-oxide
tris 1-phenyl-1,3-butanedionato Dy0.2, La0.8 1-methylimidazole
tris 1-phenyl-1,3-butanedionato Dy0.2, La0.8 triphenylphosphine oxide
tris 1-phenyl-1,3-butanedionato Dy0.2, La0.8 2,2-bipyridyl
tris 1-phenyl-1,3-butanedionato Dy0.2, La0.8 2,2-bipyridyl-N,N-dioxide
tris 1-phenyl-1,3-butanedionato Dy0.2, La0.8 phenanthroline
tris 1-phenyl-1,3-butanedionato Dy0.2, La0.8 bathocuproine
tris 1-phenyl-1,3-butanedionato Dy0.2, La0.8 bathophenanthroline
tris acetylacetonato Dy0.1, La0.9 dimethylaminopyridine
tris acetylacetonato Dy0.1, La0.9 4-picoline-N-oxide
tris acetylacetonato Dy0.1, La0.9 4-phenylpyridine
tris acetylacetonato Dy0.1, La0.9 4-cyanopyridine
tris acetylacetonato Dy0.1, La0.9 4-phenylpyridine-N-oxide
tris acetylacetonato Dy0.1, La0.9 1-methylimidazole
tris acetylacetonato Dy0.1, La0.9 triphenylphosphine oxide
tris acetylacetonato Dy0.1, La0.9 2,2-bipyridyl
tris acetylacetonato Dy0.1, La0.9 2,2-bipyridyl-N,N-dioxide
tris acetylacetonato Dy0.1, La0.9 phenanthroline
tris acetylacetonato Dy0.1, La0.9 bathocuproine
tris acetylacetonato Dy0.1, La0.9 bathophenanthroline
tris dibenzoylmethanato Dy0.1, La0.9 dimethylaminopyridine
tris dibenzoylmethanato Dy0.1i La0.9 4-picoline-N-oxide
tris dibenzoylmethanato Dy0.1, La0.9 4-phenylpyridine
tris dibenzoylmethanato Dy0.1, La0.9 4-cyanopyridine
tris dibenzoylmethanato Dy0.1, La0.9 4-phenylpyridine-N-oxide
tris dibenzoylmethanato Dy0.1, La0.9 1-methylimidazole
tris dibenzoylmethanato Dy0.1, La0.9 triphenylphosphine oxide
tris dibenzoylmethanato Dy0.1, La0.9 2,2-bipyridyl
tris dibenzoylmethanato Dy0.1, La0.9 2,2-bipyridyl-N,N-dioxide
tris dibenzoylmethanato Dy0.1, La0.9 phenanthroline
tris dibenzoylmethanato Dy0.1, La0.9 bathocuproine
tris dibenzoylmethanato Dy0.1, La0.9 bathophenanthroline
tris thenoyltrifluoroacetonato Dy0.1, La0.9 dimethylaminopyridine tris thenoyltrifluoroacetonato Dy0.1, La0.9 4-picoline-N-oxide
tris thenoyltrifluoroacetonato Dy0.1, La0.9 4-phenylpyridine
tris thenoyltrifluoroacetonato Dy0.1, La0.9 4-cyanopyridine
tris thenoyltrifluoroacetonato Dy0.1, La0.9 4-phenylpyridine-N-oxide
tris thenoyltrifluoroacetonato Dy0.1, La0.9 1-methylimidazole
tris thenoyltrifluoroacetonato Dy0.1, La0.9 triphenylphosphine oxide
tris thenoyltrifluoroacetonato Dy0.1, La0.9 2,2-bipyridyl
tris thenoyltrifluoroacetonato Dy0.1, La0.9 2,2-bipyridyl-N,N-dioxide
tris thenoyltrifluoroacetonato Dy0.1, La0.9 phenanthroline
tris thenoyltrifluoroacetonato Dy0.1, La0.9 bathocuproine
tris thenoyltrifluoroacetonato Dy0.1, La0.9 bathophenanthroline
tris 2,2,6,6-tetramethylheptanedionato Dy0.1, La0.9 dimethylaminopyridine
tris 2,2,6,6-tetramethylheptanedionato Dy0.1, La0.9 4-picoline-N-oxide
tris 2,2,6,6-tetramethylheptanedionato Dy0.1, La0.9 4-phenylpyridine
tris 2,2,6,6-tetramethylheptanedionato Dy0.1, La0.9 4-cyanopyridine
tris 2,2,6,6-tetramethylheptanedionato Dy0.1, La0.9 4-phenylpyridine-N-oxide
tris 2,2,6,6-tetramethylheptanedionato Dy0.1, La0.9 1-methylimidazole
tris 2,2,6,6-tetramethylheptanedionato Dy0.1, La0.9 triphenylphosphine oxide
tris 2,2,6,6-tetramethylheptanedionato Dy0.1, La0.9 2,2-bipyridyl
tris 2,2,6,6-tetramethylheptanedionato Dy0.1, La0.9 2,2-bipyridyl-N,N-dioxide
tris 2,2,6,6-tetramethylheptanedionato Dy0.1, La0.9 phenanthroline
tris 2,2,6,6-tetramethylheptanedionato Dy0.1, La0.9 bathocuproine
tris 2,2,6,6-tetramethylheptanedionato Dy0.1, La0.9 bathophenanthroline
tris 3-methylpentane-2,4-dionato Dy0.1, La0.9 dimethylaminopyridine
tris 3-methylpentane-2,4-dionato Dy0.1, La0.9 4-picoline-N-oxide
tris 3-methylpentane-2,4-dionato Dy0.1, La0.9 4-phenylpyridine
tris 3-methylpentane-2,4-dionato Dy0.1, La0.9 4-cyanopyridine
tris 3-methylpentane-2,4-dionato Dy0.1, La0.9 4-phenylpyridine-N-oxide
tris 3-methylpentane-2,4-dionato Dy0.1, La0.9 1-methylimidazole
tris 3-methylpentane-2,4-dionato Dy0.1, La0.9 triphenylphosphine oxide
tris 3-methylpentane-2,4-dionato Dy0.1, La0.9 2,2-bipyridyl
tris 3-methylpentane-2,4-dionato Dy0.1, La0.9 2,2-bipyridyl-N,N-dioxide
tris 3-methylpentane-2,4-dionato Dy0.1, La0.9 phenanthroline
tris 3-methylpentane-2,4-dionato Dy0.1, La0.9 bathocuproine
tris 3-methylpentane-2,4-dionato Dy0.1, La0.9 bathophenanthroline
tris 3-ethylpentane-2,4-dionato Dy0.1, La0.9 dimethylaminopyridine
tris 3-ethylpentane-2,4-dionato Dy0.1, La0.9 4-picoline-N-oxide
tris 3-ethylpentane-2,4-dionato Dy0.1, La0.9 4-phenylpyridine
tris 3-ethylpentane-2,4-dionato Dy0.1, La0.9 4-cyanopyridine
tris 3-ethylpentane-2,4-dionato Dy0.1, La0.9 4-phenylpyridine-N-oxide
tris 3-ethylpentane-2,4-dionato Dy0.1, La0.9 1-methylimidazole
tris 3-ethylpentane-2,4-dionato Dy0.1, La0.9 triphenylphosphine oxide
tris 3-ethylpentane-2,4-dionato Dy0.1, La0.9 2,2-bipyridyl
tris 3-ethylpentane-2,4-dionato Dy0.1, La0.9 2,2-bipyridyl-N,N-dioxide
tris 3-ethylpentane-2,4-dionato Dy0.1, La0.9 phenanthroline
tris 3-ethylpentane-2,4-dionato Dy0.1, La0.9 bathocuproine
tris 3-ethylpentane-2,4-dionato Dy0.1, La0.9 bathophenanthroline
tris pivaloyltrifluoroacetonato Dy0.1, La0.9 dimethylaminopyridine
tris pivaloyltrifluoroacetonato Dy0.1, La0.9 4-picoline-N-oxide
tris pivaloyltrifluoroacetonato Dy0.1, La0.9 4-phenylpyridine
tris pivaloyltrifluoroacetonato Dy0.1, La0.9 4-cyanopyridine
tris pivaloyltrifluoroacetonato Dy0.1, La0.9 4-phenylpyridine-N-oxide
tris pivaloyltrifluoroacetonato Dy0.1, La0.9 1-methylimidazole
tris pivaloyltrifluoroacetonato Dy0.1, La0.9 triphenylphosphine oxide
tris pivaloyltrifluoroacetonato Dy0.1, La0.9 2,2-bipyridyl
tris pivaloyltrifluoroacetonato Dy0.1, La0.9 2,2-bipyridyl-N,N-dioxide
tris pivaloyltrifluoroacetonato Dy0.1, La0.9 phenanthroline
tris pivaloyltrifluoroacetonato Dy0.1, La0.9 bathocuproine
tris pivaloyltrifluoroacetonato Dy0.1, La0.9 bathophenanthroline
tris trifluoroacetylacetonato Dy0.1, La0.9 dimethylaminopyridine
tris trifluoroacetylacetonato Dy0.1, La0.9 4-picoline-N-oxide
tris trifluoroacetylacetonato Dy0.1, La0.9 4-phenylpyridine
tris trifluoroacetylacetonato Dy0.1, La0.9 4-cyanopyridine
tris trifluoroacetylacetonato Dy0.1, La0.9 4-phenylpyridine-N-oxide
tris trifluoroacetylacetonato Dy0.1, La0.9 1-methylimidazole
tris trifluoroacetylacetonato Dy0.1, La0.9 triphenylphosphine oxide
tris trifluoroacetylacetonato Dy0.1, La0.9 2,2-bipyridyl
tris trifluoroacetylacetonato Dy0.1, La0.9 2,2-bipyridyl-N,N-dioxide
tris trifluoroacetylacetonato Dy0.1, La0.9 phenanthroline
tris trifluoroacetylacetonato Dy0.1, La0.9 bathocuproine
tris trifluoroacetylacetonato Dy0.1, La0.9 bathophenanthroline
tris hexafluoroacetylacetonato Dy0.1, La0.9 dimethylaminopyridine
tris hexafluoroacetylacetonato Dy0.1, La0.9 4-picoline-N-oxide
tris hexafluoroacetylacetonato Dy0.1, La0.9 4-phenylpyridine
tris hexafluoroacetylacetonato Dy0.1, La0.9 4-cyanopyridine tris hexafluoroacetylacetonato Dy0.1, La0.9 4-phenylpyridine-N-oxide
tris hexafluoroacetylacetonato Dy0.1, La0.9 1-methylimidazole
tris hexafluoroacetylacetonato Dy0.1, La0.9 triphenylphosphine oxide
tris hexafluoroacetylacetonato Dy0.1, La0.9 2,2-bipyridyl
tris hexafluoroacetylacetonato Dy0.1, La0.9 2,2-bipyridyl-N,N-dioxide
tris hexafluoroacetylacetonato Dy0.1, La0.9 phenanthroline
tris hexafluoroacetylacetonato Dy0.1, La0.9 bathocuproine
tris hexafluoroacetylacetonato Dy0.1, La0.9 bathophenanthroline
tris 6,6,7,7,8,8,8-heptafluoro-2,2-dimethyloctanedionato Dy0.1, La0.9 dimethylaminopyridine
tris 6,6,7,7,8,8,8-heptafluoro-2,2-dimethyloctanedionato Dy0.1, La0.9 4-picoline-N-oxide
tris 6,6,7,7,8,8,8-heptafluoro-2,2-dimethyloctanedionato Dy0.1, La0.9 4-phenylpyridine
tris 6,6,7,7,8,8,8-heptafluoro-2,2-dimethyloctanedionato Dy0.1, La0.9 4-cyanopyridine
tris 6,6,7,7,8,8,8-heptafluoro-2,2-dimethyloctanedionato Dy0.1, La0.9 4-phenylpyridine-N-oxide
tris 6,6,7,7,8,8,8-heptafluoro-2,2-dimethyloctanedionato Dy0.1, La0.9 1-methylimidazole
tris 6,6,7,7,8,8,8-heptafluoro-2,2-dimethyloctanedionato Dy0.1, La0.9 triphenylphosphine oxide
tris 6,6,7,7,8,8,8-heptafluoro-2,2-dimethyloctanedionato Dy0.1, La0.9 2,2-bipyridyl
tris 6,6,7,7,8,8,8-heptafluoro-2,2-dimethyloctanedionato Dy0.1, La0.9 2,2-bipyridyl-N,N-dioxide
tris 6,6,7,7,8,8,8-heptafluoro-2,2-dimethyloctanedionato Dy0.1, La0.9 phenanthroline
tris 6,6,7,7,8,8,8-heptafluoro-2,2-dimethyloctanedionato Dy0.1, La0.9 bathocuproine
tris 6,6,7,7,8,8,8-heptafluoro-2,2-dimethyloctanedionato Dy0.1, La0.9 bathophenanthroline
tris 1-phenyl-1,3-butanedionato Dy0.1, La0.9 dimethylaminopyridine
tris 1-phenyl-1,3-butanedionato Dy0.1, La0.9 4-picoline-N-oxide
tris 1-phenyl-1,3-butanedionato Dy0.1, La0.9 4-phenylpyridine
tris 1-phenyl-1,3-butanedionato Dy0.1, La0.9 4-cyanopyridine
tris 1-phenyl-1,3-butanedionato Dy0.1, La0.9 4-phenylpyridine-N-oxide
tris 1-phenyl-1,3-butanedionato Dy0.1, La0.9 1-methylimidazole
tris 1-phenyl-1,3-butanedionato Dy0.1, La0.9 triphenylphosphine oxide
tris 1-phenyl-1,3-butanedionato Dy0.1, La0.9 2,2-bipyridyl
tris 1-phenyl-1,3-butanedionato Dy0.1, La0.9 2,2-bipyridyl-N,N-dioxide
tris 1-phenyl-1,3-butanedionato Dy0.1, La0.9 phenanthroline
tris 1-phenyl-1,3-butanedionato Dy0.1, La0.9 bathocuproine
tris 1-phenyl-1,3-butanedionato Dy0.1, La0.9 bathophenanthroline
tris acetylacetonato Dy0.01, La0.99 dimethylaminopyridine
tris acetylacetonato Dy0.01, La0.99 4-picoline-N-oxide
tris acetylacetonato Dy0.01, La0.99 4-phenylpyridine
tris acetylacetonato Dy0.01, La0.99 4-cyanopyridine
tris acetylacetonato Dy0.01, La0.99 4-phenylpyridine-N-oxide
tris acetylacetonato Dy0.01, La0.99 1-methylimidazole
tris acetylacetonato Dy0.01, La0.99 triphenylphosphine oxide
tris acetylacetonato Dy0.01, La0.99 2,2-bipyridyl
tris acetylacetonato Dy0.01, La0.99 2,2-bipyridyl-N,N-dioxide
tris acetylacetonato Dy0.01, La0.99 phenanthroline
tris acetylacetonato Dy0.01, La0.99 bathocuproine
tris acetylacetonato Dy0.01, La0.99 bathophenanthroline
tris dibenzoylmethanato Dy0.01, La0.99 dimethylaminopyridine
tris dibenzoylmethanato Dy0.01, La0.99 4-picoline-N-oxide
tris dibenzoylmethanato Dy0.01, La0.99 4-phenylpyridine
tris dibenzoylmethanato Dy0.01, La0.99 4-cyanopyridine
tris dibenzoylmethanato Dy0.01, La0.99 4-phenylpyridine-N-oxide
tris dibenzoylmethanato Dy0.01, La0.99 1-methylimidazole
tris dibenzoylmethanato Dy0.01, La0.99 triphenylphosphine oxide
tris dibenzoylmethanato Dy0.01, La0.99 2,2-bipyridyl
tris dibenzoylmethanato Dy0.01, La0.99 2,2-bipyridyl-N,N-dioxide
tris dibenzoylmethanato Dy0.01, La0.99 phenanthroline
tris dibenzoylmethanato Dy0.01, La0.99 bathocuproine
tris dibenzoylmethanato Dy0.01, La0.99 bathophenanthroline
tris thenoyltrifluoroacetonato Dy0.01, La0.99 dimethylaminopyridine
tris thenoyltrifluoroacetonato Dy0.01, La0.99 4-picoline-N-oxide
tris thenoyltrifluoroacetonato Dy0.01, La0.99 4-phenylpyridine
tris thenoyltrifluoroacetonato Dy0.01, La0.99 4-cyanopyridine
tris thenoyltrifluoroacetonato Dy0.01, La0.99 4-phenylpyridine-N-oxide
tris thenoyltrifluoroacetonato Dy0.01, La0.99 1-methylimidazole
tris thenoyltrifluoroacetonato Dy0.01, La0.99 triphenylphosphine oxide
tris thenoyltrifluoroacetonato Dy0.01, La0.99 2,2-bipyridyl
tris thenoyltrifluoroacetonato Dy0.01, La0.99 2,2-bipyridyl-N,N-dioxide
tris thenoyltrifluoroacetonato Dy0.01, La0.99 phenanthroline
tris thenoyltrifluoroacetonato Dy0.01, La0.99 bathocuproine
tris thenoyltrifluoroacetonato Dy0.01, La0.99 bathophenanthroline
tris 2,2,6,6-tetramethylheptanedionato Dy0.01, La0.99 dimethylaminopyridine
tris 2,2,6,6-tetramethylheptanedionato Dy0.01, La0.99 4-picoline-N-oxide
tris 2,2,6,6-tetramethylheptanedionato Dy0.01, La0.99 4-phenylpyridine
tris 2,2,6,6-tetramethylheptanedionato Dy0.01, La0.99 4-cyanopyridine
tris 2,2,6,6-tetramethylheptanedionato Dy0.01, La0.99 4-phenylpyridine-N-oxide
tris 2,2,6,6-tetramethylheptanedionato Dy0.01, La0.99 1-methylimidazole
tris 2,2,6,6-tetramethylheptanedionato Dy0.01, La0.99 triphenylphosphine oxide
tris 2,2,6,6-tetramethylheptanedionato Dy0.01, La0.99 2,2-bipyridyl
tris 2,2,6,6-tetramethylheptanedionato Dy0.01, La0.99 2,2-bipyridyl-N,N-dioxide
tris 2,2,6,6-tetramethylheptanedionato Dy0.01, La0.99 phenanthroline tris 2,2,6,6-tetramethylheptanedionato Dy0.01, La0.99 bathocuproine
tris 2,2,6,6-tetramethylheptanedionato Dy0.01, La0.99 bathophenanthroline
tris 3-methylpentane-2,4-dionato Dy0.01, La0.99 dimethylaminopyridine
tris 3-methylpentane-2,4-dionato Dy0.01, La0.99 4-picoline-N-oxide
tris 3-methylpentane-2,4-dionato Dy0.01, La0.99 4-phenylpyridine
tris 3-methylpentane-2,4-dionato Dy0.01, La0.99 4-cyanopyridine
tris 3-methylpentane-2,4-dionato Dy0.01, La0.99 4-phenylpyridine-N-oxide
tris 3-methylpentane-2,4-dionato Dy0.01, La0.99 1-methylimidazole
tris 3-methylpentane-2,4-dionato Dy0.01, La0.99 triphenylphosphine oxide
tris 3-methylpentane-2,4-dionato Dy0.01, La0.99 2,2-bipyridyl
tris 3-methylpentane-2,4-dionato Dy0.01, La0.99 2,2-bipyridyl-N,N-dioxide
tris 3-methylpentane-2,4-dionato Dy0.01, La0.99 phenanthroline
tris 3-methylpentane-2,4-dionato Dy0.01, La0.99 bathocuproine
tris 3-methylpentane-2,4-dionato Dy0.01, La0.99 bathophenanthroline
tris 3-ethylpentane-2,4-dionato Dy0.01, La0.99 dimethylaminopyridine
tris 3-ethylpentane-2,4-dionato Dy0.01, La0.99 4-picoline-N-oxide
tris 3-ethylpentane-2,4-dionato Dy0.01, La0.99 4-phenylpyridine
tris 3-ethylpentane-2,4-dionato Dy0.01, La0.99 4-cyanopyridine
tris 3-ethylpentane-2,4-dionato Dy0.01, La0.99 4-phenylpyridine-N-oxide
tris 3-ethylpentane-2,4-dionato Dy0.01, La0.99 1-methylimidazole
tris 3-ethylpentane-2,4-dionato Dy0.01, La0.99 triphenylphosphine oxide
tris 3-ethylpentane-2,4-dionato Dy0.01, La0.99 2,2-bipyridyl
tris 3-ethylpentane-2,4-dionato Dy0.01, La0.99 2,2-bipyridyl-N,N-dioxide
tris 3-ethylpentane-2,4-dionato Dy0.01, La0.99 phenanthroline
tris 3-ethylpentane-2,4-dionato Dy0.01, La0.99 bathocuproine
tris 3-ethylpentane-2,4-dionato Dy0.01, La0.99 bathophenanthroline
tris pivaloyltrifluoroacetonato Dy0.01, La0.99 dimethylaminopyridine
tris pivaloyltrifluoroacetonato Dy0.01, La0.99 4-picoline-N-oxide
tris pivaloyltrifluoroacetonato Dy0.01, La0.99 4-phenylpyridine
tris pivaloyltrifluoroacetonato Dy0.01, La0.99 4-cyanopyridine
tris pivaloyltrifluoroacetonato Dy0.01, La0.99 4-phenylpyridine-N-oxide
tris pivaloyltrifluoroacetonato Dy0.01, La0.99 1-methylimidazole
tris pivaloyltrifluoroacetonato Dy0.01, La0.99 triphenylphosphine oxide
tris pivaloyltrifluoroacetonato Dy0.01, La0.99 2,2-bipyridyl
tris pivaloyltrifluoroacetonato Dy0.01, La0.99 2,2-bipyridyl-N,N-dioxide
tris pivaloyltrifluoroacetonato Dy0.01, La0.99 phenanthroline
tris pivaloyltrifluoroacetonato Dy0.01, La0.99 bathocuproine
tris pivaloyltrifluoroacetonato Dy0.01, La0.99 bathophenanthroline
tris trifluoroacetylacetonato Dy0.01, La0.99 dimethylaminopyridine
tris trifluoroacetylacetonato Dy0.01, La0.99 4-picoline-N-oxide
tris trifluoroacetylacetonato Dy0.01, La0.99 4-phenylpyridine
tris trifluoroacetylacetonato Dy0.01, La0.99 4-cyanopyridine
tris trifluoroacetylacetonato Dy0.01, La0.99 4-phenylpyridine-N-oxide
tris trifluoroacetylacetonato Dy0.01, La0.99 1-methylimidazole
tris trifluoroacetylacetonato Dy0.01, La0.99 triphenylphosphine oxide
tris trifluoroacetylacetonato Dy0.01, La0.99 2,2-bipyridyl
tris trifluoroacetylacetonato Dy0.01, La0.99 2,2-bipyridyl-N,N-dioxide
tris trifluoroacetylacetonato Dy0.01, La0.99 phenanthroline
tris trifluoroacetylacetonato Dy0.01, La0.99 bathocuproine
tris trifluoroacetylacetonato Dy0.01, La0.99 bathophenanthroline
tris hexafluoroacetylacetonato Dy0.01, La0.99 dimethylaminopyridine
tris hexafluoroacetylacetonato Dy0.01, La0.99 4-picoline-N-oxide
tris hexafluoroacetylacetonato Dy0.01, La0.99 4-phenylpyridine
tris hexafluoroacetylacetonato Dy0.01, La0.99 4-cyanopyridine
tris hexafluoroacetylacetonato Dy0.01, La0.99 4-phenylpyridine-N-oxide
tris hexafluoroacetylacetonato Dy0.01, La0.99 1-methylimidazole
tris hexafluoroacetylacetonato Dy0.01, La0.99 triphenylphosphine oxide
tris hexafluoroacetylacetonato Dy0.01, La0.99 2,2-bipyridyl
tris hexafluoroacetylacetonato Dy0.01, La0.99 2,2-bipyridyl-N,N-dioxide
tris hexafluoroacetylacetonato Dy0.01, La0.99 phenanthroline
tris hexafluoroacetylacetonato Dy0.01, La0.99 bathocuproine
tris hexafluoroacetylacetonato Dy0.01, La0.99 bathophenanthroline
tris 6,6,7,7,8,8,8-heptafluoro-2,2-dimethyloctanedionato Dy0.01, La0.99 dimethylaminopyridine
tris 6,6,7,7,8,8,8-heptafluoro-2,2-dimethyloctanedionato Dy0.01, La0.99 4-picoline-N-oxide
tris 6,6,7,7,8,8,8-heptafluoro-2,2-dimethyloctanedionato Dy0.01, La0.99 4-phenylpyridine
tris 6,6,7,7,8,8,8-heptafluoro-2,2-dimethyloctanedionato Dy0.01, La0.99 4-cyanopyridine
tris 6,6,7,7,8,8,8-heptafluoro-2,2-dimethyloctanedionato Dy0.01, La0.99 4-phenylpyridine-N-oxide
tris 6,6,7,7,8,8,8-heptafluoro-2,2-dimethyloctanedionato Dy0.01, La0.99 1-methylimidazole
tris 6,6,7,7,8,8,8-heptafluoro-2,2-dimethyloctanedionato Dy0.01, La0.99 triphenylphosphine oxide tris 6,6,7,7,8,8,8-heptafluoro-2,2-dimethyloctanedionato Dy0.01, La0.99 2,2-bipyridyl
tris 6,6,7,7,8,8,8-heptafluoro-2,2-dimethyloctanedionato Dy0.01, La0.99 2,2-bipyridyl-N,N-dioxide
tris 6,6,7,7,8,8,8-heptafluoro-2,2-dimethyloctanedionato Dy0.01, La0.99 phenanthroline
tris 6,6,7,7,8,8,8-heptafluoro-2,2-dimethyloctanedionato Dy0.01, La0.99 bathocuproine
tris 6,6,7,7,8,8,8-heptafluoro-2,2-dimethyloctanedionato Dy0.01, La0.99 bathophenanthroline
tris 1-phenyl-1,3-butanedionato Dy0.01, La0.99 dimethylaminopyridine
tris 1-phenyl-1,3-butanedionato Dy0.01, La0.99 4-picoline-N-oxide
tris 1-phenyl-1,3-butanedionato Dy0.01, La0.99 4-phenylpyridine
tris 1-phenyl-1,3-butanedionato Dy0.01, La0.99 4-cyanopyridine
tris 1-phenyl-1,3-butanedionato Dy0.01, La0.99 4-phenylpyridine-N-oxide
tris 1-phenyl-1,3-butanedionato Dy0.01, La0.99 1-methylimidazole
tris 1-phenyl-1,3-butanedionato Dy0.01, La0.99 triphenylphosphine oxide
tris 1-phenyl-1,3-butanedionato Dy0.01, La0.99 2,2-bipyridyl
tris 1-phenyl-1,3-butanedionato Dy0.01, La0.99 2,2-bipyridyl-N,N-dioxide
tris 1-phenyl-1,3-butanedionato Dy0.01, La0.99 phenanthroline
tris 1-phenyl-1,3-butanedionato Dy0.01, La0.99 bathocuproine
tris 1-phenyl-1,3-butanedionato Dy0.01, La0.99 bathophenanthroline
tris acetylacetonato Sm0.5, Gd0.5 dimethylaminopyridine
tris acetylacetonato Sm0.5, Gd0.5 4-picoline-N-oxide
tris acetylacetonato Sm0.5, Gd0.5 4-phenylpyridine
tris acetylacetonato Sm0.5, Gd0.5 4-cyanopyridine
tris acetylacetonato Sm0.5, Gd0.5 4-phenylpyridine-N-oxide
tris acetylacetonato Sm0.5, Gd0.5 1-methylimidazole
tris acetylacetonato Sm0.5, Gd0.5 triphenylphosphine oxide
tris acetylacetonato Sm0.5, Gd0.5 2,2-bipyridyl
tris acetylacetonato Sm0.5, Gd0.5 2,2-bipyridyl-N,N-dioxide
tris acetylacetonato Sm0.5, Gd0.5 phenanthroline
tris acetylacetonato Sm0.5, Gd0.5 bathocuproine
tris acetylacetonato Sm0.5, Gd0.5 bathophenanthroline
tris dibenzoylmethanato Sm0.5, Gd0.5 dimethylaminopyridine
tris dibenzoylmethanato Sm0.5, Gd0.5 4-picoline-N-oxide
tris dibenzoylmethanato Sm0.5, Gd0.5 4-phenylpyridine
tris dibenzoylmethanato Sm0.5, Gd0.5 4-cyanopyridine
tris dibenzoylmethanato Sm0.5, Gd0.5 4-phenylpyridine-N-oxide
tris dibenzoylmethanato Sm0.5, Gd0.5 1-methylimidazole
tris dibenzoylmethanato Sm0.5, Gd0.5 triphenylphosphine oxide
tris dibenzoylmethanato Sm0.5, Gd0.5 2,2-bipyridyl
tris dibenzoylmethanato Sm0.5, Gd0.5 2,2-bipyridyl-N,N-dioxide
tris dibenzoylmethanato Sm0.5, Gd0.5 phenanthroline
tris dibenzoylmethanato Sm0.5, Gd0.5 bathocuproine
tris dibenzoylmethanato Sm0.5, Gd0.5 bathophenanthroline
tris thenoyltrifluoroacetonato Sm0.5, Gd0.5 dimethylaminopyridine
tris thenoyltrifluoroacetonato Sm0.5, Gd0.5 4-picoline-N-oxide
tris thenoyltrifluoroacetonato Sm0.5, Gd0.5 4-phenylpyridine
tris thenoyltrifluoroacetonato Sm0.5, Gd0.5 4-cyanopyridine
tris thenoyltrifluoroacetonato Sm0.5, Gd0.5 4-phenylpyridine-N-oxide
tris thenoyltrifluoroacetonato Sm0.5, Gd0.5 1-methylimidazole
tris thenoyltrifluoroacetonato Sm0.5, Gd0.5 triphenylphosphine oxide
tris thenoyltrifluoroacetonato Sm0.5, Gd0.5 2,2-bipyridyl
tris thenoyltrifluoroacetonato Sm0.5, Gd0.5 2,2-bipyridyl-N,N-dioxide
tris thenoyltrifluoroacetonato Sm0.5, Gd0.5 phenanthroline
tris thenoyltrifluoroacetonato Sm0.5, Gd0.5 bathocuproine
tris thenoyltrifluoroacetonato Sm0.5, Gd0.5 bathophenanthroline
tris 2,2,6,6-tetramethylheptanedionato Sm0.5, Gd0.5 dimethylaminopyridine
tris 2,2,6,6-tetramethylheptanedionato Sm0.5, Gd0.5 4-picoline-N-oxide
tris 2,2,6,6-tetramethylheptanedionato Sm0.5, Gd0.5 4-phenylpyridine
tris 2,2,6,6-tetramethylheptanedionato Sm0.5, Gd0.5 4-cyanopyridine
tris 2,2,6,6-tetramethylheptanedionato Sm0.5, Gd0.5 4-phenylpyridine-N-oxide
tris 2,2,6,6-tetramethylheptanedionato Sm0.5, Gd0.5 1-methylimidazole
tris 2,2,6,6-tetramethylheptanedionato Sm0.5, Gd0.5 triphenylphosphine oxide
tris 2,2,6,6-tetramethylheptanedionato Sm0.5, Gd0.5 2,2-bipyridyl
tris 2,2,6,6-tetramethylheptanedionato Sm0.5, Gd0.5 2,2-bipyridyl-N,N-dioxide
tris 2,2,6,6-tetramethylheptanedionato Sm0.5, Gd0.5 phenanthroline
tris 2,2,6,6-tetramethylheptanedionato Sm0.5, Gd0.5 bathocuproine
tris 2,2,6,6-tetramethylheptanedionato Sm0.5, Gd0.5 bathophenanthroline
tris 3-methylpentane-2,4-dionato Sm0.5, Gd0.5 dimethylaminopyridine
tris 3-methylpentane-2,4-dionato Sm0.5, Gd0.5 4-picoline-N-oxide
tris 3-methylpentane-2,4-dionato Sm0.5, Gd0.5 4-phenylpyridine
tris 3-methylpentane-2,4-dionato Sm0.5, Gd0.5 4-cyanopyridine
tris 3-methylpentane-2,4-dionato Sm0.5, Gd0.5 4-phenylpyridine-N-oxide
tris 3-methylpentane-2,4-dionato Sm0.5, Gd0.5 1-methylimidazole
tris 3-methylpentane-2,4-dionato Sm0.5, Gd0.5 triphenylphosphine oxide
tris 3-methylpentane-2,4-dionato Sm0.5, Gd0.5 2,2-bipyridyl
tris 3-methylpentane-2,4-dionato Sm0.5, Gd0.5 2,2-bipyridyl-N,N-dioxide
tris 3-methylpentane-2,4-dionato Sm0.5, Gd0.5 phenanthroline
tris 3-methylpentane-2,4-dionato Sm0.5, Gd0.5 bathocuproine
tris 3-methylpentane-2,4-dionato Sm0.5, Gd0.5 bathophenanthroline tris 3-ethylpentane-2,4-dionato Sm0.5, Gd0.5 dimethylaminopyridine
tris 3-ethylpentane-2,4-dionato Sm0.5, Gd0.5 4-picoline-N-oxide
tris 3-ethylpentane-2,4-dionato Sm0.5, Gd0.5 4-phenylpyridine
tris 3-ethylpentane-2,4-dionato Sm0.5, Gd0.5 4-cyanopyridine
tris 3-ethylpentane-2,4-dionato Sm0.5, Gd0.5 4-phenylpyridine-N-oxide
tris 3-ethylpentane-2,4-dionato Sm0.5, Gd0.5 1-methylimidazole
tris 3-ethylpentane-2,4-dionato Sm0.5, Gd0.5 triphenylphosphine oxide
tris 3-ethylpentane-2,4-dionato Sm0.5, Gd0.5 2,2-bipyridyl
tris 3-ethylpentane-2,4-dionato Sm0.5, Gd0.5 2,2-bipyridyl-N,N-dioxide
tris 3-ethylpentane-2,4-dionato Sm0.5, Gd0.5 phenanthroline
tris 3-ethylpentane-2,4-dionato Sm0.5, Gd0.5 bathocuproine
tris 3-ethylpentane-2,4-dionato Sm0.5, Gd0.5 bathophenanthroline
tris pivaloyltrifluoroacetonato Sm0.5, Gd0.5 dimethylaminopyridine
tris pivaloyltrifluoroacetonato Sm0.5, Gd0.5 4-picoline-N-oxide
tris pivaloyltrifluoroacetonato Sm0.5, Gd0.5 4-phenylpyridine
tris pivaloyltrifluoroacetonato Sm0.5, Gd0.5 4-cyanopyridine
tris pivaloyltrifluoroacetonato Sm0.5, Gd0.5 4-phenylpyridine-N-oxide
tris pivaloyltrifluoroacetonato Sm0.5, Gd0.5 1-methylimidazole
tris pivaloyltrifluoroacetonato Sm0.5, Gd0.5 triphenylphosphine oxide
tris pivaloyltrifluoroacetonato Sm0.5, Gd0.5 2,2-bipyridyl
tris pivaloyltrifluoroacetonato Sm0.5, Gd0.5 2,2-bipyridyl-N,N-dioxide
tris pivaloyltrifluoroacetonato Sm0.5, Gd0.5 phenanthroline
tris pivaloyltrifluoroacetonato Sm0.5, Gd0.5 bathocuproine
tris pivaloyltrifluoroacetonato Sm0.5, Gd0.5 bathophenanthroline
tris trifluoroacetylacetonato Sm0.5, Gd0.5 dimethylaminopyridine
tris trifluoroacetylacetonato Sm0.5, Gd0.5 4-picoline-N-oxide
tris trifluoroacetylacetonato Sm0.5, Gd0.5 4-phenylpyridine
tris trifluoroacetylacetonato Sm0.5, Gd0.5 4-cyanopyridine
tris trifluoroacetylacetonato Sm0.5, Gd0.5 4-phenylpyridine-N-oxide
tris trifluoroacetylacetonato Sm0.5, Gd0.5 1-methylimidazole
tris trifluoroacetylacetonato Sm0.5, Gd0.5 triphenylphosphine oxide
tris trifluoroacetylacetonato Sm0.5, Gd0.5 2,2-bipyridyl
tris trifluoroacetylacetonato Sm0.5, Gd0.5 2,2-bipyridyl-N,N-dioxide
tris trifluoroacetylacetonato Sm0.5, Gd0.5 phenanthroline
tris trifluoroacetylacetonato Sm0.5, Gd0.5 bathocuproine
tris trifluoroacetylacetonato Sm0.5, Gd0.5 bathophenanthroline
tris hexafluoroacetylacetonato Sm0.5, Gd0.5 dimethylaminopyridine
tris hexafluoroacetylacetonato Sm0.5, Gd0.5 4-picoline-N-oxide
tris hexafluoroacetylacetonato Sm0.5, Gd0.5 4-phenylpyridine
tris hexafluoroacetylacetonato Sm0.5, Gd0.5 4-cyanopyridine
tris hexafluoroacetylacetonato Sm0.5, Gd0.5 4-phenylpyridine-N-oxide
tris hexafluoroacetylacetonato Sm0.5, Gd0.5 1-methylimidazole
tris hexafluoroacetylacetonato Sm0.5, Gd0.5 triphenylphosphine oxide
tris hexafluoroacetylacetonato Sm0.5, Gd0.5 2,2-bipyridyl
tris hexafluoroacetylacetonato Sm0.5, Gd0.5 2,2-bipyridyl-N,N-dioxide
tris hexafluoroacetylacetonato Sm0.5, Gd0.5 phenanthroline
tris hexafluoroacetylacetonato Sm0.5, Gd0.5 bathocuproine
tris hexafluoroacetylacetonato Sm0.5, Gd0.5 bathophenanthroline
tris 6,6,7,7,8,8,8-heptafluoro-2,2-dimethyloctanedionato Sm0.5, Gd0.5 dimethylaminopyridine
tris 6,6,7,7,8,8,8-heptafluoro-2,2-dimethyloctanedionato Sm0.5, Gd0.5 4-picoline-N-oxide
tris 6,6,7,7,8,8,8-heptafluoro-2,2-dimethyloctanedionato Sm0.5, Gd0.5 4-phenylpyridine
tris 6,6,7,7,8,8,8-heptafluoro-2,2-dimethyloctanedionato Sm0.5, Gd0.5 4-cyanopyridine
tris 6,6,7,7,8,8,8-heptafluoro-2,2-dimethyloctanedionato Sm0.5, Gd0.5 4-phenylpyridine-N-oxide
tris 6,6,7,7,8,8,8-heptafluoro-2,2-dimethyloctanedionato Sm0.5, Gd0.5 1-methylimidazole
tris 6,6,7,7,8,8,8-heptafluoro-2,2-dimethyloctanedionato Sm0.5, Gd0.5 triphenylphosphine oxide
tris 6,6,7,7,8,8,8-heptafluoro-2,2-dimethyloctanedionato Sm0.5, Gd0.5 2,2-bipyridyl
tris 6,6,7,7,8,8,8-heptafluoro-2,2-dimethyloctanedionato Sm0.5, Gd0.5 2,2-bipyridyl-N,N-dioxide
tris 6,6,7,7,8,8,8-heptafluoro-2,2-dimethyloctanedionato Sm0.5, Gd0.5 phenanthroline
tris 6,6,7,7,8,8,8-heptafluoro-2,2-dimethyloctanedionato Sm0.5, Gd0.5 bathocuproine
tris 6,6,7,7,8,8,8-heptafluoro-2,2-dimethyloctanedionato Sm0.5, Gd0.5 bathophenanthroline
tris 1-phenyl-1,3-butanedionato Sm0.5, Gd0.5 dimethylaminopyridine
tris 1-phenyl-1,3-butanedionato Sm0.5, Gd0.5 4-picoline-N-oxide
tris 1-phenyl-1,3-butanedionato Sm0.5, Gd0.5 4-phenylpyridine
tris 1-phenyl-1,3-butanedionato Sm0.5, Gd0.5 4-cyanopyridine
tris 1-phenyl-1,3-butanedionato Sm0.5, Gd0.5 4-phenylpyridine-N-oxide
tris 1-phenyl-1,3-butanedionato Sm0.5, Gd0.5 1-methylimidazole
tris 1-phenyl-1,3-butanedionato Sm0.5, Gd0.5 triphenylphosphine oxide
tris 1-phenyl-1,3-butanedionato Sm0.5, Gd0.5 2,2-bipyridyl
tris 1-phenyl-1,3-butanedionato Sm0.5, Gd0.5 2,2-bipyridyl-N,N-dioxide
tris 1-phenyl-1,3-butanedionato Sm0.5, Gd0.5 phenanthroline
tris 1-phenyl-1,3-butanedionato Sm0.5, Gd0.5 bathocuproine
tris 1-phenyl-1,3-butanedionato Sm0.5, Gd0.5 bathophenanthroline
tris acetylacetonato Sm0.2, Gd0.8 dimethylaminopyridine
tris acetylacetonato Sm0.2, Gd0.8 4-picoline-N-oxide
tris acetylacetonato Sm0.2, Gd0.8 4-phenylpyridine tris acetylacetonato Sm0.2, Gd0.8 4-cyanopyridine
tris acetylacetonato Sm0.2, Gd0.8 4-phenylpyridine-N-oxide
tris acetylacetonato Sm0.2, Gd0.8 1-methylimidazole
tris acetylacetonato Sm0.2, Gd0.8 triphenylphosphine oxide
tris acetylacetonato Sm0.2, Gd0.8 2,2-bipyridyl
tris acetylacetonato Sm0.2, Gd0.8 2,2-bipyridyl-N,N-dioxide
tris acetylacetonato Sm0.2, Gd0.8 phenanthroline
tris acetylacetonato Sm0.2, Gd0.8 bathocuproine
tris acetylacetonato Sm0.2, Gd0.8 bathophenanthroline
tris dibenzoylmethanato Sm0.2, Gd0.8 dimethylaminopyridine
tris dibenzoylmethanato Sm0.2, Gd0.8 4-picoline-N-oxide
tris dibenzoylmethanato Sm0.2, Gd0.8 4-phenylpyridine
tris dibenzoylmethanato Sm0.2, Gd0.8 4-cyanopyridine
tris dibenzoylmethanato Sm0.2, Gd0.8 4-phenylpyridine-N-oxide
tris dibenzoylmethanato Sm0.2, Gd0.8 1-methylimidazole
tris dibenzoylmethanato Sm0.2, Gd0.8 triphenylphosphine oxide
tris dibenzoylmethanato Sm0.2, Gd0.8 2,2-bipyridyl
tris dibenzoylmethanato Sm0.2, Gd0.8 2,2-bipyridyl-N,N-dioxide
tris dibenzoylmethanato Sm0.2, Gd0.8 phenanthroline
tris dibenzoylmethanato Sm0.2, Gd0.8 bathocuproine
tris dibenzoylmethanato Sm0.2, Gd0.8 bathophenanthroline
tris thenoyltrifluoroacetonato Sm0.2, Gd0.8 dimethylaminopyridine
tris thenoyltrifluoroacetonato Sm0.2, Gd0.8 4-picoline-N-oxide
tris thenoyltrifluoroacetonato Sm0.2, Gd0.8 4-phenylpyridine
tris thenoyltrifluoroacetonato Sm0.2, Gd0.8 4-cyanopyridine
tris thenoyltrifluoroacetonato Sm0.2, Gd0.8 4-phenylpyridine-N-oxide
tris thenoyltrifluoroacetonato Sm0.2, Gd0.8 1-methylimidazole
tris thenoyltrifluoroacetonato Sm0.2, Gd0.8 triphenylphosphine oxide
tris thenoyltrifluoroacetonato Sm0.2, Gd0.8 2,2-bipyridyl
tris thenoyltrifluoroacetonato Sm0.2, Gd0.8 2,2-bipyridyl-N,N-dioxide
tris thenoyltrifluoroacetonato Sm0.2, Gd0.8 phenanthroline
tris thenoyltrifluoroacetonato Sm0.2, Gd0.8 bathocuproine
tris thenoyltrifluoroacetonato Sm0.2, Gd0.8 bathophenanthroline
tris 2,2,6,6-tetramethylheptanedionato Sm0.2, Gd0.8 dimethylaminopyridine
tris 2,2,6,6-tetramethylheptanedionato Sm0.2, Gd0.8 4-picoline-N-oxide
tris 2,2,6,6-tetramethylheptanedionato Sm0.2, Gd0.8 4-phenylpyridine
tris 2,2,6,6-tetramethylheptanedionato Sm0.2, Gd0.8 4-cyanopyridine
tris 2,2,6,6-tetramethylheptanedionato Sm0.2, Gd0.8 4-phenylpyridine-N-oxide
tris 2,2,6,6-tetramethylheptanedionato Sm0.2, Gd0.8 1-methylimidazole
tris 2,2,6,6-tetramethylheptanedionato Sm0.2, Gd0.8 triphenylphosphine oxide
tris 2,2,6,6-tetramethylheptanedionato Sm0.2, Gd0.8 2,2-bipyridyl
tris 2,2,6,6-tetramethylheptanedionato Sm0.2, Gd0.8 2,2-bipyridyl-N,N-dioxide
tris 2,2,6,6-tetramethylheptanedionato Sm0.2, Gd0.8 phenanthroline
tris 2,2,6,6-tetramethylheptanedionato Sm0.2, Gd0.8 bathocuproine
tris 2,2,6,6-tetramethylheptanedionato Sm0.2, Gd0.8 bathophenanthroline
tris 3-methylpentane-2,4-dionato Sm0.2, Gd0.8 dimethylaminopyridine
tris 3-methylpentane-2,4-dionato Sm0.2, Gd0.8 4-picoline-N-oxide
tris 3-methylpentane-2,4-dionato Sm0.2, Gd0.8 4-phenylpyridine
tris 3-methylpentane-2,4-dionato Sm0.2, Gd0.8 4-cyanopyridine
tris 3-methylpentane-2,4-dionato Sm0.2, Gd0.8 4-phenylpyridine-N-oxide
tris 3-methylpentane-2,4-dionato Sm0.2, Gd0.8 1-methylimidazole
tris 3-methylpentane-2,4-dionato Sm0.2, Gd0.8 triphenylphosphine oxide
tris 3-methylpentane-2,4-dionato Sm0.2, Gd0.8 2,2-bipyridyl
tris 3-methylpentane-2,4-dionato Sm0.2, Gd0.8 2,2-bipyridyl-N,N-dioxide
tris 3-methylpentane-2,4-dionato Sm0.2, Gd0.8 phenanthroline
tris 3-methylpentane-2,4-dionato Sm0.2, Gd0.8 bathocuproine
tris 3-methylpentane-2,4-dionato Sm0.2, Gd0.8 bathophenanthroline
tris 3-ethylpentane-2,4-dionato Sm0.2, Gd0.8 dimethylaminopyridine
tris 3-ethylpentane-2,4-dionato Sm0.2, Gd0.8 4-picoline-N-oxide
tris 3-ethylpentane-2,4-dionato Sm0.2, Gd0.8 4-phenylpyridine
tris 3-ethylpentane-2,4-dionato Sm0.2, Gd0.8 4-cyanopyridine
tris 3-ethylpentane-2,4-dionato Sm0.2, Gd0.8 4-phenylpyridine-N-oxide
tris 3-ethylpentane-2,4-dionato Sm0.2, Gd0.8 1-methylimidazole
tris 3-ethylpentane-2,4-dionato Sm0.2, Gd0.8 triphenylphosphine oxide
tris 3-ethylpentane-2,4-dionato Sm0.2, Gd0.8 2,2-bipyridyl
tris 3-ethylpentane-2,4-dionato Sm0.2, Gd0.8 2,2-bipyridyl-N,N-dioxide
tris 3-ethylpentane-2,4-dionato Sm0.2, Gd0.8 phenanthroline
tris 3-ethylpentane-2,4-dionato Sm0.2, Gd0.8 bathocuproine
tris 3-ethylpentane-2,4-dionato Sm0.2, Gd0.8 bathophenanthroline
tris pivaloyltrifluoroacetonato Sm0.2, Gd0.8 dimethylaminopyridine
tris pivaloyltrifluoroacetonato Sm0.2, Gd0.8 4-picoline-N-oxide
tris pivaloyltrifluoroacetonato Sm0.2, Gd0.8 4-phenylpyridine
tris pivaloyltrifluoroacetonato Sm0.2, Gd0.8 4-cyanopyridine
tris pivaloyltrifluoroacetonato Sm0.2, Gd0.8 4-phenylpyridine-N-oxide
tris pivaloyltrifluoroacetonato Sm0.2, Gd0.8 1-methylimidazole
tris pivaloyltrifluoroacetonato Sm0.2, Gd0.8 triphenylphosphine oxide
tris pivaloyltrifluoroacetonato Sm0.2, Gd0.8 2,2-bipyridyl tris pivaloyltrifluoroacetonato Sm0.2, Gd0.8 2,2-bipyridyl-N,N-dioxide
tris pivaloyltrifluoroacetonato Sm0.2, Gd0.8 phenanthroline
tris pivaloyltrifluoroacetonato Sm0.2, Gd0.8 bathocuproine
tris pivaloyltrifluoroacetonato Sm0.2, Gd0.8 bathophenanthroline
tris trifluoroacetylacetonato Sm0.2, Gd0.8 dimethylaminopyridine
tris trifluoroacetylacetonato Sm0.2, Gd0.8 4-picoline-N-oxide
tris trifluoroacetylacetonato Sm0.2, Gd0.8 4-phenylpyridine
tris trifluoroacetylacetonato Sm0.2, Gd0.8 4-cyanopyridine
tris trifluoroacetylacetonato Sm0.2, Gd0.8 4-phenylpyridine-N-oxide
tris trifluoroacetylacetonato Sm0.2, Gd0.8 1-methylimidazole
tris trifluoroacetylacetonato Sm0.2, Gd0.8 triphenylphosphine oxide
tris trifluoroacetylacetonato Sm0.2, Gd0.8 2,2-bipyridyl
tris trifluoroacetylacetonato Sm0.2, Gd0.8 2,2-bipyridyl-N,N-dioxide
tris trifluoroacetylacetonato Sm0.2, Gd0.8 phenanthroline
tris trifluoroacetylacetonato Sm0.2, Gd0.8 bathocuproine
tris trifluoroacetylacetonato Sm0.2, Gd0.8 bathophenanthroline
tris hexafluoroacetylacetonato Sm0.2, Gd0.8 dimethylaminopyridine
tris hexafluoroacetylacetonato Sm0.2, Gd0.8 4-picoline-N-oxide
tris hexafluoroacetylacetonato Sm0.2, Gd0.8 4-phenylpyridine
tris hexafluoroacetylacetonato Sm0.2, Gd0.8 4-cyanopyridine
tris hexafluoroacetylacetonato Sm0.2, Gd0.8 4-phenylpyridine-N-oxide
tris hexafluoroacetylacetonato Sm0.2, Gd0.8 1-methylimidazole
tris hexafluoroacetylacetonato Sm0.2, Gd0.8 triphenylphosphine oxide
tris hexafluoroacetylacetonato Sm0.2, Gd0.8 2,2-bipyridyl
tris hexafluoroacetylacetonato Sm0.2, Gd0.8 2,2-bipyridyl-N,N-dioxide
tris hexafluoroacetylacetonato Sm0.2, Gd0.8 phenanthroline
tris hexafluoroacetylacetonato Sm0.2, Gd0.8 bathocuproine
tris hexafluoroacetylacetonato Sm0.2, Gd0.8 bathophenanthroline
tris 6,6,7,7,8,8,8-heptafluoro-2,2-dimethyloctanedionato Sm0.2, Gd0.8 dimethylaminopyridine
tris 6,6,7,7,8,8,8-heptafluoro-2,2-dimethyloctanedionato Sm0.2, Gd0.8 4-picoline-N-oxide
tris 6,6,7,7,8,8,8-heptafluoro-2,2-dimethyloctanedionato Sm0.2, Gd0.8 4-phenylpyridine
tris 6,6,7,7,8,8,8-heptafluoro-2,2-dimethyloctanedionato Sm0.2, Gd0.8 4-cyanopyridine
tris 6,6,7,7,8,8,8-heptafluoro-2,2-dimethyloctanedionato Sm0.2, Gd0.8 4-phenylpyridine-N-oxide
tris 6,6,7,7,8,8,8-heptafluoro-2,2-dimethyloctanedionato Sm0.2, Gd0.8 1-methylimidazole
tris 6,6,7,7,8,8,8-heptafluoro-2,2-dimethyloctanedionato Sm0.2, Gd0.8 triphenylphosphine oxide
tris 6,6,7,7,8,8,8-heptafluoro-2,2-dimethyloctanedionato Sm0.2, Gd0.8 2,2-bipyridyl
tris 6,6,7,7,8,8,8-heptafluoro-2,2-dimethyloctanedionato Sm0.2, Gd0.8 2,2-bipyridyl-N,N-dioxide
tris 6,6,7,7,8,8,8-heptafluoro-2,2-dimethyloctanedionato Sm0.2, Gd0.8 phenanthroline
tris 6,6,7,7,8,8,8-heptafluoro-2,2-dimethyloctanedionato Sm0.2, Gd0.8 bathocuproine
tris 6,6,7,7,8,8,8-heptafluoro-2,2-dimethyloctanedionato Sm0.2, Gd0.8 bathophenanthroline
tris 1-phenyl-1,3-butanedionato Sm0.2, Gd0.8 dimethylaminopyridine
tris 1-phenyl-1,3-butanedionato Sm0.2, Gd0.8 4-picoline-N-oxide
tris 1-phenyl-1,3-butanedionato Sm0.2, Gd0.8 4-phenylpyridine
tris 1-phenyl-1,3-butanedionato Sm0.2, Gd0.8 4-cyanopyridine
tris 1-phenyl-1,3-butanedionato Sm0.2, Gd0.8 4-phenylpyridine-N-oxide
tris 1-phenyl-1,3-butanedionato Sm0.2, Gd0.8 1-methylimidazole
tris 1-phenyl-1,3-butanedionato Sm0.2, Gd0.8 triphenylphosphine oxide
tris 1-phenyl-1,3-butanedionato Sm0.2, Gd0.8 2,2-bipyridyl
tris 1-phenyl-1,3-butanedionato Sm0.2, Gd0.8 2,2-bipyridyl-N,N-dioxide
tris 1-phenyl-1,3-butanedionato Sm0.2, Gd0.8 phenanthroline
tris 1-phenyl-1,3-butanedionato Sm0.2, Gd0.8 bathocuproine
tris 1-phenyl-1,3-butanedionato Sm0.2, Gd0.8 bathophenanthroline
tris acetylacetonato Sm0.1, Gd0.9 dimethylaminopyridine
tris acetylacetonato Sm0.1, Gd0.9 4-picoline-N-oxide
tris acetylacetonato Sm0.1, Gd0.9 4-phenylpyridine
tris acetylacetonato Sm0.1, Gd0.9 4-cyanopyridine
tris acetylacetonato Sm0.1, Gd0.9 4-phenylpyridine-N-oxide
tris acetylacetonato Sm0.1, Gd0.9 1-methylimidazole
tris acetylacetonato Sm0.1, Gd0.9 triphenylphosphine oxide
tris acetylacetonato Sm0.1, Gd0.9 2,2-bipyridyl
tris acetylacetonato Sm0.1, Gd0.9 2,2-bipyridyl-N,N-dioxide
tris acetylacetonato Sm0.1, Gd0.9 phenanthroline
tris acetylacetonato Sm0.1, Gd0.9 bathocuproine
tris acetylacetonato Sm0.1, Gd0.9 bathophenanthroline
tris dibenzoylmethanato Sm0.1, Gd0.9 dimethylaminopyridine
tris dibenzoylmethanato Sm0.1, Gd0.9 4-picoline-N-oxide
tris dibenzoylmethanato Sm0.1, Gd0.9 4-phenylpyridine
tris dibenzoylmethanato Sm0.1, Gd0.9 4-cyanopyridine
tris dibenzoylmethanato Sm0.1, Gd0.9 4-phenylpyridine-N-oxide
tris dibenzoylmethanato Sm0.1, Gd0.9 1-methylimidazole
tris dibenzoylmethanato Sm0.1, Gd0.9 triphenylphosphine oxide
tris dibenzoylmethanato Sm0.1, Gd0.9 2,2-bipyridyl
tris dibenzoylmethanato Sm0.1, Gd0.9 2,2-bipyridyl-N,N-dioxide
tris dibenzoylmethanato Sm0.1, Gd0.9 phenanthroline
tris dibenzoylmethanato Sm0.1, Gd0.9 bathocuproine
tris dibenzoylmethanato Sm0.1, Gd0.9 bathophenanthroline
tris thenoyltrifluoroacetonato Sm0.1, Gd0.9 dimethylaminopyridine
tris thenoyltrifluoroacetonato Sm0.1, Gd0.9 4-picoline-N-oxide
tris thenoyltrifluoroacetonato Sm0.1, Gd0.9 4-phenylpyridine
tris thenoyltrifluoroacetonato Sm0.1, Gd0.9 4-cyanopyridine
tris thenoyltrifluoroacetonato Sm0.1, Gd0.9 4-phenylpyridine-N-oxide tris thenoyltrifluoroacetonato Sm0.1, Gd0.9 1-methylimidazole
tris thenoyltrifluoroacetonato Sm0.1, Gd0.9 triphenylphosphine oxide
tris thenoyltrifluoroacetonato Sm0.1, Gd0.9 2,2-bipyridyl
tris thenoyltrifluoroacetonato Sm0.1, Gd0.9 2,2-bipyridyl-N,N-dioxide
tris thenoyltrifluoroacetonato Sm0.1, Gd0.9 phenanthroline
tris thenoyltrifluoroacetonato Sm0.1, Gd0.9 bathocuproine
tris thenoyltrifluoroacetonato Sm0.1, Gd0.9 bathophenanthroline
tris 2,2,6,6-tetramethylheptanedionato Sm0.1, Gd0.9 dimethylaminopyridine
tris 2,2,6,6-tetramethylheptanedionato Sm0.1, Gd0.9 4-picoline-N-oxide
tris 2,2,6,6-tetramethylheptanedionato Sm0.1, Gd0.9 4-phenylpyridine
tris 2,2,6,6-tetramethylheptanedionato Sm0.1, Gd0.9 4-cyanopyridine
tris 2,2,6,6-tetramethylheptanedionato Sm0.1, Gd0.9 4-phenylpyridine-N-oxide
tris 2,2,6,6-tetramethylheptanedionato Sm0.1, Gd0.9 1-methylimidazole
tris 2,2,6,6-tetramethylheptanedionato Sm0.1, Gd0.9 triphenylphosphine oxide
tris 2,2,6,6-tetramethylheptanedionato Sm0.1, Gd0.9 2,2-bipyridyl
tris 2,2,6,6-tetramethylheptanedionato Sm0.1, Gd0.9 2,2-bipyridyl-N,N-dioxide
tris 2,2,6,6-tetramethylheptanedionato Sm0.1, Gd0.9 phenanthroline
tris 2,2,6,6-tetramethylheptanedionato Sm0.1, Gd0.9 bathocuproine
tris 2,2,6,6-tetramethylheptanedionato Sm0.1, Gd0.9 bathophenanthroline
tris 3-methylpentane-2,4-dionato Sm0.1, Gd0.9 dimethylaminopyridine
tris 3-methylpentane-2,4-dionato Sm0.1, Gd0.9 4-picoline-N-oxide
tris 3-methylpentane-2,4-dionato Sm0.1, Gd0.9 4-phenylpyridine
tris 3-methylpentane-2,4-dionato Sm0.1, Gd0.9 4-cyanopyridine
tris 3-methylpentane-2,4-dionato Sm0.1, Gd0.9 4-phenylpyridine-N-oxide
tris 3-methylpentane-2,4-dionato Sm0.1, Gd0.9 1-methylimidazole
tris 3-methylpentane-2,4-dionato Sm0.1, Gd0.9 triphenylphosphine oxide
tris 3-methylpentane-2,4-dionato Sm0.1, Gd0.9 2,2-bipyridyl
tris 3-methylpentane-2,4-dionato Sm0.1, Gd0.9 2,2-bipyridyl-N,N-dioxide
tris 3-methylpentane-2,4-dionato Sm0.1, Gd0.9 phenanthroline
tris 3-methylpentane-2,4-dionato Sm0.1, Gd0.9 bathocuproine
tris 3-methylpentane-2,4-dionato Sm0.1, Gd0.9 bathophenanthroline
tris 3-ethylpentane-2,4-dionato Sm0.1, Gd0.9 dimethylaminopyridine
tris 3-ethylpentane-2,4-dionato Sm0.1, Gd0.9 4-picoline-N-oxide
tris 3-ethylpentane-2,4-dionato Sm0.1, Gd0.9 4-phenylpyridine
tris 3-ethylpentane-2,4-dionato Sm0.1, Gd0.9 4-cyanopyridine
tris 3-ethylpentane-2,4-dionato Sm0.1, Gd0.9 4-phenylpyridine-N-oxide
tris 3-ethylpentane-2,4-dionato Sm0.1, Gd0.9 1-methylimidazole
tris 3-ethylpentane-2,4-dionato Sm0.1, Gd0.9 triphenylphosphine oxide
tris 3-ethylpentane-2,4-dionato Sm0.1, Gd0.9 2,2-bipyridyl
tris 3-ethylpentane-2,4-dionato Sm0.1, Gd0.9 2,2-bipyridyl-N,N-dioxide
tris 3-ethylpentane-2,4-dionato Sm0.1, Gd0.9 phenanthroline
tris 3-ethylpentane-2,4-dionato Sm0.1, Gd0.9 bathocuproine
tris 3-ethylpentane-2,4-dionato Sm0.1, Gd0.9 bathophenanthroline
tris pivaloyltrifluoroacetonato Sm0.1, Gd0.9 dimethylaminopyridine
tris pivaloyltrifluoroacetonato Sm0.1, Gd0.9 4-picoline-N-oxide
tris pivaloyltrifluoroacetonato Sm0.1, Gd0.9 4-phenylpyridine
tris pivaloyltrifluoroacetonato Sm0.1, Gd0.9 4-cyanopyridine
tris pivaloyltrifluoroacetonato Sm0.1, Gd0.9 4-phenylpyridine-N-oxide
tris pivaloyltrifluoroacetonato Sm0.1, Gd0.9 1-methylimidazole
tris pivaloyltrifluoroacetonato Sm0.1, Gd0.9 triphenylphosphine oxide
tris pivaloyltrifluoroacetonato Sm0.1, Gd0.9 2,2-bipyridyl
tris pivaloyltrifluoroacetonato Sm0.1, Gd0.9 2,2-bipyridyl-N,N-dioxide
tris pivaloyltrifluoroacetonato Sm0.1, Gd0.9 phenanthroline
tris pivaloyltrifluoroacetonato Sm0.1, Gd0.9 bathocuproine
tris pivaloyltrifluoroacetonato Sm0.1, Gd0.9 bathophenanthroline
tris trifluoroacetylacetonato Sm0.1, Gd0.9 dimethylaminopyridine
tris trifluoroacetylacetonato Sm0.1, Gd0.9 4-picoline-N-oxide
tris trifluoroacetylacetonato Sm0.1, Gd0.9 4-phenylpyridine
tris trifluoroacetylacetonato Sm0.1, Gd0.9 4-cyanopyridine
tris trifluoroacetylacetonato Sm0.1, Gd0.9 4-phenylpyridine-N-oxide
tris trifluoroacetylacetonato Sm0.1, Gd0.9 1-methylimidazole
tris trifluoroacetylacetonato Sm0.1, Gd0.9 triphenylphosphine oxide
tris trifluoroacetylacetonato Sm0.1, Gd0.9 2,2-bipyridyl
tris trifluoroacetylacetonato Sm0.1, Gd0.9 2,2-bipyridyl-N,N-dioxide
tris trifluoroacetylacetonato Sm0.1, Gd0.9 phenanthroline
tris trifluoroacetylacetonato Sm0.1, Gd0.9 bathocuproine
tris trifluoroacetylacetonato Sm0.1, Gd0.9 bathophenanthroline
tris hexafluoroacetylacetonato Sm0.1, Gd0.9 dimethylaminopyridine
tris hexafluoroacetylacetonato Sm0.1, Gd0.9 4-picoline-N-oxide
tris hexafluoroacetylacetonato Sm0.1, Gd0.9 4-phenylpyridine
tris hexafluoroacetylacetonato Sm0.1, Gd0.9 4-cyanopyridine
tris hexafluoroacetylacetonato Sm0.1, Gd0.9 4-phenylpyridine-N-oxide
tris hexafluoroacetylacetonato Sm0.1, Gd0.9 1-methylimidazole tris hexafluoroacetylacetonato Sm0.1, Gd0.9 triphenylphosphine oxide
tris hexafluoroacetylacetonato Sm0.1, Gd0.9 2,2-bipyridyl
tris hexafluoroacetylacetonato Sm0.1, Gd0.9 2,2-bipyridyl-N,N-dioxide
tris hexafluoroacetylacetonato Sm0.1, Gd0.9 phenanthroline
tris hexafluoroacetylacetonato Sm0.1, Gd0.9 bathocuproine
tris hexafluoroacetylacetonato Sm0.1, Gd0.9 bathophenanthroline
tris 6,6,7,7,8,8,8-heptafluoro-2,2-dimethyloctanedionato Sm0.1, Gd0.9 dimethylaminopyridine
tris 6,6,7,7,8,8,8-heptafluoro-2,2-dimethyloctanedionato Sm0.1, Gd0.9 4-picoline-N-oxide
tris 6,6,7,7,8,8,8-heptafluoro-2,2-dimethyloctanedionato Sm0.1, Gd0.9 4-phenylpyridine
tris 6,6,7,7,8,8,8-heptafluoro-2,2-dimethyloctanedionato Sm0.1, Gd0.9 4-cyanopyridine
tris 6,6,7,7,8,8,8-heptafluoro-2,2-dimethyloctanedionato Sm0.1, Gd0.9 4-phenylpyridine-N-oxide
tris 6,6,7,7,8,8,8-heptafluoro-2,2-dimethyloctanedionato Sm0.1, Gd0.9 1-methylimidazole
tris 6,6,7,7,8,8,8-heptafluoro-2,2-dimethyloctanedionato Sm0.1, Gd0.9 triphenylphosphine oxide
tris 6,6,7,7,8,8,8-heptafluoro-2,2-dimethyloctanedionato Sm0.1, Gd0.9 2,2-bipyridyl
tris 6,6,7,7,8,8,8-heptafluoro-2,2-dimethyloctanedionato Sm0.1, Gd0.9 2,2-bipyridyl-N,N-dioxide
tris 6,6,7,7,8,8,8-heptafluoro-2,2-dimethyloctanedionato Sm0.1, Gd0.9 phenanthroline
tris 6,6,7,7,8,8,8-heptafluoro-2,2-dimethyloctanedionato Sm0.1, Gd0.9 bathocuproine
tris 6,6,7,7,8,8,8-heptafluoro-2,2-dimethyloctanedionato Sm0.1, Gd0.9 bathophenanthroline
tris 1-phenyl-1,3-butanedionato Sm0.1, Gd0.9 dimethylaminopyridine
tris 1-phenyl-1,3-butanedionato Sm0.1, Gd0.9 4-picoline-N-oxide
tris 1-phenyl-1,3-butanedionato Sm0.1, Gd0.9 4-phenylpyridine
tris 1-phenyl-1,3-butanedionato Sm0.1, Gd0.9 4-cyanopyridine
tris 1-phenyl-1,3-butanedionato Sm0.1, Gd0.9 4-phenylpyridine-N-oxide
tris 1-phenyl-1,3-butanedionato Sm0.1, Gd0.9 1-methylimidazole
tris 1-phenyl-1,3-butanedionato Sm0.1, Gd0.9 triphenylphosphine oxide
tris 1-phenyl-1,3-butanedionato Sm0.1, Gd0.9 2,2-bipyridyl
tris 1-phenyl-1,3-butanedionato Sm0.1, Gd0.9 2,2-bipyridyl-N,N-dioxide
tris 1-phenyl-1,3-butanedionato Sm0.1, Gd0.9 phenanthroline
tris 1-phenyl-1,3-butanedionato Sm0.1, Gd0.9 bathocuproine
tris 1-phenyl-1,3-butanedionato Sm0.1, Gd0.9 bathophenanthroline
tris acetylacetonato Sm0.01, Gd0.99 dimethylaminopyridine
tris acetylacetonato Sm0.01, Gd0.99 4-picoline-N-oxide
tris acetylacetonato Sm0.01, Gd0.99 4-phenylpyridine
tris acetylacetonato Sm0.01, Gd0.99 4-cyanopyridine
tris acetylacetonato Sm0.01, Gd0.99 4-phenylpyridine-N-oxide
tris acetylacetonato Sm0.01, Gd0.99 1-methylimidazole
tris acetylacetonato Sm0.01, Gd0.99 triphenylphosphine oxide
tris acetylacetonato Sm0.01, Gd0.99 2,2-bipyridyl
tris acetylacetonato Sm0.01, Gd0.99 2,2-bipyridyl-N,N-dioxide
tris acetylacetonato Sm0.01, Gd0.99 phenanthroline
tris acetylacetonato Sm0.01, Gd0.99 bathocuproine
tris acetylacetonato Sm0.01, Gd0.99 bathophenanthroline
tris dibenzoylmethanato Sm0.01, Gd0.99 dimethylaminopyridine
tris dibenzoylmethanato Sm0.01, Gd0.99 4-picoline-N-oxide
tris dibenzoylmethanato Sm0.01, Gd0.99 4-phenylpyridine
tris dibenzoylmethanato Sm0.01, Gd0.99 4-cyanopyridine
tris dibenzoylmethanato Sm0.01, Gd0.99 4-phenylpyridine-N-oxide
tris dibenzoylmethanato Sm0.01, Gd0.99 1-methylimidazole
tris dibenzoylmethanato Sm0.01, Gd0.99 triphenylphosphine oxide
tris dibenzoylmethanato Sm0.01, Gd0.99 2,2-bipyridyl
tris dibenzoylmethanato Sm0.01, Gd0.99 2,2-bipyridyl-N,N-dioxide
tris dibenzoylmethanato Sm0.01, Gd0.99 phenanthroline
tris dibenzoylmethanato Sm0.01, Gd0.99 bathocuproine
tris dibenzoylmethanato Sm0.01, Gd0.99 bathophenanthroline
tris thenoyltrifluoroacetonato Sm0.01, Gd0.99 dimethylaminopyridine
tris thenoyltrifluoroacetonato Sm0.01, Gd0.99 4-picoline-N-oxide
tris thenoyltrifluoroacetonato Sm0.01, Gd0.99 4-phenylpyridine
tris thenoyltrifluoroacetonato Sm0.01, Gd0.99 4-cyanopyridine
tris thenoyltrifluoroacetonato Sm0.01, Gd0.99 4-phenylpyridine-N-oxide
tris thenoyltrifluoroacetonato Sm0.01, Gd0.99 1-methylimidazole
tris thenoyltrifluoroacetonato Sm0.01, Gd0.99 triphenylphosphine oxide
tris thenoyltrifluoroacetonato Sm0.01, Gd0.99 2,2-bipyridyl
tris thenoyltrifluoroacetonato Sm0.01, Gd0.99 2,2-bipyridyl-N,N-dioxide
tris thenoyltrifluoroacetonato Sm0.01, Gd0.99 phenanthroline
tris thenoyltrifluoroacetonato Sm0.01, Gd0.99 bathocuproine
tris thenoyltrifluoroacetonato Sm0.01, Gd0.99 bathophenanthroline
tris 2,2,6,6-tetramethylheptanedionato Sm0.01, Gd0.99 dimethylaminopyridine
tris 2,2,6,6-tetramethylheptanedionato Sm0.01, Gd0.99 4-picoline-N-oxide
tris 2,2,6,6-tetramethylheptanedionato Sm0.01, Gd0.99 4-phenylpyridine
tris 2,2,6,6-tetramethylheptanedionato Sm0.01, Gd0.99 4-cyanopyridine
tris 2,2,6,6-tetramethylheptanedionato Sm0.01, Gd0.99 4-phenylpyridine-N-oxide
tris 2,2,6,6-tetramethylheptanedionato Sm0.01, Gd0.99 1-methylimidazole
tris 2,2,6,6-tetramethylheptanedionato Sm0.01, Gd0.99 triphenylphosphine oxide
tris 2,2,6,6-tetramethylheptanedionato Sm0.01, Gd0.99 2,2-bipyridyl
tris 2,2,6,6-tetramethylheptanedionato Sm0.01, Gd0.99 2,2-bipyridyl-N,N-dioxide
tris 2,2,6,6-tetramethylheptanedionato Sm0.01, Gd0.99 phenanthroline tris 2,2,6,6-tetramethylheptanedionato Sm0.01, Gd0.99 bathocuproine
tris 2,2,6,6-tetramethylheptanedionato Sm0.01, Gd0.99 bathophenanthroline
tris 3-methylpentane-2,4-dionato Sm0.01, Gd0.99 dimethylaminopyridine
tris 3-methylpentane-2,4-dionato Sm0.01, Gd0.99 4-picoline-N-oxide
tris 3-methylpentane-2,4-dionato Sm0.01, Gd0.99 4-phenylpyridine
tris 3-methylpentane-2,4-dionato Sm0.01, Gd0.99 4-cyanopyridine
tris 3-methylpentane-2,4-dionato Sm0.01, Gd0.99 4-phenylpyridine-N-oxide
tris 3-methylpentane-2,4-dionato Sm0.01, Gd0.99 1-methylimidazole
tris 3-methylpentane-2,4-dionato Sm0.01, Gd0.99 triphenylphosphine oxide
tris 3-methylpentane-2,4-dionato Sm0.01, Gd0.99 2,2-bipyridyl
tris 3-methylpentane-2,4-dionato Sm0.01, Gd0.99 2,2-bipyridyl-N,N-dioxide
tris 3-methylpentane-2,4-dionato Sm0.01, Gd0.99 phenanthroline
tris 3-methylpentane-2,4-dionato Sm0.01, Gd0.99 bathocuproine
tris 3-methylpentane-2,4-dionato Sm0.01, Gd0.99 bathophenanthroline
tris 3-ethylpentane-2,4-dionato Sm0.01, Gd0.99 dimethylaminopyridine
tris 3-ethylpentane-2,4-dionato Sm0.01, Gd0.99 4-picoline-N-oxide
tris 3-ethylpentane-2,4-dionato Sm0.01, Gd0.99 4-phenylpyridine
tris 3-ethylpentane-2,4-dionato Sm0.01, Gd0.99 4-cyanopyridine
tris 3-ethylpentane-2,4-dionato Sm0.01, Gd0.99 4-phenylpyridine-N-oxide
tris 3-ethylpentane-2,4-dionato Sm0.01, Gd0.99 1-methylimidazole
tris 3-ethylpentane-2,4-dionato Sm0.01, Gd0.99 triphenylphosphine oxide
tris 3-ethylpentane-2,4-dionato Sm0.01, Gd0.99 2,2-bipyridyl
tris 3-ethylpentane-2,4-dionato Sm0.01, Gd0.99 2,2-bipyridyl-N,N-dioxide
tris 3-ethylpentane-2,4-dionato Sm0.01, Gd0.99 phenanthroline
tris 3-ethylpentane-2,4-dionato Sm0.01, Gd0.99 bathocuproine
tris 3-ethylpentane-2,4-dionato Sm0.01, Gd0.99 bathophenanthroline
tris pivaloyltrifluoroacetonato Sm0.01, Gd0.99 dimethylaminopyridine
tris pivaloyltrifluoroacetonato Sm0.01, Gd0.99 4-picoline-N-oxide
tris pivaloyltrifluoroacetonato Sm0.01, Gd0.99 4-phenylpyridine
tris pivaloyltrifluoroacetonato Sm0.01, Gd0.99 4-cyanopyridine
tris pivaloyltrifluoroacetonato Sm0.01, Gd0.99 4-phenylpyridine-N-oxide
tris pivaloyltrifluoroacetonato Sm0.01, Gd0.99 1-methylimidazole
tris pivaloyltrifluoroacetonato Sm0.01, Gd0.99 triphenylphosphine oxide
tris pivaloyltrifluoroacetonato Sm0.01, Gd0.99 2,2-bipyridyl
tris pivaloyltrifluoroacetonato Sm0.01, Gd0.99 2,2-bipyridyl-N,N-dioxide
tris pivaloyltrifluoroacetonato Sm0.01, Gd0.99 phenanthroline
tris pivaloyltrifluoroacetonato Sm0.01, Gd0.99 bathocuproine
tris pivaloyltrifluoroacetonato Sm0.01, Gd0.99 bathophenanthroline
tris trifluoroacetylacetonato Sm0.01, Gd0.99 dimethylaminopyridine
tris trifluoroacetylacetonato Sm0.01, Gd0.99 4-picoline-N-oxide
tris trifluoroacetylacetonato Sm0.01, Gd0.99 4-phenylpyridine
tris trifluoroacetylacetonato Sm0.01, Gd0.99 4-cyanopyridine
tris trifluoroacetylacetonato Sm0.01, Gd0.99 4-phenylpyridine-N-oxide
tris trifluoroacetylacetonato Sm0.01, Gd0.99 1-methylimidazole
tris trifluoroacetylacetonato Sm0.01, Gd0.99 triphenylphosphine oxide
tris trifluoroacetylacetonato Sm0.01, Gd0.99 2,2-bipyridyl
tris trifluoroacetylacetonato Sm0.01, Gd0.99 2,2-bipyridyl-N,N-dioxide
tris trifluoroacetylacetonato Sm0.01, Gd0.99 phenanthroline
tris trifluoroacetylacetonato Sm0.01, Gd0.99 bathocuproine
tris trifluoroacetylacetonato Sm0.01, Gd0.99 bathophenanthroline
tris hexafluoroacetylacetonato Sm0.01, Gd0.99 dimethylaminopyridine
tris hexafluoroacetylacetonato Sm0.01, Gd0.99 4-picoline-N-oxide
tris hexafluoroacetylacetonato Sm0.01, Gd0.99 4-phenylpyridine
tris hexafluoroacetylacetonato Sm0.01, Gd0.99 4-cyanopyridine
tris hexafluoroacetylacetonato Sm0.01, Gd0.99 4-phenylpyridine-N-oxide
tris hexafluoroacetylacetonato Sm0.01, Gd0.99 1-methylimidazole
tris hexafluoroacetylacetonato Sm0.01, Gd0.99 triphenylphosphine oxide
tris hexafluoroacetylacetonato Sm0.01, Gd0.99 2,2-bipyridyl
tris hexafluoroacetylacetonato Sm0.01, Gd0.99 2,2-bipyridyl-N,N-dioxide
tris hexafluoroacetylacetonato Sm0.01, Gd0.99 phenanthroline
tris hexafluoroacetylacetonato Sm0.01, Gd0.99 bathocuproine
tris hexafluoroacetylacetonato Sm0.0l, Gd0.99 bathophenanthroline
tris 6,6,7,7,8,8,8-heptafluoro-2,2-dimethyloctanedionato Sm0.01, Gd0.99 dimethylaminopyridine
tris 6,6,7,7,8,8,8-heptafluoro-2,2-dimethyloctanedionato Sm0.01, Gd0.99 4-picoline-N-oxide
tris 6,6,7,7,8,8,8-heptafluoro-2,2-dimethyloctanedionato Sm0.01, Gd0.99 4-phenylpyridine
tris 6,6,7,7,8,8,8-heptafluoro-2,2-dimethyloctanedionato Sm0.01, Gd0.99 4-cyanopyridine
tris 6,6,7,7,8,8,8-heptafluoro-2,2-dimethyloctanedionato Sm0.01, Gd0.99 4-phenylpyridine-N-oxide
tris 6,6,7,7,8,8,8-heptafluoro-2,2-dimethyloctanedionato Sm0.01, Gd0.99 1-methylimidazole tris 6,6,7,7,8,8,8-heptafluoro-2,2-dimethyloctanedionato Sm0.01, Gd0.99 triphenylphosphine oxide
tris 6,6,7,7,8,8,8-heptafluoro-2,2-dimethyloctanedionato Sm0.01, Gd0.99 2,2-bipyridyl
tris 6,6,7,7,8,8,8-heptafluoro-2,2-dimethyloctanedionato Sm0.01, Gd0.99 2,2-bipyridyl-N,N-dioxide
tris 6,6,7,7,8,8,8-heptafluoro-2,2-dimethyloctanedionato Sm0.01, Gd0.99 phenanthroline
tris 6,6,7,7,8,8,8-heptafluoro-2,2-dimethyloctanedionato Sm0.01, Gd0.99 bathocuproine
tris 6,6,7,7,8,8,8-heptafluoro-2,2-dimethyloctanedionato Sm0.01, Gd0.99 bathophenanthroline
tris 1-phenyl-1,3-butanedionato Sm0.01, Gd0.99 dimethylaminopyridine
tris 1-phenyl-1,3-butanedionato Sm0.01, Gd0.99 4-picoline-N-oxide
tris 1-phenyl-1,3-butanedionato Sm0.01, Gd0.99 4-phenylpyridine
tris 1-phenyl-1,3-butanedionato Sm0.01, Gd0.99 4-cyanopyridine
tris 1-phenyl-1,3-butanedionato Sm0.01, Gd0.99 4-phenylpyridine-N-oxide
tris 1-phenyl-1,3-butanedionato Sm0.01, Gd0.99 1-methylimidazole
tris 1-phenyl-1,3-butanedionato Sm0.01, Gd0.99 triphenylphosphine oxide
tris 1-phenyl-1,3-butanedionato Sm0.01, Gd0.99 2,2-bipyridyl
tris 1-phenyl-1,3-butanedionato Sm0.01, Gd0.99 2,2-bipyridyl-N,N-dioxide
tris 1-phenyl-1,3-butanedionato Sm0.01, Gd0.99 phenanthroline
tris 1-phenyl-1,3-butanedionato Sm0.01, Gd0.99 bathocuproine
tris 1-phenyl-1,3-butanedionato Sm0.01, Gd0.99 bathophenanthroline
tris acetylacetonato Dy0.5, Gd0.5 dimethylaminopyridine
tris acetylacetonato Dy0.5, Gd0.5 4-picoline-N-oxide
tris acetylacetonato Dy0.5, Gd0.5 4-phenylpyridine
tris acetylacetonato Dy0.5, Gd0.5 4-cyanopyridine
tris acetylacetonato Dy0.5, Gd0.5 4-phenylpyridine-N-oxide
tris acetylacetonato Dy0.5, Gd0.5 1-methylimidazole
tris acetylacetonato Dy0.5, Gd0.5 triphenylphosphine oxide
tris acetylacetonato Dy0.5, Gd0.5 2,2-bipyridyl
tris acetylacetonato Dy0.5, Gd0.5 2,2-bipyridyl-N,N-dioxide
tris acetylacetonato Dy0.5, Gd0.5 phenanthroline
tris acetylacetonato Dy0.5, Gd0.5 bathocuproine
tris acetylacetonato Dy0.5, Gd0.5 bathophenanthroline
tris dibenzoylmethanato Dy0.5, Gd0.5 dimethylaminopyridine
tris dibenzoylmethanato Dy0.5, Gd0.5 4-picoline-N-oxide
tris dibenzoylmethanato Dy0.5, Gd0.5 4-phenylpyridine
tris dibenzoylmethanato Dy0.5, Gd0.5 4-cyanopyridine
tris dibenzoylmethanato Dy0.5, Gd0.5 4-phenylpyridine-N-oxide
tris dibenzoylmethanato Dy0.5, Gd0.5 1-methylimidazole
tris dibenzoylmethanato Dy0.5, Gd0.5 triphenylphosphine oxide
tris dibenzoylmethanato Dy0.5, Gd0.5 2,2-bipyridyl
tris dibenzoylmethanato Dy0.5, Gd0.5 2,2-bipyridyl-N,N-dioxide
tris dibenzoylmethanato Dy0.5, Gd0.5 phenanthroline
tris dibenzoylmethanato Dy0.5, Gd0.5 bathocuproine
tris dibenzoylmethanato Dy0.5, Gd0.5 bathophenanthroline
tris thenoyltrifluoroacetonato Dy0.5, Gd0.5 dimethylaminopyridine
tris thenoyltrifluoroacetonato Dy0.5, Gd0.5 4-picoline-N-oxide
tris thenoyltrifluoroacetonato Dy0.5, Gd0.5 4-phenylpyridine
tris thenoyltrifluoroacetonato Dy0.5, Gd0.5 4-cyanopyridine
tris thenoyltrifluoroacetonato Dy0.5, Gd0.5 4-phenylpyridine-N-oxide
tris thenoyltrifluoroacetonato Dy0.5, Gd0.5 1-methylimidazole
tris thenoyltrifluoroacetonato Dy0.5, Gd0.5 triphenylphosphine oxide
tris thenoyltrifluoroacetonato Dy0.5, Gd0.5 2,2-bipyridyl
tris thenoyltrifluoroacetonato Dy0.5, Gd0.5 2,2-bipyridyl-N,N-dioxide
tris thenoyltrifluoroacetonato Dy0.5, Gd0.5 phenanthroline
tris thenoyltrifluoroacetonato Dy0.5, Gd0.5 bathocuproine
tris thenoyltrifluoroacetonato Dy0.5, Gd0.5 bathophenanthroline
tris 2,2,6,6-tetramethylheptanedionato Dy0.5, Gd0.5 dimethylaminopyridine
tris 2,2,6,6-tetramethylheptanedionato Dy0.5, Gd0.5 4-picoline-N-oxide
tris 2,2,6,6-tetramethylheptanedionato Dy0.5, Gd0.5 4-phenylpyridine
tris 2,2,6,6-tetramethylheptanedionato Dy0.5, Gd0.5 4-cyanopyridine
tris 2,2,6,6-tetramethylheptanedionato Dy0.5, Gd0.5 4-phenylpyridine-N-oxide
tris 2,2,6,6-tetramethylheptanedionato Dy0.5, Gd0.5 1-methylimidazole
tris 2,2,6,6-tetramethylheptanedionato Dy0.5, Gd0.5 triphenylphosphine oxide
tris 2,2,6,6-tetramethylheptanedionato Dy0.5, Gd0.5 2,2-bipyridyl
tris 2,2,6,6-tetramethylheptanedionato Dy0.5, Gd0.5 2,2-bipyridyl-N,N-dioxide
tris 2,2,6,6-tetramethylheptanedionato Dy0.5, Gd0.5 phenanthroline
tris 2,2,6,6-tetramethylheptanedionato Dy0.5, Gd0.5 bathocuproine
tris 2,2,6,6-tetramethylheptanedionato Dy0.5, Gd0.5 bathophenanthroline
tris 3-methylpentane-2,4-dionato Dy0.5, Gd0.5 dimethylaminopyridine
tris 3-methylpentane-2,4-dionato Dy0.5, Gd0.5 4-picoline-N-oxide
tris 3-methylpentane-2,4-dionato Dy0.5, Gd0.5 4-phenylpyridine
tris 3-methylpentane-2,4-dionato Dy0.5, Gd0.5 4-cyanopyridine
tris 3-methylpentane-2,4-dionato Dy0.5, Gd0.5 4-phenylpyridine-N-oxide
tris 3-methylpentane-2,4-dionato Dy0.5, Gd0.5 1-methylimidazole
tris 3-methylpentane-2,4-dionato Dy0.5, Gd0.5 triphenylphosphine oxide
tris 3-methylpentane-2,4-dionato Dy0.5, Gd0.5 2,2-bipyridyl
tris 3-methylpentane-2,4-dionato Dy0.5, Gd0.5 2,2-bipyridyl-N,N-dioxide
tris 3-methylpentane-2,4-dionato Dy0.5, Gd0.5 phenanthroline
tris 3-methylpentane-2,4-dionato Dy0.5, Gd0.5 bathocuproine
tris 3-methylpentane-2,4-dionato Dy0.5, Gd0.5 bathophenanthroline tris 3-ethylpentane-2,4-dionato Dy0.5, Gd0.5 dimethylaminopyridine
tris 3-ethylpentane-2,4-dionato Dy0.5, Gd0.5 4-picoline-N-oxide
tris 3-ethylpentane-2,4-dionato Dy0.5, Gd0.5 4-phenylpyridine
tris 3-ethylpentane-2,4-dionato Dy0.5, Gd0.5 4-cyanopyridine
tris 3-ethylpentane-2,4-dionato Dy0.5, Gd0.5 4-phenylpyridine-N-oxide
tris 3-ethylpentane-2,4-dionato Dy0.5, Gd0.5 1-methylimidazole
tris 3-ethylpentane-2,4-dionato Dy0.5, Gd0.5 triphenylphosphine oxide
tris 3-ethylpentane-2,4-dionato Dy0.5, Gd0.5 2,2-bipyridyl
tris 3-ethylpentane-2,4-dionato Dy0.5, Gd0.5 2,2-bipyridyl-N,N-dioxide
tris 3-ethylpentane-2,4-dionato Dy0.5, Gd0.5 phenanthroline
tris 3-ethylpentane-2,4-dionato Dy0.5, Gd0.5 bathocuproine
tris 3-ethylpentane-2,4-dionato Dy0.5, Gd0.5 bathophenanthroline
tris pivaloyltrifluoroacetonato Dy0.5, Gd0.5 dimethylaminopyridine
tris pivaloyltrifluoroacetonato Dy0.5, Gd0.5 4-picoline-N-oxide
tris pivaloyltrifluoroacetonato Dy0.5, Gd0.5 4-phenylpyridine
tris pivaloyltrifluoroacetonato Dy0.5, Gd0.5 4-cyanopyridine
tris pivaloyltrifluoroacetonato Dy0.5, Gd0.5 4-phenylpyridine-N-oxide
tris pivaloyltrifluoroacetonato Dy0.5, Gd0.5 1-methylimidazole
tris pivaloyltrifluoroacetonato Dy0.5, Gd0.5 triphenylphosphine oxide
tris pivaloyltrifluoroacetonato Dy0.5, Gd0.5 2,2-bipyridyl
tris pivaloyltrifluoroacetonato Dy0.5, Gd0.5 2,2-bipyridyl-N,N-dioxide
tris pivaloyltrifluoroacetonato Dy0.5, Gd0.5 phenanthroline
tris pivaloyltrifluoroacetonato Dy0.5, Gd0.5 bathocuproine
tris pivaloyltrifluoroacetonato Dy0.5, Gd0.5 bathophenanthroline
tris trifluoroacetylacetonato Dy0.5, Gd0.5 dimethylaminopyridine
tris trifluoroacetylacetonato Dy0.5, Gd0.5 4-picoline-N-oxide
tris trifluoroacetylacetonato Dy0.5, Gd0.5 4-phenylpyridine
tris trifluoroacetylacetonato Dy0.5, Gd0.5 4-cyanopyridine
tris trifluoroacetylacetonato Dy0.5, Gd0.5 4-phenylpyridine-N-oxide
tris trifluoroacetylacetonato Dy0.5, Gd0.5 1-methylimidazole
tris trifluoroacetylacetonato Dy0.5, Gd0.5 triphenylphosphine oxide
tris trifluoroacetylacetonato Dy0.5, Gd0.5 2,2-bipyridyl
tris trifluoroacetylacetonato Dy0.5, Gd0.5 2,2-bipyridyl-N,N-dioxide
tris trifluoroacetylacetonato Dy0.5, Gd0.5 phenanthroline
tris trifluoroacetylacetonato Dy0.5, Gd0.5 bathocuproine
tris trifluoroacetylacetonato Dy0.5, Gd0.5 bathophenanthroline
tris hexafluoroacetylacetonato Dy0.5, Gd0.5 dimethylaminopyridine
tris hexafluoroacetylacetonato Dy0.5, Gd0.5 4-picoline-N-oxide
tris hexafluoroacetylacetonato Dy0.5, Gd0.5 4-phenylpyridine
tris hexafluoroacetylacetonato Dy0.5, Gd0.5 4-cyanopyridine
tris hexafluoroacetylacetonato Dy0.5, Gd0.5 4-phenylpyridine-N-oxide
tris hexafluoroacetylacetonato Dy0.5, Gd0.5 1-methylimidazole
tris hexafluoroacetylacetonato Dy0.5, Gd0.5 triphenylphosphine oxide
tris hexafluoroacetylacetonato Dy0.5, Gd0.5 2,2-bipyridyl
tris hexafluoroacetylacetonato Dy0.5, Gd0.5 2,2-bipyridyl-N,N-dioxide
tris hexafluoroacetylacetonato Dy0.5, Gd0.5 phenanthroline
tris hexafluoroacetylacetonato Dy0.5, Gd0.5 bathocuproine
tris hexafluoroacetylacetonato Dy0.5, Gd0.5 bathophenanthroline
tris 6,6,7,7,8,8,8-heptafluoro-2,2-dimethyloctanedionato Dy0.5, Gd0.5 dimethylaminopyridine
tris 6,6,7,7,8,8,8-heptafluoro-2,2-dimethyloctanedionato Dy0.5, Gd0.5 4-picoline-N-oxide
tris 6,6,7,7,8,8,8-heptafluoro-2,2-dimethyloctanedionato Dy0.5, Gd0.5 4-phenylpyridine
tris 6,6,7,7,8,8,8-heptafluoro-2,2-dimethyloctanedionato Dy0.5, Gd0.5 4-cyanopyridine
tris 6,6,7,7,8,8,8-heptafluoro-2,2-dimethyloctanedionato Dy0.5, Gd0.5 4-phenylpyridine-N-oxide
tris 6,6,7,7,8,8,8-heptafluoro-2,2-dimethyloctanedionato Dy0.5, Gd0.5 1-methylimidazole
tris 6,6,7,7,8,8,8-heptafluoro-2,2-dimethyloctanedionato Dy0.5, Gd0.5 triphenylphosphine oxide
tris 6,6,7,7,8,8,8-heptafluoro-2,2-dimethyloctanedionato Dy0.5, Gd0.5 2,2-bipyridyl
tris 6,6,7,7,8,8,8-heptafluoro-2,2-dimethyloctanedionato Dy0.5, Gd0.5 2,2-bipyridyl-N,N-dioxide
tris 6,6,7,7,8,8,8-heptafluoro-2,2-dimethyloctanedionato Dy0.5, Gd0.5 phenanthroline
tris 6,6,7,7,8,8,8-heptafluoro-2,2-dimethyloctanedionato Dy0.5, Gd0.5 bathocuproine
tris 6,6,7,7,8,8,8-heptafluoro-2,2-dimethyloctanedionato Dy0.5, Gd0.5 bathophenanthroline
tris 1-phenyl-1,3-butanedionato Dy0.5, Gd0.5 dimethylaminopyridine
tris 1-phenyl-1,3-butanedionato Dy0.5, Gd0.5 4-picoline-N-oxide
tris 1-phenyl-1,3-butanedionato Dy0.5, Gd0.5 4-phenylpyridine
tris 1-phenyl-1,3-butanedionato Dy0.5, Gd0.5 4-cyanopyridine
tris 1-phenyl-1,3-butanedionato Dy0.5, Gd0.5 4-phenylpyridine-N-oxide
tris 1-phenyl-1,3-butanedionato Dy0.5, Gd0.5 1-methylimidazole
tris 1-phenyl-1,3-butanedionato Dy0.5, Gd0.5 triphenylphosphine oxide
tris 1-phenyl-1,3-butanedionato Dy0.5, Gd0.5 2,2-bipyridyl
tris 1-phenyl-1,3-butanedionato Dy0.5, Gd0.5 2,2-bipyridyl-N,N-dioxide
tris 1-phenyl-1,3-butanedionato Dy0.5, Gd0.5 phenanthroline
tris 1-phenyl-1,3-butanedionato Dy0.5, Gd0.5 bathocuproine
tris 1-phenyl-1,3-butanedionato Dy0.5, Gd0.5 bathophenanthroline
tris acetylacetonato Dy0.2, Gd0.8 dimethylaminopyridine
tris acetylacetonato Dy0.2, Gd0.8 4-picoline-N-oxide
tris acetylacetonato Dy0.2, Gd0.8 4-phenylpyridine tris acetylacetonato Dy0.2, Gd0.8 4-cyanopyridine
tris acetylacetonato Dy0.2, Gd0.8 4-phenylpyridine-N-oxide
tris acetylacetonato Dy0.2, Gd0.8 1-methylimidazole
tris acetylacetonato Dy0.2, Gd0.8 triphenylphosphine oxide
tris acetylacetonato Dy0.2, Gd0.8 2,2-bipyridyl
tris acetylacetonato Dy0.2, Gd0.8 2,2-bipyridyl-N,N-dioxide
tris acetylacetonato Dy0.2, Gd0.8 phenanthroline
tris acetylacetonato Dy0.2, Gd0.8 bathocuproine
tris acetylacetonato Dy0.2, Gd0.8 bathophenanthroline
tris dibenzoylmethanato Dy0.2, Gd0.8 dimethylaminopyridine
tris dibenzoylmethanato Dy0.2, Gd0.8 4-picoline-N-oxide
tris dibenzoylmethanato Dy0.2, Gd0.8 4-phenylpyridine
tris dibenzoylmethanato Dy0.2, Gd0.8 4-cyanopyridine
tris dibenzoylmethanato Dy0.2, Gd0.8 4-phenylpyridine-N-oxide
tris dibenzoylmethanato Dy0.2, Gd0.8 1-methylimidazole
tris dibenzoylmethanato Dy0.2, Gd0.8 triphenylphosphine oxide
tris dibenzoylmethanato Dy0.2, Gd0.8 2,2-bipyridyl
tris dibenzoylmethanato Dy0.2, Gd0.8 2,2-bipyridyl-N,N-dioxide
tris dibenzoylmethanato Dy0.2, Gd0.8 phenanthroline
tris dibenzoylmethanato Dy0.2, Gd0.8 bathocuproine
tris dibenzoylmethanato Dy0.2, Gd0.8 bathophenanthroline
tris thenoyltrifluoroacetonato Dy0.2, Gd0.8 dimethylaminopyridine
tris thenoyltrifluoroacetonato Dy0.2, Gd0.8 4-picoline-N-oxide
tris thenoyltrifluoroacetonato Dy0.2, Gd0.8 4-phenylpyridine
tris thenoyltrifluoroacetonato Dy0.2, Gd0.8 4-cyanopyridine
tris thenoyltrifluoroacetonato Dy0.2, Gd0.8 4-phenylpyridine-N-oxide
tris thenoyltrifluoroacetonato Dy0.2, Gd0.8 1-methylimidazole
tris thenoyltrifluoroacetonato Dy0.2, Gd0.8 triphenylphosphine oxide
tris thenoyltrifluoroacetonato Dy0.2, Gd0.8 2,2-bipyridyl
tris thenoyltrifluoroacetonato Dy0.2, Gd0.8 2,2-bipyridyl-N,N-dioxide
tris thenoyltrifluoroacetonato Dy0.2, Gd0.8 phenanthroline
tris thenoyltrifluoroacetonato Dy0.2, Gd0.8 bathocuproine
tris thenoyltrifluoroacetonato Dy0.2, Gd0.8 bathophenanthroline
tris 2,2,6,6-tetramethylheptanedionato Dy0.2, Gd0.8 dimethylaminopyridine
tris 2,2,6,6-tetramethylheptanedionato Dy0.2, Gd0.8 4-picoline-N-oxide
tris 2,2,6,6-tetramethylheptanedionato Dy0.2, Gd0.8 4-phenylpyridine
tris 2,2,6,6-tetramethylheptanedionato Dy0.2, Gd0.8 4-cyanopyridine
tris 2,2,6,6-tetramethylheptanedionato Dy0.2, Gd0.8 4-phenylpyridine-N-oxide
tris 2,2,6,6-tetramethylheptanedionato Dy0.2, Gd0.8 1-methylimidazole
tris 2,2,6,6-tetramethylheptanedionato Dy0.2, Gd0.8 triphenylphosphine oxide
tris 2,2,6,6-tetramethylheptanedionato Dy0.2, Gd0.8 2,2-bipyridyl
tris 2,2,6,6-tetramethylheptanedionato Dy0.2, Gd0.8 2,2-bipyridyl-N,N-dioxide
tris 2,2,6,6-tetramethylheptanedionato Dy0.2, Gd0.8 phenanthroline
tris 2,2,6,6-tetramethylheptanedionato Dy0.2, Gd0.8 bathocuproine
tris 2,2,6,6-tetramethylheptanedionato Dy0.2, Gd0.8 bathophenanthroline
tris 3-methylpentane-2,4-dionato Dy0.2, Gd0.8 dimethylaminopyridine
tris 3-methylpentane-2,4-dionato Dy0.2, Gd0.8 4-picoline-N-oxide
tris 3-methylpentane-2,4-dionato Dy0.2, Gd0.8 4-phenylpyridine
tris 3-methylpentane-2,4-dionato Dy0.2, Gd0.8 4-cyanopyridine
tris 3-methylpentane-2,4-dionato Dy0.2, Gd0.8 4-phenylpyridine-N-oxide
tris 3-methylpentane-2,4-dionato Dy0.2, Gd0.8 1-methylimidazole
tris 3-methylpentane-2,4-dionato Dy0.2, Gd0.8 triphenylphosphine oxide
tris 3-methylpentane-2,4-dionato Dy0.2, Gd0.8 2,2-bipyridyl
tris 3-methylpentane-2,4-dionato Dy0.2, Gd0.8 2,2-bipyridyl-N,N-dioxide
tris 3-methylpentane-2,4-dionato Dy0.2, Gd0.8 phenanthroline
tris 3-methylpentane-2,4-dionato Dy0.2, Gd0.8 bathocuproine
tris 3-methylpentane-2,4-dionato Dy0.2, Gd0.8 bathophenanthroline
tris 3-ethylpentane-2,4-dionato Dy0.2, Gd0.8 dimethylaminopyridine
tris 3-ethylpentane-2,4-dionato Dy0.2, Gd0.8 4-picoline-N-oxide
tris 3-ethylpentane-2,4-dionato Dy0.2, Gd0.8 4-phenylpyridine
tris 3-ethylpentane-2,4-dionato Dy0.2, Gd0.8 4-cyanopyridine
tris 3-ethylpentane-2,4-dionato Dy0.2, Gd0.8 4-phenylpyridine-N-oxide
tris 3-ethylpentane-2,4-dionato Dy0.2, Gd0.8 1-methylimidazole
tris 3-ethylpentane-2,4-dionato Dy0.2, Gd0.8 triphenylphosphine oxide
tris 3-ethylpentane-2,4-dionato Dy0.2, Gd0.8 2,2-bipyridyl
tris 3-ethylpentane-2,4-dionato Dy0.2, Gd0.8 2,2-bipyridyl-N,N-dioxide
tris 3-ethylpentane-2,4-dionato Dy0.2, Gd0.8 phenanthroline
tris 3-ethylpentane-2,4-dionato Dy0.2, Gd0.8 bathocuproine
tris 3-ethylpentane-2,4-dionato Dy0.2, Gd0.8 bathophenanthroline
tris pivaloyltrifluoroacetonato Dy0.2, Gd0.8 dimethylaminopyridine
tris pivaloyltrifluoroacetonato Dy0.2, Gd0.8 4-picoline-N-oxide
tris pivaloyltrifluoroacetonato Dy0.2, Gd0.8 4-phenylpyridine
tris pivaloyltrifluoroacetonato Dy0.2, Gd0.8 4-cyanopyridine
tris pivaloyltrifluoroacetonato Dy0.2, Gd0.8 4-phenylpyridine-N-oxide
tris pivaloyltrifluoroacetonato Dy0.2, Gd0.8 1-methylimidazole
tris pivaloyltrifluoroacetonato Dy0.2, Gd0.8 triphenylphosphine oxide
tris pivaloyltrifluoroacetonato Dy0.2, Gd0.8 2,2-bipyridyl
tris pivaloyltrifluoroacetonato Dy0.2, Gd0.8 2,2-bipyridyl-N,N-dioxide tris pivaloyltrifluoroacetonato Dy0.2, Gd0.8 phenanthroline
tris pivaloyltrifluoroacetonato Dy0.2, Gd0.8 bathocuproine
tris pivaloyltrifluoroacetonato Dy0.2, Gd0.8 bathophenanthroline
tris trifluoroacetylacetonato Dy0.2, Gd0.8 dimethylaminopyridine
tris trifluoroacetylacetonato Dy0.2, Gd0.8 4-picoline-N-oxide
tris trifluoroacetylacetonato Dy0.2, Gd0.8 4-phenylpyridine
tris trifluoroacetylacetonato Dy0.2, Gd0.8 4-cyanopyridine
tris trifluoroacetylacetonato Dy0.2, Gd0.8 4-phenylpyridine-N-oxide
tris trifluoroacetylacetonato Dy0.2, Gd0.8 1-methylimidazole
tris trifluoroacetylacetonato Dy0.2, Gd0.8 triphenylphosphine oxide
tris trifluoroacetylacetonato Dy0.2, Gd0.8 2,2-bipyridyl
tris trifluoroacetylacetonato Dy0.2, Gd0.8 2,2-bipyridyl-N,N-dioxide
tris trifluoroacetylacetonato Dy0.2, Gd0.8 phenanthroline
tris trifluoroacetylacetonato Dy0.2, Gd0.8 bathocuproine
tris trifluoroacetylacetonato Dy0.2, Gd0.8 bathophenanthroline
tris hexafluoroacetylacetonato Dy0.2, Gd0.8 dimethylaminopyridine
tris hexafluoroacetylacetonato Dy0.2, Gd0.8 4-picoline-N-oxide
tris hexafluoroacetylacetonato Dy0.2, Gd0.8 4-phenylpyridine
tris hexafluoroacetylacetonato Dy0.2, Gd0.8 4-cyanopyridine
tris hexafluoroacetylacetonato Dy0.2, Gd0.8 4-phenylpyridine-N-oxide
tris hexafluoroacetylacetonato Dy0.2, Gd0.8 1-methylimidazole
tris hexafluoroacetylacetonato Dy0.2, Gd0.8 triphenylphosphine oxide
tris hexafluoroacetylacetonato Dy0.2, Gd0.8 2,2-bipyridyl
tris hexafluoroacetylacetonato Dy0.2, Gd0.8 2,2-bipyridyl-N,N-dioxide
tris hexafluoroacetylacetonato Dy0.2, Gd0.8 phenanthroline
tris hexafluoroacetylacetonato Dy0.2, Gd0.8 bathocuproine
tris hexafluoroacetylacetonato Dy0.2, Gd0.8 bathophenanthroline
tris 6,6,7,7,8,8,8-heptafluoro-2,2-dimethyloctanedionato Dy0.2, Gd0.8 dimethylaminopyridine
tris 6,6,7,7,8,8,8-heptafluoro-2,2-dimethyloctanedionato Dy0.2, Gd0.8 4-picoline-N-oxide
tris 6,6,7,7,8,8,8-heptafluoro-2,2-dimethyloctanedionato Dy0.2, Gd0.8 4-phenylpyridine
tris 6,6,7,7,8,8,8-heptafluoro-2,2-dimethyloctanedionato Dy0.2, Gd0.8 4-cyanopyridine
tris 6,6,7,7,8,8,8-heptafluoro-2,2-dimethyloctanedionato Dy0.2, Gd0.8 4-phenylpyridine-N-oxide
tris 6,6,7,7,8,8,8-heptafluoro-2,2-dimethyloctanedionato Dy0.2, Gd0.8 1-methylimidazole
tris 6,6,7,7,8,8,8-heptafluoro-2,2-dimethyloctanedionato Dy0.2, Gd0.8 triphenylphosphine oxide
tris 6,6,7,7,8,8,8-heptafluoro-2,2-dimethyloctanedionato Dy0.2, Gd0.8 2,2-bipyridyl
tris 6,6,7,7,8,8,8-heptafluoro-2,2-dimethyloctanedionato Dy0.2, Gd0.8 2,2-bipyridyl-N,N-dioxide
tris 6,6,7,7,8,8,8-heptafluoro-2,2-dimethyloctanedionato Dy0.2, Gd0.8 phenanthroline
tris 6,6,7,7,8,8,8-heptafluoro-2,2-dimethyloctanedionato Dy0.2, Gd0.8 bathocuproine
tris 6,6,7,7,8,8,8-heptafluoro-2,2-dimethyloctanedionato Dy0.2, Gd0.8 bathophenanthroline
tris 1-phenyl-1,3-butanedionato Dy0.2, Gd0.8 dimethylaminopyridine
tris 1-phenyl-1,3-butanedionato Dy0.2, Gd0.8 4-picoline-N-oxide
tris 1-phenyl-1,3-butanedionato Dy0.2, Gd0.8 4-phenylpyridine
tris 1-phenyl-1,3-butanedionato Dy0.2, Gd0.8 4-cyanopyridine
tris 1-phenyl-1,3-butanedionato Dy0.2, Gd0.8 4-phenylpyridine-N-oxide
tris 1-phenyl-1,3-butanedionato Dy0.2, Gd0.8 1-methylimidazole
tris 1-phenyl-1,3-butanedionato Dy0.2, Gd0.8 triphenylphosphine oxide
tris 1-phenyl-1,3-butanedionato Dy0.2, Gd0.8 2,2-bipyridyl
tris 1-phenyl-1,3-butanedionato Dy0.2, Gd0.8 2,2-bipyridyl-N,N-dioxide
tris 1-phenyl-1,3-butanedionato Dy0.2, Gd0.8 phenanthroline
tris 1-phenyl-1,3-butanedionato Dy0.2, Gd0.8 bathocuproine
tris 1-phenyl-1,3-butanedionato Dy0.2, Gd0.8 bathophenanthroline
tris acetylacetonato Dy0.1, Gd0.9 dimethylaminopyridine
tris acetylacetonato Dy0.1, Gd0.9 4-picoline-N-oxide
tris acetylacetonato Dy0.1, Gd0.9 4-phenylpyridine
tris acetylacetonato Dy0.1, Gd0.9 4-cyanopyridine
tris acetylacetonato Dy0.1, Gd0.9 4-phenylpyridine-N-oxide
tris acetylacetonato Dy0.1, Gd0.9 1-methylimidazole
tris acetylacetonato Dy0.1, Gd0.9 triphenylphosphine oxide
tris acetylacetonato Dy0.1, Gd0.9 2,2-bipyridyl
tris acetylacetonato Dy0.1, Gd0.9 2,2-bipyridyl-N,N-dioxide
tris acetylacetonato Dy0.1, Gd0.9 phenanthroline
tris acetylacetonato Dy0.1, Gd0.9 bathocuproine
tris acetylacetonato Dy0.1, Gd0.9 bathophenanthroline
tris dibenzoylmethanato Dy0.1, Gd0.9 dimethylaminopyridine
tris dibenzoylmethanato Dy0.1, Gd0.9 4-picoline-N-oxide
tris dibenzoylmethanato Dy0.1, Gd0.9 4-phenylpyridine
tris dibenzoylmethanato Dy0.1, Gd0.9 4-cyanopyridine
tris dibenzoylmethanato Dy0.1, Gd0.9 4-phenylpyridine-N-oxide
tris dibenzoylmethanato Dy0.1, Gd0.9 1-methylimidazole
tris dibenzoylmethanato Dy0.1, Gd0.9 triphenylphosphine oxide
tris dibenzoylmethanato Dy0.1, Gd0.9 2,2-bipyridyl
tris dibenzoylmethanato Dy0.1, Gd0.9 2,2-bipyridyl-N,N-dioxide
tris dibenzoylmethanato Dy0.1, Gd0.9 phenanthroline
tris dibenzoylmethanato Dy0.1, Gd0.9 bathocuproine
tris dibenzoylmethanato Dy0.1, Gd0.9 bathophenanthroline
tris thenoyltrifluoroacetonato Dy0.1, Gd0.9 dimethylaminopyridine
tris thenoyltrifluoroacetonato Dy0.1, Gd0.9 4-picoline-N-oxide
tris thenoyltrifluoroacetonato Dy0.1, Gd0.9 4-phenylpyridine
tris thenoyltrifluoroacetonato Dy0.1, Gd0.9 4-cyanopyridine
tris thenoyltrifluoroacetonato Dy0.1, Gd0.9 4-phenylpyridine-N-oxide
tris thenoyltrifluoroacetonato Dy0.1, Gd0.9 1-methylimidazole
tris thenoyltrifluoroacetonato Dy0.1, Gd0.9 triphenylphosphine oxide tris thenoyltrifluoroacetonato Dy0.1, Gd0.9 2,2-bipyridyl
tris thenoyltrifluoroacetonato Dy0.1, Gd0.9 2,2-bipyridyl-N,N-dioxide
tris thenoyltrifluoroacetonato Dy0.1, Gd0.9 phenanthroline
tris thenoyltrifluoroacetonato Dy0.1, Gd0.9 bathocuproine
tris thenoyltrifluoroacetonato Dy0.1, Gd0.9 bathophenanthroline
tris 2,2,6,6-tetramethylheptanedionato Dy0.1, Gd0.9 dimethylaminopyridine
tris 2,2,6,6-tetramethylheptanedionato Dy0.1, Gd0.9 4-picoline-N-oxide
tris 2,2,6,6-tetramethylheptanedionato Dy0.1, Gd0.9 4-phenylpyridine
tris 2,2,6,6-tetramethylheptanedionato Dy0.1, Gd0.9 4-cyanopyridine
tris 2,2,6,6-tetramethylheptanedionato Dy0.1, Gd0.9 4-phenylpyridine-N-oxide
tris 2,2,6,6-tetramethylheptanedionato Dy0.1, Gd0.9 1-methylimidazole
tris 2,2,6,6-tetramethylheptanedionato Dy0.1, Gd0.9 triphenylphosphine oxide
tris 2,2,6,6-tetramethylheptanedionato Dy0.1, Gd0.9 2,2-bipyridyl
tris 2,2,6,6-tetramethylheptanedionato Dy0.1, Gd0.9 2,2-bipyridyl-N,N-dioxide
tris 2,2,6,6-tetramethylheptanedionato Dy0.1, Gd0.9 phenanthroline
tris 2,2,6,6-tetramethylheptanedionato Dy0.1, Gd0.9 bathocuproine
tris 2,2,6,6-tetramethylheptanedionato Dy0.1, Gd0.9 bathophenanthroline
tris 3-methylpentane-2,4-dionato Dy0.1, Gd0.9 dimethylaminopyridine
tris 3-methylpentane-2,4-dionato Dy0.1, Gd0.9 4-picoline-N-oxide
tris 3-methylpentane-2,4-dionato Dy0.1, Gd0.9 4-phenylpyridine
tris 3-methylpentane-2,4-dionato Dy0.1, Gd0.9 4-cyanopyridine
tris 3-methylpentane-2,4-dionato Dy0.1, Gd0.9 4-phenylpyridine-N-oxide
tris 3-methylpentane-2,4-dionato Dy0.1, Gd0.9 1-methylimidazole
tris 3-methylpentane-2,4-dionato Dy0.1, Gd0.9 triphenylphosphine oxide
tris 3-methylpentane-2,4-dionato Dy0.1, Gd0.9 2,2-bipyridyl
tris 3-methylpentane-2,4-dionato Dy0.1, Gd0.9 2,2-bipyridyl-N,N-dioxide
tris 3-methylpentane-2,4-dionato Dy0.1, Gd0.9 phenanthroline
tris 3-methylpentane-2,4-dionato Dy0.1, Gd0.9 bathocuproine
tris 3-methylpentane-2,4-dionato Dy0.1, Gd0.9 bathophenanthroline
tris 3-ethylpentane-2,4-dionato Dy0.1, Gd0.9 dimethylaminopyridine
tris 3-ethylpentane-2,4-dionato Dy0.1, Gd0.9 4-picoline-N-oxide
tris 3-ethylpentane-2,4-dionato Dy0.1, Gd0.9 4-phenylpyridine
tris 3-ethylpentane-2,4-dionato Dy0.1, Gd0.9 4-cyanopyridine
tris 3-ethylpentane-2,4-dionato Dy0.1, Gd0.9 4-phenylpyridine-N-oxide
tris 3-ethylpentane-2,4-dionato Dy0.1, Gd0.9 1-methylimidazole
tris 3-ethylpentane-2,4-dionato Dy0.1, Gd0.9 triphenylphosphine oxide
tris 3-ethylpentane-2,4-dionato Dy0.1, Gd0.9 2,2-bipyridyl
tris 3-ethylpentane-2,4-dionato Dy0.1, Gd0.9 2,2-bipyridyl-N,N-dioxide
tris 3-ethylpentane-2,4-dionato Dy0.1, Gd0.9 phenanthroline
tris 3-ethylpentane-2,4-dionato Dy0.1, Gd0.9 bathocuproine
tris 3-ethylpentane-2,4-dionato Dy0.1, Gd0.9 bathophenanthroline
tris pivaloyltrifluoroacetonato Dy0.1, Gd0.9 dimethylaminopyridine
tris pivaloyltrifluoroacetonato Dy0.1, Gd0.9 4-picoline-N-oxide
tris pivaloyltrifluoroacetonato Dy0.1, Gd0.9 4-phenylpyridine
tris pivaloyltrifluoroacetonato Dy0.1, Gd0.9 4-cyanopyridine
tris pivaloyltrifluoroacetonato Dy0.1, Gd0.9 4-phenylpyridine-N-oxide
tris pivaloyltrifluoroacetonato Dy0.1, Gd0.9 1-methylimidazole
tris pivaloyltrifluoroacetonato Dy0.1, Gd0.9 triphenylphosphine oxide
tris pivaloyltrifluoroacetonato Dy0.1, Gd0.9 2,2-bipyridyl
tris pivaloyltrifluoroacetonato Dy0.1, Gd0.9 2,2-bipyridyl-N,N-dioxide
tris pivaloyltrifluoroacetonato Dy0.1, Gd0.9 phenanthroline
tris pivaloyltrifluoroacetonato Dy0.1, Gd0.9 bathocuproine
tris pivaloyltrifluoroacetonato Dy0.1, Gd0.9 bathophenanthroline
tris trifluoroacetylacetonato Dy0.1, Gd0.9 dimethylaminopyridine
tris trifluoroacetylacetonato Dy0.1, Gd0.9 4-picoline-N-oxide
tris trifluoroacetylacetonato Dy0.1, Gd0.9 4-phenylpyridine
tris trifluoroacetylacetonato Dy0.1, Gd0.9 4-cyanopyridine
tris trifluoroacetylacetonato Dy0.1, Gd0.9 4-phenylpyridine-N-oxide
tris trifluoroacetylacetonato Dy0.1, Gd0.9 1-methylimidazole
tris trifluoroacetylacetonato Dy0.1, Gd0.9 triphenylphosphine oxide
tris trifluoroacetylacetonato Dy0.1, Gd0.9 2,2-bipyridyl
tris trifluoroacetylacetonato Dy0.1, Gd0.9 2,2-bipyridyl-N,N-dioxide
tris trifluoroacetylacetonato Dy0.1, Gd0.9 phenanthroline
tris trifluoroacetylacetonato Dy0.1, Gd0.9 bathocuproine
tris trifluoroacetylacetonato Dy0.1, Gd0.9 bathophenanthroline
tris hexafluoroacetylacetonato Dy0.1, Gd0.9 dimethylaminopyridine
tris hexafluoroacetylacetonato Dy0.1, Gd0.9 4-picoline-N-oxide
tris hexafluoroacetylacetonato Dy0.1, Gd0.9 4-phenylpyridine
tris hexafluoroacetylacetonato Dy0.1, Gd0.9 4-cyanopyridine
tris hexafluoroacetylacetonato Dy0.1, Gd0.9 4-phenylpyridine-N-oxide
tris hexafluoroacetylacetonato Dy0.1, Gd0.9 1-methylimidazole
tris hexafluoroacetylacetonato Dy0.1, Gd0.9 triphenylphosphine oxide
tris hexafluoroacetylacetonato Dy0.1, Gd0.9 2,2-bipyridyl
tris hexafluoroacetylacetonato Dy0.1, Gd0.9 2,2-bipyridyl-N,N-dioxide tris hexafluoroacetylacetonato Dy0.1, Gd0.9 phenanthroline
tris hexafluoroacetylacetonato Dy0.1, Gd0.9 bathocuproine
tris hexafluoroacetylacetonato Dy0.1, Gd0.9 bathophenanthroline
tris 6,6,7,7,8,8,8-heptafluoro-2,2-dimethyloctanedionato Dy0.1, Gd0.9 dimethylaminopyridine
tris 6,6,7,7,8,8,8-heptafluoro-2,2-dimethyloctanedionato Dy0.1, Gd0.9 4-picoline-N-oxide
tris 6,6,7,7,8,8,8-heptafluoro-2,2-dimethyloctanedionato Dy0.1, Gd0.9 4-phenylpyridine
tris 6,6,7,7,8,8,8-heptafluoro-2,2-dimethyloctanedionato Dy0.1, Gd0.9 4-cyanopyridine
tris 6,6,7,7,8,8,8-heptafluoro-2,2-dimethyloctanedionato Dy0.1, Gd0.9 4-phenylpyridine-N-oxide
tris 6,6,7,7,8,8,8-heptafluoro-2,2-dimethyloctanedionato Dy0.1, Gd0.9 1-methylimidazole
tris 6,6,7,7,8,8,8-heptafluoro-2,2-dimethyloctanedionato Dy0.1, Gd0.9 triphenylphosphine oxide
tris 6,6,7,7,8,8,8-heptafluoro-2,2-dimethyloctanedionato Dy0.1, Gd0.9 2,2-bipyridyl
tris 6,6,7,7,8,8,8-heptafluoro-2,2-dimethyloctanedionato Dy0.1, Gd0.9 2,2-bipyridyl-N,N-dioxide
tris 6,6,7,7,8,8,8-heptafluoro-2,2-dimethyloctanedionato Dy0.1, Gd0.9 phenanthroline
tris 6,6,7,7,8,8,8-heptafluoro-2,2-dimethyloctanedionato Dy0.1, Gd0.9 bathocuproine
tris 6,6,7,7,8,8,8-heptafluoro-2,2-dimethyloctanedionato Dy0.1, Gd0.9 bathophenanthroline
tris 1-phenyl-1,3-butanedionato Dy0.1, Gd0.9 dimethylaminopyridine
tris 1-phenyl-1,3-butanedionato Dy0.1, Gd0.9 4-picoline-N-oxide
tris 1-phenyl-1,3-butanedionato Dy0.1, Gd0.9 4-phenylpyridine
tris 1-phenyl-1,3-butanedionato Dy0.1, Gd0.9 4-cyanopyridine
tris 1-phenyl-1,3-butanedionato Dy0.1, Gd0.9 4-phenylpyridine-N-oxide
tris 1-phenyl-1,3-butanedionato Dy0.1, Gd0.9 1-methylimidazole
tris 1-phenyl-1,3-butanedionato Dy0.1, Gd0.9 triphenylphosphine oxide
tris 1-phenyl-1,3-butanedionato Dy0.1, Gd0.9 2,2-bipyridyl
tris 1-phenyl-1,3-butanedionato Dy0.1, Gd0.9 2,2-bipyridyl-N,N-dioxide
tris 1-phenyl-1,3-butanedionato Dy0.1, Gd0.9 phenanthroline
tris 1-phenyl-1,3-butanedionato Dy0.1, Gd0.9 bathocuproine
tris 1-phenyl-1,3-butanedionato Dy0.1, Gd0.9 bathophenanthroline
tris acetylacetonato Dy0.01, Gd0.99 dimethylaminopyridine
tris acetylacetonato Dy0.01, Gd0.99 4-picoline-N-oxide
tris acetylacetonato Dy0.01, Gd0.99 4-phenylpyridine
tris acetylacetonato Dy0.01, Gd0.99 4-cyanopyridine
tris acetylacetonato Dy0.01, Gd0.99 4-phenylpyridine-N-oxide
tris acetylacetonato Dy0.01, Gd0.99 1-methylimidazole
tris acetylacetonato Dy0.01, Gd0.99 triphenylphosphine oxide
tris acetylacetonato Dy0.01, Gd0.99 2,2-bipyridyl
tris acetylacetonato Dy0.01, Gd0.99 2,2-bipyridyl-N,N-dioxide
tris acetylacetonato Dy0.01, Gd0.99 phenanthroline
tris acetylacetonato Dy0.01, Gd0.99 bathocuproine
tris acetylacetonato Dy0.01, Gd0.99 bathophenanthroline
tris dibenzoylmethanato Dy0.01, Gd0.99 dimethylaminopyridine
tris dibenzoylmethanato Dy0.01, Gd0.99 4-picoline-N-oxide
tris dibenzoylmethanato Dy0.01, Gd0.99 4-phenylpyridine
tris dibenzoylmethanato Dy0.01, Gd0.99 4-cyanopyridine
tris dibenzoylmethanato Dy0.01, Gd0.99 4-phenylpyridine-N-oxide
tris dibenzoylmethanato Dy0.01, Gd0.99 1-methylimidazole
tris dibenzoylmethanato Dy0.01, Gd0.99 triphenylphosphine oxide
tris dibenzoylmethanato Dy0.01, Gd0.99 2,2-bipyridyl
tris dibenzoylmethanato Dy0.01, Gd0.99 2,2-bipyridyl-N,N-dioxide
tris dibenzoylmethanato Dy0.01, Gd0.99 phenanthroline
tris dibenzoylmethanato Dy0.01, Gd0.99 bathocuproine
tris dibenzoylmethanato Dy0.01, Gd0.99 bathophenanthroline
tris thenoyltrifluoroacetonato Dy0.01, Gd0.99 dimethylaminopyridine
tris thenoyltrifluoroacetonato Dy0.01, Gd0.99 4-picoline-N-oxide
tris thenoyltrifluoroacetonato Dy0.01, Gd0.99 4-phenylpyridine
tris thenoyltrifluoroacetonato Dy0.01, Gd0.99 4-cyanopyridine
tris thenoyltrifluoroacetonato Dy0.01, Gd0.99 4-phenylpyridine-N-oxide
tris thenoyltrifluoroacetonato Dy0.01, Gd0.99 1-methylimidazole
tris thenoyltrifluoroacetonato Dy0.01, Gd0.99 triphenylphosphine oxide
tris thenoyltrifluoroacetonato Dy0.01, Gd0.99 2,2-bipyridyl
tris thenoyltrifluoroacetonato Dy0.01, Gd0.99 2,2-bipyridyl-N,N-dioxide
tris thenoyltrifluoroacetonato Dy0.01, Gd0.99 phenanthroline
tris thenoyltrifluoroacetonato Dy0.01, Gd0.99 bathocuproine
tris thenoyltrifluoroacetonato Dy0.01, Gd0.99 bathophenanthroline
tris 2,2,6,6-tetramethylheptanedionato Dy0.01, Gd0.99 dimethylaminopyridine
tris 2,2,6,6-tetramethylheptanedionato Dy0.01, Gd0.99 4-picoline-N-oxide
tris 2,2,6,6-tetramethylheptanedionato Dy0.01, Gd0.99 4-phenylpyridine
tris 2,2,6,6-tetramethylheptanedionato Dy0.01, Gd0.99 4-cyanopyridine
tris 2,2,6,6-tetramethylheptanedionato Dy0.01, Gd0.99 4-phenylpyridine-N-oxide
tris 2,2,6,6-tetramethylheptanedionato Dy0.01, Gd0.99 1-methylimidazole
tris 2,2,6,6-tetramethylheptanedionato Dy0.01, Gd0.99 triphenylphosphine oxide
tris 2,2,6,6-tetramethylheptanedionato Dy0.01, Gd0.99 2,2-bipyridyl
tris 2,2,6,6-tetramethylheptanedionato Dy0.01, Gd0.99 2,2-bipyridyl-N,N-dioxide
tris 2,2,6,6-tetramethylheptanedionato Dy0.01, Gd0.99 phenanthroline
tris 2,2,6,6-tetramethylheptanedionato Dy0.01, Gd0.99 bathocuproine
tris 2,2,6,6-tetramethylheptanedionato Dy0.01, Gd0.99 bathophenanthroline
tris 3-methylpentane-2,4-dionato Dy0.01, Gd0.99 dimethylaminopyridine tris 3-methylpentane-2,4-dionato Dy0.01, Gd0.99 4-picoline-N-oxide
tris 3-methylpentane-2,4-dionato Dy0.01, Gd0.99 4-phenylpyridine
tris 3-methylpentane-2,4-dionato Dy0.01, Gd0.99 4-cyanopyridine
tris 3-methylpentane-2,4-dionato Dy0.01, Gd0.99 4-phenylpyridine-N-oxide
tris 3-methylpentane-2,4-dionato Dy0.01, Gd0.99 1-methylimidazole
tris 3-methylpentane-2,4-dionato Dy0.01, Gd0.99 triphenylphosphine oxide
tris 3-methylpentane-2,4-dionato Dy0.01, Gd0.99 2,2-bipyridyl
tris 3-methylpentane-2,4-dionato Dy0.01, Gd0.99 2,2-bipyridyl-N,N-dioxide
tris 3-methylpentane-2,4-dionato Dy0.01, Gd0.99 phenanthroline
tris 3-methylpentane-2,4-dionato Dy0.01, Gd0.99 bathocuproine
tris 3-methylpentane-2,4-dionato Dy0.01, Gd0.99 bathophenanthroline
tris 3-ethylpentane-2,4-dionato Dy0.01, Gd0.99 dimethylaminopyridine
tris 3-ethylpentane-2,4-dionato Dy0.01, Gd0.99 4-picoline-N-oxide
tris 3-ethylpentane-2,4-dionato Dy0.01, Gd0.99 4-phenylpyridine
tris 3-ethylpentane-2,4-dionato Dy0.01, Gd0.99 4-cyanopyridine
tris 3-ethylpentane-2,4-dionato Dy0.01, Gd0.99 4-phenylpyridine-N-oxide
tris 3-ethylpentane-2,4-dionato Dy0.01, Gd0.99 1-methylimidazole
tris 3-ethylpentane-2,4-dionato Dy0.01, Gd0.99 triphenylphosphine oxide
tris 3-ethylpentane-2,4-dionato Dy0.01, Gd0.99 2,2-bipyridyl
tris 3-ethylpentane-2,4-dionato Dy0.01, Gd0.99 2,2-bipyridyl-N,N-dioxide
tris 3-ethylpentane-2,4-dionato Dy0.01, Gd0.99 phenanthroline
tris 3-ethylpentane-2,4-dionato Dy0.01, Gd0.99 bathocuproine
tris 3-ethylpentane-2,4-dionato Dy0.01, Gd0.99 bathophenanthroline
tris pivaloyltrifluoroacetonato Dy0.01, Gd0.99 dimethylaminopyridine
tris pivaloyltrifluoroacetonato Dy0.01, Gd0.99 4-picoline-N-oxide
tris pivaloyltrifluoroacetonato Dy0.01, Gd0.99 4-phenylpyridine
tris pivaloyltrifluoroacetonato Dy0.01, Gd0.99 4-cyanopyridine
tris pivaloyltrifluoroacetonato Dy0.01, Gd0.99 4-phenylpyridine-N-oxide
tris pivaloyltrifluoroacetonato Dy0.01, Gd0.99 1-methylimidazole
tris pivaloyltrifluoroacetonato Dy0.01, Gd0.99 triphenylphosphine oxide
tris pivaloyltrifluoroacetonato Dy0.01, Gd0.99 2,2-bipyridyl
tris pivaloyltrifluoroacetonato Dy0.01, Gd0.99 2,2-bipyridyl-N,N-dioxide
tris pivaloyltrifluoroacetonato Dy0.01, Gd0.99 phenanthroline
tris pivaloyltrifluoroacetonato Dy0.01, Gd0.99 bathocuproine
tris pivaloyltrifluoroacetonato Dy0.01, Gd0.99 bathophenanthroline
tris trifluoroacetylacetonato Dy0.01, Gd0.99 dimethylaminopyridine
tris trifluoroacetylacetonato Dy0.01, Gd0.99 4-picoline-N-oxide
tris trifluoroacetylacetonato Dy0.01, Gd0.99 4-phenylpyridine
tris trifluoroacetylacetonato Dy0.01, Gd0.99 4-cyanopyridine
tris trifluoroacetylacetonato Dy0.01, Gd0.99 4-phenylpyridine-N-oxide
tris trifluoroacetylacetonato Dy0.01, Gd0.99 1-methylimidazole
tris trifluoroacetylacetonato Dy0.01, Gd0.99 triphenylphosphine oxide
tris trifluoroacetylacetonato Dy0.01, Gd0.99 2,2-bipyridyl
tris trifluoroacetylacetonato Dy0.01, Gd0.99 2,2-bipyridyl-N,N-dioxide
tris trifluoroacetylacetonato Dy0.01, Gd0.99 phenanthroline
tris trifluoroacetylacetonato Dy0.01, Gd0.99 bathocuproine
tris trifluoroacetylacetonato Dy0.01, Gd0.99 bathophenanthroline
tris hexafluoroacetylacetonato Dy0.01, Gd0.99 dimethylaminopyridine
tris hexafluoroacetylacetonato Dy0.01, Gd0.99 4-picoline-N-oxide
tris hexafluoroacetylacetonato Dy0.01, Gd0.99 4-phenylpyridine
tris hexafluoroacetylacetonato Dy0.01, Gd0.99 4-cyanopyridine
tris hexafluoroacetylacetonato Dy0.01, Gd0.99 4-phenylpyridine-N-oxide
tris hexafluoroacetylacetonato Dy0.01, Gd0.99 1-methylimidazole
tris hexafluoroacetylacetonato Dy0.01, Gd0.99 triphenylphosphine oxide
tris hexafluoroacetylacetonato Dy0.01, Gd0.99 2,2-bipyridyl
tris hexafluoroacetylacetonato Dy0.01, Gd0.99 2,2-bipyridyl-N,N-dioxide
tris hexafluoroacetylacetonato Dy0.01, Gd0.99 phenanthroline
tris hexafluoroacetylacetonato Dy0.01, Gd0.99 bathocuproine
tris hexafluoroacetylacetonato Dy0.01, Gd0.99 bathophenanthroline
tris 6,6,7,7,8,8,8-heptafluoro-2,2-dimethyloctanedionato Dy0.01, Gd0.99 dimethylaminopyridine
tris 6,6,7,7,8,8,8-heptafluoro-2,2-dimethyloctanedionato Dy0.01, Gd0.99 4-picoline-N-oxide
tris 6,6,7,7,8,8,8-heptafluoro-2,2-dimethyloctanedionato Dy0.01, Gd0.99 4-phenylpyridine
tris 6,6,7,7,8,8,8-heptafluoro-2,2-dimethyloctanedionato Dy0.01, Gd0.99 4-cyanopyridine
tris 6,6,7,7,8,8,8-heptafluoro-2,2-dimethyloctanedionato Dy0.01, Gd0.99 4-phenylpyridine-N-oxide
tris 6,6,7,7,8,8,8-heptafluoro-2,2-dimethyloctanedionato Dy0.01, Gd0.99 1-methylimidazole
tris 6,6,7,7,8,8,8-heptafluoro-2,2-dimethyloctanedionato Dy0.01, Gd0.99 triphenylphosphine oxide
tris 6,6,7,7,8,8,8-heptafluoro-2,2-dimethyloctanedionato Dy0.01, Gd0.99 2,2-bipyridyl
tris 6,6,7,7,8,8,8-heptafluoro-2,2-dimethyloctanedionato Dy0.01, Gd0.99 2,2-bipyridyl-N,N-dioxide
tris 6,6,7,7,8,8,8-heptafluoro-2,2-dimethyloctanedionato Dy0.01, Gd0.99 phenanthroline tris 6,6,7,7,8,8,8-heptafluoro-2,2-dimethyloctanedionato Dy0.01, Gd0.99 bathocuproine
tris 6,6,7,7,8,8,8-heptafluoro-2,2-dimethyloctanedionato Dy0.01, Gd0.99 bathophenanthroline
tris 1-phenyl-1,3-butanedionato Dy0.01, Gd0.99 dimethylaminopyridine
tris 1-phenyl-1,3-butanedionato Dy0.01, Gd0.99 4-picoline-N-oxide
tris 1-phenyl-1,3-butanedionato Dy0.01, Gd0.99 4-phenylpyridine
tris 1-phenyl-1,3-butanedionato Dy0.01, Gd0.99 4-cyanopyridine
tris 1-phenyl-1,3-butanedionato Dy0.01, Gd0.99 4-phenylpyridine-N-oxide
tris 1-phenyl-1,3-butanedionato Dy0.01, Gd0.99 1-methylimidazole
tris 1-phenyl-1,3-butanedionato Dy0.01, Gd0.99 triphenylphosphine oxide
tris 1-phenyl-1,3-butanedionato Dy0.01, Gd0.99 2,2-bipyridyl
tris 1-phenyl-1,3-butanedionato Dy0.01, Gd0.99 2,2-bipyridyl-N,N-dioxide
tris 1-phenyl-1,3-butanedionato Dy0.01, Gd0.99 phenanthroline
tris 1-phenyl-1,3-butanedionato Dy0.01, Gd0.99 bathocuproine
tris 1-phenyl-1,3-butanedionato Dy0.01, Gd0.99 bathophenanthroline
tris acetylacetonato Dy0.5, Gd0.5 dimethylaminopyridine
tris acetylacetonato Dy0.5, Gd0.5 4-picoline-N-oxide
tris acetylacetonato Dy0.5, Gd0.5 4-phenylpyridine
tris acetylacetonato Dy0.5, Gd0.5 4-cyanopyridine
tris acetylacetonato Dy0.5, Gd0.5 4-phenylpyridine-N-oxide
tris acetylacetonato Dy0.5, Gd0.5 1-methylimidazole
tris acetylacetonato Dy0.5, Gd0.5 triphenylphosphine oxide
tris acetylacetonato Dy0.5, Gd0.5 2,2-bipyridyl
tris acetylacetonato Dy0.5, Gd0.5 2,2-bipyridyl-N,N-dioxide
tris acetylacetonato Dy0.5, Gd0.5 phenanthroline
tris acetylacetonato Dy0.5, Gd0.5 bathocuproine
tris acetylacetonato Dy0.5, Gd0.5 bathophenanthroline
tris dibenzoylmethanato Dy0.5, Gd0.5 dimethylaminopyridine
tris dibenzoylmethanato Dy0.5, Gd0.5 4-picoline-N-oxide
tris dibenzoylmethanato Dy0.5, Gd0.5 4-phenylpyridine
tris dibenzoylmethanato Dy0.5, Gd0.5 4-cyanopyridine
tris dibenzoylmethanato Dy0.5, Gd0.5 4-phenylpyridine-N-oxide
tris dibenzoylmethanato Dy0.5, Gd0.5 1-methylimidazole
tris dibenzoylmethanato Dy0.5, Gd0.5 triphenylphosphine oxide
tris dibenzoylmethanato Dy0.5, Gd0.5 2,2-bipyridyl
tris dibenzoylmethanato Dy0.5, Gd0.5 2,2-bipyridyl-N,N-dioxide
tris dibenzoylmethanato Dy0.5, Gd0.5 phenanthroline
tris dibenzoylmethanato Dy0.5, Gd0.5 bathocuproine
tris dibenzoylmethanato Dy0.5, Gd0.5 bathophenanthroline
tris thenoyltrifluoroacetonato Dy0.5, Gd0.5 dimethylaminopyridine
tris thenoyltrifluoroacetonato Dy0.5, Gd0.5 4-picoline-N-oxide
tris thenoyltrifluoroacetonato Dy0.5, Gd0.5 4-phenylpyridine
tris thenoyltrifluoroacetonato Dy0.5, Gd0.5 4-cyanopyridine
tris thenoyltrifluoroacetonato Dy0.5, Gd0.5 4-phenylpyridine-N-oxide
tris thenoyltrifluoroacetonato Dy0.5, Gd0.5 1-methylimidazole
tris thenoyltrifluoroacetonato Dy0.5, Gd0.5 triphenylphosphine oxide
tris thenoyltrifluoroacetonato Dy0.5, Gd0.5 2,2-bipyridyl
tris thenoyltrifluoroacetonato Dy0.5, Gd0.5 2,2-bipyridyl-N,N-dioxide
tris thenoyltrifluoroacetonato Dy0.5, Gd0.5 phenanthroline
tris thenoyltrifluoroacetonato Dy0.5, Gd0.5 bathocuproine
tris thenoyltrifluoroacetonato Dy0.5, Gd0.5 bathophenanthroline
tris 2,2,6,6-tetramethylheptanedionato Dy0.5, Gd0.5 dimethylaminopyridine
tris 2,2,6,6-tetramethylheptanedionato Dy0.5, Gd0.5 4-picoline-N-oxide
tris 2,2,6,6-tetramethylheptanedionato Dy0.5, Gd0.5 4-phenylpyridine
tris 2,2,6,6-tetramethylheptanedionato Dy0.5, Gd0.5 4-cyanopyridine
tris 2,2,6,6-tetramethylheptanedionato Dy0.5, Gd0.5 4-phenylpyridine-N-oxide
tris 2,2,6,6-tetramethylheptanedionato Dy0.5, Gd0.5 1-methylimidazole
tris 2,2,6,6-tetramethylheptanedionato Dy0.5, Gd0.5 triphenylphosphine oxide
tris 2,2,6,6-tetramethylheptanedionato Dy0.5, Gd0.5 2,2-bipyridyl
tris 2,2,6,6-tetramethylheptanedionato Dy0.5, Gd0.5 2,2-bipyridyl-N,N-dioxide
tris 2,2,6,6-tetramethylheptanedionato Dy0.5, Gd0.5 phenanthroline
tris 2,2,6,6-tetramethylheptanedionato Dy0.5, Gd0.5 bathocuproine
tris 2,2,6,6-tetramethylheptanedionato Dy0.5, Gd0.5 bathophenanthroline
tris 3-methylpentane-2,4-dionato Dy0.5, Gd0.5 dimethylaminopyridine
tris 3-methylpentane-2,4-dionato Dy0.5, Gd0.5 4-picoline-N-oxide
tris 3-methylpentane-2,4-dionato Dy0.5, Gd0.5 4-phenylpyridine
tris 3-methylpentane-2,4-dionato Dy0.5, Gd0.5 4-cyanopyridine
tris 3-methylpentane-2,4-dionato Dy0.5, Gd0.5 4-phenylpyridine-N-oxide
tris 3-methylpentane-2,4-dionato Dy0.5, Gd0.5 1-methylimidazole
tris 3-methylpentane-2,4-dionato Dy0.5, Gd0.5 triphenylphosphine oxide
tris 3-methylpentane-2,4-dionato Dy0.5, Gd0.5 2,2-bipyridyl
tris 3-methylpentane-2,4-dionato Dy0.5, Gd0.5 2,2-bipyridyl-N,N-dioxide
tris 3-methylpentane-2,4-dionato Dy0.5, Gd0.5 phenanthroline
tris 3-methylpentane-2,4-dionato Dy0.5, Gd0.5 bathocuproine
tris 3-methylpentane-2,4-dionato Dy0.5, Gd0.5 bathophenanthroline
tris 3-ethylpentane-2,4-dionato Dy0.5, Gd0.5 dimethylaminopyridine
tris 3-ethylpentane-2,4-dionato Dy0.5, Gd0.5 4-picoline-N-oxide
tris 3-ethylpentane-2,4-dionato Dy0.5, Gd0.5 4-phenylpyridine
tris 3-ethylpentane-2,4-dionato Dy0.5, Gd0.5 4-cyanopyridine tris 3-ethylpentane-2,4-dionato Dy0.5, Gd0.5 4-phenylpyridine-N-oxide
tris 3-ethylpentane-2,4-dionato Dy0.5, Gd0.5 1-methylimidazole
tris 3-ethylpentane-2,4-dionato Dy0.5, Gd0.5 triphenylphosphine oxide
tris 3-ethylpentane-2,4-dionato Dy0.5, Gd0.5 2,2-bipyridyl
tris 3-ethylpentane-2,4-dionato Dy0.5, Gd0.5 2,2-bipyridyl-N,N-dioxide
tris 3-ethylpentane-2,4-dionato Dy0.5, Gd0.5 phenanthroline
tris 3-ethylpentane-2,4-dionato Dy0.5, Gd0.5 bathocuproine
tris 3-ethylpentane-2,4-dionato Dy0.5, Gd0.5 bathophenanthroline
tris pivaloyltrifluoroacetonato Dy0.5, Gd0.5 dimethylaminopyridine
tris pivaloyltrifluoroacetonato Dy0.5, Gd0.5 4-picoline-N-oxide
tris pivaloyltrifluoroacetonato Dy0.5, Gd0.5 4-phenylpyridine
tris pivaloyltrifluoroacetonato Dy0.5, Gd0.5 4-cyanopyridine
tris pivaloyltrifluoroacetonato Dy0.5, Gd0.5 4-phenylpyridine-N-oxide
tris pivaloyltrifluoroacetonato Dy0.5, Gd0.5 1-methylimidazole
tris pivaloyltrifluoroacetonato Dy0.5, Gd0.5 triphenylphosphine oxide
tris pivaloyltrifluoroacetonato Dy0.5, Gd0.5 2,2-bipyridyl
tris pivaloyltrifluoroacetonato Dy0.5, Gd0.5 2,2-bipyridyl-N,N-dioxide
tris pivaloyltrifluoroacetonato Dy0.5, Gd0.5 phenanthroline
tris pivaloyltrifluoroacetonato Dy0.5, Gd0.5 bathocuproine
tris pivaloyltrifluoroacetonato Dy0.5, Gd0.5 bathophenanthroline
tris trifluoroacetylacetonato Dy0.5, Gd0.5 dimethylaminopyridine
tris trifluoroacetylacetonato Dy0.5, Gd0.5 4-picoline-N-oxide
tris trifluoroacetylacetonato Dy0.5, Gd0.5 4-phenylpyridine
tris trifluoroacetylacetonato Dy0.5, Gd0.5 4-cyanopyridine
tris trifluoroacetylacetonato Dy0.5, Gd0.5 4-phenylpyridine-N-oxide
tris trifluoroacetylacetonato Dy0.5, Gd0.5 1-methylimidazole
tris trifluoroacetylacetonato Dy0.5, Gd0.5 triphenylphosphine oxide
tris trifluoroacetylacetonato Dy0.5, Gd0.5 2,2-bipyridyl
tris trifluoroacetylacetonato Dy0.5, Gd0.5 2,2-bipyridyl-N,N-dioxide
tris trifluoroacetylacetonato Dy0.5, Gd0.5 phenanthroline
tris trifluoroacetylacetonato Dy0.5, Gd0.5 bathocuproine
tris trifluoroacetylacetonato Dy0.5, Gd0.5 bathophenanthroline
tris hexafluoroacetylacetonato Dy0.5, Gd0.5 dimethylaminopyridine
tris hexafluoroacetylacetonato Dy0.5, Gd0.5 4-picoline-N-oxide
tris hexafluoroacetylacetonato Dy0.5, Gd0.5 4-phenylpyridine
tris hexafluoroacetylacetonato Dy0.5, Gd0.5 4-cyanopyridine
tris hexafluoroacetylacetonato Dy0.5, Gd0.5 4-phenylpyridine-N-oxide
tris hexafluoroacetylacetonato Dy0.5, Gd0.5 1-methylimidazole
tris hexafluoroacetylacetonato Dy0.5, Gd0.5 triphenylphosphine oxide
tris hexafluoroacetylacetonato Dy0.5, Gd0.5 2,2-bipyridyl
tris hexafluoroacetylacetonato Dy0.5, Gd0.5 2,2-bipyridyl-N,N-dioxide
tris hexafluoroacetylacetonato Dy0.5, Gd0.5 phenanthroline
tris hexafluoroacetylacetonato Dy0.5, Gd0.5 bathocuproine
tris hexafluoroacetylacetonato Dy0.5, Gd0.5 bathophenanthroline
tris 6,6,7,7,8,8,8-heptafluoro-2,2-dimethyloctanedionato Dy0.5, Gd0.5 dimethylaminopyridine
tris 6,6,7,7,8,8,8-heptafluoro-2,2-dimethyloctanedionato Dy0.5, Gd0.5 4-picoline-N-oxide
tris 6,6,7,7,8,8,8-heptafluoro-2,2-dimethyloctanedionato Dy0.5, Gd0.5 4-phenylpyridine
tris 6,6,7,7,8,8,8-heptafluoro-2,2-dimethyloctanedionato Dy0.5, Gd0.5 4-cyanopyridine
tris 6,6,7,7,8,8,8-heptafluoro-2,2-dimethyloctanedionato Dy0.5, Gd0.5 4-phenylpyridine-N-oxide
tris 6,6,7,7,8,8,8-heptafluoro-2,2-dimethyloctanedionato Dy0.5, Gd0.5 1-methylimidazole
tris 6,6,7,7,8,8,8-heptafluoro-2,2-dimethyloctanedionato Dy0.5, Gd0.5 triphenylphosphine oxide
tris 6,6,7,7,8,8,8-heptafluoro-2,2-dimethyloctanedionato Dy0.5, Gd0.5 2,2-bipyridyl
tris 6,6,7,7,8,8,8-heptafluoro-2,2-dimethyloctanedionato Dy0.5, Gd0.5 2,2-bipyridyl-N,N-dioxide
tris 6,6,7,7,8,8,8-heptafluoro-2,2-dimethyloctanedionato Dy0.5, Gd0.5 phenanthroline
tris 6,6,7,7,8,8,8-heptafluoro-2,2-dimethyloctanedionato Dy0.5, Gd0.5 bathocuproine
tris 6,6,7,7,8,8,8-heptafluoro-2,2-dimethyloctanedionato Dy0.5, Gd0.5 bathophenanthroline
tris 1-phenyl-1,3-butanedionato Dy0.5, Gd0.5 dimethylaminopyridine
tris 1-phenyl-1,3-butanedionato Dy0.5, Gd0.5 4-picoline-N-oxide
tris 1-phenyl-1,3-butanedionato Dy0.5, Gd0.5 4-phenylpyridine
tris 1-phenyl-1,3-butanedionato Dy0.5, Gd0.5 4-cyanopyridine
tris 1-phenyl-1,3-butanedionato Dy0.5, Gd0.5 4-phenylpyridine-N-oxide
tris 1-phenyl-1,3-butanedionato Dy0.5, Gd0.5 1-methylimidazole
tris 1-phenyl-1,3-butanedionato Dy0.5, Gd0.5 triphenylphosphine oxide
tris 1-phenyl-1,3-butanedionato Dy0.5, Gd0.5 2,2-bipyridyl
tris 1-phenyl-1,3-butanedionato Dy0.5, Gd0.5 2,2-bipyridyl-N,N-dioxide
tris 1-phenyl-1,3-butanedionato Dy0.5, Gd0.5 phenanthroline
tris 1-phenyl-1,3-butanedionato Dy0.5, Gd0.5 bathocuproine
tris 1-phenyl-1,3-butanedionato Dy0.5, Gd0.5 bathophenanthroline
tris acetylacetonato Dy0.2, Gd0.8 dimethylaminopyridine
tris acetylacetonato Dy0.2, Gd0.8 4-picoline-N-oxide
tris acetylacetonato Dy0.2, Gd0.8 4-phenylpyridine
tris acetylacetonato Dy0.2, Gd0.8 4-cyanopyridine
tris acetylacetonato Dy0.2, Gd0.8 4-phenylpyridine-N-oxide
tris acetylacetonato Dy0.2, Gd0.8 1-methylimidazole
tris acetylacetonato Dy0.2, Gd0.8 triphenylphosphine oxide
tris acetylacetonato Dy0.2, Gd0.8 2,2-bipyridyl
tris acetylacetonato Dy0.2, Gd0.8 2,2-bipyridyl-N,N-dioxide
tris acetylacetonato Dy0.2, Gd0.8 phenanthroline tris acetylacetonato Dy0.2, Gd0.8 bathocuproine
tris acetylacetonato Dy0.2, Gd0.8 bathophenanthroline
tris dibenzoylmethanato Dy0.2, Gd0.8 dimethylaminopyridine
tris dibenzoylmethanato Dy0.2, Gd0.8 4-picoline-N-oxide
tris dibenzoylmethanato Dy0.2, Gd0.8 4-phenylpyridine
tris dibenzoylmethanato Dy0.2, Gd0.8 4-cyanopyridine
tris dibenzoylmethanato Dy0.2, Gd0.8 4-phenylpyridine-N-oxide
tris dibenzoylmethanato Dy0.2, Gd0.8 1-methylimidazole
tris dibenzoylmethanato Dy0.2, Gd0.8 triphenylphosphine oxide
tris dibenzoylmethanato Dy0.2, Gd0.8 2,2-bipyridyl
tris dibenzoylmethanato Dy0.2, Gd0.8 2,2-bipyridyl-N,N-dioxide
tris dibenzoylmethanato Dy0.2, Gd0.8 phenanthroline
tris dibenzoylmethanato Dy0.2, Gd0.8 bathocuproine
tris dibenzoylmethanato Dy0.2, Gd0.8 bathophenanthroline
tris thenoyltrifluoroacetonato Dy0.2, Gd0.8 dimethylaminopyridine
tris thenoyltrifluoroacetonato Dy0.2, Gd0.8 4-picoline-N-oxide
tris thenoyltrifluoroacetonato Dy0.2, Gd0.8 4-phenylpyridine
tris thenoyltrifluoroacetonato Dy0.2, Gd0.8 4-cyanopyridine
tris thenoyltrifluoroacetonato Dy0.2, Gd0.8 4-phenylpyridine-N-oxide
tris thenoyltrifluoroacetonato Dy0.2, Gd0.8 1-methylimidazole
tris thenoyltrifluoroacetonato Dy0.2, Gd0.8 triphenylphosphine oxide
tris thenoyltrifluoroacetonato Dy0.2, Gd0.8 2,2-bipyridyl
tris thenoyltrifluoroacetonato Dy0.2, Gd0.8 2,2-bipyridyl-N,N-dioxide
tris thenoyltrifluoroacetonato Dy0.2, Gd0.8 phenanthroline
tris thenoyltrifluoroacetonato Dy0.2, Gd0.8 bathocuproine
tris thenoyltrifluoroacetonato Dy0.2, Gd0.8 bathophenanthroline
tris 2,2,6,6-tetramethylheptanedionato Dy0.2, Gd0.8 dimethylaminopyridine
tris 2,2,6,6-tetramethylheptanedionato Dy0.2, Gd0.8 4-picoline-N-oxide
tris 2,2,6,6-tetramethylheptanedionato Dy0.2, Gd0.8 4-phenylpyridine
tris 2,2,6,6-tetramethylheptanedionato Dy0.2, Gd0.8 4-cyanopyridine
tris 2,2,6,6-tetramethylheptanedionato Dy0.2, Gd0.8 4-phenylpyridine-N-oxide
tris 2,2,6,6-tetramethylheptanedionato Dy0.2, Gd0.8 1-methylimidazole
tris 2,2,6,6-tetramethylheptanedionato Dy0.2, Gd0.8 triphenylphosphine oxide
tris 2,2,6,6-tetramethylheptanedionato Dy0.2, Gd0.8 2,2-bipyridyl
tris 2,2,6,6-tetramethylheptanedionato Dy0.2, Gd0.8 2,2-bipyridyl-N,N-dioxide
tris 2,2,6,6-tetramethylheptanedionato Dy0.2, Gd0.8 phenanthroline
tris 2,2,6,6-tetramethylheptanedionato Dy0.2, Gd0.8 bathocuproine
tris 2,2,6,6-tetramethylheptanedionato Dy0.2, Gd0.8 bathophenanthroline
tris 3-methylpentane-2,4-dionato Dy0.2, Gd0.8 dimethylaminopyridine
tris 3-methylpentane-2,4-dionato Dy0.2, Gd0.8 4-picoline-N-oxide
tris 3-methylpentane-2,4-dionato Dy0.2, Gd0.8 4-phenylpyridine
tris 3-methylpentane-2,4-dionato Dy0.2, Gd0.8 4-cyanopyridine
tris 3-methylpentane-2,4-dionato Dy0.2, Gd0.8 4-phenylpyridine-N-oxide
tris 3-methylpentane-2,4-dionato Dy0.2, Gd0.8 1-methylimidazole
tris 3-methylpentane-2,4-dionato Dy0.2, Gd0.8 triphenylphosphine oxide
tris 3-methylpentane-2,4-dionato Dy0.2, Gd0.8 2,2-bipyridyl
tris 3-methylpentane-2,4-dionato Dy0.2, Gd0.8 2,2-bipyridyl-N,N-dioxide
tris 3-methylpentane-2,4-dionato Dy0.2, Gd0.8 phenanthroline
tris 3-methylpentane-2,4-dionato Dy0.2, Gd0.8 bathocuproine
tris 3-methylpentane-2,4-dionato Dy0.2, Gd0.8 bathophenanthroline
tris 3-ethylpentane-2,4-dionato Dy0.2, Gd0.8 dimethylaminopyridine
tris 3-ethylpentane-2,4-dionato Dy0.2, Gd0.8 4-picoline-N-oxide
tris 3-ethylpentane-2,4-dionato Dy0.2, Gd0.8 4-phenylpyridine
tris 3-ethylpentane-2,4-dionato Dy0.2, Gd0.8 4-cyanopyridine
tris 3-ethylpentane-2,4-dionato Dy0.2, Gd0.8 4-phenylpyridine-N-oxide
tris 3-ethylpentane-2,4-dionato Dy0.2, Gd0.8 1-methylimidazole
tris 3-ethylpentane-2,4-dionato Dy0.2, Gd0.8 triphenylphosphine oxide
tris 3-ethylpentane-2,4-dionato Dy0.2, Gd0.8 2,2-bipyridyl
tris 3-ethylpentane-2,4-dionato Dy0.2, Gd0.8 2,2-bipyridyl-N,N-dioxide
tris 3-ethylpentane-2,4-dionato Dy0.2, Gd0.8 phenanthroline
tris 3-ethylpentane-2,4-dionato Dy0.2, Gd0.8 bathocuproine
tris 3-ethylpentane-2,4-dionato Dy0.2, Gd0.8 bathophenanthroline
tris pivaloyltrifluoroacetonato Dy0.2, Gd0.8 dimethylaminopyridine
tris pivaloyltrifluoroacetonato Dy0.2, Gd0.8 4-picoline-N-oxide
tris pivaloyltrifluoroacetonato Dy0.2, Gd0.8 4-phenylpyridine
tris pivaloyltrifluoroacetonato Dy0.2, Gd0.8 4-cyanopyridine
tris pivaloyltrifluoroacetonato Dy0.2, Gd0.8 4-phenylpyridine-N-oxide
tris pivaloyltrifluoroacetonato Dy0.2, Gd0.8 1-methylimidazole
tris pivaloyltrifluoroacetonato Dy0.2, Gd0.8 triphenylphosphine oxide
tris pivaloyltrifluoroacetonato Dy0.2, Gd0.8 2,2-bipyridyl
tris pivaloyltrifluoroacetonato Dy0.2, Gd0.8 2,2-bipyridyl-N,N-dioxide
tris pivaloyltrifluoroacetonato Dy0.2, Gd0.8 phenanthroline
tris pivaloyltrifluoroacetonato Dy0.2, Gd0.8 bathocuproine
tris pivaloyltrifluoroacetonato Dy0.2, Gd0.8 bathophenanthroline
tris trifluoroacetylacetonato Dy0.2, Gd0.8 dimethylaminopyridine
tris trifluoroacetylacetonato Dy0.2, Gd0.8 4-picoline-N-oxide tris trifluoroacetylacetonato Dy0.2, Gd0.8 4-phenylpyridine
tris trifluoroacetylacetonato Dy0.2, Gd0.8 4-cyanopyridine
tris trifluoroacetylacetonato Dy0.2, Gd0.8 4-phenylpyridine-N-oxide
tris trifluoroacetylacetonato Dy0.2, Gd0.8 1-methylimidazole
tris trifluoroacetylacetonato Dy0.2, Gd0.8 triphenylphosphine oxide
tris trifluoroacetylacetonato Dy0.2, Gd0.8 2,2-bipyridyl
tris trifluoroacetylacetonato Dy0.2, Gd0.8 2,2-bipyridyl-N,N-dioxide
tris trifluoroacetylacetonato Dy0.2, Gd0.8 phenanthroline
tris trifluoroacetylacetonato Dy0.2, Gd0.8 bathocuproine
tris trifluoroacetylacetonato Dy0.2, Gd0.8 bathophenanthroline
tris hexafluoroacetylacetonato Dy0.2, Gd0.8 dimethylaminopyridine
tris hexafluoroacetylacetonato Dy0.2, Gd0.8 4-picoline-N-oxide
tris hexafluoroacetylacetonato Dy0.2, Gd0.8 4-phenylpyridine
tris hexafluoroacetylacetonato Dy0.2, Gd0.8 4-cyanopyridine
tris hexafluoroacetylacetonato Dy0.2, Gd0.8 4-phenylpyridine-N-oxide
tris hexafluoroacetylacetonato Dy0.2, Gd0.8 1-methylimidazole
tris hexafluoroacetylacetonato Dy0.2, Gd0.8 triphenylphosphine oxide
tris hexafluoroacetylacetonato Dy0.2, Gd0.8 2,2-bipyridyl
tris hexafluoroacetylacetonato Dy0.2, Gd0.8 2,2-bipyridyl-N,N-dioxide
tris hexafluoroacetylacetonato Dy0.2, Gd0.8 phenanthroline
tris hexafluoroacetylacetonato Dy0.2, Gd0.8 bathocuproine
tris hexafluoroacetylacetonato Dy0.2, Gd0.8 bathophenanthroline
tris 6,6,7,7,8,8,8-heptafluoro-2,2-dimethyloctanedionato Dy0.2, Gd0.8 dimethylaminopyridine
tris 6,6,7,7,8,8,8-heptafluoro-2,2-dimethyloctanedionato Dy0.2, Gd0.8 4-picoline-N-oxide
tris 6,6,7,7,8,8,8-heptafluoro-2,2-dimethyloctanedionato Dy0.2, Gd0.8 4-phenylpyridine
tris 6,6,7,7,8,8,8-heptafluoro-2,2-dimethyloctanedionato Dy0.2, Gd0.8 4-cyanopyridine
tris 6,6,7,7,8,8,8-heptafluoro-2,2-dimethyloctanedionato Dy0.2, Gd0.8 4-phenylpyridine-N-oxide
tris 6,6,7,7,8,8,8-heptafluoro-2,2-dimethyloctanedionato Dy0.2, Gd0.8 1-methylimidazole
tris 6,6,7,7,8,8,8-heptafluoro-2,2-dimethyloctanedionato Dy0.2, Gd0.8 triphenylphosphine oxide
tris 6,6,7,7,8,8,8-heptafluoro-2,2-dimethyloctanedionato Dy0.2, Gd0.8 2,2-bipyridyl
tris 6,6,7,7,8,8,8-heptafluoro-2,2-dimethyloctanedionato Dy0.2, Gd0.8 2,2-bipyridyl-N,N-dioxide
tris 6,6,7,7,8,8,8-heptafluoro-2,2-dimethyloctanedionato Dy0.2, Gd0.8 phenanthroline
tris 6,6,7,7,8,8,8-heptafluoro-2,2-dimethyloctanedionato Dy0.2, Gd0.8 bathocuproine
tris 6,6,7,7,8,8,8-heptafluoro-2,2-dimethyloctanedionato Dy0.2, Gd0.8 bathophenanthroline
tris 1-phenyl-1,3-butanedionato Dy0.2, Gd0.8 dimethylaminopyridine
tris 1-phenyl-1,3-butanedionato Dy0.2, Gd0.8 4-picoline-N-oxide
tris 1-phenyl-1,3-butanedionato Dy0.2, Gd0.8 4-phenylpyridine
tris 1-phenyl-1,3-butanedionato Dy0.2, Gd0.8 4-cyanopyridine
tris 1-phenyl-1,3-butanedionato Dy0.2, Gd0.8 4-phenylpyridine-N-oxide
tris 1-phenyl-1,3-butanedionato Dy0.2, Gd0.8 1-methylimidazole
tris 1-phenyl-1,3-butanedionato Dy0.2, Gd0.8 triphenylphosphine oxide
tris 1-phenyl-1,3-butanedionato Dy0.2, Gd0.8 2,2-bipyridyl
tris 1-phenyl-1,3-butanedionato Dy0.2, Gd0.8 2,2-bipyridyl-N,N-dioxide
tris 1-phenyl-1,3-butanedionato Dy0.2, Gd0.8 phenanthroline
tris 1-phenyl-1,3-butanedionato Dy0.2, Gd0.8 bathocuproine
tris 1-phenyl-1,3-butanedionato Dy0.2, Gd0.8 bathophenanthroline
tris acetylacetonato Dy0.1, Gd0.9 dimethylaminopyridine
tris acetylacetonato Dy0.1, Gd0.9 4-picoline-N-oxide
tris acetylacetonato Dy0.1, Gd0.9 4-phenylpyridine
tris acetylacetonato Dy0.1, Gd0.9 4-cyanopyridine
tris acetylacetonato Dy0.1, Gd0.9 4-phenylpyridine-N-oxide
tris acetylacetonato Dy0.1, Gd0.9 1-methylimidazole
tris acetylacetonato Dy0.1, Gd0.9 triphenylphosphine oxide
tris acetylacetonato Dy0.1, Gd0.9 2,2-bipyridyl
tris acetylacetonato Dy0.1, Gd0.9 2,2-bipyridyl-N,N-dioxide
tris acetylacetonato Dy0.1, Gd0.9 phenanthroline
tris acetylacetonato Dy0.1, Gd0.9 bathocuproine
tris acetylacetonato Dy0.1, Gd0.9 bathophenanthroline
tris dibenzoylmethanato Dy0.1, Gd0.9 dimethylaminopyridine
tris dibenzoylmethanato Dy0.1, Gd0.9 4-picoline-N-oxide
tris dibenzoylmethanato Dy0.1, Gd0.9 4-phenylpyridine
tris dibenzoylmethanato Dy0.1, Gd0.9 4-cyanopyridine
tris dibenzoylmethanato Dy0.1, Gd0.9 4-phenylpyridine-N-oxide
tris dibenzoylmethanato Dy0.1, Gd0.9 1-methylimidazole
tris dibenzoylmethanato Dy0.1, Gd0.9 triphenylphosphine oxide
tris dibenzoylmethanato Dy0.1, Gd0.9 2,2-bipyridyl
tris dibenzoylmethanato Dy0.1, Gd0.9 2,2-bipyridyl-N,N-dioxide
tris dibenzoylmethanato Dy0.1, Gd0.9 phenanthroline
tris dibenzoylmethanato Dy0.1, Gd0.9 bathocuproine
tris dibenzoylmethanato Dy0.1, Gd0.9 bathophenanthroline
tris thenoyltrifluoroacetonato Dy0.1, Gd0.9 dimethylaminopyridine
tris thenoyltrifluoroacetonato Dy0.1, Gd0.9 4-picoline-N-oxide
tris thenoyltrifluoroacetonato Dy0.1, Gd0.9 4-phenylpyridine
tris thenoyltrifluoroacetonato Dy0.1, Gd0.9 4-cyanopyridine
tris thenoyltrifluoroacetonato Dy0.1, Gd0.9 4-phenylpyridine-N-oxide
tris thenoyltrifluoroacetonato Dy0.1, Gd0.9 1-methylimidazole
tris thenoyltrifluoroacetonato Dy0.1, Gd0.9 triphenylphosphine oxide
tris thenoyltrifluoroacetonato Dy0.1, Gd0.9 2,2-bipyridyl
tris thenoyltrifluoroacetonato Dy0.1, Gd0.9 2,2-bipyridyl-N,N-dioxide
tris thenoyltrifluoroacetonato Dy0.1, Gd0.9 phenanthroline
tris thenoyltrifluoroacetonato Dy0.1, Gd0.9 bathocuproine
tris thenoyltrifluoroacetonato Dy0.1, Gd0.9 bathophenanthroline tris 2,2,6,6-tetramethylheptanedionato Dy0.1, Gd0.9 dimethylaminopyridine
tris 2,2,6,6-tetramethylheptanedionato Dy0.1, Gd0.9 4-picoline-N-oxide
tris 2,2,6,6-tetramethylheptanedionato Dy0.1, Gd0.9 4-phenylpyridine
tris 2,2,6,6-tetramethylheptanedionato Dy0.1, Gd0.9 4-cyanopyridine
tris 2,2,6,6-tetramethylheptanedionato Dy0.1, Gd0.9 4-phenylpyridine-N-oxide
tris 2,2,6,6-tetramethylheptanedionato Dy0.1, Gd0.9 1-methylimidazole
tris 2,2,6,6-tetramethylheptanedionato Dy0.1, Gd0.9 triphenylphosphine oxide
tris 2,2,6,6-tetramethylheptanedionato Dy0.1, Gd0.9 2,2-bipyridyl
tris 2,2,6,6-tetramethylheptanedionato Dy0.1, Gd0.9 2,2-bipyridyl-N,N-dioxide
tris 2,2,6,6-tetramethylheptanedionato Dy0.1, Gd0.9 phenanthroline
tris 2,2,6,6-tetramethylheptanedionato Dy0.1, Gd0.9 bathocuproine
tris 2,2,6,6-tetramethylheptanedionato Dy0.1, Gd0.9 bathophenanthroline
tris 3-methylpentane-2,4-dionato Dy0.1, Gd0.9 dimethylaminopyridine
tris 3-methylpentane-2,4-dionato Dy0.1, Gd0.9 4-picoline-N-oxide
tris 3-methylpentane-2,4-dionato Dy0.1, Gd0.9 4-phenylpyridine
tris 3-methylpentane-2,4-dionato Dy0.1, Gd0.9 4-cyanopyridine
tris 3-methylpentane-2,4-dionato Dy0.1, Gd0.9 4-phenylpyridine-N-oxide
tris 3-methylpentane-2,4-dionato Dy0.1, Gd0.9 1-methylimidazole
tris 3-methylpentane-2,4-dionato Dy0.1, Gd0.9 triphenylphosphine oxide
tris 3-methylpentane-2,4-dionato Dy0.1, Gd0.9 2,2-bipyridyl
tris 3-methylpentane-2,4-dionato Dy0.1, Gd0.9 2,2-bipyridyl-N,N-dioxide
tris 3-methylpentane-2,4-dionato Dy0.1, Gd0.9 phenanthroline
tris 3-methylpentane-2,4-dionato Dy0.1, Gd0.9 bathocuproine
tris 3-methylpentane-2,4-dionato Dy0.1, Gd0.9 bathophenanthroline
tris 3-ethylpentane-2,4-dionato Dy0.1, Gd0.9 dimethylaminopyridine
tris 3-ethylpentane-2,4-dionato Dy0.1, Gd0.9 4-picoline-N-oxide
tris 3-ethylpentane-2,4-dionato Dy0.1, Gd0.9 4-phenylpyridine
tris 3-ethylpentane-2,4-dionato Dy0.1, Gd0.9 4-cyanopyridine
tris 3-ethylpentane-2,4-dionato Dy0.1, Gd0.9 4-phenylpyridine-N-oxide
tris 3-ethylpentane-2,4-dionato Dy0.1, Gd0.9 1-methylimidazole
tris 3-ethylpentane-2,4-dionato Dy0.1, Gd0.9 triphenylphosphine oxide
tris 3-ethylpentane-2,4-dionato Dy0.1, Gd0.9 2,2-bipyridyl
tris 3-ethylpentane-2,4-dionato Dy0.1, Gd0.9 2,2-bipyridyl-N,N-dioxide
tris 3-ethylpentane-2,4-dionato Dy0.1, Gd0.9 phenanthroline
tris 3-ethylpentane-2,4-dionato Dy0.1, Gd0.9 bathocuproine
tris 3-ethylpentane-2,4-dionato Dy0.1, Gd0.9 bathophenanthroline
tris pivaloyltrifluoroacetonato Dy0.1, Gd0.9 dimethylaminopyridine
tris pivaloyltrifluoroacetonato Dy0.1, Gd0.9 4-picoline-N-oxide
tris pivaloyltrifluoroacetonato Dy0.1, Gd0.9 4-phenylpyridine
tris pivaloyltrifluoroacetonato Dy0.1, Gd0.9 4-cyanopyridine
tris pivaloyltrifluoroacetonato Dy0.1, Gd0.9 4-phenylpyridine-N-oxide
tris pivaloyltrifluoroacetonato Dy0.1, Gd0.9 1-methylimidazole
tris pivaloyltrifluoroacetonato Dy0.1, Gd0.9 triphenylphosphine oxide
tris pivaloyltrifluoroacetonato Dy0.1, Gd0.9 2,2-bipyridyl
tris pivaloyltrifluoroacetonato Dy0.1, Gd0.9 2,2-bipyridyl-N,N-dioxide
tris pivaloyltrifluoroacetonato Dy0.1, Gd0.9 phenanthroline
tris pivaloyltrifluoroacetonato Dy0.1, Gd0.9 bathocuproine
tris pivaloyltrifluoroacetonato Dy0.1, Gd0.9 bathophenanthroline
tris trifluoroacetylacetonato Dy0.1, Gd0.9 dimethylaminopyridine
tris trifluoroacetylacetonato Dy0.1, Gd0.9 4-picoline-N-oxide
tris trifluoroacetylacetonato Dy0.1, Gd0.9 4-phenylpyridine
tris trifluoroacetylacetonato Dy0.1, Gd0.9 4-cyanopyridine
tris trifluoroacetylacetonato Dy0.1, Gd0.9 4-phenylpyridine-N-oxide
tris trifluoroacetylacetonato Dy0.1, Gd0.9 1-methylimidazole
tris trifluoroacetylacetonato Dy0.1, Gd0.9 triphenylphosphine oxide
tris trifluoroacetylacetonato Dy0.1, Gd0.9 2,2-bipyridyl
tris trifluoroacetylacetonato Dy0.1, Gd0.9 2,2-bipyridyl-N,N-dioxide
tris trifluoroacetylacetonato Dy0.1, Gd0.9 phenanthroline
tris trifluoroacetylacetonato Dy0.1, Gd0.9 bathocuproine
tris trifluoroacetylacetonato Dy0.1, Gd0.9 bathophenanthroline
tris hexafluoroacetylacetonato Dy0.1, Gd0.9 dimethylaminopyridine
tris hexafluoroacetylacetonato Dy0.1, Gd0.9 4-picoline-N-oxide
tris hexafluoroacetylacetonato Dy0.1, Gd0.9 4-phenylpyridine
tris hexafluoroacetylacetonato Dy0.1, Gd0.9 4-cyanopyridine
tris hexafluoroacetylacetonato Dy0.1, Gd0.9 4-phenylpyridine-N-oxide
tris hexafluoroacetylacetonato Dy0.1, Gd0.9 1-methylimidazole
tris hexafluoroacetylacetonato Dy0.1, Gd0.9 triphenylphosphine oxide
tris hexafluoroacetylacetonato Dy0.1, Gd0.9 2,2-bipyridyl
tris hexafluoroacetylacetonato Dy0.1, Gd0.9 2,2-bipyridyl-N,N-dioxide
tris hexafluoroacetylacetonato Dy0.1, Gd0.9 phenanthroline
tris hexafluoroacetylacetonato Dy0.1, Gd0.9 bathocuproine
tris hexafluoroacetylacetonato Dy0.1, Gd0.9 bathophenanthroline
tris 6,6,7,7,8,8,8-heptafluoro-2,2-dimethyloctanedionato Dy0.1, Gd0.9 dimethylaminopyridine tris 6,6,7,7,8,8,8-heptafluoro-2,2-dimethyloctanedionato Dy0.1, Gd0.9 4-picoline-N-oxide
tris 6,6,7,7,8,8,8-heptafluoro-2,2-dimethyloctanedionato Dy0.1, Gd0.9 4-phenylpyridine
tris 6,6,7,7,8,8,8-heptafluoro-2,2-dimethyloctanedionato Dy0.1, Gd0.9 4-cyanopyridine
tris 6,6,7,7,8,8,8-heptafluoro-2,2-dimethyloctanedionato Dy0.1, Gd0.9 4-phenylpyridine-N-oxide
tris 6,6,7,7,8,8,8-heptafluoro-2,2-dimethyloctanedionato Dy0.1, Gd0.9 1-methylimidazole
tris 6,6,7,7,8,8,8-heptafluoro-2,2-dimethyloctanedionato Dy0.1, Gd0.9 triphenylphosphine oxide
tris 6,6,7,7,8,8,8-heptafluoro-2,2-dimethyloctanedionato Dy0.1, Gd0.9 2,2-bipyridyl
tris 6,6,7,7,8,8,8-heptafluoro-2,2-dimethyloctanedionato Dy0.1, Gd0.9 2,2-bipyridyl-N,N-dioxide
tris 6,6,7,7,8,8,8-heptafluoro-2,2-dimethyloctanedionato Dy0.1, Gd0.9 phenanthroline
tris 6,6,7,7,8,8,8-heptafluoro-2,2-dimethyloctanedionato Dy0.1, Gd0.9 bathocuproine
tris 6,6,7,7,8,8,8-heptafluoro-2,2-dimethyloctanedionato Dy0.1, Gd0.9 bathophenanthroline
tris 1-phenyl-1,3-butanedionato Dy0.1, Gd0.9 dimethylaminopyridine
tris 1-phenyl-1,3-butanedionato Dy0.1, Gd0.9 4-picoline-N-oxide
tris 1-phenyl-1,3-butanedionato Dy0.1, Gd0.9 4-phenylpyridine
tris 1-phenyl-1,3-butanedionato Dy0.1, Gd0.9 4-cyanopyridine
tris 1-phenyl-1,3-butanedionato Dy0.1, Gd0.9 4-phenylpyridine-N-oxide
tris 1-phenyl-1,3-butanedionato Dy0.1, Gd0.9 1-methylimidazole
tris 1-phenyl-1,3-butanedionato Dy0.1, Gd0.9 triphenylphosphine oxide
tris 1-phenyl-1,3-butanedionato Dy0.1, Gd0.9 2,2-bipyridyl
tris 1-phenyl-1,3-butanedionato Dy0.1, Gd0.9 2,2-bipyridyl-N,N-dioxide
tris 1-phenyl-1,3-butanedionato Dy0.1, Gd0.9 phenanthroline
tris 1-phenyl-1,3-butanedionato Dy0.1, Gd0.9 bathocuproine
tris 1-phenyl-1,3-butanedionato Dy0.1, Gd0.9 bathophenanthroline
tris acetylacetonato Dy0.01, Gd0.99 dimethylaminopyridine
tris acetylacetonato Dy0.01, Gd0.99 4-picoline-N-oxide
tris acetylacetonato Dy0.01, Gd0.99 4-phenylpyridine
tris acetylacetonato Dy0.01, Gd0.99 4-cyanopyridine
tris acetylacetonato Dy0.01, Gd0.99 4-phenylpyridine-N-oxide
tris acetylacetonato Dy0.01, Gd0.99 1-methylimidazole
tris acetylacetonato Dy0.01, Gd0.99 triphenylphosphine oxide
tris acetylacetonato Dy0.01, Gd0.99 2,2-bipyridyl
tris acetylacetonato Dy0.01, Gd0.99 2,2-bipyridyl-N,N-dioxide
tris acetylacetonato Dy0.01, Gd0.99 phenanthroline
tris acetylacetonato Dy0.01, Gd0.99 bathocuproine
tris acetylacetonato Dy0.01, Gd0.99 bathophenanthroline
tris dibenzoylmethanato Dy0.01, Gd0.99 dimethylaminopyridine
tris dibenzoylmethanato Dy0.01, Gd0.99 4-picoline-N-oxide
tris dibenzoylmethanato Dy0.01, Gd0.99 4-phenylpyridine
tris dibenzoylmethanato Dy0.01, Gd0.99 4-cyanopyridine
tris dibenzoylmethanato Dy0.01, Gd0.99 4-phenylpyridine-N-oxide
tris dibenzoylmethanato Dy0.01, Gd0.99 1-methylimidazole
tris dibenzoylmethanato Dy0.01, Gd0.99 triphenylphosphine oxide
tris dibenzoylmethanato Dy0.01, Gd0.99 2,2-bipyridyl
tris dibenzoylmethanato Dy0.01, Gd0.99 2,2-bipyridyl-N,N-dioxide
tris dibenzoylmethanato Dy0.01, Gd0.99 phenanthroline
tris dibenzoylmethanato Dy0.01, Gd0.99 bathocuproine
tris dibenzoylmethanato Dy0.01, Gd0.99 bathophenanthroline
tris thenoyltrifluoroacetonato Dy0.01, Gd0.99 dimethylaminopyridine
tris thenoyltrifluoroacetonato Dy0.01, Gd0.99 4-picoline-N-oxide
tris thenoyltrifluoroacetonato Dy0.01, Gd0.99 4-phenylpyridine
tris thenoyltrifluoroacetonato Dy0.01, Gd0.99 4-cyanopyridine
tris thenoyltrifluoroacetonato Dy0.01, Gd0.99 4-phenylpyridine-N-oxide
tris thenoyltrifluoroacetonato Dy0.01, Gd0.99 1-methylimidazole
tris thenoyltrifluoroacetonato Dy0.01, Gd0.99 triphenylphosphine oxide
tris thenoyltrifluoroacetonato Dy0.01, Gd0.99 2,2-bipyridyl
tris thenoyltrifluoroacetonato Dy0.01, Gd0.99 2,2-bipyridyl-N,N-dioxide
tris thenoyltrifluoroacetonato Dy0.01, Gd0.99 phenanthroline
tris thenoyltrifluoroacetonato Dy0.01, Gd0.99 bathocuproine
tris thenoyltrifluoroacetonato Dy0.01, Gd0.99 bathophenanthroline
tris 2,2,6,6-tetramethylheptanedionato Dy0.01, Gd0.99 dimethylaminopyridine
tris 2,2,6,6-tetramethylheptanedionato Dy0.01, Gd0.99 4-picoline-N-oxide
tris 2,2,6,6-tetramethylheptanedionato Dy0.01, Gd0.99 4-phenylpyridine
tris 2,2,6,6-tetramethylheptanedionato Dy0.01, Gd0.99 4-cyanopyridine
tris 2,2,6,6-tetramethylheptanedionato Dy0.01, Gd0.99 4-phenylpyridine-N-oxide
tris 2,2,6,6-tetramethylheptanedionato Dy0.01, Gd0.99 1-methylimidazole
tris 2,2,6,6-tetramethylheptanedionato Dy0.01, Gd0.99 triphenylphosphine oxide
tris 2,2,6,6-tetramethylheptanedionato Dy0.01, Gd0.99 2,2-bipyridyl
tris 2,2,6,6-tetramethylheptanedionato Dy0.01, Gd0.99 2,2-bipyridyl-N,N-dioxide
tris 2,2,6,6-tetramethylheptanedionato Dy0.01, Gd0.99 phenanthroline
tris 2,2,6,6-tetramethylheptanedionato Dy0.01, Gd0.99 bathocuproine
tris 2,2,6,6-tetramethylheptanedionato Dy0.01, Gd0.99 bathophenanthroline
tris 3-methylpentane-2,4-dionato Dy0.01, Gd0.99 dimethylaminopyridine
tris 3-methylpentane-2,4-dionato Dy0.01, Gd0.99 4-picoline-N-oxide
tris 3-methylpentane-2,4-dionato Dy0.01, Gd0.99 4-phenylpyridine
tris 3-methylpentane-2,4-dionato Dy0.01, Gd0.99 4-cyanopyridine tris 3-methylpentane-2,4-dionato Dy0.01, Gd0.99 4-phenylpyridine-N-oxide
tris 3-methylpentane-2,4-dionato Dy0.01, Gd0.99 1-methylimidazole
tris 3-methylpentane-2,4-dionato Dy0.01, Gd0.99 triphenylphosphine oxide
tris 3-methylpentane-2,4-dionato Dy0.01, Gd0.99 2,2-bipyridyl
tris 3-methylpentane-2,4-dionato Dy0.01, Gd0.99 2,2-bipyridyl-N,N-dioxide
tris 3-methylpentane-2,4-dionato Dy0.01, Gd0.99 phenanthroline
tris 3-methylpentane-2,4-dionato Dy0.01, Gd0.99 bathocuproine
tris 3-methylpentane-2,4-dionato Dy0.01, Gd0.99 bathophenanthroline
tris 3-ethylpentane-2,4-dionato Dy0.01, Gd0.99 dimethylaminopyridine
tris 3-ethylpentane-2,4-dionato Dy0.01, Gd0.99 4-picoline-N-oxide
tris 3-ethylpentane-2,4-dionato Dy0.01, Gd0.99 4-phenylpyridine
tris 3-ethylpentane-2,4-dionato Dy0.01, Gd0.99 4-cyanopyridine
tris 3-ethylpentane-2,4-dionato Dy0.01, Gd0.99 4-phenylpyridine-N-oxide
tris 3-ethylpentane-2,4-dionato Dy0.01, Gd0.99 1-methylimidazole
tris 3-ethylpentane-2,4-dionato Dy0.01, Gd0.99 triphenylphosphine oxide
tris 3-ethylpentane-2,4-dionato Dy0.01, Gd0.99 2,2-bipyridyl
tris 3-ethylpentane-2,4-dionato Dy0.01, Gd0.99 2,2-bipyridyl-N,N-dioxide
tris 3-ethylpentane-2,4-dionato Dy0.01, Gd0.99 phenanthroline
tris 3-ethylpentane-2,4-dionato Dy0.01, Gd0.99 bathocuproine
tris 3-ethylpentane-2,4-dionato Dy0.01, Gd0.99 bathophenanthroline
tris pivaloyltrifluoroacetonato Dy0.01, Gd0.99 dimethylaminopyridine
tris pivaloyltrifluoroacetonato Dy0.01, Gd0.99 4-picoline-N-oxide
tris pivaloyltrifluoroacetonato Dy0.01, Gd0.99 4-phenylpyridine
tris pivaloyltrifluoroacetonato Dy0.01, Gd0.99 4-cyanopyridine
tris pivaloyltrifluoroacetonato Dy0.01, Gd0.99 4-phenylpyridine-N-oxide
tris pivaloyltrifluoroacetonato Dy0.01, Gd0.99 1-methylimidazole
tris pivaloyltrifluoroacetonato Dy0.01, Gd0.99 triphenylphosphine oxide
tris pivaloyltrifluoroacetonato Dy0.01, Gd0.99 2,2-bipyridyl
tris pivaloyltrifluoroacetonato Dy0.01, Gd0.99 2,2-bipyridyl-N,N-dioxide
tris pivaloyltrifluoroacetonato Dy0.01, Gd0.99 phenanthroline
tris pivaloyltrifluoroacetonato Dy0.01, Gd0.99 bathocuproine
tris pivaloyltrifluoroacetonato Dy0.01, Gd0.99 bathophenanthroline
tris trifluoroacetylacetonato Dy0.01, Gd0.99 dimethylaminopyridine
tris trifluoroacetylacetonato Dy0.01, Gd0.99 4-picoline-N-oxide
tris trifluoroacetylacetonato Dy0.01, Gd0.99 4-phenylpyridine
tris trifluoroacetylacetonato Dy0.01, Gd0.99 4-cyanopyridine
tris trifluoroacetylacetonato Dy0.01, Gd0.99 4-phenylpyridine-N-oxide
tris trifluoroacetylacetonato Dy0.01, Gd0.99 1-methylimidazole
tris trifluoroacetylacetonato Dy0.01, Gd0.99 triphenylphosphine oxide
tris trifluoroacetylacetonato Dy0.01, Gd0.99 2,2-bipyridyl
tris trifluoroacetylacetonato Dy0.01, Gd0.99 2,2-bipyridyl-N,N-dioxide
tris trifluoroacetylacetonato Dy0.01, Gd0.99 phenanthroline
tris trifluoroacetylacetonato Dy0.01, Gd0.99 bathocuproine
tris trifluoroacetylacetonato Dy0.01, Gd0.99 bathophenanthroline
tris hexafluoroacetylacetonato Dy0.01, Gd0.99 dimethylaminopyridine
tris hexafluoroacetylacetonato Dy0.01, Gd0.99 4-picoline-N-oxide
tris hexafluoroacetylacetonato Dy0.01, Gd0.99 4-phenylpyridine
tris hexafluoroacetylacetonato Dy0.01, Gd0.99 4-cyanopyridine
tris hexafluoroacetylacetonato Dy0.01, Gd0.99 4-phenylpyridine-N-oxide
tris hexafluoroacetylacetonato Dy0.01, Gd0.99 1-methylimidazole
tris hexafluoroacetylacetonato Dy0.01, Gd0.99 triphenylphosphine oxide
tris hexafluoroacetylacetonato Dy0.01, Gd0.99 2,2-bipyridyl
tris hexafluoroacetylacetonato Dy0.01, Gd0.99 2,2-bipyridyl-N,N-dioxide
tris hexafluoroacetylacetonato Dy0.01, Gd0.99 phenanthroline
tris hexafluoroacetylacetonato Dy0.01, Gd0.99 bathocuproine
tris hexafluoroacetylacetonato Dy0.01, Gd0.99 bathophenanthroline
tris 6,6,7,7,8,8,8-heptafluoro-2,2-dimethyloctanedionato Dy0.01, Gd0.99 dimethylaminopyridine
tris 6,6,7,7,8,8,8-heptafluoro-2,2-dimethyloctanedionato Dy0.01, Gd0.99 4-picoline-N-oxide
tris 6,6,7,7,8,8,8-heptafluoro-2,2-dimethyloctanedionato Dy0.01, Gd0.99 4-phenylpyridine
tris 6,6,7,7,8,8,8-heptafluoro-2,2-dimethyloctanedionato Dy0.01, Gd0.99 4-cyanopyridine
tris 6,6,7,7,8,8,8-heptafluoro-2,2-dimethyloctanedionato Dy0.01, Gd0.99 4-phenylpyridine-N-oxide
tris 6,6,7,7,8,8,8-heptafluoro-2,2-dimethyloctanedionato Dy0.01, Gd0.99 1-methylimidazole
tris 6,6,7,7,8,8,8-heptafluoro-2,2-dimethyloctanedionato Dy0.01, Gd0.99 triphenylphosphine oxide
tris 6,6,7,7,8,8,8-heptafluoro-2,2-dimethyloctanedionato Dy0.01, Gd0.99 2,2-bipyridyl
tris 6,6,7,7,8,8,8-heptafluoro-2,2-dimethyloctanedionato Dy0.01, Gd0.99 2,2-bipyridyl-N,N-dioxide
tris 6,6,7,7,8,8,8-heptafluoro-2,2-dimethyloctanedionato Dy0.01, Gd0.99 phenanthroline
tris 6,6,7,7,8,8,8-heptafluoro-2,2-dimethyloctanedionato Dy0.01, Gd0.99 bathocuproine
tris 6,6,7,7,8,8,8-heptafluoro-2,2-dimethyloctanedionato Dy0.01, Gd0.99 bathophenanthroline
tris 1-phenyl-1,3-butanedionato Dy0.01, Gd0.99 dimethylaminopyridine tris 1-phenyl-1,3-butanedionato Dy0.01, Gd0.99 4-picoline-N-oxide
tris 1-phenyl-1,3-butanedionato Dy0.01, Gd0.99 4-phenylpyridine
tris 1-phenyl-1,3-butanedionato Dy0.01, Gd0.99 4-cyanopyridine
tris 1-phenyl-1,3-butanedionato Dy0.01, Gd0.99 4-phenylpyridine-N-oxide
tris 1-phenyl-1,3-butanedionato Dy0.01, Gd0.99 1-methylimidazole
tris 1-phenyl-1,3-butanedionato Dy0.01, Gd0.99 triphenylphosphine oxide
tris 1-phenyl-1,3-butanedionato Dy0.01, Gd0.99 2,2-bipyridyl
tris 1-phenyl-1,3-butanedionato Dy0.01, Gd0.99 2,2-bipyridyl-N,N-dioxide
tris 1-phenyl-1,3-butanedionato Dy0.01, Gd0.99 phenanthroline
tris 1-phenyl-1,3-butanedionato Dy0.01, Gd0.99 bathocuproine
tris 1-phenyl-1,3-butanedionato Dy0.01, Gd0.99 bathophenanthroline Lanthanum(III) chloride heptahydrate (3.7 gm), terbium chloride hexahydrate (0.037 gm) and antipyrine (11.3 gm) were dissolved in 100 ml of distilled water. The solution was heated to boiling, and potassium iodide (5 gm) dissolved in the minimum quantity of distilled water was added. The solution was cooled overnight and the resulting light yellow crystals filtered and dried to provide hexakis antipyrine Tb0.01, La0.99 iodide. The product gave strong green photoluminescence when excited with UV light of wavelength 365 nm, and bright green triboluminescence when the crystals were crushed.

In the same way, the following compounds were prepared:
hexakis antipyrine Tb iodide (comparative example); brightness=8
hexakis antipyrine Tb0.5, Y0.5 iodide
hexakis antipyrine Tb0.2, Y0.8 iodide
hexakis antipyrine Tb0.1, Y0.9 iodide; brightness=7
hexakis antipyrine Tb0.01, Y0.99 iodide; brightness=5
hexakis antipyrine Tb0.5, La0.5 iodide
hexakis antipyrine Tb0.2, La0.8 iodide
hexakis antipyrine Tb0.1, La0.9 iodide; brightness=8
hexakis antipyrine Tb0.01, La0.99 iodide; brightness=6
hexakis antipyrine Tb0.5, Gd0.5 iodide
hexakis antipyrine Tb0.2, Gd0.8 iodide
hexakis antipyrine Tb0.1, Gd0.9 iodide; brightness=7
hexakis antipyrine Tb0.01, Gd0.99 iodide; brightness=7
hexakis antipyrine Tb0.5, Lu0.5 iodide
hexakis antipyrine Tb0.2, Lu0.8 iodide
hexakis antipyrine Tb0.1, Lu0.9 iodide; brightness=6
hexakis antipyrine Tb0.01, Lu0.99 iodide; brightness=6

Synthesis 3

Anhydrous europium chloride (0.1 gm), anhydrous gadolinium chloride (0.9 gm) and dibenzoylmethane (3.4 gm) were dissolved in 90 mls anhydrous ethanol. Triethylamine (1.55 gm) was added, and the solution raised briefly to reflux. The solution was cooled first to room temperature overnight, and then to 5° C. in a refrigerator. The crystalline solid which separated was filtered off, washed with cold anhydrous ethanol, and dried to provide triethylammonium tetrakis dibenzoylmethanato Tb0.1, Gd0.9 as a light yellow solid. The product was compared with the corresponding compound containing 100% europium, and on crushing side by side in a semi-darkened room, appeared to show brighter triboluminescent emission than the latter.

The following were prepared in like manner:
triethylammonium tetrakis acetylacetonato Tb (comparative example)
triethylammonium tetrakis dibenzoylmethanato Tb (comparative example)
triethylammonium tetrakis thenoyltrifluoroacetonato Tb (comparative example)
triethylammonium tetrakis 2,2,6,6-tetramethylheptanedionato Tb (comparative example)
triethylammonium tetrakis 3-methylpentane-2,4-dionato Tb (comparative example)
triethylammonium tetrakis 3-ethylpentane-2,4-dionato Tb (comparative example)
triethylammonium tetrakis pivaloyltrifluoroacetonato Tb (comparative example)
triethylammonium tetrakis trifluoroacetylacetonato Tb (comparative example)
triethylammonium tetrakis hexafluoroacetylacetonato Tb (comparative example)
triethylammonium tetrakis 6,6,7,7,8,8,8-heptafluoro-2,2-dimethyloctanedionato Tb (comparative example)
triethylammonium tetrakis 1-phenyl-1,3-butanedionato Tb (comparative example)
morpholinium tetrakis acetylacetonato Tb (comparative example)
morpholinium tetrakis dibenzoylmethanato Tb (comparative example)
morpholinium tetrakis thenoyltrifluoroacetonato Tb (comparative example)
morpholinium tetrakis 2,2,6,6-tetramethylheptanedionato Tb (comparative example)
morpholinium tetrakis 3-methylpentane-2,4-dionato Tb (comparative example)
morpholinium tetrakis 3-ethylpentane-2,4-dionato Tb (comparative example)
morpholinium tetrakis pivaloyltrifluoroacetonato Tb (comparative example)
morpholinium tetrakis trifluoroacetylacetonato Tb (comparative example)
morpholinium tetrakis hexafluoroacetylacetonato Tb (comparative example)
morpholinium tetrakis 6,6,7,7,8,8,8-heptafluoro-2,2-dimethyloctanedionato Tb (comparative example)
morpholinium tetrakis 1-phenyl-1,3-butanedionato Tb (comparative example)
dimethylbenzylammonium tetrakis acetylacetonato Tb (comparative example)
dimethylbenzylammonium tetrakis dibenzoylmethanato Tb (comparative example)
dimethylbenzylammonium tetrakis thenoyltrifluoroacetonato Tb (comparative example)
dimethylbenzylammonium tetrakis 2,2,6,6-tetramethylheptanedionato Tb (comparative example)
dimethylbenzylammonium tetrakis 3-methylpentane-2,4-dionato Tb (comparative example)
dimethylbenzylammonium tetrakis 3-ethylpentane-2,4-dionato Tb (comparative example)
dimethylbenzylammonium tetrakis pivaloyltrifluoroacetonato Tb (comparative example)
dimethylbenzylammonium tetrakis trifluoroacetylacetonato Tb (comparative example)
dimethylbenzylammonium tetrakis hexafluoroacetylacetonato Tb (comparative example)
dimethylbenzylammonium tetrakis 6,6,7,7,8,8,8-heptafluoro-2,2-dimethyloctanedionato Tb (comparative example)

dimethylbenzylammonium tetrakis 1-phenyl-1,3-butanedionato Tb (comparative example)
triallylammonium tetrakis acetylacetonato Tb (comparative example)
triallylammonium tetrakis dibenzoylmethanato Tb (comparative example)
triallylammonium tetrakis thenoyltrifluoroacetonato Tb (comparative example)
triallylammonium tetrakis 2,2,6,6-tetramethylheptanedionato Tb (comparative example)
triallylammonium tetrakis 3-methylpentane-2,4-dionato Tb (comparative example)
triallylammonium tetrakis 3-ethylpentane-2,4-dionato Tb (comparative example)
triallylammonium tetrakis pivaloyltrifluoroacetonato Tb (comparative example)
triallylammonium tetrakis trifluoroacetylacetonato Tb (comparative example)
triallylammonium tetrakis hexafluoroacetylacetonato Tb (comparative example)
triallylammonium tetrakis 6,6,7,7,8,8,8-heptafluoro-2,2-dimethyloctanedionato Tb (comparative example)
triallylammonium tetrakis 1-phenyl-1,3-butanedionato Tb (comparative example)
anilinium tetrakis acetylacetonato Tb (comparative example)
anilinium tetrakis dibenzoylmethanato Tb (comparative example)
anilinium tetrakis thenoyltrifluoroacetonato Tb (comparative example)
anilinium tetrakis 2,2,6,6-tetramethylheptanedionato Tb (comparative example)
anilinium tetrakis 3-methylpentane-2,4-dionato Tb (comparative example)
anilinium tetrakis 3-ethylpentane-2,4-dionato Tb (comparative example)
anilinium tetrakis pivaloyltrifluoroacetonato Tb (comparative example)
anilinium tetrakis trifluoroacetylacetonato Tb (comparative example)
anilinium tetrakis hexafluoroacetylacetonato Tb (comparative example)
anilinium tetrakis 6,6,7,7,8,8,8-heptafluoro-2,2-dimethyloctanedionato Tb (comparative example)
anilinium tetrakis 1-phenyl-1,3-butanedionato Tb (comparative example)
triethylammonium tetrakis acetylacetonato Eu (comparative example)
triethylammonium tetrakis dibenzoylmethanato Eu (comparative example); brightness=9
triethylammonium tetrakis thenoyltrifluoroacetonato Eu (comparative example)
triethylammonium tetrakis 2,2,6,6-tetramethylheptanedionato Eu (comparative example)
triethylammonium tetrakis 3-methylpentane-2,4-dionato Eu (comparative example)
triethylammonium tetrakis 3-ethylpentane-2,4-dionato Eu (comparative example)
triethylammonium tetrakis pivaloyltrifluoroacetonato Eu (comparative example)
triethylammonium tetrakis trifluoroacetylacetonato Eu (comparative example)
triethylammonium tetrakis hexafluoroacetylacetonato Eu (comparative example)
triethylammonium tetrakis 6,6,7,7,8,8,8-heptafluoro-2,2-dimethyloctanedionato Eu (comparative example)
triethylammonium tetrakis 1-phenyl-1,3-butanedionato Eu (comparative example)
morpholinium tetrakis acetylacetonato Eu (comparative example)
morpholinium tetrakis dibenzoylmethanato Eu (comparative example); brightness=9
morpholinium tetrakis thenoyltrifluoroacetonato Eu (comparative example)
morpholinium tetrakis 2,2,6,6-tetramethylheptanedionato Eu (comparative example)
morpholinium tetrakis 3-methylpentane-2,4-dionato Eu (comparative example)
morpholinium tetrakis 3-ethylpentane-2,4-dionato Eu (comparative example)
morpholinium tetrakis pivaloyltrifluoroacetonato Eu (comparative example)
morpholinium tetrakis trifluoroacetylacetonato Eu (comparative example)
morpholinium tetrakis hexafluoroacetylacetonato Eu (comparative example)
morpholinium tetrakis 6,6,7,7,8,8,8-heptafluoro-2,2-dimethyloctanedionato Eu (comparative example)
morpholinium tetrakis 1-phenyl-1,3-butanedionato Eu (comparative example)
dimethylbenzylammonium tetrakis acetylacetonato Eu (comparative example)
dimethylbenzylammonium tetrakis dibenzoylmethanato Eu (comparative example)
dimethylbenzylammonium tetrakis thenoyltrifluoroacetonato Eu (comparative example)
dimethylbenzylammonium tetrakis 2,2,6,6-tetramethylheptanedionato Eu (comparative example)
dimethylbenzylammonium tetrakis 3-methylpentane-2,4-dionato Eu (comparative example)
dimethylbenzylammonium tetrakis 3-ethylpentane-2,4-dionato Eu (comparative example)
dimethylbenzylammonium tetrakis pivaloyltrifluoroacetonato Eu (comparative example)
dimethylbenzylammonium tetrakis trifluoroacetylacetonato Eu (comparative example)
dimethylbenzylammonium tetrakis hexafluoroacetylacetonato Eu (comparative example)
dimethylbenzylammonium tetrakis 6,6,7,7,8,8,8-heptafluoro-2,2-dimethyloctanedionato Eu (comparative example)
dimethylbenzylammonium tetrakis 1-phenyl-1,3-butanedionato Eu (comparative example)
triallylammonium tetrakis acetylacetonato Eu (comparative example)
triallylammonium tetrakis dibenzoylmethanato Eu (comparative example)
triallylammonium tetrakis thenoyltrifluoroacetonato Eu (comparative example)
triallylammonium tetrakis 2,2,6,6-tetramethylheptanedionato Eu (comparative example)
triallylammonium tetrakis 3-methylpentane-2,4-dionato Eu (comparative example)
triallylammonium tetrakis 3-ethylpentane-2,4-dionato Eu (comparative example)
triallylammonium tetrakis pivaloyltrifluoroacetonato Eu (comparative example)
triallylammonium tetrakis trifluoroacetylacetonato Eu (comparative example)
triallylammonium tetrakis hexafluoroacetylacetonato Eu (comparative example)
triallylammonium tetrakis 6,6,7,7,8,8,8-heptafluoro-2,2-dimethyloctanedionato Eu (comparative example)

triallylammonium tetrakis 1-phenyl-1,3-butanedionato Eu (comparative example)
anilinium tetrakis acetylacetonato Eu (comparative example)
anilinium tetrakis dibenzoylmethanato Eu (comparative example)
anilinium tetrakis thenoyltrifluoroacetonato Eu (comparative example)
anilinium tetrakis 2,2,6,6-tetramethylheptanedionato Eu (comparative example)
anilinium tetrakis 3-methylpentane-2,4-dionato Eu (comparative example)
anilinium tetrakis 3-ethylpentane-2,4-dionato Eu (comparative example)
anilinium tetrakis pivaloyltrifluoroacetonato Eu (comparative example)
anilinium tetrakis trifluoroacetylacetonato Eu (comparative example)
anilinium tetrakis hexafluoroacetylacetonato Eu (comparative example)
anilinium tetrakis 6,6,7,7,8,8,8-heptafluoro-2,2-dimethyloctanedionato Eu (comparative example)
anilinium tetrakis 1-phenyl-1,3-butanedionato Eu (comparative example)
triethylammonium tetrakis acetylacetonato Sm (comparative example)
triethylammonium tetrakis dibenzoylmethanato Sm (comparative example)
triethylammonium tetrakis thenoyltrifluoroacetonato Sm (comparative example)
triethylammonium tetrakis 2,2,6,6-tetramethylheptanedionato Sm (comparative example)
triethylammonium tetrakis 3-methylpentane-2,4-dionato Sm (comparative example)
triethylammonium tetrakis 3-ethylpentane-2,4-dionato Sm (comparative example)
triethylammonium tetrakis pivaloyltrifluoroacetonato Sm (comparative example)
triethylammonium tetrakis trifluoroacetylacetonato Sm (comparative example)
triethylammonium tetrakis hexafluoroacetylacetonato Sm (comparative example)
triethylammonium tetrakis 6,6,7,7,8,8,8-heptafluoro-2,2-dimethyloctanedionato Sm (comparative example)
triethylammonium tetrakis 1-phenyl-1,3-butanedionato Sm (comparative example)
morpholinium tetrakis acetylacetonato Sm (comparative example)
morpholinium tetrakis dibenzoylmethanato Sm (comparative example)
morpholinium tetrakis thenoyltrifluoroacetonato Sm (comparative example)
morpholinium tetrakis 2,2,6,6-tetramethylheptanedionato Sm (comparative example)
morpholinium tetrakis 3-methylpentane-2,4-dionato Sm (comparative example)
morpholinium tetrakis 3-ethylpentane-2,4-dionato Sm (comparative example)
morpholinium tetrakis pivaloyltrifluoroacetonato Sm (comparative example)
morpholinium tetrakis trifluoroacetylacetonato Sm (comparative example)
morpholinium tetrakis hexafluoroacetylacetonato Sm (comparative example)
morpholinium tetrakis 6,6,7,7,8,8,8-heptafluoro-2,2-dimethyloctanedionato Sm (comparative example)
morpholinium tetrakis 1-phenyl-1,3-butanedionato Sm (comparative example)
dimethylbenzylammonium tetrakis acetylacetonato Sm (comparative example)
dimethylbenzylammonium tetrakis dibenzoylmethanato Sm (comparative example)
dimethylbenzylammonium tetrakis thenoyltrifluoroacetonato Sm (comparative example)
dimethylbenzylammonium tetrakis 2,2,6,6-tetramethylheptanedionato Sm (comparative example)
dimethylbenzylammonium tetrakis 3-methylpentane-2,4-dionato Sm (comparative example)
dimethylbenzylammonium tetrakis 3-ethylpentane-2,4-dionato Sm (comparative example)
dimethylbenzylammonium tetrakis pivaloyltrifluoroacetonato Sm (comparative example)
dimethylbenzylammonium tetrakis trifluoroacetylacetonato Sm (comparative example)
dimethylbenzylammonium tetrakis hexafluoroacetylacetonato Sm (comparative example)
dimethylbenzylammonium tetrakis 6,6,7,7,8,8,8-heptafluoro-2,2-dimethyloctanedionato Sm (comparative example)
dimethylbenzylammonium tetrakis 1-phenyl-1,3-butanedionato Sm (comparative example)
triallylammonium tetrakis acetylacetonato Sm (comparative example)
triallylammonium tetrakis dibenzoylmethanato Sm (comparative example)
triallylammonium tetrakis thenoyltrifluoroacetonato Sm (comparative example)
triallylammonium tetrakis 2,2,6,6-tetramethylheptanedionato Sm (comparative example)
triallylammonium tetrakis 3-methylpentane-2,4-dionato Sm (comparative example)
triallylammonium tetrakis 3-ethylpentane-2,4-dionato Sm (comparative example)
triallylammonium tetrakis pivaloyltrifluoroacetonato Sm (comparative example)
triallylammonium tetrakis trifluoroacetylacetonato Sm (comparative example)
triallylammonium tetrakis hexafluoroacetylacetonato Sm (comparative example)
triallylammonium tetrakis 6,6,7,7,8,8,8-heptafluoro-2,2-dimethyloctanedionato Sm (comparative example)
triallylammonium tetrakis 1-phenyl-1,3-butanedionato Sm (comparative example)
anilinium tetrakis acetylacetonato Sm (comparative example)
anilinium tetrakis dibenzoylmethanato Sm (comparative example)
anilinium tetrakis thenoyltrifluoroacetonato Sm (comparative example)
anilinium tetrakis 2,2,6,6-tetramethylheptanedionato Sm (comparative example)
anilinium tetrakis 3-methylpentane-2,4-dionato Sm (comparative example)
anilinium tetrakis 3-ethylpentane-2,4-dionato Sm (comparative example)
anilinium tetrakis pivaloyltrifluoroacetonato Sm (comparative example)
anilinium tetrakis trifluoroacetylacetonato Sm (comparative example)
anilinium tetrakis hexafluoroacetylacetonato Sm (comparative example)
anilinium tetrakis 6,6,7,7,8,8,8-heptafluoro-2,2-dimethyloctanedionato Sm (comparative example)

anilinium tetrakis 1-phenyl-1,3-butanedionato Sm (comparative example)
triethylammonium tetrakis acetylacetonato Dy (comparative example)
triethylammonium tetrakis dibenzoylmethanato Dy (comparative example)
triethylammonium tetrakis thenoyltrifluoroacetonato Dy (comparative example)
triethylammonium tetrakis 2,2,6,6-tetramethylheptanedionato Dy (comparative example)
triethylammonium tetrakis 3-methylpentane-2,4-dionato Dy (comparative example)
triethylammonium tetrakis 3-ethylpentane-2,4-dionato Dy (comparative example)
triethylammonium tetrakis pivaloyltrifluoroacetonato Dy (comparative example)
triethylammonium tetrakis trifluoroacetylacetonato Dy (comparative example)
triethylammonium tetrakis hexafluoroacetylacetonato Dy (comparative example)
triethylammonium tetrakis 6,6,7,7,8,8,8-heptafluoro-2,2-dimethyloctanedionato Dy (comparative example)
triethylammonium tetrakis 1-phenyl-1,3-butanedionato Dy (comparative example)
morpholinium tetrakis acetylacetonato Dy (comparative example)
morpholinium tetrakis dibenzoylmethanato Dy (comparative example)
morpholinium tetrakis thenoyltrifluoroacetonato Dy (comparative example)
morpholinium tetrakis 2,2,6,6-tetramethylheptanedionato Dy (comparative example)
morpholinium tetrakis 3-methylpentane-2,4-dionato Dy (comparative example)
morpholinium tetrakis 3-ethylpentane-2,4-dionato Dy (comparative example)
morpholinium tetrakis pivaloyltrifluoroacetonato Dy (comparative example)
morpholinium tetrakis trifluoroacetylacetonato Dy (comparative example)
morpholinium tetrakis hexafluoroacetylacetonato Dy (comparative example)
morpholinium tetrakis 6,6,7,7,8,8,8-heptafluoro-2,2-dimethyloctanedionato Dy (comparative example)
morpholinium tetrakis 1-phenyl-1,3-butanedionato Dy (comparative example)
dimethylbenzylammonium tetrakis acetylacetonato Dy (comparative example)
dimethylbenzylammonium tetrakis dibenzoylmethanato Dy (comparative example)
dimethylbenzylammonium tetrakis thenoyltrifluoroacetonato Dy (comparative example)
dimethylbenzylammonium tetrakis 2,2,6,6-tetramethylheptanedionato Dy (comparative example)
dimethylbenzylammonium tetrakis 3-methylpentane-2,4-dionato Dy (comparative example)
dimethylbenzylammonium tetrakis 3-ethylpentane-2,4-dionato Dy (comparative example)
dimethylbenzylammonium tetrakis pivaloyltrifluoroacetonato Dy (comparative example)
dimethylbenzylammonium tetrakis trifluoroacetylacetonato Dy (comparative example)
dimethylbenzylammonium tetrakis hexafluoroacetylacetonato Dy (comparative example)
dimethylbenzylammonium tetrakis 6,6,7,7,8,8,8-heptafluoro-2,2-dimethyloctanedionato Dy (comparative example)
dimethylbenzylammonium tetrakis 1-phenyl-1,3-butanedionato Dy (comparative example)
triallylammonium tetrakis acetylacetonato Dy (comparative example)
triallylammonium tetrakis dibenzoylmethanato Dy (comparative example)
triallylammonium tetrakis thenoyltrifluoroacetonato Dy (comparative example)
triallylammonium tetrakis 2,2,6,6-tetramethylheptanedionato Dy (comparative example)
triallylammonium tetrakis 3-methylpentane-2,4-dionato Dy (comparative example)
triallylammonium tetrakis 3-ethylpentane-2,4-dionato Dy (comparative example)
triallylammonium tetrakis pivaloyltrifluoroacetonato Dy (comparative example)
triallylammonium tetrakis trifluoroacetylacetonato Dy (comparative example)
triallylammonium tetrakis hexafluoroacetylacetonato Dy (comparative example)
triallylammonium tetrakis 6,6,7,7,8,8,8-heptafluoro-2,2-dimethyloctanedionato Dy (comparative example)
triallylammonium tetrakis 1-phenyl-1,3-butanedionato Dy (comparative example)
anilinium tetrakis acetylacetonato Dy (comparative example)
anilinium tetrakis dibenzoylmethanato Dy (comparative example)
anilinium tetrakis thenoyltrifluoroacetonato Dy (comparative example)
anilinium tetrakis 2,2,6,6-tetramethylheptanedionato Dy (comparative example)
anilinium tetrakis 3-methylpentane-2,4-dionato Dy (comparative example)
anilinium tetrakis 3-ethylpentane-2,4-dionato Dy (comparative example)
anilinium tetrakis pivaloyltrifluoroacetonato Dy (comparative example)
anilinium tetrakis trifluoroacetylacetonato Dy (comparative example)
anilinium tetrakis hexafluoroacetylacetonato Dy (comparative example)
anilinium tetrakis 6,6,7,7,8,8,8-heptafluoro-2,2-dimethyloctanedionato Dy (comparative example)
anilinium tetrakis 1-phenyl-1,3-butanedionato Dy (comparative example)
triethylammonium tetrakis acetylacetonato Tb0.5, Y0.5
triethylammonium tetrakis dibenzoylmethanato Tb0.5, Y0.5
triethylammonium tetrakis thenoyltrifluoroacetonato Tb0.5, Y0.5
triethylammonium tetrakis 2,2,6,6-tetramethylheptanedionato Tb0.5, Y0.5
triethylammonium tetrakis 3-methylpentane-2,4-dionato Tb0.5, Y0.5
triethylammonium tetrakis 3-ethylpentane-2,4-dionato Tb0.5, Y0.5
triethylammonium tetrakis pivaloyltrifluoroacetonato Tb0.5, Y0.5
triethylammonium tetrakis trifluoroacetylacetonato Tb0.5, Y0.5
triethylammonium tetrakis hexafluoroacetylacetonato Tb0.5, Y0.5
triethylammonium tetrakis 6,6,7,7,8,8,8-heptafluoro-2,2-dimethyloctanedionato Tb0.5, Y0.5
triethylammonium tetrakis 1-phenyl-1,3-butanedionato Tb0.5, Y0.5
morpholinium tetrakis acetylacetonato Tb0.5, Y0.5 morpholinium tetrakis dibenzoylmethanato Tb0.5, Y0.5
morpholinium tetrakis thenoyltrifluoroacetonato Tb0.5, Y0.5
morpholinium tetrakis 2,2,6,6-tetramethylheptanedionato Tb0.5, Y0.5
morpholinium tetrakis 3-methylpentane-2,4-dionato Tb0.5, Y0.5
morpholinium tetrakis 3-ethylpentane-2,4-dionato Tb0.5, Y0.5
morpholinium tetrakis pivaloyltrifluoroacetonato Tb0.5, Y0.5
morpholinium tetrakis trifluoroacetylacetonato Tb0.5, Y0.5
morpholinium tetrakis hexafluoroacetylacetonato Tb0.5, Y0.5
morpholinium tetrakis 6,6,7,7,8,8,8-heptafluoro-2,2-dimethyloctanedionato Tb0.5, Y0.5
morpholinium tetrakis 1-phenyl-1,3-butanedionato Tb0.5, Y0.5
dimethylbenzylammonium tetrakis acetylacetonato Tb0.5, Y0.5
dimethylbenzylammonium tetrakis dibenzoylmethanato Tb0.5, Y0.5
dimethylbenzylammonium tetrakis thenoyltrifluoroacetonato Tb0.5, Y0.5
dimethylbenzylammonium tetrakis 2,2,6,6-tetramethylheptanedionato Tb0.5, Y0.5
dimethylbenzylammonium tetrakis 3-methylpentane-2,4-dionato Tb0.5, Y0.5
dimethylbenzylammonium tetrakis 3-ethylpentane-2,4-dionato Tb0.5, Y0.5
dimethylbenzylammonium tetrakis pivaloyltrifluoroacetonato Tb0.5, Y0.5
dimethylbenzylammonium tetrakis trifluoroacetylacetonato Tb0.5, Y0.5
dimethylbenzylammonium tetrakis hexafluoroacetylacetonato Tb0.5, Y0.5
dimethylbenzylammonium tetrakis 6,6,7,7,8,8,8-heptafluoro-2,2-dimethyloctanedionato Tb0.5, Y0.5
dimethylbenzylammonium tetrakis 1-phenyl-1,3-butanedionato Tb0.5, Y0.5
triallylammonium tetrakis acetylacetonato Tb0.5, Y0.5
triallylammonium tetrakis dibenzoylmethanato Tb0.5, Y0.5
triallylammonium tetrakis thenoyltrifluoroacetonato Tb0.5, Y0.5
triallylammonium tetrakis 2,2,6,6-tetramethylheptanedionato Tb0.5, Y0.5
triallylammonium tetrakis 3-methylpentane-2,4-dionato Tb0.5, Y0.5
triallylammonium tetrakis 3-ethylpentane-2,4-dionato Tb0.5, Y0.5
triallylammonium tetrakis pivaloyltrifluoroacetonato Tb0.5, Y0.5
triallylammonium tetrakis trifluoroacetylacetonato Tb0.5, Y0.5
triallylammonium tetrakis hexafluoroacetylacetonato Tb0.5, Y0.5
triallylammonium tetrakis 6,6,7,7,8,8,8-heptafluoro-2,2-dimethyloctanedionato Tb0.5, Y0.5
triallylammonium tetrakis 1-phenyl-1,3-butanedionato Tb0.5, Y0.5
anilinium tetrakis acetylacetonato Tb0.5, Y0.5
anilinium tetrakis dibenzoylmethanato Tb0.5, Y0.5
anilinium tetrakis thenoyltrifluoroacetonato Tb0.5, Y0.5
anilinium tetrakis 2,2,6,6-tetramethylheptanedionato Tb0.5, Y0.5
anilinium tetrakis 3-methylpentane-2,4-dionato Tb0.5, Y0.5
anilinium tetrakis 3-ethylpentane-2,4-dionato Tb0.5, Y0.5
anilinium tetrakis pivaloyltrifluoroacetonato Tb0.5, Y0.5
anilinium tetrakis trifluoroacetylacetonato Tb0.5, Y0.5
anilinium tetrakis hexafluoroacetylacetonato Tb0.5, Y0.5
anilinium tetrakis 6,6,7,7,8,8,8-heptafluoro-2,2-dimethyloctanedionato Tb0.5, Y0.5
anilinium tetrakis 1-phenyl-1,3-butanedionato Tb0.5, Y0.5
triethylammonium tetrakis acetylacetonato Tb0.2, Y0.8
triethylammonium tetrakis dibenzoylmethanato Tb0.2, Y0.8
triethylammonium tetrakis thenoyltrifluoroacetonato Tb0.2, Y0.8
triethylammonium tetrakis 2,2,6,6-tetramethylheptanedionato Tb0.2, Y0.8
triethylammonium tetrakis 3-methylpentane-2,4-dionato Tb0.2, Y0.8
triethylammonium tetrakis 3-ethylpentane-2,4-dionato Tb0.2, Y0.8
triethylammonium tetrakis pivaloyltrifluoroacetonato Tb0.2, Y0.8
triethylammonium tetrakis trifluoroacetylacetonato Tb0.2, Y0.8
triethylammonium tetrakis hexafluoroacetylacetonato Tb0.2, Y0.8
triethylammonium tetrakis 6,6,7,7,8,8,8-heptafluoro-2,2-dimethyloctanedionato Tb0.2, Y0.8
triethylammonium tetrakis 1-phenyl-1,3-butanedionato Tb0.2, Y0.8
morpholinium tetrakis acetylacetonato Tb0.2, Y0.8
morpholinium tetrakis dibenzoylmethanato Tb0.2, Y0.8
morpholinium tetrakis thenoyltrifluoroacetonato Tb0.2, Y0.8
morpholinium tetrakis 2,2,6,6-tetramethylheptanedionato Tb0.2, Y0.8
morpholinium tetrakis 3-methylpentane-2,4-dionato Tb0.2, Y0.8
morpholinium tetrakis 3-ethylpentane-2,4-dionato Tb0.2, Y0.8
morpholinium tetrakis pivaloyltrifluoroacetonato Tb0.2, Y0.8
morpholinium tetrakis trifluoroacetylacetonato Tb0.2, Y0.8
morpholinium tetrakis hexafluoroacetylacetonato Tb0.2, Y0.8
morpholinium tetrakis 6,6,7,7,8,8,8-heptafluoro-2,2-dimethyloctanedionato Tb0.2, Y0.8
morpholinium tetrakis 1-phenyl-1,3-butanedionato Tb0.2, Y0.8
dimethylbenzylammonium tetrakis acetylacetonato Tb0.2, Y0.8
dimethylbenzylammonium tetrakis dibenzoylmethanato Tb0.2, Y0.8
dimethylbenzylammonium tetrakis thenoyltrifluoroacetonato Tb0.2, Y0.8
dimethylbenzylammonium tetrakis 2,2,6,6-tetramethylheptanedionato Tb0.2, Y0.8
dimethylbenzylammonium tetrakis 3-methylpentane-2,4-dionato Tb0.2, Y0.8
dimethylbenzylammonium tetrakis 3-ethylpentane-2,4-dionato Tb0.2, Y0.8
dimethylbenzylammonium tetrakis pivaloyltrifluoroacetonato Tb0.2, Y0.8
dimethylbenzylammonium tetrakis trifluoroacetylacetonato Tb0.2, Y0.8
dimethylbenzylammonium tetrakis hexafluoroacetylacetonato Tb0.2, Y0.8
dimethylbenzylammonium tetrakis 6,6,7,7,8,8,8-heptafluoro-2,2-dimethyloctanedionato Tb0.2, Y0.8
dimethylbenzylammonium tetrakis 1-phenyl-1,3-butanedionato Tb0.2, Y0.8 triallylammonium tetrakis acetylacetonato Tb0.2, Y0.8
triallylammonium tetrakis dibenzoylmethanato Tb0.2, Y0.8
triallylammonium tetrakis thenoyltrifluoroacetonato Tb0.2, Y0.8
triallylammonium tetrakis 2,2,6,6-tetramethylheptanedionato Tb0.2, Y0.8
triallylammonium tetrakis 3-methylpentane-2,4-dionato Tb0.2, Y0.8
triallylammonium tetrakis 3-ethylpentane-2,4-dionato Tb0.2, Y0.8
triallylammonium tetrakis pivaloyltrifluoroacetonato Tb0.2, Y0.8
triallylammonium tetrakis trifluoroacetylacetonato Tb0.2, Y0.8
triallylammonium tetrakis hexafluoroacetylacetonato Tb0.2, Y0.8
triallylammonium tetrakis 6,6,7,7,8,8-heptafluoro-2,2-dimethyloctanedionato Tb0.2, Y0.8
triallylammonium tetrakis 1-phenyl-1,3-butanedionato Tb0.2, Y0.8
anilinium tetrakis acetylacetonato Tb0.2, Y0.8
anilinium tetrakis dibenzoylmethanato Tb0.2, Y0.8
anilinium tetrakis thenoyltrifluoroacetonato Tb0.2, Y0.8
anilinium tetrakis 2,2,6,6-tetramethylheptanedionato Tb0.2, Y0.8
anilinium tetrakis 3-methylpentane-2,4-dionato Tb0.2, Y0.8
anilinium tetrakis 3-ethylpentane-2,4-dionato Tb0.2, Y0.8
anilinium tetrakis pivaloyltrifluoroacetonato Tb0.2, Y0.8
anilinium tetrakis trifluoroacetylacetonato Tb0.2, Y0.8
anilinium tetrakis hexafluoroacetylacetonato Tb0.2, Y0.8
anilinium tetrakis 6,6,7,7,8,8-heptafluoro-2,2-dimethyloctanedionato Tb0.2, Y0.8
anilinium tetrakis 1-phenyl-1,3-butanedionato Tb0.2, Y0.8
triethylammonium tetrakis acetylacetonato Tb0.1, Y0.9
triethylammonium tetrakis dibenzoylmethanato Tb0.1, Y0.9
triethylammonium tetrakis thenoyltrifluoroacetonato Tb0.1, Y0.9
triethylammonium tetrakis 2,2,6,6-tetramethylheptanedionato Tb0.1, Y0.9
triethylammonium tetrakis 3-methylpentane-2,4-dionato Tb0.1, Y0.9
triethylammonium tetrakis 3-ethylpentane-2,4-dionato Tb0.1, Y0.9
triethylammonium tetrakis pivaloyltrifluoroacetonato Tb0.1, Y0.9
triethylammonium tetrakis trifluoroacetylacetonato Tb0.1, Y0.9
triethylammonium tetrakis hexafluoroacetylacetonato Tb0.1, Y0.9
triethylammonium tetrakis 6,6,7,7,8,8-heptafluoro-2,2-dimethyloctanedionato Tb0.1, Y0.9
triethylammonium tetrakis 1-phenyl-1,3-butanedionato Tb0.1, Y0.9
morpholinium tetrakis acetylacetonato Tb0.1, Y0.9
morpholinium tetrakis dibenzoylmethanato Tb0.1, Y0.9
morpholinium tetrakis thenoyltrifluoroacetonato Tb0.1, Y0.9
morpholinium tetrakis 2,2,6,6-tetramethylheptanedionato Tb0.1, Y0.9
morpholinium tetrakis 3-methylpentane-2,4-dionato Tb0.1, Y0.9
morpholinium tetrakis 3-ethylpentane-2,4-dionato Tb0.1, Y0.9
morpholinium tetrakis pivaloyltrifluoroacetonato Tb0.1, Y0.9
morpholinium tetrakis trifluoroacetylacetonato Tb0.1, Y0.9
morpholinium tetrakis hexafluoroacetylacetonato Tb0.1, Y0.9
morpholinium tetrakis 6,6,7,7,8,8-heptafluoro-2,2-dimethyloctanedionato Tb0.1, Y0.9
morpholinium tetrakis 1-phenyl-1,3-butanedionato Tb0.1, Y0.9
dimethylbenzylammonium tetrakis acetylacetonato Tb0.1, Y0.9
dimethylbenzylammonium tetrakis dibenzoylmethanato Tb0.1, Y0.9
dimethylbenzylammonium tetrakis thenoyltrifluoroacetonato Tb0.1, Y0.9
dimethylbenzylammonium tetrakis 2,2,6,6-tetramethylheptanedionato Tb0.1, Y0.9
dimethylbenzylammonium tetrakis 3-methylpentane-2,4-dionato Tb0.1, Y0.9
dimethylbenzylammonium tetrakis 3-ethylpentane-2,4-dionato Tb0.1, Y0.9
dimethylbenzylammonium tetrakis pivaloyltrifluoroacetonato Tb0.1, Y0.9
dimethylbenzylammonium tetrakis trifluoroacetylacetonato Tb0.1, Y0.9
dimethylbenzylammonium tetrakis hexafluoroacetylacetonato Tb0.1, Y0.9
dimethylbenzylammonium tetrakis 6,6,7,7,8,8-heptafluoro-2,2-dimethyloctanedionato Tb0.1, Y0.9
dimethylbenzylammonium tetrakis 1-phenyl-1,3-butanedionato Tb0.1, Y0.9
triallylammonium tetrakis acetylacetonato Tb0.1, Y0.9
triallylammonium tetrakis dibenzoylmethanato Tb0.1, Y0.9
triallylammonium tetrakis thenoyltrifluoroacetonato Tb0.1, Y0.9
triallylammonium tetrakis 2,2,6,6-tetramethylheptanedionato Tb0.1, Y0.9
triallylammonium tetrakis 3-methylpentane-2,4-dionato Tb0.1, Y0.9
triallylammonium tetrakis 3-ethylpentane-2,4-dionato Tb0.1, Y0.9
triallylammonium tetrakis pivaloyltrifluoroacetonato Tb0.1, Y0.9
triallylammonium tetrakis trifluoroacetylacetonato Tb0.1, Y0.9
triallylammonium tetrakis hexafluoroacetylacetonato Tb0.1, Y0.9
triallylammonium tetrakis 6,6,7,7,8,8-heptafluoro-2,2-dimethyloctanedionato Tb0.1, Y0.9
triallylammonium tetrakis 1-phenyl-1,3-butanedionato Tb0.1, Y0.9
anilinium tetrakis acetylacetonato Tb0.1, Y0.9
anilinium tetrakis dibenzoylmethanato Tb0.1, Y0.9
anilinium tetrakis thenoyltrifluoroacetonato Tb0.1, Y0.9
anilinium tetrakis 2,2,6,6-tetramethylheptanedionato Tb0.1, Y0.9
anilinium tetrakis 3-methylpentane-2,4-dionato Tb0.1, Y0.9
anilinium tetrakis 3-ethylpentane-2,4-dionato Tb0.1, Y0.9
anilinium tetrakis pivaloyltrifluoroacetonato Tb0.1, Y0.9
anilinium tetrakis trifluoroacetylacetonato Tb0.1, Y0.9
anilinium tetrakis hexafluoroacetylacetonato Tb0.1, Y0.9
anilinium tetrakis 6,6,7,7,8,8-heptafluoro-2,2-dimethyloctanedionato Tb0.1, Y0.9
anilinium tetrakis 1-phenyl-1,3-butanedionato Tb0.1, Y0.9
triethylammonium tetrakis acetylacetonato Tb0.01, Y0.99
triethylammonium tetrakis dibenzoylmethanato Tb0.01, Y0.99
triethylammonium tetrakis thenoyltrifluoroacetonato Tb0.01, Y0.99 triethylammonium tetrakis 2,2,6,6-tetramethylheptanedionato Tb0.01, Y0.99
triethylammonium tetrakis 3-methylpentane-2,4-dionato Tb0.01, Y0.99
triethylammonium tetrakis 3-ethylpentane-2,4-dionato Tb0.01, Y0.99
triethylammonium tetrakis pivaloyltrifluoroacetonato Tb0.01, Y0.99
triethylammonium tetrakis trifluoroacetylacetonato Tb0.01, Y0.99
triethylammonium tetrakis hexafluoroacetylacetonato Tb0.01, Y0.99
triethylammonium tetrakis 6,6,7,7,8,8,8-heptafluoro-2,2-dimethyloctanedionato Tb0.01, Y0.99
triethylammonium tetrakis 1-phenyl-1,3-butanedionato Tb0.01, Y0.99
morpholinium tetrakis acetylacetonato Tb0.01, Y0.99
morpholinium tetrakis dibenzoylmethanato Tb0.01, Y0.99
morpholinium tetrakis thenoyltrifluoroacetonato Tb0.01, Y0.99
morpholinium tetrakis 2,2,6,6-tetramethylheptanedionato Tb0.01, Y0.99
morpholinium tetrakis 3-methylpentane-2,4-dionato Tb0.01, Y0.99
morpholinium tetrakis 3-ethylpentane-2,4-dionato Tb0.01, Y0.99
morpholinium tetrakis pivaloyltrifluoroacetonato Tb0.01, Y0.99
morpholinium tetrakis trifluoroacetylacetonato Tb0.01, Y0.99
morpholinium tetrakis hexafluoroacetylacetonato Tb0.01, Y0.99
morpholinium tetrakis 6,6,7,7,8,8,8-heptafluoro-2,2-dimethyloctanedionato Tb0.01, Y0.99
morpholinium tetrakis 1-phenyl-1,3-butanedionato Tb0.01, Y0.99
dimethylbenzylammonium tetrakis acetylacetonato Tb0.01, Y0.99
dimethylbenzylammonium tetrakis dibenzoylmethanato Tb0.01, Y0.99
dimethylbenzylammonium tetrakis thenoyltrifluoroacetonato Tb0.01, Y0.99
dimethylbenzylammonium tetrakis 2,2,6,6-tetramethylheptanedionato Tb0.01, Y0.99
dimethylbenzylammonium tetrakis 3-methylpentane-2,4-dionato Tb0.01, Y0.99
dimethylbenzylammonium tetrakis 3-ethylpentane-2,4-dionato Tb0.01, Y0.99
dimethylbenzylammonium tetrakis pivaloyltrifluoroacetonato Tb0.01, Y0.99
dimethylbenzylammonium tetrakis trifluoroacetylacetonato Tb0.01, Y0.99
dimethylbenzylammonium tetrakis hexafluoroacetylacetonato Tb0.01, Y0.99
dimethylbenzylammonium tetrakis 6,6,7,7,8,8,8-heptafluoro-2,2-dimethyloctanedionato Tb0.01, Y0.99
dimethylbenzylammonium tetrakis 1-phenyl-1,3-butanedionato Tb0.01, Y0.99
triallylammonium tetrakis acetylacetonato Tb0.01, Y0.99
triallylammonium tetrakis dibenzoylmethanato Tb0.01, Y0.99
triallylammonium tetrakis thenoyltrifluoroacetonato Tb0.01, Y0.99
triallylammonium tetrakis 2,2,6,6-tetramethylheptanedionato Tb0.01, Y0.99
triallylammonium tetrakis 3-methylpentane-2,4-dionato Tb0.01, Y0.99
triallylammonium tetrakis 3-ethylpentane-2,4-dionato Tb0.01, Y0.99
triallylammonium tetrakis pivaloyltrifluoroacetonato Tb0.01, Y0.99
triallylammonium tetrakis trifluoroacetylacetonato Tb0.01, Y0.99
triallylammonium tetrakis hexafluoroacetylacetonato Tb0.01, Y0.99
triallylammonium tetrakis 6,6,7,7,8,8,8-heptafluoro-2,2-dimethyloctanedionato Tb0.01, Y0.99
triallylammonium tetrakis 1-phenyl-1,3-butanedionato Tb0.01, Y0.99
anilinium tetrakis acetylacetonato Tb0.01, Y0.99
anilinium tetrakis dibenzoylmethanato Tb0.01, Y0.99
anilinium tetrakis thenoyltrifluoroacetonato Tb0.01, Y0.99
anilinium tetrakis 2,2,6,6-tetramethylheptanedionato Tb0.01, Y0.99
anilinium tetrakis 3-methylpentane-2,4-dionato Tb0.01, Y0.99
anilinium tetrakis 3-ethylpentane-2,4-dionato Tb0.01, Y0.99
anilinium tetrakis pivaloyltrifluoroacetonato Tb0.01, Y0.99
anilinium tetrakis trifluoroacetylacetonato Tb0.01, Y0.99
anilinium tetrakis hexafluoroacetylacetonato Tb0.01, Y0.99
anilinium tetrakis 6,6,7,7,8,8,8-heptafluoro-2,2-dimethyloctanedionato Tb0.01, Y0.99
anilinium tetrakis 1-phenyl-1,3-butanedionato Tb0.01, Y0.99
triethylammonium tetrakis acetylacetonato Eu0.5, Y0.5
triethylammonium tetrakis dibenzoylmethanato Eu0.5, Y0.5
triethylammonium tetrakis thenoyltrifluoroacetonato Eu0.5, Y0.5
triethylammonium tetrakis 2,2,6,6-tetramethylheptanedionato Eu0.5, Y0.5
triethylammonium tetrakis 3-methylpentane-2,4-dionato Eu0.5, Y0.5
triethylammonium tetrakis 3-ethylpentane-2,4-dionato Eu0.5, Y0.5
triethylammonium tetrakis pivaloyltrifluoroacetonato Eu0.5, Y0.5
triethylammonium tetrakis trifluoroacetylacetonato Eu0.5, Y0.5
triethylammonium tetrakis hexafluoroacetylacetonato Eu0.5, Y0.5
triethylammonium tetrakis 6,6,7,7,8,8,8-heptafluoro-2,2-dimethyloctanedionato Eu0.5, Y0.5
triethylammonium tetrakis 1-phenyl-1,3-butanedionato Eu0.5, Y0.5
morpholinium tetrakis acetylacetonato Eu0.5, Y0.5
morpholinium tetrakis dibenzoylmethanato Eu0.5, Y0.5
morpholinium tetrakis thenoyltrifluoroacetonato Eu0.5, Y0.5
morpholinium tetrakis 2,2,6,6-tetramethylheptanedionato Eu0.5, Y0.5
morpholinium tetrakis 3-methylpentane-2,4-dionato Eu0.5, Y0.5
morpholinium tetrakis 3-ethylpentane-2,4-dionato Eu0.5, Y0.5
morpholinium tetrakis pivaloyltrifluoroacetonato Eu0.5, Y0.5
morpholinium tetrakis trifluoroacetylacetonato Eu0.5, Y0.5
morpholinium tetrakis hexafluoroacetylacetonato Eu0.5, Y0.5
morpholinium tetrakis 6,6,7,7,8,8,8-heptafluoro-2,2-dimethyloctanedionato Eu0.5, Y0.5
morpholinium tetrakis 1-phenyl-1,3-butanedionato Eu0.5, Y0.5 dimethylbenzylammonium tetrakis acetylacetonato Eu0.5, Y0.5
dimethylbenzylammonium tetrakis dibenzoylmethanato Eu0.5, Y0.5
dimethylbenzylammonium tetrakis thenoyltrifluoroacetonato Eu0.5, Y0.5
dimethylbenzylammonium tetrakis 2,2,6,6-tetramethylheptanedionato Eu0.5, Y0.5
dimethylbenzylammonium tetrakis 3-methylpentane-2,4-dionato Eu0.5, Y0.5
dimethylbenzylammonium tetrakis 3-ethylpentane-2,4-dionato Eu0.5, Y0.5
dimethylbenzylammonium tetrakis pivaloyltrifluoroacetonato Eu0.5, Y0.5
dimethylbenzylammonium tetrakis trifluoroacetylacetonato Eu0.5, Y0.5
dimethylbenzylammonium tetrakis hexafluoroacetylacetonato Eu0.5, Y0.5
dimethylbenzylammonium tetrakis 6,6,7,7,8,8,8-heptafluoro-2,2-dimethyloctanedionato Eu0.5, Y0.5
dimethylbenzylammonium tetrakis 1-phenyl-1,3-butanedionato Eu0.5, Y0.5
triallylammonium tetrakis acetylacetonato Eu0.5, Y0.5
triallylammonium tetrakis dibenzoylmethanato Eu0.5, Y0.5
triallylammonium tetrakis thenoyltrifluoroacetonato Eu0.5, Y0.5
triallylammonium tetrakis 2,2,6,6-tetramethylheptanedionato Eu0.5, Y0.5
triallylammonium tetrakis 3-methylpentane-2,4-dionato Eu0.5, Y0.5
triallylammonium tetrakis 3-ethylpentane-2,4-dionato Eu0.5, Y0.5
triallylammonium tetrakis pivaloyltrifluoroacetonato Eu0.5, Y0.5
triallylammonium tetrakis trifluoroacetylacetonato Eu0.5, Y0.5
triallylammonium tetrakis hexafluoroacetylacetonato Eu0.5, Y0.5
triallylammonium tetrakis 6,6,7,7,8,8,8-heptafluoro-2,2-dimethyloctanedionato Eu0.5, Y0.5
triallylammonium tetrakis 1-phenyl-1,3-butanedionato Eu0.5, Y0.5
anilinium tetrakis acetylacetonato Eu0.5, Y0.5
anilinium tetrakis dibenzoylmethanato Eu0.5, Y0.5
anilinium tetrakis thenoyltrifluoroacetonato Eu0.5, Y0.5
anilinium tetrakis 2,2,6,6-tetramethylheptanedionato Eu0.5, Y0.5
anilinium tetrakis 3-methylpentane-2,4-dionato Eu0.5, Y0.5
anilinium tetrakis 3-ethylpentane-2,4-dionato Eu0.5, Y0.5
anilinium tetrakis pivaloyltrifluoroacetonato Eu0.5, Y0.5
anilinium tetrakis trifluoroacetylacetonato Eu0.5, Y0.5
anilinium tetrakis hexafluoroacetylacetonato Eu0.5, Y0.5
anilinium tetrakis 6,6,7,7,8,8,8-heptafluoro-2,2-dimethyloctanedionato Eu0.5, Y0.5
anilinium tetrakis 1-phenyl-1,3-butanedionato Eu0.5, Y0.5
triethylammonium tetrakis acetylacetonato Eu0.2, Y0.8
triethylammonium tetrakis dibenzoylmethanato Eu0.2, Y0.8
triethylammonium tetrakis thenoyltrifluoroacetonato Eu0.2, Y0.8
triethylammonium tetrakis 2,2,6,6-tetramethylheptanedionato Eu0.2, Y0.8
triethylammonium tetrakis 3-methylpentane-2,4-dionato Eu0.2, Y0.8
triethylammonium tetrakis 3-ethylpentane-2,4-dionato Eu0.2, Y0.8
triethylammonium tetrakis pivaloyltrifluoroacetonato Eu0.2, Y0.8
triethylammonium tetrakis trifluoroacetylacetonato Eu0.2, Y0.8
triethylammonium tetrakis hexafluoroacetylacetonato Eu0.2, Y0.8
triethylammonium tetrakis 6,6,7,7,8,8,8-heptafluoro-2,2-dimethyloctanedionato Eu0.2, Y0.8
triethylammonium tetrakis 1-phenyl-1,3-butanedionato Eu0.2, Y0.8
morpholinium tetrakis acetylacetonato Eu0.2, Y0.8
morpholinium tetrakis dibenzoylmethanato Eu0.2, Y0.8
morpholinium tetrakis thenoyltrifluoroacetonato Eu0.2, Y0.8
morpholinium tetrakis 2,2,6,6-tetramethylheptanedionato Eu0.2, Y0.8
morpholinium tetrakis 3-methylpentane-2,4-dionato Eu0.2, Y0.8
morpholinium tetrakis 3-ethylpentane-2,4-dionato Eu0.2, Y0.8
morpholinium tetrakis pivaloyltrifluoroacetonato Eu0.2, Y0.8
morpholinium tetrakis trifluoroacetylacetonato Eu0.2, Y0.8
morpholinium tetrakis hexafluoroacetylacetonato Eu0.2, Y0.8
morpholinium tetrakis 6,6,7,7,8,8,8-heptafluoro-2,2-dimethyloctanedionato Eu0.2, Y0.8
morpholinium tetrakis 1-phenyl-1,3-butanedionato Eu0.2, Y0.8
dimethylbenzylammonium tetrakis acetylacetonato Eu0.2, Y0.8
dimethylbenzylammonium tetrakis dibenzoylmethanato Eu0.2, Y0.8
dimethylbenzylammonium tetrakis thenoyltrifluoroacetonato Eu0.2, Y0.8
dimethylbenzylammonium tetrakis 2,2,6,6-tetramethylheptanedionato Eu0.2, Y0.8
dimethylbenzylammonium tetrakis 3-methylpentane-2,4-dionato Eu0.2, Y0.8
dimethylbenzylammonium tetrakis 3-ethylpentane-2,4-dionato Eu0.2, Y0.8
dimethylbenzylammonium tetrakis pivaloyltrifluoroacetonato Eu0.2, Y0.8
dimethylbenzylammonium tetrakis trifluoroacetylacetonato Eu0.2, Y0.8
dimethylbenzylammonium tetrakis hexafluoroacetylacetonato Eu0.2, Y0.8
dimethylbenzylammonium tetrakis 6,6,7,7,8,8,8-heptafluoro-2,2-dimethyloctanedionato Eu0.2, Y0.8
dimethylbenzylammonium tetrakis 1-phenyl-1,3-butanedionato Eu0.2, Y0.8
triallylammonium tetrakis acetylacetonato Eu0.2, Y0.8
triallylammonium tetrakis dibenzoylmethanato Eu0.2, Y0.8
triallylammonium tetrakis thenoyltrifluoroacetonato Eu0.2, Y0.8
triallylammonium tetrakis 2,2,6,6-tetramethylheptanedionato Eu0.2, Y0.8
triallylammonium tetrakis 3-methylpentane-2,4-dionato Eu0.2, Y0.8
triallylammonium tetrakis 3-ethylpentane-2,4-dionato Eu0.2, Y0.8
triallylammonium tetrakis pivaloyltrifluoroacetonato Eu0.2, Y0.8
triallylammonium tetrakis trifluoroacetylacetonato Eu0.2, Y0.8
triallylammonium tetrakis hexafluoroacetylacetonato Eu0.2, Y0.8
triallylammonium tetrakis 6,6,7,7,8,8,8-heptafluoro-2,2-dimethyloctanedionato Eu0.2, Y0.8 triallylammonium tetrakis 1-phenyl-1,3-butanedionato Eu0.2, Y0.8
anilinium tetrakis acetylacetonato Eu0.2, Y0.8
anilinium tetrakis dibenzoylmethanato Eu0.2, Y0.8
anilinium tetrakis thenoyltrifluoroacetonato Eu0.2, Y0.8
anilinium tetrakis 2,2,6,6-tetramethylheptanedionato Eu0.2, Y0.8
anilinium tetrakis 3-methylpentane-2,4-dionato Eu0.2, Y0.8
anilinium tetrakis 3-ethylpentane-2,4-dionato Eu0.2, Y0.8
anilinium tetrakis pivaloyltrifluoroacetonato Eu0.2, Y0.8
anilinium tetrakis trifluoroacetylacetonato Eu0.2, Y0.8
anilinium tetrakis hexafluoroacetylacetonato Eu0.2, Y0.8
anilinium tetrakis 6,6,7,7,8,8,8-heptafluoro-2,2-dimethyloctanedionato Eu0.2, Y0.8
anilinium tetrakis 1-phenyl-1,3-butanedionato Eu0.2, Y0.8
triethylammonium tetrakis acetylacetonato Eu0.1, Y0.9
triethylammonium tetrakis dibenzoylmethanato Eu0.1, Y0.9
triethylammonium tetrakis thenoyltrifluoroacetonato Eu0.1, Y0.9
triethylammonium tetrakis 2,2,6,6-tetramethylheptanedionato Eu0.1, Y0.9
triethylammonium tetrakis 3-methylpentane-2,4-dionato Eu0.1, Y0.9
triethylammonium tetrakis 3-ethylpentane-2,4-dionato Eu0.1, Y0.9
triethylammonium tetrakis pivaloyltrifluoroacetonato Eu0.1, Y0.9
triethylammonium tetrakis trifluoroacetylacetonato Eu0.1, Y0.9
triethylammonium tetrakis hexafluoroacetylacetonato Eu0.1, Y0.9
triethylammonium tetrakis 6,6,7,7,8,8,8-heptafluoro-2,2-dimethyloctanedionato Eu0.1, Y0.9
triethylammonium tetrakis 1-phenyl-1,3-butanedionato Eu0.1, Y0.9
morpholinium tetrakis acetylacetonato Eu0.1, Y0.9
morpholinium tetrakis dibenzoylmethanato Eu0.1, Y0.9; brightness=8
morpholinium tetrakis thenoyltrifluoroacetonato Eu0.1, Y0.9
morpholinium tetrakis 2,2,6,6-tetramethylheptanedionato Eu0.1, Y0.9
morpholinium tetrakis 3-methylpentane-2,4-dionato Eu0.1, Y0.9
morpholinium tetrakis 3-ethylpentane-2,4-dionato Eu0.1, Y0.9
morpholinium tetrakis pivaloyltrifluoroacetonato Eu0.1, Y0.9
morpholinium tetrakis trifluoroacetylacetonato Eu0.1, Y0.9
morpholinium tetrakis hexafluoroacetylacetonato Eu0.1, Y0.9
morpholinium tetrakis 6,6,7,7,8,8,8-heptafluoro-2,2-dimethyloctanedionato Eu0.1, Y0.9
morpholinium tetrakis 1-phenyl-1,3-butanedionato Eu0.1, Y0.9
dimethylbenzylammonium tetrakis acetylacetonato Eu0.1, Y0.9
dimethylbenzylammonium tetrakis dibenzoylmethanato Eu0.1, Y0.9
dimethylbenzylammonium tetrakis thenoyltrifluoroacetonato Eu0.1, Y0.9
dimethylbenzylammonium tetrakis 2,2,6,6-tetramethylheptanedionato Eu0.1, Y0.9
dimethylbenzylammonium tetrakis 3-methylpentane-2,4-dionato Eu0.1, Y0.9
dimethylbenzylammonium tetrakis 3-ethylpentane-2,4-dionato Eu0.1, Y0.9
dimethylbenzylammonium tetrakis pivaloyltrifluoroacetonato Eu0.1, Y0.9
dimethylbenzylammonium tetrakis trifluoroacetylacetonato Eu0.1, Y0.9
dimethylbenzylammonium tetrakis hexafluoroacetylacetonato Eu0.1, Y0.9
dimethylbenzylammonium tetrakis 6,6,7,7,8,8,8-heptafluoro-2,2-dimethyloctanedionato Eu0.1, Y0.9
dimethylbenzylammonium tetrakis 1-phenyl-1,3-butanedionato Eu0.1, Y0.9
triallylammonium tetrakis acetylacetonato Eu0.1, Y0.9
triallylammonium tetrakis dibenzoylmethanato Eu0.1, Y0.9
triallylammonium tetrakis thenoyltrifluoroacetonato Eu0.1, Y0.9
triallylammonium tetrakis 2,2,6,6-tetramethylheptanedionato Eu0.1, Y0.9
triallylammonium tetrakis 3-methylpentane-2,4-dionato Eu0.1, Y0.9
triallylammonium tetrakis 3-ethylpentane-2,4-dionato Eu0.1, Y0.9
triallylammonium tetrakis pivaloyltrifluoroacetonato Eu0.1, Y0.9
triallylammonium tetrakis trifluoroacetylacetonato Eu0.1, Y0.9
triallylammonium tetrakis hexafluoroacetylacetonato Eu0.1, Y0.9
triallylammonium tetrakis 6,6,7,7,8,8,8-heptafluoro-2,2-dimethyloctanedionato Eu0.1, Y0.9
triallylammonium tetrakis 1-phenyl-1,3-butanedionato Eu0.1, Y0.9
anilinium tetrakis acetylacetonato Eu0.1, Y0.9
anilinium tetrakis dibenzoylmethanato Eu0.1, Y0.9
anilinium tetrakis thenoyltrifluoroacetonato Eu0.1, Y0.9
anilinium tetrakis 2,2,6,6-tetramethylheptanedionato Eu0.1, Y0.9
anilinium tetrakis 3-methylpentane-2,4-dionato Eu0.1, Y0.9
anilinium tetrakis 3-ethylpentane-2,4-dionato Eu0.1, Y0.9
anilinium tetrakis pivaloyltrifluoroacetonato Eu0.1, Y0.9
anilinium tetrakis trifluoroacetylacetonato Eu0.1, Y0.9
anilinium tetrakis hexafluoroacetylacetonato Eu0.1, Y0.9
anilinium tetrakis 6,6,7,7,8,8,8-heptafluoro-2,2-dimethyloctanedionato Eu0.1, Y0.9
anilinium tetrakis 1-phenyl-1,3-butanedionato Eu0.1, Y0.9
triethylammonium tetrakis acetylacetonato Eu0.01, Y0.99
triethylammonium tetrakis dibenzoylmethanato Eu0.01, Y0.99
triethylammonium tetrakis thenoyltrifluoroacetonato Eu0.01, Y0.99
triethylammonium tetrakis 2,2,6,6-tetramethylheptanedionato Eu0.01, Y0.99
triethylammonium tetrakis 3-methylpentane-2,4-dionato Eu0.01, Y0.99
triethylammonium tetrakis 3-ethylpentane-2,4-dionato Eu0.01, Y0.99
triethylammonium tetrakis pivaloyltrifluoroacetonato Eu0.01, Y0.99
triethylammonium tetrakis trifluoroacetylacetonato Eu0.01, Y0.99
triethylammonium tetrakis hexafluoroacetylacetonato Eu0.01, Y0.99
triethylammonium tetrakis 6,6,7,7,8,8,8-heptafluoro-2,2-dimethyloctanedionato Eu0.01, Y0.99
triethylammonium tetrakis 1-phenyl-1,3-butanedionato Eu0.01, Y0.99
morpholinium tetrakis acetylacetonato Eu0.01, Y0.99
morpholinium tetrakis dibenzoylmethanato Eu0.01, Y0.99 morpholinium tetrakis thenoyltrifluoroacetonato Eu0.01, Y0.99
morpholinium tetrakis 2,2,6,6-tetramethylheptanedionato Eu0.01, Y0.99
morpholinium tetrakis 3-methylpentane-2,4-dionato Eu0.01, Y0.99
morpholinium tetrakis 3-ethylpentane-2,4-dionato Eu0.01, Y0.99
morpholinium tetrakis pivaloyltrifluoroacetonato Eu0.01, Y0.99
morpholinium tetrakis trifluoroacetylacetonato Eu0.01, Y0.99
morpholinium tetrakis hexafluoroacetylacetonato Eu0.01, Y0.99
morpholinium tetrakis 6,6,7,7,8,8,8-heptafluoro-2,2-dimethyloctanedionato Eu0.01, Y0.99
morpholinium tetrakis 1-phenyl-1,3-butanedionato Eu0.01, Y0.99
dimethylbenzylammonium tetrakis acetylacetonato Eu0.01, Y0.99
dimethylbenzylammonium tetrakis dibenzoylmethanato Eu0.01, Y0.99
dimethylbenzylammonium tetrakis thenoyltrifluoroacetonato Eu0.01, Y0.99
dimethylbenzylammonium tetrakis 2,2,6,6-tetramethylheptanedionato Eu0.01, Y0.99
dimethylbenzylammonium tetrakis 3-methylpentane-2,4-dionato Eu0.01, Y0.99
dimethylbenzylammonium tetrakis 3-ethylpentane-2,4-dionato Eu0.01, Y0.99
dimethylbenzylammonium tetrakis pivaloyltrifluoroacetonato Eu0.01, Y0.99
dimethylbenzylammonium tetrakis trifluoroacetylacetonato Eu0.01, Y0.99
dimethylbenzylammonium tetrakis hexafluoroacetylacetonato Eu0.01, Y0.99
dimethylbenzylammonium tetrakis 6,6,7,7,8,8,8-heptafluoro-2,2-dimethyloctanedionato Eu0.01, Y0.99
dimethylbenzylammonium tetrakis 1-phenyl-1,3-butanedionato Eu0.01, Y0.99
triallylammonium tetrakis acetylacetonato Eu0.01, Y0.99
triallylammonium tetrakis dibenzoylmethanato Eu0.01, Y0.99
triallylammonium tetrakis thenoyltrifluoroacetonato Eu0.01, Y0.99
triallylammonium tetrakis 2,2,6,6-tetramethylheptanedionato Eu0.01, Y0.99
triallylammonium tetrakis 3-methylpentane-2,4-dionato Eu0.01, Y0.99
triallylammonium tetrakis 3-ethylpentane-2,4-dionato Eu0.01, Y0.99
triallylammonium tetrakis pivaloyltrifluoroacetonato Eu0.01, Y0.99
triallylammonium tetrakis trifluoroacetylacetonato Eu0.01, Y0.99
triallylammonium tetrakis hexafluoroacetylacetonato Eu0.01, Y0.99
triallylammonium tetrakis 6,6,7,7,8,8,8-heptafluoro-2,2-dimethyloctanedionato Eu0.01, Y0.99
triallylammonium tetrakis 1-phenyl-1,3-butanedionato Eu0.01, Y0.99
anilinium tetrakis acetylacetonato Eu0.01, Y0.99
anilinium tetrakis dibenzoylmethanato Eu0.01, Y0.99
anilinium tetrakis thenoyltrifluoroacetonato Eu0.01, Y0.99
anilinium tetrakis 2,2,6,6-tetramethylheptanedionato Eu0.01, Y0.99
anilinium tetrakis 3-methylpentane-2,4-dionato Eu0.01, Y0.99
anilinium tetrakis 3-ethylpentane-2,4-dionato Eu0.01, Y0.99
anilinium tetrakis pivaloyltrifluoroacetonato Eu0.01, Y0.99
anilinium tetrakis trifluoroacetylacetonato Eu0.01, Y0.99
anilinium tetrakis hexafluoroacetylacetonato Eu0.01, Y0.99
anilinium tetrakis 6,6,7,7,8,8,8-heptafluoro-2,2-dimethyloctanedionato Eu0.01, Y0.99
anilinium tetrakis 1-phenyl-1,3-butanedionato Eu0.01, Y0.99
triethylammonium tetrakis acetylacetonato Eu0.5, Y0.5
triethylammonium tetrakis dibenzoylmethanato Eu0.5, Y0.5
triethylammonium tetrakis thenoyltrifluoroacetonato Eu0.5, Y0.5
triethylammonium tetrakis 2,2,6,6-tetramethylheptanedionato Eu0.5, Y0.5
triethylammonium tetrakis 3-methylpentane-2,4-dionato Eu0.5, Y0.5
triethylammonium tetrakis 3-ethylpentane-2,4-dionato Eu0.5, Y0.5
triethylammonium tetrakis pivaloyltrifluoroacetonato Eu0.5, Y0.5
triethylammonium tetrakis trifluoroacetylacetonato Eu0.5, Y0.5
triethylammonium tetrakis hexafluoroacetylacetonato Eu0.5, Y0.5
triethylammonium tetrakis 6,6,7,7,8,8,8-heptafluoro-2,2-dimethyloctanedionato Eu0.5, Y0.5
triethylammonium tetrakis 1-phenyl-1,3-butanedionato Eu0.5, Y0.5
morpholinium tetrakis acetylacetonato Eu0.5, Y0.5
morpholinium tetrakis dibenzoylmethanato Eu0.5, Y0.5
morpholinium tetrakis thenoyltrifluoroacetonato Eu0.5, Y0.5
morpholinium tetrakis 2,2,6,6-tetramethylheptanedionato Eu0.5, Y0.5
morpholinium tetrakis 3-methylpentane-2,4-dionato Eu0.5, Y0.5
morpholinium tetrakis 3-ethylpentane-2,4-dionato Eu0.5, Y0.5
morpholinium tetrakis pivaloyltrifluoroacetonato Eu0.5, Y0.5
morpholinium tetrakis trifluoroacetylacetonato Eu0.5, Y0.5
morpholinium tetrakis hexafluoroacetylacetonato Eu0.5, Y0.5
morpholinium tetrakis 6,6,7,7,8,8,8-heptafluoro-2,2-dimethyloctanedionato Eu0.5, Y0.5
morpholinium tetrakis 1-phenyl-1,3-butanedionato Eu0.5, Y0.5
dimethylbenzylammonium tetrakis acetylacetonato Eu0.5, Y0.5
dimethylbenzylammonium tetrakis dibenzoylmethanato Eu0.5, Y0.5
dimethylbenzylammonium tetrakis thenoyltrifluoroacetonato Eu0.5, Y0.5
dimethylbenzylammonium tetrakis 2,2,6,6-tetramethylheptanedionato Eu0.5, Y0.5
dimethylbenzylammonium tetrakis 3-methylpentane-2,4-dionato Eu0.5, Y0.5
dimethylbenzylammonium tetrakis 3-ethylpentane-2,4-dionato Eu0.5, Y0.5
dimethylbenzylammonium tetrakis pivaloyltrifluoroacetonato Eu0.5, Y0.5
dimethylbenzylammonium tetrakis trifluoroacetylacetonato Eu0.5, Y0.5
dimethylbenzylammonium tetrakis hexafluoroacetylacetonato Eu0.5, Y0.5 dimethylbenzylammonium tetrakis 6,6,7,7,8,8,8-heptafluoro-2,2-dimethyloctanedionato Eu0.5, Y0.5
dimethylbenzylammonium tetrakis 1-phenyl-1,3-butanedionato Eu0.5, Y0.5
triallylammonium tetrakis acetylacetonato Eu0.5, Y0.5
triallylammonium tetrakis dibenzoylmethanato Eu0.5, Y0.5
triallylammonium tetrakis thenoyltrifluoroacetonato Eu0.5, Y0.5
triallylammonium tetrakis 2,2,6,6-tetramethylheptanedionato Eu0.5, Y0.5
triallylammonium tetrakis 3-methylpentane-2,4-dionato Eu0.5, Y0.5
triallylammonium tetrakis 3-ethylpentane-2,4-dionato Eu0.5, Y0.5
triallylammonium tetrakis pivaloyltrifluoroacetonato Eu0.5, Y0.5
triallylammonium tetrakis trifluoroacetylacetonato Eu0.5, Y0.5
triallylammonium tetrakis hexafluoroacetylacetonato Eu0.5, Y0.5
triallylammonium tetrakis 6,6,7,7,8,8,8-heptafluoro-2,2-dimethyloctanedionato Eu0.5, Y0.5
triallylammonium tetrakis 1-phenyl-1,3-butanedionato Eu0.5, Y0.5
anilinium tetrakis acetylacetonato Eu0.5, Y0.5
anilinium tetrakis dibenzoylmethanato Eu0.5, Y0.5
anilinium tetrakis thenoyltrifluoroacetonato Eu0.5, Y0.5
anilinium tetrakis 2,2,6,6-tetramethylheptanedionato Eu0.5, Y0.5
anilinium tetrakis 3-methylpentane-2,4-dionato Eu0.5, Y0.5
anilinium tetrakis 3-ethylpentane-2,4-dionato Eu0.5, Y0.5
anilinium tetrakis pivaloyltrifluoroacetonato Eu0.5, Y0.5
anilinium tetrakis trifluoroacetylacetonato Eu0.5, Y0.5
anilinium tetrakis hexafluoroacetylacetonato Eu0.5, Y0.5
anilinium tetrakis 6,6,7,7,8,8,8-heptafluoro-2,2-dimethyloctanedionato Eu0.5, Y0.5
anilinium tetrakis 1-phenyl-1,3-butanedionato Eu0.5, Y0.5
triethylammonium tetrakis acetylacetonato Eu0.2, Y0.8
triethylammonium tetrakis dibenzoylmethanato Eu0.2, Y0.8
triethylammonium tetrakis thenoyltrifluoroacetonato Eu0.2, Y0.8
triethylammonium tetrakis 2,2,6,6-tetramethylheptanedionato Eu0.2, Y0.8
triethylammonium tetrakis 3-methylpentane-2,4-dionato Eu0.2, Y0.8
triethylammonium tetrakis 3-ethylpentane-2,4-dionato Eu0.2, Y0.8
triethylammonium tetrakis pivaloyltrifluoroacetonato Eu0.2, Y0.8
triethylammonium tetrakis trifluoroacetylacetonato Eu0.2, Y0.8
triethylammonium tetrakis hexafluoroacetylacetonato Eu0.2, Y0.8
triethylammonium tetrakis 6,6,7,7,8,8,8-heptafluoro-2,2-dimethyloctanedionato Eu0.2, Y0.8
triethylammonium tetrakis 1-phenyl-1,3-butanedionato Eu0.2, Y0.8
morpholinium tetrakis acetylacetonato Eu0.2, Y0.8
morpholinium tetrakis dibenzoylmethanato Eu0.2, Y0.8
morpholinium tetrakis thenoyltrifluoroacetonato Eu0.2, Y0.8
morpholinium tetrakis 2,2,6,6-tetramethylheptanedionato Eu0.2, Y0.8
morpholinium tetrakis 3-methylpentane-2,4-dionato Eu0.2, Y0.8
morpholinium tetrakis 3-ethylpentane-2,4-dionato Eu0.2, Y0.8
morpholinium tetrakis pivaloyltrifluoroacetonato Eu0.2, Y0.8
morpholinium tetrakis trifluoroacetylacetonato Eu0.2, Y0.8
morpholinium tetrakis hexafluoroacetylacetonato Eu0.2, Y0.8
morpholinium tetrakis 6,6,7,7,8,8,8-heptafluoro-2,2-dimethyloctanedionato Eu0.2, Y0.8
morpholinium tetrakis 1-phenyl-1,3-butanedionato Eu0.2, Y0.8
dimethylbenzylammonium tetrakis acetylacetonato Eu0.2, Y0.8
dimethylbenzylammonium tetrakis dibenzoylmethanato Eu0.2, Y0.8
dimethylbenzylammonium tetrakis thenoyltrifluoroacetonato Eu0.2, Y0.8
dimethylbenzylammonium tetrakis 2,2,6,6-tetramethylheptanedionato Eu0.2, Y0.8
dimethylbenzylammonium tetrakis 3-methylpentane-2,4-dionato Eu0.2, Y0.8
dimethylbenzylammonium tetrakis 3-ethylpentane-2,4-dionato Eu0.2, Y0.8
dimethylbenzylammonium tetrakis pivaloyltrifluoroacetonato Eu0.2, Y0.8
dimethylbenzylammonium tetrakis trifluoroacetylacetonato Eu0.2, Y0.8
dimethylbenzylammonium tetrakis hexafluoroacetylacetonato Eu0.2, Y0.8
dimethylbenzylammonium tetrakis 6,6,7,7,8,8,8-heptafluoro-2,2-dimethyloctanedionato Eu0.2, Y0.8
dimethylbenzylammonium tetrakis 1-phenyl-1,3-butanedionato Eu0.2, Y0.8
triallylammonium tetrakis acetylacetonato Eu0.2, Y0.8
triallylammonium tetrakis dibenzoylmethanato Eu0.2, Y0.8
triallylammonium tetrakis thenoyltrifluoroacetonato Eu0.2, Y0.8
triallylammonium tetrakis 2,2,6,6-tetramethylheptanedionato Eu0.2, Y0.8
triallylammonium tetrakis 3-methylpentane-2,4-dionato Eu0.2, Y0.8
triallylammonium tetrakis 3-ethylpentane-2,4-dionato Eu0.2, Y0.8
triallylammonium tetrakis pivaloyltrifluoroacetonato Eu0.2, Y0.8
triallylammonium tetrakis trifluoroacetylacetonato Eu0.2, Y0.8
triallylammonium tetrakis hexafluoroacetylacetonato Eu0.2, Y0.8
triallylammonium tetrakis 6,6,7,7,8,8,8-heptafluoro-2,2-dimethyloctanedionato Eu0.2, Y0.8
triallylammonium tetrakis 1-phenyl-1,3-butanedionato Eu0.2, Y0.8
anilinium tetrakis acetylacetonato Eu0.2, Y0.8
anilinium tetrakis dibenzoylmethanato Eu0.2, Y0.8
anilinium tetrakis thenoyltrifluoroacetonato Eu0.2, Y0.8
anilinium tetrakis 2,2,6,6-tetramethylheptanedionato Eu0.2, Y0.8
anilinium tetrakis 3-methylpentane-2,4-dionato Eu0.2, Y0.8
anilinium tetrakis 3-ethylpentane-2,4-dionato Eu0.2, Y0.8
anilinium tetrakis pivaloyltrifluoroacetonato Eu0.2, Y0.8
anilinium tetrakis trifluoroacetylacetonato Eu0.2, Y0.8
anilinium tetrakis hexafluoroacetylacetonato Eu0.2, Y0.8
anilinium tetrakis 6,6,7,7,8,8,8-heptafluoro-2,2-dimethyloctanedionato Eu0.2, Y0.8
anilinium tetrakis 1-phenyl-1,3-butanedionato Eu0.2, Y0.8
triethylammonium tetrakis acetylacetonato Eu0.1, Y0.9
triethylammonium tetrakis dibenzoylmethanato Eu0.1, Y0.9 triethylammonium tetrakis thenoyltrifluoroacetonato Eu0.1, Y0.9
triethylammonium tetrakis 2,2,6,6-tetramethylheptanedionato Eu0.1, Y0.9
triethylammonium tetrakis 3-methylpentane-2,4-dionato Eu0.1, Y0.9
triethylammonium tetrakis 3-ethylpentane-2,4-dionato Eu0.1, Y0.9
triethylammonium tetrakis pivaloyltrifluoroacetonato Eu0.1, Y0.9
triethylammonium tetrakis trifluoroacetylacetonato Eu0.1, Y0.9
triethylammonium tetrakis hexafluoroacetylacetonato Eu0.1, Y0.9
triethylammonium tetrakis 6,6,7,7,8,8,8-heptafluoro-2,2-dimethyloctanedionato Eu0.1, Y0.9
triethylammonium tetrakis 1-phenyl-1,3-butanedionato Eu0.1, Y0.9
morpholinium tetrakis acetylacetonato Eu0.1, Y0.9
morpholinium tetrakis dibenzoylmethanato Eu0.1, Y0.9
morpholinium tetrakis thenoyltrifluoroacetonato Eu0.1, Y0.9
morpholinium tetrakis 2,2,6,6-tetramethylheptanedionato Eu0.1, Y0.9
morpholinium tetrakis 3-methylpentane-2,4-dionato Eu0.1, Y0.9
morpholinium tetrakis 3-ethylpentane-2,4-dionato Eu0.1, Y0.9
morpholinium tetrakis pivaloyltrifluoroacetonato Eu0.1, Y0.9
morpholinium tetrakis trifluoroacetylacetonato Eu0.1, Y0.9
morpholinium tetrakis hexafluoroacetylacetonato Eu0.1, Y0.9
morpholinium tetrakis 6,6,7,7,8,8,8-heptafluoro-2,2-dimethyloctanedionato Eu0.1, Y0.9
morpholinium tetrakis 1-phenyl-1,3-butanedionato Eu0.1, Y0.9
dimethylbenzylammonium tetrakis acetylacetonato Eu0.1, Y0.9
dimethylbenzylammonium tetrakis dibenzoylmethanato Eu0.1, Y0.9
dimethylbenzylammonium tetrakis thenoyltrifluoroacetonato Eu0.1, Y0.9
dimethylbenzylammonium tetrakis 2,2,6,6-tetramethylheptanedionato Eu0.1, Y0.9
dimethylbenzylammonium tetrakis 3-methylpentane-2,4-dionato Eu0.1, Y0.9
dimethylbenzylammonium tetrakis 3-ethylpentane-2,4-dionato Eu0.1, Y0.9
dimethylbenzylammonium tetrakis pivaloyltrifluoroacetonato Eu0.1, Y0.9
dimethylbenzylammonium tetrakis trifluoroacetylacetonato Eu0.1, Y0.9
dimethylbenzylammonium tetrakis hexafluoroacetylacetonato Eu0.1, Y0.9
dimethylbenzylammonium tetrakis 6,6,7,7,8,8,8-heptafluoro-2,2-dimethyloctanedionato Eu0.1, Y0.9
dimethylbenzylammonium tetrakis 1-phenyl-1,3-butanedionato Eu0.1, Y0.9
triallylammonium tetrakis acetylacetonato Eu0.1, Y0.9
triallylammonium tetrakis dibenzoylmethanato Eu0.1, Y0.9
triallylammonium tetrakis thenoyltrifluoroacetonato Eu0.1, Y0.9
triallylammonium tetrakis 2,2,6,6-tetramethylheptanedionato Eu0.1, Y0.9
triallylammonium tetrakis 3-methylpentane-2,4-dionato Eu0.1, Y0.9
triallylammonium tetrakis 3-ethylpentane-2,4-dionato Eu0.1, Y0.9
triallylammonium tetrakis pivaloyltrifluoroacetonato Eu0.1, Y0.9
triallylammonium tetrakis trifluoroacetylacetonato Eu0.1, Y0.9
triallylammonium tetrakis hexafluoroacetylacetonato Eu0.1, Y0.9
triallylammonium tetrakis 6,6,7,7,8,8,8-heptafluoro-2,2-dimethyloctanedionato Eu0.1, Y0.9
triallylammonium tetrakis 1-phenyl-1,3-butanedionato Eu0.1, Y0.9
anilinium tetrakis acetylacetonato Eu0.1, Y0.9
anilinium tetrakis dibenzoylmethanato Eu0.1, Y0.9
anilinium tetrakis thenoyltrifluoroacetonato Eu0.1, Y0.9
anilinium tetrakis 2,2,6,6-tetramethylheptanedionato Eu0.1, Y0.9
anilinium tetrakis 3-methylpentane-2,4-dionato Eu0.1, Y0.9
anilinium tetrakis 3-ethylpentane-2,4-dionato Eu0.1, Y0.9
anilinium tetrakis pivaloyltrifluoroacetonato Eu0.1, Y0.9
anilinium tetrakis trifluoroacetylacetonato Eu0.1, Y0.9
anilinium tetrakis hexafluoroacetylacetonato Eu0.1, Y0.9
anilinium tetrakis 6,6,7,7,8,8,8-heptafluoro-2,2-dimethyloctanedionato Eu0.1, Y0.9
anilinium tetrakis 1-phenyl-1,3-butanedionato Eu0.1, Y0.9
triethylammonium tetrakis acetylacetonato Eu0.01, Y0.99
triethylammonium tetrakis dibenzoylmethanato Eu0.01, Y0.99
triethylammonium tetrakis thenoyltrifluoroacetonato Eu0.01, Y0.99
triethylammonium tetrakis 2,2,6,6-tetramethylheptanedionato Eu0.01, Y0.99
triethylammonium tetrakis 3-methylpentane-2,4-dionato Eu0.01, Y0.99
triethylammonium tetrakis 3-ethylpentane-2,4-dionato Eu0.01, Y0.99
triethylammonium tetrakis pivaloyltrifluoroacetonato Eu0.01, Y0.99
triethylammonium tetrakis trifluoroacetylacetonato Eu0.01, Y0.99
triethylammonium tetrakis hexafluoroacetylacetonato Eu0.01, Y0.99
triethylammonium tetrakis 6,6,7,7,8,8,8-heptafluoro-2,2-dimethyloctanedionato Eu0.01, Y0.99
triethylammonium tetrakis 1-phenyl-1,3-butanedionato Eu0.01, Y0.99
morpholinium tetrakis acetylacetonato Eu0.01, Y0.99
morpholinium tetrakis dibenzoylmethanato Eu0.01, Y0.99
morpholinium tetrakis thenoyltrifluoroacetonato Eu0.01, Y0.99
morpholinium tetrakis 2,2,6,6-tetramethylheptanedionato Eu0.01, Y0.99
morpholinium tetrakis 3-methylpentane-2,4-dionato Eu0.01, Y0.99
morpholinium tetrakis 3-ethylpentane-2,4-dionato Eu0.01, Y0.99
morpholinium tetrakis pivaloyltrifluoroacetonato Eu0.01, Y0.99
morpholinium tetrakis trifluoroacetylacetonato Eu0.01, Y0.99
morpholinium tetrakis hexafluoroacetylacetonato Eu0.01, Y0.99
morpholinium tetrakis 6,6,7,7,8,8,8-heptafluoro-2,2-dimethyloctanedionato Eu0.01, Y0.99
morpholinium tetrakis 1-phenyl-1,3-butanedionato Eu0.01, Y0.99 dimethylbenzylammonium tetrakis acetylacetonato Eu0.01, Y0.99
dimethylbenzylammonium tetrakis dibenzoylmethanato Eu0.01, Y0.99
dimethylbenzylammonium tetrakis thenoyltrifluoroacetonato Eu0.01, Y0.99
dimethylbenzylammonium tetrakis 2,2,6,6-tetramethylheptanedionato Eu0.01, Y0.99
dimethylbenzylammonium tetrakis 3-methylpentane-2,4-dionato Eu0.01, Y0.99
dimethylbenzylammonium tetrakis 3-ethylpentane-2,4-dionato Eu0.01, Y0.99
dimethylbenzylammonium tetrakis pivaloyltrifluoroacetonato Eu0.01, Y0.99
dimethylbenzylammonium tetrakis trifluoroacetylacetonato Eu0.01, Y0.99
dimethylbenzylammonium tetrakis hexafluoroacetylacetonato Eu0.01, Y0.99
dimethylbenzylammonium tetrakis 6,6,7,7,8,8,8-heptafluoro-2,2-dimethyloctanedionato Eu0.01, Y0.99
dimethylbenzylammonium tetrakis 1-phenyl-1,3-butanedionato Eu0.01, Y0.99
triallylammonium tetrakis acetylacetonato Eu0.01, Y0.99
triallylammonium tetrakis dibenzoylmethanato Eu0.01, Y0.99
triallylammonium tetrakis thenoyltrifluoroacetonato Eu0.01, Y0.99
triallylammonium tetrakis 2,2,6,6-tetramethylheptanedionato Eu0.01, Y0.99
triallylammonium tetrakis 3-methylpentane-2,4-dionato Eu0.01, Y0.99
triallylammonium tetrakis 3-ethylpentane-2,4-dionato Eu0.01, Y0.99
triallylammonium tetrakis pivaloyltrifluoroacetonato Eu0.01, Y0.99
triallylammonium tetrakis trifluoroacetylacetonato Eu0.01, Y0.99
triallylammonium tetrakis hexafluoroacetylacetonato Eu0.01, Y0.99
triallylammonium tetrakis 6,6,7,7,8,8,8-heptafluoro-2,2-dimethyloctanedionato Eu0.01, Y0.99
triallylammonium tetrakis 1-phenyl-1,3-butanedionato Eu0.01, Y0.99
anilinium tetrakis acetylacetonato Eu0.01, Y0.99
anilinium tetrakis dibenzoylmethanato Eu0.01, Y0.99
anilinium tetrakis thenoyltrifluoroacetonato Eu0.01, Y0.99
anilinium tetrakis 2,2,6,6-tetramethylheptanedionato Eu0.01, Y0.99
anilinium tetrakis 3-methylpentane-2,4-dionato Eu0.01, Y0.99
anilinium tetrakis 3-ethylpentane-2,4-dionato Eu0.01, Y0.99
anilinium tetrakis pivaloyltrifluoroacetonato Eu0.01, Y0.99
anilinium tetrakis trifluoroacetylacetonato Eu0.01, Y0.99
anilinium tetrakis hexafluoroacetylacetonato Eu0.01, Y0.99
anilinium tetrakis 6,6,7,7,8,8,8-heptafluoro-2,2-dimethyloctanedionato Eu0.01, Y0.99
anilinium tetrakis 1-phenyl-1,3-butanedionato Eu0.01, Y0.99
triethylammonium tetrakis acetylacetonato Tb0.5, La0.5
triethylammonium tetrakis dibenzoylmethanato Tb0.5, La0.5
triethylammonium tetrakis thenoyltrifluoroacetonato Tb0.5, La0.5
triethylammonium tetrakis 2,2,6,6-tetramethylheptanedionato Tb0.5, La0.5
triethylammonium tetrakis 3-methylpentane-2,4-dionato Tb0.5, La0.5
triethylammonium tetrakis 3-ethylpentane-2,4-dionato Tb0.5, La0.5
triethylammonium tetrakis pivaloyltrifluoroacetonato Tb0.5, La0.5
triethylammonium tetrakis trifluoroacetylacetonato Tb0.5, La0.5
triethylammonium tetrakis hexafluoroacetylacetonato Tb0.5, La0.5
triethylammonium tetrakis 6,6,7,7,8,8,8-heptafluoro-2,2-dimethyloctanedionato Tb0.5, La0.5
triethylammonium tetrakis 1-phenyl-1,3-butanedionato Tb0.5, La0.5
morpholinium tetrakis acetylacetonato Tb0.5, La0.5
morpholinium tetrakis dibenzoylmethanato Tb0.5, La0.5
morpholinium tetrakis thenoyltrifluoroacetonato Tb0.5, La0.5
morpholinium tetrakis 2,2,6,6-tetramethylheptanedionato Tb0.5, La0.5
morpholinium tetrakis 3-methylpentane-2,4-dionato Tb0.5, La0.5
morpholinium tetrakis 3-ethylpentane-2,4-dionato Tb0.5, La0.5
morpholinium tetrakis pivaloyltrifluoroacetonato Tb0.5, La0.5
morpholinium tetrakis trifluoroacetylacetonato Tb0.5, La0.5
morpholinium tetrakis hexafluoroacetylacetonato Tb0.5, La0.5
morpholinium tetrakis 6,6,7,7,8,8,8-heptafluoro-2,2-dimethyloctanedionato Tb0.5, La0.5
morpholinium tetrakis 1-phenyl-1,3-butanedionato Tb0.5, La0.5
dimethylbenzylammonium tetrakis acetylacetonato Tb0.5, La0.5
dimethylbenzylammonium tetrakis dibenzoylmethanato Tb0.5, La0.5
dimethylbenzylammonium tetrakis thenoyltrifluoroacetonato Tb0.5, La0.5
dimethylbenzylammonium tetrakis 2,2,6,6-tetramethylheptanedionato Tb0.5, La0.5
dimethylbenzylammonium tetrakis 3-methylpentane-2,4-dionato Tb0.5, La0.5
dimethylbenzylammonium tetrakis 3-ethylpentane-2,4-dionato Tb0.5, La0.5
dimethylbenzylammonium tetrakis pivaloyltrifluoroacetonato Tb0.5, La0.5
dimethylbenzylammonium tetrakis trifluoroacetylacetonato Tb0.5, La0.5
dimethylbenzylammonium tetrakis hexafluoroacetylacetonato Tb0.5, La0.5
dimethylbenzylammonium tetrakis 6,6,7,7,8,8,8-heptafluoro-2,2-dimethyloctanedionato Tb0.5, La0.5
dimethylbenzylammonium tetrakis 1-phenyl-1,3-butanedionato Tb0.5, La0.5
triallylammonium tetrakis acetylacetonato Tb0.5, La0.5
triallylammonium tetrakis dibenzoylmethanato Tb0.5, La0.5
triallylammonium tetrakis thenoyltrifluoroacetonato Tb0.5, La0.5
triallylammonium tetrakis 2,2,6,6-tetramethylheptanedionato Tb0.5, La0.5
triallylammonium tetrakis 3-methylpentane-2,4-dionato Tb0.5, La0.5
triallylammonium tetrakis 3-ethylpentane-2,4-dionato Tb0.5, La0.5
triallylammonium tetrakis pivaloyltrifluoroacetonato Tb0.5, La0.5
triallylammonium tetrakis trifluoroacetylacetonato Tb0.5, La0.5 triallylammonium tetrakis hexafluoroacetylacetonato Tb0.5, La0.5
triallylammonium tetrakis 6,6,7,7,8,8,8-heptafluoro-2,2-dimethyloctanedionato Tb0.5, La0.5
triallylammonium tetrakis 1-phenyl-1,3-butanedionato Tb0.5, La0.5
anilinium tetrakis acetylacetonato Tb0.5, La0.5
anilinium tetrakis dibenzoylmethanato Tb0.5, La0.5
anilinium tetrakis thenoyltrifluoroacetonato Tb0.5, La0.5
anilinium tetrakis 2,2,6,6-tetramethylheptanedionato Tb0.5, La0.5
anilinium tetrakis 3-methylpentane-2,4-dionato Tb0.5, La0.5
anilinium tetrakis 3-ethylpentane-2,4-dionato Tb0.5, La0.5
anilinium tetrakis pivaloyltrifluoroacetonato Tb0.5, La0.5
anilinium tetrakis trifluoroacetylacetonato Tb0.5, La0.5
anilinium tetrakis hexafluoroacetylacetonato Tb0.5, La0.5
anilinium tetrakis 6,6,7,7,8,8,8-heptafluoro-2,2-dimethyloctanedionato Tb0.5, La0.5
anilinium tetrakis 1-phenyl-1,3-butanedionato Tb0.5, La0.5
triethylammonium tetrakis acetylacetonato Tb0.2, La0.8
triethylammonium tetrakis dibenzoylmethanato Tb0.2, La0.8
triethylammonium tetrakis thenoyltrifluoroacetonato Tb0.2, La0.8
triethylammonium tetrakis 2,2,6,6-tetramethylheptanedionato Tb0.2, La0.8
triethylammonium tetrakis 3-methylpentane-2,4-dionato Tb0.2, La0.8
triethylammonium tetrakis 3-ethylpentane-2,4-dionato Tb0.2, La0.8
triethylammonium tetrakis pivaloyltrifluoroacetonato Tb0.2, La0.8
triethylammonium tetrakis trifluoroacetylacetonato Tb0.2, La0.8
triethylammonium tetrakis hexafluoroacetylacetonato Tb0.2, La0.8
triethylammonium tetrakis 6,6,7,7,8,8,8-heptafluoro-2,2-dimethyloctanedionato Tb0.2, La0.8
triethylammonium tetrakis 1-phenyl-1,3-butanedionato Tb0.2, La0.8
morpholinium tetrakis acetylacetonato Tb0.2, La0.8
morpholinium tetrakis dibenzoylmethanato Tb0.2, La0.8
morpholinium tetrakis thenoyltrifluoroacetonato Tb0.2, La0.8
morpholinium tetrakis 2,2,6,6-tetramethylheptanedionato Tb0.2, La0.8
morpholinium tetrakis 3-methylpentane-2,4-dionato Tb0.2, La0.8
morpholinium tetrakis 3-ethylpentane-2,4-dionato Tb0.2, La0.8
morpholinium tetrakis pivaloyltrifluoroacetonato Tb0.2, La0.8
morpholinium tetrakis trifluoroacetylacetonato Tb0.2, La0.8
morpholinium tetrakis hexafluoroacetylacetonato Tb0.2, La0.8
morpholinium tetrakis 6,6,7,7,8,8,8-heptafluoro-2,2-dimethyloctanedionato Tb0.2, La0.8
morpholinium tetrakis 1-phenyl-1,3-butanedionato Tb0.2, La0.8
dimethylbenzylammonium tetrakis acetylacetonato Tb0.2, La0.8
dimethylbenzylammonium tetrakis dibenzoylmethanato Tb0.2, La0.8
dimethylbenzylammonium tetrakis thenoyltrifluoroacetonato Tb0.2, La0.8
dimethylbenzylammonium tetrakis 2,2,6,6-tetramethylheptanedionato Tb0.2, La0.8
dimethylbenzylammonium tetrakis 3-methylpentane-2,4-dionato Tb0.2, La0.8
dimethylbenzylammonium tetrakis 3-ethylpentane-2,4-dionato Tb0.2, La0.8
dimethylbenzylammonium tetrakis pivaloyltrifluoroacetonato Tb0.2, La0.8
dimethylbenzylammonium tetrakis trifluoroacetylacetonato Tb0.2, La0.8
dimethylbenzylammonium tetrakis hexafluoroacetylacetonato Tb0.2, La0.8
dimethylbenzylammonium tetrakis 6,6,7,7,8,8,8-heptafluoro-2,2-dimethyloctanedionato Tb0.2, La0.8
dimethylbenzylammonium tetrakis 1-phenyl-1,3-butanedionato Tb0.2, La0.8
triallylammonium tetrakis acetylacetonato Tb0.2, La0.8
triallylammonium tetrakis dibenzoylmethanato Tb0.2, La0.8
triallylammonium tetrakis thenoyltrifluoroacetonato Tb0.2, La0.8
triallylammonium tetrakis 2,2,6,6-tetramethylheptanedionato Tb0.2, La0.8
triallylammonium tetrakis 3-methylpentane-2,4-dionato Tb0.2, La0.8
triallylammonium tetrakis 3-ethylpentane-2,4-dionato Tb0.2, La0.8
triallylammonium tetrakis pivaloyltrifluoroacetonato Tb0.2, La0.8
triallylammonium tetrakis trifluoroacetylacetonato Tb0.2, La0.8
triallylammonium tetrakis hexafluoroacetylacetonato Tb0.2, La0.8
triallylammonium tetrakis 6,6,7,7,8,8,8-heptafluoro-2,2-dimethyloctanedionato Tb0.2, La0.8
triallylammonium tetrakis 1-phenyl-1,3-butanedionato Tb0.2, La0.8
anilinium tetrakis acetylacetonato Tb0.2, La0.8
anilinium tetrakis dibenzoylmethanato Tb0.2, La0.8
anilinium tetrakis thenoyltrifluoroacetonato Tb0.2, La0.8
anilinium tetrakis 2,2,6,6-tetramethylheptanedionato Tb0.2, La0.8
anilinium tetrakis 3-methylpentane-2,4-dionato Tb0.2, La0.8
anilinium tetrakis 3-ethylpentane-2,4-dionato Tb0.2, La0.8
anilinium tetrakis pivaloyltrifluoroacetonato Tb0.2, La0.8
anilinium tetrakis trifluoroacetylacetonato Tb0.2, La0.8
anilinium tetrakis hexafluoroacetylacetonato Tb0.2, La0.8
anilinium tetrakis 6,6,7,7,8,8,8-heptafluoro-2,2-dimethyloctanedionato Tb0.2, La0.8
anilinium tetrakis 1-phenyl-1,3-butanedionato Tb0.2, La0.8
triethylammonium tetrakis acetylacetonato Tb0.1, La0.9
triethylammonium tetrakis dibenzoylmethanato Tb0.1, La0.9
triethylammonium tetrakis thenoyltrifluoroacetonato Tb0.1, La0.9
triethylammonium tetrakis 2,2,6,6-tetramethylheptanedionato Tb0.1, La0.9
triethylammonium tetrakis 3-methylpentane-2,4-dionato Tb0.1, La0.9
triethylammonium tetrakis 3-ethylpentane-2,4-dionato Tb0.1, La0.9
triethylammonium tetrakis pivaloyltrifluoroacetonato Tb0.1, La0.9
triethylammonium tetrakis trifluoroacetylacetonato Tb0.1, La0.9
triethylammonium tetrakis hexafluoroacetylacetonato Tb0.1, La0.9 triethylammonium tetrakis 6,6,7,7,8,8,8-heptafluoro-2,2-dimethyloctanedionato Tb0.1, La0.9
triethylammonium tetrakis 1-phenyl-1,3-butanedionato Tb0.1, La0.9
morpholinium tetrakis acetylacetonato Tb0.1, La0.9
morpholinium tetrakis dibenzoylmethanato Tb0.1, La0.9
morpholinium tetrakis thenoyltrifluoroacetonato Tb0.1, La0.9
morpholinium tetrakis 2,2,6,6-tetramethylheptanedionato Tb0.1, La0.9
morpholinium tetrakis 3-methylpentane-2,4-dionato Tb0.1, La0.9
morpholinium tetrakis 3-ethylpentane-2,4-dionato Tb0.1, La0.9
morpholinium tetrakis pivaloyltrifluoroacetonato Tb0.1, La0.9
morpholinium tetrakis trifluoroacetylacetonato Tb0.1, La0.9
morpholinium tetrakis hexafluoroacetylacetonato Tb0.1, La0.9
morpholinium tetrakis 6,6,7,7,8,8,8-heptafluoro-2,2-dimethyloctanedionato Tb0.1, La0.9
morpholinium tetrakis 1-phenyl-1,3-butanedionato Tb0.1, La0.9
dimethylbenzylammonium tetrakis acetylacetonato Tb0.1, La0.9
dimethylbenzylammonium tetrakis dibenzoylmethanato Tb0.1, La0.9
dimethylbenzylammonium tetrakis thenoyltrifluoroacetonato Tb0.1, La0.9
dimethylbenzylammonium tetrakis 2,2,6,6-tetramethylheptanedionato Tb0.1, La0.9
dimethylbenzylammonium tetrakis 3-methylpentane-2,4-dionato Tb0.1, La0.9
dimethylbenzylammonium tetrakis 3-ethylpentane-2,4-dionato Tb0.1, La0.9
dimethylbenzylammonium tetrakis pivaloyltrifluoroacetonato Tb0.1, La0.9
dimethylbenzylammonium tetrakis trifluoroacetylacetonato Tb0.1, La0.9
dimethylbenzylammonium tetrakis hexafluoroacetylacetonato Tb0.1, La0.9
dimethylbenzylammonium tetrakis 6,6,7,7,8,8,8-heptafluoro-2,2-dimethyloctanedionato Tb0.1, La0.9
dimethylbenzylammonium tetrakis 1-phenyl-1,3-butanedionato Tb0.1, La0.9
triallylammonium tetrakis acetylacetonato Tb0.1, La0.9
triallylammonium tetrakis dibenzoylmethanato Tb0.1, La0.9
triallylammonium tetrakis thenoyltrifluoroacetonato Tb0.1, La0.9
triallylammonium tetrakis 2,2,6,6-tetramethylheptanedionato Tb0.1, La0.9
triallylammonium tetrakis 3-methylpentane-2,4-dionato Tb0.1, La0.9
triallylammonium tetrakis 3-ethylpentane-2,4-dionato Tb0.1, La0.9
triallylammonium tetrakis pivaloyltrifluoroacetonato Tb0.1, La0.9
triallylammonium tetrakis trifluoroacetylacetonato Tb0.1, La0.9
triallylammonium tetrakis hexafluoroacetylacetonato Tb0.1, La0.9
triallylammonium tetrakis 6,6,7,7,8,8,8-heptafluoro-2,2-dimethyloctanedionato Tb0.1, La0.9
triallylammonium tetrakis 1-phenyl-1,3-butanedionato Tb0.1, La0.9
anilinium tetrakis acetylacetonato Tb0.1, La0.9
anilinium tetrakis dibenzoylmethanato Tb0.1, La0.9
anilinium tetrakis thenoyltrifluoroacetonato Tb0.1, La0.9
anilinium tetrakis 2,2,6,6-tetramethylheptanedionato Tb0.1, La0.9
anilinium tetrakis 3-methylpentane-2,4-dionato Tb0.1, La0.9
anilinium tetrakis 3-ethylpentane-2,4-dionato Tb0.1, La0.9
anilinium tetrakis pivaloyltrifluoroacetonato Tb0.1, La0.9
anilinium tetrakis trifluoroacetylacetonato Tb0.1, La0.9
anilinium tetrakis hexafluoroacetylacetonato Tb0.1, La0.9
anilinium tetrakis 6,6,7,7,8,8,8-heptafluoro-2,2-dimethyloctanedionato Tb0.1, La0.9
anilinium tetrakis 1-phenyl-1,3-butanedionato Tb0.1, La0.9
triethylammonium tetrakis acetylacetonato Tb0.01, La0.99
triethylammonium tetrakis dibenzoylmethanato Tb0.01, La0.99
triethylammonium tetrakis thenoyltrifluoroacetonato Tb0.01, La0.99
triethylammonium tetrakis 2,2,6,6-tetramethylheptanedionato Tb0.01, La0.99
triethylammonium tetrakis 3-methylpentane-2,4-dionato Tb0.01, La0.99
triethylammonium tetrakis 3-ethylpentane-2,4-dionato Tb0.01, La0.99
triethylammonium tetrakis pivaloyltrifluoroacetonato Tb0.01, La0.99
triethylammonium tetrakis trifluoroacetylacetonato Tb0.01, La0.99
triethylammonium tetrakis hexafluoroacetylacetonato Tb0.01, La0.99
triethylammonium tetrakis 6,6,7,7,8,8,8-heptafluoro-2,2-dimethyloctanedionato Tb0.01, La0.99
triethylammonium tetrakis 1-phenyl-1,3-butanedionato Tb0.01, La0.99
morpholinium tetrakis acetylacetonato Tb0.01, La0.99
morpholinium tetrakis dibenzoylmethanato Tb0.01, La0.99
morpholinium tetrakis thenoyltrifluoroacetonato Tb0.01, La0.99
morpholinium tetrakis 2,2,6,6-tetramethylheptanedionato Tb0.01, La0.99
morpholinium tetrakis 3-methylpentane-2,4-dionato Tb0.01, La0.99
morpholinium tetrakis 3-ethylpentane-2,4-dionato Tb0.01, La0.99
morpholinium tetrakis pivaloyltrifluoroacetonato Tb0.01, La0.99
morpholinium tetrakis trifluoroacetylacetonato Tb0.01, La0.99
morpholinium tetrakis hexafluoroacetylacetonato Tb0.01, La0.99
morpholinium tetrakis 6,6,7,7,8,8,8-heptafluoro-2,2-dimethyloctanedionato Tb0.01, La0.99
morpholinium tetrakis 1-phenyl-1,3-butanedionato Tb0.01, La0.99
dimethylbenzylammonium tetrakis acetylacetonato Tb0.01, La0.99
dimethylbenzylammonium tetrakis dibenzoylmethanato Tb0.01, La0.99
dimethylbenzylammonium tetrakis thenoyltrifluoroacetonato Tb0.01, La0.99
dimethylbenzylammonium tetrakis 2,2,6,6-tetramethylheptanedionato Tb0.01, La0.99
dimethylbenzylammonium tetrakis 3-methylpentane-2,4-dionato Tb0.01, La0.99
dimethylbenzylammonium tetrakis 3-ethylpentane-2,4-dionato Tb0.01, La0.99
dimethylbenzylammonium tetrakis pivaloyltrifluoroacetonato Tb0.01, La0.99 dimethylbenzylammonium tetrakis trifluoroacetylacetonato Tb0.01, La0.99
dimethylbenzylammonium tetrakis hexafluoroacetylacetonato Tb0.01, La0.99
dimethylbenzylammonium tetrakis 6,6,7,7,8,8,8-heptafluoro-2,2-dimethyloctanedionato Tb0.01, La0.99
dimethylbenzylammonium tetrakis 1-phenyl-1,3-butanedionato Tb0.01, La0.99
triallylammonium tetrakis acetylacetonato Tb0.01, La0.99
triallylammonium tetrakis dibenzoylmethanato Tb0.01, La0.99
triallylammonium tetrakis thenoyltrifluoroacetonato Tb0.01, La0.99
triallylammonium tetrakis 2,2,6,6-tetramethylheptanedionato Tb0.01, La0.99
triallylammonium tetrakis 3-methylpentane-2,4-dionato Tb0.01, La0.99
triallylammonium tetrakis 3-ethylpentane-2,4-dionato Tb0.01, La0.99
triallylammonium tetrakis pivaloyltrifluoroacetonato Tb0.01, La0.99
triallylammonium tetrakis trifluoroacetylacetonato Tb0.01, La0.99
triallylammonium tetrakis hexafluoroacetylacetonato Tb0.01, La0.99
triallylammonium tetrakis 6,6,7,7,8,8,8-heptafluoro-2,2-dimethyloctanedionato Tb0.01, La0.99
triallylammonium tetrakis 1-phenyl-1,3-butanedionato Tb0.01, La0.99
anilinium tetrakis acetylacetonato Tb0.01, La0.99
anilinium tetrakis dibenzoylmethanato Tb0.01, La0.99
anilinium tetrakis thenoyltrifluoroacetonato Tb0.01, La0.99
anilinium tetrakis 2,2,6,6-tetramethylheptanedionato Tb0.01, La0.99
anilinium tetrakis 3-methylpentane-2,4-dionato Tb0.01, La0.99
anilinium tetrakis 3-ethylpentane-2,4-dionato Tb0.01, La0.99
anilinium tetrakis pivaloyltrifluoroacetonato Tb0.01, La0.99
anilinium tetrakis trifluoroacetylacetonato Tb0.01, La0.99
anilinium tetrakis hexafluoroacetylacetonato Tb0.01, La0.99
anilinium tetrakis 6,6,7,7,8,8,8-heptafluoro-2,2-dimethyloctanedionato Tb0.01, La0.99
anilinium tetrakis 1-phenyl-1,3-butanedionato Tb0.01, La0.99
triethylammonium tetrakis acetylacetonato Eu0.5, La0.5
triethylammonium tetrakis dibenzoylmethanato Eu0.5, La0.5
triethylammonium tetrakis thenoyltrifluoroacetonato Eu0.5, La0.5
triethylammonium tetrakis 2,2,6,6-tetramethylheptanedionato Eu0.5, La0.5
triethylammonium tetrakis 3-methylpentane-2,4-dionato Eu0.5, La0.5
triethylammonium tetrakis 3-ethylpentane-2,4-dionato Eu0.5, La0.5
triethylammonium tetrakis pivaloyltrifluoroacetonato Eu0.5, La0.5
triethylammonium tetrakis trifluoroacetylacetonato Eu0.5, La0.5
triethylammonium tetrakis hexafluoroacetylacetonato Eu0.5, La0.5
triethylammonium tetrakis 6,6,7,7,8,8,8-heptafluoro-2,2-dimethyloctanedionato Eu0.5, La0.5
triethylammonium tetrakis 1-phenyl-1,3-butanedionato Eu0.5, La0.5
morpholinium tetrakis acetylacetonato Eu0.5, La0.5
morpholinium tetrakis dibenzoylmethanato Eu0.5, La0.5
morpholinium tetrakis thenoyltrifluoroacetonato Eu0.5, La0.5
morpholinium tetrakis 2,2,6,6-tetramethylheptanedionato Eu0.5, La0.5
morpholinium tetrakis 3-methylpentane-2,4-dionato Eu0.5, La0.5
morpholinium tetrakis 3-ethylpentane-2,4-dionato Eu0.5, La0.5
morpholinium tetrakis pivaloyltrifluoroacetonato Eu0.5, La0.5
morpholinium tetrakis trifluoroacetylacetonato Eu0.5, La0.5
morpholinium tetrakis hexafluoroacetylacetonato Eu0.5, La0.5
morpholinium tetrakis 6,6,7,7,8,8,8-heptafluoro-2,2-dimethyloctanedionato Eu0.5, La0.5
morpholinium tetrakis 1-phenyl-1,3-butanedionato Eu0.5, La0.5
dimethylbenzylammonium tetrakis acetylacetonato Eu0.5, La0.5
dimethylbenzylammonium tetrakis dibenzoylmethanato Eu0.5, La0.5
dimethylbenzylammonium tetrakis thenoyltrifluoroacetonato Eu0.5, La0.5
dimethylbenzylammonium tetrakis 2,2,6,6-tetramethylheptanedionato Eu0.5, La0.5
dimethylbenzylammonium tetrakis 3-methylpentane-2,4-dionato Eu0.5, La0.5
dimethylbenzylammonium tetrakis 3-ethylpentane-2,4-dionato Eu0.5, La0.5
dimethylbenzylammonium tetrakis pivaloyltrifluoroacetonato Eu0.5, La0.5
dimethylbenzylammonium tetrakis trifluoroacetylacetonato Eu0.5, La0.5
dimethylbenzylammonium tetrakis hexafluoroacetylacetonato Eu0.5, La0.5
dimethylbenzylammonium tetrakis 6,6,7,7,8,8,8-heptafluoro-2,2-dimethyloctanedionato Eu0.5, La0.5
dimethylbenzylammonium tetrakis 1-phenyl-1,3-butanedionato Eu0.5, La0.5
triallylammonium tetrakis acetylacetonato Eu0.5, La0.5
triallylammonium tetrakis dibenzoylmethanato Eu0.5, La0.5
triallylammonium tetrakis thenoyltrifluoroacetonato Eu0.5, La0.5
triallylammonium tetrakis 2,2,6,6-tetramethylheptanedionato Eu0.5, La0.5
triallylammonium tetrakis 3-methylpentane-2,4-dionato Eu0.5, La0.5
triallylammonium tetrakis 3-ethylpentane-2,4-dionato Eu0.5, La0.5
triallylammonium tetrakis pivaloyltrifluoroacetonato Eu0.5, La0.5
triallylammonium tetrakis trifluoroacetylacetonato Eu0.5, La0.5
triallylammonium tetrakis hexafluoroacetylacetonato Eu0.5, La0.5
triallylammonium tetrakis 6,6,7,7,8,8,8-heptafluoro-2,2-dimethyloctanedionato Eu0.5, La0.5
triallylammonium tetrakis 1-phenyl-1,3-butanedionato Eu0.5, La0.5
anilinium tetrakis acetylacetonato Eu0.5, La0.5
anilinium tetrakis dibenzoylmethanato Eu0.5, La0.5
anilinium tetrakis thenoyltrifluoroacetonato Eu0.5, La0.5
anilinium tetrakis 2,2,6,6-tetramethylheptanedionato Eu0.5, La0.5
anilinium tetrakis 3-methylpentane-2,4-dionato Eu0.5, La0.5 anilinium tetrakis 3-ethylpentane-2,4-dionato Eu0.5, La0.5
anilinium tetrakis pivaloyltrifluoroacetonato Eu0.5, La0.5
anilinium tetrakis trifluoroacetylacetonato Eu0.5, La0.5
anilinium tetrakis hexafluoroacetylacetonato Eu0.5, La0.5
anilinium tetrakis 6,6,7,7,8,8,8-heptafluoro-2,2-dimethyloctanedionato Eu0.5, La0.5
anilinium tetrakis 1-phenyl-1,3-butanedionato Eu0.5, La0.5
triethylammonium tetrakis acetylacetonato Eu0.2, La0.8
triethylammonium tetrakis dibenzoylmethanato Eu0.2, La0.8
triethylammonium tetrakis thenoyltrifluoroacetonato Eu0.2, La0.8
triethylammonium tetrakis 2,2,6,6-tetramethylheptanedionato Eu0.2, La0.8
triethylammonium tetrakis 3-methylpentane-2,4-dionato Eu0.2, La0.8
triethylammonium tetrakis 3-ethylpentane-2,4-dionato Eu0.2, La0.8
triethylammonium tetrakis pivaloyltrifluoroacetonato Eu0.2, La0.8
triethylammonium tetrakis trifluoroacetylacetonato Eu0.2, La0.8
triethylammonium tetrakis hexafluoroacetylacetonato Eu0.2, La0.8
triethylammonium tetrakis 6,6,7,7,8,8,8-heptafluoro-2,2-dimethyloctanedionato Eu0.2, La0.8
triethylammonium tetrakis 1-phenyl-1,3-butanedionato Eu0.2, La0.8
morpholinium tetrakis acetylacetonato Eu0.2, La0.8
morpholinium tetrakis dibenzoylmethanato Eu0.2, La0.8
morpholinium tetrakis thenoyltrifluoroacetonato Eu0.2, La0.8
morpholinium tetrakis 2,2,6,6-tetramethylheptanedionato Eu0.2, La0.8
morpholinium tetrakis 3-methylpentane-2,4-dionato Eu0.2, La0.8
morpholinium tetrakis 3-ethylpentane-2,4-dionato Eu0.2, La0.8
morpholinium tetrakis pivaloyltrifluoroacetonato Eu0.2, La0.8
morpholinium tetrakis trifluoroacetylacetonato Eu0.2, La0.8
morpholinium tetrakis hexafluoroacetylacetonato Eu0.2, La0.8
morpholinium tetrakis 6,6,7,7,8,8,8-heptafluoro-2,2-dimethyloctanedionato Eu0.2, La0.8
morpholinium tetrakis 1-phenyl-1,3-butanedionato Eu0.2, La0.8
dimethylbenzylammonium tetrakis acetylacetonato Eu0.2, La0.8
dimethylbenzylammonium tetrakis dibenzoylmethanato Eu0.2, La0.8
dimethylbenzylammonium tetrakis thenoyltrifluoroacetonato Eu0.2, La0.8
dimethylbenzylammonium tetrakis 2,2,6,6-tetramethylheptanedionato Eu0.2, La0.8
dimethylbenzylammonium tetrakis 3-methylpentane-2,4-dionato Eu0.2, La0.8
dimethylbenzylammonium tetrakis 3-ethylpentane-2,4-dionato Eu0.2, La0.8
dimethylbenzylammonium tetrakis pivaloyltrifluoroacetonato Eu0.2, La0.8
dimethylbenzylammonium tetrakis trifluoroacetylacetonato Eu0.2, La0.8
dimethylbenzylammonium tetrakis hexafluoroacetylacetonato Eu0.2, La0.8
dimethylbenzylammonium tetrakis 6,6,7,7,8,8,8-heptafluoro-2,2-dimethyloctanedionato Eu0.2, La0.8
dimethylbenzylammonium tetrakis 1-phenyl-1,3-butanedionato Eu0.2, La0.8
triallylammonium tetrakis acetylacetonato Eu0.2, La0.8
triallylammonium tetrakis dibenzoylmethanato Eu0.2, La0.8
triallylammonium tetrakis thenoyltrifluoroacetonato Eu0.2, La0.8
triallylammonium tetrakis 2,2,6,6-tetramethylheptanedionato Eu0.2, La0.8
triallylammonium tetrakis 3-methylpentane-2,4-dionato Eu0.2, La0.8
triallylammonium tetrakis 3-ethylpentane-2,4-dionato Eu0.2, La0.8
triallylammonium tetrakis pivaloyltrifluoroacetonato Eu0.2, La0.8
triallylammonium tetrakis trifluoroacetylacetonato Eu0.2, La0.8
triallylammonium tetrakis hexafluoroacetylacetonato Eu0.2, La0.8
triallylammonium tetrakis 6,6,7,7,8,8,8-heptafluoro-2,2-dimethyloctanedionato Eu0.2, La0.8
triallylammonium tetrakis 1-phenyl-1,3-butanedionato Eu0.2, La0.8
anilinium tetrakis acetylacetonato Eu0.2, La0.8
anilinium tetrakis dibenzoylmethanato Eu0.2, La0.8
anilinium tetrakis thenoyltrifluoroacetonato Eu0.2, La0.8
anilinium tetrakis 2,2,6,6-tetramethylheptanedionato Eu0.2, La0.8
anilinium tetrakis 3-methylpentane-2,4-dionato Eu0.2, La0.8
anilinium tetrakis 3-ethylpentane-2,4-dionato Eu0.2, La0.8
anilinium tetrakis pivaloyltrifluoroacetonato Eu0.2, La0.8
anilinium tetrakis trifluoroacetylacetonato Eu0.2, La0.8
anilinium tetrakis hexafluoroacetylacetonato Eu0.2, La0.8
anilinium tetrakis 6,6,7,7,8,8,8-heptafluoro-2,2-dimethyloctanedionato Eu0.2, La0.8
anilinium tetrakis 1-phenyl-1,3-butanedionato Eu0.2, La0.8
triethylammonium tetrakis acetylacetonato Eu0.1, La0.9
triethylammonium tetrakis dibenzoylmethanato Eu0.1, La0.9
triethylammonium tetrakis thenoyltrifluoroacetonato Eu0.1, La0.9
triethylammonium tetrakis 2,2,6,6-tetramethylheptanedionato Eu0.1, La0.9
triethylammonium tetrakis 3-methylpentane-2,4-dionato Eu0.1, La0.9
triethylammonium tetrakis 3-ethylpentane-2,4-dionato Eu0.1, La0.9
triethylammonium tetrakis pivaloyltrifluoroacetonato Eu0.1, La0.9
triethylammonium tetrakis trifluoroacetylacetonato Eu0.1, La0.9
triethylammonium tetrakis hexafluoroacetylacetonato Eu0.1, La0.9
triethylammonium tetrakis 6,6,7,7,8,8,8-heptafluoro-2,2-dimethyloctanedionato Eu0.1, La0.9
triethylammonium tetrakis 1-phenyl-1,3-butanedionato Eu0.1, La0.9
morpholinium tetrakis acetylacetonato Eu0.1, La0.9
morpholinium tetrakis dibenzoylmethanato Eu0.1, La0.9
morpholinium tetrakis thenoyltrifluoroacetonato Eu0.1, La0.9
morpholinium tetrakis 2,2,6,6-tetramethylheptanedionato Eu0.1, La0.9
morpholinium tetrakis 3-methylpentane-2,4-dionato Eu0.1, La0.9
morpholinium tetrakis 3-ethylpentane-2,4-dionato Eu0.1, La0.9 morpholinium tetrakis pivaloyltrifluoroacetonato Eu0.1, La0.9
morpholinium tetrakis trifluoroacetylacetonato Eu0.1, La0.9
morpholinium tetrakis hexafluoroacetylacetonato Eu0.1, La0.9
morpholinium tetrakis 6,6,7,7,8,8,8-heptafluoro-2,2-dimethyloctanedionato Eu0.1, La0.9
morpholinium tetrakis 1-phenyl-1,3-butanedionato Eu0.1, La0.9
dimethylbenzylammonium tetrakis acetylacetonato Eu0.1, La0.9
dimethylbenzylammonium tetrakis dibenzoylmethanato Eu0.1, La0.9
dimethylbenzylammonium tetrakis thenoyltrifluoroacetonato Eu0.1, La0.9
dimethylbenzylammonium tetrakis 2,2,6,6-tetramethylheptanedionato Eu0.1, La0.9
dimethylbenzylammonium tetrakis 3-methylpentane-2,4-dionato Eu0.1, La0.9
dimethylbenzylammonium tetrakis 3-ethylpentane-2,4-dionato Eu0.1, La0.9
dimethylbenzylammonium tetrakis pivaloyltrifluoroacetonato Eu0.1, La0.9
dimethylbenzylammonium tetrakis trifluoroacetylacetonato Eu0.1, La0.9
dimethylbenzylammonium tetrakis hexafluoroacetylacetonato Eu0.1, La0.9
dimethylbenzylammonium tetrakis 6,6,7,7,8,8,8-heptafluoro-2,2-dimethyloctanedionato Eu0.1, La0.9
dimethylbenzylammonium tetrakis 1-phenyl-1,3-butanedionato Eu0.1, La0.9
triallylammonium tetrakis acetylacetonato Eu0.1, La0.9
triallylammonium tetrakis dibenzoylmethanato Eu0.1, La0.9
triallylammonium tetrakis thenoyltrifluoroacetonato Eu0.1, La0.9
triallylammonium tetrakis 2,2,6,6-tetramethylheptanedionato Eu0.1, La0.9
triallylammonium tetrakis 3-methylpentane-2,4-dionato Eu0.1, La0.9
triallylammonium tetrakis 3-ethylpentane-2,4-dionato Eu0.1, La0.9
triallylammonium tetrakis pivaloyltrifluoroacetonato Eu0.1, La0.9
triallylammonium tetrakis trifluoroacetylacetonato Eu0.1, La0.9
triallylammonium tetrakis hexafluoroacetylacetonato Eu0.1, La0.9
triallylammonium tetrakis 6,6,7,7,8,8,8-heptafluoro-2,2-dimethyloctanedionato Eu0.1, La0.9
triallylammonium tetrakis 1-phenyl-1,3-butanedionato Eu0.1, La0.9
anilinium tetrakis acetylacetonato Eu0.1, La0.9
anilinium tetrakis dibenzoylmethanato Eu0.1, La0.9
anilinium tetrakis thenoyltrifluoroacetonato Eu0.1, La0.9
anilinium tetrakis 2,2,6,6-tetramethylheptanedionato Eu0.1, La0.9
anilinium tetrakis 3-methylpentane-2,4-dionato Eu0.1, La0.9
anilinium tetrakis 3-ethylpentane-2,4-dionato Eu0.1, La0.9
anilinium tetrakis pivaloyltrifluoroacetonato Eu0.1, La0.9
anilinium tetrakis trifluoroacetylacetonato Eu0.1, La0.9
anilinium tetrakis hexafluoroacetylacetonato Eu0.1, La0.9
anilinium tetrakis 6,6,7,7,8,8,8-heptafluoro-2,2-dimethyloctanedionato Eu0.1, La0.9
anilinium tetrakis 1-phenyl-1,3-butanedionato Eu0.1, La0.9
triethylammonium tetrakis acetylacetonato Eu0.01, La0.99
triethylammonium tetrakis dibenzoylmethanato Eu0.01, La0.99
triethylammonium tetrakis thenoyltrifluoroacetonato Eu0.01, La0.99
triethylammonium tetrakis 2,2,6,6-tetramethylheptanedionato Eu0.01, La0.99
triethylammonium tetrakis 3-methylpentane-2,4-dionato Eu0.01, La0.99
triethylammonium tetrakis 3-ethylpentane-2,4-dionato Eu0.01, La0.99
triethylammonium tetrakis pivaloyltrifluoroacetonato Eu0.01, La0.99
triethylammonium tetrakis trifluoroacetylacetonato Eu0.01, La0.99
triethylammonium tetrakis hexafluoroacetylacetonato Eu0.01, La0.99
triethylammonium tetrakis 6,6,7,7,8,8,8-heptafluoro-2,2-dimethyloctanedionato Eu0.01, La0.99
triethylammonium tetrakis 1-phenyl-1,3-butanedionato Eu0.01, La0.99
morpholinium tetrakis acetylacetonato Eu0.01, La0.99
morpholinium tetrakis dibenzoylmethanato Eu0.01, La0.99
morpholinium tetrakis thenoyltrifluoroacetonato Eu0.01, La0.99
morpholinium tetrakis 2,2,6,6-tetramethylheptanedionato Eu0.01, La0.99
morpholinium tetrakis 3-methylpentane-2,4-dionato Eu0.01, La0.99
morpholinium tetrakis 3-ethylpentane-2,4-dionato Eu0.01, La0.99
morpholinium tetrakis pivaloyltrifluoroacetonato Eu0.01, La0.99
morpholinium tetrakis trifluoroacetylacetonato Eu0.01, La0.99
morpholinium tetrakis hexafluoroacetylacetonato Eu0.01, La0.99
morpholinium tetrakis 6,6,7,7,8,8,8-heptafluoro-2,2-dimethyloctanedionato Eu0.01, La0.99
morpholinium tetrakis 1-phenyl-1,3-butanedionato Eu0.01, La0.99
dimethylbenzylammonium tetrakis acetylacetonato Eu0.01, La0.99
dimethylbenzylammonium tetrakis dibenzoylmethanato Eu0.01, La0.99
dimethylbenzylammonium tetrakis thenoyltrifluoroacetonato Eu0.01, La0.99
dimethylbenzylammonium tetrakis 2,2,6,6-tetramethylheptanedionato Eu0.01, La0.99
dimethylbenzylammonium tetrakis 3-methylpentane-2,4-dionato Eu0.01, La0.99
dimethylbenzylammonium tetrakis 3-ethylpentane-2,4-dionato Eu0.01, La0.99
dimethylbenzylammonium tetrakis pivaloyltrifluoroacetonato Eu0.01, La0.99
dimethylbenzylammonium tetrakis trifluoroacetylacetonato Eu0.01, La0.99
dimethylbenzylammonium tetrakis hexafluoroacetylacetonato Eu0.01, La0.99
dimethylbenzylammonium tetrakis 6,6,7,7,8,8,8-heptafluoro-2,2-dimethyloctanedionato Eu0.01, La0.99
dimethylbenzylammonium tetrakis 1-phenyl-1,3-butanedionato Eu0.01, La0.99
triallylammonium tetrakis acetylacetonato Eu0.01, La0.99
triallylammonium tetrakis dibenzoylmethanato Eu0.01, La0.99
triallylammonium tetrakis thenoyltrifluoroacetonato Eu0.01, La0.99 triallylammonium tetrakis 2,2,6,6-tetramethylheptanedionato Eu0.01, La0.99
triallylammonium tetrakis 3-methylpentane-2,4-dionato Eu0.01, La0.99
triallylammonium tetrakis 3-ethylpentane-2,4-dionato Eu0.01, La0.99
triallylammonium tetrakis pivaloyltrifluoroacetonato Eu0.01, La0.99
triallylammonium tetrakis trifluoroacetylacetonato Eu0.01, La0.99
triallylammonium tetrakis hexafluoroacetylacetonato Eu0.01, La0.99
triallylammonium tetrakis 6,6,7,7,8,8,8-heptafluoro-2,2-dimethyloctanedionato Eu0.01, La0.99
triallylammonium tetrakis 1-phenyl-1,3-butanedionato Eu0.01, La0.99
anilinium tetrakis acetylacetonato Eu0.01, La0.99
anilinium tetrakis dibenzoylmethanato Eu0.01, La0.99
anilinium tetrakis thenoyltrifluoroacetonato Eu0.01, La0.99
anilinium tetrakis 2,2,6,6-tetramethylheptanedionato Eu0.01, La0.99
anilinium tetrakis 3-methylpentane-2,4-dionato Eu0.01, La0.99
anilinium tetrakis 3-ethylpentane-2,4-dionato Eu0.01, La0.99
anilinium tetrakis pivaloyltrifluoroacetonato Eu0.01, La0.99
anilinium tetrakis trifluoroacetylacetonato Eu0.01, La0.99
anilinium tetrakis hexafluoroacetylacetonato Eu0.01, La0.99
anilinium tetrakis 6,6,7,7,8,8,8-heptafluoro-2,2-dimethyloctanedionato Eu0.01, La0.99
anilinium tetrakis 1-phenyl-1,3-butanedionato Eu0.01, La0.99
triethylammonium tetrakis acetylacetonato Eu0.5, La0.5
triethylammonium tetrakis dibenzoylmethanato Eu0.5, La0.5
triethylammonium tetrakis thenoyltrifluoroacetonato Eu0.5, La0.5
triethylammonium tetrakis 2,2,6,6-tetramethylheptanedionato Eu0.5, La0.5
triethylammonium tetrakis 3-methylpentane-2,4-dionato Eu0.5, La0.5
triethylammonium tetrakis 3-ethylpentane-2,4-dionato Eu0.5, La0.5
triethylammonium tetrakis pivaloyltrifluoroacetonato Eu0.5, La0.5
triethylammonium tetrakis trifluoroacetylacetonato Eu0.5, La0.5
triethylammonium tetrakis hexafluoroacetylacetonato Eu0.5, La0.5
triethylammonium tetrakis 6,6,7,7,8,8,8-heptafluoro-2,2-dimethyloctanedionato Eu0.5, La0.5
triethylammonium tetrakis 1-phenyl-1,3-butanedionato Eu0.5, La0.5
morpholinium tetrakis acetylacetonato Eu0.5, La0.5
morpholinium tetrakis dibenzoylmethanato Eu0.5, La0.5
morpholinium tetrakis thenoyltrifluoroacetonato Eu0.5, La0.5
morpholinium tetrakis 2,2,6,6-tetramethylheptanedionato Eu0.5, La0.5
morpholinium tetrakis 3-methylpentane-2,4-dionato Eu0.5, La0.5
morpholinium tetrakis 3-ethylpentane-2,4-dionato Eu0.5, La0.5
morpholinium tetrakis pivaloyltrifluoroacetonato Eu0.5, La0.5
morpholinium tetrakis trifluoroacetylacetonato Eu0.5, La0.5
morpholinium tetrakis hexafluoroacetylacetonato Eu0.5, La0.5
morpholinium tetrakis 6,6,7,7,8,8,8-heptafluoro-2,2-dimethyloctanedionato Eu0.5, La0.5
morpholinium tetrakis 1-phenyl-1,3-butanedionato Eu0.5, La0.5
dimethylbenzylammonium tetrakis acetylacetonato Eu0.5, La0.5
dimethylbenzylammonium tetrakis dibenzoylmethanato Eu0.5, La0.5
dimethylbenzylammonium tetrakis thenoyltrifluoroacetonato Eu0.5, La0.5
dimethylbenzylammonium tetrakis 2,2,6,6-tetramethylheptanedionato Eu0.5, La0.5
dimethylbenzylammonium tetrakis 3-methylpentane-2,4-dionato Eu0.5, La0.5
dimethylbenzylammonium tetrakis 3-ethylpentane-2,4-dionato Eu0.5, La0.5
dimethylbenzylammonium tetrakis pivaloyltrifluoroacetonato Eu0.5, La0.5
dimethylbenzylammonium tetrakis trifluoroacetylacetonato Eu0.5, La0.5
dimethylbenzylammonium tetrakis hexafluoroacetylacetonato Eu0.5, La0.5
dimethylbenzylammonium tetrakis 6,6,7,7,8,8,8-heptafluoro-2,2-dimethyloctanedionato Eu0.5, La0.5
dimethylbenzylammonium tetrakis 1-phenyl-1,3-butanedionato Eu0.5, La0.5
triallylammonium tetrakis acetylacetonato Eu0.5, La0.5
triallylammonium tetrakis dibenzoylmethanato Eu0.5, La0.5
triallylammonium tetrakis thenoyltrifluoroacetonato Eu0.5, La0.5
triallylammonium tetrakis 2,2,6,6-tetramethylheptanedionato Eu0.5, La0.5
triallylammonium tetrakis 3-methylpentane-2,4-dionato Eu0.5, La0.5
triallylammonium tetrakis 3-ethylpentane-2,4-dionato Eu0.5, La0.5
triallylammonium tetrakis pivaloyltrifluoroacetonato Eu0.5, La0.5
triallylammonium tetrakis trifluoroacetylacetonato Eu0.5, La0.5
triallylammonium tetrakis hexafluoroacetylacetonato Eu0.5, La0.5
triallylammonium tetrakis 6,6,7,7,8,8,8-heptafluoro-2,2-dimethyloctanedionato Eu0.5, La0.5
triallylammonium tetrakis 1-phenyl-1,3-butanedionato Eu0.5, La0.5
anilinium tetrakis acetylacetonato Eu0.5, La0.5
anilinium tetrakis dibenzoylmethanato Eu0.5, La0.5
anilinium tetrakis thenoyltrifluoroacetonato Eu0.5, La0.5
anilinium tetrakis 2,2,6,6-tetramethylheptanedionato Eu0.5, La0.5
anilinium tetrakis 3-methylpentane-2,4-dionato Eu0.5, La0.5
anilinium tetrakis 3-ethylpentane-2,4-dionato Eu0.5, La0.5
anilinium tetrakis pivaloyltrifluoroacetonato Eu0.5, La0.5
anilinium tetrakis trifluoroacetylacetonato Eu0.5, La0.5
anilinium tetrakis hexafluoroacetylacetonato Eu0.5, La0.5
anilinium tetrakis 6,6,7,7,8,8,8-heptafluoro-2,2-dimethyloctanedionato Eu0.5, La0.5
anilinium tetrakis 1-phenyl-1,3-butanedionato Eu0.5, La0.5
triethylammonium tetrakis acetylacetonato Eu0.2, La0.8
triethylammonium tetrakis dibenzoylmethanato Eu0.2, La0.8
triethylammonium tetrakis thenoyltrifluoroacetonato Eu0.2, La0.8 triethylammonium tetrakis 2,2,6,6-tetramethylheptanedionato Eu0.2, La0.8
triethylammonium tetrakis 3-methylpentane-2,4-dionato Eu0.2, La0.8
triethylammonium tetrakis 3-ethylpentane-2,4-dionato Eu0.2, La0.8
triethylammonium tetrakis pivaloyltrifluoroacetonato Eu0.2, La0.8
triethylammonium tetrakis trifluoroacetylacetonato Eu0.2, La0.8
triethylammonium tetrakis hexafluoroacetylacetonato Eu0.2, La0.8
triethylammonium tetrakis 6,6,7,7,8,8,8-heptafluoro-2,2-dimethyloctanedionato Eu0.2, La0.8
triethylammonium tetrakis 1-phenyl-1,3-butanedionato Eu0.2, La0.8
morpholinium tetrakis acetylacetonato Eu0.2, La0.8
morpholinium tetrakis dibenzoylmethanato Eu0.2, La0.8
morpholinium tetrakis thenoyltrifluoroacetonato Eu0.2, La0.8
morpholinium tetrakis 2,2,6,6-tetramethylheptanedionato Eu0.2, La0.8
morpholinium tetrakis 3-methylpentane-2,4-dionato Eu0.2, La0.8
morpholinium tetrakis 3-ethylpentane-2,4-dionato Eu0.2, La0.8
morpholinium tetrakis pivaloyltrifluoroacetonato Eu0.2, La0.8
morpholinium tetrakis trifluoroacetylacetonato Eu0.2, La0.8
morpholinium tetrakis hexafluoroacetylacetonato Eu0.2, La0.8
morpholinium tetrakis 6,6,7,7,8,8,8-heptafluoro-2,2-dimethyloctanedionato Eu0.2, La0.8
morpholinium tetrakis 1-phenyl-1,3-butanedionato Eu0.2, La0.8
dimethylbenzylammonium tetrakis acetylacetonato Eu0.2, La0.8
dimethylbenzylammonium tetrakis dibenzoylmethanato Eu0.2, La0.8
dimethylbenzylammonium tetrakis thenoyltrifluoroacetonato Eu0.2, La0.8
dimethylbenzylammonium tetrakis 2,2,6,6-tetramethylheptanedionato Eu0.2, La0.8
dimethylbenzylammonium tetrakis 3-methylpentane-2,4-dionato Eu0.2, La0.8
dimethylbenzylammonium tetrakis 3-ethylpentane-2,4-dionato Eu0.2, La0.8
dimethylbenzylammonium tetrakis pivaloyltrifluoroacetonato Eu0.2, La0.8
dimethylbenzylammonium tetrakis trifluoroacetylacetonato Eu0.2, La0.8
dimethylbenzylammonium tetrakis hexafluoroacetylacetonato Eu0.2, La0.8
dimethylbenzylammonium tetrakis 6,6,7,7,8,8,8-heptafluoro-2,2-dimethyloctanedionato Eu0.2, La0.8
dimethylbenzylammonium tetrakis 1-phenyl-1,3-butanedionato Eu0.2, La0.8
triallylammonium tetrakis acetylacetonato Eu0.2, La0.8
triallylammonium tetrakis dibenzoylmethanato Eu0.2, La0.8
triallylammonium tetrakis thenoyltrifluoroacetonato Eu0.2, La0.8
triallylammonium tetrakis 2,2,6,6-tetramethylheptanedionato Eu0.2, La0.8
triallylammonium tetrakis 3-methylpentane-2,4-dionato Eu0.2, La0.8
triallylammonium tetrakis 3-ethylpentane-2,4-dionato Eu0.2, La0.8
triallylammonium tetrakis pivaloyltrifluoroacetonato Eu0.2, La0.8
triallylammonium tetrakis trifluoroacetylacetonato Eu0.2, La0.8
triallylammonium tetrakis hexafluoroacetylacetonato Eu0.2, La0.8
triallylammonium tetrakis 6,6,7,7,8,8,8-heptafluoro-2,2-dimethyloctanedionato Eu0.2, La0.8
triallylammonium tetrakis 1-phenyl-1,3-butanedionato Eu0.2, La0.8
anilinium tetrakis acetylacetonato Eu0.2, La0.8
anilinium tetrakis dibenzoylmethanato Eu0.2, La0.8
anilinium tetrakis thenoyltrifluoroacetonato Eu0.2, La0.8
anilinium tetrakis 2,2,6,6-tetramethylheptanedionato Eu0.2, La0.8
anilinium tetrakis 3-methylpentane-2,4-dionato Eu0.2, La0.8
anilinium tetrakis 3-ethylpentane-2,4-dionato Eu0.2, La0.8
anilinium tetrakis pivaloyltrifluoroacetonato Eu0.2, La0.8
anilinium tetrakis trifluoroacetylacetonato Eu0.2, La0.8
anilinium tetrakis hexafluoroacetylacetonato Eu0.2, La0.8
anilinium tetrakis 6,6,7,7,8,8,8-heptafluoro-2,2-dimethyloctanedionato Eu0.2, La0.8
anilinium tetrakis 1-phenyl-1,3-butanedionato Eu0.2, La0.8
triethylammonium tetrakis acetylacetonato Eu0.1, La0.9
triethylammonium tetrakis dibenzoylmethanato Eu0.1, La0.9
triethylammonium tetrakis thenoyltrifluoroacetonato Eu0.1, La0.9
triethylammonium tetrakis 2,2,6,6-tetramethylheptanedionato Eu0.1, La0.9
triethylammonium tetrakis 3-methylpentane-2,4-dionato Eu0.1, La0.9
triethylammonium tetrakis 3-ethylpentane-2,4-dionato Eu0.1, La0.9
triethylammonium tetrakis pivaloyltrifluoroacetonato Eu0.1, La0.9
triethylammonium tetrakis trifluoroacetylacetonato Eu0.1, La0.9
triethylammonium tetrakis hexafluoroacetylacetonato Eu0.1, La0.9
triethylammonium tetrakis 6,6,7,7,8,8,8-heptafluoro-2,2-dimethyloctanedionato Eu0.1, La0.9
triethylammonium tetrakis 1-phenyl-1,3-butanedionato Eu0.1, La0.9
morpholinium tetrakis acetylacetonato Eu0.1, La0.9
morpholinium tetrakis dibenzoylmethanato Eu0.1, La0.9
morpholinium tetrakis thenoyltrifluoroacetonato Eu0.1, La0.9
morpholinium tetrakis 2,2,6,6-tetramethylheptanedionato Eu0.1, La0.9
morpholinium tetrakis 3-methylpentane-2,4-dionato Eu0.1, La0.9
morpholinium tetrakis 3-ethylpentane-2,4-dionato Eu0.1, La0.9
morpholinium tetrakis pivaloyltrifluoroacetonato Eu0.1, La0.9
morpholinium tetrakis trifluoroacetylacetonato Eu0.1, La0.9
morpholinium tetrakis hexafluoroacetylacetonato Eu0.1, La0.9
morpholinium tetrakis 6,6,7,7,8,8,8-heptafluoro-2,2-dimethyloctanedionato Eu0.1, La0.9
morpholinium tetrakis 1-phenyl-1,3-butanedionato Eu0.1, La0.9
dimethylbenzylammonium tetrakis acetylacetonato Eu0.1, La0.9 dimethylbenzylammonium tetrakis dibenzoylmethanato Eu0.1, La0.9
dimethylbenzylammonium tetrakis thenoyltrifluoroacetonato Eu0.1, La0.9
dimethylbenzylammonium tetrakis 2,2,6,6-tetramethylheptanedionato Eu0.1, La0.9
dimethylbenzylammonium tetrakis 3-methylpentane-2,4-dionato Eu0.1, La0.9
dimethylbenzylammonium tetrakis 3-ethylpentane-2,4-dionato Eu0.1, La0.9
dimethylbenzylammonium tetrakis pivaloyltrifluoroacetonato Eu0.1, La0.9
dimethylbenzylammonium tetrakis trifluoroacetylacetonato Eu0.1, La0.9
dimethylbenzylammonium tetrakis hexafluoroacetylacetonato Eu0.1, La0.9
dimethylbenzylammonium tetrakis 6,6,7,7,8,8,8-heptafluoro-2,2-dimethyloctanedionato Eu0.1, La0.9
dimethylbenzylammonium tetrakis 1-phenyl-1,3-butanedionato Eu0.1, La0.9
triallylammonium tetrakis acetylacetonato Eu0.1, La0.9
triallylammonium tetrakis dibenzoylmethanato Eu0.1, La0.9
triallylammonium tetrakis thenoyltrifluoroacetonato Eu0.1, La0.9
triallylammonium tetrakis 2,2,6,6-tetramethylheptanedionato Eu0.1, La0.9
triallylammonium tetrakis 3-methylpentane-2,4-dionato Eu0.1, La0.9
triallylammonium tetrakis 3-ethylpentane-2,4-dionato Eu0.1, La0.9
triallylammonium tetrakis pivaloyltrifluoroacetonato Eu0.1, La0.9
triallylammonium tetrakis trifluoroacetylacetonato Eu0.1, La0.9
triallylammonium tetrakis hexafluoroacetylacetonato Eu0.1, La0.9
triallylammonium tetrakis 6,6,7,7,8,8,8-heptafluoro-2,2-dimethyloctanedionato Eu0.1, La0.9
triallylammonium tetrakis 1-phenyl-1,3-butanedionato Eu0.1, La0.9
anilinium tetrakis acetylacetonato Eu0.1, La0.9
anilinium tetrakis dibenzoylmethanato Eu0.1, La0.9
anilinium tetrakis thenoyltrifluoroacetonato Eu0.1, La0.9
anilinium tetrakis 2,2,6,6-tetramethylheptanedionato Eu0.1, La0.9
anilinium tetrakis 3-methylpentane-2,4-dionato Eu0.1, La0.9
anilinium tetrakis 3-ethylpentane-2,4-dionato Eu0.1, La0.9
anilinium tetrakis pivaloyltrifluoroacetonato Eu0.1, La0.9
anilinium tetrakis trifluoroacetylacetonato Eu0.1, La0.9
anilinium tetrakis hexafluoroacetylacetonato Eu0.1, La0.9
anilinium tetrakis 6,6,7,7,8,8,8-heptafluoro-2,2-dimethyloctanedionato Eu0.1, La0.9
anilinium tetrakis 1-phenyl-1,3-butanedionato Eu0.1, La0.9
triethylammonium tetrakis acetylacetonato Eu0.01, La0.99
triethylammonium tetrakis dibenzoylmethanato Eu0.01, La0.99
triethylammonium tetrakis thenoyltrifluoroacetonato Eu0.01, La0.99
triethylammonium tetrakis 2,2,6,6-tetramethylheptanedionato Eu0.01, La0.99
triethylammonium tetrakis 3-methylpentane-2,4-dionato Eu0.01, La0.99
triethylammonium tetrakis 3-ethylpentane-2,4-dionato Eu0.01, La0.99
triethylammonium tetrakis pivaloyltrifluoroacetonato Eu0.01, La0.99
triethylammonium tetrakis trifluoroacetylacetonato Eu0.01, La0.99
triethylammonium tetrakis hexafluoroacetylacetonato Eu0.01, La0.99
triethylammonium tetrakis 6,6,7,7,8,8,8-heptafluoro-2,2-dimethyloctanedionato Eu0.01, La0.99
triethylammonium tetrakis 1-phenyl-1,3-butanedionato Eu0.01, La0.99
morpholinium tetrakis acetylacetonato Eu0.01, La0.99
morpholinium tetrakis dibenzoylmethanato Eu0.01, La0.99
morpholinium tetrakis thenoyltrifluoroacetonato Eu0.01, La0.99
morpholinium tetrakis 2,2,6,6-tetramethylheptanedionato Eu0.01, La0.99
morpholinium tetrakis 3-methylpentane-2,4-dionato Eu0.01, La0.99
morpholinium tetrakis 3-ethylpentane-2,4-dionato Eu0.01, La0.99
morpholinium tetrakis pivaloyltrifluoroacetonato Eu0.01, La0.99
morpholinium tetrakis trifluoroacetylacetonato Eu0.01, La0.99
morpholinium tetrakis hexafluoroacetylacetonato Eu0.01, La0.99
morpholinium tetrakis 6,6,7,7,8,8,8-heptafluoro-2,2-dimethyloctanedionato Eu0.01, La0.99
morpholinium tetrakis 1-phenyl-1,3-butanedionato Eu0.01, La0.99
dimethylbenzylammonium tetrakis acetylacetonato Eu0.01, La0.99
dimethylbenzylammonium tetrakis dibenzoylmethanato Eu0.01, La0.99
dimethylbenzylammonium tetrakis thenoyltrifluoroacetonato Eu0.01, La0.99
dimethylbenzylammonium tetrakis 2,2,6,6-tetramethylheptanedionato Eu0.01, La0.99
dimethylbenzylammonium tetrakis 3-methylpentane-2,4-dionato Eu0.01, La0.99
dimethylbenzylammonium tetrakis 3-ethylpentane-2,4-dionato Eu0.01, La0.99
dimethylbenzylammonium tetrakis pivaloyltrifluoroacetonato Eu0.01, La0.99
dimethylbenzylammonium tetrakis trifluoroacetylacetonato Eu0.01, La0.99
dimethylbenzylammonium tetrakis hexafluoroacetylacetonato Eu0.01, La0.99
dimethylbenzylammonium tetrakis 6,6,7,7,8,8,8-heptafluoro-2,2-dimethyloctanedionato Eu0.01, La0.99
dimethylbenzylammonium tetrakis 1-phenyl-1,3-butanedionato Eu0.01, La0.99
triallylammonium tetrakis acetylacetonato Eu0.01, La0.99
triallylammonium tetrakis dibenzoylmethanato Eu0.01, La0.99
triallylammonium tetrakis thenoyltrifluoroacetonato Eu0.01, La0.99
triallylammonium tetrakis 2,2,6,6-tetramethylheptanedionato Eu0.01, La0.99
triallylammonium tetrakis 3-methylpentane-2,4-dionato Eu0.01, La0.99
triallylammonium tetrakis 3-ethylpentane-2,4-dionato Eu0.01, La0.99
triallylammonium tetrakis pivaloyltrifluoroacetonato Eu0.01, La0.99
triallylammonium tetrakis trifluoroacetylacetonato Eu0.01, La0.99
triallylammonium tetrakis hexafluoroacetylacetonato Eu0.01, La0.99 triallylammonium tetrakis 6,6,7,7,8,8,8-heptafluoro-2,2-dimethyloctanedionato Eu0.01, La0.99
triallylammonium tetrakis 1-phenyl-1,3-butanedionato Eu0.01, La0.99
anilinium tetrakis acetylacetonato Eu0.01, La0.99
anilinium tetrakis dibenzoylmethanato Eu0.01, La0.99
anilinium tetrakis thenoyltrifluoroacetonato Eu0.01, La0.99
anilinium tetrakis 2,2,6,6-tetramethylheptanedionato Eu0.01, La0.99
anilinium tetrakis 3-methylpentane-2,4-dionato Eu0.01, La0.99
anilinium tetrakis 3-ethylpentane-2,4-dionato Eu0.01, La0.99
anilinium tetrakis pivaloyltrifluoroacetonato Eu0.01, La0.99
anilinium tetrakis trifluoroacetylacetonato Eu0.01, La0.99
anilinium tetrakis hexafluoroacetylacetonato Eu0.01, La0.99
anilinium tetrakis 6,6,7,7,8,8,8-heptafluoro-2,2-dimethyloctanedionato Eu0.01, La0.99
anilinium tetrakis 1-phenyl-1,3-butanedionato Eu0.01, La0.99
triethylammonium tetrakis acetylacetonato Tb0.5, Gd0.5
triethylammonium tetrakis dibenzoylmethanato Tb0.5, Gd0.5
triethylammonium tetrakis thenoyltrifluoroacetonato Tb0.5, Gd0.5
triethylammonium tetrakis 2,2,6,6-tetramethylheptanedionato Tb0.5, Gd0.5
triethylammonium tetrakis 3-methylpentane-2,4-dionato Tb0.5, Gd0.5
triethylammonium tetrakis 3-ethylpentane-2,4-dionato Tb0.5, Gd0.5
triethylammonium tetrakis pivaloyltrifluoroacetonato Tb0.5, Gd0.5
triethylammonium tetrakis trifluoroacetylacetonato Tb0.5, Gd0.5
triethylammonium tetrakis hexafluoroacetylacetonato Tb0.5, Gd0.5
triethylammonium tetrakis 6,6,7,7,8,8,8-heptafluoro-2,2-dimethyloctanedionato Tb0.5, Gd0.5
triethylammonium tetrakis 1-phenyl-1,3-butanedionato Tb0.5, Gd0.5
morpholinium tetrakis acetylacetonato Tb0.5, Gd0.5
morpholinium tetrakis dibenzoylmethanato Tb0.5, Gd0.5
morpholinium tetrakis thenoyltrifluoroacetonato Tb0.5, Gd0.5
morpholinium tetrakis 2,2,6,6-tetramethylheptanedionato Tb0.5, Gd0.5
morpholinium tetrakis 3-methylpentane-2,4-dionato Tb0.5, Gd0.5
morpholinium tetrakis 3-ethylpentane-2,4-dionato Tb0.5, Gd0.5
morpholinium tetrakis pivaloyltrifluoroacetonato Tb0.5, Gd0.5
morpholinium tetrakis trifluoroacetylacetonato Tb0.5, Gd0.5
morpholinium tetrakis hexafluoroacetylacetonato Tb0.5, Gd0.5
morpholinium tetrakis 6,6,7,7,8,8,8-heptafluoro-2,2-dimethyloctanedionato Tb0.5, Gd0.5
morpholinium tetrakis 1-phenyl-1,3-butanedionato Tb0.5, Gd0.5
dimethylbenzylammonium tetrakis acetylacetonato Tb0.5, Gd0.5
dimethylbenzylammonium tetrakis dibenzoylmethanato Tb0.5, Gd0.5
dimethylbenzylammonium tetrakis thenoyltrifluoroacetonato Tb0.5, Gd0.5
dimethylbenzylammonium tetrakis 2,2,6,6-tetramethylheptanedionato Tb0.5, Gd0.5
dimethylbenzylammonium tetrakis 3-methylpentane-2,4-dionato Tb0.5, Gd0.5
dimethylbenzylammonium tetrakis 3-ethylpentane-2,4-dionato Tb0.5, Gd0.5
dimethylbenzylammonium tetrakis pivaloyltrifluoroacetonato Tb0.5, Gd0.5
dimethylbenzylammonium tetrakis trifluoroacetylacetonato Tb0.5, Gd0.5
dimethylbenzylammonium tetrakis hexafluoroacetylacetonato Tb0.5, Gd0.5
dimethylbenzylammonium tetrakis 6,6,7,7,8,8,8-heptafluoro-2,2-dimethyloctanedionato Tb0.5, Gd0.5
dimethylbenzylammonium tetrakis 1-phenyl-1,3-butanedionato Tb0.5, Gd0.5
triallylammonium tetrakis acetylacetonato Tb0.5, Gd0.5
triallylammonium tetrakis dibenzoylmethanato Tb0.5, Gd0.5
triallylammonium tetrakis thenoyltrifluoroacetonato Tb0.5, Gd0.5
triallylammonium tetrakis 2,2,6,6-tetramethylheptanedionato Tb0.5, Gd0.5
triallylammonium tetrakis 3-methylpentane-2,4-dionato Tb0.5, Gd0.5
triallylammonium tetrakis 3-ethylpentane-2,4-dionato Tb0.5, Gd0.5
triallylammonium tetrakis pivaloyltrifluoroacetonato Tb0.5, Gd0.5
triallylammonium tetrakis trifluoroacetylacetonato Tb0.5, Gd0.5
triallylammonium tetrakis hexafluoroacetylacetonato Tb0.5, Gd0.5
triallylammonium tetrakis 6,6,7,7,8,8,8-heptafluoro-2,2-dimethyloctanedionato Tb0.5, Gd0.5
triallylammonium tetrakis 1-phenyl-1,3-butanedionato Tb0.5, Gd0.5
anilinium tetrakis acetylacetonato Tb0.5, Gd0.5
anilinium tetrakis dibenzoylmethanato Tb0.5, Gd0.5
anilinium tetrakis thenoyltrifluoroacetonato Tb0.5, Gd0.5
anilinium tetrakis 2,2,6,6-tetramethylheptanedionato Tb0.5, Gd0.5
anilinium tetrakis 3-methylpentane-2,4-dionato Tb0.5, Gd0.5
anilinium tetrakis 3-ethylpentane-2,4-dionato Tb0.5, Gd0.5
anilinium tetrakis pivaloyltrifluoroacetonato Tb0.5, Gd0.5
anilinium tetrakis trifluoroacetylacetonato Tb0.5, Gd0.5
anilinium tetrakis hexafluoroacetylacetonato Tb0.5, Gd0.5
anilinium tetrakis 6,6,7,7,8,8,8-heptafluoro-2,2-dimethyloctanedionato Tb0.5, Gd0.5
anilinium tetrakis 1-phenyl-1,3-butanedionato Tb0.5, Gd0.5
triethylammonium tetrakis acetylacetonato Tb0.2, Gd0.8
triethylammonium tetrakis dibenzoylmethanato Tb0.2, Gd0.8
triethylammonium tetrakis thenoyltrifluoroacetonato Tb0.2, Gd0.8
triethylammonium tetrakis 2,2,6,6-tetramethylheptanedionato Tb0.2, Gd0.8
triethylammonium tetrakis 3-methylpentane-2,4-dionato Tb0.2, Gd0.8
triethylammonium tetrakis 3-ethylpentane-2,4-dionato Tb0.2, Gd0.8
triethylammonium tetrakis pivaloyltrifluoroacetonato Tb0.2, Gd0.8
triethylammonium tetrakis trifluoroacetylacetonato Tb0.2, Gd0.8 triethylammonium tetrakis hexafluoroacetylacetonato Tb0.2, Gd0.8
triethylammonium tetrakis 6,6,7,7,8,8,8-heptafluoro-2,2-dimethyloctanedionato Tb0.2, Gd0.8
triethylammonium tetrakis 1-phenyl-1,3-butanedionato Tb0.2, Gd0.8
morpholinium tetrakis acetylacetonato Tb0.2, Gd0.8
morpholinium tetrakis dibenzoylmethanato Tb0.2, Gd0.8
morpholinium tetrakis thenoyltrifluoroacetonato Tb0.2, Gd0.8
morpholinium tetrakis 2,2,6,6-tetramethylheptanedionato Tb0.2, Gd0.8
morpholinium tetrakis 3-methylpentane-2,4-dionato Tb0.2, Gd0.8
morpholinium tetrakis 3-ethylpentane-2,4-dionato Tb0.2, Gd0.8
morpholinium tetrakis pivaloyltrifluoroacetonato Tb0.2, Gd0.8
morpholinium tetrakis trifluoroacetylacetonato Tb0.2, Gd0.8
morpholinium tetrakis hexafluoroacetylacetonato Tb0.2, Gd0.8
morpholinium tetrakis 6,6,7,7,8,8,8-heptafluoro-2,2-dimethyloctanedionato Tb0.2, Gd0.8
morpholinium tetrakis 1-phenyl-1,3-butanedionato Tb0.2, Gd0.8
dimethylbenzylammonium tetrakis acetylacetonato Tb0.2, Gd0.8
dimethylbenzylammonium tetrakis dibenzoylmethanato Tb0.2, Gd0.8
dimethylbenzylammonium tetrakis thenoyltrifluoroacetonato Tb0.2, Gd0.8
dimethylbenzylammonium tetrakis 2,2,6,6-tetramethylheptanedionato Tb0.2, Gd0.8
dimethylbenzylammonium tetrakis 3-methylpentane-2,4-dionato Tb0.2, Gd0.8
dimethylbenzylammonium tetrakis 3-ethylpentane-2,4-dionato Tb0.2, Gd0.8
dimethylbenzylammonium tetrakis pivaloyltrifluoroacetonato Tb0.2, Gd0.8
dimethylbenzylammonium tetrakis trifluoroacetylacetonato Tb0.2, Gd0.8
dimethylbenzylammonium tetrakis hexafluoroacetylacetonato Tb0.2, Gd0.8
dimethylbenzylammonium tetrakis 6,6,7,7,8,8,8-heptafluoro-2,2-dimethyloctanedionato Tb0.2, Gd0.8
dimethylbenzylammonium tetrakis 1-phenyl-1,3-butanedionato Tb0.2, Gd0.8
triallylammonium tetrakis acetylacetonato Tb0.2, Gd0.8
triallylammonium tetrakis dibenzoylmethanato Tb0.2, Gd0.8
triallylammonium tetrakis thenoyltrifluoroacetonato Tb0.2, Gd0.8
triallylammonium tetrakis 2,2,6,6-tetramethylheptanedionato Tb0.2, Gd0.8
triallylammonium tetrakis 3-methylpentane-2,4-dionato Tb0.2, Gd0.8
triallylammonium tetrakis 3-ethylpentane-2,4-dionato Tb0.2, Gd0.8
triallylammonium tetrakis pivaloyltrifluoroacetonato Tb0.2, Gd0.8
triallylammonium tetrakis trifluoroacetylacetonato Tb0.2, Gd0.8
triallylammonium tetrakis hexafluoroacetylacetonato Tb0.2, Gd0.8
triallylammonium tetrakis 6,6,7,7,8,8,8-heptafluoro-2,2-dimethyloctanedionato Tb0.2, Gd0.8
triallylammonium tetrakis 1-phenyl-1,3-butanedionato Tb0.2, Gd0.8
anilinium tetrakis acetylacetonato Tb0.2, Gd0.8
anilinium tetrakis dibenzoylmethanato Tb0.2, Gd0.8
anilinium tetrakis thenoyltrifluoroacetonato Tb0.2, Gd0.8
anilinium tetrakis 2,2,6,6-tetramethylheptanedionato Tb0.2, Gd0.8
anilinium tetrakis 3-methylpentane-2,4-dionato Tb0.2, Gd0.8
anilinium tetrakis 3-ethylpentane-2,4-dionato Tb0.2, Gd0.8
anilinium tetrakis pivaloyltrifluoroacetonato Tb0.2, Gd0.8
anilinium tetrakis trifluoroacetylacetonato Tb0.2, Gd0.8
anilinium tetrakis hexafluoroacetylacetonato Tb0.2, Gd0.8
anilinium tetrakis 6,6,7,7,8,8,8-heptafluoro-2,2-dimethyloctanedionato Tb0.2, Gd0.8
anilinium tetrakis 1-phenyl-1,3-butanedionato Tb0.2, Gd0.8
triethylammonium tetrakis acetylacetonato Tb0.1, Gd0.9
triethylammonium tetrakis thenoyltrifluoroacetonato Tb0.1, Gd0.9
triethylammonium tetrakis 2,2,6,6-tetramethylheptanedionato Tb0.1, Gd0.9
triethylammonium tetrakis 3-methylpentane-2,4-dionato Tb0.1, Gd0.9
triethylammonium tetrakis 3-ethylpentane-2,4-dionato Tb0.1, Gd0.9
triethylammonium tetrakis pivaloyltrifluoroacetonato Tb0.1, Gd0.9
triethylammonium tetrakis trifluoroacetylacetonato Tb0.1, Gd0.9
triethylammonium tetrakis hexafluoroacetylacetonato Tb0.1, Gd0.9
triethylammonium tetrakis 6,6,7,7,8,8,8-heptafluoro-2,2-dimethyloctanedionato Tb0.1, Gd0.9
triethylammonium tetrakis 1-phenyl-1,3-butanedionato Tb0.1, Gd0.9
morpholinium tetrakis acetylacetonato Tb0.1, Gd0.9
morpholinium tetrakis dibenzoylmethanato Tb0.1, Gd0.9
morpholinium tetrakis thenoyltrifluoroacetonato Tb0.1, Gd0.9
morpholinium tetrakis 2,2,6,6-tetramethylheptanedionato Tb0.1, Gd0.9
morpholinium tetrakis 3-methylpentane-2,4-dionato Tb0.1, Gd0.9
morpholinium tetrakis 3-ethylpentane-2,4-dionato Tb0.1, Gd0.9
morpholinium tetrakis pivaloyltrifluoroacetonato Tb0.1, Gd0.9
morpholinium tetrakis trifluoroacetylacetonato Tb0.1, Gd0.9
morpholinium tetrakis hexafluoroacetylacetonato Tb0.1, Gd0.9
morpholinium tetrakis 6,6,7,7,8,8,8-heptafluoro-2,2-dimethyloctanedionato Tb0.1, Gd0.9
morpholinium tetrakis 1-phenyl-1,3-butanedionato Tb0.1, Gd0.9
dimethylbenzylammonium tetrakis acetylacetonato Tb0.1, Gd0.9
dimethylbenzylammonium tetrakis dibenzoylmethanato Tb0.1, Gd0.9
dimethylbenzylammonium tetrakis thenoyltrifluoroacetonato Tb0.1, Gd0.9
dimethylbenzylammonium tetrakis 2,2,6,6-tetramethylheptanedionato Tb0.1, Gd0.9
dimethylbenzylammonium tetrakis 3-methylpentane-2,4-dionato Tb0.1, Gd0.9
dimethylbenzylammonium tetrakis 3-ethylpentane-2,4-dionato Tb0.1, Gd0.9 dimethylbenzylammonium tetrakis pivaloyltrifluoroacetonato Tb0.1, Gd0.9
dimethylbenzylammonium tetrakis trifluoroacetylacetonato Tb0.1, Gd0.9
dimethylbenzylammonium tetrakis hexafluoroacetylacetonato Tb0.1, Gd0.9
dimethylbenzylammonium tetrakis 6,6,7,7,8,8,8-heptafluoro-2,2-dimethyloctanedionato Tb0.1, Gd0.9
dimethylbenzylammonium tetrakis 1-phenyl-1,3-butanedionato Tb0.1, Gd0.9
triallylammonium tetrakis acetylacetonato Tb0.1, Gd0.9
triallylammonium tetrakis dibenzoylmethanato Tb0.1, Gd0.9
triallylammonium tetrakis thenoyltrifluoroacetonato Tb0.1, Gd0.9
triallylammonium tetrakis 2,2,6,6-tetramethylheptanedionato Tb0.1, Gd0.9
triallylammonium tetrakis 3-methylpentane-2,4-dionato Tb0.1, Gd0.9
triallylammonium tetrakis 3-ethylpentane-2,4-dionato Tb0.1, Gd0.9
triallylammonium tetrakis pivaloyltrifluoroacetonato Tb0.1, Gd0.9
triallylammonium tetrakis trifluoroacetylacetonato Tb0.1, Gd0.9
triallylammonium tetrakis hexafluoroacetylacetonato Tb0.1, Gd0.9
triallylammonium tetrakis 6,6,7,7,8,8,8-heptafluoro-2,2-dimethyloctanedionato Tb0.1, Gd0.9
triallylammonium tetrakis 1-phenyl-1,3-butanedionato Tb0.1, Gd0.9
anilinium tetrakis acetylacetonato Tb0.1, Gd0.9
anilinium tetrakis dibenzoylmethanato Tb0.1, Gd0.9
anilinium tetrakis thenoyltrifluoroacetonato Tb0.1, Gd0.9
anilinium tetrakis 2,2,6,6-tetramethylheptanedionato Tb0.1, Gd0.9
anilinium tetrakis 3-methylpentane-2,4-dionato Tb0.1, Gd0.9
anilinium tetrakis 3-ethylpentane-2,4-dionato Tb0.1, Gd0.9
anilinium tetrakis pivaloyltrifluoroacetonato Tb0.1, Gd0.9
anilinium tetrakis trifluoroacetylacetonato Tb0.1, Gd0.9
anilinium tetrakis hexafluoroacetylacetonato Tb0.1, Gd0.9
anilinium tetrakis 6,6,7,7,8,8,8-heptafluoro-2,2-dimethyloctanedionato Tb0.1, Gd0.9
anilinium tetrakis 1-phenyl-1,3-butanedionato Tb0.1, Gd0.9
triethylammonium tetrakis acetylacetonato Tb0.01, Gd0.99
triethylammonium tetrakis dibenzoylmethanato Tb0.01, Gd0.99
triethylammonium tetrakis thenoyltrifluoroacetonato Tb0.01, Gd0.99
triethylammonium tetrakis 2,2,6,6-tetramethylheptanedionato Tb0.01, Gd0.99
triethylammonium tetrakis 3-methylpentane-2,4-dionato Tb0.01, Gd0.99
triethylammonium tetrakis 3-ethylpentane-2,4-dionato Tb0.01, Gd0.99
triethylammonium tetrakis pivaloyltrifluoroacetonato Tb0.01, Gd0.99
triethylammonium tetrakis trifluoroacetylacetonato Tb0.01, Gd0.99
triethylammonium tetrakis hexafluoroacetylacetonato Tb0.01, Gd0.99
triethylammonium tetrakis 6,6,7,7,8,8,8-heptafluoro-2,2-dimethyloctanedionato Tb0.01, Gd0.99
triethylammonium tetrakis 1-phenyl-1,3-butanedionato Tb0.01, Gd0.99
morpholinium tetrakis acetylacetonato Tb0.01, Gd0.99
morpholinium tetrakis dibenzoylmethanato Tb0.01, Gd0.99
morpholinium tetrakis thenoyltrifluoroacetonato Tb0.01, Gd0.99
morpholinium tetrakis 2,2,6,6-tetramethylheptanedionato Tb0.01, Gd0.99
morpholinium tetrakis 3-methylpentane-2,4-dionato Tb0.01, Gd0.99
morpholinium tetrakis 3-ethylpentane-2,4-dionato Tb0.01, Gd0.99
morpholinium tetrakis pivaloyltrifluoroacetonato Tb0.01, Gd0.99
morpholinium tetrakis trifluoroacetylacetonato Tb0.01, Gd0.99
morpholinium tetrakis hexafluoroacetylacetonato Tb0.01, Gd0.99
morpholinium tetrakis 6,6,7,7,8,8,8-heptafluoro-2,2-dimethyloctanedionato Tb0.01, Gd0.99
morpholinium tetrakis 1-phenyl-1,3-butanedionato Tb0.01, Gd0.99
dimethylbenzylammonium tetrakis acetylacetonato Tb0.01, Gd0.99
dimethylbenzylammonium tetrakis dibenzoylmethanato Tb0.01, Gd0.99
dimethylbenzylammonium tetrakis thenoyltrifluoroacetonato Tb0.01, Gd0.99
dimethylbenzylammonium tetrakis 2,2,6,6-tetramethylheptanedionato Tb0.01, Gd0.99
dimethylbenzylammonium tetrakis 3-methylpentane-2,4-dionato Tb0.01, Gd0.99
dimethylbenzylammonium tetrakis 3-ethylpentane-2,4-dionato Tb0.01, Gd0.99
dimethylbenzylammonium tetrakis pivaloyltrifluoroacetonato Tb0.01, Gd0.99
dimethylbenzylammonium tetrakis trifluoroacetylacetonato Tb0.01, Gd0.99
dimethylbenzylammonium tetrakis hexafluoroacetylacetonato Tb0.01, Gd0.99
dimethylbenzylammonium tetrakis 6,6,7,7,8,8,8-heptafluoro-2,2-dimethyloctanedionato Tb0.01, Gd0.99
dimethylbenzylammonium tetrakis 1-phenyl-1,3-butanedionato Tb0.01, Gd0.99
triallylammonium tetrakis acetylacetonato Tb0.01, Gd0.99
triallylammonium tetrakis dibenzoylmethanato Tb0.01, Gd0.99
triallylammonium tetrakis thenoyltrifluoroacetonato Tb0.01, Gd0.99
triallylammonium tetrakis 2,2,6,6-tetramethylheptanedionato Tb0.01, Gd0.99
triallylammonium tetrakis 3-methylpentane-2,4-dionato Tb0.01, Gd0.99
triallylammonium tetrakis 3-ethylpentane-2,4-dionato Tb0.01, Gd0.99
triallylammonium tetrakis pivaloyltrifluoroacetonato Tb0.01, Gd0.99
triallylammonium tetrakis trifluoroacetylacetonato Tb0.01, Gd0.99
triallylammonium tetrakis hexafluoroacetylacetonato Tb0.01, Gd0.99
triallylammonium tetrakis 6,6,7,7,8,8,8-heptafluoro-2,2-dimethyloctanedionato Tb0.01, Gd0.99
triallylammonium tetrakis 1-phenyl-1,3-butanedionato Tb0.01, Gd0.99
anilinium tetrakis acetylacetonato Tb0.01, Gd0.99
anilinium tetrakis dibenzoylmethanato Tb0.01, Gd0.99
anilinium tetrakis thenoyltrifluoroacetonato Tb0.01, Gd0.99
anilinium tetrakis 2,2,6,6-tetramethylheptanedionato Tb0.01, Gd0.99 anilinium tetrakis 3-methylpentane-2,4-dionato Tb0.01, Gd0.99
anilinium tetrakis 3-ethylpentane-2,4-dionato Tb0.01, Gd0.99
anilinium tetrakis pivaloyltrifluoroacetonato Tb0.01, Gd0.99
anilinium tetrakis trifluoroacetylacetonato Tb0.01, Gd0.99
anilinium tetrakis hexafluoroacetylacetonato Tb0.01, Gd0.99
anilinium tetrakis 6,6,7,7,8,8,8-heptafluoro-2,2-dimethyloctanedionato Tb0.01, Gd0.99
anilinium tetrakis 1-phenyl-1,3-butanedionato Tb0.01, Gd0.99
triethylammonium tetrakis acetylacetonato Eu0.5, Gd0.5
triethylammonium tetrakis dibenzoylmethanato Eu0.5, Gd0.5
triethylammonium tetrakis thenoyltrifluoroacetonato Eu0.5, Gd0.5
triethylammonium tetrakis 2,2,6,6-tetramethylheptanedionato Eu0.5, Gd0.5
triethylammonium tetrakis 3-methylpentane-2,4-dionato Eu0.5, Gd0.5
triethylammonium tetrakis 3-ethylpentane-2,4-dionato Eu0.5, Gd0.5
triethylammonium tetrakis pivaloyltrifluoroacetonato Eu0.5, Gd0.5
triethylammonium tetrakis trifluoroacetylacetonato Eu0.5, Gd0.5
triethylammonium tetrakis hexafluoroacetylacetonato Eu0.5, Gd0.5
triethylammonium tetrakis 6,6,7,7,8,8,8-heptafluoro-2,2-dimethyloctanedionato Eu0.5, Gd0.5
triethylammonium tetrakis 1-phenyl-1,3-butanedionato Eu0.5, Gd0.5
morpholinium tetrakis acetylacetonato Eu0.5, Gd0.5
morpholinium tetrakis dibenzoylmethanato Eu0.5, Gd0.5
morpholinium tetrakis thenoyltrifluoroacetonato Eu0.5, Gd0.5
morpholinium tetrakis 2,2,6,6-tetramethylheptanedionato Eu0.5, Gd0.5
morpholinium tetrakis 3-methylpentane-2,4-dionato Eu0.5, Gd0.5
morpholinium tetrakis 3-ethylpentane-2,4-dionato Eu0.5, Gd0.5
morpholinium tetrakis pivaloyltrifluoroacetonato Eu0.5, Gd0.5
morpholinium tetrakis trifluoroacetylacetonato Eu0.5, Gd0.5
morpholinium tetrakis hexafluoroacetylacetonato Eu0.5, Gd0.5
morpholinium tetrakis 6,6,7,7,8,8,8-heptafluoro-2,2-dimethyloctanedionato Eu0.5, Gd0.5
morpholinium tetrakis 1-phenyl-1,3-butanedionato Eu0.5, Gd0.5
dimethylbenzylammonium tetrakis acetylacetonato Eu0.5, Gd0.5
dimethylbenzylammonium tetrakis dibenzoylmethanato Eu0.5, Gd0.5
dimethylbenzylammonium tetrakis thenoyltrifluoroacetonato Eu0.5, Gd0.5
dimethylbenzylammonium tetrakis 2,2,6,6-tetramethylheptanedionato Eu0.5, Gd0.5
dimethylbenzylammonium tetrakis 3-methylpentane-2,4-dionato Eu0.5, Gd0.5
dimethylbenzylammonium tetrakis 3-ethylpentane-2,4-dionato Eu0.5, Gd0.5
dimethylbenzylammonium tetrakis pivaloyltrifluoroacetonato Eu0.5, Gd0.5
dimethylbenzylammonium tetrakis trifluoroacetylacetonato Eu0.5, Gd0.5
dimethylbenzylammonium tetrakis hexafluoroacetylacetonato Eu0.5, Gd0.5
dimethylbenzylammonium tetrakis 6,6,7,7,8,8,8-heptafluoro-2,2-dimethyloctanedionato Eu0.5, Gd0.5
dimethylbenzylammonium tetrakis 1-phenyl-1,3-butanedionato Eu0.5, Gd0.5
triallylammonium tetrakis acetylacetonato Eu0.5, Gd0.5
triallylammonium tetrakis dibenzoylmethanato Eu0.5, Gd0.5
triallylammonium tetrakis thenoyltrifluoroacetonato Eu0.5, Gd0.5
triallylammonium tetrakis 2,2,6,6-tetramethylheptanedionato Eu0.5, Gd0.5
triallylammonium tetrakis 3-methylpentane-2,4-dionato Eu0.5, Gd0.5
triallylammonium tetrakis 3-ethylpentane-2,4-dionato Eu0.5, Gd0.5
triallylammonium tetrakis pivaloyltrifluoroacetonato Eu0.5, Gd0.5
triallylammonium tetrakis trifluoroacetylacetonato Eu0.5, Gd0.5
triallylammonium tetrakis hexafluoroacetylacetonato Eu0.5, Gd0.5
triallylammonium tetrakis 6,6,7,7,8,8,8-heptafluoro-2,2-dimethyloctanedionato Eu0.5, Gd0.5
triallylammonium tetrakis 1-phenyl-1,3-butanedionato Eu0.5, Gd0.5
anilinium tetrakis acetylacetonato Eu0.5, Gd0.5
anilinium tetrakis dibenzoylmethanato Eu0.5, Gd0.5
anilinium tetrakis thenoyltrifluoroacetonato Eu0.5, Gd0.5
anilinium tetrakis 2,2,6,6-tetramethylheptanedionato Eu0.5, Gd0.5
anilinium tetrakis 3-methylpentane-2,4-dionato Eu0.5, Gd0.5
anilinium tetrakis 3-ethylpentane-2,4-dionato Eu0.5, Gd0.5
anilinium tetrakis pivaloyltrifluoroacetonato Eu0.5, Gd0.5
anilinium tetrakis trifluoroacetylacetonato Eu0.5, Gd0.5
anilinium tetrakis hexafluoroacetylacetonato Eu0.5, Gd0.5
anilinium tetrakis 6,6,7,7,8,8,8-heptafluoro-2,2-dimethyloctanedionato Eu0.5, Gd0.5
anilinium tetrakis 1-phenyl-1,3-butanedionato Eu0.5, Gd0.5
triethylammonium tetrakis acetylacetonato Eu0.2, Gd0.8
triethylammonium tetrakis dibenzoylmethanato Eu0.2, Gd0.8
triethylammonium tetrakis thenoyltrifluoroacetonato Eu0.2, Gd0.8
triethylammonium tetrakis 2,2,6,6-tetramethylheptanedionato Eu0.2, Gd0.8
triethylammonium tetrakis 3-methylpentane-2,4-dionato Eu0.2, Gd0.8
triethylammonium tetrakis 3-ethylpentane-2,4-dionato Eu0.2, Gd0.8
triethylammonium tetrakis pivaloyltrifluoroacetonato Eu0.2, Gd0.8
triethylammonium tetrakis trifluoroacetylacetonato Eu0.2, Gd0.8
triethylammonium tetrakis hexafluoroacetylacetonato Eu0.2, Gd0.8
triethylammonium tetrakis 6,6,7,7,8,8,8-heptafluoro-2,2-dimethyloctanedionato Eu0.2, Gd0.8
triethylammonium tetrakis 1-phenyl-1,3-butanedionato Eu0.2, Gd0.8
morpholinium tetrakis acetylacetonato Eu0.2, Gd0.8 morpholinium tetrakis dibenzoylmethanato Eu0.2, Gd0.8
morpholinium tetrakis thenoyltrifluoroacetonato Eu0.2, Gd0.8
morpholinium tetrakis 2,2,6,6-tetramethylheptanedionato Eu0.2, Gd0.8
morpholinium tetrakis 3-methylpentane-2,4-dionato Eu0.2, Gd0.8
morpholinium tetrakis 3-ethylpentane-2,4-dionato Eu0.2, Gd0.8
morpholinium tetrakis pivaloyltrifluoroacetonato Eu0.2, Gd0.8
morpholinium tetrakis trifluoroacetylacetonato Eu0.2, Gd0.8
morpholinium tetrakis hexafluoroacetylacetonato Eu0.2, Gd0.8
morpholinium tetrakis 6,6,7,7,8,8,8-heptafluoro-2,2-dimethyloctanedionato Eu0.2, Gd0.8
morpholinium tetrakis 1-phenyl-1,3-butanedionato Eu0.2, Gd0.8
dimethylbenzylammonium tetrakis acetylacetonato Eu0.2, Gd0.8
dimethylbenzylammonium tetrakis dibenzoylmethanato Eu0.2, Gd0.8
dimethylbenzylammonium tetrakis thenoyltrifluoroacetonato Eu0.2, Gd0.8
dimethylbenzylammonium tetrakis 2,2,6,6-tetramethylheptanedionato Eu0.2, Gd0.8
dimethylbenzylammonium tetrakis 3-methylpentane-2,4-dionato Eu0.2, Gd0.8
dimethylbenzylammonium tetrakis 3-ethylpentane-2,4-dionato Eu0.2, Gd0.8
dimethylbenzylammonium tetrakis pivaloyltrifluoroacetonato Eu0.2, Gd0.8
dimethylbenzylammonium tetrakis trifluoroacetylacetonato Eu0.2, Gd0.8
dimethylbenzylammonium tetrakis hexafluoroacetylacetonato Eu0.2, Gd0.8
dimethylbenzylammonium tetrakis 6,6,7,7,8,8,8-heptafluoro-2,2-dimethyloctanedionato Eu0.2, Gd0.8
dimethylbenzylammonium tetrakis 1-phenyl-1,3-butanedionato Eu0.2, Gd0.8
triallylammonium tetrakis acetylacetonato Eu0.2, Gd0.8
triallylammonium tetrakis dibenzoylmethanato Eu0.2, Gd0.8
triallylammonium tetrakis thenoyltrifluoroacetonato Eu0.2, Gd0.8
triallylammonium tetrakis 2,2,6,6-tetramethylheptanedionato Eu0.2, Gd0.8
triallylammonium tetrakis 3-methylpentane-2,4-dionato Eu0.2, Gd0.8
triallylammonium tetrakis 3-ethylpentane-2,4-dionato Eu0.2, Gd0.8
triallylammonium tetrakis pivaloyltrifluoroacetonato Eu0.2, Gd0.8
triallylammonium tetrakis trifluoroacetylacetonato Eu0.2, Gd0.8
triallylammonium tetrakis hexafluoroacetylacetonato Eu0.2, Gd0.8
triallylammonium tetrakis 6,6,7,7,8,8,8-heptafluoro-2,2-dimethyloctanedionato Eu0.2, Gd0.8
triallylammonium tetrakis 1-phenyl-1,3-butanedionato Eu0.2, Gd0.8
anilinium tetrakis acetylacetonato Eu0.2, Gd0.8
anilinium tetrakis dibenzoylmethanato Eu0.2, Gd0.8
anilinium tetrakis thenoyltrifluoroacetonato Eu0.2, Gd0.8
anilinium tetrakis 2,2,6,6-tetramethylheptanedionato Eu0.2, Gd0.8
anilinium tetrakis 3-methylpentane-2,4-dionato Eu0.2, Gd0.8
anilinium tetrakis 3-ethylpentane-2,4-dionato Eu0.2, Gd0.8
anilinium tetrakis pivaloyltrifluoroacetonato Eu0.2, Gd0.8
anilinium tetrakis trifluoroacetylacetonato Eu0.2, Gd0.8
anilinium tetrakis hexafluoroacetylacetonato Eu0.2, Gd0.8
anilinium tetrakis 6,6,7,7,8,8,8-heptafluoro-2,2-dimethyloctanedionato Eu0.2, Gd0.8
anilinium tetrakis 1-phenyl-1,3-butanedionato Eu0.2, Gd0.8
triethylammonium tetrakis acetylacetonato Eu0.1, Gd0.9
triethylammonium tetrakis dibenzoylmethanato Eu0.1, Gd0.9; brightness=9
triethylammonium tetrakis thenoyltrifluoroacetonato Eu0.1, Gd0.9
triethylammonium tetrakis 2,2,6,6-tetramethylheptanedionato Eu0.1, Gd0.9
triethylammonium tetrakis 3-methylpentane-2,4-dionato Eu0.1, Gd0.9
triethylammonium tetrakis 3-ethylpentane-2,4-dionato Eu0.1, Gd0.9
triethylammonium tetrakis pivaloyltrifluoroacetonato Eu0.1, Gd0.9
triethylammonium tetrakis trifluoroacetylacetonato Eu0.1, Gd0.9
triethylammonium tetrakis hexafluoroacetylacetonato Eu0.1, Gd0.9
triethylammonium tetrakis 6,6,7,7,8,8,8-heptafluoro-2,2-dimethyloctanedionato Eu0.1, Gd0.9
triethylammonium tetrakis 1-phenyl-1,3-butanedionato Eu0.1, Gd0.9
morpholinium tetrakis acetylacetonato Eu0.1, Gd0.9
morpholinium tetrakis dibenzoylmethanato Eu0.1, Gd0.9; brightness=8
morpholinium tetrakis thenoyltrifluoroacetonato Eu0.1, Gd0.9
morpholinium tetrakis 2,2,6,6-tetramethylheptanedionato Eu0.1, Gd0.9
morpholinium tetrakis 3-methylpentane-2,4-dionato Eu0.1, Gd0.9
morpholinium tetrakis 3-ethylpentane-2,4-dionato Eu0.1, Gd0.9
morpholinium tetrakis pivaloyltrifluoroacetonato Eu0.1, Gd0.9
morpholinium tetrakis trifluoroacetylacetonato Eu0.1, Gd0.9
morpholinium tetrakis hexafluoroacetylacetonato Eu0.1, Gd0.9
morpholinium tetrakis 6,6,7,7,8,8,8-heptafluoro-2,2-dimethyloctanedionato Eu0.1, Gd0.9
morpholinium tetrakis 1-phenyl-1,3-butanedionato Eu0.1, Gd0.9
dimethylbenzylammonium tetrakis acetylacetonato Eu0.1, Gd0.9
dimethylbenzylammonium tetrakis dibenzoylmethanato Eu0.1, Gd0.9
dimethylbenzylammonium tetrakis thenoyltrifluoroacetonato Eu0.1, Gd 0.9
dimethylbenzylammonium tetrakis 2,2,6,6-tetramethylheptanedionato Eu0.1, Gd0.9
dimethylbenzylammonium tetrakis 3-methylpentane-2,4-dionato Eu0.1, Gd0.9
dimethylbenzylammonium tetrakis 3-ethylpentane-2,4-dionato Eu0.1, Gd0.9
dimethylbenzylammonium tetrakis pivaloyltrifluoroacetonato Eu0.1, Gd0.9
dimethylbenzylammonium tetrakis trifluoroacetylacetonato Eu0.1, Gd0.9 dimethylbenzylammonium tetrakis hexafluoroacetylacetonato Eu0.1, Gd0.9
dimethylbenzylammonium tetrakis 6,6,7,7,8,8,8-heptafluoro-2,2-dimethyloctanedionato Eu0.1, Gd0.9
dimethylbenzylammonium tetrakis 1-phenyl-1,3-butanedionato Eu0.1, Gd0.9
triallylammonium tetrakis acetylacetonato Eu0.1, Gd0.9
triallylammonium tetrakis dibenzoylmethanato Eu0.1, Gd0.9
triallylammonium tetrakis thenoyltrifluoroacetonato Eu0.1, Gd0.9
triallylammonium tetrakis 2,2,6,6-tetramethylheptanedionato Eu0.1, Gd0.9
triallylammonium tetrakis 3-methylpentane-2,4-dionato Eu0.1, Gd0.9
triallylammonium tetrakis 3-ethylpentane-2,4-dionato Eu0.1, Gd0.9
triallylammonium tetrakis pivaloyltrifluoroacetonato Eu0.1, Gd0.9
triallylammonium tetrakis trifluoroacetylacetonato Eu0.1, Gd0.9
triallylammonium tetrakis hexafluoroacetylacetonato Eu0.1, Gd0.9
triallylammonium tetrakis 6,6,7,7,8,8,8-heptafluoro-2,2-dimethyloctanedionato Eu0.1, Gd0.9
triallylammonium tetrakis 1-phenyl-1,3-butanedionato Eu0.1, Gd0.9
anilinium tetrakis acetylacetonato Eu0.1, Gd0.9
anilinium tetrakis dibenzoylmethanato Eu0.1, Gd0.9
anilinium tetrakis thenoyltrifluoroacetonato Eu0.1, Gd0.9
anilinium tetrakis 2,2,6,6-tetramethylheptanedionato Eu0.1, Gd0.9
anilinium tetrakis 3-methylpentane-2,4-dionato Eu0.1, Gd0.9
anilinium tetrakis 3-ethylpentane-2,4-dionato Eu0.1, Gd0.9.
anilinium tetrakis pivaloyltrifluoroacetonato Eu0.1, Gd0.9
anilinium tetrakis trifluoroacetylacetonato Eu0.1, Gd0.9
anilinium tetrakis hexafluoroacetylacetonato Eu0.1, Gd0.9
anilinium tetrakis 6,6,7,7,8,8,8-heptafluoro-2,2-dimethyloctanedionato Eu0.1, Gd0.9
anilinium tetrakis 1-phenyl-1,3-butanedionato Eu0.1, Gd0.9
triethylammonium tetrakis acetylacetonato Eu0.01, Gd0.99
triethylammonium tetrakis dibenzoylmethanato Eu0.01, Gd0.99
triethylammonium tetrakis thenoyltrifluoroacetonato Eu0.01, Gd0.99
triethylammonium tetrakis 2,2,6,6-tetramethylheptanedionato Eu0.01, Gd0.99
triethylammonium tetrakis 3-methylpentane-2,4-dionato Eu0.01, Gd0.99
triethylammonium tetrakis 3-ethylpentane-2,4-dionato Eu0.01, Gd0.99
triethylammonium tetrakis pivaloyltrifluoroacetonato Eu0.01, Gd0.99
triethylammonium tetrakis trifluoroacetylacetonato Eu0.01, Gd0.99
triethylammonium tetrakis hexafluoroacetylacetonato Eu0.01, Gd0.99
triethylammonium tetrakis 6,6,7,7,8,8,8-heptafluoro-2,2-dimethyloctanedionato Eu0.01, Gd0.99
triethylammonium tetrakis 1-phenyl-1,3-butanedionato Eu0.01, Gd0.99
morpholinium tetrakis acetylacetonato Eu0.01, Gd0.99
morpholinium tetrakis dibenzoylmethanato Eu0.01, Gd0.99
morpholinium tetrakis thenoyltrifluoroacetonato Eu0.01, Gd0.99
morpholinium tetrakis 2,2,6,6-tetramethylheptanedionato Eu0.01, Gd0.99
morpholinium tetrakis 3-methylpentane-2,4-dionato Eu0.01, Gd0.99
morpholinium tetrakis 3-ethylpentane-2,4-dionato Eu0.01, Gd0.99
morpholinium tetrakis pivaloyltrifluoroacetonato Eu0.01, Gd0.99
morpholinium tetrakis trifluoroacetylacetonato Eu0.01, Gd0.99
morpholinium tetrakis hexafluoroacetylacetonato Eu0.01, Gd0.99
morpholinium tetrakis 6,6,7,7,8,8,8-heptafluoro-2,2-dimethyloctanedionato Eu0.01, Gd0.99
morpholinium tetrakis 1-phenyl-1,3-butanedionato Eu0.01, Gd0.99
dimethylbenzylammonium tetrakis acetylacetonato Eu0.01, Gd0.99
dimethylbenzylammonium tetrakis dibenzoylmethanato Eu0.01, Gd0.99
dimethylbenzylammonium tetrakis thenoyltrifluoroacetonato Eu0.01, Gd0.99
dimethylbenzylammonium tetrakis 2,2,6,6-tetramethylheptanedionato Eu0.01, Gd0.99
dimethylbenzylammonium tetrakis 3-methylpentane-2,4-dionato Eu0.01, Gd0.99
dimethylbenzylammonium tetrakis 3-ethylpentane-2,4-dionato Eu0.01, Gd0.99
dimethylbenzylammonium tetrakis pivaloyltrifluoroacetonato Eu0.01, Gd0.99
dimethylbenzylammonium tetrakis trifluoroacetylacetonato Eu0.01, Gd0.99
dimethylbenzylammonium tetrakis hexafluoroacetylacetonato Eu0.01, Gd0.99
dimethylbenzylammonium tetrakis 6,6,7,7,8,8,8-heptafluoro-2,2-dimethyloctanedionato Eu0.01, Gd0.99
dimethylbenzylammonium tetrakis 1-phenyl-1,3-butanedionato Eu0.01, Gd0.99
triallylammonium tetrakis acetylacetonato Eu0.01, Gd0.99
triallylammonium tetrakis dibenzoylmethanato Eu0.01, Gd0.99
triallylammonium tetrakis thenoyltrifluoroacetonato Eu0.01, Gd0.99
triallylammonium tetrakis 2,2,6,6-tetramethylheptanedionato Eu0.01, Gd0.99
triallylammonium tetrakis 3-methylpentane-2,4-dionato Eu0.01, Gd0.99
triallylammonium tetrakis 3-ethylpentane-2,4-dionato Eu0.01, Gd0.99
triallylammonium tetrakis pivaloyltrifluoroacetonato Eu0.01, Gd0.99
triallylammonium tetrakis trifluoroacetylacetonato Eu0.01, Gd0.99
triallylammonium tetrakis hexafluoroacetylacetonato Eu0.01, Gd0.99
triallylammonium tetrakis 6,6,7,7,8,8,8-heptafluoro-2,2-dimethyloctanedionato Eu0.01, Gd0.99
triallylammonium tetrakis 1-phenyl-1,3-butanedionato Eu0.01, Gd0.99
anilinium tetrakis acetylacetonato Eu0.01, Gd0.99
anilinium tetrakis dibenzoylmethanato Eu0.01, Gd0.99
anilinium tetrakis thenoyltrifluoroacetonato Eu0.01, Gd0.99
anilinium tetrakis 2,2,6,6-tetramethylheptanedionato Eu0.01, Gd0.99
anilinium tetrakis 3-methylpentane-2,4-dionato Eu0.01, Gd0.99 anilinium tetrakis 3-ethylpentane-2,4-dionato Eu0.01, Gd0.99
anilinium tetrakis pivaloyltrifluoroacetonato Eu0.01, Gd0.99
anilinium tetrakis trifluoroacetylacetonato Eu0.01, Gd0.99
anilinium tetrakis hexafluoroacetylacetonato Eu0.01, Gd0.99
anilinium tetrakis 6,6,7,7,8,8,8-heptafluoro-2,2-dimethyloctanedionato Eu0.01, Gd0.99
anilinium tetrakis 1-phenyl-1,3-butanedionato Eu0.01, Gd0.99
triethylammonium tetrakis acetylacetonato Eu0.5, Gd0.5
triethylammonium tetrakis dibenzoylmethanato Eu0.5, Gd0.5
triethylammonium tetrakis thenoyltrifluoroacetonato Eu0.5, Gd0.5
triethylammonium tetrakis 2,2,6,6-tetramethylheptanedionato Eu0.5, Gd0.5
triethylammonium tetrakis 3-methylpentane-2,4-dionato Eu0.5, Gd0.5
triethylammonium tetrakis 3-ethylpentane-2,4-dionato Eu0.5, Gd0.5
triethylammonium tetrakis pivaloyltrifluoroacetonato Eu0.5, Gd0.5
triethylammonium tetrakis trifluoroacetylacetonato Eu0.5, Gd0.5
triethylammonium tetrakis hexafluoroacetylacetonato Eu0.5, Gd0.5
triethylammonium tetrakis 6,6,7,7,8,8,8-heptafluoro-2,2-dimethyloctanedionato Eu0.5, Gd0.5
triethylammonium tetrakis 1-phenyl-1,3-butanedionato Eu0.5, Gd0.5
morpholinium tetrakis acetylacetonato Eu0.5, Gd0.5
morpholinium tetrakis dibenzoylmethanato Eu0.5, Gd0.5
morpholinium tetrakis thenoyltrifluoroacetonato Eu0.5, Gd0.5
morpholinium tetrakis 2,2,6,6-tetramethylheptanedionato Eu0.5, Gd0.5
morpholinium tetrakis 3-methylpentane-2,4-dionato Eu0.5, Gd0.5
morpholinium tetrakis 3-ethylpentane-2,4-dionato Eu0.5, Gd0.5
morpholinium tetrakis pivaloyltrifluoroacetonato Eu0.5, Gd0.5
morpholinium tetrakis trifluoroacetylacetonato Eu0.5, Gd0.5
morpholinium tetrakis hexafluoroacetylacetonato Eu0.5, Gd0.5
morpholinium tetrakis 6,6,7,7,8,8,8-heptafluoro-2,2-dimethyloctanedionato Eu0.5, Gd0.5
morpholinium tetrakis 1-phenyl-1,3-butanedionato Eu0.5, Gd0.5
dimethylbenzylammonium tetrakis acetylacetonato Eu0.5, Gd0.5
dimethylbenzylammonium tetrakis dibenzoylmethanato Eu0.5, Gd0.5
dimethylbenzylammonium tetrakis thenoyltrifluoroacetonato Eu0.5, Gd0.5
dimethylbenzylammonium tetrakis 2,2,6,6-tetramethylheptanedionato Eu0.5, Gd0.5
dimethylbenzylammonium tetrakis 3-methylpentane-2,4-dionato Eu0.5, Gd0.5
dimethylbenzylammonium tetrakis 3-ethylpentane-2,4-dionato Eu0.5, Gd0.5
dimethylbenzylammonium tetrakis pivaloyltrifluoroacetonato Eu0.5, Gd0.5
dimethylbenzylammonium tetrakis trifluoroacetylacetonato Eu0.5, Gd0.5
dimethylbenzylammonium tetrakis hexafluoroacetylacetonato Eu0.5, Gd0.5
dimethylbenzylammonium tetrakis 6,6,7,7,8,8,8-heptafluoro-2,2-dimethyloctanedionato Eu0.5, Gd0.5
dimethylbenzylammonium tetrakis 1-phenyl-1,3-butanedionato Eu0.5, Gd0.5
triallylammonium tetrakis acetylacetonato Eu0.5, Gd0.5
triallylammonium tetrakis dibenzoylmethanato Eu0.5, Gd0.5
triallylammonium tetrakis thenoyltrifluoroacetonato Eu0.5, Gd0.5
triallylammonium tetrakis 2,2,6,6-tetramethylheptanedionato Eu0.5, Gd0.5
triallylammonium tetrakis 3-methylpentane-2,4-dionato Eu0.5, Gd0.5
triallylammonium tetrakis 3-ethylpentane-2,4-dionato Eu0.5, Gd0.5
triallylammonium tetrakis pivaloyltrifluoroacetonato Eu0.5, Gd0.5
triallylammonium tetrakis trifluoroacetylacetonato Eu0.5, Gd0.5
triallylammonium tetrakis hexafluoroacetylacetonato Eu0.5, Gd0.5
triallylammonium tetrakis 6,6,7,7,8,8,8-heptafluoro-2,2-dimethyloctanedionato Eu0.5, Gd0.5
triallylammonium tetrakis 1-phenyl-1,3-butanedionato Eu0.5, Gd0.5
anilinium tetrakis acetylacetonato Eu0.5, Gd0.5
anilinium tetrakis dibenzoylmethanato Eu0.5, Gd0.5
anilinium tetrakis thenoyltrifluoroacetonato Eu0.5, Gd0.5
anilinium tetrakis 2,2,6,6-tetramethylheptanedionato Eu0.5, Gd0.5
anilinium tetrakis 3-methylpentane-2,4-dionato Eu0.5, Gd0.5
anilinium tetrakis 3-ethylpentane-2,4-dionato Eu0.5, Gd0.5
anilinium tetrakis pivaloyltrifluoroacetonato Eu0.5, Gd0.5
anilinium tetrakis trifluoroacetylacetonato Eu0.5, Gd0.5
anilinium tetrakis hexafluoroacetylacetonato Eu0.5, Gd0.5
anilinium tetrakis 6,6,7,7,8,8,8-heptafluoro-2,2-dimethyloctanedionato Eu0.5, Gd0.5
anilinium tetrakis 1-phenyl-1,3-butanedionato Eu0.5, Gd0.5
triethylammonium tetrakis acetylacetonato Eu0.2, Gd0.8
triethylammonium tetrakis dibenzoylmethanato Eu0.2, Gd0.8
triethylammonium tetrakis thenoyltrifluoroacetonato Eu0.2, Gd0.8
triethylammonium tetrakis 2,2,6,6-tetramethylheptanedionato Eu0.2, Gd0.8
triethylammonium tetrakis 3-methylpentane-2,4-dionato Eu0.2, Gd0.8
triethylammonium tetrakis 3-ethylpentane-2,4-dionato Eu0.2, Gd0.8
triethylammonium tetrakis pivaloyltrifluoroacetonato Eu0.2, Gd0.8
triethylammonium tetrakis trifluoroacetylacetonato Eu0.2, Gd0.8
triethylammonium tetrakis hexafluoroacetylacetonato Eu0.2, Gd0.8
triethylammonium tetrakis 6,6,7,7,8,8,8-heptafluoro-2,2-dimethyloctanedionato Eu0.2, Gd0.8
triethylammonium tetrakis 1-phenyl-1,3-butanedionato Eu0.2, Gd0.8
morpholinium tetrakis acetylacetonato Eu0.2, Gd0.8
morpholinium tetrakis dibenzoylmethanato Eu0.2, Gd0.8 morpholinium tetrakis thenoyltrifluoroacetonato Eu0.2, Gd0.8
morpholinium tetrakis 2,2,6,6-tetramethylheptanedionato Eu0.2, Gd0.8
morpholinium tetrakis 3-methylpentane-2,4-dionato Eu0.2, Gd0.8
morpholinium tetrakis 3-ethylpentane-2,4-dionato Eu0.2, Gd0.8
morpholinium tetrakis pivaloyltrifluoroacetonato Eu0.2, Gd0.8
morpholinium tetrakis trifluoroacetylacetonato Eu0.2, Gd0.8
morpholinium tetrakis hexafluoroacetylacetonato Eu0.2, Gd0.8
morpholinium tetrakis 6,6,7,7,8,8,8-heptafluoro-2,2-dimethyloctanedionato Eu0.2, Gd0.8
morpholinium tetrakis 1-phenyl-1,3-butanedionato Eu0.2, Gd0.8
dimethylbenzylammonium tetrakis acetylacetonato Eu0.2, Gd0.8
dimethylbenzylammonium tetrakis dibenzoylmethanato Eu0.2, Gd0.8
dimethylbenzylammonium tetrakis thenoyltrifluoroacetonato Eu0.2, Gd0.8
dimethylbenzylammonium tetrakis 2,2,6,6-tetramethylheptanedionato Eu0.2, Gd0.8
dimethylbenzylammonium tetrakis 3-methylpentane-2,4-dionato Eu0.2, Gd0.8
dimethylbenzylammonium tetrakis 3-ethylpentane-2,4-dionato Eu0.2, Gd0.8
dimethylbenzylammonium tetrakis pivaloyltrifluoroacetonato Eu0.2, Gd0.8
dimethylbenzylammonium tetrakis trifluoroacetylacetonato Eu0.2, Gd0.8
dimethylbenzylammonium tetrakis hexafluoroacetylacetonato Eu0.2, Gd0.8
dimethylbenzylammonium tetrakis 6,6,7,7,8,8,8-heptafluoro-2,2-dimethyloctanedionato Eu0.2, Gd0.8
dimethylbenzylammonium tetrakis 1-phenyl-1,3-butanedionato Eu0.2, Gd0.8
triallylammonium tetrakis acetylacetonato Eu0.2, Gd0.8
triallylammonium tetrakis dibenzoylmethanato Eu0.2, Gd0.8
triallylammonium tetrakis thenoyltrifluoroacetonato Eu0.2, Gd0.8
triallylammonium tetrakis 2,2,6,6-tetramethylheptanedionato Eu0.2, Gd0.8
triallylammonium tetrakis 3-methylpentane-2,4-dionato Eu0.2, Gd0.8
triallylammonium tetrakis 3-ethylpentane-2,4-dionato Eu0.2, Gd0.8
triallylammonium tetrakis pivaloyltrifluoroacetonato Eu0.2, Gd0.8
triallylammonium tetrakis trifluoroacetylacetonato Eu0.2, Gd0.8
triallylammonium tetrakis hexafluoroacetylacetonato Eu0.2, Gd0.8
triallylammonium tetrakis 6,6,7,7,8,8,8-heptafluoro-2,2-dimethyloctanedionato Eu0.2, Gd0.8
triallylammonium tetrakis 1-phenyl-1,3-butanedionato Eu0.2, Gd0.8
anilinium tetrakis acetylacetonato Eu0.2, Gd0.8
anilinium tetrakis dibenzoylmethanato Eu0.2, Gd0.8
anilinium tetrakis thenoyltrifluoroacetonato Eu0.2, Gd0.8
anilinium tetrakis 2,2,6,6-tetramethylheptanedionato Eu0.2, Gd0.8
anilinium tetrakis 3-methylpentane-2,4-dionato Eu0.2, Gd0.8
anilinium tetrakis 3-ethylpentane-2,4-dionato Eu0.2, Gd0.8
anilinium tetrakis pivaloyltrifluoroacetonato Eu0.2, Gd0.8
anilinium tetrakis trifluoroacetylacetonato Eu0.2, Gd0.8
anilinium tetrakis hexafluoroacetylacetonato Eu0.2, Gd0.8
anilinium tetrakis 6,6,7,7,8,8,8-heptafluoro-2,2-dimethyloctanedionato Eu0.2, Gd0.8
anilinium tetrakis 1-phenyl-1,3-butanedionato Eu0.2, Gd0.8
triethylammonium tetrakis acetylacetonato Eu0.1, Gd0.9
triethylammonium tetrakis dibenzoylmethanato Eu0.1, Gd0.9
triethylammonium tetrakis thenoyltrifluoroacetonato Eu0.1, Gd0.9
triethylammonium tetrakis 2,2,6,6-tetramethylheptanedionato Eu0.1, Gd0.9
triethylammonium tetrakis 3-methylpentane-2,4-dionato Eu0.1, Gd0.9
triethylammonium tetrakis 3-ethylpentane-2,4-dionato Eu0.1, Gd0.9
triethylammonium tetrakis pivaloyltrifluoroacetonato Eu0.1, Gd0.9
triethylammonium tetrakis trifluoroacetylacetonato Eu0.1, Gd0.9
triethylammonium tetrakis hexafluoroacetylacetonato Eu0.1, Gd0.9
triethylammonium tetrakis 6,6,7,7,8,8,8-heptafluoro-2,2-dimethyloctanedionato Eu0.1, Gd0.9
triethylammonium tetrakis 1-phenyl-1,3-butanedionato Eu0.1, Gd0.9
morpholinium tetrakis acetylacetonato Eu0.1, Gd0.9
morpholinium tetrakis dibenzoylmethanato Eu0.1, Gd0.9
morpholinium tetrakis thenoyltrifluoroacetonato Eu0.1, Gd0.9
morpholinium tetrakis 2,2,6,6-tetramethylheptanedionato Eu0.1, Gd0.9
morpholinium tetrakis 3-methylpentane-2,4-dionato Eu0.1, Gd0.9
morpholinium tetrakis 3-ethylpentane-2,4-dionato Eu0.1, Gd0.9
morpholinium tetrakis pivaloyltrifluoroacetonato Eu0.1, Gd0.9
morpholinium tetrakis trifluoroacetylacetonato Eu0.1, Gd0.9
morpholinium tetrakis hexafluoroacetylacetonato Eu0.1, Gd0.9
morpholinium tetrakis 6,6,7,7,8,8,8-heptafluoro-2,2-dimethyloctanedionato Eu0.1, Gd0.9
morpholinium tetrakis 1-phenyl-1,3-butanedionato Eu0.1, Gd0.9
dimethylbenzylammonium tetrakis acetylacetonato Eu0.1, Gd0.9
dimethylbenzylammonium tetrakis dibenzoylmethanato Eu0.1, Gd0.9
dimethylbenzylammonium tetrakis thenoyltrifluoroacetonato Eu0.1, Gd0.9
dimethylbenzylammonium tetrakis 2,2,6,6-tetramethylheptanedionato Eu0.1, Gd0.9
dimethylbenzylammonium tetrakis 3-methylpentane-2,4-dionato Eu0.1, Gd0.9
dimethylbenzylammonium tetrakis 3-ethylpentane-2,4-dionato Eu0.1, Gd0.9
dimethylbenzylammonium tetrakis pivaloyltrifluoroacetonato Eu0.1, Gd0.9
dimethylbenzylammonium tetrakis trifluoroacetylacetonato Eu0.1, Gd0.9 dimethylbenzylammonium tetrakis hexafluoroacetylacetonato Eu0.1, Gd0.9
dimethylbenzylammonium tetrakis 6,6,7,7,8,8,8-heptafluoro-2,2-dimethyloctanedionato Eu0.1, Gd0.9
dimethylbenzylammonium tetrakis 1-phenyl-1,3-butanedionato Eu0.1, Gd0.9
triallylammonium tetrakis acetylacetonato Eu0.1, Gd0.9
triallylammonium tetrakis dibenzoylmethanato Eu0.1, Gd0.9
triallylammonium tetrakis thenoyltrifluoroacetonato Eu0.1, Gd0.9
triallylammonium tetrakis 2,2,6,6-tetramethylheptanedionato Eu0.1, Gd0.9
triallylammonium tetrakis 3-methylpentane-2,4-dionato Eu0.1, Gd0.9
triallylammonium tetrakis 3-ethylpentane-2,4-dionato Eu0.1, Gd0.9
triallylammonium tetrakis pivaloyltrifluoroacetonato Eu0.1, Gd0.9
triallylammonium tetrakis trifluoroacetylacetonato Eu0.1, Gd0.9
triallylammonium tetrakis hexafluoroacetylacetonato Eu0.1, Gd0.9
triallylammonium tetrakis 6,6,7,7,8,8,8-heptafluoro-2,2-dimethyloctanedionato Eu0.1, Gd0.9
triallylammonium tetrakis 1-phenyl-1,3-butanedionato Eu0.1, Gd0.9
anilinium tetrakis acetylacetonato Eu0.1, Gd0.9
anilinium tetrakis dibenzoylmethanato Eu0.1, Gd0.9
anilinium tetrakis thenoyltrifluoroacetonato Eu0.1, Gd0.9
anilinium tetrakis 2,2,6,6-tetramethylheptanedionato Eu0.1, Gd0.9
anilinium tetrakis 3-methylpentane-2,4-dionato Eu0.1, Gd0.9
anilinium tetrakis 3-ethylpentane-2,4-dionato Eu0.1, Gd0.9
anilinium tetrakis pivaloyltrifluoroacetonato Eu0.1, Gd0.9
anilinium tetrakis trifluoroacetylacetonato Eu0.1, Gd0.9
anilinium tetrakis hexafluoroacetylacetonato Eu0.1, Gd0.9
anilinium tetrakis 6,6,7,7,8,8,8-heptafluoro-2,2-dimethyloctanedionato Eu0.1, Gd0.9
anilinium tetrakis 1-phenyl-1,3-butanedionato Eu0.1, Gd0.9
triethylammonium tetrakis acetylacetonato Eu0.01, Gd0.99
triethylammonium tetrakis dibenzoylmethanato Eu0.01, Gd0.99
triethylammonium tetrakis thenoyltrifluoroacetonato Eu0.01, Gd0.99
triethylammonium tetrakis 2,2,6,6-tetramethylheptanedionato Eu0.01, Gd0.99
triethylammonium tetrakis 3-methylpentane-2,4-dionato Eu0.01, Gd0.99
triethylammonium tetrakis 3-ethylpentane-2,4-dionato Eu0.01, Gd0.99
triethylammonium tetrakis pivaloyltrifluoroacetonato Eu0.01, Gd0.99
triethylammonium tetrakis trifluoroacetylacetonato Eu0.01, Gd0.99
triethylammonium tetrakis hexafluoroacetylacetonato Eu0.01, Gd0.99
triethylammonium tetrakis 6,6,7,7,8,8,8-heptafluoro-2,2-dimethyloctanedionato Eu0.01, Gd0.99
triethylammonium tetrakis 1-phenyl-1,3-butanedionato Eu0.01, Gd0.99
morpholinium tetrakis acetylacetonato Eu0.01, Gd0.99
morpholinium tetrakis dibenzoylmethanato Eu0.01, Gd0.99
morpholinium tetrakis thenoyltrifluoroacetonato Eu0.01, Gd0.99
morpholinium tetrakis 2,2,6,6-tetramethylheptanedionato Eu0.01, Gd0.99
morpholinium tetrakis 3-methylpentane-2,4-dionato Eu0.01, Gd0.99
morpholinium tetrakis 3-ethylpentane-2,4-dionato Eu0.01, Gd0.99
morpholinium tetrakis pivaloyltrifluoroacetonato Eu0.01, Gd0.99
morpholinium tetrakis trifluoroacetylacetonato Eu0.01, Gd0.99
morpholinium tetrakis hexafluoroacetylacetonato Eu0.01, Gd0.99
morpholinium tetrakis 6,6,7,7,8,8,8-heptafluoro-2,2-dimethyloctanedionato Eu0.01, Gd0.99
morpholinium tetrakis 1-phenyl-1,3-butanedionato Eu0.01, Gd0.99
dimethylbenzylammonium tetrakis acetylacetonato Eu0.01, Gd0.99
dimethylbenzylammonium tetrakis dibenzoylmethanato Eu0.01, Gd0.99
dimethylbenzylammonium tetrakis thenoyltrifluoroacetonato Eu0.01, Gd0.99
dimethylbenzylammonium tetrakis 2,2,6,6-tetramethylheptanedionato Eu0.01, Gd0.99
dimethylbenzylammonium tetrakis 3-methylpentane-2,4-dionato Eu0.01, Gd0.99
dimethylbenzylammonium tetrakis 3-ethylpentane-2,4-dionato Eu0.01, Gd0.99
dimethylbenzylammonium tetrakis pivaloyltrifluoroacetonato Eu0.01, Gd0.99
dimethylbenzylammonium tetrakis trifluoroacetylacetonato Eu0.01, Gd0.99
dimethylbenzylammonium tetrakis hexafluoroacetylacetonato Eu0.01, Gd0.99
dimethylbenzylammonium tetrakis 6,6,7,7,8,8,8-heptafluoro-2,2-dimethyloctanedionato Eu0.01, Gd0.99
dimethylbenzylammonium tetrakis 1-phenyl-1,3-butanedionato Eu0.01, Gd0.99
triallylammonium tetrakis acetylacetonato Eu0.01, Gd0.99
triallylammonium tetrakis dibenzoylmethanato Eu0.01, Gd0.99
triallylammonium tetrakis thenoyltrifluoroacetonato Eu0.01, Gd0.99
triallylammonium tetrakis 2,2,6,6-tetramethylheptanedionato Eu0.01, Gd0.99
triallylammonium tetrakis 3-methylpentane-2,4-dionato Eu0.01, Gd0.99
triallylammonium tetrakis 3-ethylpentane-2,4-dionato Eu0.01, Gd0.99
triallylammonium tetrakis pivaloyltrifluoroacetonato Eu0.01, Gd0.99
triallylammonium tetrakis trifluoroacetylacetonato Eu0.01, Gd0.99
triallylammonium tetrakis hexafluoroacetylacetonato Eu0.01, Gd0.99
triallylammonium tetrakis 6,6,7,7,8,8,8-heptafluoro-2,2-dimethyloctanedionato Eu0.01, Gd0.99
triallylammonium tetrakis 1-phenyl-1,3-butanedionato Eu0.01, Gd0.99
anilinium tetrakis acetylacetonato Eu0.01, Gd0.99
anilinium tetrakis dibenzoylmethanato Eu0.01, Gd0.99
anilinium tetrakis thenoyltrifluoroacetonato Eu0.01, Gd0.99
anilinium tetrakis 2,2,6,6-tetramethylheptanedionato Eu0.01, Gd0.99
anilinium tetrakis 3-methylpentane-2,4-dionato Eu0.01, Gd0.99 anilinium tetrakis 3-ethylpentane-2,4-dionato Eu0.01, Gd0.99
anilinium tetrakis pivaloyltrifluoroacetonato Eu0.01, Gd0.99
anilinium tetrakis trifluoroacetylacetonato Eu0.01, Gd0.99
anilinium tetrakis hexafluoroacetylacetonato Eu0.01, Gd0.99
anilinium tetrakis 6,6,7,7,8,8,8-heptafluoro-2,2-dimethyloctanedionato Eu0.01, Gd0.99
anilinium tetrakis 1-phenyl-1,3-butanedionato Eu0.01, Gd0.99
triethylammonium tetrakis acetylacetonato Sm0.5, Y0.5
triethylammonium tetrakis dibenzoylmethanato Sm0.5, Y0.5
triethylammonium tetrakis thenoyltrifluoroacetonato Sm0.5, Y0.5
triethylammonium tetrakis 2,2,6,6-tetramethylheptanedionato Sm0.5, Y0.5
triethylammonium tetrakis 3-methylpentane-2,4-dionato Sm0.5, Y0.5
triethylammonium tetrakis 3-ethylpentane-2,4-dionato Sm0.5, Y0.5
triethylammonium tetrakis pivaloyltrifluoroacetonato Sm0.5, Y0.5
triethylammonium tetrakis trifluoroacetylacetonato Sm0.5, Y0.5
triethylammonium tetrakis hexafluoroacetylacetonato Sm0.5, Y0.5
triethylammonium tetrakis 6,6,7,7,8,8,8-heptafluoro-2,2-dimethyloctanedionato Sm0.5, Y0.5
triethylammonium tetrakis 1-phenyl-1,3-butanedionato Sm0.5, Y0.5
morpholinium tetrakis acetylacetonato Sm0.5, Y0.5
morpholinium tetrakis dibenzoylmethanato Sm0.5, Y0.5
morpholinium tetrakis thenoyltrifluoroacetonato Sm0.5, Y0.5
morpholinium tetrakis 2,2,6,6-tetramethylheptanedionato Sm0.5, Y0.5
morpholinium tetrakis 3-methylpentane-2,4-dionato Sm0.5, Y0.5
morpholinium tetrakis 3-ethylpentane-2,4-dionato Sm0.5, Y0.5
morpholinium tetrakis pivaloyltrifluoroacetonato Sm0.5, Y0.5
morpholinium tetrakis trifluoroacetylacetonato Sm0.5, Y0.5
morpholinium tetrakis hexafluoroacetylacetonato Sm0.5, Y0.5
morpholinium tetrakis 6,6,7,7,8,8,8-heptafluoro-2,2-dimethyloctanedionato Sm0.5, Y0.5
morpholinium tetrakis 1-phenyl-1,3-butanedionato Sm0.5, Y0.5
dimethylbenzylammonium tetrakis acetylacetonato Sm0.5, Y0.5
dimethylbenzylammonium tetrakis dibenzoylmethanato Sm0.5, Y0.5
dimethylbenzylammonium tetrakis thenoyltrifluoroacetonato Sm0.5, Y0.5
dimethylbenzylammonium tetrakis 2,2,6,6-tetramethylheptanedionato Sm0.5, Y0.5
dimethylbenzylammonium tetrakis 3-methylpentane-2,4-dionato Sm0.5, Y0.5
dimethylbenzylammonium tetrakis 3-ethylpentane-2,4-dionato Sm0.5, Y0.5
dimethylbenzylammonium tetrakis pivaloyltrifluoroacetonato Sm0.5, Y0.5
dimethylbenzylammonium tetrakis trifluoroacetylacetonato Sm0.5, Y0.5
dimethylbenzylammonium tetrakis hexafluoroacetylacetonato Sm0.5, Y0.5
dimethylbenzylammonium tetrakis 6,6,7,7,8,8,8-heptafluoro-2,2-dimethyloctanedionato Sm0.5, Y0.5
dimethylbenzylammonium tetrakis 1-phenyl-1,3-butanedionato Sm0.5, Y0.5
triallylammonium tetrakis acetylacetonato Sm0.5, Y0.5
triallylammonium tetrakis dibenzoylmethanato Sm0.5, Y0.5
triallylammonium tetrakis thenoyltrifluoroacetonato Sm0.5, Y0.5
triallylammonium tetrakis 2,2,6,6-tetramethylheptanedionato Sm0.5, Y0.5
triallylammonium tetrakis 3-methylpentane-2,4-dionato Sm0.5, Y0.5
triallylammonium tetrakis 3-ethylpentane-2,4-dionato Sm0.5, Y0.5
triallylammonium tetrakis pivaloyltrifluoroacetonato Sm0.5, Y0.5
triallylammonium tetrakis trifluoroacetylacetonato Sm0.5, Y0.5
triallylammonium tetrakis hexafluoroacetylacetonato Sm0.5, Y0.5
triallylammonium tetrakis 6,6,7,7,8,8,8-heptafluoro-2,2-dimethyloctanedionato Sm0.5, Y0.5
triallylammonium tetrakis 1-phenyl-1,3-butanedionato Sm0.5, Y0.5
anilinium tetrakis acetylacetonato Sm0.5, Y0.5
anilinium tetrakis dibenzoylmethanato Sm0.5, Y0.5
anilinium tetrakis thenoyltrifluoroacetonato Sm0.5, Y0.5
anilinium tetrakis 2,2,6,6-tetramethylheptanedionato Sm0.5, Y0.5
anilinium tetrakis 3-methylpentane-2,4-dionato Sm0.5, Y0.5
anilinium tetrakis 3-ethylpentane-2,4-dionato Sm0.5, Y0.5
anilinium tetrakis pivaloyltrifluoroacetonato Sm0.5, Y0.5
anilinium tetrakis trifluoroacetylacetonato Sm0.5, Y0.5
anilinium tetrakis hexafluoroacetylacetonato Sm0.5, Y0.5
anilinium tetrakis 6,6,7,7,8,8,8-heptafluoro-2,2-dimethyloctanedionato Sm0.5, Y0.5
anilinium tetrakis 1-phenyl-1,3-butanedionato Sm0.5, Y0.5
triethylammonium tetrakis acetylacetonato Sm0.2, Y0.8
triethylammonium tetrakis dibenzoylmethanato Sm0.2, Y0.8
triethylammonium tetrakis thenoyltrifluoroacetonato Sm0.2, Y0.8
triethylammonium tetrakis 2,2,6,6-tetramethylheptanedionato Sm0.2, Y0.8
triethylammonium tetrakis 3-methylpentane-2,4-dionato Sm0.2, Y0.8
triethylammonium tetrakis 3-ethylpentane-2,4-dionato Sm0.2, Y0.8
triethylammonium tetrakis pivaloyltrifluoroacetonato Sm0.2, Y0.8
triethylammonium tetrakis trifluoroacetylacetonato Sm0.2, Y0.8
triethylammonium tetrakis hexafluoroacetylacetonato Sm0.2, Y0.8
triethylammonium tetrakis 6,6,7,7,8,8,8-heptafluoro-2,2-dimethyloctanedionato Sm0.2, Y0.8
triethylammonium tetrakis 1-phenyl-1,3-butanedionato Sm0.2, Y0.8
morpholinium tetrakis acetylacetonato Sm0.2, Y0.8
morpholinium tetrakis dibenzoylmethanato Sm0.2, Y0.8
morpholinium tetrakis thenoyltrifluoroacetonato Sm0.2, Y0.8
morpholinium tetrakis 2,2,6,6-tetramethylheptanedionato Sm0.2, Y0.8 morpholinium tetrakis 3-methylpentane-2,4-dionato Sm0.2, Y0.8
morpholinium tetrakis 3-ethylpentane-2,4-dionato Sm0.2, Y0.8
morpholinium tetrakis pivaloyltrifluoroacetonato Sm0.2, Y0.8
morpholinium tetrakis trifluoroacetylacetonato Sm0.2, Y0.8
morpholinium tetrakis hexafluoroacetylacetonato Sm0.2, Y0.8
morpholinium tetrakis 6,6,7,7,8,8,8-heptafluoro-2,2-dimethyloctanedionato Sm0.2, Y0.8
morpholinium tetrakis 1-phenyl-1,3-butanedionato Sm0.2, Y0.8
dimethylbenzylammonium tetrakis acetylacetonato Sm0.2, Y0.8
dimethylbenzylammonium tetrakis dibenzoylmethanato Sm0.2, Y0.8
dimethylbenzylammonium tetrakis thenoyltrifluoroacetonato Sm0.2, Y0.8
dimethylbenzylammonium tetrakis 2,2,6,6-tetramethylheptanedionato Sm0.2, Y0.8
dimethylbenzylammonium tetrakis 3-methylpentane-2,4-dionato Sm0.2, Y0.8
dimethylbenzylammonium tetrakis 3-ethylpentane-2,4-dionato Sm0.2, Y0.8
dimethylbenzylammonium tetrakis pivaloyltrifluoroacetonato Sm0.2, Y0.8
dimethylbenzylammonium tetrakis trifluoroacetylacetonato Sm0.2, Y0.8
dimethylbenzylammonium tetrakis hexafluoroacetylacetonato Sm0.2, Y0.8
dimethylbenzylammonium tetrakis 6,6,7,7,8,8,8-heptafluoro-2,2-dimethyloctanedionato Sm0.2, Y0.8
dimethylbenzylammonium tetrakis 1-phenyl-1,3-butanedionato Sm0.2, Y0.8
triallylammonium tetrakis acetylacetonato Sm0.2, Y0.8
triallylammonium tetrakis dibenzoylmethanato Sm0.2, Y0.8
triallylammonium tetrakis thenoyltrifluoroacetonato Sm0.2, Y0.8
triallylammonium tetrakis 2,2,6,6-tetramethylheptanedionato Sm0.2, Y0.8
triallylammonium tetrakis 3-methylpentane-2,4-dionato Sm0.2, Y0.8
triallylammonium tetrakis 3-ethylpentane-2,4-dionato Sm0.2, Y0.8
triallylammonium tetrakis pivaloyltrifluoroacetonato Sm0.2, Y0.8
triallylammonium tetrakis trifluoroacetylacetonato Sm0.2, Y0.8
triallylammonium tetrakis hexafluoroacetylacetonato Sm0.2, Y0.8
triallylammonium tetrakis 6,6,7,7,8,8,8-heptafluoro-2,2-dimethyloctanedionato Sm0.2, Y0.8
triallylammonium tetrakis 1-phenyl-1,3-butanedionato Sm0.2, Y0.8
anilinium tetrakis acetylacetonato Sm0.2, Y0.8
anilinium tetrakis dibenzoylmethanato Sm0.2, Y0.8
anilinium tetrakis thenoyltrifluoroacetonato Sm0.2, Y0.8
anilinium tetrakis 2,2,6,6-tetramethylheptanedionato Sm0.2, Y0.8
anilinium tetrakis 3-methylpentane-2,4-dionato Sm0.2, Y0.8
anilinium tetrakis 3-ethylpentane-2,4-dionato Sm0.2, Y0.8
anilinium tetrakis pivaloyltrifluoroacetonato Sm0.2, Y0.8
anilinium tetrakis trifluoroacetylacetonato Sm0.2, Y0.8
anilinium tetrakis hexafluoroacetylacetonato Sm0.2, Y0.8
anilinium tetrakis 6,6,7,7,8,8,8-heptafluoro-2,2-dimethyloctanedionato Sm0.2, Y0.8
anilinium tetrakis 1-phenyl-1,3-butanedionato Sm0.2, Y0.8
triethylammonium, tetrakis acetylacetonato Sm0.1, Y0.9
triethylammonium tetrakis dibenzoylmethanato Sm0.1, Y0.9
triethylammonium tetrakis thenoyltrifluoroacetonato Sm0.1, Y0.9
triethylammonium tetrakis 2,2,6,6-tetramethylheptanedionato Sm0.1, Y0.9
triethylammonium tetrakis 3-methylpentane-2,4-dionato Sm0.1, Y0.9
triethylammonium tetrakis 3-ethylpentane-2,4-dionato Sm0.1, Y0.9
triethylammonium tetrakis pivaloyltrifluoroacetonato Sm0.1, Y0.9
triethylammonium tetrakis trifluoroacetylacetonato Sm0.1, Y0.9
triethylammonium tetrakis hexafluoroacetylacetonato Sm0.1, Y0.9
triethylammonium tetrakis 6,6,7,7,8,8,8-heptafluoro-2,2-dimethyloctanedionato Sm0.1, Y0.9
triethylammonium tetrakis 1-phenyl-1,3-butanedionato Sm0.1, Y0.9
morpholinium tetrakis acetylacetonato Sm0.1, Y0.9
morpholinium tetrakis dibenzoylmethanato Sm0.1, Y0.9
morpholinium tetrakis thenoyltrifluoroacetonato Sm0.1, Y0.9
morpholinium tetrakis 2,2,6,6-tetramethylheptanedionato Sm0.1, Y0.9
morpholinium tetrakis 3-methylpentane-2,4-dionato Sm0.1, Y0.9
morpholinium tetrakis 3-ethylpentane-2,4-dionato Sm0.1, Y0.9
morpholinium tetrakis pivaloyltrifluoroacetonato Sm0.1, Y0.9
morpholinium tetrakis trifluoroacetylacetonato Sm0.1, Y0.9
morpholinium tetrakis hexafluoroacetylacetonato Sm0.1, Y0.9
morpholinium tetrakis 6,6,7,7,8,8,8-heptafluoro-2,2-dimethyloctanedionato Sm0.1, Y0.9
morpholinium tetrakis 1-phenyl-1,3-butanedionato Sm0.1, Y0.9
dimethylbenzylammonium tetrakis acetylacetonato Sm0.1, Y0.9
dimethylbenzylammonium tetrakis dibenzoylmethanato Sm0.1, Y0.9
dimethylbenzylammonium tetrakis thenoyltrifluoroacetonato Sm0.1, Y0.9
dimethylbenzylammonium tetrakis 2,2,6,6-tetramethylheptanedionato Sm0.1, Y0.9
dimethylbenzylammonium tetrakis 3-methylpentane-2,4-dionato Sm0.1, Y0.9
dimethylbenzylammonium tetrakis 3-ethylpentane-2,4-dionato Sm0.1, Y0.9
dimethylbenzylammonium tetrakis pivaloyltrifluoroacetonato Sm0.1, Y0.9
dimethylbenzylammonium tetrakis trifluoroacetylacetonato Sm0.1, Y0.9
dimethylbenzylammonium tetrakis hexafluoroacetylacetonato Sm0.1, Y0.9
dimethylbenzylammonium tetrakis 6,6,7,7,8,8,8-heptafluoro-2,2-dimethyloctanedionato Sm0.1, Y0.9
dimethylbenzylammonium tetrakis 1-phenyl-1,3-butanedionato Sm0.1, Y0.9
triallylammonium tetrakis acetylacetonato Sm0.1, Y0.9
triallylammonium tetrakis dibenzoylmethanato Sm0.1, Y0.9
triallylammonium tetrakis thenoyltrifluoroacetonato Sm0.1, Y0.9 triallylammonium tetrakis 2,2,6,6-tetramethylheptanedionato Sm0.1, Y0.9
triallylammonium tetrakis 3-methylpentane-2,4-dionato Sm0.1, Y0.9
triallylammonium tetrakis 3-ethylpentane-2,4-dionato Sm0.1, Y0.9
triallylammonium tetrakis pivaloyltrifluoroacetonato Sm0.1, Y0.9
triallylammonium tetrakis trifluoroacetylacetonato Sm0.1, Y0.9
triallylammonium tetrakis hexafluoroacetylacetonato Sm0.1, Y0.9
triallylammonium tetrakis 6,6,7,7,8,8,8-heptafluoro-2,2-dimethyloctanedionato Sm0.1, Y0.9
triallylammonium tetrakis 1-phenyl-1,3-butanedionato Sm0.1, Y0.9
anilinium tetrakis acetylacetonato Sm0.1, Y0.9
anilinium tetrakis dibenzoylmethanato Sm0.1, Y0.9
anilinium tetrakis thenoyltrifluoroacetonato Sm0.1, Y0.9
anilinium tetrakis 2,2,6,6-tetramethylheptanedionato Sm0.1, Y0.9
anilinium tetrakis 3-methylpentane-2,4-dionato Sm0.1, Y0.9
anilinium tetrakis 3-ethylpentane-2,4-dionato Sm0.1, Y0.9
anilinium tetrakis pivaloyltrifluoroacetonato Sm0.1, Y0.9
anilinium tetrakis trifluoroacetylacetonato Sm0.1, Y0.9
anilinium tetrakis hexafluoroacetylacetonato Sm0.1, Y0.9
anilinium tetrakis 6,6,7,7,8,8,8-heptafluoro-2,2-dimethyloctanedionato Sm0.1, Y0.9
anilinium tetrakis 1-phenyl-1,3-butanedionato Sm0.1, Y0.9
triethylammonium tetrakis acetylacetonato Sm0.01, Y0.99
triethylammonium tetrakis dibenzoylmethanato Sm0.01, Y0.99
triethylammonium tetrakis thenoyltrifluoroacetonato Sm0.01, Y0.99
triethylammonium tetrakis 2,2,6,6-tetramethylheptanedionato Sm0.01, Y0.99
triethylammonium tetrakis 3-methylpentane-2,4-dionato Sm0.01, Y0.99
triethylammonium tetrakis 3-ethylpentane-2,4-dionato Sm0.01, Y0.99
triethylammonium tetrakis pivaloyltrifluoroacetonato Sm0.01, Y0.99
triethylammonium tetrakis trifluoroacetylacetonato Sm0.01, Y0.99
triethylammonium tetrakis hexafluoroacetylacetonato Sm0.01, Y0.99
triethylammonium tetrakis 6,6,7,7,8,8,8-heptafluoro-2,2-dimethyloctanedionato Sm0.01, Y0.99
triethylammonium tetrakis 1-phenyl-1,3-butanedionato Sm0.01, Y0.99
morpholinium tetrakis acetylacetonato Sm0.01, Y0.99
morpholinium tetrakis dibenzoylmethanato Sm0.01, Y0.99
morpholinium tetrakis thenoyltrifluoroacetonato Sm0.01, Y0.99
morpholinium tetrakis 2,2,6,6-tetramethylheptanedionato Sm0.01, Y0.99
morpholinium tetrakis 3-methylpentane-2,4-dionato Sm0.01, Y0.99
morpholinium tetrakis 3-ethylpentane-2,4-dionato Sm0.01, Y0.99
morpholinium tetrakis pivaloyltrifluoroacetonato Sm0.01, Y0.99
morpholinium tetrakis trifluoroacetylacetonato Sm0.01, Y0.99
morpholinium tetrakis hexafluoroacetylacetonato Sm0.01, Y0.99
morpholinium tetrakis 6,6,7,7,8,8,8-heptafluoro-2,2-dimethyloctanedionato Sm0.01, Y0.99
morpholinium tetrakis 1-phenyl-1,3-butanedionato Sm0.01, Y0.99
dimethylbenzylammonium tetrakis acetylacetonato Sm0.01, Y0.99
dimethylbenzylammonium tetrakis dibenzoylmethanato Sm0.01, Y0.99
dimethylbenzylammonium tetrakis thenoyltrifluoroacetonato Sm0.01, Y0.99
dimethylbenzylammonium tetrakis 2,2,6,6-tetramethylheptanedionato Sm0.01, Y0.99
dimethylbenzylammonium tetrakis 3-methylpentane-2,4-dionato Sm0.01, Y0.99
dimethylbenzylammonium tetrakis 3-ethylpentane-2,4-dionato Sm0.01, Y0.99
dimethylbenzylammonium tetrakis pivaloyltrifluoroacetonato Sm0.01, Y0.99
dimethylbenzylammonium tetrakis trifluoroacetylacetonato Sm0.01, Y0.99
dimethylbenzylammonium tetrakis hexafluoroacetylacetonato Sm0.01, Y0.99
dimethylbenzylammonium tetrakis 6,6,7,7,8,8,8-heptafluoro-2,2-dimethyloctanedionato Sm0.01, Y0.99
dimethylbenzylammonium tetrakis 1-phenyl-1,3-butanedionato Sm0.01, Y0.99
triallylammonium tetrakis acetylacetonato Sm0.01, Y0.99
triallylammonium tetrakis dibenzoylmethanato Sm0.01, Y0.99
triallylammonium tetrakis thenoyltrifluoroacetonato Sm0.01, Y0.99
triallylammonium tetrakis 2,2,6,6-tetramethylheptanedionato Sm0.01, Y0.99
triallylammonium tetrakis 3-methylpentane-2,4-dionato Sm0.01, Y0.99
triallylammonium tetrakis 3-ethylpentane-2,4-dionato Sm0.01, Y0.99
triallylammonium tetrakis pivaloyltrifluoroacetonato Sm0.01, Y0.99
triallylammonium tetrakis trifluoroacetylacetonato Sm0.01, Y0.99
triallylammonium tetrakis hexafluoroacetylacetonato Sm0.01, Y0.99
triallylammonium tetrakis 6,6,7,7,8,8,8-heptafluoro-2,2-dimethyloctanedionato Sm0.01, Y0.99
triallylammonium tetrakis 1-phenyl-1,3-butanedionato Sm0.01, Y0.99
anilinium tetrakis acetylacetonato Sm0.01, Y0.99
anilinium tetrakis dibenzoylmethanato Sm0.01, Y0.99
anilinium tetrakis thenoyltrifluoroacetonato Sm0.01, Y0.99
anilinium tetrakis 2,2,6,6-tetramethylheptanedionato Sm0.01, Y0.99
anilinium tetrakis 3-methylpentane-2,4-dionato Sm0.01, Y0.99
anilinium tetrakis 3-ethylpentane-2,4-dionato Sm0.01, Y0.99
anilinium tetrakis pivaloyltrifluoroacetonato Sm0.01, Y0.99
anilinium tetrakis trifluoroacetylacetonato Sm0.01, Y0.99
anilinium tetrakis hexafluoroacetylacetonato Sm0.01, Y0.99
anilinium tetrakis 6,6,7,7,8,8,8-heptafluoro-2,2-dimethyloctanedionato Sm0.01, Y0.99
anilinium tetrakis 1-phenyl-1,3-butanedionato Sm0.01, Y0.99
triethylammonium tetrakis acetylacetonato Dy0.5, Y0.5
triethylammonium tetrakis dibenzoylmethanato Dy0.5, Y0.5
triethylammonium tetrakis thenoyltrifluoroacetonato Dy0.5, Y0.5 triethylammonium tetrakis 2,2,6,6-tetramethylheptanedionato Dy0.5, Y0.5
triethylammonium tetrakis 3-methylpentane-2,4-dionato Dy0.5, Y0.5
triethylammonium tetrakis 3-ethylpentane-2,4-dionato Dy0.5, Y0.5
triethylammonium tetrakis pivaloyltrifluoroacetonato Dy0.5, Y0.5
triethylammonium tetrakis trifluoroacetylacetonato Dy0.5, Y0.5
triethylammonium tetrakis hexafluoroacetylacetonato Dy0.5, Y0.5
triethylammonium tetrakis 6,6,7,7,8,8,8-heptafluoro-2,2-dimethyloctanedionato Dy0.5, Y0.5
triethylammonium tetrakis 1-phenyl-1,3-butanedionato Dy0.5, Y0.5
morpholinium tetrakis acetylacetonato Dy0.5, Y0.5
morpholinium tetrakis dibenzoylmethanato Dy0.5, Y0.5
morpholinium tetrakis thenoyltrifluoroacetonato Dy0.5, Y0.5
morpholinium tetrakis 2,2,6,6-tetramethylheptanedionato Dy0.5, Y0.5
morpholinium tetrakis 3-methylpentane-2,4-dionato Dy0.5, Y0.5
morpholinium tetrakis 3-ethylpentane-2,4-dionato Dy0.5, Y0.5
morpholinium tetrakis pivaloyltrifluoroacetonato Dy0.5, Y0.5
morpholinium tetrakis trifluoroacetylacetonato Dy0.5, Y0.5
morpholinium tetrakis hexafluoroacetylacetonato Dy0.5, Y0.5
morpholinium tetrakis 6,6,7,7,8,8,8-heptafluoro-2,2-dimethyloctanedionato Dy0.5, Y0.5
morpholinium tetrakis 1-phenyl-1,3-butanedionato Dy0.5, Y0.5
dimethylbenzylammonium tetrakis acetylacetonato Dy0.5, Y0.5
dimethylbenzylammonium tetrakis dibenzoylmethanato Dy0.5, Y0.5
dimethylbenzylammonium tetrakis thenoyltrifluoroacetonato Dy0.5, Y0.5
dimethylbenzylammonium tetrakis 2,2,6,6-tetramethylheptanedionato Dy0.5, Y0.5
dimethylbenzylammonium tetrakis 3-methylpentane-2,4-dionato Dy0.5, Y0.5
dimethylbenzylammonium tetrakis 3-ethylpentane-2,4-dionato Dy0.5, Y0.5
dimethylbenzylammonium tetrakis pivaloyltrifluoroacetonato Dy0.5, Y0.5
dimethylbenzylammonium tetrakis trifluoroacetylacetonato Dy0.5, Y0.5
dimethylbenzylammonium tetrakis hexafluoroacetylacetonato Dy0.5, Y0.5
dimethylbenzylammonium tetrakis 6,6,7,7,8,8,8-heptafluoro-2,2-dimethyloctanedionato Dy0.5, Y0.5
dimethylbenzylammonium tetrakis 1-phenyl-1,3-butanedionato Dy0.5, Y0.5
triallylammonium tetrakis acetylacetonato Dy0.5, Y0.5
triallylammonium tetrakis dibenzoylmethanato Dy0.5, Y0.5
triallylammonium tetrakis thenoyltrifluoroacetonato Dy0.5, Y0.5
triallylammonium tetrakis 2,2,6,6-tetramethylheptanedionato Dy0.5, Y0.5
triallylammonium tetrakis 3-methylpentane-2,4-dionato Dy0.5, Y0.5
triallylammonium tetrakis 3-ethylpentane-2,4-dionato Dy0.5, Y0.5
triallylammonium tetrakis pivaloyltrifluoroacetonato Dy0.5, Y0.5
triallylammonium tetrakis trifluoroacetylacetonato Dy0.5, Y0.5
triallylammonium tetrakis hexafluoroacetylacetonato Dy0.5, Y0.5
triallylammonium tetrakis 6,6,7,7,8,8,8-heptafluoro-2,2-dimethyloctanedionato Dy0.5, Y0.5
triallylammonium tetrakis 1-phenyl-1,3-butanedionato Dy0.5, Y0.5
anilinium tetrakis acetylacetonato Dy0.5, Y0.5
anilinium tetrakis dibenzoylmethanato Dy0.5, Y0.5
anilinium tetrakis thenoyltrifluoroacetonato Dy0.5, Y0.5
anilinium tetrakis 2,2,6,6-tetramethylheptanedionato Dy0.5, Y0.5
anilinium tetrakis 3-methylpentane-2,4-dionato Dy0.5, Y0.5
anilinium tetrakis 3-ethylpentane-2,4-dionato Dy0.5, Y0.5
anilinium tetrakis pivaloyltrifluoroacetonato Dy0.5, Y0.5
anilinium tetrakis trifluoroacetylacetonato Dy0.5, Y0.5
anilinium tetrakis hexafluoroacetylacetonato Dy0.5, Y0.5
anilinium tetrakis 6,6,7,7,8,8,8-heptafluoro-2,2-dimethyloctanedionato Dy0.5, Y0.5
anilinium tetrakis 1-phenyl-1,3-butanedionato Dy0.5, Y0.5
triethylammonium tetrakis acetylacetonato Dy0.2, Y0.8
triethylammonium tetrakis dibenzoylmethanato Dy0.2, Y0.8
triethylammonium tetrakis thenoyltrifluoroacetonato Dy0.2, Y0.8
triethylammonium tetrakis 2,2,6,6-tetramethylheptanedionato Dy0.2, Y0.8
triethylammonium tetrakis 3-methylpentane-2,4-dionato Dy0.2, Y0.8
triethylammonium tetrakis 3-ethylpentane-2,4-dionato Dy0.2, Y0.8
triethylammonium tetrakis pivaloyltrifluoroacetonato Dy0.2, Y0.8
triethylammonium tetrakis trifluoroacetylacetonato Dy0.2, Y0.8
triethylammonium tetrakis hexafluoroacetylacetonato Dy0.2, Y0.8
triethylammonium tetrakis 6,6,7,7,8,8,8-heptafluoro-2,2-dimethyloctanedionato Dy0.2, Y0.8
triethylammonium tetrakis 1-phenyl-1,3-butanedionato Dy0.2, Y0.8
morpholinium tetrakis acetylacetonato Dy0.2, Y0.8
morpholinium tetrakis dibenzoylmethanato Dy0.2, Y0.8
morpholinium tetrakis thenoyltrifluoroacetonato Dy0.2, Y0.8
morpholinium tetrakis 2,2,6,6-tetramethylheptanedionato Dy0.2, Y0.8
morpholinium tetrakis 3-methylpentane-2,4-dionato Dy0.2, Y0.8
morpholinium tetrakis 3-ethylpentane-2,4-dionato Dy0.2, Y0.8
morpholinium tetrakis pivaloyltrifluoroacetonato Dy0.2, Y0.8
morpholinium tetrakis trifluoroacetylacetonato Dy0.2, Y0.8
morpholinium tetrakis hexafluoroacetylacetonato Dy0.2, Y0.8
morpholinium tetrakis 6,6,7,7,8,8,8-heptafluoro-2,2-dimethyloctanedionato Dy0.2, Y0.8
morpholinium tetrakis 1-phenyl-1,3-butanedionato Dy0.2, Y0.8
dimethylbenzylammonium tetrakis acetylacetonato Dy0.2, Y0.8
dimethylbenzylammonium tetrakis dibenzoylmethanato Dy0.2, Y0.8 dimethylbenzylammonium tetrakis thenoyltrifluoroacetonato Dy0.2, Y0.8
dimethylbenzylammonium tetrakis 2,2,6,6-tetramethylheptanedionato Dy0.2, Y0.8
dimethylbenzylammonium tetrakis 3-methylpentane-2,4-dionato Dy0.2, Y0.8
dimethylbenzylammonium tetrakis 3-ethylpentane-2,4-dionato Dy0.2, Y0.8
dimethylbenzylammonium tetrakis pivaloyltrifluoroacetonato Dy0.2, Y0.8
dimethylbenzylammonium tetrakis trifluoroacetylacetonato Dy0.2, Y0.8
dimethylbenzylammonium tetrakis hexafluoroacetylacetonato Dy0.2, Y0.8
dimethylbenzylammonium tetrakis 6,6,7,7,8,8,8-heptafluoro-2,2-dimethyloctanedionato Dy0.2, Y0.8
dimethylbenzylammonium tetrakis 1-phenyl-1,3-butanedionato Dy0.2, Y0.8
triallylammonium tetrakis acetylacetonato Dy0.2, Y0.8
triallylammonium tetrakis dibenzoylmethanato Dy0.2, Y0.8
triallylammonium tetrakis thenoyltrifluoroacetonato Dy0.2, Y0.8
triallylammonium tetrakis 2,2,6,6-tetramethylheptanedionato Dy0.2, Y0.8
triallylammonium tetrakis 3-methylpentane-2,4-dionato Dy0.2, Y0.8
triallylammonium tetrakis 3-ethylpentane-2,4-dionato Dy0.2, Y0.8
triallylammonium tetrakis pivaloyltrifluoroacetonato Dy0.2, Y0.8
triallylammonium tetrakis trifluoroacetylacetonato Dy0.2, Y0.8
triallylammonium tetrakis hexafluoroacetylacetonato Dy0.2, Y0.8
triallylammonium tetrakis 6,6,7,7,8,8,8-heptafluoro-2,2-dimethyloctanedionato Dy0.2, Y0.8
triallylammonium tetrakis 1-phenyl-1,3-butanedionato Dy0.2, Y0.8
anilinium tetrakis acetylacetonato Dy0.2, Y0.8
anilinium tetrakis dibenzoylmethanato Dy0.2, Y0.8
anilinium tetrakis thenoyltrifluoroacetonato Dy0.2, Y0.8
anilinium tetrakis 2,2,6,6-tetramethylheptanedionato Dy0.2, Y0.8
anilinium tetrakis 3-methylpentane-2,4-dionato Dy0.2, Y0.8
anilinium tetrakis 3-ethylpentane-2,4-dionato Dy0.2, Y0.8
anilinium tetrakis pivaloyltrifluoroacetonato Dy0.2, Y0.8
anilinium tetrakis trifluoroacetylacetonato Dy0.2, Y0.8
anilinium tetrakis hexafluoroacetylacetonato Dy0.2, Y0.8
anilinium tetrakis 6,6,7,7,8,8,8-heptafluoro-2,2-dimethyloctanedionato Dy0.2, Y0.8
anilinium tetrakis 1-phenyl-1,3-butanedionato Dy0.2, Y0.8
triethylammonium tetrakis acetylacetonato Dy0.1, Y0.9
triethylammonium tetrakis dibenzoylmethanato Dy0.1, Y0.9
triethylammonium tetrakis thenoyltrifluoroacetonato Dy0.1, Y0.9
triethylammonium tetrakis 2,2,6,6-tetramethylheptanedionato Dy0.1, Y0.9
triethylammonium tetrakis 3-methylpentane-2,4-dionato Dy0.1, Y0.9
triethylammonium tetrakis 3-ethylpentane-2,4-dionato Dy0.1, Y0.9
triethylammonium tetrakis pivaloyltrifluoroacetonato Dy0.1, Y0.9
triethylammonium tetrakis trifluoroacetylacetonato Dy0.1, Y0.9
triethylammonium tetrakis hexafluoroacetylacetonato Dy0.1, Y0.9
triethylammonium tetrakis 6,6,7,7,8,8,8-heptafluoro-2,2-dimethyloctanedionato Dy0.1, Y0.9
triethylammonium tetrakis 1-phenyl-1,3-butanedionato Dy0.1, Y0.9
morpholinium tetrakis acetylacetonato Dy0.1, Y0.9
morpholinium tetrakis dibenzoylmethanato Dy0.1, Y0.9
morpholinium tetrakis thenoyltrifluoroacetonato Dy0.1, Y0.9
morpholinium tetrakis 2,2,6,6-tetramethylheptanedionato Dy0.1, Y0.9
morpholinium tetrakis 3-methylpentane-2,4-dionato Dy0.1, Y0.9
morpholinium tetrakis 3-ethylpentane-2,4-dionato Dy0.1, Y0.9
morpholinium tetrakis pivaloyltrifluoroacetonato Dy0.1, Y0.9
morpholinium tetrakis trifluoroacetylacetonato Dy0.1, Y0.9
morpholinium tetrakis hexafluoroacetylacetonato Dy0.1, Y0.9
morpholinium tetrakis 6,6,7,7,8,8,8-heptafluoro-2,2-dimethyloctanedionato Dy0.1, Y0.9
morpholinium tetrakis 1-phenyl-1,3-butanedionato Dy0.1, Y0.9
dimethylbenzylammonium tetrakis acetylacetonato Dy0.1, Y0.9
dimethylbenzylammonium tetrakis dibenzoylmethanato Dy0.1, Y0.9
dimethylbenzylammonium tetrakis thenoyltrifluoroacetonato Dy0.1, Y0.9
dimethylbenzylammonium tetrakis 2,2,6,6-tetramethylheptanedionato Dy0.1, Y0.9
dimethylbenzylammonium tetrakis 3-methylpentane-2,4-dionato Dy0.1, Y0.9
dimethylbenzylammonium tetrakis 3-ethylpentane-2,4-dionato Dy0.1, Y0.9
dimethylbenzylammonium tetrakis pivaloyltrifluoroacetonato Dy0.1, Y0.9
dimethylbenzylammonium tetrakis trifluoroacetylacetonato Dy0.1, Y0.9
dimethylbenzylammonium tetrakis hexafluoroacetylacetonato Dy0.1, Y0.9
dimethylbenzylammonium tetrakis 6,6,7,7,8,8,8-heptafluoro-2,2-dimethyloctanedionato Dy0.1, Y0.9
dimethylbenzylammonium tetrakis 1-phenyl-1,3-butanedionato Dy0.1, Y0.9
triallylammonium tetrakis acetylacetonato Dy0.1, Y0.9
triallylammonium tetrakis dibenzoylmethanato Dy0.1, Y0.9
triallylammonium tetrakis thenoyltrifluoroacetonato Dy0.1, Y0.9
triallylammonium tetrakis 2,2,6,6-tetramethylheptanedionato Dy0.1, Y0.9
triallylammonium tetrakis 3-methylpentane-2,4-dionato Dy0.1, Y0.9
triallylammonium tetrakis 3-ethylpentane-2,4-dionato Dy0.1, Y0.9
triallylammonium tetrakis pivaloyltrifluoroacetonato Dy0.1, Y0.9
triallylammonium tetrakis trifluoroacetylacetonato Dy0.1, Y0.9
triallylammonium tetrakis hexafluoroacetylacetonato Dy0.1, Y0.9
triallylammonium tetrakis 6,6,7,7,8,8,8-heptafluoro-2,2-dimethyloctanedionato Dy0.1, Y0.9
triallylammonium tetrakis 1-phenyl-1,3-butanedionato Dy0.1, Y0.9
anilinium tetrakis acetylacetonato Dy0.1, Y0.9
anilinium tetrakis dibenzoylmethanato Dy0.1, Y0.9 anilinium tetrakis thenoyltrifluoroacetonato Dy0.1, Y0.9
anilinium tetrakis 2,2,6,6-tetramethylheptanedionato Dy0.1, Y0.9
anilinium tetrakis 3-methylpentane-2,4-dionato Dy0.1, Y0.9
anilinium tetrakis 3-ethylpentane-2,4-dionato Dy0.1, Y0.9
anilinium tetrakis pivaloyltrifluoroacetonato Dy0.1, Y0.9
anilinium tetrakis trifluoroacetylacetonato Dy0.1, Y0.9
anilinium tetrakis hexafluoroacetylacetonato Dy0.1, Y0.9
anilinium tetrakis 6,6,7,7,8,8,8-heptafluoro-2,2-dimethyloctanedionato Dy0.1, Y0.9
anilinium tetrakis 1-phenyl-1,3-butanedionato Dy0.1, Y0.9
triethylammonium tetrakis acetylacetonato Dy0.01, Y0.99
triethylammonium tetrakis dibenzoylmethanato Dy0.01, Y0.99
triethylammonium tetrakis thenoyltrifluoroacetonato Dy0.01, Y0.99
triethylammonium tetrakis 2,2,6,6-tetramethylheptanedionato Dy0.01, Y0.99
triethylammonium tetrakis 3-methylpentane-2,4-dionato Dy0.01, Y0.99
triethylammonium tetrakis 3-ethylpentane-2,4-dionato Dy0.01, Y0.99
triethylammonium tetrakis pivaloyltrifluoroacetonato Dy0.01, Y0.99
triethylammonium tetrakis trifluoroacetylacetonato Dy0.01, Y0.99
triethylammonium tetrakis hexafluoroacetylacetonato Dy0.01, Y0.99
triethylammonium tetrakis 6,6,7,7,8,8,8-heptafluoro-2,2-dimethyloctanedionato Dy0.01, Y0.99
triethylammonium tetrakis 1-phenyl-1,3-butanedionato Dy0.01, Y0.99
morpholinium tetrakis acetylacetonato Dy0.01, Y0.99
morpholinium tetrakis dibenzoylmethanato Dy0.01, Y0.99
morpholinium tetrakis thenoyltrifluoroacetonato Dy0.01, Y0.99
morpholinium tetrakis 2,2,6,6-tetramethylheptanedionato Dy0.01, Y0.99
morpholinium tetrakis 3-methylpentane-2,4-dionato Dy0.01, Y0.99
morpholinium tetrakis 3-ethylpentane-2,4-dionato Dy0.01, Y0.99
morpholinium tetrakis pivaloyltrifluoroacetonato Dy0.01, Y0.99
morpholinium tetrakis trifluoroacetylacetonato Dy0.01, Y0.99
morpholinium tetrakis hexafluoroacetylacetonato Dy0.01, Y0.99
morpholinium tetrakis 6,6,7,7,8,8,8-heptafluoro-2,2-dimethyloctanedionato Dy0.01, Y0.99
morpholinium tetrakis 1-phenyl-1,3-butanedionato Dy0.01, Y0.99
dimethylbenzylammonium tetrakis acetylacetonato Dy0.01, Y0.99
dimethylbenzylammonium tetrakis dibenzoylmethanato Dy0.01, Y0.99
dimethylbenzylammonium tetrakis thenoyltrifluoroacetonato Dy0.01, Y0.99
dimethylbenzylammonium tetrakis 2,2,6,6-tetramethylheptanedionato Dy0.01, Y0.99
dimethylbenzylammonium tetrakis 3-methylpentane-2,4-dionato Dy0.01, Y0.99
dimethylbenzylammonium tetrakis 3-ethylpentane-2,4-dionato Dy0.01, Y0.99
dimethylbenzylammonium tetrakis pivaloyltrifluoroacetonato Dy0.01, Y0.99
dimethylbenzylammonium tetrakis trifluoroacetylacetonato Dy0.01, Y0.99
dimethylbenzylammonium tetrakis hexafluoroacetylacetonato Dy0.01, Y0.99
dimethylbenzylammonium tetrakis 6,6,7,7,8,8,8-heptafluoro-2,2-dimethyloctanedionato Dy0.01, Y0.99
dimethylbenzylammonium tetrakis 1-phenyl-1,3-butanedionato Dy0.01, Y0.99
triallylammonium tetrakis acetylacetonato Dy0.01, Y0.99
triallylammonium tetrakis dibenzoylmethanato Dy0.01, Y0.99
triallylammonium tetrakis thenoyltrifluoroacetonato Dy0.01, Y0.99
triallylammonium tetrakis 2,2,6,6-tetramethylheptanedionato Dy0.01, Y0.99
triallylammonium tetrakis 3-methylpentane-2,4-dionato Dy0.01, Y0.99
triallylammonium tetrakis 3-ethylpentane-2,4-dionato Dy0.01, Y0.99
triallylammonium tetrakis pivaloyltrifluoroacetonato Dy0.01, Y0.99
triallylammonium tetrakis trifluoroacetylacetonato Dy0.01, Y0.99
triallylammonium tetrakis hexafluoroacetylacetonato Dy0.01, Y0.99
triallylammonium tetrakis 6,6,7,7,8,8,8-heptafluoro-2,2-dimethyloctanedionato Dy0.01, Y0.99
triallylammonium tetrakis 1-phenyl-1,3-butanedionato Dy0.01, Y0.99
anilinium tetrakis acetylacetonato Dy0.01, Y0.99
anilinium tetrakis dibenzoylmethanato Dy0.01, Y0.99
anilinium tetrakis thenoyltrifluoroacetonato Dy0.01, Y0.99
anilinium tetrakis 2,2,6,6-tetramethylheptanedionato Dy0.01, Y0.99
anilinium tetrakis 3-methylpentane-2,4-dionato Dy0.01, Y0.99
anilinium tetrakis 3-ethylpentane-2,4-dionato Dy0.01, Y0.99
anilinium tetrakis pivaloyltrifluoroacetonato Dy0.01, Y0.99
anilinium tetrakis trifluoroacetylacetonato Dy0.01, Y0.99
anilinium tetrakis hexafluoroacetylacetonato Dy0.01, Y0.99
anilinium tetrakis 6,6,7,7,8,8,8-heptafluoro-2,2-dimethyloctanedionato Dy0.01, Y0.99
anilinium tetrakis 1-phenyl-1,3-butanedionato Dy0.01, Y0.99
triethylammonium tetrakis acetylacetonato Dy0.5, Y0.5
triethylammonium tetrakis dibenzoylmethanato Dy0.5, Y0.5
triethylammonium tetrakis thenoyltrifluoroacetonato Dy0.5, Y0.5
triethylammonium tetrakis 2,2,6,6-tetramethylheptanedionato Dy0.5, Y0.5
triethylammonium tetrakis 3-methylpentane-2,4-dionato Dy0.5, Y0.5
triethylammonium tetrakis 3-ethylpentane-2,4-dionato Dy0.5, Y0.5
triethylammonium tetrakis pivaloyltrifluoroacetonato Dy0.5, Y0.5
triethylammonium tetrakis trifluoroacetylacetonato Dy0.5, Y0.5
triethylammonium tetrakis hexafluoroacetylacetonato Dy0.5, Y0.5
triethylammonium tetrakis 6,6,7,7,8,8,8-heptafluoro-2,2-dimethyloctanedionato Dy0.5, Y0.5
triethylammonium tetrakis 1-phenyl-1,3-butanedionato Dy0.5, Y0.5
morpholinium tetrakis acetylacetonato Dy0.5, Y0.5
morpholinium tetrakis dibenzoylmethanato Dy0.5, Y0.5 morpholinium tetrakis thenoyltrifluoroacetonato Dy0.5, Y0.5
morpholinium tetrakis 2,2,6,6-tetramethylheptanedionato Dy0.5, Y0.5
morpholinium tetrakis 3-methylpentane-2,4-dionato Dy0.5, Y0.5
morpholinium tetrakis 3-ethylpentane-2,4-dionato Dy0.5, Y0.5
morpholinium tetrakis pivaloyltrifluoroacetonato Dy0.5, Y0.5
morpholinium tetrakis trifluoroacetylacetonato Dy0.5, Y0.5
morpholinium tetrakis hexafluoroacetylacetonato Dy0.5, Y0.5
morpholinium tetrakis 6,6,7,7,8,8,8-heptafluoro-2,2-dimethyloctanedionato Dy0.5, Y0.5
morpholinium tetrakis 1-phenyl-1,3-butanedionato Dy0.5, Y0.5
dimethylbenzylammonium tetrakis acetylacetonato Dy0.5, Y0.5
dimethylbenzylammonium tetrakis dibenzoylmethanato Dy0.5, Y0.5
dimethylbenzylammonium tetrakis thenoyltrifluoroacetonato Dy0.5, Y0.5
dimethylbenzylammonium tetrakis 2,2,6,6-tetramethylheptanedionato Dy0.5, Y0.5
dimethylbenzylammonium tetrakis 3-methylpentane-2,4-dionato Dy0.5, Y0.5
dimethylbenzylammonium tetrakis 3-ethylpentane-2,4-dionato Dy0.5, Y0.5
dimethylbenzylammonium tetrakis pivaloyltrifluoroacetonato Dy0.5, Y0.5
dimethylbenzylammonium tetrakis trifluoroacetylacetonato Dy0.5, Y0.5
dimethylbenzylammonium tetrakis hexafluoroacetylacetonato Dy0.5, Y0.5
dimethylbenzylammonium tetrakis 6,6,7,7,8,8,8-heptafluoro-2,2-dimethyloctanedionato Dy0.5, Y0.5
dimethylbenzylammonium tetrakis 1-phenyl-1,3-butanedionato Dy0.5, Y0.5
triallylammonium tetrakis acetylacetonato Dy0.5, Y0.5
triallylammonium tetrakis dibenzoylmethanato Dy0.5, Y0.5
triallylammonium tetrakis thenoyltrifluoroacetonato Dy0.5, Y0.5
triallylammonium tetrakis 2,2,6,6-tetramethylheptanedionato Dy0.5, Y0.5
triallylammonium tetrakis 3-methylpentane-2,4-dionato Dy0.5, Y0.5
triallylammonium tetrakis 3-ethylpentane-2,4-dionato Dy0.5, Y0.5
triallylammonium tetrakis pivaloyltrifluoroacetonato Dy0.5, Y0.5
triallylammonium tetrakis trifluoroacetylacetonato Dy0.5, Y0.5
triallylammonium tetrakis hexafluoroacetylacetonato Dy0.5, Y0.5
triallylammonium tetrakis 6,6,7,7,8,8,8-heptafluoro-2,2-dimethyloctanedionato Dy0.5, Y0.5
triallylammonium tetrakis 1-phenyl-1,3-butanedionato Dy0.5, Y0.5
anilinium tetrakis acetylacetonato Dy0.5, Y0.5
anilinium tetrakis dibenzoylmethanato Dy0.5, Y0.5
anilinium tetrakis thenoyltrifluoroacetonato Dy0.5, Y0.5
anilinium tetrakis 2,2,6,6-tetramethylheptanedionato Dy0.5, Y0.5
anilinium tetrakis 3-methylpentane-2,4-dionato Dy0.5, Y0.5
anilinium tetrakis 3-ethylpentane-2,4-dionato Dy0.5, Y0.5
anilinium tetrakis pivaloyltrifluoroacetonato Dy0.5, Y0.5
anilinium tetrakis trifluoroacetylacetonato Dy0.5, Y0.5
anilinium tetrakis hexafluoroacetylacetonato Dy0.5, Y0.5
anilinium tetrakis 6,6,7,7,8,8,8-heptafluoro-2,2-dimethyloctanedionato Dy0.5, Y0.5
anilinium tetrakis 1-phenyl-1,3-butanedionato Dy0.5, Y0.5
triethylammonium tetrakis acetylacetonato Dy0.2, Y0.8
triethylammonium tetrakis dibenzoylmethanato Dy0.2, Y0.8
triethylammonium tetrakis thenoyltrifluoroacetonato Dy0.2, Y0.8
triethylammonium tetrakis 2,2,6,6-tetramethylheptanedionato Dy0.2, Y0.8
triethylammonium tetrakis 3-methylpentane-2,4-dionato Dy0.2, Y0.8
triethylammonium tetrakis 3-ethylpentane-2,4-dionato Dy0.2, Y0.8
triethylammonium tetrakis pivaloyltrifluoroacetonato Dy0.2, Y0.8
triethylammonium tetrakis trifluoroacetylacetonato Dy0.2, Y0.8
triethylammonium tetrakis hexafluoroacetylacetonato Dy0.2, Y0.8
triethylammonium tetrakis 6,6,7,7,8,8,8-heptafluoro-2,2-dimethyloctanedionato Dy0.2, Y0.8
triethylammonium tetrakis 1-phenyl-1,3-butanedionato Dy0.2, Y0.8
morpholinium tetrakis acetylacetonato Dy0.2, Y0.8
morpholinium tetrakis dibenzoylmethanato Dy0.2, Y0.8
morpholinium tetrakis thenoyltrifluoroacetonato Dy0.2, Y0.8
morpholinium tetrakis 2,2,6,6-tetramethylheptanedionato Dy0.2, Y0.8
morpholinium tetrakis 3-methylpentane-2,4-dionato Dy0.2, Y0.8
morpholinium tetrakis 3-ethylpentane-2,4-dionato Dy0.2, Y0.8
morpholinium tetrakis pivaloyltrifluoroacetonato Dy0.2, Y0.8
morpholinium tetrakis trifluoroacetylacetonato Dy0.2, Y0.8
morpholinium tetrakis hexafluoroacetylacetonato Dy0.2, Y0.8
morpholinium tetrakis 6,6,7,7,8,8,8-heptafluoro-2,2-dimethyloctanedionato Dy0.2, Y0.8
morpholinium tetrakis 1-phenyl-1,3-butanedionato Dy0.2, Y0.8
dimethylbenzylammonium tetrakis acetylacetonato Dy0.2, Y0.8
dimethylbenzylammonium tetrakis dibenzoylmethanato Dy0.2, Y0.8
dimethylbenzylammonium tetrakis thenoyltrifluoroacetonato Dy0.2, Y0.8
dimethylbenzylammonium tetrakis 2,2,6,6-tetramethylheptanedionato Dy0.2, Y0.8
dimethylbenzylammonium tetrakis 3-methylpentane-2,4-dionato Dy0.2, Y0.8
dimethylbenzylammonium tetrakis 3-ethylpentane-2,4-dionato Dy0.2, Y0.8
dimethylbenzylammonium tetrakis pivaloyltrifluoroacetonato Dy0.2, Y0.8
dimethylbenzylammonium tetrakis trifluoroacetylacetonato Dy0.2, Y0.8
dimethylbenzylammonium tetrakis hexafluoroacetylacetonato Dy0.2, Y0.8
dimethylbenzylammonium tetrakis 6,6,7,7,8,8,8-heptafluoro-2,2-dimethyloctanedionato Dy0.2, Y0.8
dimethylbenzylammonium tetrakis 1-phenyl-1,3-butanedionato Dy0.2, Y0.8
triallylammonium tetrakis acetylacetonato Dy0.2, Y0.8 triallylammonium tetrakis dibenzoylmethanato Dy0.2, Y0.8
triallylammonium tetrakis thenoyltrifluoroacetonato Dy0.2, Y0.8
triallylammonium tetrakis 2,2,6,6-tetramethylheptanedionato Dy0.2, Y0.8
triallylammonium tetrakis 3-methylpentane-2,4-dionato Dy0.2, Y0.8
triallylammonium tetrakis 3-ethylpentane-2,4-dionato Dy0.2, Y0.8
triallylammonium tetrakis pivaloyltrifluoroacetonato Dy0.2, Y0.8
triallylammonium tetrakis trifluoroacetylacetonato Dy0.2, Y0.8
triallylammonium tetrakis hexafluoroacetylacetonato Dy0.2, Y0.8
triallylammonium tetrakis 6,6,7,7,8,8,8-heptafluoro-2,2-dimethyloctanedionato Dy0.2, Y0.8
triallylammonium tetrakis 1-phenyl-1,3-butanedionato Dy0.2, Y0.8
anilinium tetrakis acetylacetonato Dy0.2, Y0.8
anilinium tetrakis dibenzoylmethanato Dy0.2, Y0.8
anilinium tetrakis thenoyltrifluoroacetonato Dy0.2, Y0.8
anilinium tetrakis 2,2,6,6-tetramethylheptanedionato Dy0.2, Y0.8
anilinium tetrakis 3-methylpentane-2,4-dionato Dy0.2, Y0.8
anilinium tetrakis 3-ethylpentane-2,4-dionato Dy0.2, Y0.8
anilinium tetrakis pivaloyltrifluoroacetonato Dy0.2, Y0.8
anilinium tetrakis trifluoroacetylacetonato Dy0.2, Y0.8
anilinium tetrakis hexafluoroacetylacetonato Dy0.2, Y0.8
anilinium tetrakis 6,6,7,7,8,8,8-heptafluoro-2,2-dimethyloctanedionato Dy0.2, Y0.8
anilinium tetrakis 1-phenyl-1,3-butanedionato Dy0.2, Y0.8
triethylammonium tetrakis acetylacetonato Dy0.1, Y0.9
triethylammonium tetrakis dibenzoylmethanato Dy0.1, Y0.9
triethylammonium tetrakis thenoyltrifluoroacetonato Dy0.1, Y0.9
triethylammonium tetrakis 2,2,6,6-tetramethylheptanedionato Dy0.1, Y0.9
triethylammonium tetrakis 3-methylpentane-2,4-dionato Dy0.1, Y0.9
triethylammonium tetrakis 3-ethylpentane-2,4-dionato Dy0.1, Y0.9
triethylammonium tetrakis pivaloyltrifluoroacetonato Dy0.1, Y0.9
triethylammonium tetrakis trifluoroacetylacetonato Dy0.1, Y0.9
triethylammonium tetrakis hexafluoroacetylacetonato Dy0.1, Y0.9
triethylammonium tetrakis 6,6,7,7,8,8,8-heptafluoro-2,2-dimethyloctanedionato Dy0.1, Y0.9
triethylammonium tetrakis 1-phenyl-1,3-butanedionato Dy0.1, Y0.9
morpholinium tetrakis acetylacetonato Dy0.1, Y0.9
morpholinium tetrakis dibenzoylmethanato Dy0.1, Y0.9
morpholinium tetrakis thenoyltrifluoroacetonato Dy0.1, Y0.9
morpholinium tetrakis 2,2,6,6-tetramethylheptanedionato Dy0.1, Y0.9
morpholinium tetrakis 3-methylpentane-2,4-dionato Dy0.1, Y0.9
morpholinium tetrakis 3-ethylpentane-2,4-dionato Dy0.1, Y0.9
morpholinium tetrakis pivaloyltrifluoroacetonato Dy0.1, Y0.9
morpholinium tetrakis trifluoroacetylacetonato Dy0.1, Y0.9
morpholinium tetrakis hexafluoroacetylacetonato Dy0.1, Y0.9
morpholinium tetrakis 6,6,7,7,8,8,8-heptafluoro-2,2-dimethyloctanedionato Dy0.1, Y0.9
morpholinium tetrakis 1-phenyl-1,3-butanedionato Dy0.1, Y0.9
dimethylbenzylammonium tetrakis acetylacetonato Dy0.1, Y0.9
dimethylbenzylammonium tetrakis dibenzoylmethanato Dy0.1, Y0.9
dimethylbenzylammonium tetrakis thenoyltrifluoroacetonato Dy0.1, Y0.9
dimethylbenzylammonium tetrakis 2,2,6,6-tetramethylheptanedionato Dy0.1, Y0.9
dimethylbenzylammonium tetrakis 3-methylpentane-2,4-dionato Dy0.1, Y0.9
dimethylbenzylammonium tetrakis 3-ethylpentane-2,4-dionato Dy0.1, Y0.9
dimethylbenzylammonium tetrakis pivaloyltrifluoroacetonato Dy0.1, Y0.9
dimethylbenzylammonium tetrakis trifluoroacetylacetonato Dy0.1, Y0.9
dimethylbenzylammonium tetrakis hexafluoroacetylacetonato Dy0.1, Y0.9
dimethylbenzylammonium tetrakis 6,6,7,7,8,8,8-heptafluoro-2,2-dimethyloctanedionato Dy0.1, Y0.9
dimethylbenzylammonium tetrakis 1-phenyl-1,3-butanedionato Dy0.1, Y0.9
triallylammonium tetrakis acetylacetonato Dy0.1, Y0.9
triallylammonium tetrakis dibenzoylmethanato Dy0.1, Y0.9
triallylammonium tetrakis thenoyltrifluoroacetonato Dy0.1, Y0.9
triallylammonium tetrakis 2,2,6,6-tetramethylheptanedionato Dy0.1, Y0.9
triallylammonium tetrakis 3-methylpentane-2,4-dionato Dy0.1, Y0.9
triallylammonium tetrakis 3-ethylpentane-2,4-dionato Dy0.1, Y0.9
triallylammonium tetrakis pivaloyltrifluoroacetonato Dy0.1, Y0.9
triallylammonium tetrakis trifluoroacetylacetonato Dy0.1, Y0.9
triallylammonium tetrakis hexafluoroacetylacetonato Dy0.1, Y0.9
triallylammonium tetrakis 6,6,7,7,8,8,8-heptafluoro-2,2-dimethyloctanedionato Dy0.1, Y0.9
triallylammonium tetrakis 1-phenyl-1,3-butanedionato Dy0.1, Y0.9
anilinium tetrakis acetylacetonato Dy0.1, Y0.9
anilinium tetrakis dibenzoylmethanato Dy0.1, Y0.9
anilinium tetrakis thenoyltrifluoroacetonato Dy0.1, Y0.9
anilinium tetrakis 2,2,6,6-tetramethylheptanedionato Dy0.1, Y0.9
anilinium tetrakis 3-methylpentane-2,4-dionato Dy0.1, Y0.9
anilinium tetrakis 3-ethylpentane-2,4-dionato Dy0.1, Y0.9
anilinium tetrakis pivaloyltrifluoroacetonato Dy0.1, Y0.9
anilinium tetrakis trifluoroacetylacetonato Dy0.1, Y0.9
anilinium tetrakis hexafluoroacetylacetonato Dy0.1, Y0.9
anilinium tetrakis 6,6,7,7,8,8,8-heptafluoro-2,2-dimethyloctanedionato Dy0.1, Y0.9
anilinium tetrakis 1-phenyl-1,3-butanedionato Dy0.1, Y0.9
triethylammonium tetrakis acetylacetonato Dy0.01, Y0.99
triethylammonium tetrakis dibenzoylmethanato Dy0.01, Y0.99
triethylammonium tetrakis thenoyltrifluoroacetonato Dy0.01, Y0.99
triethylammonium tetrakis 2,2,6,6-tetramethylheptanedionato Dy0.01, Y0.99 triethylammonium tetrakis 3-methylpentane-2,4-dionato Dy0.01, Y0.99
triethylammonium tetrakis 3-ethylpentane-2,4-dionato Dy0.01, Y0.99
triethylammonium tetrakis pivaloyltrifluoroacetonato Dy0.01, Y0.99
triethylammonium tetrakis trifluoroacetylacetonato Dy0.01, Y0.99
triethylammonium tetrakis hexafluoroacetylacetonato Dy0.01, Y0.99
triethylammonium tetrakis 6,6,7,7,8,8,8-heptafluoro-2,2-dimethyloctanedionato Dy0.01, Y0.99
triethylammonium tetrakis 1-phenyl-1,3-butanedionato Dy0.01, Y0.99
morpholinium tetrakis acetylacetonato Dy0.01, Y0.99
morpholinium tetrakis dibenzoylmethanato Dy0.01, Y0.99
morpholinium tetrakis thenoyltrifluoroacetonato Dy0.01, Y0.99
morpholinium tetrakis 2,2,6,6-tetramethylheptanedionato Dy0.01, Y0.99
morpholinium tetrakis 3-methylpentane-2,4-dionato Dy0.01, Y0.99
morpholinium tetrakis 3-ethylpentane-2,4-dionato Dy0.01, Y0.99
morpholinium tetrakis pivaloyltrifluoroacetonato Dy0.01, Y0.99
morpholinium tetrakis trifluoroacetylacetonato Dy0.01, Y0.99
morpholinium tetrakis hexafluoroacetylacetonato Dy0.01, Y0.99
morpholinium tetrakis 6,6,7,7,8,8,8-heptafluoro-2,2-dimethyloctanedionato Dy0.01, Y0.99
morpholinium tetrakis 1-phenyl-1,3-butanedionato Dy0.01, Y0.99
dimethylbenzylammonium tetrakis acetylacetonato Dy0.01, Y0.99
dimethylbenzylammonium tetrakis dibenzoylmethanato Dy0.01, Y0.99
dimethylbenzylammonium tetrakis thenoyltrifluoroacetonato Dy0.01, Y0.99
dimethylbenzylammonium tetrakis 2,2,6,6-tetramethylheptanedionato Dy0.01, Y0.99
dimethylbenzylammonium tetrakis 3-methylpentane-2,4-dionato Dy0.01, Y0.99
dimethylbenzylammonium tetrakis 3-ethylpentane-2,4-dionato Dy0.01, Y0.99
dimethylbenzylammonium tetrakis pivaloyltrifluoroacetonato Dy0.01, Y0.99
dimethylbenzylammonium tetrakis trifluoroacetylacetonato Dy0.01, Y0.99
dimethylbenzylammonium tetrakis hexafluoroacetylacetonato Dy0.01, Y0.99
dimethylbenzylammonium tetrakis 6,6,7,7,8,8,8-heptafluoro-2,2-dimethyloctanedionato Dy0.01, Y0.99
dimethylbenzylammonium tetrakis 1-phenyl-1,3-butanedionato Dy0.01, Y0.99
triallylammonium tetrakis acetylacetonato Dy0.01, Y0.99
triallylammonium tetrakis dibenzoylmethanato Dy0.01Y0.99
triallylammonium tetrakis thenoyltrifluoroacetonato Dy0.01, Y0.99
triallylammonium tetrakis 2,2,6,6-tetramethylheptanedionato Dy0.01, Y0.99
triallylammonium tetrakis 3-methylpentane-2,4-dionato Dy0.01, Y0.99
triallylammonium tetrakis 3-ethylpentane-2,4-dionato Dy0.01, Y0.99
triallylammonium tetrakis pivaloyltrifluoroacetonato Dy0.01, Y0.99
triallylammonium tetrakis trifluoroacetylacetonato Dy0.01, Y0.99
triallylammonium tetrakis hexafluoroacetylacetonato Dy0.01, Y0.99
triallylammonium tetrakis 6,6,7,7,8,8,8-heptafluoro-2,2-dimethyloctanedionato Dy0.01, Y0.99
triallylammonium tetrakis 1-phenyl-1,3-butanedionato Dy0.01, Y0.99
anilinium tetrakis acetylacetonato Dy0.01, Y0.99
anilinium tetrakis dibenzoylmethanato Dy0.01, Y0.99
anilinium tetrakis thenoyltrifluoroacetonato Dy0.01, Y0.99
anilinium tetrakis 2,2,6,6-tetramethylheptanedionato Dy0.01, Y0.99
anilinium tetrakis 3-methylpentane-2,4-dionato Dy0.01, Y0.99
anilinium tetrakis 3-ethylpentane-2,4-dionato Dy0.01, Y0.99
anilinium tetrakis pivaloyltrifluoroacetonato Dy0.01, Y0.99
anilinium tetrakis trifluoroacetylacetonato Dy0.01, Y0.99
anilinium tetrakis hexafluoroacetylacetonato Dy0.01, Y0.99
anilinium tetrakis 6,6,7,7,8,8,8-heptafluoro-2,2-dimethyloctanedionato Dy0.01, Y0.99
anilinium tetrakis 1-phenyl-1,3-butanedionato Dy0.01, Y0.99
triethylammonium tetrakis acetylacetonato Sm0.5, La0.5
triethylammonium tetrakis dibenzoylmethanato Sm0.5, La0.5
triethylammonium tetrakis thenoyltrifluoroacetonato Sm0.5, La0.5
triethylammonium tetrakis 2,2,6,6-tetramethylheptanedionato Sm0.5, La0.5
triethylammonium tetrakis 3-methylpentane-2,4-dionato Sm0.5, La0.5
triethylammonium tetrakis 3-ethylpentane-2,4-dionato Sm0.5, La0.5
triethylammonium tetrakis pivaloyltrifluoroacetonato Sm0.5, La0.5
triethylammonium tetrakis trifluoroacetylacetonato Sm0.5, La0.5
triethylammonium tetrakis hexafluoroacetylacetonato Sm0.5, La0.5
triethylammonium tetrakis 6,6,7,7,8,8,8-heptafluoro-2,2-dimethyloctanedionato Sm0.5, La0.5
triethylammonium tetrakis 1-phenyl-1,3-butanedionato Sm0.5, La0.5
morpholinium tetrakis acetylacetonato Sm0.5, La0.5
morpholinium tetrakis dibenzoylmethanato Sm0.5, La0.5
morpholinium tetrakis thenoyltrifluoroacetonato Sm0.5, La0.5
morpholinium tetrakis 2,2,6,6-tetramethylheptanedionato Sm0.5, La0.5
morpholinium tetrakis 3-methylpentane-2,4-dionato Sm0.5, La0.5
morpholinium tetrakis 3-ethylpentane-2,4-dionato Sm0.5, La0.5
morpholinium tetrakis pivaloyltrifluoroacetonato Sm0.5, La0.5
morpholinium tetrakis trifluoroacetylacetonato Sm0.5, La0.5
morpholinium tetrakis hexafluoroacetylacetonato Sm0.5, La0.5
morpholinium tetrakis 6,6,7,7,8,8,8-heptafluoro-2,2-dimethyloctanedionato Sm0.5, La0.5
morpholinium tetrakis 1-phenyl-1,3-butanedionato Sm0.5, La0.5 dimethylbenzylammonium tetrakis acetylacetonato Sm0.5, La0.5
dimethylbenzylammonium tetrakis dibenzoylmethanato Sm0.5, La0.5
dimethylbenzylammonium tetrakis thenoyltrifluoroacetonato Sm0.5, La0.5
dimethylbenzylammonium tetrakis 2,2,6,6-tetramethylheptanedionato Sm0.5, La0.5
dimethylbenzylammonium tetrakis 3-methylpentane-2,4-dionato Sm0.5, La0.5
dimethylbenzylammonium tetrakis 3-ethylpentane-2,4-dionato Sm0.5, La0.5
dimethylbenzylammonium tetrakis pivaloyltrifluoroacetonato Sm0.5, La0.5
dimethylbenzylammonium tetrakis trifluoroacetylacetonato Sm0.5, La0.5
dimethylbenzylammonium tetrakis hexafluoroacetylacetonato Sm0.5, La0.5
dimethylbenzylammonium tetrakis 6,6,7,7,8,8,8-heptafluoro-2,2-dimethyloctanedionato Sm0.5, La0.5
dimethylbenzylammonium tetrakis 1-phenyl-1,3-butanedionato Sm0.5, La0.5
triallylammonium tetrakis acetylacetonato Sm0.5, La0.5
triallylammonium tetrakis dibenzoylmethanato Sm0.5, La0.5
triallylammonium tetrakis thenoyltrifluoroacetonato Sm0.5, La0.5
triallylammonium tetrakis 2,2,6,6-tetramethylheptanedionato Sm0.5, La0.5
triallylammonium tetrakis 3-methylpentane-2,4-dionato Sm0.5, La0.5
triallylammonium tetrakis 3-ethylpentane-2,4-dionato Sm0.5, La0.5
triallylammonium tetrakis pivaloyltrifluoroacetonato Sm0.5, La0.5
triallylammonium tetrakis trifluoroacetylacetonato Sm0.5, La0.5
triallylammonium tetrakis hexafluoroacetylacetonato Sm0.5, La0.5
triallylammonium tetrakis 6,6,7,7,8,8,8-heptafluoro-2,2-dimethyloctanedionato Sm0.5, La0.5
triallylammonium tetrakis 1-phenyl-1,3-butanedionato Sm0.5, La0.5
anilinium tetrakis acetylacetonato Sm0.5, La0.5
anilinium tetrakis dibenzoylmethanato Sm0.5, La0.5
anilinium tetrakis thenoyltrifluoroacetonato Sm0.5, La0.5
anilinium tetrakis 2,2,6,6-tetramethylheptanedionato Sm0.5, La0.5
anilinium tetrakis 3-methylpentane-2,4-dionato Sm0.5, La0.5
anilinium tetrakis 3-ethylpentane-2,4-dionato Sm0.5, La0.5
anilinium tetrakis pivaloyltrifluoroacetonato Sm0.5, La0.5
anilinium tetrakis trifluoroacetylacetonato Sm0.5, La0.5
anilinium tetrakis hexafluoroacetylacetonato Sm0.5, La0.5
anilinium tetrakis 6,6,7,7,8,8,8-heptafluoro-2,2-dimethyloctanedionato Sm0.5, La0.5
anilinium tetrakis 1-phenyl-1,3-butanedionato Sm0.5, La0.5
triethylammonium tetrakis acetylacetonato Sm0.2, La0.8
triethylammonium tetrakis dibenzoylmethanato Sm0.2, La0.8
triethylammonium tetrakis thenoyltrifluoroacetonato Sm0.2, La0.8
triethylammonium tetrakis 2,2,6,6-tetramethylheptanedionato Sm0.2, La0.8
triethylammonium tetrakis 3-methylpentane-2,4-dionato Sm0.2, La0.8
triethylammonium tetrakis 3-ethylpentane-2,4-dionato Sm0.2, La0.8
triethylammonium tetrakis pivaloyltrifluoroacetonato Sm0.2, La0.8
triethylammonium tetrakis trifluoroacetylacetonato Sm0.2, La0.8
triethylammonium tetrakis hexafluoroacetylacetonato Sm0.2, La0.8
triethylammonium tetrakis 6,6,7,7,8,8,8-heptafluoro-2,2-dimethyloctanedionato Sm0.2, La0.8
triethylammonium tetrakis 1-phenyl-1,3-butanedionato Sm0.2, La0.8
morpholinium tetrakis acetylacetonato Sm0.2, La0.8
morpholinium tetrakis dibenzoylmethanato Sm0.2, La0.8
morpholinium tetrakis thenoyltrifluoroacetonato Sm0.2, La0.8
morpholinium tetrakis 2,2,6,6-tetramethylheptanedionato Sm0.2, La0.8
morpholinium tetrakis 3-methylpentane-2,4-dionato Sm0.2, La0.8
morpholinium tetrakis 3-ethylpentane-2,4-dionato Sm0.2, La0.8
morpholinium tetrakis pivaloyltrifluoroacetonato Sm0.2, La0.8
morpholinium tetrakis trifluoroacetylacetonato Sm0.2, La0.8
morpholinium tetrakis hexafluoroacetylacetonato Sm0.2, La0.8
morpholinium tetrakis 6,6,7,7,8,8,8-heptafluoro-2,2-dimethyloctanedionato Sm0.2, La0.8
morpholinium tetrakis 1-phenyl-1,3-butanedionato Sm0.2, La0.8
dimethylbenzylammonium tetrakis acetylacetonato Sm0.2, La0.8
dimethylbenzylammonium tetrakis dibenzoylmethanato Sm0.2, La0.8
dimethylbenzylammonium tetrakis thenoyltrifluoroacetonato Sm0.2, La0.8
dimethylbenzylammonium tetrakis 2,2,6,6-tetramethylheptanedionato Sm0.2, La0.8
dimethylbenzylammonium tetrakis 3-methylpentane-2,4-dionato Sm0.2, La0.8
dimethylbenzylammonium tetrakis 3-ethylpentane-2,4-dionato Sm0.2, La0.8
dimethylbenzylammonium tetrakis pivaloyltrifluoroacetonato Sm0.2, La0.8
dimethylbenzylammonium tetrakis trifluoroacetylacetonato Sm0.2, La0.8
dimethylbenzylammonium tetrakis hexafluoroacetylacetonato Sm0.2, La0.8
dimethylbenzylammonium tetrakis 6,6,7,7,8,8,8-heptafluoro-2,2-dimethyloctanedionato Sm0.2, La0.8
dimethylbenzylammonium tetrakis 1-phenyl-1,3-butanedionato Sm0.2, La0.8
triallylammonium tetrakis acetylacetonato Sm0.2, La0.8
triallylammonium tetrakis dibenzoylmethanato Sm0.2, La0.8
triallylammonium tetrakis thenoyltrifluoroacetonato Sm0.2, La0.8
triallylammonium tetrakis 2,2,6,6-tetramethylheptanedionato Sm0.2, La0.8
triallylammonium tetrakis 3-methylpentane-2,4-dionato Sm0.2, La0.8
triallylammonium tetrakis 3-ethylpentane-2,4-dionato Sm0.2, La0.8
triallylammonium tetrakis pivaloyltrifluoroacetonato Sm0.2, La0.8 triallylammonium tetrakis trifluoroacetylacetonato Sm0.2, La0.8
triallylammonium tetrakis hexafluoroacetylacetonato Sm0.2, La0.8
triallylammonium tetrakis 6,6,7,7,8,8,8-heptafluoro-2,2-dimethyloctanedionato Sm0.2, La0.8
triallylammonium tetrakis 1-phenyl-1,3-butanedionato Sm0.2, La0.8
anilinium tetrakis acetylacetonato Sm0.2, La0.8
anilinium tetrakis dibenzoylmethanato Sm0.2, La0.8
anilinium tetrakis thenoyltrifluoroacetonato Sm0.2, La0.8
anilinium tetrakis 2,2,6,6-tetramethylheptanedionato Sm0.2, La0.8
anilinium tetrakis 3-methylpentane-2,4-dionato Sm0.2, La0.8
anilinium tetrakis 3-ethylpentane-2,4-dionato Sm0.2, La0.8
anilinium tetrakis pivaloyltrifluoroacetonato Sm0.2, La0.8
anilinium tetrakis trifluoroacetylacetonato Sm0.2, La0.8
anilinium tetrakis hexafluoroacetylacetonato Sm0.2, La0.8
anilinium tetrakis 6,6,7,7,8,8,8-heptafluoro-2,2-dimethyloctanedionato Sm0.2, La0.8
anilinium tetrakis 1-phenyl-1,3-butanedionato Sm0.2, La0.8
triethylammonium tetrakis acetylacetonato Sm0.1, La0.9
triethylammonium tetrakis dibenzoylmethanato Sm0.1, La0.9
triethylammonium tetrakis thenoyltrifluoroacetonato Sm0.1, La0.9
triethylammonium tetrakis 2,2,6,6-tetramethylheptanedionato Sm0.1, La0.9
triethylammonium tetrakis 3-methylpentane-2,4-dionato Sm0.1, La0.9
triethylammonium tetrakis 3-ethylpentane-2,4-dionato Sm0.1, La0.9
triethylammonium tetrakis pivaloyltrifluoroacetonato Sm0.1, La0.9
triethylammonium tetrakis trifluoroacetylacetonato Sm0.1, La0.9
triethylammonium tetrakis hexafluoroacetylacetonato Sm0.1, La0.9
triethylammonium tetrakis 6,6,7,7,8,8,8-heptafluoro-2,2-dimethyloctanedionato Sm0.1, La0.9
triethylammonium tetrakis 1-phenyl-1,3-butanedionato Sm0.1, La0.9
morpholinium tetrakis acetylacetonato Sm0.1, La0.9
morpholinium tetrakis dibenzoylmethanato Sm0.1, La0.9
morpholinium tetrakis thenoyltrifluoroacetonato Sm0.1, La0.9
morpholinium tetrakis 2,2,6,6-tetramethylheptanedionato Sm0.1, La0.9
morpholinium tetrakis 3-methylpentane-2,4-dionato Sm0.1, La0.9
morpholinium tetrakis 3-ethylpentane-2,4-dionato Sm0.1, La0.9
morpholinium tetrakis pivaloyltrifluoroacetonato Sm0.1, La0.9
morpholinium tetrakis trifluoroacetylacetonato Sm0.1, La0.9
morpholinium tetrakis hexafluoroacetylacetonato Sm0.1, La0.9
morpholinium tetrakis 6,6,7,7,8,8,8-heptafluoro-2,2-dimethyloctanedionato Sm0.1, La0.9
morpholinium tetrakis 1-phenyl-1,3-butanedionato Sm0.1, La0.9
dimethylbenzylammonium tetrakis acetylacetonato Sm0.1, La0.9
dimethylbenzylammonium tetrakis dibenzoylmethanato Sm0.1, La0.9
dimethylbenzylammonium tetrakis thenoyltrifluoroacetonato Sm0.1, La0.9
dimethylbenzylammonium tetrakis 2,2,6,6-tetramethylheptanedionato Sm0.1, La0.9
dimethylbenzylammonium tetrakis 3-methylpentane-2,4-dionato Sm0.1, La0.9
dimethylbenzylammonium tetrakis 3-ethylpentane-2,4-dionato Sm0.1, La0.9
dimethylbenzylammonium tetrakis pivaloyltrifluoroacetonato Sm0.1, La0.9
dimethylbenzylammonium tetrakis trifluoroacetylacetonato Sm0.1, La0.9
dimethylbenzylammonium tetrakis hexafluoroacetylacetonato Sm0.1, La0.9
dimethylbenzylammonium tetrakis 6,6,7,7,8,8,8-heptafluoro-2,2-dimethyloctanedionato Sm0.1, La0.9
dimethylbenzylammonium tetrakis 1-phenyl-1,3-butanedionato Sm0.1, La0.9
triallylammonium tetrakis acetylacetonato Sm0.1, La0.9
triallylammonium tetrakis dibenzoylmethanato Sm0.1, La0.9
triallylammonium tetrakis thenoyltrifluoroacetonato Sm0.1, La0.9
triallylammonium tetrakis 2,2,6,6-tetramethylheptanedionato Sm0.1, La0.9
triallylammonium tetrakis 3-methylpentane-2,4-dionato Sm0.1, La0.9
triallylammonium tetrakis 3-ethylpentane-2,4-dionato Sm0.1, La0.9
triallylammonium tetrakis pivaloyltrifluoroacetonato Sm0.1, La0.9
triallylammonium tetrakis trifluoroacetylacetonato Sm0.1, La0.9
triallylammonium tetrakis hexafluoroacetylacetonato Sm0.1, La0.9
triallylammonium tetrakis 6,6,7,7,8,8,8-heptafluoro-2,2-dimethyloctanedionato Sm0.1, La0.9
triallylammonium tetrakis 1-phenyl-1,3-butanedionato Sm0.1, La0.9
anilinium tetrakis acetylacetonato Sm0.1, La0.9
anilinium tetrakis dibenzoylmethanato Sm0.1, La0.9
anilinium tetrakis thenoyltrifluoroacetonato Sm0.1, La0.9
anilinium tetrakis 2,2,6,6-tetramethylheptanedionato Sm0.1, La0.9
anilinium tetrakis 3-methylpentane-2,4-dionato Sm0.1, La0.9
anilinium tetrakis 3-ethylpentane-2,4-dionato Sm0.1, La0.9
anilinium tetrakis pivaloyltrifluoroacetonato Sm0.1, La0.9
anilinium tetrakis trifluoroacetylacetonato Sm0.1, La0.9
anilinium tetrakis hexafluoroacetylacetonato Sm0.1, La0.9
anilinium tetrakis 6,6,7,7,8,8,8-heptafluoro-2,2-dimethyloctanedionato Sm0.1, La0.9
anilinium tetrakis 1-phenyl-1,3-butanedionato Sm0.1, La0.9
triethylammonium tetrakis acetylacetonato Sm0.01, La0.99
triethylammonium tetrakis dibenzoylmethanato Sm0.01, La0.99
triethylammonium tetrakis thenoyltrifluoroacetonato Sm0.01, La0.99
triethylammonium tetrakis 2,2,6,6-tetramethylheptanedionato Sm0.01, La0.99
triethylammonium tetrakis 3-methylpentane-2,4-dionato Sm0.01, La0.99
triethylammonium tetrakis 3-ethylpentane-2,4-dionato Sm0.01, La0.99
triethylammonium tetrakis pivaloyltrifluoroacetonato Sm0.01, La0.99 triethylammonium tetrakis trifluoroacetylacetonato Sm0.01, La0.99
triethylammonium tetrakis hexafluoroacetylacetonato Sm0.01, La0.99
triethylammonium tetrakis 6,6,7,7,8,8,8-heptafluoro-2,2-dimethyloctanedionato Sm0.01, La0.99
triethylammonium tetrakis 1-phenyl-1,3-butanedionato Sm0.01, La0.99
morpholinium tetrakis acetylacetonato Sm0.01, La0.99
morpholinium tetrakis dibenzoylmethanato Sm0.01, La0.99
morpholinium tetrakis thenoyltrifluoroacetonato Sm0.01, La0.99
morpholinium tetrakis 2,2,6,6-tetramethylheptanedionato Sm0.01, La0.99
morpholinium tetrakis 3-methylpentane-2,4-dionato Sm0.01, La0.99
morpholinium tetrakis 3-ethylpentane-2,4-dionato Sm0.01, La0.99
morpholinium tetrakis pivaloyltrifluoroacetonato Sm0.01, La0.99
morpholinium tetrakis trifluoroacetylacetonato Sm0.01, La0.99
morpholinium tetrakis hexafluoroacetylacetonato Sm0.01, La0.99
morpholinium tetrakis 6,6,7,7,8,8,8-heptafluoro-2,2-dimethyloctanedionato Sm0.01, La0.99
morpholinium tetrakis 1-phenyl-1,3-butanedionato Sm0.01, La0.99
dimethylbenzylammonium tetrakis acetylacetonato Sm0.01, La0.99
dimethylbenzylammonium tetrakis dibenzoylmethanato Sm0.01, La0.99
dimethylbenzylammonium tetrakis thenoyltrifluoroacetonato Sm0.01, La0.99
dimethylbenzylammonium tetrakis 2,2,6,6-tetramethylheptanedionato Sm0.01, La0.99
dimethylbenzylammonium tetrakis 3-methylpentane-2,4-dionato Sm0.01, La0.99
dimethylbenzylammonium tetrakis 3-ethylpentane-2,4-dionato Sm0.01, La0.99
dimethylbenzylammonium tetrakis pivaloyltrifluoroacetonato Sm0.01, La0.99
dimethylbenzylammonium tetrakis trifluoroacetylacetonato Sm0.01, La0.99
dimethylbenzylammonium tetrakis hexafluoroacetylacetonato Sm0.01, La0.99
dimethylbenzylammonium tetrakis 6,6,7,7,8,8,8-heptafluoro-2,2-dimethyloctanedionato Sm0.01, La0.99
dimethylbenzylammonium tetrakis 1-phenyl-1,3-butanedionato Sm0.01, La0.99
triallylammonium tetrakis acetylacetonato Sm0.01, La0.99
triallylammonium tetrakis dibenzoylmethanato Sm0.01, La0.99
triallylammonium tetrakis thenoyltrifluoroacetonato Sm0.01, La0.99
triallylammonium tetrakis 2,2,6,6-tetramethylheptanedionato Sm0.01, La0.99
triallylammonium tetrakis 3-methylpentane-2,4-dionato Sm0.01, La0.99
triallylammonium tetrakis 3-ethylpentane-2,4-dionato Sm0.01, La0.99
triallylammonium tetrakis pivaloyltrifluoroacetonato Sm0.01, La0.99
triallylammonium tetrakis trifluoroacetylacetonato Sm0.01, La0.99
triallylammonium tetrakis hexafluoroacetylacetonato Sm0.01, La0.99
triallylammonium tetrakis 6,6,7,7,8,8,8-heptafluoro-2,2-dimethyloctanedionato Sm0.01, La0.99
triallylammonium tetrakis 1-phenyl-1,3-butanedionato Sm0.01, La0.99
anilinium tetrakis acetylacetonato Sm0.01, La0.99
anilinium tetrakis dibenzoylmethanato Sm0.01, La0.99
anilinium tetrakis thenoyltrifluoroacetonato Sm0.01, La0.99
anilinium tetrakis 2,2,6,6-tetramethylheptanedionato Sm0.01, La0.99
anilinium tetrakis 3-methylpentane-2,4-dionato Sm0.01, La0.99
anilinium tetrakis 3-ethylpentane-2,4-dionato Sm0.01, La0.99
anilinium tetrakis pivaloyltrifluoroacetonato Sm0.01, La0.99
anilinium tetrakis trifluoroacetylacetonato Sm0.01, La0.99
anilinium tetrakis hexafluoroacetylacetonato Sm0.01, La0.99
anilinium tetrakis 6,6,7,7,8,8,8-heptafluoro-2,2-dimethyloctanedionato Sm0.01, La0.99
anilinium tetrakis 1-phenyl-1,3-butanedionato Sm0.01, La0.99
triethylammonium tetrakis acetylacetonato Dy0.5, La0.5
triethylammonium tetrakis dibenzoylmethanato Dy0.5, La0.5
triethylammonium tetrakis thenoyltrifluoroacetonato Dy0.5, La0.5
triethylammonium tetrakis 2,2,6,6-tetramethylheptanedionato Dy0.5, La0.5
triethylammonium tetrakis 3-methylpentane-2,4-dionato Dy0.5, La0.5
triethylammonium tetrakis 3-ethylpentane-2,4-dionato Dy0.5, La0.5
triethylammonium tetrakis pivaloyltrifluoroacetonato Dy0.5, La0.5
triethylammonium tetrakis trifluoroacetylacetonato Dy0.5, La0.5
triethylammonium tetrakis hexafluoroacetylacetonato Dy0.5, La0.5
triethylammonium tetrakis 6,6,7,7,8,8,8-heptafluoro-2,2-dimethyloctanedionato Dy0.5, La0.5
triethylammonium tetrakis 1-phenyl-1,3-butanedionato Dy0.5, La0.5
morpholinium tetrakis acetylacetonato Dy0.5, La0.5
morpholinium tetrakis dibenzoylmethanato Dy0.5, La0.5
morpholinium tetrakis thenoyltrifluoroacetonato Dy0.5, La0.5
morpholinium tetrakis 2,2,6,6-tetramethylheptanedionato Dy0.5, La0.5
morpholinium tetrakis 3-methylpentane-2,4-dionato Dy0.5, La0.5
morpholinium tetrakis 3-ethylpentane-2,4-dionato Dy0.5, La0.5
morpholinium tetrakis pivaloyltrifluoroacetonato Dy0.5, La0.5
morpholinium tetrakis trifluoroacetylacetonato Dy0.5, La0.5
morpholinium tetrakis hexafluoroacetylacetonato Dy0.5, La0.5
morpholinium tetrakis 6,6,7,7,8,8,8-heptafluoro-2,2-dimethyloctanedionato Dy0.5, La0.5
morpholinium tetrakis 1-phenyl-1,3-butanedionato Dy0.5, La0.5
dimethylbenzylammonium tetrakis acetylacetonato Dy0.5, La0.5
dimethylbenzylammonium tetrakis dibenzoylmethanato Dy0.5, La0.5 dimethylbenzylammonium tetrakis thenoyltrifluoroacetonato Dy0.5, La0.5
dimethylbenzylammonium tetrakis 2,2,6,6-tetramethylheptanedionato Dy0.5, La0.5
dimethylbenzylammonium tetrakis 3-methylpentane-2,4-dionato Dy0.5, La0.5
dimethylbenzylammonium tetrakis 3-ethylpentane-2,4-dionato Dy0.5, La0.5
dimethylbenzylammonium tetrakis pivaloyltrifluoroacetonato Dy0.5, La0.5
dimethylbenzylammonium tetrakis trifluoroacetylacetonato Dy0.5, La0.5
dimethylbenzylammonium tetrakis hexafluoroacetylacetonato Dy0.5, La0.5
dimethylbenzylammonium tetrakis 6,6,7,7,8,8,8-heptafluoro-2,2-dimethyloctanedionato Dy0.5, La0.5
dimethylbenzylammonium tetrakis 1-phenyl-1,3-butanedionato Dy0.5, La0.5
triallylammonium tetrakis acetylacetonato Dy0.5, La0.5
triallylammonium tetrakis dibenzoylmethanato Dy0.5, La0.5
triallylammonium tetrakis thenoyltrifluoroacetonato Dy0.5, La0.5
triallylammonium tetrakis 2,2,6,6-tetramethylheptanedionato Dy0.5, La0.5
triallylammonium tetrakis 3-methylpentane-2,4-dionato Dy0.5, La0.5
triallylammonium tetrakis 3-ethylpentane-2,4-dionato Dy0.5, La0.5
triallylammonium tetrakis pivaloyltrifluoroacetonato Dy0.5, La0.5
triallylammonium tetrakis trifluoroacetylacetonato Dy0.5, La0.5
triallylammonium tetrakis hexafluoroacetylacetonato Dy0.5, La0.5
triallylammonium tetrakis 6,6,7,7,8,8,8-heptafluoro-2,2-dimethyloctanedionato Dy0.5, La0.5
triallylammonium tetrakis 1-phenyl-1,3-butanedionato Dy0.5, La0.5
anilinium tetrakis acetylacetonato Dy0.5, La0.5
anilinium tetrakis dibenzoylmethanato Dy0.5, La0.5
anilinium tetrakis thenoyltrifluoroacetonato Dy0.5, La0.5
anilinium tetrakis 2,2,6,6-tetramethylheptanedionato Dy0.5, La0.5
anilinium tetrakis 3-methylpentane-2,4-dionato Dy0.5, La0.5
anilinium tetrakis 3-ethylpentane-2,4-dionato Dy0.5, La0.5
anilinium tetrakis pivaloyltrifluoroacetonato Dy0.5, La0.5
anilinium tetrakis trifluoroacetylacetonato Dy0.5, La0.5
anilinium tetrakis hexafluoroacetylacetonato Dy0.5, La0.5
anilinium tetrakis 6,6,7,7,8,8,8-heptafluoro-2,2-dimethyloctanedionato Dy0.5, La0.5
anilinium tetrakis 1-phenyl-1,3-butanedionato Dy0.5, La0.5
triethylammonium tetrakis acetylacetonato Dy0.2, La0.8
triethylammonium tetrakis dibenzoylmethanato Dy0.2, La0.8
triethylammonium tetrakis thenoyltrifluoroacetonato Dy0.2, La0.8
triethylammonium tetrakis 2,2,6,6-tetramethylheptanedionato Dy0.2, La0.8
triethylammonium tetrakis 3-methylpentane-2,4-dionato Dy0.2, La0.8
triethylammonium tetrakis 3-ethylpentane-2,4-dionato Dy0.2, La0.8
triethylammonium tetrakis pivaloyltrifluoroacetonato Dy0.2, La0.8
triethylammonium tetrakis trifluoroacetylacetonato Dy0.2, La0.8
triethylammonium tetrakis hexafluoroacetylacetonato Dy0.2, La0.8
triethylammonium tetrakis 6,6,7,7,8,8,8-heptafluoro-2,2-dimethyloctanedionato Dy0.2, La0.8
triethylammonium tetrakis 1-phenyl-1,3-butanedionato Dy0.2, La0.8
morpholinium tetrakis acetylacetonato Dy0.2, La0.8
morpholinium tetrakis dibenzoylmethanato Dy0.2, La0.8
morpholinium tetrakis thenoyltrifluoroacetonato Dy0.2, La0.8
morpholinium tetrakis 2,2,6,6-tetramethylheptanedionato Dy0.2, La0.8
morpholinium tetrakis 3-methylpentane-2,4-dionato Dy0.2, La0.8
morpholinium tetrakis 3-ethylpentane-2,4-dionato Dy0.2, La0.8
morpholinium tetrakis pivaloyltrifluoroacetonato Dy0.2, La0.8
morpholinium tetrakis trifluoroacetylacetonato Dy0.2, La0.8
morpholinium tetrakis hexafluoroacetylacetonato Dy0.2, La0.8
morpholinium tetrakis 6,6,7,7,8,8,8-heptafluoro-2,2-dimethyloctanedionato Dy0.2, La0.8
morpholinium tetrakis 1-phenyl-1,3-butanedionato Dy0.2, La0.8
dimethylbenzylammonium tetrakis acetylacetonato Dy0.2, La0.8
dimethylbenzylammonium tetrakis dibenzoylmethanato Dy0.2, La0.8
dimethylbenzylammonium tetrakis thenoyltrifluoroacetonato Dy0.2, La0.8
dimethylbenzylammonium tetrakis 2,2,6,6-tetramethylheptanedionato Dy0.2, La0.8
dimethylbenzylammonium tetrakis 3-methylpentane-2,4-dionato Dy0.2, La0.8
dimethylbenzylammonium tetrakis 3-ethylpentane-2,4-dionato Dy0.2, La0.8
dimethylbenzylammonium tetrakis pivaloyltrifluoroacetonato Dy0.2, La0.8
dimethylbenzylammonium tetrakis trifluoroacetylacetonato Dy0.2, La0.8
dimethylbenzylammonium tetrakis hexafluoroacetylacetonato Dy0.2, La0.8
dimethylbenzylammonium tetrakis 6,6,7,7,8,8,8-heptafluoro-2,2-dimethyloctanedionato Dy0.2, La0.8
dimethylbenzylammonium tetrakis 1-phenyl-1,3-butanedionato Dy0.2, La0.8
triallylammonium tetrakis acetylacetonato Dy0.2, La0.8
triallylammonium tetrakis dibenzoylmethanato Dy0.2, La0.8
triallylammonium tetrakis thenoyltrifluoroacetonato Dy0.2, La0.8
triallylammonium tetrakis 2,2,6,6-tetramethylheptanedionato Dy0.2, La0.8
triallylammonium tetrakis 3-methylpentane-2,4-dionato Dy0.2, La0.8
triallylammonium tetrakis 3-ethylpentane-2,4-dionato Dy0.2, La0.8
triallylammonium tetrakis pivaloyltrifluoroacetonato Dy0.2, La0.8
triallylammonium tetrakis trifluoroacetylacetonato Dy0.2, La0.8
triallylammonium tetrakis hexafluoroacetylacetonato Dy0.2, La0.8 triallylammonium tetrakis 6,6,7,7,8,8,8-heptafluoro-2,2-dimethyloctanedionato Dy0.2, La0.8
triallylammonium tetrakis 1-phenyl-1,3-butanedionato Dy0.2, La0.8
anilinium tetrakis acetylacetonato Dy0.2, La0.8
anilinium tetrakis dibenzoylmethanato Dy0.2, La0.8
anilinium tetrakis thenoyltrifluoroacetonato Dy0.2, La0.8
anilinium tetrakis 2,2,6,6-tetramethylheptanedionato Dy0.2, La0.8
anilinium tetrakis 3-methylpentane-2,4-dionato Dy0.2, La0.8
anilinium tetrakis 3-ethylpentane-2,4-dionato Dy0.2, La0.8
anilinium tetrakis pivaloyltrifluoroacetonato Dy0.2, La0.8
anilinium tetrakis trifluoroacetylacetonato Dy0.2, La0.8
anilinium tetrakis hexafluoroacetylacetonato Dy0.2, La0.8
anilinium tetrakis 6,6,7,7,8,8,8-heptafluoro-2,2-dimethyloctanedionato Dy0.2, La0.8
anilinium tetrakis 1-phenyl-1,3-butanedionato Dy0.2, La0.8
triethylammonium tetrakis acetylacetonato Dy0.1, La0.9
triethylammonium tetrakis dibenzoylmethanato Dy0.1, La0.9
triethylammonium tetrakis thenoyltrifluoroacetonato Dy0.1, La0.9
triethylammonium tetrakis 2,2,6,6-tetramethylheptanedionato Dy0.1, La0.9
triethylammonium tetrakis 3-methylpentane-2,4-dionato Dy0.1, La0.9
triethylammonium tetrakis 3-ethylpentane-2,4-dionato Dy0.1, La0.9
triethylammonium tetrakis pivaloyltrifluoroacetonato Dy0.1, La0.9
triethylammonium tetrakis trifluoroacetylacetonato Dy0.1, La0.9
triethylammonium tetrakis hexafluoroacetylacetonato Dy0.1, La0.9
triethylammonium tetrakis 6,6,7,7,8,8,8-heptafluoro-2,2-dimethyloctanedionato Dy0.1, La0.9
triethylammonium tetrakis 1-phenyl-1,3-butanedionato Dy0.1, La0.9
morpholinium tetrakis acetylacetonato Dy0.1, La0.9
morpholinium tetrakis dibenzoylmethanato Dy0.1, La0.9
morpholinium tetrakis thenoyltrifluoroacetonato Dy0.1, La0.9
morpholinium tetrakis 2,2,6,6-tetramethylheptanedionato Dy0.1, La0.9
morpholinium tetrakis 3-methylpentane-2,4-dionato Dy0.1, La0.9
morpholinium tetrakis 3-ethylpentane-2,4-dionato Dy0.1, La0.9
morpholinium tetrakis pivaloyltrifluoroacetonato Dy0.1, La0.9
morpholinium tetrakis trifluoroacetylacetonato Dy0.1, La0.9
morpholinium tetrakis hexafluoroacetylacetonato Dy0.1, La0.9
morpholinium tetrakis 6,6,7,7,8,8,8-heptafluoro-2,2-dimethyloctanedionato Dy0.1, La0.9
morpholinium tetrakis 1-phenyl-1,3-butanedionato Dy0.1, La0.9
dimethylbenzylammonium tetrakis acetylacetonato Dy0.1, La0.9
dimethylbenzylammonium tetrakis dibenzoylmethanato Dy0.1, La0.9
dimethylbenzylammonium tetrakis thenoyltrifluoroacetonato Dy0.1, La0.9
dimethylbenzylammonium tetrakis 2,2,6,6-tetramethylheptanedionato Dy0.1, La0.9
dimethylbenzylammonium tetrakis 3-methylpentane-2,4-dionato Dy0.1, La0.9
dimethylbenzylammonium tetrakis 3-ethylpentane-2,4-dionato Dy0.1, La0.9
dimethylbenzylammonium tetrakis pivaloyltrifluoroacetonato Dy0.1, La0.9
dimethylbenzylammonium tetrakis trifluoroacetylacetonato Dy0.1, La0.9
dimethylbenzylammonium tetrakis hexafluoroacetylacetonato Dy0.1, La0.9
dimethylbenzylammonium tetrakis 6,6,7,7,8,8,8-heptafluoro-2,2-dimethyloctanedionato Dy0.1, La0.9
dimethylbenzylammonium tetrakis 1-phenyl-1,3-butanedionato Dy0.1, La0.9
triallylammonium tetrakis acetylacetonato Dy0.1, La0.9
triallylammonium tetrakis dibenzoylmethanato Dy0.1, La0.9
triallylammonium tetrakis thenoyltrifluoroacetonato Dy0.1, La0.9
triallylammonium tetrakis 2,2,66-tetramethylheptanedionato Dy0.1, La0.9
triallylammonium tetrakis 3-methylpentane-2,4-dionato Dy0.1, La0.9
triallylammonium tetrakis 3-ethylpentane-2,4-dionato Dy0.1, La0.9
triallylammonium tetrakis pivaloyltrifluoroacetonato Dy0.1, La0.9
triallylammonium tetrakis trifluoroacetylacetonato Dy0.1, La0.9
triallylammonium tetrakis hexafluoroacetylacetonato Dy0.1, La0.9
triallylammonium tetrakis 6,6,7,7,8,8,8-heptafluoro-2,2-dimethyloctanedionato Dy0.1, La0.9
triallylammonium tetrakis 1-phenyl-1,3-butanedionato Dy0.1, La0.9
anilinium tetrakis acetylacetonato Dy0.1, La0.9
anilinium tetrakis dibenzoylmethanato Dy0.1, La0.9
anilinium tetrakis thenoyltrifluoroacetonato Dy0.1, La0.9
anilinium tetrakis 2,2,6,6-tetramethylheptanedionato Dy0.1, La0.9
anilinium tetrakis 3-methylpentane-2,4-dionato Dy0.1, La0.9
anilinium tetrakis 3-ethylpentane-2,4-dionato Dy0.1, La0.9
anilinium tetrakis pivaloyltrifluoroacetonato Dy0.1, La0.9
anilinium tetrakis trifluoroacetylacetonato Dy0.1, La0.9
anilinium tetrakis hexafluoroacetylacetonato Dy0.1, La0.9
anilinium tetrakis 6,6,7,7,8,8,8-heptafluoro-2,2-dimethyloctanedionato Dy0.1, La0.9
anilinium tetrakis 1-phenyl-1,3-butanedionato Dy0.1, La0.9
triethylammonium tetrakis acetylacetonato Dy0.01, La0.99
triethylammonium tetrakis dibenzoylmethanato Dy0.01, La0.99
triethylammonium tetrakis thenoyltrifluoroacetonato Dy0.01, La0.99
triethylammonium tetrakis 2,2,6,6-tetramethylheptanedionato Dy0.01, La0.99
triethylammonium tetrakis 3-methylpentane-2,4-dionato Dy0.01, La0.99
triethylammonium tetrakis 3-ethylpentane-2,4-dionato Dy0.01, La0.99
triethylammonium tetrakis pivaloyltrifluoroacetonato Dy0.01, La0.99
triethylammonium tetrakis trifluoroacetylacetonato Dy0.01, La0.99
triethylammonium tetrakis hexafluoroacetylacetonato Dy0.01, La0.99 triethylammonium tetrakis 6,6,7,7,8,8,8-heptafluoro-2,2-dimethyloctanedionato Dy0.01, La0.99
triethylammonium tetrakis 1-phenyl-1,3-butanedionato Dy0.01, La0.99
morpholinium tetrakis acetylacetonato Dy0.01, La0.99
morpholinium tetrakis dibenzoylmethanato Dy0.01, La0.99
morpholinium tetrakis thenoyltrifluoroacetonato Dy0.01, La0.99
morpholinium tetrakis 2,2,6,6-tetramethylheptanedionato Dy0.01, La0.99
morpholinium tetrakis 3-methylpentane-2,4-dionato Dy0.01, La0.99
morpholinium tetrakis 3-ethylpentane-2,4-dionato Dy0.01, La0.99
morpholinium tetrakis pivaloyltrifluoroacetonato Dy0.01, La0.99
morpholinium tetrakis trifluoroacetylacetonato Dy0.01, La0.99
morpholinium tetrakis hexafluoroacetylacetonato Dy0.01, La0.99
morpholinium tetrakis 6,6,7,7,8,8,8-heptafluoro-2,2-dimethyloctanedionato Dy0.01, La0.99
morpholinium tetrakis 1-phenyl-1,3-butanedionato Dy0.01, La0.99
dimethylbenzylammonium tetrakis acetylacetonato Dy0.01, La0.99
dimethylbenzylammonium tetrakis dibenzoylmethanato Dy0.01, La0.99
dimethylbenzylammonium tetrakis thenoyltrifluoroacetonato Dy0.01, La0.99
dimethylbenzylammonium tetrakis 2,2,6,6-tetramethylheptanedionato Dy0.01, La0.99
dimethylbenzylammonium tetrakis 3-methylpentane-2,4-dionato Dy0.01, La0.99
dimethylbenzylammonium tetrakis 3-ethylpentane-2,4-dionato Dy0.01, La0.99
dimethylbenzylammonium tetrakis pivaloyltrifluoroacetonato Dy0.01, La0.99
dimethylbenzylammonium tetrakis trifluoroacetylacetonato Dy0.01, La0.99
dimethylbenzylammonium tetrakis hexafluoroacetylacetonato Dy0.01, La0.99
dimethylbenzylammonium tetrakis 6,6,7,7,8,8,8-heptafluoro-2,2-dimethyloctanedionato Dy0.01, La0.99
dimethylbenzylammonium tetrakis 1-phenyl-1,3-butanedionato Dy0.01, La0.99
triallylammonium tetrakis acetylacetonato Dy0.01, La0.99
triallylammonium tetrakis dibenzoylmethanato Dy0.01, La0.99
triallylammonium tetrakis thenoyltrifluoroacetonato Dy0.01, La0.99
triallylammonium tetrakis 2,2,6,6-tetramethylheptanedionato Dy0.01, La0.99
triallylammonium tetrakis 3-methylpentane-2,4-dionato Dy0.01, La0.99
triallylammonium tetrakis 3-ethylpentane-2,4-dionato Dy0.01, La0.99
triallylammonium tetrakis pivaloyltrifluoroacetonato Dy0.01, La0.99
triallylammonium tetrakis trifluoroacetylacetonato Dy0.01, La0.99
triallylammonium tetrakis hexafluoroacetylacetonato Dy0.01, La0.99
triallylammonium tetrakis 6,6,7,7,8,8,8-heptafluoro-2,2-dimethyloctanedionato Dy0.01, La0.99
triallylammonium tetrakis 1-phenyl-1,3-butanedionato Dy0.01, La0.99
anilinium tetrakis acetylacetonato Dy0.01, La0.99
anilinium tetrakis dibenzoylmethanato Dy0.01, La0.99
anilinium tetrakis thenoyltrifluoroacetonato Dy0.01, La0.99
anilinium tetrakis 2,2,6,6-tetramethylheptanedionato Dy0.01, La0.99
anilinium tetrakis 3-methylpentane-2,4-dionato Dy0.01, La0.99
anilinium tetrakis 3-ethylpentane-2,4-dionato Dy0.01, La0.99
anilinium tetrakis pivaloyltrifluoroacetonato Dy0.01, La0.99
anilinium tetrakis trifluoroacetylacetonato Dy0.01, La0.99
anilinium tetrakis hexafluoroacetylacetonato Dy0.01, La0.99
anilinium tetrakis 6,6,7,7,8,8,8-heptafluoro-2,2-dimethyloctanedionato Dy0.01, La0.99
anilinium tetrakis 1-phenyl-1,3-butanedionato Dy0.01, La0.99
triethylammonium tetrakis acetylacetonato Dy0.5, La0.5
triethylammonium tetrakis dibenzoylmethanato Dy0.5, La0.5
triethylammonium tetrakis thenoyltrifluoroacetonato Dy0.5, La0.5
triethylammonium tetrakis 2,2,6,6-tetramethylheptanedionato Dy0.5, La0.5
triethylammonium tetrakis 3-methylpentane-2,4-dionato Dy0.5, La0.5
triethylammonium tetrakis 3-ethylpentane-2,4-dionato Dy0.5, La0.5
triethylammonium tetrakis pivaloyltrifluoroacetonato Dy0.5, La0.5
triethylammonium tetrakis trifluoroacetylacetonato Dy0.5, La0.5
triethylammonium tetrakis hexafluoroacetylacetonato Dy0.5, La0.5
triethylammonium tetrakis 6,6,7,7,8,8,8-heptafluoro-2,2-dimethyloctanedionato Dy0.5, La0.5
triethylammonium tetrakis 1-phenyl-1,3-butanedionato Dy0.5, La0.5
morpholinium tetrakis acetylacetonato Dy0.5, La0.5
morpholinium tetrakis dibenzoylmethanato Dy0.5, La0.5
morpholinium tetrakis thenoyltrifluoroacetonato Dy0.5, La0.5
morpholinium tetrakis 2,2,6,6-tetramethylheptanedionato Dy0.5, La0.5
morpholinium tetrakis 3-methylpentane-2,4-dionato Dy0.5, La0.5
morpholinium tetrakis 3-ethylpentane-2,4-dionato Dy0.5, La0.5
morpholinium tetrakis pivaloyltrifluoroacetonato Dy0.5, La0.5
morpholinium tetrakis trifluoroacetylacetonato Dy0.5, La0.5
morpholinium tetrakis hexafluoroacetylacetonato Dy0.5, La0.5
morpholinium tetrakis 6,6,7,7,8,8,8-heptafluoro-2,2-dimethyloctanedionato Dy0.5, La0.5
morpholinium tetrakis 1-phenyl-1,3-butanedionato Dy0.5, La0.5
dimethylbenzylammonium tetrakis acetylacetonato Dy0.5, La0.5
dimethylbenzylammonium tetrakis dibenzoylmethanato Dy0.5, La0.5
dimethylbenzylammonium tetrakis thenoyltrifluoroacetonato Dy0.5, La0.5
dimethylbenzylammonium tetrakis 2,2,6,6-tetramethylheptanedionato Dy0.5, La0.5
dimethylbenzylammonium tetrakis 3-methylpentane-2,4-dionato Dy0.5, La0.5 dimethylbenzylammonium tetrakis 3-ethylpentane-2,4-dionato Dy0.5, La0.5
dimethylbenzylammonium tetrakis pivaloyltrifluoroacetonato Dy0.5, La0.5
dimethylbenzylammonium tetrakis trifluoroacetylacetonato Dy0.5, La0.5
dimethylbenzylammonium tetrakis hexafluoroacetylacetonato Dy0.5, La0.5
dimethylbenzylammonium tetrakis 6,6,7,7,8,8,8-heptafluoro-2,2-dimethyloctanedionato Dy0.5, La0.5
dimethylbenzylammonium tetrakis 1-phenyl-1,3-butanedionato Dy0.5, La0.5
triallylammonium tetrakis acetylacetonato Dy0.5, La0.5
triallylammonium tetrakis dibenzoylmethanato Dy0.5, La0.5
triallylammonium tetrakis thenoyltrifluoroacetonato Dy0.5, La0.5
triallylammonium tetrakis 2,2,6,6-tetramethylheptanedionato Dy0.5, La0.5
triallylammonium tetrakis 3-methylpentane-2,4-dionato Dy0.5, La0.5
triallylammonium tetrakis 3-ethylpentane-2,4-dionato Dy0.5, La0.5
triallylammonium tetrakis pivaloyltrifluoroacetonato Dy0.5, La0.5
triallylammonium tetrakis trifluoroacetylacetonato Dy0.5, La0.5
triallylammonium tetrakis hexafluoroacetylacetonato Dy0.5, La0.5
triallylammonium tetrakis 6,6,7,7,8,8,8-heptafluoro-2,2-dimethyloctanedionato Dy0.5, La0.5
triallylammonium tetrakis 1-phenyl-1,3-butanedionato Dy0.5, La0.5
anilinium tetrakis acetylacetonato Dy0.5, La0.5
anilinium tetrakis dibenzoylmethanato Dy0.5i La0.5
anilinium tetrakis thenoyltrifluoroacetonato Dy0.5, La0.5
anilinium tetrakis 2,2,6,6-tetramethylheptanedionato Dy0.5, La0.5
anilinium tetrakis 3-methylpentane-2,4-dionato Dy0.5, La0.5
anilinium tetrakis 3-ethylpentane-2,4-dionato Dy0.5, La0.5
anilinium tetrakis pivaloyltrifluoroacetonato Dy0.5, La0.5
anilinium tetrakis trifluoroacetylacetonato Dy0.5, La0.5
anilinium tetrakis hexafluoroacetylacetonato Dy0.5, La0.5
anilinium tetrakis 6,6,7,7,8,8,8-heptafluoro-2,2-dimethyloctanedionato Dy0.5, La0.5
anilinium tetrakis 1-phenyl-1,3-butanedionato Dy0.5, La0.5
triethylammonium tetrakis acetylacetonato Dy0.2, La0.8
triethylammonium tetrakis dibenzoylmethanato Dy0.2, La0.8
triethylammonium tetrakis thenoyltrifluoroacetonato Dy0.2, La0.8
triethylammonium tetrakis 2,2,6,6-tetramethylheptanedionato Dy0.2, La0.8
triethylammonium tetrakis 3-methylpentane-2,4-dionato Dy0.2, La0.8
triethylammonium tetrakis 3-ethylpentane-2,4-dionato Dy0.2, La0.8
triethylammonium tetrakis pivaloyltrifluoroacetonato Dy0.2, La0.8
triethylammonium tetrakis trifluoroacetylacetonato Dy0.2, La0.8
triethylammonium tetrakis hexafluoroacetylacetonato Dy0.2, La0.8
triethylammonium tetrakis 6,6,7,7,8,8,8-heptafluoro-2,2-dimethyloctanedionato Dy0.2, La0.8
triethylammonium tetrakis 1-phenyl-1,3-butanedionato Dy0.2, La0.8
morpholinium tetrakis acetylacetonato Dy0.2, La0.8
morpholinium tetrakis dibenzoylmethanato Dy0.2, La0.8
morpholinium tetrakis thenoyltrifluoroacetonato Dy0.2, La0.8
morpholinium tetrakis 2,2,6,6-tetramethylheptanedionato Dy0.2, La0.8
morpholinium tetrakis 3-methylpentane-2,4-dionato Dy0.2, La0.8
morpholinium tetrakis 3-ethylpentane-2,4-dionato Dy0.2, La0.8
morpholinium tetrakis pivaloyltrifluoroacetonato Dy0.2, La0.8
morpholinium tetrakis trifluoroacetylacetonato Dy0.2, La0.8
morpholinium tetrakis hexafluoroacetylacetonato Dy0.2, La0.8
morpholinium tetrakis 6,6,7,7,8,8,8-heptafluoro-2,2-dimethyloctanedionato Dy0.2, La0.8
morpholinium tetrakis 1-phenyl-1,3-butanedionato Dy0.2, La0.8
dimethylbenzylammonium tetrakis acetylacetonato Dy0.2, La0.8
dimethylbenzylammonium tetrakis dibenzoylmethanato Dy0.2, La0.8
dimethylbenzylammonium tetrakis thenoyltrifluoroacetonato Dy0.2, La0.8
dimethylbenzylammonium tetrakis 2,2,6,6-tetramethylheptanedionato Dy0.2, La0.8
dimethylbenzylammonium tetrakis 3-methylpentane-2,4-dionato Dy0.2, La0.8
dimethylbenzylammonium tetrakis 3-ethylpentane-2,4-dionato Dy0.2, La0.8
dimethylbenzylammonium tetrakis pivaloyltrifluoroacetonato Dy0.2, La0.8
dimethylbenzylammonium tetrakis trifluoroacetylacetonato Dy0.2, La0.8
dimethylbenzylammonium tetrakis hexafluoroacetylacetonato Dy0.2, La0.8
dimethylbenzylammonium tetrakis 6,6,7,7,8,8,8-heptafluoro-2,2-dimethyloctanedionato Dy0.2, La0.8
dimethylbenzylammonium tetrakis 1-phenyl-1,3-butanedionato Dy0.2, La0.8
triallylammonium tetrakis acetylacetonato Dy0.2, La0.8
triallylammonium tetrakis dibenzoylmethanato Dy0.2, La0.8
triallylammonium tetrakis thenoyltrifluoroacetonato Dy0.2, La0.8
triallylammonium tetrakis 2,2,6,6-tetramethylheptanedionato Dy0.2, La0.8
triallylammonium tetrakis 3-methylpentane-2,4-dionato Dy0.2, La0.8
triallylammonium tetrakis 3-ethylpentane-2,4-dionato Dy0.2, La0.8
triallylammonium tetrakis pivaloyltrifluoroacetonato Dy0.2, La0.8
triallylammonium tetrakis trifluoroacetylacetonato Dy0.2, La0.8
triallylammonium tetrakis hexafluoroacetylacetonato Dy0.2, La0.8
triallylammonium tetrakis 6,6,7,7,8,8,8-heptafluoro-2,2-dimethyloctanedionato Dy0.2, La0.8
triallylammonium tetrakis 1-phenyl-1,3-butanedionato Dy0.2, La0.8
anilinium tetrakis acetylacetonato Dy0.2, La0.8
anilinium tetrakis dibenzoylmethanato Dy0.2, La0.8
anilinium tetrakis thenoyltrifluoroacetonato Dy0.2, La0.8 anilinium tetrakis 2,2,6,6-tetramethylheptanedionato Dy0.2, La0.8
anilinium tetrakis 3-methylpentane-2,4-dionato Dy0.2, La0.8
anilinium tetrakis 3-ethylpentane-2,4-dionato Dy0.2, La0.8
anilinium tetrakis pivaloyltrifluoroacetonato Dy0.2, La0.8
anilinium tetrakis trifluoroacetylacetonato Dy0.2, La0.8
anilinium tetrakis hexafluoroacetylacetonato Dy0.2, La0.8
anilinium tetrakis 6,6,7,7,8,8,8-heptafluoro-2,2-dimethyloctanedionato Dy0.2, La0.8
anilinium tetrakis 1-phenyl-1,3-butanedionato Dy0.2, La0.8
triethylammonium tetrakis acetylacetonato Dy0.1, La0.9
triethylammonium tetrakis dibenzoylmethanato Dy0.1, La0.9
triethylammonium tetrakis thenoyltrifluoroacetonato Dy0.1, La0.9
triethylammonium tetrakis 2,2,6,6-tetramethylheptanedionato Dy0.1, La0.9
triethylammonium tetrakis 3-methylpentane-2,4-dionato Dy0.1, La0.9
triethylammonium tetrakis 3-ethylpentane-2,4-dionato Dy0.1, La0.9
triethylammonium tetrakis pivaloyltrifluoroacetonato Dy0.1, La0.9
triethylammonium tetrakis trifluoroacetylacetonato Dy0.1, La0.9
triethylammonium tetrakis hexafluoroacetylacetonato Dy0.1, La0.9
triethylammonium tetrakis 6,6,7,7,8,8,8-heptafluoro-2,2-dimethyloctanedionato Dy0.1, La0.9
triethylammonium tetrakis 1-phenyl-1,3-butanedionato Dy0.1, La0.9
morpholinium tetrakis acetylacetonato Dy0.1, La0.9
morpholinium tetrakis dibenzoylmethanato Dy0.1, La0.9
morpholinium tetrakis thenoyltrifluoroacetonato Dy0.1, La0.9
morpholinium tetrakis 2,2,6,6-tetramethylheptanedionato Dy0.1, La0.9
morpholinium tetrakis 3-methylpentane-2,4-dionato Dy0.1, La0.9
morpholinium tetrakis 3-ethylpentane-2,4-dionato Dy0.1, La0.9
morpholinium tetrakis pivaloyltrifluoroacetonato Dy0.1, La0.9
morpholinium tetrakis trifluoroacetylacetonato Dy0.1, La0.9
morpholinium tetrakis hexafluoroacetylacetonato Dy0.1, La0.9
morpholinium tetrakis 6,6,7,7,8,8,8-heptafluoro-2,2-dimethyloctanedionato Dy0.1, La0.9
morpholinium tetrakis 1-phenyl-1,3-butanedionato Dy0.1, La0.9
dimethylbenzylammonium tetrakis acetylacetonato Dy0.1, La0.9
dimethylbenzylammonium tetrakis dibenzoylmethanato Dy0.1, La0.9
dimethylbenzylammonium tetrakis thenoyltrifluoroacetonato Dy0.1, La0.9
dimethylbenzylammonium tetrakis 2,2,6,6-tetramethylheptanedionato Dy0.1, La0.9
dimethylbenzylammonium tetrakis 3-methylpentane-2,4-dionato Dy0.1, La0.9
dimethylbenzylammonium tetrakis 3-ethylpentane-2,4-dionato Dy0.1, La0.9
dimethylbenzylammonium tetrakis pivaloyltrifluoroacetonato Dy0.1, La0.9
dimethylbenzylammonium tetrakis trifluoroacetylacetonato Dy0.1, La0.9
dimethylbenzylammonium tetrakis hexafluoroacetylacetonato Dy0.1, La0.9
dimethylbenzylammonium tetrakis 6,6,7,7,8,8,8-heptafluoro-2,2-dimethyloctanedionato Dy0.1, La0.9
dimethylbenzylammonium tetrakis 1-phenyl-1,3-butanedionato Dy0.1, La0.9
triallylammonium tetrakis acetylacetonato Dy0.1, La0.9
triallylammonium tetrakis dibenzoylmethanato Dy0.1, La0.9
triallylammonium tetrakis thenoyltrifluoroacetonato Dy0.1, La0.9
triallylammonium tetrakis 2,2,6,6-tetramethylheptanedionato Dy0.1, La0.9
triallylammonium tetrakis 3-methylpentane-2,4-dionato Dy0.1, La0.9
triallylammonium tetrakis 3-ethylpentane-2,4-dionato Dy0.1, La0.9
triallylammonium tetrakis pivaloyltrifluoroacetonato Dy0.1, La0.9
triallylammonium tetrakis trifluoroacetylacetonato Dy0.1, La0.9
triallylammonium tetrakis hexafluoroacetylacetonato Dy0.1, La0.9
triallylammonium tetrakis 6,6,7,7,8,8,8-heptafluoro-2,2-dimethyloctanedionato Dy0.1, La0.9
triallylammonium tetrakis 1-phenyl-1,3-butanedionato Dy0.1, La0.9
anilinium tetrakis acetylacetonato Dy0.1, La0.9
anilinium tetrakis dibenzoylmethanato Dy0.1, La0.9
anilinium tetrakis thenoyltrifluoroacetonato Dy0.1, La0.9
anilinium tetrakis 2,2,6,6-tetramethylheptanedionato Dy0.1, La0.9
anilinium tetrakis 3-methylpentane-2,4-dionato Dy0.1, La0.9
anilinium tetrakis 3-ethylpentane-2,4-dionato Dy0.1, La0.9
anilinium tetrakis pivaloyltrifluoroacetonato Dy0.1, La0.9
anilinium tetrakis trifluoroacetylacetonato Dy0.1, La0.9
anilinium tetrakis hexafluoroacetylacetonato Dy0.1, La0.9
anilinium tetrakis 6,6,7,7,8,8,8-heptafluoro-2,2-dimethyloctanedionato Dy0.1, La0.9
anilinium tetrakis 1-phenyl-1,3-butanedionato Dy0.1, La0.9
triethylammonium tetrakis acetylacetonato Dy0.01, La0.99
triethylammonium tetrakis dibenzoylmethanato Dy0.01, La0.99
triethylammonium tetrakis thenoyltrifluoroacetonato Dy0.01, La0.99
triethylammonium tetrakis 2,2,6,6-tetramethylheptanedionato Dy0.01, La0.99
triethylammonium tetrakis 3-methylpentane-2,4-dionato Dy0.01, La0.99
triethylammonium tetrakis 3-ethylpentane-2,4-dionato Dy0.01, La0.99
triethylammonium tetrakis pivaloyltrifluoroacetonato Dy0.01, La0.99
triethylammonium tetrakis trifluoroacetylacetonato Dy0.01, La0.99
triethylammonium tetrakis hexafluoroacetylacetonato Dy0.01, La0.99
triethylammonium tetrakis 6,6,7,7,8,8,8-heptafluoro-2,2-dimethyloctanedionato Dy0.01, La0.99
triethylammonium tetrakis 1-phenyl-1,3-butanedionato Dy0.01, La0.99
morpholinium tetrakis acetylacetonato Dy0.01, La0.99
morpholinium tetrakis dibenzoylmethanato Dy0.01, La0.99
morpholinium tetrakis thenoyltrifluoroacetonato Dy0.01, La0.99 morpholinium tetrakis 2,2,6,6-tetramethylheptanedionato Dy0.01, La0.99
morpholinium tetrakis 3-methylpentane-2,4-dionato Dy0.01, La0.99
morpholinium tetrakis 3-ethylpentane-2,4-dionato Dy0.01, La0.99
morpholinium tetrakis pivaloyltrifluoroacetonato Dy0.01, La0.99
morpholinium tetrakis trifluoroacetylacetonato Dy0.01, La0.99
morpholinium tetrakis hexafluoroacetylacetonato Dy0.01, La0.99
morpholinium tetrakis 6,6,7,7,8,8,8-heptafluoro-2,2-dimethyloctanedionato Dy0.01, La0.99
morpholinium tetrakis 1-phenyl-1,3-butanedionato Dy0.01, La0.99
dimethylbenzylammonium tetrakis acetylacetonato Dy0.01, La0.99
dimethylbenzylammonium tetrakis dibenzoylmethanato Dy0.01, La0.99
dimethylbenzylammonium tetrakis thenoyltrifluoroacetonato Dy0.01, La0.99
dimethylbenzylammonium tetrakis 2,2,6,6-tetramethylheptanedionato Dy0.01, La0.99
dimethylbenzylammonium tetrakis 3-methylpentane-2,4-dionato Dy0.01, La0.99
dimethylbenzylammonium tetrakis 3-ethylpentane2,4-dionato Dy0.01, La0.99
dimethylbenzylammonium tetrakis pivaloyltrifluoroacetonato Dy0.01, La0.99
dimethylbenzylammonium tetrakis trifluoroacetylacetonato Dy0.01, La0.99
dimethylbenzylammonium tetrakis hexafluoroacetylacetonato Dy0.01, La0.99
dimethylbenzylammonium tetrakis 6,6,7,7,8,8,8-heptafluoro-2,2-dimethyloctanedionato Dy0.01, La0.99
dimethylbenzylammonium tetrakis 1-phenyl-1,3-butanedionato Dy0.01, La0.99
triallylammonium tetrakis acetylacetonato Dy0.01, La0.99
triallylammonium tetrakis dibenzoylmethanato Dy0.01, La0.99
triallylammonium tetrakis thenoyltrifluoroacetonato Dy0.01, La0.99
triallylammonium tetrakis 2,2,6,6-tetramethylheptanedionato Dy0.01, La0.99
triallylammonium tetrakis 3-methylpentane-2,4-dionato Dy0.01, La0.99
triallylammonium tetrakis 3-ethylpentane-2,4-dionato Dy0.01, La0.99
triallylammonium tetrakis pivaloyltrifluoroacetonato Dy0.01, La0.99
triallylammonium tetrakis trifluoroacetylacetonato Dy0.01, La0.99
triallylammonium tetrakis hexafluoroacetylacetonato Dy0.01, La0.99
triallylammonium tetrakis 6,6,7,7,8,8,8-heptafluoro-2,2-dimethyloctanedionato Dy0.01, La0.99
triallylammonium tetrakis 1-phenyl-1,3-butanedionato Dy0.01, La0.99
anilinium tetrakis acetylacetonato Dy0.01, La0.99
anilinium tetrakis dibenzoylmethanato Dy0.01, La0.99
anilinium tetrakis thenoyltrifluoroacetonato Dy0.01, La0.99
anilinium tetrakis 2,2,6,6-tetramethylheptanedionato Dy0.01, La0.99
anilinium tetrakis 3-methylpentane-2,4-dionato Dy0.01, La0.99
anilinium tetrakis 3-ethylpentane-2,4-dionato Dy0.01, La0.99
anilinium tetrakis pivaloyltrifluoroacetonato Dy0.01, La0.99
anilinium tetrakis trifluoroacetylacetonato Dy0.01, La0.99
anilinium tetrakis hexafluoroacetylacetonato Dy0.01, La0.99
anilinium tetrakis 6,6,7,7,8,8,8-heptafluoro-2,2-dimethyloctanedionato Dy0.01, La0.99
anilinium tetrakis 1-phenyl-1,3-butanedionato Dy0.01, La0.99
triethylammonium tetrakis acetylacetonato Sm0.5, Gd0.5
triethylammonium tetrakis dibenzoylmethanato Sm0.5, Gd0.5
triethylammonium tetrakis thenoyltrifluoroacetonato Sm0.5, Gd0.5
triethylammonium tetrakis 2,2,6,6-tetramethylheptanedionato Sm0.5, Gd0.5
triethylammonium tetrakis 3-methylpentane-2,4-dionato Sm0.5, Gd0.5
triethylammonium tetrakis 3-ethylpentane-2,4-dionato Sm0.5, Gd0.5
triethylammonium tetrakis pivaloyltrifluoroacetonato Sm0.5, Gd0.5
triethylammonium tetrakis trifluoroacetylacetonato Sm0.5, Gd0.5
triethylammonium tetrakis hexafluoroacetylacetonato Sm0.5, Gd0.5
triethylammonium tetrakis 6,6,7,7,8,8,8-heptafluoro-2,2-dimethyloctanedionato Sm0.5, Gd0.5
triethylammonium tetrakis 1-phenyl-1,3-butanedionato Sm0.5, Gd0.5
morpholinium tetrakis acetylacetonato Sm0.5, Gd0.5
morpholinium tetrakis dibenzoylmethanato Sm0.5, Gd0.5
morpholinium tetrakis thenoyltrifluoroacetonato Sm0.5, Gd0.5
morpholinium tetrakis 2,2,6,6-tetramethylheptanedionato Sm0.5, Gd0.5
morpholinium tetrakis 3-methylpentane-2,4-dionato Sm0.5, Gd0.5
morpholinium tetrakis 3-ethylpentane-2,4-dionato Sm0.5, Gd0.5
morpholinium tetrakis pivaloyltrifluoroacetonato Sm0.5, Gd0.5
morpholinium tetrakis trifluoroacetylacetonato Sm0.5, Gd0.5
morpholinium tetrakis hexafluoroacetylacetonato Sm0.5, Gd0.5
morpholinium tetrakis 6,6,7,7,8,8,8-heptafluoro-2,2-dimethyloctanedionato Sm0.5, Gd0.5
morpholinium tetrakis 1-phenyl-1,3-butanedionato Sm0.5, Gd0.5
dimethylbenzylammonium tetrakis acetylacetonato Sm0.5, Gd0.5
dimethylbenzylammonium tetrakis dibenzoylmethanato Sm0.5, Gd0.5
dimethylbenzylammonium tetrakis thenoyltrifluoroacetonato Sm0.5, Gd0.5
dimethylbenzylammonium tetrakis 2,2,6,6-tetramethylheptanedionato Sm0.5, Gd0.5
dimethylbenzylammonium tetrakis 3-methylpentane-2,4-dionato Sm0.5, Gd0.5
dimethylbenzylammonium tetrakis 3-ethylpentane-2,4-dionato Sm0.5, Gd0.5
dimethylbenzylammonium tetrakis pivaloyltrifluoroacetonato Sm0.5, Gd0.5
dimethylbenzylammonium tetrakis trifluoroacetylacetonato Sm0.5, Gd0.5 dimethylbenzylammonium tetrakis hexafluoroacetylacetonato Sm0.5, Gd0.5
dimethylbenzylammonium tetrakis 6,6,7,7,8,8,8-heptafluoro-2,2-dimethyloctanedionato Sm0.5, Gd0.5
dimethylbenzylammonium tetrakis 1-phenyl-1,3-butanedionato Sm0.5, Gd0.5
triallylammonium tetrakis acetylacetonato Sm0.5, Gd0.5
triallylammonium tetrakis dibenzoylmethanato Sm0.5, Gd0.5
triallylammonium tetrakis thenoyltrifluoroacetonato Sm0.5, Gd0.5
triallylammonium tetrakis 2,2,6,6-tetramethylheptanedionato Sm0.5, Gd0.5
triallylammonium tetrakis 3-methylpentane-2,4-dionato Sm0.5, Gd0.5
triallylammonium tetrakis 3-ethylpentane-2,4-dionato Sm0.5, Gd0.5
triallylammonium tetrakis pivaloyltrifluoroacetonato Sm0.5, Gd0.5
triallylammonium tetrakis trifluoroacetylacetonato Sm0.5, Gd0.5
triallylammonium tetrakis hexafluoroacetylacetonato Sm0.5, Gd0.5
triallylammonium tetrakis 6,6,7,7,8,8,8-heptafluoro-2,2-dimethyloctanedionato Sm0.5, Gd0.5
triallylammonium tetrakis 1-phenyl-1,3-butanedionato Sm0.5, Gd0.5
anilinium tetrakis acetylacetonato Sm0.5, Gd0.5
anilinium tetrakis dibenzoylmethanato Sm0.5, Gd0.5
anilinium tetrakis thenoyltrifluoroacetonato Sm0.5, Gd0.5
anilinium tetrakis 2,2,6,6-tetramethylheptanedionato Sm0.5, Gd0.5
anilinium tetrakis 3-methylpentane-2,4-dionato Sm0.5, Gd0.5
anilinium tetrakis 3-ethylpentane-2,4-dionato Sm0.5, Gd0.5
anilinium tetrakis pivaloyltrifluoroacetonato Sm0.5, Gd0.5
anilinium tetrakis trifluoroacetylacetonato Sm0.5, Gd0.5
anilinium tetrakis hexafluoroacetylacetonato Sm0.5, Gd0.5
anilinium tetrakis 6,6,7,7,8,8,8-heptafluoro-2,2-dimethyloctanedionato Sm0.5, Gd0.5
anilinium tetrakis 1-phenyl-1,3-butanedionato Sm0.5, Gd0.5
triethylammonium tetrakis acetylacetonato Sm0.2, Gd0.8
triethylammonium tetrakis dibenzoylmethanato Sm0.2, Gd0.8
triethylammonium tetrakis thenoyltrifluoroacetonato Sm0.2, Gd0.8
triethylammonium tetrakis 2,2,6,6-tetramethylheptanedionato Sm0.2, Gd0.8
triethylammonium tetrakis 3-methylpentane-2,4-dionato Sm0.2, Gd0.8
triethylammonium tetrakis 3-ethylpentane-2,4-dionato Sm0.2, Gd0.8
triethylammonium tetrakis pivaloyltrifluoroacetonato Sm0.2, Gd0.8
triethylammonium tetrakis trifluoroacetylacetonato Sm0.2, Gd0.8
triethylammonium tetrakis hexafluoroacetylacetonato Sm0.2, Gd0.8
triethylammonium tetrakis 6,6,7,7,8,8,8-heptafluoro-2,2-dimethyloctanedionato Sm0.2, Gd0.8
triethylammonium tetrakis 1-phenyl-1,3-butanedionato Sm0.2, Gd0.8
morpholinium tetrakis acetylacetonato Sm0.2, Gd0.8
morpholinium tetrakis dibenzoylmethanato Sm0.2, Gd0.8
morpholinium tetrakis thenoyltrifluoroacetonato Sm0.2, Gd0.8
morpholinium tetrakis 2,2,6,6-tetramethylheptanedionato Sm0.2, Gd0.8
morpholinium tetrakis 3-methylpentane-2,4-dionato Sm0.2, Gd0.8
morpholinium tetrakis 3-ethylpentane-2,4-dionato Sm0.2, Gd0.8
morpholinium tetrakis pivaloyltrifluoroacetonato Sm0.2, Gd0.8
morpholinium tetrakis trifluoroacetylacetonato Sm0.2, Gd0.8
morpholinium tetrakis hexafluoroacetylacetonato Sm0.2, Gd0.8
morpholinium tetrakis 6,6,7,7,8,8,8-heptafluoro-2,2-dimethyloctanedionato Sm0.2, Gd0.8
morpholinium tetrakis 1-phenyl-1,3-butanedionato Sm0.2, Gd0.8
dimethylbenzylammonium tetrakis acetylacetonato Sm0.2, Gd0.8
dimethylbenzylammonium tetrakis dibenzoylmethanato Sm0.2, Gd0.8
dimethylbenzylammonium tetrakis thenoyltrifluoroacetonato Sm0.2, Gd0.8
dimethylbenzylammonium tetrakis 2,2,6,6-tetramethylheptanedionato Sm0.2, Gd0.8
dimethylbenzylammonium tetrakis 3-methylpentane-2,4-dionato Sm0.2, Gd0.8
dimethylbenzylammonium tetrakis 3-ethylpentane-2,4-dionato Sm0.2, Gd0.8
dimethylbenzylammonium tetrakis pivaloyltrifluoroacetonato Sm0.2, Gd0.8
dimethylbenzylammonium tetrakis trifluoroacetylacetonato Sm0.2, Gd0.8
dimethylbenzylammonium tetrakis hexafluoroacetylacetonato Sm0.2, Gd0.8
dimethylbenzylammonium tetrakis 6,6,7,7,8,8,8-heptafluoro-2,2-dimethyloctanedionato Sm0.2, Gd0.8
dimethylbenzylammonium tetrakis 1-phenyl-1,3-butanedionato Sm0.2, Gd0.8
triallylammonium tetrakis acetylacetonato Sm0.2, Gd0.8
triallylammonium tetrakis dibenzoylmethanato Sm0.2, Gd0.8
triallylammonium tetrakis thenoyltrifluoroacetonato Sm0.2, Gd0.8
triallylammonium tetrakis 2,2,6,6-tetramethylheptanedionato Sm0.2, Gd0.8
triallylammonium tetrakis 3-methylpentane-2,4-dionato Sm0.2, Gd0.8
triallylammonium tetrakis 3-ethylpentane-2,4-dionato Sm0.2, Gd0.8
triallylammonium tetrakis pivaloyltrifluoroacetonato Sm0.2, Gd0.8
triallylammonium tetrakis trifluoroacetylacetonato Sm0.2, Gd0.8
triallylammonium tetrakis hexafluoroacetylacetonato Sm0.2, Gd0.8
triallylammonium tetrakis 6,6,7,7,8,8,8-heptafluoro-2,2-dimethyloctanedionato Sm0.2, Gd0.8
triallylammonium tetrakis 1-phenyl-1,3-butanedionato Sm0.2, Gd0.8
anilinium tetrakis acetylacetonato Sm0.2, Gd0.8
anilinium tetrakis dibenzoylmethanato Sm0.2, Gd0.8
anilinium tetrakis thenoyltrifluoroacetonato Sm0.2, Gd0.8
anilinium tetrakis 2,2,6,6-tetramethylheptanedionato Sm0.2, Gd0.8
anilinium tetrakis 3-methylpentane-2,4-dionato Sm0.2, Gd0.8
anilinium tetrakis 3-ethylpentane-2,4-dionato Sm0.2, Gd0.8 anilinium tetrakis pivaloyltrifluoroacetonato Sm0.2, Gd0.8
anilinium tetrakis trifluoroacetylacetonato Sm0.2, Gd0.8
anilinium tetrakis hexafluoroacetylacetonato Sm0.2, Gd0.8
anilinium tetrakis 6,6,7,7,8,8,8-heptafluoro-2,2-dimethyloctanedionato Sm0.2, Gd0.8
anilinium tetrakis 1-phenyl-1,3-butanedionato Sm0.2, Gd0.8
triethylammonium tetrakis acetylacetonato Sm0.1, Gd0.9
triethylammonium tetrakis dibenzoylmethanato Sm0.1, Gd0.9
triethylammonium tetrakis thenoyltrifluoroacetonato Sm0.1, Gd0.9
triethylammonium tetrakis 2,2,6,6-tetramethylheptanedionato Sm0.1, Gd0.9
triethylammonium tetrakis 3-methylpentane-2,4-dionato Sm0.1, Gd0.9
triethylammonium tetrakis 3-ethylpentane-2,4-dionato Sm0.1, Gd0.9
triethylammonium tetrakis pivaloyltrifluoroacetonato Sm0.1, Gd0.9
triethylammonium tetrakis trifluoroacetylacetonato Sm0.1, Gd0.9
triethylammonium tetrakis hexafluoroacetylacetonato Sm0.1, Gd0.9
triethylammonium tetrakis 6,6,7,7,8,8,8-heptafluoro-2,2-dimethyloctanedionato Sm0.1, Gd0.9
triethylammonium tetrakis 1-phenyl-1,3-butanedionato Sm0.1, Gd0.9
morpholinium tetrakis acetylacetonato Sm0.1, Gd0.9
morpholinium tetrakis dibenzoylmethanato Sm0.1, Gd0.9
morpholinium tetrakis thenoyltrifluoroacetonato Sm0.1, Gd0.9
morpholinium tetrakis 2,2,6,6-tetramethylheptanedionato Sm0.1, Gd0.9
morpholinium tetrakis 3-methylpentane-2,4-dionato Sm0.1, Gd0.9
morpholinium tetrakis 3-ethylpentane-2,4-dionato Sm0.1, Gd0.9
morpholinium tetrakis pivaloyltrifluoroacetonato Sm0.1, Gd0.9
morpholinium tetrakis trifluoroacetylacetonato Sm0.1, Gd0.9
morpholinium tetrakis hexafluoroacetylacetonato Sm0.1, Gd0.9
morpholinium tetrakis 6,6,7,7,8,8,8-heptafluoro-2,2-dimethyloctanedionato Sm0.1, Gd0.9
morpholinium tetrakis 1-phenyl-1,3-butanedionato Sm0.1, Gd0.9
dimethylbenzylammonium tetrakis acetylacetonato Sm0.1, Gd0.9
dimethylbenzylammonium tetrakis dibenzoylmethanato Sm0.1, Gd0.9
dimethylbenzylammonium tetrakis thenoyltrifluoroacetonato Sm0.1, Gd0.9
dimethylbenzylammonium tetrakis 2,2,6,6-tetramethylheptanedionato Sm0.1, Gd0.9
dimethylbenzylammonium tetrakis 3-methylpentane-2,4-dionato Sm0.1, Gd0.9
dimethylbenzylammonium tetrakis 3-ethylpentane-2,4-dionato Sm0.1, Gd0.9
dimethylbenzylammonium tetrakis pivaloyltrifluoroacetonato Sm0.1, Gd0.9
dimethylbenzylammonium tetrakis trifluoroacetylacetonato Sm0.1, Gd0.9
dimethylbenzylammonium tetrakis hexafluoroacetylacetonato Sm0.1, Gd0.9
dimethylbenzylammonium tetrakis 6,6,7,7,8,8,8-heptafluoro-2,2-dimethyloctanedionato Sm0.1, Gd0.9
dimethylbenzylammonium tetrakis 1-phenyl-1,3-butanedionato Sm0.1, Gd0.9
triallylammonium tetrakis acetylacetonato Sm0.1, Gd0.9
triallylammonium tetrakis dibenzoylmethanato Sm0.1, Gd0.9
triallylammonium tetrakis thenoyltrifluoroacetonato Sm0.1, Gd0.9
triallylammonium tetrakis 2,2,6,6-tetramethylheptanedionato Sm0.1, Gd0.9
triallylammonium tetrakis 3-methylpentane-2,4-dionato Sm0.1, Gd0.9
triallylammonium tetrakis 3-ethylpentane-2,4-dionato Sm0.1, Gd0.9
triallylammonium tetrakis pivaloyltrifluoroacetonato Sm0.1, Gd0.9
triallylammonium tetrakis trifluoroacetylacetonato Sm0.1, Gd0.9
triallylammonium tetrakis hexafluoroacetylacetonato Sm0.1, Gd0.9
triallylammonium tetrakis 6,6,7,7,8,8,8-heptafluoro-2,2-dimethyloctanedionato Sm0.1, Gd0.9
triallylammonium tetrakis 1-phenyl-1,3-butanedionato Sm0.1, Gd0.9
anilinium tetrakis acetylacetonato Sm0.1, Gd0.9
anilinium tetrakis dibenzoylmethanato Sm0.1, Gd0.9
anilinium tetrakis thenoyltrifluoroacetonato Sm0.1, Gd0.9
anilinium tetrakis 2,2,6,6-tetramethylheptanedionato Sm0.1, Gd0.9
anilinium tetrakis 3-methylpentane-2,4-dionato Sm0.1, Gd0.9
anilinium tetrakis 3-ethylpentane-2,4-dionato Sm0.1, Gd0.9
anilinium tetrakis pivaloyltrifluoroacetonato Sm0.1, Gd0.9
anilinium tetrakis trifluoroacetylacetonato Sm0.1, Gd0.9
anilinium tetrakis hexafluoroacetylacetonato Sm0.1, Gd0.9
anilinium tetrakis 6,6,7,7,8,8,8-heptafluoro-2,2-dimethyloctanedionato Sm0.1, Gd0.9
anilinium tetrakis 1-phenyl-1,3-butanedionato Sm0.1, Gd0.9
triethylammonium tetrakis acetylacetonato Sm0.01, Gd0.99
triethylammonium tetrakis dibenzoylmethanato Sm0.01, Gd0.99
triethylammonium tetrakis thenoyltrifluoroacetonato Sm0.01, Gd0.99
triethylammonium tetrakis 2,2,6,6-tetramethylheptanedionato Sm0.01, Gd0.99
triethylammonium tetrakis 3-methylpentane-2,4-dionato Sm0.01, Gd0.99
triethylammonium tetrakis 3-ethylpentane-2,4-dionato Sm0.01, Gd0.99
triethylammonium tetrakis pivaloyltrifluoroacetonato Sm0.01, Gd0.99
triethylammonium tetrakis trifluoroacetylacetonato Sm0.01, Gd0.99
triethylammonium tetrakis hexafluoroacetylacetonato Sm0.01, Gd0.99
triethylammonium tetrakis 6,6,7,7,8,8,8-heptafluoro-2,2-dimethyloctanedionato Sm0.01, Gd0.99
triethylammonium tetrakis 1-phenyl-1,3-butanedionato Sm0.01, Gd0.99
morpholinium tetrakis acetylacetonato Sm0.01, Gd0.99
morpholinium tetrakis dibenzoylmethanato Sm0.01, Gd0.99
morpholinium tetrakis thenoyltrifluoroacetonato Sm0.01, Gd0.99
morpholinium tetrakis 2,2,6,6-tetramethylheptanedionato Sm0.01, Gd0.99 morpholinium tetrakis 3-methylpentane-2,4-dionato Sm0.01, Gd0.99
morpholinium tetrakis 3-ethylpentane-2,4-dionato Sm0.01, Gd0.99
morpholinium tetrakis pivaloyltrifluoroacetonato Sm0.01, Gd0.99
morpholinium tetrakis trifluoroacetylacetonato Sm0.01, Gd0.99
morpholinium tetrakis hexafluoroacetylacetonato Sm0.01, Gd0.99
morpholinium tetrakis 6,6,7,7,8,8,8-heptafluoro-2,2-dimethyloctanedionato Sm0.01, Gd0.99
morpholinium tetrakis 1-phenyl-1,3-butanedionato Sm0.01, Gd0.99
dimethylbenzylammonium tetrakis acetylacetonato Sm0.01, Gd0.99
dimethylbenzylammonium tetrakis dibenzoylmethanato Sm0.01, Gd0.99
dimethylbenzylammonium tetrakis thenoyltrifluoroacetonato Sm0.01, Gd0.99
dimethylbenzylammonium tetrakis 2,2,6,6-tetramethylheptanedionato Sm0.01, Gd0.99
dimethylbenzylammonium tetrakis 3-methylpentane-2,4-dionato Sm0.01, Gd0.99
dimethylbenzylammonium tetrakis 3-ethylpentane-2,4-dionato Sm0.01, Gd0.99
dimethylbenzylammonium tetrakis pivaloyltrifluoroacetonato Sm0.01, Gd0.99
dimethylbenzylammonium tetrakis trifluoroacetylacetonato Sm0.01, Gd0.99
dimethylbenzylammonium tetrakis hexafluoroacetylacetonato Sm0.01, Gd0.99
dimethylbenzylammonium tetrakis 6,6,7,7,8,8,8-heptafluoro-2,2-dimethyloctanedionato Sm0.01, Gd0.99
dimethylbenzylammonium tetrakis 1-phenyl-1,3-butanedionato Sm0.01, Gd0.99
triallylammonium tetrakis acetylacetonato Sm0.01, Gd0.99
triallylammonium tetrakis dibenzoylmethanato Sm0.01, Gd0.99
triallylammonium tetrakis thenoyltrifluoroacetonato Sm0.01, Gd0.99
triallylammonium tetrakis 2,2,6,6-tetramethylheptanedionato Sm0.01, Gd0.99
triallylammonium tetrakis 3-methylpentane-2,4-dionato Sm0.01, Gd0.99
triallylammonium tetrakis 3-ethylpentane-2,4-dionato Sm0.01, Gd0.99
triallylammonium tetrakis pivaloyltrifluoroacetonato Sm0.01, Gd0.99
triallylammonium tetrakis trifluoroacetylacetonato Sm0.01, Gd0.99
triallylammonium tetrakis hexafluoroacetylacetonato Sm0.01, Gd0.99
triallylammonium tetrakis 6,6,7,7,8,8,8-heptafluoro-2,2-dimethyloctanedionato Sm0.01, Gd0.99
triallylammonium tetrakis 1-phenyl-1,3-butanedionato Sm0.01, Gd0.99
anilinium tetrakis acetylacetonato Sm0.01, Gd0.99
anilinium tetrakis dibenzoylmethanato Sm0.01, Gd0.99
anilinium tetrakis thenoyltrifluoroacetonato Sm0.01, Gd0.99
anilinium tetrakis 2,2,6,6-tetramethylheptanedionato Sm0.01, Gd0.99
anilinium tetrakis 3-methylpentane-2,4-dionato Sm0.01, Gd0.99
anilinium tetrakis 3-ethylpentane-2,4-dionato Sm0.01, Gd0.99
anilinium tetrakis pivaloyltrifluoroacetonato Sm0.01, Gd0.99
anilinium tetrakis trifluoroacetylacetonato Sm0.01, Gd0.99
anilinium tetrakis hexafluoroacetylacetonato Sm0.01, Gd0.99
anilinium tetrakis 6,6,7,7,8,8,8-heptafluoro-2,2-dimethyloctanedionato Sm0.01, Gd0.99
anilinium tetrakis 1-phenyl-1,3-butanedionato Sm0.01, Gd0.99
triethylammonium tetrakis acetylacetonato Dy0.5, Gd0.5
triethylammonium tetrakis dibenzoylmethanato Dy0.5, Gd0.5
triethylammonium tetrakis thenoyltrifluoroacetonato Dy0.5, Gd0.5
triethylammonium tetrakis 2,2,6,6-tetramethylheptanedionato Dy0.5, Gd0.5
triethylammonium tetrakis 3-methylpentane-2,4-dionato Dy0.5, Gd0.5
triethylammonium tetrakis 3-ethylpentane-2,4-dionato Dy0.5, Gd0.5
triethylammonium tetrakis pivaloyltrifluoroacetonato Dy0.5, Gd0.5
triethylammonium tetrakis trifluoroacetylacetonato Dy0.5, Gd0.5
triethylammonium tetrakis hexafluoroacetylacetonato Dy0.5, Gd0.5
triethylammonium tetrakis 6,6,7,7,8,8,8-heptafluoro-2,2-dimethyloctanedionato Dy0.5, Gd0.5
triethylammonium tetrakis 1-phenyl-1,3-butanedionato Dy0.5, Gd0.5
morpholinium tetrakis acetylacetonato Dy0.5, Gd0.5
morpholinium tetrakis dibenzoylmethanato Dy0.5, Gd0.5
morpholinium tetrakis thenoyltrifluoroacetonato Dy0.5, Gd0.5
morpholinium tetrakis 2,2,6,6-tetramethylheptanedionato Dy0.5, Gd0.5
morpholinium tetrakis 3-methylpentane-2,4-dionato Dy0.5, Gd0.5
morpholinium tetrakis 3-ethylpentane-2,4-dionato Dy0.5, Gd0.5
morpholinium tetrakis pivaloyltrifluoroacetonato Dy0.5, Gd0.5
morpholinium tetrakis trifluoroacetylacetonato Dy0.5, Gd0.5
morpholinium tetrakis hexafluoroacetylacetonato Dy0.5, Gd0.5
morpholinium tetrakis 6,6,7,7,8,8,8-heptafluoro-2,2-dimethyloctanedionato Dy0.5, Gd0.5
morpholinium tetrakis 1-phenyl-1,3-butanedionato Dy0.5, Gd0.5
dimethylbenzylammonium tetrakis acetylacetonato Dy0.5, Gd0.5
dimethylbenzylammonium tetrakis dibenzoylmethanato Dy0.5, Gd0.5
dimethylbenzylammonium tetrakis thenoyltrifluoroacetonato Dy0.5, Gd0.5
dimethylbenzylammonium tetrakis 2,2,6,6-tetramethylheptanedionato Dy0.5, Gd0.5
dimethylbenzylammonium tetrakis 3-methylpentane-2,4-dionato Dy0.5, Gd0.5
dimethylbenzylammonium tetrakis 3-ethylpentane-2,4-dionato Dy0.5, Gd0.5
dimethylbenzylammonium tetrakis pivaloyltrifluoroacetonato Dy0.5, Gd0.5
dimethylbenzylammonium tetrakis trifluoroacetylacetonato Dy0.5, Gd0.5 dimethylbenzylammonium tetrakis hexafluoroacetylacetonato Dy0.5, Gd0.5
dimethylbenzylammonium tetrakis 6,6,7,7,8,8,8-heptafluoro-2,2-dimethyloctanedionato Dy0.5, Gd0.5
dimethylbenzylammonium tetrakis 1-phenyl-1,3-butanedionato Dy0.5, Gd0.5
triallylammonium tetrakis acetylacetonato Dy0.5, Gd0.5
triallylammonium tetrakis dibenzoylmethanato Dy0.5, Gd0.5
triallylammonium tetrakis thenoyltrifluoroacetonato Dy0.5, Gd0.5
triallylammonium tetrakis 2,2,6,6-tetramethylheptanedionato Dy0.5, Gd0.5
triallylammonium tetrakis 3-methylpentane-2,4-dionato Dy0.5, Gd0.5
triallylammonium tetrakis 3-ethylpentane-2,4-dionato Dy0.5, Gd0.5
triallylammonium tetrakis pivaloyltrifluoroacetonato Dy0.5, Gd0.5
triallylammonium tetrakis trifluoroacetylacetonato Dy0.5, Gd0.5
triallylammonium tetrakis hexafluoroacetylacetonato Dy0.5, Gd0.5
triallylammonium tetrakis 6,6,7,7,8,8,8-heptafluoro-2,2-dimethyloctanedionato Dy0.5, Gd0.5
triallylammonium tetrakis 1-phenyl-1,3-butanedionato Dy0.5, Gd0.5
anilinium tetrakis acetylacetonato Dy0.5, Gd0.5
anilinium tetrakis dibenzoylmethanato Dy0.5, Gd0.5
anilinium tetrakis thenoyltrifluoroacetonato Dy0.5, Gd0.5
anilinium tetrakis 2,2,6,6-tetramethylheptanedionato Dy0.5, Gd0.5
anilinium tetrakis 3-methylpentane-2,4-dionato Dy0.5, Gd0.5
anilinium tetrakis 3-ethylpentane-2,4-dionato Dy0.5, Gd0.5
anilinium tetrakis pivaloyltrifluoroacetonato Dy0.5, Gd0.5
anilinium tetrakis trifluoroacetylacetonato Dy0.5, Gd0.5
anilinium tetrakis hexafluoroacetylacetonato Dy0.5, Gd0.5
anilinium tetrakis 6,6,7,7,8,8,8-heptafluoro-2,2-dimethyloctanedionato Dy0.5, Gd0.5
anilinium tetrakis 1-phenyl-1,3-butanedionato Dy0.5, Gd0.5
triethylammonium tetrakis acetylacetonato Dy0.2, Gd0.8
triethylammonium tetrakis dibenzoylmethanato Dy0.2, Gd0.8
triethylammonium tetrakis thenoyltrifluoroacetonato Dy0.2, Gd0.8
triethylammonium tetrakis 2,2,6,6-tetramethylheptanedionato Dy0.2, Gd0.8
triethylammonium tetrakis 3-methylpentane-2,4-dionato Dy0.2, Gd0.8
triethylammonium tetrakis 3-ethylpentane-2,4-dionato Dy0.2, Gd0.8
triethylammonium tetrakis pivaloyltrifluoroacetonato Dy0.2, Gd0.8
triethylammonium tetrakis trifluoroacetylacetonato Dy0.2, Gd0.8
triethylammonium tetrakis hexafluoroacetylacetonato Dy0.2, Gd0.8
triethylammonium tetrakis 6,6,7,7,8,8,8-heptafluoro-2,2-dimethyloctanedionato Dy0.2, Gd0.8
triethylammonium tetrakis 1-phenyl-1,3-butanedionato Dy0.2, Gd0.8
morpholinium tetrakis acetylacetonato Dy0.2, Gd0.8
morpholinium tetrakis dibenzoylmethanato Dy0.2, Gd0.8
morpholinium tetrakis thenoyltrifluoroacetonato Dy0.2, Gd0.8
morpholinium tetrakis 2,2,6,6-tetramethylheptanedionato Dy0.2, Gd0.8
morpholinium tetrakis 3-methylpentane-2,4-dionato Dy0.2, Gd0.8
morpholinium tetrakis 3-ethylpentane-2,4-dionato Dy0.2, Gd0.8
morpholinium tetrakis pivaloyltrifluoroacetonato Dy0.2, Gd0.8
morpholinium tetrakis trifluoroacetylacetonato Dy0.2, Gd0.8
morpholinium tetrakis hexafluoroacetylacetonato Dy0.2, Gd0.8
morpholinium tetrakis 6,6,7,7,8,8,8-heptafluoro-2,2-dimethyloctanedionato Dy0.2, Gd0.8
morpholinium tetrakis 1-phenyl-1,3-butanedionato Dy0.2, Gd0.8
dimethylbenzylammonium tetrakis acetylacetonato Dy0.2, Gd0.8
dimethylbenzylammonium tetrakis dibenzoylmethanato Dy0.2, Gd0.8
dimethylbenzylammonium tetrakis thenoyltrifluoroacetonato Dy0.2, Gd0.8
dimethylbenzylammonium tetrakis 2,2,6,6-tetramethylheptanedionato Dy0.2, Gd0.8
dimethylbenzylammonium tetrakis 3-methylpentane-2,4-dionato Dy0.2, Gd0.8
dimethylbenzylammonium tetrakis 3-ethylpentane-2,4-dionato Dy0.2, Gd0.8
dimethylbenzylammonium tetrakis pivaloyltrifluoroacetonato Dy0.2, Gd0.8
dimethylbenzylammonium tetrakis trifluoroacetylacetonato Dy0.2, Gd0.8
dimethylbenzylammonium tetrakis hexafluoroacetylacetonato Dy0.2, Gd0.8
dimethylbenzylammonium tetrakis 6,6,7,7,8,8,8-heptafluoro-2,2-dimethyloctanedionato Dy0.2, Gd0.8
dimethylbenzylammonium tetrakis 1-phenyl-1,3-butanedionato Dy0.2, Gd0.8
triallylammonium tetrakis acetylacetonato Dy0.2, Gd0.8
triallylammonium tetrakis dibenzoylmethanato Dy0.2, Gd0.8
triallylammonium tetrakis thenoyltrifluoroacetonato Dy0.2, Gd0.8
triallylammonium tetrakis 2,2,6,6-tetramethylheptanedionato Dy0.2, Gd0.8
triallylammonium tetrakis 3-methylpentane-2,4-dionato Dy0.2, Gd0.8
triallylammonium tetrakis 3-ethylpentane-2,4-dionato Dy0.2, Gd0.8
triallylammonium tetrakis pivaloyltrifluoroacetonato Dy0.2, Gd0.8
triallylammonium tetrakis trifluoroacetylacetonato Dy0.2, Gd0.8
triallylammonium tetrakis hexafluoroacetylacetonato Dy0.2, Gd0.8
triallylammonium tetrakis 6,6,7,7,8,8,8-heptafluoro-2,2-dimethyloctanedionato Dy0.2, Gd0.8
triallylammonium tetrakis 1-phenyl-1,3-butanedionato Dy0.2, Gd0.8
anilinium tetrakis acetylacetonato Dy0.2, Gd0.8
anilinium tetrakis dibenzoylmethanato Dy0.2, Gd0.8
anilinium tetrakis thenoyltrifluoroacetonato Dy0.2, Gd0.8
anilinium tetrakis 2,2,6,6-tetramethylheptanedionato Dy0.2, Gd0.8
anilinium tetrakis 3-methylpentane-2,4-dionato Dy0.2, Gd0.8
anilinium tetrakis 3-ethylpentane-2,4-dionato Dy0.2, Gd0.8 anilinium tetrakis pivaloyltrifluoroacetonato Dy0.2, Gd0.8
anilinium tetrakis trifluoroacetylacetonato Dy0.2, Gd0.8
anilinium tetrakis hexafluoroacetylacetonato Dy0.2, Gd0.8
anilinium tetrakis 6,6,7,7,8,8,8-heptafluoro-2,2-dimethyloctanedionato Dy0.2, Gd0.8
anilinium tetrakis 1-phenyl-1,3-butanedionato Dy0.2, Gd0.8
triethylammonium tetrakis acetylacetonato Dy0.1, Gd0.9
triethylammonium tetrakis dibenzoylmethanato Dy0.1, Gd0.9
triethylammonium tetrakis thenoyltrifluoroacetonato Dy0.1, Gd0.9
triethylammonium tetrakis 2,2,6,6-tetramethylheptanedionato Dy0.1, Gd0.9
triethylammonium tetrakis 3-methylpentane-2,4-dionato Dy0.1, Gd0.9
triethylammonium tetrakis 3-ethylpentane-2,4-dionato Dy0.1, Gd0.9
triethylammonium tetrakis pivaloyltrifluoroacetonato Dy0.1, Gd0.9
triethylammonium tetrakis trifluoroacetylacetonato Dy0.1, Gd0.9
triethylammonium tetrakis hexafluoroacetylacetonato Dy0.1, Gd0.9
triethylammonium tetrakis 6,6,7,7,8,8,8-heptafluoro-2,2-dimethyloctanedionato Dy0.1, Gd0.9
triethylammonium tetrakis 1-phenyl-1,3-butanedionato Dy0.1, Gd0.9
morpholinium tetrakis acetylacetonato Dy0.1, Gd0.9
morpholinium tetrakis dibenzoylmethanato Dy0.1, Gd0.9
morpholinium tetrakis thenoyltrifluoroacetonato Dy0.1, Gd0.9
morpholinium tetrakis 2,2,6,6-tetramethylheptanedionato Dy0.1, Gd0.9
morpholinium tetrakis 3-methylpentane-2,4-dionato Dy0.1, Gd0.9
morpholinium tetrakis 3-ethylpentane-2,4-dionato Dy0.1, Gd0.9
morpholinium tetrakis pivaloyltrifluoroacetonato Dy0.1, Gd0.9
morpholinium tetrakis trifluoroacetylacetonato Dy0.1, Gd0.9
morpholinium tetrakis hexafluoroacetylacetonato Dy0.1, Gd0.9
morpholinium tetrakis 6,6,7,7,8,8,8-heptafluoro-2,2-dimethyloctanedionato Dy0.1, Gd0.9
morpholinium tetrakis 1-phenyl-1,3-butanedionato Dy0.1, Gd0.9
dimethylbenzylammonium tetrakis acetylacetonato Dy0.1, Gd0.9
dimethylbenzylammonium tetrakis dibenzoylmethanato Dy0.1, Gd0.9
dimethylbenzylammonium tetrakis thenoyltrifluoroacetonato Dy0.1, Gd0.9
dimethylbenzylammonium tetrakis 2,2,6,6-tetramethylheptanedionato Dy0.1, Gd0.9
dimethylbenzylammonium tetrakis 3-methylpentane-2,4-dionato Dy0.1, Gd0.9
dimethylbenzylammonium tetrakis 3-ethylpentane-2,4-dionato Dy0.1, Gd0.9
dimethylbenzylammonium tetrakis pivaloyltrifluoroacetonato Dy0.1, Gd0.9
dimethylbenzylammonium tetrakis trifluoroacetylacetonato Dy0.1, Gd0.9
dimethylbenzylammonium tetrakis hexafluoroacetylacetonato Dy0.1, Gd0.9
dimethylbenzylammonium tetrakis 6,6,7,7,8,8,8-heptafluoro-2,2-dimethyloctanedionato Dy0.1, Gd0.9
dimethylbenzylammonium tetrakis 1-phenyl-1,3-butanedionato Dy0.1, Gd0.9
triallylammonium tetrakis acetylacetonato Dy0.1, Gd0.9
triallylammonium tetrakis dibenzoylmethanato Dy0.1, Gd0.9
triallylammonium tetrakis thenoyltrifluoroacetonato Dy0.1, Gd0.9
triallylammonium tetrakis 2,2,6,6-tetramethylheptanedionato Dy0.1, Gd0.9
triallylammonium tetrakis 3-methylpentane-2,4-dionato Dy0.1, Gd0.9
triallylammonium tetrakis 3-ethylpentane-2,4-dionato Dy0.1, Gd0.9
triallylammonium tetrakis pivaloyltrifluoroacetonato Dy0.1, Gd0.9
triallylammonium tetrakis trifluoroacetylacetonato Dy0.1, Gd0.9
triallylammonium tetrakis hexafluoroacetylacetonato Dy0.1, Gd0.9
triallylammonium tetrakis 6,6,7,7,8,8,8-heptafluoro-2,2-dimethyloctanedionato Dy0.1, Gd0.9
triallylammonium tetrakis 1-phenyl-1,3-butanedionato Dy0.1, Gd0.9
anilinium tetrakis acetylacetonato Dy0.1, Gd0.9
anilinium tetrakis dibenzoylmethanato Dy0.1, Gd0.9
anilinium tetrakis thenoyltrifluoroacetonato Dy0.1, Gd0.9
anilinium tetrakis 2,2,6,6-tetramethylheptanedionato Dy0.1, Gd0.9
anilinium tetrakis 3-methylpentane-2,4-dionato Dy0.1, Gd0.9
anilinium tetrakis 3-ethylpentane-2,4-dionato Dy0.1, Gd0.9
anilinium tetrakis pivaloyltrifluoroacetonato Dy0.1, Gd0.9
anilinium tetrakis trifluoroacetylacetonato Dy0.1, Gd0.9
anilinium tetrakis hexafluoroacetylacetonato Dy0.1, Gd0.9
anilinium tetrakis 6,6,7,7,8,8,8-heptafluoro-2,2-dimethyloctanedionato Dy0.1, Gd0.9
anilinium tetrakis 1-phenyl-1,3-butanedionato Dy0.1, Gd0.9
triethylammonium tetrakis acetylacetonato Dy0.01, Gd0.99
triethylammonium tetrakis dibenzoylmethanato Dy0.01, Gd0.99
triethylammonium tetrakis thenoyltrifluoroacetonato Dy0.01, Gd0.99
triethylammonium tetrakis 2,2,6,6-tetramethylheptanedionato Dy0.01, Gd0.99
triethylammonium tetrakis 3-methylpentane-2,4-dionato Dy0.01, Gd0.99
triethylammonium tetrakis 3-ethylpentane-2,4-dionato Dy0.01, Gd0.99
triethylammonium tetrakis pivaloyltrifluoroacetonato Dy0.01, Gd0.99
triethylammonium tetrakis trifluoroacetylacetonato Dy0.01, Gd0.99
triethylammonium tetrakis hexafluoroacetylacetonato Dy0.01, Gd0.99
triethylammonium tetrakis 6,6,7,7,8,8,8-heptafluoro-2,2-dimethyloctanedionato Dy0.01, Gd0.99
triethylammonium tetrakis 1-phenyl-1,3-butanedionato Dy0.01, Gd0.99
morpholinium tetrakis acetylacetonato Dy0.01, Gd0.99
morpholinium tetrakis dibenzoylmethanato Dy0.01, Gd0.99
morpholinium tetrakis thenoyltrifluoroacetonato Dy0.01, Gd0.99
morpholinium tetrakis 2,2,6,6-tetramethylheptanedionato Dy0.01, Gd0.99
morpholinium tetrakis 3-methylpentane-2,4-dionato Dy0.01, Gd0.99 morpholinium tetrakis 3-ethylpentane-2,4-dionato Dy0.01, Gd0.99
morpholinium tetrakis pivaloyltrifluoroacetonato Dy0.01, Gd0.99
morpholinium tetrakis trifluoroacetylacetonato Dy0.01, Gd0.99
morpholinium tetrakis hexafluoroacetylacetonato Dy0.01, Gd0.99
morpholinium tetrakis 6,6,7,7,8,8,8-heptafluoro-2,2-dimethyloctanedionato Dy0.01, Gd0.99
morpholinium tetrakis 1-phenyl-1,3-butanedionato Dy0.01, Gd0.99
dimethylbenzylammonium tetrakis acetylacetonato Dy0.01, Gd0.99
dimethylbenzylammonium tetrakis dibenzoylmethanato Dy0.01, Gd0.99
dimethylbenzylammonium tetrakis thenoyltrifluoroacetonato Dy0.01, Gd0.99
dimethylbenzylammonium tetrakis 2,2,6,6-tetramethylheptanedionato Dy0.01, Gd0.99
dimethylbenzylammonium tetrakis 3-methylpentane-2,4-dionato Dy0.01, Gd0.99
dimethylbenzylammonium tetrakis 3-ethylpentane-2,4-dionato Dy0.01, Gd0.99
dimethylbenzylammonium tetrakis pivaloyltrifluoroacetonato Dy0.01, Gd0.99
dimethylbenzylammonium tetrakis trifluoroacetylacetonato Dy0.01, Gd0.99
dimethylbenzylammonium tetrakis hexafluoroacetylacetonato Dy0.01, Gd0.99
dimethylbenzylammonium tetrakis 6,6,7,7,8,8,8-heptafluoro-2,2-dimethyloctanedionato Dy0.01, Gd0.99
dimethylbenzylammonium tetrakis 1-phenyl-1,3-butanedionato Dy0.01, Gd0.99
triallylammonium tetrakis acetylacetonato Dy0.01, Gd0.99
triallylammonium tetrakis dibenzoylmethanato Dy0.01, Gd0.99
triallylammonium tetrakis thenoyltrifluoroacetonato Dy0.01, Gd0.99
triallylammonium tetrakis 2,2,6,6-tetramethylheptanedionato Dy0.01, Gd0.99
triallylammonium tetrakis 3-methylpentane-2,4-dionato Dy0.01, Gd0.99
triallylammonium tetrakis 3-ethylpentane-2,4-dionato Dy0.01, Gd0.99
triallylammonium tetrakis pivaloyltrifluoroacetonato Dy0.01, Gd0.99
triallylammonium tetrakis trifluoroacetylacetonato Dy0.01, Gd0.99
triallylammonium tetrakis hexafluoroacetylacetonato Dy0.01, Gd0.99
triallylammonium tetrakis 6,6,7,7,8,8,8-heptafluoro-2,2-dimethyloctanedionato Dy0.01, Gd0.99
triallylammonium tetrakis 1-phenyl-1,3-butanedionato Dy0.01, Gd0.99
anilinium tetrakis acetylacetonato Dy0.01, Gd0.99
anilinium tetrakis dibenzoylmethanato Dy0.01, Gd0.99
anilinium tetrakis thenoyltrifluoroacetonato Dy0.01, Gd0.99
anilinium tetrakis 2,2,6,6-tetramethylheptanedionato Dy0.01, Gd0.99
anilinium tetrakis 3-methylpentane-2,4-dionato Dy0.01, Gd0.99
anilinium tetrakis 3-ethylpentane-2,4-dionato Dy0.01, Gd0.99
anilinium tetrakis pivaloyltrifluoroacetonato Dy0.01, Gd0.99
anilinium tetrakis trifluoroacetylacetonato Dy0.01, Gd0.99
anilinium tetrakis hexafluoroacetylacetonato Dy0.01, Gd0.99
anilinium tetrakis 6,6,7,7,8,8,8-heptafluoro-2,2-dimethyloctanedionato Dy0.01, Gd0.99
anilinium tetrakis 1-phenyl-1,3-butanedionato Dy0.01, Gd0.99
triethylammonium tetrakis acetylacetonato Dy0.5, Gd0.5
triethylammonium tetrakis dibenzoylmethanato Dy0.5, Gd0.5
triethylammonium tetrakis thenoyltrifluoroacetonato Dy0.5, Gd0.5
triethylammonium tetrakis 2,2,6,6-tetramethylheptanedionato Dy0.5, Gd0.5
triethylammonium tetrakis 3-methylpentane-2,4-dionato Dy0.5, Gd0.5
triethylammonium tetrakis 3-ethylpentane-2,4-dionato Dy0.5, Gd0.5
triethylammonium tetrakis pivaloyltrifluoroacetonato Dy0.5, Gd0.5
triethylammonium tetrakis trifluoroacetylacetonato Dy0.5, Gd0.5
triethylammonium tetrakis hexafluoroacetylacetonato Dy0.5, Gd0.5
triethylammonium tetrakis 6,6,7,7,8,8,8-heptafluoro-2,2-dimethyloctanedionato Dy0.5, Gd0.5
triethylammonium tetrakis 1-phenyl-1,3-butanedionato Dy0.5, Gd0.5
morpholinium tetrakis acetylacetonato Dy0.5, Gd0.5
morpholinium tetrakis dibenzoylmethanato Dy0.5, Gd0.5
morpholinium tetrakis thenoyltrifluoroacetonato Dy0.5, Gd0.5
morpholinium tetrakis 2,2,6,6-tetramethylheptanedionato Dy0.5, Gd0.5
morpholinium tetrakis 3-methylpentane-2,4-dionato Dy0.5, Gd0.5
morpholinium tetrakis 3-ethylpentane-2,4-dionato Dy0.5, Gd0.5
morpholinium tetrakis pivaloyltrifluoroacetonato Dy0.5, Gd0.5
morpholinium tetrakis trifluoroacetylacetonato Dy0.5, Gd0.5
morpholinium tetrakis hexafluoroacetylacetonato Dy0.5, Gd0.5
morpholinium tetrakis 6,6,7,7,8,8,8-heptafluoro-2,2-dimethyloctanedionato Dy0.5, Gd0.5
morpholinium tetrakis 1-phenyl-1,3-butanedionato Dy0.5, Gd0.5
dimethylbenzylammonium tetrakis acetylacetonato Dy0.5, Gd0.5
dimethylbenzylammonium tetrakis dibenzoylmethanato Dy0.5, Gd0.5
dimethylbenzylammonium tetrakis thenoyltrifluoroacetonato Dy0.5, Gd0.5
dimethylbenzylammonium tetrakis 2,2,6,6-tetramethylheptanedionato Dy0.5, Gd0.5
dimethylbenzylammonium tetrakis 3-methylpentane-2,4-dionato Dy0.5, Gd0.5
dimethylbenzylammonium tetrakis 3-ethylpentane-2,4-dionato Dy0.5, Gd0.5
dimethylbenzylammonium tetrakis pivaloyltrifluoroacetonato Dy0.5, Gd0.5
dimethylbenzylammonium tetrakis trifluoroacetylacetonato Dy0.5, Gd0.5
dimethylbenzylammonium tetrakis hexafluoroacetylacetonato Dy0.5, Gd0.5
dimethylbenzylammonium tetrakis 6,6,7,7,8,8,8-heptafluoro-2,2-dimethyloctanedionato Dy0.5, Gd0.5 dimethylbenzylammonium tetrakis 1-phenyl-1,3-butanedionato Dy0.5, Gd0.5
triallylammonium tetrakis acetylacetonato Dy0.5, Gd0.5
triallylammonium tetrakis dibenzoylmethanato Dy0.5, Gd0.5
triallylammonium tetrakis thenoyltrifluoroacetonato Dy0.5, Gd0.5
triallylammonium tetrakis 2,2,6,6-tetramethylheptanedionato Dy0.5, Gd0.5
triallylammonium tetrakis 3-methylpentane-2,4-dionato Dy0.5, Gd0.5
triallylammonium tetrakis 3-ethylpentane-2,4-dionato Dy0.5, Gd0.5
triallylammonium tetrakis pivaloyltrifluoroacetonato Dy0.5, Gd0.5
triallylammonium tetrakis trifluoroacetylacetonato Dy0.5, Gd0.5
triallylammonium tetrakis hexafluoroacetylacetonato Dy0.5, Gd0.5
triallylammonium tetrakis 6,6,7,7,8,8,8-heptafluoro-2,2-dimethyloctanedionato Dy0.5, Gd0.5
triallylammonium tetrakis 1-phenyl-1,3-butanedionato Dy0.5, Gd0.5
anilinium tetrakis acetylacetonato Dy0.5, Gd0.5
anilinium tetrakis dibenzoylmethanato Dy0.5, Gd0.5
anilinium tetrakis thenoyltrifluoroacetonato Dy0.5, Gd0.5
anilinium tetrakis 2,2,6,6-tetramethylheptanedionato Dy0.5, Gd0.5
anilinium tetrakis 3-methylpentane-2,4-dionato Dy0.5, Gd0.5
anilinium tetrakis 3-ethylpentane-2,4-dionato Dy0.5, Gd0.5
anilinium tetrakis pivaloyltrifluoroacetonato Dy0.5, Gd0.5
anilinium tetrakis trifluoroacetylacetonato Dy0.5, Gd0.5
anilinium tetrakis hexafluoroacetylacetonato Dy0.5, Gd0.5
anilinium tetrakis 6,6,7,7,8,8,8-heptafluoro-2,2-dimethyloctanedionato Dy0.5, Gd0.5
anilinium tetrakis 1-phenyl-1,3-butanedionato Dy0.5, Gd0.5
triethylammonium tetrakis acetylacetonato Dy0.2, Gd0.8
triethylammonium tetrakis dibenzoylmethanato Dy0.2, Gd0.8
triethylammonium tetrakis thenoyltrifluoroacetonato Dy0.2, Gd0.8
triethylammonium tetrakis 2,2,6,6-tetramethylheptanedionato Dy0.2, Gd0.8
triethylammonium tetrakis 3-methylpentane-2,4-dionato Dy0.2, Gd0.8
triethylammonium tetrakis 3-ethylpentane-2,4-dionato Dy0.2, Gd0.8
triethylammonium tetrakis pivaloyltrifluoroacetonato Dy0.2, Gd0.8
triethylammonium tetrakis trifluoroacetylacetonato Dy0.2, Gd0.8
triethylammonium tetrakis hexafluoroacetylacetonato Dy0.2, Gd0.8
triethylammonium tetrakis 6,6,7,7,8,8,8-heptafluoro-2,2-dimethyloctanedionato Dy0.2, Gd0.8
triethylammonium tetrakis 1-phenyl-1,3-butanedionato Dy0.2, Gd0.8
morpholinium tetrakis acetylacetonato Dy0.2, Gd0.8
morpholinium tetrakis dibenzoylmethanato Dy0.2, Gd0.8
morpholinium tetrakis thenoyltrifluoroacetonato Dy0.2, Gd0.8
morpholinium tetrakis 2,2,6,6-tetramethylheptanedionato Dy0.2, Gd0.8
morpholinium tetrakis 3-methylpentane-2,4-dionato Dy0.2, Gd0.8
morpholinium tetrakis 3-ethylpentane-2,4-dionato Dy0.2, Gd0.8
morpholinium tetrakis pivaloyltrifluoroacetonato Dy0.2, Gd0.8
morpholinium tetrakis trifluoroacetylacetonato Dy0.2, Gd0.8
morpholinium tetrakis hexafluoroacetylacetonato Dy0.2, Gd0.8
morpholinium tetrakis 6,6,7,7,8,8,8-heptafluoro-2,2-dimethyloctanedionato Dy0.2, Gd0.8
morpholinium tetrakis 1-phenyl-1,3-butanedionato Dy0.2, Gd0.8
dimethylbenzylammonium tetrakis acetylacetonato Dy0.2, Gd0.8
dimethylbenzylammonium tetrakis dibenzoylmethanato Dy0.2, Gd0.8
dimethylbenzylammonium tetrakis thenoyltrifluoroacetonato Dy0.2, Gd0.8
dimethylbenzylammonium tetrakis 2,2,6,6-tetramethylheptanedionato Dy0.2, Gd0.8
dimethylbenzylammonium tetrakis 3-methylpentane-2,4-dionato Dy0.2, Gd0.8
dimethylbenzylammonium tetrakis 3-ethylpentane-2,4-dionato Dy0.2, Gd0.8
dimethylbenzylammonium tetrakis pivaloyltrifluoroacetonato Dy0.2, Gd0.8
dimethylbenzylammonium tetrakis trifluoroacetylacetonato Dy0.2, Gd0.8
dimethylbenzylammonium tetrakis hexafluoroacetylacetonato Dy0.2, Gd0.8
dimethylbenzylammonium tetrakis 6,6,7,7,8,8,8-heptafluoro-2,2-dimethyloctanedionato Dy0.2, Gd0.8
dimethylbenzylammonium tetrakis 1-phenyl-1,3-butanedionato Dy0.2, Gd0.8
triallylammonium tetrakis acetylacetonato Dy0.2, Gd0.8
triallylammonium tetrakis dibenzoylmethanato Dy0.2, Gd0.8
triallylammonium tetrakis thenoyltrifluoroacetonato Dy0.2, Gd0.8
triallylammonium tetrakis 2,2,6,6-tetramethylheptanedionato Dy0.2, Gd0.8
triallylammonium tetrakis 3-methylpentane-2,4-dionato Dy0.2, Gd0.8
triallylammonium tetrakis 3-ethylpentane-2,4-dionato Dy0.2, Gd0.8
triallylammonium tetrakis pivaloyltrifluoroacetonato Dy0.2, Gd0.8
triallylammonium tetrakis trifluoroacetylacetonato Dy0.2, Gd0.8
triallylammonium tetrakis hexafluoroacetylacetonato Dy0.2, Gd0.8
triallylammonium tetrakis 6,6,7,7,8,8,8-heptafluoro-2,2-dimethyloctanedionato Dy0.2, Gd0.8
triallylammonium tetrakis 1-phenyl-1,3-butanedionato Dy0.2, Gd0.8
anilinium tetrakis acetylacetonato Dy0.2, Gd0.8
anilinium tetrakis dibenzoylmethanato Dy0.2, Gd0.8
anilinium tetrakis thenoyltrifluoroacetonato Dy0.2, Gd0.8
anilinium tetrakis 2,2,6,6-tetramethylheptanedionato Dy0.2, Gd0.8
anilinium tetrakis 3-methylpentane-2,4-dionato Dy0.2, Gd0.8
anilinium tetrakis 3-ethylpentane-2,4-dionato Dy0.2, Gd0.8
anilinium tetrakis pivaloyltrifluoroacetonato Dy0.2, Gd0.8
anilinium tetrakis trifluoroacetylacetonato Dy0.2, Gd0.8
anilinium tetrakis hexafluoroacetylacetonato Dy0.2, Gd0.8 anilinium tetrakis 6,6,7,7,8,8,8-heptafluoro-2,2-dimethyloctanedionato Dy0.2, Gd0.8
anilinium tetrakis 1-phenyl-1,3-butanedionato Dy0.2, Gd0.8
triethylammonium tetrakis acetylacetonato Dy0.1, Gd0.9
triethylammonium tetrakis dibenzoylmethanato Dy0.1, Gd0.9
triethylammonium tetrakis thenoyltrifluoroacetonato Dy0.1, Gd0.9
triethylammonium tetrakis 2,2,6,6-tetramethylheptanedionato Dy0.1, Gd0.9
triethylammonium tetrakis 3-methylpentane-2,4-dionato Dy0.1, Gd0.9
triethylammonium tetrakis 3-ethylpentane-2,4-dionato Dy0.1, Gd0.9
triethylammonium tetrakis pivaloyltrifluoroacetonato Dy0.1, Gd0.9
triethylammonium tetrakis trifluoroacetylacetonato Dy0.1, Gd0.9
triethylammonium tetrakis hexafluoroacetylacetonato Dy0.1, Gd0.9
triethylammonium tetrakis 6,6,7,7,8,8,8-heptafluoro-2,2-dimethyloctanedionato Dy0.1, Gd0.9
triethylammonium tetrakis 1-phenyl-1,3-butanedionato Dy0.1, Gd0.9
morpholinium tetrakis acetylacetonato Dy0.1, Gd0.9
morpholinium tetrakis dibenzoylmethanato Dy0.1, Gd0.9
morpholinium tetrakis thenoyltrifluoroacetonato Dy0.1, Gd0.9
morpholinium tetrakis 2,2,6,6-tetramethylheptanedionato Dy0.1, Gd0.9
morpholinium tetrakis 3-methylpentane-2,4-dionato Dy0.1, Gd0.9
morpholinium tetrakis 3-ethylpentane-2,4-dionato Dy0.1, Gd0.9
morpholinium tetrakis pivaloyltrifluoroacetonato Dy0.1, Gd0.9
morpholinium tetrakis trifluoroacetylacetonato Dy0.1, Gd0.9
morpholinium tetrakis hexafluoroacetylacetonato Dy0.1, Gd0.9
morpholinium tetrakis 6,6,7,7,8,8,8-heptafluoro-2,2-dimethyloctanedionato Dy0.1, Gd0.9
morpholinium tetrakis 1-phenyl-1,3-butanedionato Dy0.1, Gd0.9
dimethylbenzylammonium tetrakis acetylacetonato Dy0.1, Gd0.9
dimethylbenzylammonium tetrakis dibenzoylmethanato Dy0.1, Gd0.9
dimethylbenzylammonium tetrakis thenoyltrifluoroacetonato Dy0.1, Gd0.9
dimethylbenzylammonium tetrakis 2,2,6,6-tetramethylheptanedionato Dy0.1, Gd0.9
dimethylbenzylammonium tetrakis 3-methylpentane-2,4-dionato Dy0.1, Gd0.9
dimethylbenzylammonium tetrakis 3-ethylpentane-2,4-dionato Dy0.1, Gd0.9
dimethylbenzylammonium tetrakis pivaloyltrifluoroacetonato Dy0.1, Gd0.9
dimethylbenzylammonium tetrakis trifluoroacetylacetonato Dy0.1, Gd0.9
dimethylbenzylammonium tetrakis hexafluoroacetylacetonato Dy0.1, Gd0.9
dimethylbenzylammonium tetrakis 6,6,7,7,8,8,8-heptafluoro-2,2-dimethyloctanedionato Dy0.1, Gd0.9
dimethylbenzylammonium tetrakis 1-phenyl-1,3-butanedionato Dy0.1, Gd0.9
triallylammonium tetrakis acetylacetonato Dy0.1, Gd0.9
triallylammonium tetrakis dibenzoylmethanato Dy0.1, Gd0.9
triallylammonium tetrakis thenoyltrifluoroacetonato Dy0.1, Gd0.9
triallylammonium tetrakis 2,2,6,6-tetramethylheptanedionato Dy0.1, Gd0.9
triallylammonium tetrakis 3-methylpentane-2,4-dionato Dy0.1, Gd0.9
triallylammonium tetrakis 3-ethylpentane-2,4-dionato Dy0.1, Gd0.9
triallylammonium tetrakis pivaloyltrifluoroacetonato Dy0.1, Gd0.9
triallylammonium tetrakis trifluoroacetylacetonato Dy0.1, Gd0.9
triallylammonium tetrakis hexafluoroacetylacetonato Dy0.1, Gd0.9
triallylammonium tetrakis 6,6,7,7,8,8,8-heptafluoro-2,2-dimethyloctanedionato Dy0.1, Gd0.9
triallylammonium tetrakis 1-phenyl-1,3-butanedionato Dy0.1, Gd0.9
anilinium tetrakis acetylacetonato Dy0.1, Gd0.9
anilinium tetrakis dibenzoylmethanato Dy0.1, Gd0.9
anilinium tetrakis thenoyltrifluoroacetonato Dy0.1, Gd0.9
anilinium tetrakis 2,2,6,6-tetramethylheptanedionato Dy0.1, Gd0.9
anilinium tetrakis 3-methylpentane-2,4-dionato Dy0.1, Gd0.9
anilinium tetrakis 3-ethylpentane-2,4-dionato Dy0.1, Gd0.9
anilinium tetrakis pivaloyltrifluoroacetonato Dy0.1, Gd0.9
anilinium tetrakis trifluoroacetylacetonato Dy0.1, Gd0.9
anilinium tetrakis hexafluoroacetylacetonato Dy0.1, Gd0.9
anilinium tetrakis 6,6,7,7,8,8,8-heptafluoro-2,2-dimethyloctanedionato Dy0.1, Gd0.9
anilinium tetrakis 1-phenyl-1,3-butanedionato Dy0.1, Gd0.9
triethylammonium tetrakis acetylacetonato Dy0.01, Gd0.99
triethylammonium tetrakis dibenzoylmethanato Dy0.01, Gd0.99
triethylammonium tetrakis thenoyltrifluoroacetonato Dy0.01, Gd0.99
triethylammonium tetrakis 2,2,6,6-tetramethylheptanedionato Dy0.01, Gd0.99
triethylammonium tetrakis 3-methylpentane-2,4-dionato Dy0.01, Gd0.99
triethylammonium tetrakis 3-ethylpentane-2,4-dionato Dy0.01, Gd0.99
triethylammonium tetrakis pivaloyltrifluoroacetonato Dy0.01, Gd0.99
triethylammonium tetrakis trifluoroacetylacetonato Dy0.01, Gd0.99
triethylammonium tetrakis hexafluoroacetylacetonato Dy0.01, Gd0.99
triethylammonium tetrakis 6,6,7,7,8,8,8-heptafluoro-2,2-dimethyloctanedionato Dy0.01, Gd0.99
triethylammonium tetrakis 1-phenyl-1,3-butanedionato Dy0.01, Gd0.99
morpholinium tetrakis acetylacetonato Dy0.01, Gd0.99
morpholinium tetrakis dibenzoylmethanato Dy0.01, Gd0.99
morpholinium tetrakis thenoyltrifluoroacetonato Dy0.01, Gd0.99
morpholinium tetrakis 2,2,6,6-tetramethylheptanedionato Dy0.01, Gd0.99
morpholinium tetrakis 3-methylpentane-2,4-dionato Dy0.01, Gd0.99
morpholinium tetrakis 3-ethylpentane-2,4-dionato Dy0.01, Gd0.99
morpholinium tetrakis pivaloyltrifluoroacetonato Dy0.01, Gd0.99 morpholinium tetrakis trifluoroacetylacetonato Dy0.01, Gd0.99
morpholinium tetrakis hexafluoroacetylacetonato Dy0.01, Gd0.99
morpholinium tetrakis 6,6,7,7,8,8,8-heptafluoro-2,2-dimethyloctanedionato Dy0.01, Gd0.99
morpholinium tetrakis 1-phenyl-1,3-butanedionato Dy0.01, Gd0.99
dimethylbenzylammonium tetrakis acetylacetonato Dy0.01, Gd0.99
dimethylbenzylammonium tetrakis dibenzoylmethanato Dy0.01, Gd0.99
dimethylbenzylammonium tetrakis thenoyltrifluoroacetonato Dy0.01, Gd0.99
dimethylbenzylammonium tetrakis 2,2,6,6-tetramethylheptanedionato Dy0.01, Gd0.99
dimethylbenzylammonium tetrakis 3-methylpentane-2,4-dionato Dy0.01, Gd0.99
dimethylbenzylammonium tetrakis 3-ethylpentane-2,4-dionato Dy0.01, Gd0.99
dimethylbenzylammonium tetrakis pivaloyltrifluoroacetonato Dy0.01, Gd0.99
dimethylbenzylammonium tetrakis trifluoroacetylacetonato Dy0.01, Gd0.99
dimethylbenzylammonium tetrakis hexafluoroacetylacetonato Dy0.01, Gd0.99
dimethylbenzylammonium tetrakis 6,6,7,7,8,8,8-heptafluoro-2,2-dimethyloctanedionato Dy0.01, Gd0.99
dimethylbenzylammonium tetrakis 1-phenyl-1,3-butanedionato Dy0.01, Gd0.99
triallylammonium tetrakis acetylacetonato Dy0.01, Gd0.99
triallylammonium tetrakis dibenzoylmethanato Dy0.01, Gd0.99
triallylammonium tetrakis thenoyltrifluoroacetonato Dy0.01, Gd0.99
triallylammonium tetrakis 2,2,6,6-tetramethylheptanedionato Dy0.01, Gd0.99
triallylammonium tetrakis 3-methylpentane-2,4-dionato Dy0.01, Gd0.99
triallylammonium tetrakis 3-ethylpentane-2,4-dionato Dy0.01, Gd0.99
triallylammonium tetrakis pivaloyltrifluoroacetonato Dy0.01, Gd0.99
triallylammonium tetrakis trifluoroacetylacetonato Dy0.01, Gd0.99
triallylammonium tetrakis hexafluoroacetylacetonato Dy0.01, Gd0.99
triallylammonium tetrakis 6,6,7,7,8,8,8-heptafluoro-2,2-dimethyloctanedionato Dy0.01, Gd0.99
triallylammonium tetrakis 1-phenyl-1,3-butanedionato Dy0.01, Gd0.99
anilinium tetrakis acetylacetonato Dy0.01, Gd0.99
anilinium tetrakis dibenzoylmethanato Dy0.01, Gd0.99
anilinium tetrakis thenoyltrifluoroacetonato Dy0.01, Gd0.99
anilinium tetrakis 2,2,6,6-tetramethylheptanedionato Dy0.01, Gd0.99
anilinium tetrakis 3-methylpentane-2,4-dionato Dy0.01, Gd0.99
anilinium tetrakis 3-ethylpentane-2,4-dionato Dy0.01, Gd0.99
anilinium tetrakis pivaloyltrifluoroacetonato Dy0.01, Gd0.99
anilinium tetrakis trifluoroacetylacetonato Dy0.01, Gd0.99
anilinium tetrakis hexafluoroacetylacetonato Dy0.01, Gd0.99
anilinium tetrakis 6,6,7,7,8,8,8-heptafluoro-2,2-dimethyloctanedionato Dy0.01, Gd0.99
anilinium tetrakis 1-phenyl-1,3-butanedionato Dy0.01, Gd0.99

Unpublished patent applications GB 0102879.4 and GB 0102870.0 disclose applications of triboluminescent materials in adhesives and paper respectively.

With respect to Formula II the $I_3$ anion may be replaced with other suitable anions such as tetrafluoroborate. When the anion is other than $I_3$ then the general formula will be referred to as Formula IV.

The invention claimed is:

1. A triboluminescent material comprising M wherein M is selected from Tb, Eu, Sm, or Dy and from 75% to 99.99% of M is replaced by at least one of Y, Gd, La or Lu, wherein the triboluminescent material is given by:

(i) Formula I:

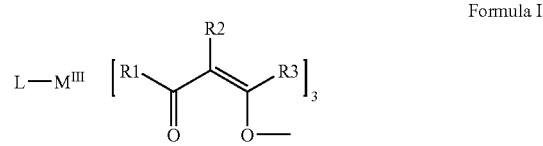

Formula I wherein:
R2 is H or C1-C6 alkyl or phenyl;
R1 and R3 are independently of each other selected from phenyl, naphthyl, H and C1-C6 branched or straight chain alkyl, thiophene and C1-C6 fluorinated alkyl wherein the fluorination may be in 1 or all positions or any intermediate value, substituted phenyl wherein the substituents are independently selected from C1-C4 straight or branched chain alkyl, Cl, Br, F, I and the phenyl group may be substituted in 1, 2 or 3 positions;
L is Formula IA:

Formula IA wherein the arrow indicates that the oxygen coordinates to M and wherein
x is 1 or 2
R4 and R5 are independently of each other selected from phenyl, tolyl, naphthyl, C1-C6 branched or straight chain alkyl and substituted phenyl wherein the substituents are independently selected from C1-C4 straight or branched chain alkyl and the phenyl group may be substituted in 1, 2 or 3 positions;
R6 is selected from phenyl, tolyl, naphthyl, C1-C6 branched or straight chain alkyl, —(CH$_2$)$_n$P(O) R7 R8, wherein n=1 to 4 and —N=(P R7 R8 R9), wherein R7, R8 and R9 are independently selected from phenyl, naphthyl, C1-C6 branched or straight chain alkyl and substituted phenyl wherein the substituents are independently selected from C1-C4 straight or branched chain alkyl and the phenyl group may be substituted in 1, 2 or 3 positions;
R6 is also selected from substituted phenyl wherein the substituents are independently selected from C1-C4 straight or branched chain alkyl and the phenyl group may be substituted in 1, 2 or 3 positions.

2. A triboluminescent material according to claim 1 wherein from 85 to 99.99% of M is replaced.

3. A triboluminescent material according to claim 2 wherein from 95 to 99.99% of M is replaced.

4. A method of making paper that emits light when torn and/or pressed and/or gripped and/or folded comprising the steps of coating and/or impregnating the paper with tribolu minescent material selected from a material according to claim 1.

5. Paper comprising one or more triboluminescent materials according to claim 1 such that the paper triboluminesces when the paper is torn and/or pressed and/or gripped and/or folded.

6. A product comprising paper according to claim 5.

* * * * *